(12) United States Patent
Brubaker et al.

(10) Patent No.: US 9,328,099 B2
(45) Date of Patent: May 3, 2016

(54) CYANOMETHYLPYRAZOLE CARBOXAMIDES AS JANUS KINASE INHIBITORS

(71) Applicants: Jason Brubaker, Cambridge, MA (US); Matthew Lloyd Childers, Medfield, MA (US); Matthew Christopher, Brookline, MA (US); Joshua T. Close, Franklin, MA (US); Jason David Katz, Newton Highlands, MA (US); Joon Jung, Newton, MA (US); Scott Peterson, Salem, MA (US); Phieng Siliphaivanh, Newton, MA (US); Tony Siu, Brookline, MA (US); Graham Frank Smith, Sudbury, MA (US); Luis E. Torres, Norwood, MA (US); Hyun Chong Woo, Natick, MA (US); Jonathan R. Young, Southborough, MA (US); Hongjun Zhang, Newton, MA (US)

(72) Inventors: Jason Brubaker, Cambridge, MA (US); Matthew Lloyd Childers, Medfield, MA (US); Matthew Christopher, Brookline, MA (US); Joshua T. Close, Franklin, MA (US); Jason David Katz, Newton Highlands, MA (US); Joon Jung, Newton, MA (US); Scott Peterson, Salem, MA (US); Phieng Siliphaivanh, Newton, MA (US); Tony Siu, Brookline, MA (US); Graham Frank Smith, Sudbury, MA (US); Luis E. Torres, Norwood, MA (US); Hyun Chong Woo, Natick, MA (US); Jonathan R. Young, Southborough, MA (US); Hongjun Zhang, Newton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 197 days.

(21) Appl. No.: 14/345,978

(22) PCT Filed: Sep. 21, 2012

(86) PCT No.: PCT/US2012/056478
§ 371 (c)(1),
(2) Date: Mar. 20, 2014

(87) PCT Pub. No.: WO2013/043962
PCT Pub. Date: Mar. 28, 2013

(65) Prior Publication Data
US 2014/0228348 A1 Aug. 14, 2014

Related U.S. Application Data

(60) Provisional application No. 61/537,978, filed on Sep. 22, 2011.

(51) Int. Cl.
| | | |
|---|---|---|
| C07D 231/38 | (2006.01) |
| C07D 405/04 | (2006.01) |
| C07D 401/14 | (2006.01) |
| C07D 401/04 | (2006.01) |
| C07D 403/04 | (2006.01) |
| C07D 405/08 | (2006.01) |
| C07D 403/12 | (2006.01) |
| C07D 401/12 | (2006.01) |
| C07D 403/08 | (2006.01) |
| C07D 405/12 | (2006.01) |
| C07D 409/12 | (2006.01) |
| C07D 413/12 | (2006.01) |
| C07D 401/06 | (2006.01) |
| C07D 403/06 | (2006.01) |
| C07D 405/06 | (2006.01) |
| C07D 405/14 | (2006.01) |
| C07D 409/04 | (2006.01) |
| C07D 413/14 | (2006.01) |
| C07D 417/14 | (2006.01) |

(52) U.S. Cl.
CPC ............ *C07D 405/08* (2013.01); *C07D 231/38* (2013.01); *C07D 401/04* (2013.01); *C07D 401/06* (2013.01); *C07D 401/12* (2013.01); *C07D 401/14* (2013.01); *C07D 403/04* (2013.01); *C07D 403/06* (2013.01); *C07D 403/08* (2013.01); *C07D 403/12* (2013.01); *C07D 405/04* (2013.01); *C07D 405/06* (2013.01); *C07D 405/12* (2013.01); *C07D 405/14* (2013.01); *C07D 409/04* (2013.01); *C07D 409/12* (2013.01); *C07D 413/12* (2013.01); *C07D 413/14* (2013.01); *C07D 417/14* (2013.01)

(58) Field of Classification Search
None
See application file for complete search history.

(56) References Cited

U.S. PATENT DOCUMENTS

2010/0022522 A1  1/2010  Rodgers et al.
2011/0224190 A1  9/2011  Huang et al.

FOREIGN PATENT DOCUMENTS

WO     2010014453 A1     2/2010

*Primary Examiner* — Michael Barker
*Assistant Examiner* — Po-Chih Chen
(74) *Attorney, Agent, or Firm* — Patricia A. Shatynski; Catherine D. Fitch

(57) ABSTRACT

The instant invention provides compounds of formula I which are JAK inhibitors, and as such are useful for the treatment of JAK-mediated diseases such as rheumatoid arthritis, asthma, COPD and cancer.

19 Claims, No Drawings

CYANOMETHYLPYRAZOLE CARBOXAMIDES AS JANUS KINASE INHIBITORS

CROSS REFERENCE TO RELATED APPLICATIONS

This application is a U.S. National Phase application under 35 U.S.C. §371 of PCT Application No. PCT/US2012/056478, filed Sep. 21, 2012, which claims priority under 35 U.S.C. §119(e) from U.S. Provisional Application Ser. No. 61/537,978, filed Sep. 21, 2011.

BACKGROUND OF THE INVENTION

Protein kinases are a group of enzymes that regulate the activity of their target proteins by the addition of phosphate groups to the protein substrate. Kinases play an essential role in many physiological processes including cell division, differentiation, cellular homeostasis and signal transduction. Kinases can be subdivided by their target into Serine/Threonine kinases and Tyrosine kinases. Tyrosine kinases are further subdivided into receptor tyrosine kinases and non-receptor tyrosine kinases. The mammalian Janus kinase (JAK) family members are non-receptor tyrosine kinases.

The JAK family has four members; JAK1, JAK2, JAK3 and TYK2. JAK1, JAK2 and TYK2 are universally expressed, whereas JAK3 expression is limited to hematopoetic cells. The JAK family is involved in intracellular signal transduction from >70 different cytokines. Cytokines bind to their cell surface receptors resulting in receptor dimerization and subsequent activation/phosphorylation of JAK tyrosine kinases. The JAKs are either constitutively associated with the receptor or are recruited upon cytokine binding. Specific tyrosine residues on the receptor are then phosphorylated by activated JAKs and serve as docking sites for STAT proteins. STATs are phosphorylated by JAKs, dimerize, then translocate to the nucleus where they bind specific DNA elements and activate gene transcription. JAK1 signals in conjunction with all JAK isoforms in a cytokine dependent manner.

JAKs are essential for multiple physiological functions. This has been demonstrated using genetically engineered mouse models that are deficient in specific JAKs. Jak1$^{-/-}$ mice die perinatally, while Jak2$^{-/-}$ mice have deficiencies in erythropoesis and die around day E12. Jak3$^{-/-}$ mice are viable, but have a SCID phenotype with deficiencies in T cells, B cells and NK cells. TYK2$^{-/-}$ mice exhibit features of hyper IgE syndrome. These phenotypes demonstrate the essential and non-redundant roles of JAK activity in vivo (K. Ghoreschi, A. Laurence, J. J. O'Shea, *Immunol. Rev.* 228, 273 (2009)).

Furthermore, mutations in the JAK enzymes have been associated with diseases in humans. Inactivating mutations in JAK3 (or the cognate common gamma chain cytokine receptor) cause a severe SCID phenotype (J. J. O'Shea, M. Pesu, D. C. Borie, P. S. Changelian, *Nat. Rev. Drug Discov.* 3, 555 (2004)). Deletions of TYK2 result in hyper IgG syndrome and increased infection risk (Y. Minegishi et al., *Immunity.* 25, 745 (2006)). No inactivating mutations have been reported for JAK1 or JAK2, consistent with the data from mice that demonstrates that JAK1 and JAK2 deficient mice are not viable. However, several mutations that result in constitutively active JAK2 have been identified, resulting in myeloproliferative diseases and confirming the central role of JAK2 in hematopoesis (O. bdel-Wahab, *Curr. Opin. Hematol.* 18, 117 (2011)). JAK2 is the sole JAK family member involved in signal transduction of the critical hematopoetic cytokines IL-3, GMCSF, EPO and TPO.

The wealth of mouse and human genetic data demonstrating a central role for JAK kinase activity in autoimmune disease, hematopoesis and oncology has been supported by the use of pan-JAK inhibitors in clinical trials for autoimmune diseases and neoplasms (See K. Ghoreschi, et al, *Immunol. Rev.* 228, 273 (2009), and A. Quintas-Cardama, H. Kantarjian, J. Cortes, S. Verstovsek, *Nat. Rev. Drug Discov.* 10, 127 (2011)). However, several adverse events have been reported that may be associated with inhibition of JAK2 signaling such as anemia, neutropenia and thrombocytopenia. Thus new or improved agents that selectively inhibit JAK1 activity but spare JAK2 activity are required for the treatment of several human diseases with an improved therapeutic index.

A considerable body of literature has accumulated that link the Jak/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

SUMMARY OF THE INVENTION

The present invention provides novel compounds which are inhibitors of JAKs. The invention also provides a method for the treatment and prevention of JAK-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts, or stereoisomers thereof:

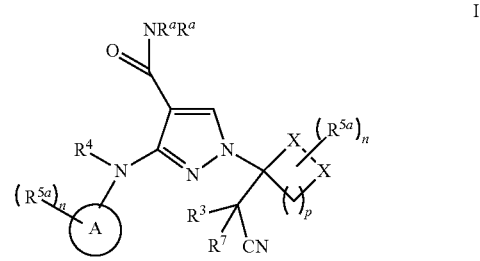

$R^a$ and $R^4$ are each independently selected from hydrogen and $C_{1-4}$alkyl;
A is selected from aryl, and heteroaryl;
n is independently 0, 1, 2, 3, or 4;
p is 0, 1, 2, or 3;
X is independently selected from C, N, O and S;
$R^3$ and $R^7$ are each independently selected from
  hydrogen,
  halogen,
  $C_{1-10}$ alkyl,
  $C_{2-10}$ alkenyl,
  $C_{1-10}$ heteroalkyl,
  aryl $C_{0-10}$ alkyl$C_{0-10}$ alkyl,
  $C_{3-8}$ cycloalkyl$C_{0-10}$ alkyl,
  heteroaryl $C_{0-10}$ alkyl,
  $(C_{3-8})$heterocycloalkyl $C_{0-10}$ alkyl, and wherein each of $R^3$ and $R^7$ are independently substituted with 0, 1, 2, 3, or 4 $R^{5a}$ substituents;

$R^{5a}$ is selected from:
halogen,
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
aryl $C_{2-10}$ alkenyl(oxy)$_{0-1}$(carbonyl)$_{0-1}C_{0-10}$ alkyl,
aryl $C_{2-10}$ alkynyl(oxy)$_{0-1}$(carbonyl)$_{0-1}C_{0-10}$ alkyl,
$C_{3-8}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-8})$heterocycloalkyl $C_{0-10}$ alkyl(oxy)$_{0-1}$(carbonyl)$_{0-1}C_{0-10}$ alkyl,
$C_{1-10}$ alkyl(carbonyl)$_{0-1}$oxy$C_{0-10}$ alkyl,
$C_{1-10}$ heteroalkyl(carbonyl)$_{0-1}$ oxy$C_{0-10}$ alkyl,
$C_{2-10}$ alkenyl(carbonyl)$_{0-1}$oxy$C_{0-10}$ alkyl,
$C_{1-10}$ hetero alkyl(carbonyl)$_{0-1}$oxy$C_{0-10}$ alkyl,
aryl $C_{0-10}$ alkyl(carbonyl)$_{0-1}$oxy$C_{0-10}$ alkyl,
$(C_{3-8})$cycloalkyl $C_{0-10}$ alkyl(carbonyl)$_{0-1}$oxy$C_{0-10}$ alkyl,
heteroaryl$C_{0-10}$ alkyl(carbonyl)$_{0-1}$oxy$C_{0-10}$ alkyl,
$(C_{3-8})$heterocycloalkyl $C_{0-10}$ alkyl(carbonyl)$_{0-1}$oxy$C_{0-10}$ alkyl,
$((C_{0-10})$alkyl$)_{1-2}$aminocarbonyloxy,
$(C_{0-10})$heteroalkylaminocarbonyloxy,
aryl $(C_{0-10})$alkylaminocarbonyloxy,
$(C_{3-8})$cycloalkyl$(C_{0-10})$alkylaminocarbonyloxy,
heteroaryl$(C_{0-10})$alkylaminocarbonyloxy,
$(C_{3-8})$heterocycloalkyl$(C_{0-10})$alkylaminocarbonyloxy,
$C_{0-10}$ alkylamino(oxy)$_{0-1}$carbonyl$C_{0-10}$ alkyl,
$(C_{0-10})$heteroalkylamino(oxy)$_{0-1}$carbonyl$C_{0-10}$ alkyl,
$C_{3-8}$cycloalkyl $C_{0-10}$ alkylamino(oxy)$_{0-1}$carbonyl$C_{0-10}$ alkyl,
aryl $C_{0-10}$alkylamino(oxy)$_{0-1}$carbonyl$C_{0-10}$ alkyl,
heteroaryl$C_{0-10}$ alkylamino(oxy)$_{0-1}$carbonyl$C_{0-10}$ alkyl,
$(C_{3-8})$heterocycloalkyl$C_{0-10}$alkylamino(oxy)$_{0-1}$carbonyl$C_{0-10}$ alkyl,
$C_{1-10}$ alkyl(oxy)$_{0-1}$(carbonyl)$_{0-1}$amino$C_{0-10}$ alkyl,
$C_{1-10}$ heteroalkyl(oxy)$_{0-1}$(carbonyl)$_{0-1}$amino$C_{0-10}$ alkyl,
$C_{3-8}$ cycloalkyl $C_{0-10}$ alkyl(oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl))$_{0-1}$ amino$C_{0-10}$ alkyl,
$(C_{3-8})$heterocycloalkyl $C_{0-10}$ alkyl(oxy)$_{0-1}$(carbonyl)$_{0-1}$amino$C_{0-10}$ alkyl,
—$CO_2(C_{0-10}$ alkyl),
—$(C_{0-10}$ alkyl)$CO_2H$,
Oxo (=O);
$C_{1-10}$ alkylsulfonyl,
$C_{1-10}$ heteroalkylsulfonyl,
$(C_{3-8})$ cycloalkylsulfonyl,
$(C_{3-8})$ cycloheteroalkylsulfonyl,
heteroarylsulfonyl,
arylsulfonyl,
aminosulfonyl,
—$SO_2N(C_{1-6}$alkyl$)_{1-2}$,
—$SO_2C_{1-6}$alkyl,
—$SO_2CF_3$,
—$SO_2CF_2H$,
$C_{1-10}$ alkylsulfinyl,
—Si$(CH_3)_3$,
amino,
$(C_{0-10}$ alkyl$)_{1-2}$ amino,
$C_{1-4}$ acylamino $C_{0-10}$ alkyl,
hydroxy,
$(C_{1-10}$ alkyl)OH,
$C_{0-10}$ alkylalkoxy,
cyano,
$(C_{1-6}$alkyl)cyano, and
$C_{1-6}$ haloalkyl;

wherein two $R^{5a}$ and the atom to which they are attached may optionally form a −4, −5, or −6 member saturated ring system;

wherein $R^{5a}$ is each optionally substituted with 1, 2, 3, or 4 $R^6$ substituents and $R^6$ is independently selected from:
halogen,
$C_{1-10}$ alkyl(oxy)$_{0-1}$ (carbonyl)$_{0-1}C_{0-10}$ alkyl,
$C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
aryl $C_{2-10}$ alkenyl(oxy)$_{0-1}$(carbonyl)$_{0-1}C_{0-10}$ alkyl,
aryl $C_{2-10}$ alkynyl(oxy)$_{0-1}$(carbonyl)$_{0-1}C_{0-10}$ alkyl,
$C_{3-8}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-8})$heterocycloalkyl $C_{0-10}$ alkyl(oxy)$_{0-1}$(carbonyl)$_{0-1}C_{0-10}$ alkyl,
$C_{1-10}$ alkyl(carbonyl)$_{0-1}$oxy$C_{0-10}$ alkyl,
$C_{2-10}$ alkenyl(carbonyl)$_{0-1}$oxy$C_{0-10}$ alkyl,
$C_{1-10}$ heteroalkyl(carbonyl)$_{0-1}$oxy$C_{0-10}$ alkyl,
aryl $C_{0-10}$ alkyl(carbonyl)$_{0-1}$oxy$C_{0-10}$ alkyl,
$(C_{3-8})$cycloalkyl $C_{0-10}$ alkyl(carbonyl)$_{0-1}$oxy$C_{0-10}$ alkyl,
heteroaryl$C_{0-10}$ alkyl(carbonyl)$_{0-1}$oxy$C_{0-10}$ alkyl,
$(C_{3-8})$heterocycloalkyl $C_{0-10}$ alkyl(carbonyl)$_{0-1}$oxy$C_{0-10}$ alkyl,
$((C_{0-10})$alkyl$)_{1-2}$aminocarbonyloxy,
aryl $(C_{0-10})$alkylaminocarbonyloxy,
$(C_{3-8})$cycloalkyl$(C_{0-10})$alkylaminocarbonyloxy,
heteroaryl$(C_{0-10})$alkylaminocarbonyloxy,
$(C_{3-8})$heterocycloalkyl$(C_{0-10})$alkylaminocarbonyloxy,
$C_{0-10}$ alkylamino(oxy)$_{0-1}$carbonyl$C_{0-10}$ alkyl,
$C_{3-8}$ cycloalkyl $C_{0-10}$ alkylamino(oxy)$_{0-1}$carbonyl$C_{0-10}$ alkyl,
aryl $C_{0-10}$ alkylamino(oxy)$_{0-1}$carbonyl$C_{0-10}$ alkyl,
heteroaryl $C_{0-10}$ alkylamino(oxy)$_{0-1}$carbonyl$C_{0-10}$ alkyl,
$(C_{3-8})$heterocycloalkyl $C_{0-10}$ alkylamino(oxy)$_{0-1}$carbonyl$C_{0-10}$ alkyl,
$C_{1-10}$ alkyl(oxy)$_{0-1}$carbonylamino$C_{0-10}$ alkyl,
$C_{3-8}$ cycloalkyl $C_{0-10}$ alkyl(oxy)$_{0-1}$carbonylamino$C_{0-10}$ alkyl,
aryl $C_{0-10}$ alkyl(oxy)$_{0-1}$carbonylamino$C_{0-10}$ alkyl,
heteroaryl $C_{0-10}$ alkyl(oxy)$_{0-1}$carbonylamino$C_{0-10}$ alkyl,
$(C_{3-8})$heterocycloalkyl $C_{0-10}$ alkyl(oxy)$_{0-1}$carbonylamino$C_{0-10}$ alkyl,
—$CO_2(C_{0-10}$ alkyl),
—$(C_{0-10}$ alkyl)$CO_2H$,
Oxo (=O),
$C_{1-10}$ alkylsulfonyl,
$C_{1-10}$ heteroalkylsulfonyl,
$(C_{3-8})$ cycloalkylsulfonyl,
$(C_{3-8})$ cycloheteroalkylsulfonyl,
heteroarylsulfonyl,
arylsulfonyl,
aminosulfonyl,
—$SO_2N(C_{1-6}$ alkyl$)_{1-2}$,
—$SO_2C_{1-6}$ alkyl,
—$SO_2CF_3$,
—$SO_2CF_2H$,
$C_{1-10}$ alkylsulfinyl,
—OSi$(C_{1-10}$alkyl$)_3$,
—Si$(CH_3)_3$,
amino, (C$_{0-10}$ alkyl)$_{1-2}$ amino,
-(oxy)$_{0-1}$(carbonyl)$_{0-1}$N(C$_{0-10}$ alkyl)$_{1-2}$
C$_{1-4}$ acylamino C$_{0-10}$ alkyl,
hydroxy,
(C$_{1-10}$ alkyl)OH,
C$_{1-10}$ alkoxy,
(C$_{1-10}$ alkyl)cyano,
cyano, and
C$_{1-6}$haloalkyl; and
wherein two R$^6$ and the atoms to which they are attached may optionally form a 3-, 4-, 5-, or 6-membered saturated ring system; and R$^6$ is optionally substituted with 1, 2, or 3 substituents selected from hydrogen, hydroxy, (C$_{1-6}$)alkyl, (C$_{1-6}$)alkoxy, (C$_{1-10}$ alkyl)OH, halogen, CO$_2$H, —(C$_{0-6}$)alkylCN, —O(C=O)C$_1$-C$_6$ alkyl, NO$_2$, trifluoromethoxy, trifluoroethoxy, trifluoromethyl, trifluoroethyl, —N—C(O)O(C$_{0-6}$) alkyl, C$_{1-10}$ alkylsulfonyl, C$_{1-10}$ heteroalkylsulfonyl, oxo (O=), (C$_{3-8}$) cycloalkylsulfonyl, (C$_{3-8}$) cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —Si(CH$_3$)$_3$, —SO$_2$CF$_2$H, —C$_{1-10}$ alkylsulfinyl, —OSi(C$_{1-10}$alkyl)$_3$, —O$_{(0-1)}$(C$_{1-10}$)haloalkyl, amino (C$_{1-6}$alkyl)$_{0-2}$ and NH$_2$; with the proviso that the compound of formula I other than:

1-[3-(cyanomethyl)-1-(ethylsulfonyl)azetidin-3-yl]-3-({4-[(1,1-dioxidothiomorpholin-4-yl)carbonyl]phenyl}amino)-1H-pyrazole-4-carboxamide; and 1-[3-(cyanomethyl)-1-(naphthalene-2-ylsulfonyl)azetidin-3-yl]-3-(phenylamino)-1H-pyrazole-4-carboxamide.

Representative compounds of the instant invention include, but are not limited to the following compounds and their pharmaceutically acceptable salts and stereoisomers thereof:

tert-Butyl 4-[4-carbamoyl-3-(phenylamino)-1H-pyrazol-1-yl]-4-(cyanomethyl)piperidine-1-carboxylate;
tert-butyl 4-{3-[(4-bromophenyl)amino]-4-carbamoyl-1H-pyrazol-1-yl}-4-(cyanomethyl)piperidine-1-carboxylate;
tert-butyl 3-[4-carbamoyl-3-(phenylamino)-1H-pyrazol-1-yl]-3-(cyanomethyl)azetidine-1-carboxylate;
tert-butyl 4-(3-{[3-(1H-benzotriazol-1-ylmethyl)phenyl]amino}-4-carbamoyl-1H-pyrazol-1-yl)-4-(cyanomethyl)piperidine-1-carboxylate;
tert-butyl 3-(4-carbamoyl-3-{[4-(methylsulfonyl)phenyl]amino}-1H-pyrazol-1-yl)-3-(cyanomethyl)azetidine-1-carboxylate;
tert-butyl 4-[4-carbamoyl-3-({4-[(1,1-dioxidothiomorpholin-4-yl)carbonyl]phenyl}amino)-1H-pyrazol-1-yl]-4-(cyanomethyl)piperidine-1-carboxylate;
tert-butyl 4-[4-carbamoyl-3-(pyridin-4-ylamino)-1H-pyrazol-1-yl]-4-(cyanomethyl)piperidine-1-carboxylate;
tert-butyl 3-[4-carbamoyl-3-({4-[(1,1-dioxidothiomorpholin-4-yl)carbonyl]phenyl}amino)-1H-pyrazol-1-yl]-3-(cyanomethyl)azetidine-1-carboxylate;
tert-Butyl-4-[4-carbamoyl-3-(phenylamino)-1H-pyrazol-1-yl]-4-(cyanomethyl)-3-methylpiperidine-1-carboxylate;
1-[3-(cyanomethyl)-1-(ethylsulfonyl)azetidin-3-yl]-3-(phenylamino)-1H-pyrazole-4-carboxamide;
1-[3-(cyanomethyl)-1-(ethylsulfonyl)azetidin-3-yl]-3-({4-[(1,1-dioxidothiomorpholin-4-yl)carbonyl]phenyl}amino)-1H-pyrazole-4-carboxamide;
1-[1-(cyanomethyl)cyclohexyl]-3-{[4-(methylsulfonyl)phenyl]amino}-1H-pyrazole-4-carboxamide;
1-[1-(cyanomethyl)cyclohexyl]-3-(phenylamino)-1H-pyrazole-4-carboxamide;
tert-butyl 3-(4-carbamoyl-3-{[4-(methylsulfonyl)phenyl]amino}-1H-pyrazol-1-yl)-3-(cyanomethyl)pyrrolidine-1-carboxylate;
tert-butyl 3-[4-carbamoyl-3-(phenylamino)-1H-pyrazol-1-yl]-3-(cyanomethyl)pyrrolidine-1-carboxylate;
tert-butyl 4-[4-carbamoyl-3-(phenylamino)-1H-pyrazol-1-yl]-4-(cyanomethyl)cyclohexanecarboxylate;
tert-butyl {4-[4-carbamoyl-3-(phenylamino)-1H-pyrazol-1-yl]-4-(cyanomethyl)cyclohexyl}carbamate;
1-[3-(cyanomethyl)oxetan-3-yl]-3-(phenylamino)-1H-pyrazole-4-carboxamide;
1-(3-cyano-1-(cyanomethyl)cyclobutyl)-3-(phenylamino)-1H-pyrazole-4-carboxamide;
1-(3-cyano-1-(cyanomethyl)cyclobutyl)-3-((4-(methylsulfonyl)phenyl)amino)-1H-pyrazole-4-carboxamide;
tert-butyl 6-[4-carbamoyl-3-(phenylamino)-1H-pyrazol-1-yl]-6-(cyanomethyl)-2-azaspiro[3.3]heptane-2-carboxylate;
1-[4-(Cyanomethyl)-1-(3,4-dimethoxyphenyl)piperidin-4-yl]-3-[(4-fluorophenyl)amino]-1H-pyrazole-4-carboxamide;
1-[4-(cyanomethyl)-1-isoquinolin-4-ylpiperidin-4-yl]-3-[(4-fluorophenyl)amino]-1H-pyrazole-4-carboxamide;
1-[4-(cyanomethyl)-1-quinolin-4-ylpiperidin-4-yl]-3-[(4-fluorophenyl)amino]-1H-pyrazole-4-carboxamide;
1-[4-(cyanomethyl)-1-(2-methylpyridin-4-yl)piperidin-4-yl]-3-[(4-fluorophenyl)amino]-1H-pyrazole-4-carboxamide;
1-[4-(cyanomethyl)-1-(5-fluoropyridin-3-yl)piperidin-4-yl]-3-[(4-fluorophenyl)amino]-1H-pyrazole-4-carboxamide;
1-[4-(cyanomethyl)-1-(2-methoxypyridin-4-yl)piperidin-4-yl]-3-[(4-fluorophenyl)amino]-1H-pyrazole-4-carboxamide;
1-{4-(cyanomethyl)-1-[6-(1-hydroxy-1-methylethyl)pyridin-2-yl]piperidin-4-yl}-3-[(4-fluorophenyl)amino]-1H-pyrazole-4-carboxamide;
1-{4-(cyanomethyl)-1-[5-(trifluoromethyl)pyridin-3-yl]piperidin-4-yl}-3-[(4-fluorophenyl)amino]-1H-pyrazole-4-carboxamide;
1-{4-(cyanomethyl)-1-[4-(2,2,2-trifluoro-1-hydroxyethyl)phenyl]piperidin-4-yl}-3-[(4-fluorophenyl)amino]-1H-pyrazole-4-carboxamide;
1-{4-(cyanomethyl)-1-[6-(2-hydroxyethoxy)pyridin-2-yl]piperidin-4-yl}-3-[(4-fluorophenyl)amino]-1H-pyrazole-4-carboxamide;
1-[4-(cyanomethyl)-1-(4-fluoro-3-methoxyphenyl)piperidin-4-yl]-3-[(4-fluorophenyl)amino]-1H-pyrazole-4-carboxamide;
1-[4-(cyanomethyl)-1-(3-fluoro-5-methoxyphenyl)piperidin-4-yl]-3-[(4-fluorophenyl)amino]-1H-pyrazole-4-carboxamide;
1-{4-(cyanomethyl)-1-[6-(difluoromethoxy)pyridin-3-yl]piperidin-4-yl}-3-[(4-fluorophenyl)amino]-1H-pyrazole-4-carboxamide;
1-[4-(cyanomethyl)-1-(5,6-dimethylpyridin-3-yl)piperidin-4-yl]-3-[(4-fluorophenyl)amino]-1H-pyrazole-4-carboxamide;
1-{4-(cyanomethyl)-1-[6-(1-methylethoxy)pyridin-2-yl]piperidin-4-yl}-3-[(4-fluorophenyl)amino]-1H-pyrazole-4-carboxamide;
1-[4-(cyanomethyl)-1-(6-ethoxypyridin-2-yl)piperidin-4-yl]-3-[(4-fluorophenyl)amino]-1H-pyrazole-4-carboxamide;
1-[4-(cyanomethyl)-1-(3-cyclopropylphenyl)piperidin-4-yl]-3-[(4-fluorophenyl)amino]-1H-pyrazole-4-carboxamide;

1-[4-(cyanomethyl)-1-(6-cyanopyridin-2-yl)piperidin-4-yl]-3-[(4-fluorophenyl)amino]-1H-pyrazole-4-carboxamide;

1-{4-(cyanomethyl)-1-[5-(difluoromethoxy)pyridin-2-yl]piperidin-4-yl}-3-[(4-fluorophenyl)amino]-1H-pyrazole-4-carboxamide;

1-[4-(cyanomethyl)-1-(6-methylpyridin-2-yl)piperidin-4-yl]-3-[(4-fluorophenyl)amino]-1H-pyrazole-4-carboxamide;

1-[4-(cyanomethyl)-1-(5-cyanopyridin-3-yl)piperidin-4-yl]-3-[(4-fluorophenyl)amino]-1H-pyrazole-4-carboxamide;

1-[4-(cyanomethyl)-1-(6-fluoropyridin-3-yl)piperidin-4-yl]-3-[(4-fluorophenyl)amino]-1H-pyrazole-4-carboxamide;

1-[4-(cyanomethyl)-1-(3-methoxypyridin-2-yl)piperidin-4-yl]-3-[(4-fluorophenyl)amino]-1H-pyrazole-4-carboxamide;

1 [4-(cyanomethyl)-1-pyrimidin-5-ylpiperidin-4-yl]-3-[(4-fluorophenyl)amino]-1H-pyrazole-4-carboxamide;

1-[4-(cyanomethyl)-1-(2-methoxypyrimidin-5-yl)piperidin-4-yl]-3-[(4-fluorophenyl)amino]-1H-pyrazole-4-carboxamide;

1-[4-(cyanomethyl)-1-(4-cyanophenyl)piperidin-4-yl]-3-[(4-fluorophenyl)amino]-1H-pyrazole-4-carboxamide;

1-[4-(cyanomethyl)-1-(3-fluorophenyl)piperidin-4-yl]-3-[(4-fluorophenyl)amino]-1H-pyrazole-4-carboxamide;

1-{4-(cyanomethyl)-1-[6-(trifluoromethyl)pyridin-3-yl]piperidin-4-yl}-3-[(4-fluorophenyl)amino]-1H-pyrazole-4-carboxamide;

1-[4-(cyanomethyl)-1-(2-methylpyridin-3-yl)piperidin-4-yl]-3-[(4-fluorophenyl)amino]-1H-pyrazole-4-carboxamide;

1-[4-(cyanomethyl)-1-pyridin-3-ylpiperidin-4-yl]-3-[(4-fluorophenyl)amino]-1H-pyrazole-4-carboxamide;

1-[4-(cyanomethyl)-1-(4-methylpyridin-2-yl)piperidin-4-yl]-3 [(4-fluorophenyl)amino]-1H-pyrazole-4-carboxamide;

1-[4-(cyanomethyl)-1-(5-fluoro-2-methylphenyl)piperidin-4-yl]-3-[(4-fluorophenyl)amino]-1H-pyrazole-4-carboxamide;

1-[4-(cyanomethyl)-1-(4-methylpyridin-3-yl)piperidin-4-yl]-3-[(4-fluorophenyl)amino]-1H-pyrazole-4-carboxamide;

1-[4-(cyanomethyl)-1-(3-fluoro-4-methylphenyl)piperidin-4-yl]-3-[(4-fluorophenyl)amino]-1H-pyrazole-4-carboxamide;

methyl 6-[4-{4-carbamoyl-3-[(4-fluorophenyl)amino]-1H-pyrazol-1-yl}-4-(cyanomethyl)piperidin-1-yl]pyridine-2-carboxylate;

1-[4-(cyanomethyl)-1-(6-ethoxypyridin-3-yl)piperidin-4-yl]-3-[(4-fluorophenyl)amino]-1H-pyrazole-4-carboxamide;

1-[4-(cyanomethyl)-1-(5-methoxypyridin-3-yl)piperidin-4-yl]-3-[(4-fluorophenyl)amino]-1H-pyrazole-4-carboxamide;

1-[4-(cyanomethyl)-1-(4-fluorophenyl)piperidin-4-yl]-3-[(4-fluorophenyl)amino]-1H-pyrazole-4-carboxamide;

1-[4-(cyanomethyl)-1-(4-methylphenyl)piperidin-4-yl]-3-[(4-fluorophenyl)amino]-1H-pyrazole-4-carboxamide;

1-[4-(cyanomethyl)-1-(3,5-difluorophenyl)piperidin-4-yl]-3-[(4-fluorophenyl)amino]-1H-pyrazole-4-carboxamide;

1-[4-(cyanomethyl)-1-(2-methoxyphenyl)piperidin-4-yl]-3-[(4-fluorophenyl)amino]-1H-pyrazole-4-carboxamide;

1-[4-(cyanomethyl)-1-(4-fluoro-3-methylphenyl)piperidin-4-yl]-3-[(4-fluorophenyl)amino]-1H-pyrazole-4-carboxamide;

1-[4-(cyanomethyl)-1-(2-fluoro-3-methylphenyl)piperidin-4-yl]-3-[(4-fluorophenyl)amino]-1H-pyrazole-4-carboxamide;

1-[4-(cyanomethyl)-1-(4-fluoropyridin-2-yl)piperidin-4-yl]-3-[(4-fluorophenyl)amino]-1H-pyrazole-4-carboxamide;

1-[4-(cyanomethyl)-1-(3,4-difluorophenyl)piperidin-4-yl]-3-[(4-fluorophenyl)amino]-1H-pyrazole-4-carboxamide;

1-[4-(cyanomethyl)-1-pyridin-4-ylpiperidin-4-yl]-3-[(4-fluorophenyl)amino]-1H-pyrazole-4-carboxamide;

1-[4-(cyanomethyl)-1-(4-methylpyrimidin-5-yl)piperidin-4-yl]-3-[(4-fluorophenyl)amino]-1H-pyrazole-4-carboxamide;

1-[4-(cyanomethyl)-1-(5-methylpyridin-3-yl)piperidin-4-yl]-3-[(4-fluorophenyl)amino]-1H-pyrazole-4-carboxamide;

1-{4-(cyanomethyl)-1-[6-(2-hydroxy-2-methylpropyl)pyridin-2-yl]piperidin-4-yl}-3-[(4-fluorophenyl)amino]-1H-pyrazole-4-carboxamide;

1-{4-(cyanomethyl)-1-[6-(fluoromethyl)pyridin-2-yl]piperidin-4-yl}-3-[(4-fluorophenyl)amino]-1H-pyrazole-4-carboxamide;

1-[4-(cyanomethyl)-1-(2-fluoropyridin-3-yl)piperidin-4-yl]-3-[(4-fluorophenyl)amino]-1H-pyrazole-4-carboxamide;

1-[4-(cyanomethyl)-1-(6-methylpyridin-3-yl)piperidin-4-yl]-3-[(4-fluorophenyl)amino]-1H-pyrazole-4-carboxamide;

1-[4-(cyanomethyl)-1-(6-methoxypyridin-3-yl)piperidin-4-yl]-3-[(4-fluorophenyl)amino]-1H-pyrazole-4-carboxamide;

1-[4-(cyanomethyl)-1-(6-fluoropyridin-2-yl)piperidin-4-yl]-3-[(4-fluorophenyl)amino]-1H-pyrazole-4-carboxamide;

1-{4-(cyanomethyl)-1-[4-(trifluoromethyl)pyridin-2-yl]piperidin-4-yl}-3-[(4-fluorophenyl)amino]-1H-pyrazole-4-carboxamide;

1-[4-(cyanomethyl)-1-(6-fluoro-5-methylpyridin-3-yl)piperidin-4-yl]-3-[(4-fluorophenyl)amino]-1H-pyrazole-4-carboxamide;

tert-Butyl 4-(4-carbamoyl-3-{[4-(methylsulfonyl)phenyl]amino}-1H-pyrazol-1-yl)-4-(cyanomethyl)piperidine-1-carboxylate;

tert-butyl 4-[4-carbamoyl-3-({4-[(1-methylethoxy)carbonyl]phenyl}amino)-1H-pyrazol-1-yl]-4-(cyanomethyl)piperidine-1-carboxylate;

tert-butyl 4-(4-carbamoyl-3-{[3-(1H-imidazol-1-ylmethyl)phenyl]amino}-1H-pyrazol-1-yl)-4-(cyanomethyl)piperidine-1-carboxylate;

2,2,2-trifluoroethyl 4-(3-{[3-(1H-benzotriazol-1-ylmethyl)phenyl]amino}-4-carbamoyl-1H-pyrazol-1-yl)-4-(cyanomethyl)piperidine-1-carboxylate;

1-[4-(cyanomethyl)tetrahydro-2H-pyran-4-yl]-3-{[4-(methylsulfonyl)phenyl]amino}-1H-pyrazole-4-carboxamide;

tert-butyl 4-{4-carbamoyl-3-[(2-cyanopyrimidin-5-yl)amino]-1H-pyrazol-1-yl}-4-(cyanomethyl)piperidine-1-carboxylate;

tert-Butyl 4-(4-carbamoyl-3-((4-fluorophenyl)amino)-1H-pyrazol-1-yl)-4-(1-cyanoethyl)piperidine-1-carboxylate;

tert-butyl 4-{4-carbamoyl-3-[(4-fluorophenyl)amino]-1H-pyrazol-1-yl}-4-[cyano(cyclopropyl)methyl]piperidine-1-carboxylate;

tert-butyl-4-{4-carbamoyl-3-[(4-fluorophenyl)amino]-1H-pyrazol-1-yl}-4-(cyanomethyl)-3-fluoropiperidine-1-carboxylate;

1-[4-(cyanomethyl)tetrahydro-2H-pyran-4-yl]-3-(phenylamino)-1H-pyrazole-4-carboxamide;

1-[8-(cyanomethyl)-1,4-dioxaspiro[4.5]dec-8-yl]-3-[(4-fluorophenyl)amino]-1H-pyrazole-4-carboxamide;

1-[8-(cyanomethyl)-1,4-dioxaspiro[4.5]dec-8-yl]-3-{[4-(methylsulfonyl)phenyl]amino}-1H-pyrazole-4-carboxamide;

1-(4-(Cyanomethyl)tetrahydro-2H-thiopyran-4-yl)-3-((4-fluorophenyl)amino)-1H-pyrazole-4-carboxamide;

1-(4-(Cyanomethyl)-1,1-dioxidotetrahydro-2H-thiopyran-4-yl)-3-((4-fluorophenyl)amino)-1H-pyrazole-4-carboxamide;

tert-Butyl 4-{4-carbamoyl-3-[(2-fluoropyridin-4-yl)amino]-1H-pyrazol-1-yl}-4-(cyanomethyl)piperidine-1-carboxylate;

tert-butyl 4-(4-carbamoyl-3-{[4-(methoxycarbonyl)phenyl]amino}-1H-pyrazol-1-yl)-4-(cyanomethyl)piperidine-1-carboxylate;

tert-butyl 4-{4-carbamoyl-3-[(4-fluorophenyl)amino]-1H-pyrazol-1-yl}-4-(cyanomethyl)piperidine-1-carboxylate;

tert-Butyl 4-[4-(aminocarbonyl)-34 {4-[(methylamino)carbonyl]phenyl}amino)-1H-pyrazol-1-yl]-4-(cyanomethyl)piperidine-1-carboxylate;

tert-butyl 4-{4-carbamoyl-3-[(4-cyanophenyl)amino]-1H-pyrazol-1-yl}-4-(cyanomethyl)piperidine-1-carboxylate;

tert-butyl 4-(4-carbamoyl-3-(6-(2-hydroxypropan-2-yl)pyridin-3-ylamino)-1H-pyrazol-1-yl)-4-(cyanomethyl)piperidine-1-carboxylate;

tert-butyl 4-(4-carbamoyl-3-(6-(1-hydroxyethyl)pyridin-3-ylamino)-1H-pyrazol-1-yl)-4-(cyanomethyl)piperidine-1-carboxylate;

tert-butyl 4-(4-carbamoyl-3-(4-(2-hydroxypropan-2-yl)phenylamino)-1H-pyrazol-1-yl)-4-(cyanomethyl)piperidine-1-carboxylate;

tert-butyl 4-(4-carbamoyl-3-(4-(1-hydroxyethyl)phenylamino)-1H-pyrazol-1-yl)-4-(cyanomethyl)piperidine-1-carboxylate;

tert-butyl 4-(3-(4-acetylphenylamino)-4-carbamoyl-1H-pyrazol-1-yl)-4-(cyanomethyl)piperidine-1-carboxylate;

tert-butyl 4-(4-carbamoyl-3-{[4-(trifluoroacetyl)phenyl]amino}-1H-pyrazol-1-yl)-4-(cyanomethyl)piperidine-1-carboxylate;

tert-butyl 4-{4-carbamoyl-3-[(6-cyanopyridin-3-yl)amino]-1H-pyrazol-1-yl}-4-(cyanomethyl)piperidine-1-carboxylate;

tert-butyl 4-(4-carbamoyl-3-{[4-(1-methyl-1H-pyrazol-3-yl)phenyl]amino}-1H-pyrazol-1-yl)-4-(cyanomethyl)piperidine-1-carboxylate;

tert-butyl 4-{3-[(2-aminopyridin-4-yl)amino]-4-carbamoyl-1H-pyrazol-1-yl}-4-(cyanomethyl)piperidine-1-carboxylate;

tert-butyl 4-[4-carbamoyl-3-({4-[(trifluoromethyl)sulfonyl]phenyl}amino)-1H-pyrazol-1-yl]-4-(cyanomethyl)piperidine-1-carboxylate;

tert-butyl 4-[4-carbamoyl-3-({4-[(difluoromethyl)sulfonyl]phenyl}amino)-1H-pyrazol-1-yl]-4-(cyanomethyl)piperidine-1-carboxylate;

tert-butyl 4-{4-carbamoyl-3-[(2-methylpyridin-4-yl)amino]-1H-pyrazol-1-yl}-4-(cyanomethyl)piperidine-1-carboxylate;

tert-butyl 4-(4-carbamoyl-3-{[2-(hydroxymethyl)pyridin-4-yl]amino}-1H-pyrazol-1-yl)-4-(cyanomethyl)piperidine-1-carboxylate;

tert-butyl 4-{4-carbamoyl-3-[(2-methoxypyridin-4-yl)amino]-1H-pyrazol-1-yl}-4-(cyanomethyl)piperidine-1-carboxylate;

tert-butyl 4-{4-carbamoyl-3-[(4-sulfamoylphenyl)amino]-1H-pyrazol-1-yl}-4-(cyanomethyl)piperidine-1-carboxylate;

tert-butyl 4-(4-carbamoyl-3-{[4-(dimethylsulfamoyl)phenyl]amino}-1H-pyrazol-1-yl)-4-(cyanomethyl)piperidine-1-carboxylate;

tert-butyl 4-(4-carbamoyl-3-{[4-(dimethylcarbamoyl)phenyl]amino}-1H-pyrazol-1-yl)-4-(cyanomethyl)piperidine-1-carboxylate;

tert-butyl 4-(4-carbamoyl-3-{[2-(trifluoromethyl)pyridin-4-yl]amino}-1H-pyrazol-1-yl)-4-(cyanomethyl)piperidine-1-carboxylate;

tert-butyl 4-(4-carbamoyl-3-{[3-fluoro-4-(morpholin-4-ylcarbonyl)phenyl]amino}-1H-pyrazol-1-yl)-4-(cyanomethyl)piperidine-1-carboxylate;

tert-butyl 4-(4-carbamoyl-3-{[4-(morpholin-4-ylcarbonyl)phenyl]amino}-1H-pyrazol-1-yl)-4-(cyanomethyl)piperidine-1-carboxylate;

tert-butyl 4-{4-carbamoyl-3-[(4-cyano-3-fluorophenyl)amino]-1H-pyrazol-1-yl}-4-(cyanomethyl)piperidine-1-carboxylate;

tert-butyl 4-{4-carbamoyl-3-[(2-carbamoylpyridin-4-yl)amino]-1H-pyrazol-1-yl}-4-(cyanomethyl)piperidine-1-carboxylate;

tert-butyl 4-{4-carbamoyl-3-[(3,4-difluorophenyl)amino]-1H-pyrazol-1-yl}-4-(cyanomethyl)piperidine-1-carboxylate;

tert-butyl 4-{4-carbamoyl-3-[(2-chloropyridin-4-yl)amino]-1H-pyrazol-1-yl}-4-(cyanomethyl)piperidine-1-carboxylate;

tert-butyl 4-(4-carbamoyl-3-{[4-(3-methyl-1,2,4-oxadiazol-5-yl)phenyl]amino}-1H-pyrazol-1-yl)-4-(cyanomethyl)piperidine-1-carboxylate;

tert-butyl 4-{4-carbamoyl-3-[(2,6-dichloropyridin-4-yl)amino]-1H-pyrazol-1-yl}-4-(cyanomethyl)piperidine-1-carboxylate;

tert-butyl 4-(4-carbamoyl-3-{[4-(5-methyl-1,2,4-oxadiazol-3-yl)phenyl]amino}-1H-pyrazol-1-yl)-4-(cyanomethyl)piperidine-1-carboxylate;

tert-butyl 4-{4-carbamoyl-3-[(2-cyanopyridin-4-yl)amino]-1H-pyrazol-1-yl}-4-(cyanomethyl)piperidine-1-carboxylate;

tert-butyl 4-[4-carbamoyl-3-(pyridin-3-ylamino)-1H-pyrazol-1-yl]-4-(cyanomethyl)piperidine-1-carboxylate;

tert-butyl 4-{4-carbamoyl-3-[(5-fluoropyridin-3-yl)amino]-1H-pyrazol-1-yl}-4-(cyanomethyl)piperidine-1-carboxylate;

tert-butyl 4-{4-carbamoyl-3-[(5-chloropyridin-3-yl)amino]-1H-pyrazol-1-yl}-4-(cyanomethyl)piperidine-1-carboxylate;

2,2-difluoroethyl 4-(4-carbamoyl-3-{[6-(cyclobutyloxy)pyridin-3-yl]amino}-1H-pyrazol-1-yl)-4-(cyanomethyl)piperidine-1-carboxylate;

2,2-difluoroethyl 4-{4-carbamoyl-3-[(6-cyclobutylpyridin-3-yl)amino]-1H-pyrazol-1-yl}-4-(cyanomethyl)piperidine-1-carboxylate;

2,2-difluoroethyl 4-{4-carbamoyl-3-[(2-methoxypyridin-4-yl)amino]-1H-pyrazol-1-yl}-4-(cyanomethyl)piperidine-1-carboxylate;

2,2-difluoroethyl 4-{4-carbamoyl-3-[(6-cyclopropylpyridin-3-yl)amino]-1H-pyrazol-1-yl}-4-(cyanomethyl)piperidine-1-carboxylate;

2,2-difluoroethyl 4-{4-carbamoyl-3-[(2-cyclopropylpyridin-4-yl)amino]-1H-pyrazol-1-yl}-4-(cyanomethyl)piperidine-1-carboxylate;

2,2,2-Trifluoroethyl 4-(4-carbamoyl-3-(6-(2-hydroxypropan-2-yl)pyridin-3-ylamino)-1H-pyrazol-1-yl)-4-(cyanomethyl)piperidine-1-carboxylate;

2,2,2-trifluoroethyl 4-(4-carbamoyl-3-(4-(trifluoromethylsulfonyl)phenylamino)-1H-pyrazol-1-yl)-4-(cyanomethyl)piperidine-1-carboxylate;

2,2,2-trifluoroethyl 4-(4-carbamoyl-3-(6-(2,2,2-trifluoro-1-hydroxyethyl)pyridin-3-ylamino)-1H-pyrazol-1-yl)-4-(cyanomethyl)piperidine-1-carboxylate;
2,2,2-trifluoroethyl 4-(3-(3-(1H-pyrazol-3-yl)phenylamino)-4-carbamoyl-1H-pyrazol-1-yl)-4-(cyanomethyl)piperidine-1-carboxylate;
2,2,2-trifluoroethyl 4-(4-carbamoyl-3-(3-(1-methyl-1H-pyrazol-4-yl)phenylamino)-1H-pyrazol-1-yl)-4-(cyanomethyl)piperidine-1-carboxylate;
2,2,2-trifluoroethyl 4-(4-carbamoyl-3-(5-(1-methyl-1H-pyrazol-4-yl)pyridinl-3-ylamino)-1H-pyrazol-1-yl)-4-(cyanomethyl)piperidine-1-carboxylate;
2,2,2-trifluoroethyl 4-(4-carbamoyl-3-(pyridin-3-ylamino)-1H-pyrazol-1-yl)-4-(cyanomethyl)piperidine-1-carboxylate;
2,2,2-trifluoroethyl 4-(4-carbamoyl-3-(5-fluoropyridin-3-ylamino)-1H-pyrazol-1-yl)-4-(cyanomethyl)piperidine-1-carboxylate;
2,2,2-trifluoroethyl 4-{4-carbamoyl-3-[(5-chloropyridin-3-yl)amino]-1H-pyrazol-1-yl}-4-(cyanomethyl)piperidine-1-carboxylate;
2,2,2-Trifluoroethyl 4-(4-carbamoyl-3-{[6-(1-methyl-1H-pyrazol-4-yl)pyridin-3-yl]amino}-1H-pyrazol-1-yl)-4-(cyanomethyl)piperidine-1-carboxylate;
2,2,2-trifluoroethyl 4-(4-carbamoyl-3-{[6-(1H-pyrazol-4-yl)pyridin-3-yl]amino}-1H-pyrazol-1-yl)-4-(cyanomethyl)piperidine-1-carboxylate;
tert-Butyl 4-{3-[(3-bromophenyl)amino]-4-carbamoyl-1H-pyrazol-1-yl}-4-(cyanomethyl)piperidine-1-carboxylate;
tert-butyl 4-(4-carbamoyl-3-{[4-(2-methoxy-2-oxoethyl)phenyl]amino}-1H-pyrazol-1-yl)-4-(cyanomethyl)piperidine-1-carboxylate;
tert-butyl 4-{4-carbamoyl-3-[(3,5-difluorophenyl)amino]-1H-pyrazol-1-yl}-4-(cyanomethyl)piperidine-1-carboxylate;
tert-butyl 4-(4-carbamoyl-3-{[6-(morpholin-4-yl)aphthal-3-yl]amino}-1H-pyrazol-1-yl)-4-(cyanomethyl)piperidine-1-carboxylate;
tert-butyl 4-{4-carbamoyl-3-[(6-fluoropyridin-3-yl)amino]-1H-pyrazol-1-yl}-4-(cyanomethyl)piperidine-1-carboxylate;
tert-butyl 4-[4-carbamoyl-3-(pyridazin-4-ylamino)-1H-pyrazol-1-yl]-4-(cyanomethyl)piperidine-1-carboxylate;
tert-butyl 4-{4-carbamoyl-3-[(1-oxo-2,3-dihydro-1H-isoindol-5-yl)amino]-1H-pyrazol-1-yl}-4-(cyanomethyl)piperidine-1-carboxylate;
tert-Butyl 4-(4-carbamoyl-3-(pyrimidin-4-ylamino)-1H-pyrazol-1-yl)-4-(cyanomethyl)piperidine-1-carboxylate;
tert-butyl 4-(4-carbamoyl-3-(6-methylpyridin-2-ylamino)-1H-pyrazol-1-yl)-4-(cyanomethyl)piperidine-1-carboxylate;
tert-butyl 4-(4-carbamoyl-3-(pyridin-2-ylamino)-1H-pyrazol-1-yl)-4-(cyanomethyl)piperidine-1-carboxylate;
tert-butyl 4-(4-carbamoyl-3-(5-fluoropyridin-2-ylamino)-1H-pyrazol-1-yl)-4-(cyanomethyl)piperidine-1-carboxylate;
tert-butyl 4-(4-carbamoyl-3-(4-fluoropyridin-2-ylamino)-1H-pyrazol-1-yl)-4-(cyanomethyl)piperidine-1-carboxylate;
tert-butyl 4-(4-carbamoyl-3-(pyridazin-3-ylamino)-1H-pyrazol-1-yl)-4-(cyanomethyl)piperidine-1-carboxylate;
tert-butyl 4-(4-carbamoyl-3-(pyrazine-2-ylamino)-1H-pyrazol-1-yl)-4-(cyanomethyl)piperidine-1-carboxylate;
tert-butyl 4-(4-carbamoyl-3-(6-methylpyrazine-2-ylamino)-1H-pyrazol-1-yl)-4-(cyanomethyl)piperidine-1-carboxylate;
tert-butyl 4-(4-carbamoyl-3-(6-methoxypyridin-2-ylamino)-1H-pyrazol-1-yl)-4-(cyanomethyl)piperidine-1-carboxylate;
tert-butyl 4-(4-carbamoyl-3-(2,6-dimethylpyrimidin-4-ylamino)-1H-pyrazol-1-yl)-4-(cyanomethyl)piperidine-1-carboxylate;
tert-butyl 4-(4-carbamoyl-3-(6-methylpyrimidin-4-ylamino)-1H-pyrazol-1-yl)-4-(cyanomethyl)piperidine-1-carboxylate;
tert-butyl 4-(4-carbamoyl-3-((5-fluoropyridin-3-yl)amino)-1H-pyrazol-1-yl)-4-(cyanomethyl)piperidine-1-carboxylate;
tert-Butyl 4-(4-carbamoyl-3-{[4-(3,5-dimethylisoxazol-4-yl)phenyl]amino}-1H-pyrazol-1-yl)-4-(cyanomethyl)piperidine-1-carboxylate;
tert-Butyl 4-{4-carbamoyl-3-[(4'-chlorobiphenyl-3-yl)amino]-1H-pyrazol-1-yl}-4-(cyanomethyl)piperidine-1-carboxylate;
tert-butyl 4-{4-carbamoyl-3-[(4'-fluorobiphenyl-3-yl)amino]-1H-pyrazol-1-yl}-4-(cyanomethyl)piperidine-1-carboxylate;
tert-butyl 4-[3-(biphenyl-3-ylamino)-4-carbamoyl-1H-pyrazol-1-yl]-4-(cyanomethyl)piperidine-1-carboxylate;
tert-butyl 4-{4-carbamoyl-3-[(4'-methoxybiphenyl-3-yl)amino]-1H-pyrazol-1-yl}-4-(cyanomethyl)piperidine-1-carboxylate;
tert-butyl 4-{4-carbamoyl-3-[(4'-hydroxybiphenyl-3-yl)amino]-1H-pyrazol-1-yl}-4-(cyanomethyl)piperidine-1-carboxylate;
tert-butyl 4-{4-carbamoyl-3-[(4'-methylbiphenyl-3-yl)amino]-1H-pyrazol-1-yl}-4-(cyanomethyl)piperidine-1-carboxylate;
tert-butyl 4-{4-carbamoyl-3-[(2'-methylbiphenyl-3-yl)amino]-1H-pyrazol-1-yl}-4-(cyanomethyl)piperidine-1-carboxylate;
tert-butyl 4-{4-carbamoyl-3-[(3'-chlorobiphenyl-3-yl)amino]-1H-pyrazol-1-yl}-4-(cyanomethyl)piperidine-1-carboxylate;
tert-butyl 4-{4-carbamoyl-3-[(3-naphthalen-2-ylphenyl)amino]-1H-pyrazol-1-yl}-4-(cyanomethyl)piperidine-1-carboxylate;
tert-butyl 4-{4-carbamoyl-3-[(2'-fluorobiphenyl-3-yl)amino]-1H-pyrazol-1-yl}-4-(cyanomethyl)piperidine-1-carboxylate;
tert-butyl 4-{4-carbamoyl-3-[(2'-hydroxybiphenyl-3-yl)amino]-1H-pyrazol-1-yl}-4-(cyanomethyl)piperidine-1-carboxylate;
[4-({1-[1-(tert-Butoxycarbonyl)-4-(cyanomethyl)piperidin-4-yl]-4-carbamoyl-1H-pyrazol-3-yl}amino)phenyl]acetic acid;
1-[3-(Cyanomethyl)-1-(2,2,2-trifluoroethyl)azetidin-3-yl]-3-(phenylamino)-1H-pyrazole-4-carboxamide;
1-[3-(Cyanomethyl)-1-methylazetidin-3-yl]-3-(phenylamino)-1H-pyrazole-4-carboxamide;
1-[1-(Biphenyl-4-ylmethyl)-4-(cyanomethyl)piperidin-4-yl]-3-(phenylamino)-1H-pyrazole-4-carboxamide;
1-[4-(cyanomethyl)-1-(pyridin-3-ylmethyl)piperidin-4-yl]-3-(phenylamino)-1H-pyrazole-4-carboxamide;
1-[1-(3-cyanobenzyl)-4-(cyanomethyl)piperidin-4-yl]-3-(phenylamino)-1H-pyrazole-4-carboxamide;
1-[1-(4-cyanobenzyl)-4-(cyanomethyl)piperidin-4-yl]-3-(phenylamino)-1H-pyrazole-4-carboxamide;
1-[4-(cyanomethyl)-1-(3-cyanopropyl)piperidin-4-yl]-3-(phenylamino)-1H-pyrazole-4-carboxamide;
1-[1-(2-chlorobenzyl)-4-(cyanomethyl)piperidin-4-yl]-3-(phenylamino)-1H-pyrazole-4-carboxamide;

1-[4-(cyanomethyl)-1-(4-methylbenzyl)piperidin-4-yl]-3-(phenylamino)-1H-pyrazole-4-carboxamide;
1-[4-(cyanomethyl)-1-(naphthalene-1-ylmethyl)piperidin-4-yl]-3-(phenylamino)-1H-pyrazole-4-carboxamide;
1-[4-(cyanomethyl)-1-(cyclohexylmethyl)piperidin-4-yl]-3-(phenylamino)-1H-pyrazole-4-carboxamide;
1-[1-(1,3-benzodioxol-5-ylmethyl)-4-(cyanomethyl)piperidin-4-yl]-3-(phenylamino)-1H-pyrazole-4-carboxamide;
1-[4-(cyanomethyl)-1-(3-hydroxybenzyl)piperidin-4-yl]-3-(phenylamino)-1H-pyrazole-4-carboxamide;
1-{1-[4-(acetylamino)benzyl]-4-(cyanomethyl)piperidin-4-yl}-3-(phenylamino)-1H-pyrazole-4-carboxamide;
1-{4-(cyanomethyl)-1-[(6-methoxynaphthalen-2-yl)methyl]piperidin-4-yl}-3-(phenylamino)-1H-pyrazole-4-carboxamide;
1-[4-(cyanomethyl)-1-(2,6-dichlorobenzyl)piperidin-4-yl]-3-(phenylamino)-1H-pyrazole-4-carboxamide;
1-{4-(cyanomethyl)-1-[3-(methylsulfanyl)propyl]piperidin-4-yl}-3-(phenylamino)-1H-pyrazole-4-carboxamide;
1-[4-(cyanomethyl)-1-(2-ethoxybenzyl)piperidin-4-yl]-3-(phenylamino)-1H-pyrazole-4-carboxamide;
1-{4-(cyanomethyl)-1-[(2E)-3-phenylprop-2-en-1-yl]piperidin-4-yl}-3-(phenylamino)-1H-pyrazole-4-carboxamide;
1-{4-(cyanomethyl)-1-(3-fluorobenzyl)piperidin-4-yl]-3-(phenylamino)-1H-pyrazole-4-carboxamide;
1-{4-(cyanomethyl)-1-[4-(trifluoromethyl)benzyl]piperidin-4-yl}-3-(phenylamino)-1H-pyrazole-4-carboxamide;
1-[1-(1-benzofuran-2-ylmethyl)-4-(cyanomethyl)piperidin-4-yl]-3-(phenylamino)-1H-pyrazole-4-carboxamide;
1-[1-(4-chloro-2-fluorobenzyl)-4-(cyanomethyl)piperidin-4-yl]-3-(phenylamino)-1H-pyrazole-4-carboxamide;
1-[4-(cyanomethyl)-1-(4-propylbenzyl)piperidin-4-yl]-3-(phenylamino)-1H-pyrazole-4-carboxamide;
1-[4-(cyanomethyl)-1-(2,6-difluorobenzyl)piperidin-4-yl]-3-(phenylamino)-1H-pyrazole-4-carboxamide;
1-{4-(cyanomethyl)-1-[4-(1-methylethyl)benzyl]piperidin-4-yl}-3-(phenylamino)-1H-pyrazole-4-carboxamide;
1-[4-(cyanomethyl)-1-(3-phenylprop-2-yn-1-yl)piperidin-4-yl]-3-(phenylamino)-1H-pyrazole-4-carboxamide;
1-[4-(cyanomethyl)-1-(2,3,6-trifluorobenzyl)piperidin-4-yl]-3-(phenylamino)-1H-pyrazole-4-carboxamide;
1-{4-(cyanomethyl)-1-[4-(1-methylethoxy)benzyl]piperidin-4-yl}-3-(phenylamino)-1H-pyrazole-4-carboxamide;
1-[4-(cyanomethyl)-1-(3,4-dimethylbenzyl)piperidin-4-yl]-3-(phenylamino)-1H-pyrazole-4-carboxamide;
methyl 2-({4-[4-carbamoyl-3-(phenylamino)-1H-pyrazol-1-yl]-4-(cyanomethyl)piperidin-1-yl}methyl)benzoate;
1-(4-(Cyanomethyl)-1-((1-ethyl-1H-imidazol-2-yl)methyl)piperidin-4-yl)-3-((2-fluoropyridin-4-yl)amino)-1H-pyrazole-4-carboxamide;
1-[4-(cyanomethyl)-1-(pyridin-3-ylmethyl)piperidin-4-yl]-3-[(2-fluoropyridin-4-yl)amino]-1H-pyrazole-4-carboxamide;
1-[4-(cyanomethyl)-1-(cyclohexylmethyl)piperidin-4-yl]-3-[(2-fluoropyridin-4-yl)amino]-1H-pyrazole-4-carboxamide;
1-{4-(cyanomethyl)-1-[(4-methyl-1H-imidazol-2-yl)methyl]piperidin-4-yl}-3-[(2-fluoropyridin-4-yl)amino]-1H-pyrazole-4-carboxamide;
1-[4-(cyanomethyl)-1-(1H-pyrazol-4-ylmethyl)piperidin-4-yl]-3-[(2-fluoropyridin-4-yl)amino]-1H-pyrazole-4-carboxamide;
1-[4-(cyanomethyl)-1-(cyclohexylmethyl)piperidin-4-yl]-3-[(4-fluorophenyl)amino]-1H-pyrazole-4-carboxamide;
1-[1-benzyl-4-(cyanomethyl)piperidin-4-yl]-3-[(4-fluorophenyl)amino]-1H-pyrazole-4-carboxamide;
1-[1-benzyl-4-(cyanomethyl)piperidin-4-yl]-3-[(2-fluoropyridin-4-yl)amino]-1H-pyrazole-4-carboxamide;
1-[4-(cyanomethyl)-1-(2-fluorobenzyl)piperidin-4-yl]-3-[(2-fluoropyridin-4-yl)amino]-1H-pyrazole-4-carboxamide;
1-[4-(cyanomethyl)-1-(3-fluorobenzyl)piperidin-4-yl]-3-[(2-fluoropyridin-4-yl)amino]-1H-pyrazole-4-carboxamide;
1-[4-(cyanomethyl)-1-(4-fluorobenzyl)piperidin-4-yl]-3-[(2-fluoropyridin-4-yl)amino]-1H-pyrazole-4-carboxamide;
1-[4-(cyanomethyl)-1-(imidazo[1,2-a]pyridin-2-ylmethyl)piperidin-4-yl]-3-[(2-fluoropyridin-4-yl)amino]-1H-pyrazole-4-carboxamide;
1-[4-(cyanomethyl)-1-(1H-pyrazol-5-ylmethyl)piperidin-4-yl]-3-[(2-fluoropyridin-4-yl)amino]-1H-pyrazole-4-carboxamide;
1-[4-(cyanomethyl)-1-(pyrazin-2-ylmethyl)piperidin-4-yl]-3-[(2-fluoropyridin-4-yl)amino]-1H-pyrazole-4-carboxamide;
1-{4-(cyanomethyl)-1-[(2-methyl-1,3-thiazol-5-yl)methyl]piperidin-4-yl}-3-[(2-fluoropyridin-4-yl)amino]-1H-pyrazole-4-carboxamide;
1-{4-(cyanomethyl)-1-[(2,2-dimethyltetrahydro-2H-pyran-4-yl)methyl]piperidin-4-yl}-3-[(2-fluoropyridin-4-yl)amino]-1H-pyrazole-4-carboxamide;
1-[4-(cyanomethyl)-1-(pyrazolo[1,5-a]pyridin-3-ylmethyl)piperidin-4-yl]-3-[(2-fluoropyridin-4-yl)amino]-1H-pyrazole-4-carboxamide;
1-[4-(cyanomethyl)-1-(1H-pyrrolo[2,3-b]pyridin-4-ylmethyl)piperidin-4-yl]-3-[(2-fluoropyridin-4-yl)amino]-1H-pyrazole-4-carboxamide;
1-[4-(cyanomethyl)-1-(furan-2-ylmethyl)piperidin-4-yl]-3-[(2-fluoropyridin-4-yl)amino]-1H-pyrazole-4-carboxamide;
1-[4-(cyanomethyl)-1-(1H-indol-5-ylmethyl)piperidin-4-yl]-3-[(2-fluoropyridin-4-yl)amino]-1H-pyrazole-4-carboxamide;
1-[4-(cyanomethyl)-1-(1H-indol-7-ylmethyl)piperidin-4-yl]-3-[(2-fluoropyridin-4-yl)amino]-1H-pyrazole-4-carboxamide;
1-{4-(cyanomethyl)-1-[(2-fluoro-5-methylpyridin-3-yl)methyl]piperidin-4-yl}-3-[(2-fluoropyridin-4-yl)amino]-1H-pyrazole-4-carboxamide;
1-{4-(cyanomethyl)-1-[(2-fluoropyridin-3-yl)methyl]piperidin-4-yl}-3-[(2-fluoropyridin-4-yl)amino]-1H-pyrazole-4-carboxamide;
1-[4-(cyanomethyl)-1-{[3-(1-hydroxy-1-methylethyl)cyclobutyl]methyl}piperidin-4-yl]-3-[(2-fluoropyridin-4-yl)amino]-1H-pyrazole-4-carboxamide;
1-[4-(cyanomethyl)-1-(1,3-thiazol-4-ylmethyl)piperidin-4-yl]-3-[(2-fluoropyridin-4-yl)amino]-1H-pyrazole-4-carboxamide;
1-[4-(cyanomethyl)-1-(1,3-oxazol-4-ylmethyl)piperidin-4-yl]-3-[(2-fluoropyridin-4-yl)amino]-1H-pyrazole-4-carboxamide;
1-{4-(cyanomethyl)-1-[(5-methylisoxazol-3-yl)methyl]piperidin-4-yl}-3-[(2-fluoropyridin-4-yl)amino]-1H-pyrazole-4-carboxamide;
1-[4-(cyanomethyl)-1-(1,3-oxazol-2-ylmethyl)piperidin-4-yl]-3-[(2-fluoropyridin-4-yl)amino]-1H-pyrazole-4-carboxamide;
1-{4-(cyanomethyl)-1-[(1-methyl-1H-pyrazol-5-yl)methyl]piperidin-4-yl}-3-[(2-fluoropyridin-4-yl)amino]-1H-pyrazole-4-carboxamide;

1-{4-(cyanomethyl)-1-[(1-methyl-1H-pyrazol-3-yl)methyl]piperidin-4-yl}-3-[(2-fluoropyridin-4-yl)amino]-1H-pyrazole-4-carboxamide;

1-[4-(cyanomethyl)-1-(isoxazol-3-ylmethyl)piperidin-4-yl]-3-[(2-fluoropyridin-4-yl)amino]-1H-pyrazole-4-carboxamide;

1-{4-(cyanomethyl)-1-[(6-fluoropyridin-2-yl)methyl]piperidin-4-yl}-3-[(2-fluoropyridin-4-yl)amino]-1H-pyrazole-4-carboxamide;

1-[4-(cyanomethyl)-1-(pyrazolo pyridin-7-ylmethyl)piperidin-4-yl]-3-[(2-fluoropyridin-4-yl)amino]-1H-pyrazole-4-carboxamide;

1-[4-(cyanomethyl)-1-(pyrazolo[1,5-a]pyridin-2-ylmethyl)piperidin-4-yl]-3-[(2-fluoropyridin-4-yl)amino]-1H-pyrazole-4-carboxamide;

1-[4-(cyanomethyl)-1-(pyridazin-3-ylmethyl)piperidin-4-yl]-3-[(2-fluoropyridin-4-yl)amino]-1H-pyrazole-4-carboxamide;

1-{4-(cyanomethyl)-1-[(5-fluoropyridin-2-yl)methyl]piperidin-4-yl}-3-[(2-fluoropyridin-4-yl)amino]-1H-pyrazole-4-carboxamide;

1-{4-(cyanomethyl)-1-[(3-methoxycyclobutyl)methyl]piperidin-4-yl}-3-[(2-fluoropyridin-4-yl)amino]-1H-pyrazole-4-carboxamide;

1-{4-(cyanomethyl)-1-[(5-fluoropyridin-3-yl)methyl]piperidin-4-yl}-3-[(2-fluoropyridin-4-yl)amino]-1H-pyrazole-4-carboxamide;

1-[4-(cyanomethyl)-1-(1H-indol-2-ylmethyl)piperidin-4-yl]-3-[(2-fluoropyridin-4-yl)amino]-1H-pyrazole-4-carboxamide;

1-{4-(cyanomethyl)-1-[(1,5-dimethyl-1H-pyrazol-4-yl)methyl]piperidin-4-yl}-3-[(2-fluoropyridin-4-yl)amino]-1H-pyrazole-4-carboxamide;

1-[1-(1H-benzimidazol-2-ylmethyl)-4-(cyanomethyl)piperidin-4-yl]-3-[(2-fluoropyridin-4-yl)amino]-1H-pyrazole-4-carboxamide;

1-{4-(cyanomethyl)-1-[(3-methyl-4,5-dihydroisoxazol-5-yl)methyl]piperidin-4-yl}-3-[(2-fluoropyridin-4-yl)amino]-1H-pyrazole-4-carboxamide;

1-[4-(cyanomethyl)-1-(1H-indol-2-ylmethyl)piperidin-4-yl]-3-[(4-fluorophenyl)amino]-1H-pyrazole-4-carboxamide;

1-{4-(cyanomethyl)-1-[(2-fluoro-5-methylpyridin-3-yl)methyl]piperidin-4-yl}-3-[(4-fluorophenyl)amino]-1H-pyrazole-4-carboxamide;

1-[4-(cyanomethyl)-1-(isoxazol-3-ylmethyl)piperidin-4-yl]-3-[(4-fluorophenyl)amino]-1H-pyrazole-4-carboxamide;

1-{4-(cyanomethyl)-1-[(6-fluoropyridin-2-yl)methyl]piperidin-4-yl}-3-[(4-fluorophenyl)amino]-1H-pyrazole-4-carboxamide;

1-[4-(cyanomethyl)-1-(pyridazin-3-ylmethyl)piperidin-4-yl]-3-[(4-fluorophenyl)amino]-1H-pyrazole-4-carboxamide;

1-{4-(cyanomethyl)-1-[(5-fluoropyridin-2-yl)methyl]piperidin-4-yl}-3-[(4-fluorophenyl)amino]-1H-pyrazole-4-carboxamide;

1-{4-(cyanomethyl)-1-[(5-fluoropyridin-3-yl)methyl]piperidin-4-yl}-3-[(4-fluorophenyl)amino]-1H-pyrazole-4-carboxamide;

1-{4-(cyanomethyl)-1-[(4-fluoropyridin-2-yl)methyl]piperidin-4-yl}-3-[(4-fluorophenyl)amino]-1H-pyrazole-4-carboxamide;

1-[4-(cyanomethyl)-1-(pyridin-3-ylmethyl)piperidin-4-yl]-3-[(4-fluorophenyl)amino]-1H-pyrazole-4-carboxamide;

1-[4-(cyanomethyl)-1-(pyrazin-2-ylmethyl)piperidin-4-yl]-3-[(4-fluorophenyl)amino]-1H-pyrazole-4-carboxamide;

1-[4-(cyanomethyl)-1-(1H-pyrrolo[2,3-b]pyridin-4-ylmethyl)piperidin-4-yl]-3-[(4-fluorophenyl)amino]-1H-pyrazole-4-carboxamide;

1-[4-(cyanomethyl)-1-(furan-2-ylmethyl)piperidin-4-yl]-3-[(4-fluorophenyl)amino]-1H-pyrazole-4-carboxamide;

1-[4-(cyanomethyl)-1-(1H-indol-5-ylmethyl)piperidin-4-yl]-3-[(4-fluorophenyl)amino]-1H-pyrazole-4-carboxamide;

1-[4-(cyanomethyl)-1-(1H-indol-6-ylmethyl)piperidin-4-yl]-3-[(4-fluorophenyl)amino]-1H-pyrazole-4-carboxamide;

1-[4-(cyanomethyl)-1-(1H-indol-4-ylmethyl)piperidin-4-yl]-3-[(4-fluorophenyl)amino]-1H-pyrazole-4-carboxamide;

1-[4-(cyanomethyl)-1-(1H-indol-7-ylmethyl)piperidin-4-yl]-3-[(4-fluorophenyl)amino]-1H-pyrazole-4-carboxamide;

1-[1-(2-chlorobenzyl)-4-(cyanomethyl)piperidin-4-yl]-3-[(2-fluoropyridin-4-yl)amino]-1H-pyrazole-4-carboxamide;

1-[4-(cyanomethyl)-1-(4-hydroxybenzyl)piperidin-4-yl]-3-[(2-fluoropyridin-4-yl)amino]-1H-pyrazole-4-carboxamide;

1-[1-(3-chlorobenzyl)-4-(cyanomethyl)piperidin-4-yl]-3-[(2-fluoropyridin-4-yl)amino]-1H-pyrazole-4-carboxamide;

1-[1-(3-cyanobenzyl)-4-(cyanomethyl)piperidin-4-yl]-3-[(2-fluoropyridin-4-yl)amino]-1H-pyrazole-4-carboxamide;

1-[4-(cyanomethyl)-1-(3-methoxybenzyl)piperidin-4-yl]-3-[(2-fluoropyridin-4-yl)amino]-1H-pyrazole-4-carboxamide;

1-[4-(cyanomethyl)-1-(2-phenylethyl)piperidin-4-yl]-3-[(2-fluoropyridin-4-yl)amino]-1H-pyrazole-4-carboxamide;

1-[4-(cyanomethyl)-1-(4-methoxybenzyl)piperidin-4-yl]-3-[(2-fluoropyridin-4-yl)amino]-1H-pyrazole-4-carboxamide;

1-[4-(cyanomethyl)-1-(2-methoxybenzyl)piperidin-4-yl]-3-[(2-fluoropyridin-4-yl)amino]-1H-pyrazole-4-carboxamide;

1-{4-(cyanomethyl)-1-[(6-oxo-1,6-dihydropyridin-2-yl)methyl]piperidin-4-yl}-3-[(2-fluoropyridin-4-yl)amino]-1H-pyrazole-4-carboxamide;

1-{4-(cyanomethyl)-1-[(6-hydroxypyridin-3-yl)methyl]piperidin-4-yl}-3-[(2-fluoropyridin-4-yl)amino]-1H-pyrazole-4-carboxamide;

1-[1-(4-cyanobenzyl)-4-(cyanomethyl)piperidin-4-yl]-3-[(2-fluoropyridin-4-yl)amino]-1H-pyrazole-4-carboxamide;

1-[4-(cyanomethyl)-1-(3-hydroxybenzyl)piperidin-4-yl]-3-[(2-fluoropyridin-4-yl)amino]-1H-pyrazole-4-carboxamide;

1-[1-(4-chlorobenzyl)-4-(cyanomethyl)piperidin-4-yl]-3-[(2-fluoropyridin-4-yl)amino]-1H-pyrazole-4-carboxamide;

1-[1-(2-cyanobenzyl)-4-(cyanomethyl)piperidin-4-yl]-3-[(2-fluoropyridin-4-yl)amino]-1H-pyrazole-4-carboxamide;

1-(4-(Cyanomethyl)-1-(1-phenylethyl)piperidin-4-yl)-3-((4-fluorophenyl)amino)-1H-pyrazole-4-carboxamide;

1-(4-(Cyanomethyl)-1-(2-fluoroethyl)piperidin-4-yl)-3-((4-fluorophenyl)amino)-1H-pyrazole-4-carboxamide;

1-[4-(cyanomethyl)-1-(cyclopropylmethyl)piperidin-4-yl]-3-[(4-fluorophenyl)amino]-1H-pyrazole-4-carboxamide;

1-(4-(Cyanomethyl)-1-(pyridin-2-yl)piperidin-4-yl)-3-(4-fluorophenylamino)-1H-pyrazole-4-carboxamide;

1-[4-(Cyanomethyl)-1-pyrimidin-4-ylpiperidin-4-yl]-3-[(4-fluorophenyl)amino]-1H-pyrazole-4-carboxamide;

Methyl 4-(4-carbamoyl-3-(4-(trifluoromethylsulfonyl)phenylamino)-1H-pyrazol-1-yl)-4-(cyanomethyl)piperidine-1-carboxylate;

2-methoxyethyl 4-(4-carbamoyl-3-(4-(trifluoromethylsulfonyl)phenylamino)-1H-pyrazol-1-yl)-4-(cyanomethyl)piperidine-1-carboxylate;

methyl 4-(4-carbamoyl-3-{[4-(methylsulfonyl)phenyl]amino}-1H-pyrazol-1-yl)-4-(cyanomethyl)piperidine-1-carboxylate;

benzyl 4-[4-carbamoyl-3-(phenylamino)-1H-pyrazol-1-yl]-4-(cyanomethyl)piperidine-1-carboxylate;

methyl 4-[4-carbamoyl-3-(phenylamino)-1H-pyrazol-1-yl]-4-(cyanomethyl)piperidine-1-carboxylate;

2-Methoxy-1,1-dimethylethyl 4-{4-carbamoyl-3-[(4-fluorophenyl)amino]-1H-pyrazol-1-yl}-4-(cyanomethyl)piperidine-1-carboxylate;

1-Hydroxy-2-methylpropan-2-yl 4-{4-carbamoyl-3-[(4-fluorophenyl)amino]-1H-pyrazol-1-yl}-4-(cyanomethyl)piperidine-1-carboxylate;

2,2,2-Trifluoroethyl 4-{4-carbamoyl-3-[(2-fluoropyridin-4-yl)amino]-1H-pyrazol-1-yl}-4-(cyanomethyl)piperidine-1-carboxylate;

2,2,2-trifluoroethyl 4-(4-carbamoyl-3-(4-fluorophenylamino)-1H-pyrazol-1-yl)-4-(cyanomethyl)piperidine-1-carboxylate;

1,1,1-trifluoropropan-2-yl 4-(4-carbamoyl-3-(4-fluorophenylamino)-1H-pyrazol-1-yl)-4-(cyanomethyl)piperidine-1-carboxylate;

cyclobutyl 4-(4-carbamoyl-3-(4-fluorophenylamino)-1H-pyrazol-1-yl)-4-(cyanomethyl)piperidine-1-carboxylate;

cyclobutylmethyl 4-(4-carbamoyl-3-(4-fluorophenylamino)-1H-pyrazol-1-yl)-4-(cyanomethyl)piperidine-1-carboxylate;

(2,2-difluorocyclopropyl)methyl 4-(4-carbamoyl-3-(4-fluorophenylamino)-1H-pyrazol-1-yl)-4-(cyanomethyl)piperidine-1-carboxylate;

2,2-difluoroethyl 4-(4-carbamoyl-3-(4-fluorophenylamino)-1H-pyrazol-1-yl)-4-(cyanomethyl)piperidine-1-carboxylate;

(1-methylcyclopropyl)methyl 4-(4-carbamoyl-3-(4-fluorophenylamino)-1H-pyrazol-1-yl)-4-(cyanomethyl)piperidine-1-carboxylate;

1,3-difluoropropan-2-yl 4-(4-carbamoyl-3-(4-fluorophenylamino)-1H-pyrazol-1-yl)-4-(cyanomethyl)piperidine-1-carboxylate;

(trimethylsilyl)methyl 4-(4-carbamoyl-3-(4-fluorophenylamino)-1H-pyrazol-1-yl)-4-(cyanomethyl)piperidine-1-carboxylate;

2,2-difluoro-3-hydroxypropyl 4-(4-carbamoyl-3-(4-fluorophenylamino)-1H-pyrazol-1-yl)-4-(cyanomethyl)piperidine-1-carboxylate;

1-cyclopropylethyl 4-(4-carbamoyl-3-(4-fluorophenylamino)-1H-pyrazol-1-yl)-4-(cyanomethyl)piperidine-1-carboxylate;

(1-hydroxycyclopropyl)methyl 4-(4-carbamoyl-3-yl)-4-(cyanomethyl)piperidine-1-carboxylate;

1,1,1-trifluoropropan-2-yl 4-(4-carbamoyl-3-(4-fluorophenylamino)-1H-pyrazol-1-yl)-4-(cyanomethyl)piperidine-1-carboxylate;

2,2-difluoroethyl 4-(4-carbamoyl-3-fluoropyridin-3-ylamino)-1H-pyrazol-1-yl)-4-(cyanomethyl)piperidine-1-carboxylate;

tetrahydrofuran-3-yl 4-{4-carbamoyl-3-[(2-fluoropyridin-4-yl)amino]-1H-pyrazol-1-yl}-4-(cyanomethyl)piperidine-1-carboxylate;

tetrahydro-2H-pyran-4-yl 4-{4-carbamoyl-3-[(2-fluoropyridin-4-yl)amino]-1H-pyrazol-1-yl}-4-(cyanomethyl)piperidine-1-carboxylate;

oxetan-3-yl 4-{4-carbamoyl-3-[(4-fluorophenyl)amino]-1H-pyrazol-1-yl}-4-(cyanomethyl)piperidine-1-carboxylate;

cyclopropylmethyl 4-{4-carbamoyl-3-[(4-fluorophenyl)amino]-1H-pyrazol-1-yl}-4-(cyanomethyl)piperidine-1-carboxylate;

(3-methyloxetan-3-yl)methyl 4-{4-carbamoyl-3-[(4-fluorophenyl)amino]-1H-pyrazol-1-yl}-4-(cyanomethyl)piperidine-1-carboxylate;

tetrahydro-2H-pyran-4-ylmethyl 4-{4-carbamoyl-3-[(4-fluorophenyl)amino]-1H-pyrazol-1-yl}-4-(cyanomethyl)piperidine-1-carboxylate;

tetrahydrofuran-3-ylmethyl 4-{4-carbamoyl-3-[(4-fluorophenyl)amino]-1H-pyrazol-1-yl}-4-(cyanomethyl)piperidine-1-carboxylate;

1-methoxypropan-2-yl 4-{4-carbamoyl-3-[(4-fluorophenyl)amino]-1H-pyrazol-1-yl}-4-(cyanomethyl)piperidine-1-carboxylate;

2-methoxypropyl 4-{4-carbamoyl-3-[(4-fluorophenyl)amino]-1H-pyrazol-1-yl}-4-(cyanomethyl)piperidine-1-carboxylate;

tetrahydro-2H-pyran-3-yl 4-{4-carbamoyl-3-[(4-fluorophenyl)amino]-1H-pyrazol-1-yl}-4-(cyanomethyl)piperidine-1-carboxylate;

oxetan-3-yl 4-(4-carbamoyl-3-(4-(trifluoromethylsulfonyl)phenylamino)-1H-pyrazol-1-yl)-4-(cyanomethyl)piperidine-1-carboxylate;

2,2-difluoroethyl 4-(4-carbamoyl-3-(2-fluoropyridin-4-ylamino)-1H-pyrazol-1-yl)-4-(cyanomethyl)piperidine-1-carboxylate;

2-methylpropyl 4-[4-carbamoyl-3-(phenylamino)-1H-pyrazol-1-yl]-4-(cyanomethyl)piperidine-1-carboxylate;

2,2-dimethylpropyl 4-[4-carbamoyl-3-(phenylamino)-1H-pyrazol-1-yl]-4-(cyanomethyl)piperidine-1-carboxylate;

cyclopentyl 4-[4-carbamoyl-3-(phenylamino)-1H-pyrazol-1-yl]-4-(cyanomethyl)piperidine-1-carboxylate;

cyclohexyl 4-[4-carbamoyl-3-(phenylamino)-1H-pyrazol-1-yl]-4-(cyanomethyl)piperidine-1-carboxylate;

3-fluorobenzyl 4-[4-carbamoyl-3-(phenylamino)-1H-pyrazol-1-yl]-4-(cyanomethyl)piperidine-1-carboxylate;

2-fluorobenzyl 4-[4-carbamoyl-3-(phenylamino)-1H-pyrazol-1-yl]-4-(cyanomethyl)piperidine-1-carboxylate;

2,3-dihydro-1H-inden-2-yl 4-[4-carbamoyl-3-(phenylamino)-1H-pyrazol-1-yl]-4-(cyanomethyl)piperidine-1-carboxylate;

2-methoxyethyl 4-[4-carbamoyl-3-(phenylamino)-1H-pyrazol-1-yl]-4-(cyanomethyl)piperidine-1-carboxylate;

4-carbamoyl-1-[4-(cyanomethyl)-1-{[tetrahydrofuran-3-yloxy]carbonyl}piperidin-4-yl]-3-(phenylamino)-1H-pyrazol-2-ium;

tetrahydro-2H-pyran-4-yl 4-[4-carbamoyl-3-(phenylamino)-1H-pyrazol-1-yl]-4-(cyanomethyl)piperidine-1-carboxylate;

pyridin-3-ylmethyl 4-[4-carbamoyl-3-(phenylamino)-1H-pyrazol-1-yl]-4-(cyanomethyl)piperidine-1-carboxylate;

pyridin-3-ylmethyl 4-[4-carbamoyl-3-(phenylamino)-1H-pyrazol-1-yl]-4-(cyanomethyl)piperidine-1-carboxylate;

pyridin-4-ylmethyl 4-[4-carbamoyl-3-(phenylamino)-1H-pyrazol-1-yl]-4-(cyanomethyl)piperidine-1-carboxylate;

2-morpholin-4-ylethyl 4-[4-carbamoyl-3-(phenylamino)-1H-pyrazol-1-yl]-4-(cyanomethyl)piperidine-1-carboxylate;

1-methylpiperidin-4-yl 4-[4-carbamoyl-3-(phenylamino)-1H-pyrazol-1-yl]-4-(cyanomethyl)piperidine-1-carboxylate;

2-(4-methylpiperazin-1-yl)ethyl 4-[4-carbamoyl-3-(phenylamino)-1H-pyrazol-1-yl]-4-(cyanomethyl)piperidine-1-carboxylate;

(1-methylpiperidin-4-yl)methyl 4-[4-carbamoyl-3-(phenylamino)-1H-pyrazol-1-yl]-4-(cyanomethyl)piperidine-1-carboxylate;

3,3,3-Trifluoropropyl 4-{4-carbamoyl-3-[(4-fluorophenyl)amino]-1H-pyrazol-1-yl}-4-(cyanomethyl)piperidine-1-carboxylate;

tetrahydrofuran-3-yl 4-{4-carbamoyl-3-[(4-fluorophenyl)amino]-1H-pyrazol-1-yl}-4-(cyanomethyl)piperidine-1-carboxylate;

tetrahydro-2H-pyran-4-yl 4-{4-carbamoyl-3-[(4-fluorophenyl)amino]-1H-pyrazol-1-yl}-4-(cyanomethyl)piperidine-1-carboxylate;

2-methoxyethyl 4-{4-carbamoyl-3-[(4-fluorophenyl)amino]-1H-pyrazol-1-yl}-4-(cyanomethyl)piperidine-1-carboxylate;

Cyclopropylmethyl 4-{4-carbamoyl-3-[(2-fluoropyridin-4-yl)amino]-1H-pyrazol-1-yl}-4-(cyanomethyl)piperidine-1-carboxylate;

2-fluoroethyl 3-[4-carbamoyl-3-(phenylamino)-1H pyrazol-1-yl]-3-(cyanomethyl)azetidine-1-carboxylate;

2-methylpropyl 3-[4-carbamoyl-3-(phenylamino)-1H-pyrazol-1-yl]-3-(cyanomethyl)azetidine-1-carboxylate;

cyclopentyl 3-[4-carbamoyl-3-(phenylamino)-1H-pyrazol-1-yl]-3-(cyanomethyl)azetidine-1-carboxylate;

benzyl 3-[4-carbamoyl-3-(phenylamino)-1H-pyrazol-1-yl]-3-(cyanomethyl)azetidine-1-carboxylate;

2-naphthalen-1-ylethyl 3-[4-carbamoyl-3-(phenylamino)-1H-pyrazol-1-yl]-3-(cyanomethyl)azetidine-1-carboxylate;

2-morpholin-4-ylethyl 3-[4-carbamoyl-3-(phenylamino)-1H-pyrazol-1-yl]-3-(cyanomethyl)azetidine-1-carboxylate;

2,2-dimethylpropyl 3-[4-carbamoyl-3-(phenylamino)-1H-pyrazol-1-yl]-3-(cyanomethyl)azetidine-1-carboxylate;

cyclohexyl 3-[4-carbamoyl-3-(phenylamino)-1H-pyrazol-1-yl]-3-(cyanomethyl)azetidine-1-carboxylate;

2-phenylethyl 3-[4-carbamoyl-3-(phenylamino)-1H-pyrazol-1-yl]-3-(cyanomethyl)azetidine-1-carboxylate;

2-methoxyethyl 3-[4-carbamoyl-3-(phenylamino)-1H-pyrazol-1-yl]-3-(cyanomethyl)azetidine-1-carboxylate;

2-ethoxy-2-oxoethyl 3-[4-carbamoyl-3-(phenylamino)-1H-pyrazol-1-yl]-3-(cyanomethyl)azetidine-1-carboxylate;

3-methoxypropyl 3-[4-carbamoyl-3-(phenylamino)-1H-pyrazol-1-yl]-3-(cyanomethyl)azetidine-1-carboxylate;

tetrahydrofuran-3-yl 3-[4-carbamoyl-3-(phenylamino)-1H-pyrazol-1-yl]-3-(cyanomethyl)azetidine-1-carboxylate;

tetrahydro-2H-pyran-4-yl 3-[4-carbamoyl-3-(phenylamino)-1H-pyrazol-1-yl]-3-(cyanomethyl)azetidine-1-carboxylate;

2-(2-oxopyrrolidin-1-yl)ethyl 3-[4-carbamoyl-3-(phenylamino)-1H-pyrazol-1-yl]-3-(cyanomethyl)azetidine-1-carboxylate;

pyridin-3-ylmethyl 3-[4-carbamoyl-3-(phenylamino)-1H-pyrazol-1-yl]-3-(cyanomethyl)azetidine-1-carboxylate;

pyridin-4-ylmethyl 3-[4-carbamoyl-3-(phenylamino)-1H-pyrazol-1-yl]-3-(cyanomethyl)azetidine-1-carboxylate;

2-pyridin-2-ylethyl 3-[4-carbamoyl-3-(phenylamino)-1H-pyrazol-1-yl]-3-(cyanomethyl)azetidine-1-carboxylate;

3-pyridin-3-ylpropyl 3-[4-carbamoyl-3-(phenylamino)-1H-pyrazol-1-yl]-3-(cyanomethyl)azetidine-1-carboxylate;

2-methoxybenzyl 3-[4-carbamoyl-3-(phenylamino)-1H-pyrazol-1-yl]-3-(cyanomethyl)azetidine-1-carboxylate;

3-methoxybenzyl 3-[4-carbamoyl-3-(phenylamino)-1H-pyrazol-1-yl]-3-(cyanomethyl)azetidine-1-carboxylate;

3-(dimethylamino)propyl 3-[4-carbamoyl-3-(phenylamino)-1H-pyrazol-1-yl]-3-(cyanomethyl)azetidine-1-carboxylate;

2-(4-methylpiperazin-1-yl)ethyl 3-[4-carbamoyl-3-(phenylamino)-1H-pyrazol-1-yl]-3-(cyanomethyl)azetidine-1-carboxylate;

(1-methylpiperidin-4-yl)methyl 3-[4-carbamoyl-3-(phenylamino)-1H-pyrazol-1-yl]-3-(cyanomethyl)azetidine-1-carboxylate;

cyclopentyl 3-(4-carbamoyl-3-{[4-(methylsulfonyl)phenyl]amino}-1H-pyrazol-1-yl)-3-(cyanomethyl)azetidine-1-carboxylate;

tetrahydrofuran-3-yl 3-(4-carbamoyl-3-{[4-(methylsulfonyl)phenyl]amino}-1H-pyrazol-1-yl)-3-(cyanomethyl)azetidine-1-carboxylate;

tetrahydro-2H-pyran-4-yl 3-(4-carbamoyl-3-{[4-(methylsulfonyl)phenyl]amino}-1H-pyrazol-1-yl)-3-(cyanomethyl)azetidine-1-carboxylate;

1-cyclopropylethyl 4-{4-carbamoyl-3-[(2-fluoropyridin-4-yl)amino]-1H-pyrazol-1-yl}-4-(cyanomethyl)piperidine-1-carboxylate;

2-Hydroxy-1-methylethyl 4-{4-carbamoyl-3-[(4-fluorophenyl)amino]-1H-pyrazol-1-yl}-4-(cyanomethyl)piperidine-1-carboxylate;

1-[1-Acetyl-3-(cyanomethyl)azetidin-3-yl]-3-(phenylamino)-1H-pyrazole-4-carboxamide;

1-[4-(Cyanomethyl)-1-propanoylpiperidin-4-yl]-3-(phenylamino)-1H-pyrazole-4-carboxamide;

1-{1-[(2E)-but-2-enoyl]-4-(cyanomethyl)piperidin-4-yl}-3-(phenylamino)-1H-pyrazole-4-carboxamide;

1-[4-(Cyanomethyl)-1-(cyclopropylcarbonyl)piperidin-4-yl]-3-(phenylamino)-1H-pyrazole-4-carboxamide;

1-[4-(cyanomethyl)-1-(methoxyacetyl)piperidin-4-yl]-3-(phenylamino)-1H-pyrazole-4-carboxamide;

1-[4-(cyanomethyl)-1-(2,2-dimethylpropanoyl)piperidin-4-yl]-3-(phenylamino)-1H-pyrazole-4-carboxamide;

1-[4-(cyanomethyl)-1-pentanoylpiperidin-4-yl]-3-(phenylamino)-1H-pyrazole-4-carboxamide;

1-[4-(cyanomethyl)-1-(N,N-dimethylglycyl)piperidin-4-yl]-3-(phenylamino)-1H-pyrazole-4-carboxamide;

1-[4-(cyanomethyl)-1-(tetrahydrofuran-2-ylcarbonyl)piperidin-4-yl]-3-(phenylamino)-1H-pyrazole-4-carboxamide;

1-[4-(cyanomethyl)-1-(phenylcarbonyl)piperidin-4-yl]-3-(phenylamino)-1H-pyrazole-4-carboxamide;

1-[4-(cyanomethyl)-1-(pyridin-3-ylcarbonyl)piperidin-4-yl]-3-(phenylamino)-1H-pyrazole-4-carboxamide;

1-[4-(cyanomethyl)-1-(pyridin-2-ylcarbonyl)piperidin-4-yl]-3-(phenylamino)-1H-pyrazole-4-carboxamide;

1-[4-(cyanomethyl)-1-(pyridin-4-ylcarbonyl)piperidin-4-yl]-3-(phenylamino)-1H-pyrazole-4-carboxamide;

1-[4-(cyanomethyl)-1-(pyrazin-2-ylcarbonyl)piperidin-4-yl]-3-(phenylamino)-1H-pyrazole-4-carboxamide;

1-{4-(cyanomethyl)-1-[(5-methylisoxazol-3-yl)carbonyl]piperidin-4-yl}-3-(phenylamino)-1H-pyrazole-4-carboxamide;

1-[4-(cyanomethyl)-1-(cyclohexylcarbonyl)piperidin-4-yl]-3-(phenylamino)-1H-pyrazole-4-carboxamide;

1-[4-(cyanomethyl)-1-(thiophen-2-ylcarbonyl)piperidin-4-yl]-3-(phenylamino)-1H-pyrazole-4-carboxamide;

1-{4-(cyanomethyl)-1-[(2-oxopyrrolidin-1-yl)acetyl]piperidin-4-yl}-3-(phenylamino)-1H-pyrazole-4-carboxamide;

1-[4-(cyanomethyl)-1-(thiophen-3-ylcarbonyl)piperidin-4-yl]-3-(phenylamino)-1H-pyrazole-4-carboxamide;

1-{4-(cyanomethyl)-1-[(2E)-3-pyridin-3-ylprop-2-enoyl]piperidin-4-yl}-3-(phenylamino)-1H-pyrazole-4-carboxamide;

1-{4-(cyanomethyl)-1-[(4-methoxyphenyl)carbonyl]piperidin-4-yl}-3-(phenylamino)-1H-pyrazole-4-carboxamide;
1-{1-[(4-chlorophenyl)carbonyl]-4-(cyanomethyl)piperidin-4-yl}-3-(phenylamino)-1H-pyrazole-4-carboxamide;
1-{1-[(2-chlorophenyl)carbonyl]-4-(cyanomethyl)piperidin-4-yl}-3-(phenylamino)-1H-pyrazole-4-carboxamide;
1-{1-[(3-chlorophenyl)carbonyl]-4-(cyanomethyl)piperidin-4-yl}-3-(phenylamino)-1H-pyrazole-4-carboxamide;
1-[4-(cyanomethyl)-1-(1H-indol-2-ylcarbonyl)piperidin-4-yl]-3-(phenylamino)-1H-pyrazole-4-carboxamide;
1-[4-(cyanomethyl)-1-[4-(dimethylamino)phenyl]carbonyl piperidin-4-yl]-3-(phenylamino)-1H-pyrazole-4-carboxamide;
1-{4-(cyanomethyl)-1-[(4-methoxyphenyl)acetyl]piperidin-4-yl}-3-(phenylamino)-1H-pyrazole-4-carboxamide;
1-[4-(cyanomethyl)-1-(naphthalene-1-ylcarbonyl)piperidin-4-yl]-3-(phenylamino)-1H-pyrazole-4-carboxamide;
1-{4-(cyanomethyl)-1-[(1-methyl-1H-indol-2-yl)carbonyl]piperidin-4-yl}-3-(phenylamino)-1H-pyrazole-4-carboxamide;
1-{4-(cyanomethyl)-1-[(3,4-dimethoxyphenyl)carbonyl]piperidin-4-yl}-3-(phenylamino)-1H-pyrazole-4-carboxamide;
1-{4-(cyanomethyl)-1-[(3-morpholin-4-ylphenyl)carbonyl]piperidin-4-yl}-3-(phenylamino)-1H-pyrazole-4-carboxamide;
1-[1-(biphenyl-2-ylcarbonyl)-4-(cyanomethyl)piperidin-4-yl]-3-(phenylamino)-1H-pyrazole-4-carboxamide;
1-[4-(cyanomethyl)-1-{[4-(trifluoromethyl)phenyl]acetyl}piperidin-4-yl]-3-(phenylamino)-1H-pyrazole-4-carboxamide;
1-{4-(cyanomethyl)-1-[(4-morpholin-4-ylphenyl)carbonyl]piperidin-4-yl}-3-(phenylamino)-1H-pyrazole-4-carboxamide;
1-[4-(cyanomethyl)-1-(quinolin-2-ylcarbonyl)piperidin-4-yl]-3-(phenylamino)-1H-pyrazole-4-carboxamide;
1-[4-(cyanomethyl)-1-(diphenylacetyl)piperidin-4-yl]-3-(phenylamino)-1H-pyrazole-4-carboxamide;
1-[4-(cyanomethyl)-1-{[4-(4-methylpiperazin-1-yl)phenyl]carbonyl}piperidin-4-yl]-3-(phenylamino)-1H-pyrazole-4-carboxamide;
1-[4-(cyanomethyl)-1-(hydroxyacetyl)piperidin-4-yl]-3-(phenylamino)-1H-pyrazole-4-carboxamide;
1-[3-(cyanomethyl)-1-propanoylazetidin-3-yl]-3-(phenylamino)-1H pyrazole-4-carboxamide;
1-[3-(cyanomethyl)-1-(2,2-dimethylpropanoyl)azetidin-3-yl]-3-(phenylamino)-1H-pyrazole-4-carboxamide;
1-[3-(cyanomethyl)-1-(pyridin-2-ylcarbonyl)azetidin-3-yl]-3-(phenylamino)-1H-pyrazole-4-carboxamide;
1-[4-(cyanomethyl)-1-(tetrahydrofuran-2-ylacetyl)piperidin-4-yl]-3-[(2-fluoropyridin-4-yl)amino]-1H-pyrazole-4-carboxamide;
1-[4-(cyanomethyl)-1-(2,2-difluoropropanoyl)piperidin-4-yl]-3-[(2-fluoropyridin-4-yl)amino]-1H-pyrazole-4-carboxamide;
1-{4-(cyanomethyl)-1-[3-fluoro-2-(fluoromethyl)-2-methylpropanoyl]piperidin-4-yl}-3-[(2-fluoropyridin-4-yl)amino]-1H-pyrazole-4-carboxamide;
1-[4-(cyanomethyl)-1-(methoxyacetyl)piperidin-4-yl]-3-[(2-fluoropyridin-4-yl)amino]-1H-pyrazole-4-carboxamide;
1-[4-(cyanomethyl)-1-(2-hydroxy-2-methylpropanoyl)piperidin-4-yl]-3-[(2-fluoropyridin-4-yl)amino]-1H-pyrazole-4-carboxamide;
1-{4-(cyanomethyl)-1-[(1-methyl-1H-pyrazol-4-yl)carbonyl]piperidin-4-yl}-3-[(2-fluoropyridin-4-yl)amino]-1H-pyrazole-4-carboxamide;
1-[4-(cyanomethyl)-1-(cyclopropylacetyl)piperidin-4-yl]-3-[(2-fluoropyridin-4-yl)amino]-1H-pyrazole-4-carboxamide;
1-{4-(cyanomethyl)-1-[(2R)-2-hydroxy-3-methylbutanoyl]piperidin-4-yl}-3-[(2-fluoropyridin-4-yl)amino]-1H-pyrazole-4-carboxamide;
1-{4-(cyanomethyl)-1-[(2S)-2-hydroxy-3-methylbutanoyl]piperidin-4-yl}-3-[(2-fluoropyridin-4-yl)amino]-1H-pyrazole-4-carboxamide;
1-[4-(cyanomethyl)-1-(3,3,3-trifluoro-2-methylpropanoyl)piperidin-4-yl]-3-[(2-fluoropyridin-4-yl)amino]-1H-pyrazole-4-carboxamide;
1-[1-(cyanoacetyl)-4-(cyanomethyl)piperidin-4-yl]-3-[(2-fluoropyridin-4-yl)amino]-1H-pyrazole-4-carboxamide;
1-[4-(cyanomethyl)-1-(3-hydroxy-3-methylbutanoyl)piperidin-4-yl]-3-[(2-fluoropyridin-4-yl)amino]-1H-pyrazole-4-carboxamide;
1-[4-(cyanomethyl)-1-{[1-(trifluoromethyl)cyclobutyl]carbonyl}piperidin-4-yl]-3-[(2-fluoropyridin-4-yl)amino]-1H-pyrazole-4-carboxamide;
1-[4-(cyano methyl)-1-(1H-imidazol-1-ylacetyl)piperidin-4-yl]-3-[(2-fluoropyridin-4-yl)amino]-1H-pyrazole-4-carboxamide;
1-{4-(cyanomethyl)-1-[(3,3-difluorocyclobutyl)carbonyl]piperidin-4-yl}-3-[(2-fluoropyridin-4-yl)amino]-1H-pyrazole-4-carboxamide;
1-[4-(cyano methyl)-1-(3,3-dimethylbutanoyl)piperidin-4-yl]-3-[(2-fluoropyridin-4-yl)amino]-1H-pyrazole-4-carboxamide;
1-[4-(cyanomethyl)-1-(3,3,3-trifluoro-2,2-dimethylpropanoyl)piperidin-4-yl]-3-[(2-fluoropyridin-4-yl)amino]-1H-pyrazole-4-carboxamide;
1-[4-(cyanomethyl)-1-{[1-(trifluoromethyl)cyclopropyl]carbonyl}piperidin-4-yl]-3-[(2-fluoropyridin-4-yl)amino]-1H-pyrazole-4-carboxamide;
1-[4-(cyanomethyl)-1-(4,4,4-trifluorobutanoyl)piperidin-4-yl]-3-[(2-fluoropyridin-4-yl)amino]-1H-pyrazole-4-carboxamide;
1-{4-(cyanomethyl)-1-[(methylsulfonyl)acetyl]piperidin-4-yl}-3-[(2-fluoropyridin-4-yl)amino]-1H-pyrazole-4-carboxamide;
1-[4-(cyanomethyl)-1-(2,2-difluorobutanoyl)piperidin-4-yl]-3-[(2-fluoropyridin-4-yl)amino]-1H-pyrazole-4-carboxamide;
1-{4-(cyanomethyl)-1-[(1-methylcyclobutyl)carbonyl]piperidin-4-yl}-3-[(2-fluoropyridin-4-yl)amino]-1H-pyrazole-4-carboxamide;
1-[4-(cyano methyl)-1-(3,3-difluoro-2-hydroxy-2-methylpropanoyl)piperidin-4-yl]-3-[(2-fluoropyridin-4-yl)amino]-1H-pyrazole-4-carboxamide;
1-{4-(cyanomethyl)-1-[(3R)-3-hydroxybutanoyl]piperidin-4-yl}-3-[(2-fluoropyridin-4-yl)amino]-1H-pyrazole-4-carboxamide;
1-(4-(Cyanomethyl)-1-(3,3,3-trifluoropropanoyl)piperidin-4-yl)-3-(4-fluorophenylamino)-1H-pyrazole-4-carboxamide;
1-(4-(cyanomethyl)-1-(3,3,3-trifluoropropanoyl)piperidin-4-yl)-3-(2-fluoropyridin-4-ylamino)-1H-pyrazole-4-carboxamide;
1-(4-(cyanomethyl)-1-(3,3,3-trifluoropropanoyl)piperidin-4-yl)-3-(5-fluoropyridin-3-ylamino)-1H-pyrazole-4-carboxamide;
1-[1-(Cyanoacetyl)-4-(cyanomethyl)piperidin-4-yl]-3-(phenylamino)-1H-pyrazole-4-carboxamide;
1-[1-(cyanoacetyl)-4-(cyanomethyl)piperidin-4-yl]-3-{[4-(methylsulfonyl)phenyl]amino}-1H-pyrazole-4-carboxamide;

1-[4-(Cyanomethyl)-1-(isopropylsulfonyl)piperidin-4-yl]-3-(phenylamino)-1H-pyrazole-4-carboxamide;
1-[4-(cyanomethyl)-1-(methylsulfonyl)piperidin-4-yl]-3-(phenylamino)-1H-pyrazole-4-carboxamide;
1-[4-(cyanomethyl)-1-(ethylsulfonyl)piperidin-4-yl]-3-(phenylamino)-1H-pyrazole-4-carboxamide;
1-[4-(cyanomethyl)-1-(furan-2-ylsulfonyl)piperidin-4-yl]-3-(phenylamino)-1H-pyrazole-4-carboxamide;
1-{4-(cyanomethyl)-1-[(trifluoromethyl)sulfonyl]piperidin-4-yl}-3-(phenylamino)-1H-pyrazole-4-carboxamide;
1-[4-(cyanomethyl)-1-(phenylsulfonyl)piperidin-4-yl]-3-(phenylamino)-1H-pyrazole-4-carboxamide;
1-{4-(cyanomethyl)-1-[(1-methyl-1H-imidazol-4-yl)sulfonyl]piperidin-4-yl}-3-(phenylamino)-1H-pyrazole-4-carboxamide;
1-[1-(benzylsulfonyl)-4-(cyanomethyl)piperidin-4-yl]-3-(phenylamino)-1H-pyrazole-4-carboxamide;
1-{4-(cyanomethyl)-1-[(4-methoxyphenyl)sulfonyl]piperidin-4-yl}-3-(phenylamino)-1H-pyrazole-4-carboxamide;
1-{4-(cyanomethyl)-1-[(3-methoxyphenyl)sulfonyl]piperidin-4-yl}-3-(phenylamino)-1H-pyrazole-4-carboxamide;
1-{1-[(3-chlorophenyl)sulfonyl]-4-(cyanomethyl)piperidin-4-yl}-3-(phenylamino)-1H-pyrazole-4-carboxamide;
1-{1-[(2-chlorophenyl)sulfonyl]-4-(cyanomethyl)piperidin-4-yl}-3-(phenylamino)-1H-pyrazole-4-carboxamide
1-[4-(cyanomethyl)-1-{[4-(trifluoromethyl)phenyl]sulfonyl}piperidin-4-yl]-3-(phenylamino)-1H-pyrazole-4-carboxamide;
1-[1-(biphenyl-4-ylsulfonyl)-4-(cyanomethyl)piperidin-4-yl]-3-(phenylamino)-1H-pyrazole-4-carboxamide;
1-[4-(cyanomethyl)-1-(cyclopropylsulfonyl)piperidin-4-yl]-3-(phenylamino)-1H-pyrazole-4-carboxamide;
1-[3-(cyanomethyl)-1-(methylsulfonyl)azetidin-3-yl]-3-(phenylamino)-1H pyrazole-4-carboxamide;
1-[3-(cyanomethyl)-1-(furan-2-ylsulfonyl)azetidin-3-yl]-3-(phenylamino)-1H-pyrazole-4-carboxamide;
1-{3-(cyanomethyl)-1-[(trifluoromethyl)sulfonyl]azetidin-3-yl}-3-(phenylamino)-1H-pyrazole-4-carboxamide;
1-[3-(cyanomethyl)-1-(phenylsulfonyl)azetidin-3-yl]-3-(phenylamino)-1H-pyrazole-4-carboxamide;
1-[1-(benzylsulfonyl)-3-(cyanomethyl)azetidin-3-yl]-3-(phenylamino)-1H-pyrazole-4-carboxamide;
1-{3-(Cyanomethyl)-1-[(3-fluorophenyl)carbamoyl]azetidin-3-yl}-3-(phenylamino)-1H pyrazole-4-carboxamide;
1-[3-(cyanomethyl)-1-(cyclohexylcarbamoyl)azetidin-3-yl]-3-(phenylamino)-1H-pyrazole-4-carboxamide;
1-{3-(cyanomethyl)-1-[(1-methylethyl)carbamoyl]azetidin-3-yl}-3-(phenylamino)-1H-pyrazole-4-carboxamide;
1-{3-(cyanomethyl)-1-[(3,4-dimethylphenyl)carbamoyl]azetidin-3-yl}-3-(phenylamino)-1H-pyrazole-4-carboxamide;
1-[1-(butylcarbamoyl)-3-(cyanomethyl)azetidin-3-yl]-3-(phenylamino)-1H-pyrazole-4-carboxamide;
1-{3-(cyanomethyl)-1-[(4-methylphenyl)carbamoyl]azetidin-3-yl}-3-(phenylamino)-1H-pyrazole-4-carboxamide;
1-[3-(cyanomethyl)-1-{[4-(1-methylethyl)phenyl]carbamoyl}azetidin-3-yl]-3-(phenylamino)-1H-pyrazole-4-carboxamide;
1-[3-(cyanomethyl)-1-{[2-(1-methylethyl)phenyl]carbamoyl}azetidin-3-yl]-3-(phenylamino)-1H-pyrazole-4-carboxamide;
ethyl N-({3-[4-carbamoyl-3-(phenylamino)-1H-pyrazol-1-yl]-3-(cyanomethyl)azetidin-1-yl}carbonyl)alaninate;
1-{3-(cyanomethyl)-1-[(2,5-difluorophenyl)carbamoyl]azetidin-3-yl}-3-(phenylamino)-1H-pyrazole-4-carboxamide;
1-{3-(cyanomethyl)-1-[(3-methylphenyl)carbamoyl]azetidin-3-yl}-3-(phenylamino)-1H-pyrazole-4-carboxamide;
1-{3-(cyanomethyl)-1-[(2,4,6-trimethylphenyl)carbamoyl]azetidin-3-yl}-3-(phenylamino)-1H-pyrazole-4-carboxamide;
1-{1-[(3-chloro-4-methylphenyl)carbamoyl]-3-(cyanomethyl)azetidin-3-yl}-3-(phenylamino)-1H-pyrazole-4-carboxamide;
1-{1-[(4-chloro-2-methylphenyl)carbamoyl]-3-(cyanomethyl)azetidin-3-yl}-3-(phenylamino)-1H-pyrazole-4-carboxamide;
1-{3-(cyanomethyl)-1-[(4-cyanophenyl)carbamoyl]azetidin-3-yl}-3-(phenylamino)-1H-pyrazole-4-carboxamide;
1-{3-(cyanomethyl)-1-[(2,5-dimethylphenyl)carbamoyl]azetidin-3-yl}-3-(phenylamino)-1H-pyrazole-4-carboxamide;
1-{1-[(5-chloro-2-methylphenyl)carbamoyl]-3-(cyanomethyl)azetidin-3-yl}-3-(phenylamino)-1H-pyrazole-4-carboxamide;
1-[3-(cyanomethyl)-1-(propylcarbamoyl)azetidin-3-yl]-3-(phenylamino)-1H-pyrazole-4-carboxamide;
1-{3-(cyanomethyl)-1-[(2,4-dimethylphenyl)carbamoyl]azetidin-3-yl}-3-(phenylamino)-1H-pyrazole-4-carboxamide;
1-{3-(cyanomethyl)-1-[(3,5-dimethylphenyl)carbamoyl]azetidin-3-yl}-3-(phenylamino)-1H-pyrazole-4-carboxamide;
1-{3-(cyanomethyl)-1-[(3,4-difluorophenyl)carbamoyl]azetidin-3-yl}-3-(phenylamino)-1H-pyrazole-4-carboxamide;
1-{1-[(3-chloro-2-methylphenyl)carbamoyl]-3-(cyanomethyl)azetidin-3-yl}-3-(phenylamino)-1H-pyrazole-4-carboxamide;
1-{3-(cyanomethyl)-1-[(2-ethyl-6-methylphenyl)carbamoyl]azetidin-3-yl}-3-(phenylamino)-1H-pyrazole-4-carboxamide;
1-{1-[(2-chloro-6-methylphenyl)carbamoyl]-3-(cyanomethyl)azetidin-3-yl}-3-(phenylamino)-1H-pyrazole-4-carboxamide;
1-{3-(cyanomethyl)-1-[(2-methoxy-5-methylphenyl)carbamoyl]azetidin-3-yl}-3-(phenylamino)-1H-pyrazole-4-carboxamide;
1-{3-(cyanomethyl)-1-[(4-ethoxyphenyl)carbamoyl]azetidin-3-yl}-3-(phenylamino)-1H-pyrazole-4-carboxamide;
1-{3-(cyanomethyl)-1-[(2-methylphenyl)carbamoyl]azetidin-3-yl}-3-(phenylamino)-1H-pyrazole-4-carboxamide;
1-{3-(cyanomethyl)-1-[(2,4-difluorophenyl)carbamoyl]azetidin-3-yl}-3-(phenylamino)-1H-pyrazole-4-carboxamide;
1-{3-(cyanomethyl)-1-[(1,1,3,3-tetramethylbutyl)carbamoyl]azetidin-3-yl}-3-(phenylamino)-1H-pyrazole-4-carboxamide;
1-{3-(cyanomethyl)-1-[(2-ethoxyphenyl)carbamoyl]azetidin-3-yl}-3-(phenylamino)-1H-pyrazole-4-carboxamide;
1-{3-(cyanomethyl)-1-[(2,6-dimethylphenyl)carbamoyl]azetidin-3-yl}-3-(phenylamino)-1H-pyrazole-4-carboxamide;
1-{1-[(3-acetylphenyl)carbamoyl]-3-(cyanomethyl)azetidin-3-yl}-3-(phenylamino)-1H-pyrazole-4-carboxamide;
1-[3-(cyanomethyl)-1-{[(1R)-1-phenylethyl]carbamoyl}azetidin-3-yl]-3-(phenylamino)-1H-pyrazole-4-carboxamide;
1-{3-(cyanomethyl)-1-[(4-ethylphenyl)carbamoyl]azetidin-3-yl}-3-(phenylamino)-1H-pyrazole-4-carboxamide;
1-{3-(cyanomethyl)-1-[(3-ethylphenyl)carbamoyl]azetidin-3-yl}-3-(phenylamino)-1H-pyrazole-4-carboxamide;

1-{3-(cyanomethyl)-1-[(4-methoxy-2-methylphenyl)carbamoyl]azetidin-3-yl}-3-(phenylamino)-1H-pyrazole-4-carboxamide;
1-{3-(cyanomethyl)-1-[(3-fluoro-4-methylphenyl)carbamoyl]azetidin-3-yl}-3-(phenylamino)-1H-pyrazole-4-carboxamide;
1-{3-(cyanomethyl)-1-[(5-fluoro-2-methylphenyl)carbamoyl]azetidin-3-yl}-3-(phenylamino)-1H-pyrazole-4-carboxamide;
1-{3-(cyanomethyl)-1-[(2-ethylphenyl)carbamoyl]azetidin-3-yl}-3-(phenylamino)-1H-pyrazole-4-carboxamide;
1-{1-[(3-chloro-4-fluorophenyl)carbamoyl]-3-(cyanomethyl)azetidin-3-yl}-3-(phenylamino)-1H-pyrazole-4-carboxamide;
1-{3-(cyanomethyl)-1-[(4-methylphenyl)carbamoyl]azetidin-3-yl}-3-{[4-(methylsulfonyl)phenyl]amino}-1H-pyrazole-4-carboxamide;
1-{3-(cyanomethyl)-1-[(2,5-difluorophenyl)carbamoyl]azetidin-3-yl}-3-{[4-(methylsulfonyl)phenyl]amino}-1H-pyrazole-4-carboxamide;
1-[1-(butylcarbamoyl)-3-(cyanomethyl)azetidin-3-yl]-3-{[4-(methylsulfonyl)phenyl]amino}-1H-pyrazole-4-carboxamide;
4-(4-carbamoyl-3-(4-(trifluoromethylsulfonyl)phenylamino)-1H-pyrazol-1-yl)-4-(cyanomethyl)-N-isopropylpiperidine-1-carboxamide;
4-(4-carbamoyl-3-(4-(trifluoromethylsulfonyl)phenylamino)-1H-pyrazol-1-yl)-4-(cyanomethyl)-N-(4-cyanophenyl)piperidine-1-carboxamide;
4-[4-Carbamoyl-3-(phenylamino)-1H-pyrazol-1-yl]-4-(cyanomethyl)-N-(1-methylethyl)piperidine-1-carboxamide;
4-[4-carbamoyl-3-(phenylamino)-1H-pyrazol-1-yl]-4-(cyanomethyl)-N-(4-cyanophenyl)piperidine-1-carboxamide;
3-((4-chlorophenyl)amino)-1-(1-(cyanomethyl)-4-(3-fluoroazetidin-1-yl)cyclohexyl)-1H-pyrazole-4-carboxamide;
1-[1-(cyanomethyl)-4-(3-fluoro azetidin-1-yl)cyclohexyl]-3-{[4-(trifluoromethyl)phenyl]amino}-1H-pyrazole-4-carboxamide;
1-(1-(cyanomethyl)-4-(cyclohexylamino)cyclohexyl-3-((4-fluorophenyl)amino)-1H-pyrazole-4-carboxamide;
1-{1-(cyanomethyl)-4-[(3-fluorophenyl)amino]cyclohexyl}-3-[(4-fluorophenyl)amino]-1H-pyrazole-4-carboxamide;
1-[1-(cyanomethyl)-4-(pyridin-2-ylamino)cyclohexyl]-3-[(2-fluoropyridin-4-yl)amino]-1H-pyrazole-4-carboxamide;
1-[1-(cyanomethyl)-4-(tetrahydro-2H-pyran-4-ylamino)cyclohexyl]-3-[(4-fluorophenyl)amino]-1H-pyrazole-4-carboxamide;
1-[1-(cyanomethyl)-4-(pyridin-3-ylamino)cyclohexyl]-3-[(2-fluoropyridin-4-yl)amino]-1H-pyrazole-4-carboxamide;
1-{1-(cyanomethyl)-4-[(4-hydroxyphenyl)amino]cyclohexyl}-3-({4-[(difluoromethyl)sulfonyl]phenyl}amino)-1H-pyrazole-4-carboxamide;
1-[1-(cyanomethyl)-4-(pyridin-3-ylamino)cyclohexyl]-3-({4-[(difluoromethyl)sulfonyl]phenyl}amino)-1H-pyrazole-4-carboxamide;
1-[1-(cyanomethyl)-4-(pyridin-3-ylamino)cyclohexyl]-34{4-[(difluoromethyl)sulfonyl]phenyl}amino)-1H-pyrazole-4-carboxamide;
1-{1-(cyanomethyl)-4-[(2,5-difluorophenyl)amino]cyclohexyl}-3-[(2-fluoropyridin-4-yl)amino]-1H-pyrazole-4-carboxamide;
1-{4-[(2-chlorophenyl)amino]-1-(cyanomethyl)cyclohexyl}-3-[(2-fluoropyridin-4-yl)amino]-1H-pyrazole-4-carboxamide;
1-[1-(cyanomethyl)-4-(pyridin-2-ylamino)cyclohexyl]-3-[(4-fluorophenyl)amino]-1H-pyrazole-4-carboxamide;
1-[1-(cyanomethyl)-4-(4-hydroxypiperidin-1-yl)cyclohexyl]-3-[(2-fluoropyridin-4-yl)amino]-1H-pyrazole-4-carboxamide;
1-{1-(cyanomethyl)-4-[(3-hydroxyphenyl)amino]cyclohexyl}-3-({4-[(difluoromethyl)sulfonyl]phenyl}amino)-1H-pyrazole-4-carboxamide;
1-{1-(cyanomethyl)-4-[methyl(phenyl)amino]cyclohexyl}-3-[(2-fluoropyridin-4-yl)amino]-1H-pyrazole-4-carboxamide;
1-{1-(cyanomethyl)-4-[(3-fluorophenyl)amino]cyclohexyl}-3-[(4-fluorophenyl)amino]-1H-pyrazole-4-carboxamide;
1-{1-(cyanomethyl)-4-[(2-fluorophenyl)amino]cyclohexyl}-3-[(2-fluoropyridin-4-yl)amino]-1H-pyrazole-4-carboxamide;
1-{1-(cyanomethyl)-4-[(4-fluorophenyl)amino]cyclohexyl}-3-[(4-fluorophenyl)amino]-1H-pyrazole-4-carboxamide;
1-{1-(cyanomethyl)-4-[(4-fluorophenyl)amino]cyclohexyl}-3-[(4-fluorophenyl)amino]-1H-pyrazole-4-carboxamide;
1-{1-(cyanomethyl)-4-[(3,4-difluorophenyl)amino]cyclohexyl}-3-[(2-fluoropyridin-4-yl)amino]-1H-pyrazole-4-carboxamide;
1-[1-(cyanomethyl)-4-(2,3-dihydro-1H-indol-1-yl)cyclohexyl]-3-[(4-fluorophenyl)amino]-1H-pyrazole-4-carboxamide;
1-[1-(cyanomethyl)-4-(pyridin-2-ylamino)cyclohexyl]-3-[(2-fluoropyridin-4-yl)amino]-1H-pyrazole-4-carboxamide;
1-[1-(cyanomethyl)-4-(cyclohexylamino)cyclohexyl]-3-[(2-fluoropyridin-4-yl)amino]-1H-pyrazole-4-carboxamide;
1-{1-(cyanomethyl)-4-[(2-fluorophenyl)amino]cyclohexyl}-3-[(2-fluoropyridin-4-yl)amino]-1H-pyrazole-4-carboxamide;
1-{4-[(2-chlorophenyl)amino]-1-(cyanomethyl)cyclohexyl}-3-[(2-fluoropyridin-4-yl)amino]-1H-pyrazole-4-carboxamide;
1-[1-(cyanomethyl)-4-(tetrahydro-2H-pyran-4-ylamino)cyclohexyl]-3-({4-[(difluoromethyl)sulfonyl]phenyl}amino)-1H-pyrazole-4-carboxamide;
1-[1-(cyanomethyl)-4-(4-hydroxypiperidin-1-yl)cyclohexyl]-3-[(4-fluorophenyl)amino]-1H-pyrazole-4-carboxamide;
1-[1-(cyanomethyl)-4-(cyclohexylamino)cyclohexyl]-3-({4-[(difluoromethyl)sulfonyl]phenyl}amino)-1H-pyrazole-4-carboxamide;
1-{4-[(3-chlorophenyl)amino]-1-(cyanomethyl)cyclohexyl}-3-[(2-fluoropyridin-4-yl)amino]-1H-pyrazole-4-carboxamide;
1-[1-(cyanomethyl)-4-(2,3-dihydro-1H-indol-1-yl)cyclohexyl]-3-[(2-fluoropyridin-4-yl)amino]-1H-pyrazole-4-carboxamide;
1-[1-(cyanomethyl)-4-(4,4-difluoropiperidin-1-yl)cyclohexyl]-3-({4-[(difluoromethyl)sulfonyl]phenyl}amino)-1H-pyrazole-4-carboxamide;
1-{1-(cyanomethyl)-4-[(2-hydroxyphenyl)amino]cyclohexyl}-3-({4-[(difluoromethyl)sulfonyl]phenyl}amino)-1H-pyrazole-4-carboxamide;
1-{1-(cyanomethyl)-4-[(2,4-difluorophenyl)amino]cyclohexyl}-3-[(2-fluoropyridin-4-yl)amino]-1H-pyrazole-4-carboxamide;
1-{1-(cyanomethyl)-4-[methyl(phenyl)amino]cyclohexyl}-3-[(2-fluoropyridin-4-yl)amino]-1H-pyrazole-4-carboxamide;

1-{1-(cyanomethyl)-4-[(3,4-difluorophenyl)amino]cyclohexyl}-3-[(4-fluorophenyl)amino]-1H-pyrazole-4-carboxamide;

1-{1-(cyanomethyl)-4-[(3,4-difluorophenyl)amino]cyclohexyl}-3-[(2-fluoropyridin-4-yl)amino]-1H-pyrazole-4-carboxamide;

1-{1-(cyanomethyl)-4-[(2,4-difluorophenyl)amino]cyclohexyl}-3-[(2-fluoropyridin-4-yl)amino]-1H-pyrazole-4-carboxamide;

1-[1-(cyanomethyl)-4-(tetrahydro-2H-pyran-4-ylamino)cyclohexyl]-3-[(2-fluoropyridin-4-yl)amino]-1H-pyrazole-4-carboxamide;

1-[1-(cyanomethyl)-4-(pyridin-3-ylamino)cyclohexyl]-3-[(4-fluorophenyl)amino]-1H-pyrazole-4-carboxamide;

1-{1-(cyanomethyl)-4-[(4-fluorophenyl)amino]cyclohexyl}-3-[(2-fluoropyridin-4-yl)amino]-1H-pyrazole-4-carboxamide;

1-[1-(cyanomethyl)-4-(4-hydroxypiperidin-1-yl)cyclohexyl]-3-[(4-fluorophenyl)amino]-1H-pyrazole-4-carboxamide;

1-[1-(cyanomethyl)-4-(4,4-difluoropiperidin-1-yl)cyclohexyl]-3-({4-[(difluoromethyl)sulfonyl]phenyl}amino)-1H-pyrazole-4-carboxamide;

1-[1-(cyanomethyl)-4-(4-hydroxypiperidin-1-yl)cyclohexyl]-3-({4-[(difluoromethyl)sulfonyl]phenyl}amino)-1H-pyrazole-4-carboxamide;

1-{1-(cyanomethyl)-4-[(3-hydroxyphenyl)amino]cyclohexyl}-3-({4-[(difluoromethyl)sulfonyl]phenyl}amino)-1H-pyrazole-4-carboxamide;

1-{4-[(4-chlorophenyl)amino]-1-(cyanomethyl)cyclohexyl}-3-[(2-fluoropyridin-4-yl)amino]-1H-pyrazole-4-carboxamide;

1-{4-[(3-chlorophenyl)amino]-1-(cyanomethyl)cyclohexyl}-3-[(4-fluorophenyl)amino]-1H-pyrazole-4-carboxamide;

1-{1-(cyanomethyl)-4-[(4-fluorophenyl)amino]cyclohexyl}-3-[(2-fluoropyridin-4-yl)amino]-1H-pyrazole-4-carboxamide;

1-{1-(cyanomethyl)-4-[(2-hydroxyphenyl)amino]cyclohexyl}-3-({4-[(difluoromethyl)sulfonyl]phenyl}amino)-1H-pyrazole-4-carboxamide;

1-[1-(cyanomethyl)-4-(2,3-dihydro-1H-indol-1-yl)cyclohexyl]-3-[(4-fluorophenyl)amino]-1H-pyrazole-4-carboxamide;

1-{1-(cyanomethyl)-4-[(2,5-difluorophenyl)amino]cyclohexyl}-3-[(4-fluorophenyl)amino]-1H-pyrazole-4-carboxamide;

1-[1-(cyanomethyl)-4-(cyclohexylamino)cyclohexyl]-3-[(2-fluoropyridin-4-yl)amino]-1H-pyrazole-4-carboxamide;

1-{4-[(4-chlorophenyl)amino]-1-(cyanomethyl)cyclohexyl}-3-[(4-fluorophenyl)amino]-1H-pyrazole-4-carboxamide;

1-{4-[(4-chlorophenyl)amino]-1-(cyanomethyl)cyclohexyl}-3-[(4-fluorophenyl)amino]-1H-pyrazole-4-carboxamide;

1-[1-(cyanomethyl)-4-(2,3-dihydro-1H-indol-1-yl)cyclohexyl]-3-[(2-fluoropyridin-4-yl)amino]-1H-pyrazole-4-carboxamide;

1-{1-(cyanomethyl)-4-[(3-fluorophenyl)amino]cyclohexyl}-3-[(2-fluoropyridin-4-yl)amino]-1H-pyrazole-4-carboxamide;

1-[1-(cyanomethyl)-4-(4-hydroxypiperidin-1-yl)cyclohexyl]-3-[(2-fluoropyridin-4-yl)amino]-1H-pyrazole-4-carboxamide;

1-[1-(cyanomethyl)-4-(cyclohexylamino)cyclohexyl]-3-({4-[(difluoromethyl)sulfonyl]phenyl}amino)-1H-pyrazole-4-carboxamide;

1-{1-(cyanomethyl)-4-[(2-fluorophenyl)amino]cyclohexyl}-3-[(4-fluorophenyl)amino]-1H-pyrazole-4-carboxamide;

1-{1-(cyanomethyl)-4-[(4-hydroxyphenyl)amino]cyclohexyl}-3-({4-[(difluoromethyl)sulfonyl]phenyl}amino)-1H-pyrazole-4-carboxamide;

1-{1-(cyanomethyl)-4-[(2-fluorophenyl)amino]cyclohexyl}-3-[(4-fluorophenyl)amino]-1H-pyrazole-4-carboxamide;

1-{4-[(4-chlorophenyl)amino]-1-(cyanomethyl)cyclohexyl}-3-[(2-fluoropyridin-4-yl)amino]-1H-pyrazole-4-carboxamide;

1-{4-[(3-chlorophenyl)amino]-1-(cyanomethyl)cyclohexyl}-3-[(2-fluoropyridin-4-yl)amino]-1H-pyrazole-4-carboxamide;

1-{1-(cyanomethyl)-4-[(2,5-difluorophenyl)amino]cyclohexyl}-3-[(2-fluoropyridin-4-yl)amino]-1H-pyrazole-4-carboxamide;

1-{1-(cyanomethyl)-4-[(3-fluorophenyl)amino]cyclohexyl}-3-[(2-fluoropyridin-4-yl)amino]-1H-pyrazole-4-carboxamide;

1-[1-(cyanomethyl)-4-(tetrahydro-2H-pyran-4-ylamino)cyclohexyl]-3-[(4-fluorophenyl)amino]-1H-pyrazole-4-carboxamide;

1-[1-(cyanomethyl)-4-(tetrahydro-2H-pyran-4-ylamino)cyclohexyl]-3-({4-[(difluoromethyl)sulfonyl]phenyl}amino)-1H-pyrazole-4-carboxamide;

1-[1-(cyanomethyl)-4-(4-hydroxypiperidin-1-yl)cyclohexyl]-34 {4-[(difluoromethyl)sulfonyl]phenyl}amino)-1H-pyrazole-4-carboxamide;

1-{1-(cyanomethyl)-4-[(2-hydroxyethyl)amino]cyclohexyl}-3-[(4-fluorophenyl)amino]-1H-pyrazole-4-carboxamide;

1-{1-(cyanomethyl)-4-[(cyclopropylmethyl)amino]cyclohexyl}-3-[(4-fluorophenyl)amino]-1H-pyrazole-4-carboxamide;

1-[1-(cyanomethyl)-4-(4,4-difluoropiperidin-1-yl)cyclohexyl]-3-[(4-fluorophenyl)amino]-1H-pyrazole-4-carboxamide;

1-{1-(cyanomethyl)-4-[(2-methoxyethyl)amino]cyclohexyl}-3-[(4-fluorophenyl)amino]-1H-pyrazole-4-carboxamide;

1-[1-(cyanomethyl)-4-{methyl[2-(methylsulfonyl)ethyl]amino}cyclohexyl]-3-[(4-fluorophenyl)amino]-1H-pyrazole-4-carboxamide;

1-[1-(cyanomethyl)-4-{[4-(trifluoromethyl)phenyl]amino}cyclohexyl]-3-[(4-fluorophenyl)amino]-1H-pyrazole-4-carboxamide;

1-[1-(cyanomethyl)-4-(3-methoxyazetidin-1-yl)cyclohexyl]-3-[(4-fluorophenyl)amino]-1H-pyrazole-4-carboxamide;

1-[1-(cyanomethyl)-4-(pyridin-3-ylamino)cyclohexyl]-3-[(4-fluorophenyl)amino]-1H-pyrazole-4-carboxamide;

1-[4-(4-acetylpiperazin-1-yl)-1-(cyanomethyl)cyclohexyl]-3-[(4-fluorophenyl)amino]-1H-pyrazole-4-carboxamide;

1-{1-(cyanomethyl)-4-[(2,2-difluoroethyl)amino]cyclohexyl}-3-[(4-fluorophenyl)amino]-1H-pyrazole-4-carboxamide;

1-[1-(cyanomethyl)-4-(methylamino)cyclohexyl]-3-[(4-fluorophenyl)amino]-1H-pyrazole-4-carboxamide;

1-{1-(cyanomethyl)-4-[(2-fluoroethyl)amino]cyclohexyl}-3-[(4-fluorophenyl)amino]-1H-pyrazole-4-carboxamide;

1-[4-azetidin-1-yl-1-(cyanomethyl)cyclohexyl]-3-[(4-fluorophenyl)amino]-1H-pyrazole-4-carboxamide;

1-[1-(cyanomethyl)-4-(3-methoxyazetidin-1-yl)cyclohexyl]-3-[(2-fluoropyridin-4-yl)amino]-1H-pyrazole-4-carboxamide;

1-[1-(cyanomethyl)-4-(3-fluoroazetidin-1-yl)cyclohexyl]-3-[(2-fluoropyridin-4-yl)amino]-1H-pyrazole-4-carboxamide;
1-[1-(cyanomethyl)-4-(phenylamino)cyclohexyl]-3-[(2-fluoropyridin-4-yl)amino]-1H-pyrazole-4-carboxamide;
1-{1-(cyanomethyl)-4-[(2,2-difluoroethyl)amino]cyclohexyl}-3-({4-[(difluoromethyl)sulfonyl]phenyl}amino)-1H-pyrazole-4-carboxamide;
1-{1-(cyanomethyl)-4-[(2,2,2-trifluoroethyl)amino]cyclohexyl}-3-({4-[(difluoromethyl)sulfonyl]phenyl}amino)-1H-pyrazole-4-carboxamide;
1-[1-(cyanomethyl)-4-(phenylamino)cyclohexyl]-3-[(2-fluoropyridin-4-yl)amino]-1H-pyrazole-4-carboxamide;
1-{1-(cyanomethyl)-4-[(2,2-difluoroethyl)amino]cyclohexyl}-3-[(2-fluoropyridin-4-yl)amino]-1H-pyrazole-4-carboxamide;
1-[1-(cyanomethyl)-4-(phenylamino)cyclohexyl]-3-({4-[(difluoromethyl)sulfonyl]phenyl}amino)-1H-pyrazole-4-carboxamide;
1-{1-(cyanomethyl)-4-[(2,2,2-trifluoroethyl)amino]cyclohexyl}-3-({4-[(difluoromethyl)sulfonyl]phenyl}amino)-1H-pyrazole-4-carboxamide;
1-[1-(cyanomethyl)-4-(1,3-dihydro-2H-isoindol-2-yl)cyclohexyl]-3-[(4-fluorophenyl)amino]-1H-pyrazole-4-carboxamide;
1-[1-(cyanomethyl)-4-(3-fluoroazetidin-1-yl)cyclohexyl]-3-({4-[(difluoromethyl)sulfonyl]phenyl}amino)-1H-pyrazole-4-carboxamide;
1-[4-(benzylamino)-1-(cyanomethyl)cyclohexyl]-3-[(4-fluorophenyl)amino]-1H-pyrazole-4-carboxamide;
1-{1-(cyanomethyl)-4-[(2,2,2-trifluoroethyl)amino]cyclohexyl}-3-[(2-fluoropyridin-4-yl)amino]-1H-pyrazole-4-carboxamide;
1-[1-(cyanomethyl)-4-(3-methoxyazetidin-1-yl)cyclohexyl]-3-[(2-fluoropyridin-4-yl)amino]-1H-pyrazole-4-carboxamide;
1-{1-(cyanomethyl)-4-[(2,2,2-trifluoroethyl)amino]cyclohexyl}-3-[(2-fluoropyridin-4-yl)amino]-1H-pyrazole-4-carboxamide;
1-[1-(cyanomethyl)-4-(phenylamino)cyclohexyl]-3-[(4-fluorophenyl)amino]-1H-pyrazole-4-carboxamide;
1-{4-[(4-cyanobenzyl)amino]-1-(cyanomethyl)cyclohexyl}-3-[(4-fluorophenyl)amino]-1H-pyrazole-4-carboxamide;
1-{1-(cyanomethyl)-4-[(2,2,2-trifluoroethyl)amino]cyclohexyl}-3-[(4-fluorophenyl)amino]-1H-pyrazole-4-carboxamide;
1-{1-(cyanomethyl)-4-[(2,2-difluoroethyl)amino]cyclohexyl}-3-({4-[(difluoromethyl)sulfonyl]phenyl}amino)-1H-pyrazole-4-carboxamide;
1-[1-(cyanomethyl)-4-(3-fluoroazetidin-1-yl)cyclohexyl]-3-[(4-fluorophenyl)amino]-1H-pyrazole-4-carboxamide;
1-{1-(cyanomethyl)-4-[(2,2,2-trifluoroethyl)amino]cyclohexyl}-3-[(4-fluorophenyl)amino]-1H-pyrazole-4-carboxamide;
1-[1-(cyanomethyl)-4-(phenylamino)cyclohexyl]-3-({4-[(difluoromethyl)sulfonyl]phenyl}amino)-1H-pyrazole-4-carboxamide;
1-[1-(cyanomethyl)-4-(phenylamino)cyclohexyl]-3-[(4-fluorophenyl)amino]-1H-pyrazole-4-carboxamide;
1-[1-(cyanomethyl)-4-(3-fluoroazetidin-1-yl)cyclohexyl]-3-[(2-fluoropyridin-4-yl)amino]-1H-pyrazole-4-carboxamide;
1-[1-(cyanomethyl)-4-(3-fluoroazetidin-1-yl)cyclohexyl]-3-({4-[(difluoromethyl)sulfonyl]phenyl}amino)-1H-pyrazole-4-carboxamide;
1-{1-(cyanomethyl)-4-[(2,2-difluoroethyl)amino]cyclohexyl}-3-[(2-fluoropyridin-4-yl)amino]-1H-pyrazole-4-carboxamide;
1-[1-(cyanomethyl)-4-(3-fluoroazetidin-1-yl)cyclohexyl]-3-[(4-fluorophenyl)amino]-1H-pyrazole-4-carboxamide;
1-[cis-4-(benzylamino)-1-(cyanomethyl)cyclohexyl]-3-[(4-fluorophenyl)amino]-1H-pyrazole-4-carboxamide;
1-(1-(cyanomethyl)-4-((2,4-difluorobenzyl)amino)cyclohexyl)-3-((2-fluoropyridin-4-yl)amino)-1H-pyrazole-4-carboxamide;
1-[4-amino-1-(cyanomethyl)cyclohexyl]-3-({4-[(difluoromethyl)sulfonyl]phenyl}amino)-1H-pyrazole-4-carboxamide;
1-{1-(cyanomethyl)-4-[(2,4-difluorobenzyl)amino]cyclohexyl}-3-[(2-fluoropyridin-4-yl)amino]-1H-pyrazole-4-carboxamide;
1-{1-(cyanomethyl)-4-[(3-hydroxybenzyl)amino]cyclohexyl}-3-[(2-fluoropyridin-4-yl)amino]-1H-pyrazole-4-carboxamide;
1-{4-[(4-cyanobenzyl)amino]-1-(cyanomethyl)cyclohexyl}-3-[(2-fluoropyridin-4-yl)amino]-1H-pyrazole-4-carboxamide;
1-{1-(cyanomethyl)-4-[(2-hydroxybenzyl)amino]cyclohexyl}-3-[(2-fluoropyridin-4-yl)amino]-1 H-pyrazole-4-carboxamide;
1-{1-(cyanomethyl)-4-[(cyclohexylmethyl)amino]cyclohexyl}-3-[(2-fluoropyridin-4-yl)amino]-1H-pyrazole-4-carboxamide;
1-{4-[(4-chlorobenzyl)amino]-1-(cyanomethyl)cyclohexyl}-3-[(2-fluoropyridin-4-yl)amino]-1H-pyrazole-4-carboxamide;
1-{4-[(2-chlorobenzyl)amino]-1-(cyanomethyl)cyclohexyl}-3-[(2-fluoropyridin-4-yl)amino]-1H-pyrazole-4-carboxamide;
1-{1-(cyanomethyl)-4-[(2-fluorobenzyl)amino]cyclohexyl}-3-[(2-fluoropyridin-4-yl)amino]-1H-pyrazole-4-carboxamide;
1-{1-(cyanomethyl)-4-[(4-fluorobenzyl)amino]cyclohexyl}-3-[(2-fluoropyridin-4-yl)amino]-1H-pyrazole-4-carboxamide;
1-{1-(cyanomethyl)-4-[(pyridin-4-ylmethyl)amino]cyclohexyl}-3-[(2-fluoropyridin-4-yl)amino]-1H-pyrazole-4-carboxamide;
1-{4-[(3-cyanobenzyl)amino]-1-(cyanomethyl)cyclohexyl}-3-[(2-fluoropyridin-4-yl)amino]-1H-pyrazole-4-carboxamide;
1-{4-[(4-chlorobenzyl)amino]-1-(cyanomethyl)cyclohexyl}-3-[(2-fluoropyridin-4-yl)amino]-1H-pyrazole-4-carboxamide;
1-{4-[(2-chlorobenzyl)amino]-1-(cyanomethyl)cyclohexyl}-3-[(2-fluoropyridin-4-yl)amino]-1H-pyrazole-4-carboxamide;
1-{1-(cyanomethyl)-4-[(pyridin-2-ylmethyl)amino]cyclohexyl}-3-[(2-fluoropyridin-4-yl)amino]-1H-pyrazole-4-carboxamide;
1-[4-(benzylamino)-1-(cyanomethyl)cyclohexyl]-3-[(2-fluoropyridin-4-yl)amino]-1H-pyrazole-4-carboxamide;
1-{1-(cyanomethyl)-4-[(3-fluorobenzyl)amino]cyclohexyl}-3-[(2-fluoropyridin-4-yl)amino]-1H-pyrazole-4-carboxamide;
1-{4-[(3-chlorobenzyl)amino]-1-(cyanomethyl)cyclohexyl}-3-[(2-fluoropyridin-4-yl)amino]-1H-pyrazole-4-carboxamide;
1-{1-(cyanomethyl)-4-[(2-fluorobenzyl)amino]cyclohexyl}-3-[(2-fluoropyridin-4-yl)amino]-1H-pyrazole-4-carboxamide;

1-{1-(cyanomethyl)-4-[(pyridin-3-ylmethyl)amino]cyclohexyl}-3-[(2-fluoropyridin-4-yl)amino]-1H-pyrazole-4-carboxamide;
1-{4-[(3-chlorobenzyl)amino]-1-(cyanomethyl)cyclohexyl}-3-[(2-fluoropyridin-4-yl)amino]-1H-pyrazole-4-carboxamide;
1-{1-(cyanomethyl)-4-[(3-fluorobenzyl)amino]cyclohexyl}-3-[(2-fluoropyridin-4-yl)amino]-1H-pyrazole-4-carboxamide;
1-{1-(cyanomethyl)-4-[(4-fluorobenzyl)amino]cyclohexyl}-3-[(2-fluoropyridin-4-yl)amino]-1H-pyrazole-4-carboxamide;
1-{1-(cyanomethyl)-4-[(4-hydroxybenzyl)amino]cyclohexyl}-3-[(2-fluoropyridin-4-yl)amino]-1H-pyrazole-4-carboxamide;
1-{4-[(2-cyanobenzyl)amino]-1-(cyanomethyl)cyclohexyl}-3-[(2-fluoropyridin-4-yl)amino]-1H-pyrazole-4-carboxamide;
1-[4-(benzylamino)-1-(cyanomethyl)cyclohexyl]-3-[(2-fluoropyridin-4-yl)amino]-1H-pyrazole-4-carboxamide;
1-(1-(Cyanomethyl)-4-(3-fluorophenylsulfonamido)cyclohexyl)-3-((2-fluoropyridin-4-yl)amino)-1H-pyrazole-4-carboxamide;
1-(4-(Cyanomethyl)-1-(2,2-difluoropropanoyl)-3-fluoropiperidin-4-yl)-3-((6-fluoropyridin-3-yl)amino)-1H-pyrazole-4-carboxamide;
1-(4-(cyanomethyl)-1-(2,2-difluoropropanoyl)-3-fluoropiperidin-4-yl)-3-((6-fluoropyridin-3-yl)amino)-1H-pyrazole-4-carboxamide;
1-(4-(cyanomethyl)-1-(2,2-difluoropropanoyl)-3-fluoropiperidin-4-yl)-3-((6-fluoropyridin-3-yl)amino)-1H-pyrazole-4-carboxamide;
1-[1-(cyanomethyl)-4-(4-cyclopropyl-1H-1,2,3-triazol-1-yl)cyclohexyl]-3-[(4-fluorophenyl)amino]-1H-pyrazole-4-carboxamide;
1-{1-(cyanomethyl)-4-[(2,2,2-trifluoroethyl)carbamoyl]cyclohexyl}-3-(phenylamino)-1H-pyrazole-4-carboxamide;
2,2-Difluoroethyl 4-(4-carbamoyl-3 ((2-fluoropyridin-4-yl)amino)-1H-pyrazol-1-yl)-4-(cyanomethyl)-3-fluoropiperidine-1-carboxylate;
1-(4-amino-1-(cyanomethyl)cyclohexyl)-3-((2-fluoropyridin-4-yl)amino)-1H-pyrazole-4-carboxamide;
4-amino-1-(cyanomethyl)cyclohexyl)-3-((4-((difluoromethyl)sulfonyl)phenyl)amino)-1H-pyrazole-4-carboxamide;
tert-butyl-4-{4-carbamoyl-3-[(4-fluorophenyl)amino]-1H-pyrazol-1-yl}-4-(cyanomethyl)-3-fluoropiperidine-1-carboxylate;
tert-butyl-4-[4-carbamoyl-3-(phenylamino)-1H-pyrazol-1-yl]-4-(cyanomethyl)-3-methylpiperidine-1-carboxylate;
tetrahydrofuran-3-yl 4-{4-carbamoyl-3-[(2-fluoropyridin-4-yl)amino]-1H-pyrazol-1-yl}-4-(cyanomethyl)piperidine-1-carboxylate; and
tetrahydrofuran-3-yl 4-{4-carbamoyl-3-[(4-fluorophenyl)amino]-1H-pyrazol-1-yl}-4-(cyanomethyl)piperidine-1-carboxylate.

In one embodiment of the invention, representative compounds include, but are not limited to the following compounds and their pharmaceutically acceptable salts and stereoisomers thereof:
tert-Butyl 4-[4-carbamoyl-3-(phenylamino)-1H-pyrazol-1-yl]-4-(cyanomethyl)piperidine-1-carboxylate;
tert-Butyl-4-[4-carbamoyl-3-(phenylamino)-1H-pyrazol-1-yl]-4-(cyanomethyl)-3-methylpiperidine-1-carboxylate;
1-{4-(cyanomethyl)-1-[5-(trifluoromethyl)pyridin-3-yl]piperidin-4-yl}-3-[(4-fluorophenyl)amino]-1H-pyrazole-4-carboxamide;
1-[4-(cyanomethyl)-1-(4-methylphenyl)piperidin-4-yl]-3-[(4-fluorophenyl)amino]-1H-pyrazole-4-carboxamide;
tert-butyl-4-{4-carbamoyl-3-[(4-fluorophenyl)amino]-1H-pyrazol-1-yl}-4-(cyanomethyl)-3-fluoropiperidine-1-carboxylate;
tert-butyl-4-{4-carbamoyl-3-[(4-fluorophenyl)amino]-1H-pyrazol-1-yl}-4-(cyanomethyl)-3-fluoropiperidine-1-carboxylate;
tert-Butyl 4-{4-carbamoyl-3-[(2-fluoropyridin-4-yl)amino]-1H-pyrazol-1-yl}-4-(cyanomethyl)piperidine-1-carboxylate;
tert-butyl 4-{4-carbamoyl-3-[(2,6-dichloropyridin-4-yl)amino]-1H-pyrazol-1-yl}-4-(cyanomethyl)piperidine-1-carboxylate;
tert-Butyl 4-(4-carbamoyl-3-(pyrimidin-4-ylamino)-1H-pyrazol-1-yl)-4-(cyanomethyl)piperidine-1-carboxylate;
[4-({1-[1-(tert-Butoxycarbonyl)-4-(cyanomethyl)piperidin-4-yl]-4-carbamoyl-1H-pyrazol-3-yl}amino)phenyl]acetic acid;
1-{1-[4-(acetylamino)benzyl]-4-(cyanomethyl)piperidin-4-yl}-3-(phenylamino)-1H-pyrazole-4-carboxamide;
1-[4-(cyanomethyl)-1-(cyclohexylmethyl)piperidin-4-yl]-3-[(2-fluoropyridin-4-yl)amino]-1H-pyrazole-4-carboxamide;
1-[4-(cyanomethyl)-1-(2-fluorobenzyl)piperidin-4-yl]-3-[(2-fluoropyridin-4-yl)amino]-1H-pyrazole-4-carboxamide;
1-{4-(cyanomethyl)-1-[(5-fluoropyridin-3-yl)methyl]piperidin-4-yl}-3-[(2-fluoropyridin-4-yl)amino]-1H-pyrazole-4-carboxamide;
1-[4-(Cyanomethyl)-1-pyrimidin-4-ylpiperidin-4-yl]-3-[(4-fluorophenyl)amino]-1H-pyrazole-4-carboxamide;
2,2,2-Trifluoroethyl 4-{4-carbamoyl-3-[(2-fluoropyridin-4-yl)amino]-1H-pyrazol-1-yl}-4-(cyanomethyl)piperidine-1-carboxylate;
2,2-difluoroethyl 4-(4-carbamoyl-3-(4-fluorophenylamino)-1H-pyrazol-1-yl)-4-(cyanomethyl)piperidine-1-carboxylate;
2,2-difluoroethyl 4-(4-carbamoyl-3-(2-fluoropyridin-4-ylamino)-1H-pyrazol-1-yl)-4-(cyanomethyl)piperidine-1-carboxylate;
cyclopropylmethyl 4-{4-carbamoyl-3-[(2-fluoropyridin-4-yl)amino]-1H-pyrazol-1-yl}-4-(cyanomethyl)piperidine-1-carboxylate;
1-cyclopropylethyl 4-{4-carbamoyl-3-[(2-fluoropyridin-4-yl)amino]-1H-pyrazol-1-yl}-4-(cyanomethyl)piperidine-1-carboxylate;
1-[4-(cyanomethyl)-1-[4-(trifluoromethyl)phenyl]acetyl piperidin-4-yl]-3-(phenylamino)-1H-pyrazole-4-carboxamide;
1-(4-(cyanomethyl)-1-(3,3,3-trifluoropropanoyl)piperidin-4-yl)-3-(4-fluorophenylamino)-1H-pyrazole-4-carboxamide;
1-(4-(cyanomethyl)-1-(3,3,3-trifluoropropanoyl)piperidin-4-yl)-3-(2-fluoropyridin-4-ylamino)-1H-pyrazole-4-carboxamide;
3-((4-chlorophenyl)amino)-1-(1-(cyanomethyl)-4-(3-fluoroazetidin-1-yl)cyclohexyl)-1H-pyrazole-4-carboxamide;
1-[1-(cyanomethyl)-4-(3-fluoroazetidin-1-yl)cyclohexyl]-3-{[4-(trifluoromethyl)phenyl]amino}-1H-pyrazole-4-carboxamide;
1-[1-(cyanomethyl)-4-(cyclohexylamino)cyclohexyl]-3-[(2-fluoropyridin-4-yl)amino]-1H-pyrazole-4-carboxamide;
1-{4-[(3-chlorophenyl)amino]-1-(cyanomethyl)cyclohexyl}-3-[(4-fluorophenyl)amino]-1H-pyrazole-4-carboxamide;

1-{1-(cyanomethyl)-4-[(cyclohexylmethyl)amino]cyclohexyl}-3-[(2-fluoropyridin-4-yl)amino]-1H-pyrazole-4-carboxamide; and 2,2-Difluoroethyl 4-(4-carbamoyl-3-((2-fluoropyridin-4-yl)amino)-1H-pyrazol-1-yl)-4-(cyanomethyl)-3-fluoropiperidine-1-carboxylate.

The invention also encompasses pharmaceutical compositions containing a compound of formula I, and methods for treatment or prevention of JAK mediated diseases using compounds of formula I.

The invention is described using the following definitions unless otherwise indicated.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

"Acyl" means a C(O)R radical Where R is optionally substituted alkyl, alkenyl, cycloalkyl, heterocycloalkyl, aryl heteroaryl, etc.

"Acylamino" means a NRR' radical where R is H, OH, or alkoxy and R' is acyl, as defined herein.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like.

The term "heteroalkyl" refers to an alkyl group where 1, 2, or 3 of the carbon atoms is substituted by a heteroatom independently selected from N, O, or S.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$ alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

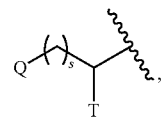

wherein s is an integer equal to zero, 1 or 2, the structure is

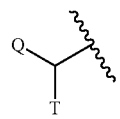

when s is zero.

The term "$C_{3-8}$cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

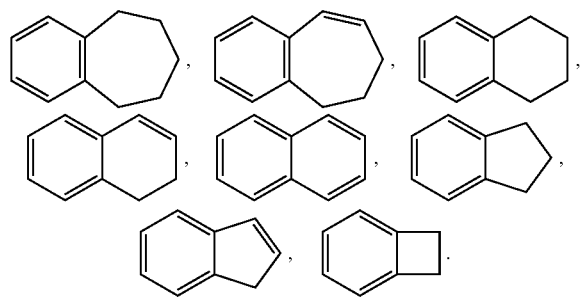

"Cyanoalkyl" refers to an alkyl group as described above in which one hydrogen atom has been replaced by a cyano group. Examples include $CH_2CN$, $CH_2CH_2CN$ and $CH(CN)CH_3$.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$haloalkyl, for example, includes —$CF_3$, —$CF_2CF_3$, $CHFCH_3$, and the like.

"Heterocycle", "heterocyclic" or "heterocyclyl" represents a monocyclic or bicyclic 3-12 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point(s) of attachment to the rest of the molecule may be on either ring. "Heterocyclyl" therefore includes heteroaryls, as well as dihydro and tetrahydro analogs thereof. Attachment of a heterocyclyl substituent can occur via a carbon atom or via a heteroatom.

Examples of heterocycles (heterocyclyl) include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Saturated heterocyclics form a subset of the heterocycles; i.e., the terms "saturated heterocyclic and $(C_{3-12})$heterocycloalkyl" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl)

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsaturated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-c]-pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

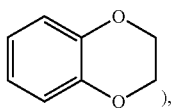

imidazo(2,1-b)(1,3)thiazole. (i.e.,

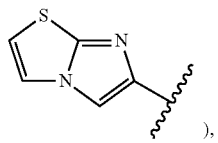 [SMILES: *c1cn2ccsc2n1]

and benzo-1,3-dioxolyl (i.e.,

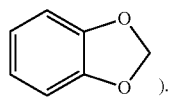

In certain contexts herein,

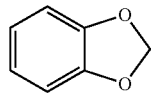

is alternatively referred to as phenyl having as a substituent methylenedioxy attached to two adjacent carbon atoms.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

Structural representations of compounds having substituents terminating with a methyl group may display the terminal methyl group either using the characters "$CH_3$", e.g. "—$CH_3$" or using a straight line representing the presence of the methyl group, e.g. "———", i.e.,

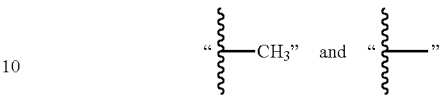

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

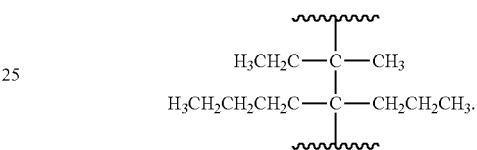

In one embodiment of the invention, $R^a$ is hydrogen or methyl. In a variant of this embodiment, $R^a$ is hydrogen.

In one embodiment of the invention $R^4$ is hydrogen or methyl. In a variant of this embodiment, $R^4$ is hydrogen. In another embodiment $R^4$ is methyl.

In one embodiment, p is 2 or 3.

In one embodiment, $R^3$ and $R^7$ are each independently selected from hydrogen, halogen, $C_{1-10}$ alkyl, and $C_{3-8}$cycloalkyl$C_{0-10}$ alkyl.

In a further embodiment, $R^2$ and $R^7$ are each independently selected from hydrogen, $C_{3-8}$ cycloalkyl$C_{0-10}$ alkyl, and $C_{1-10}$ alkyl. In one embodiment of the invention, $R^3$ and $R^7$ are each independently selected from hydrogen, ethyl, propyl, butyl, pentyl, methyl, cyclopropyl, cyclobutyl, cyclopentyl or cyclohexyl. In a variant of this embodiment, $R^3$ and $R^7$ are each independently selected from hydrogen, cyclopropyl, or methyl. In another variant, $R^3$ is hydrogen.

In one embodiment A is selected from: furanyl, thienyl, pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, quinoxalinyl, quinazolinyl, benzoxazolyl, benzisoxazolyl, 5,6,7,8-tetrahydroquinolinyl, imidazo[1,2-c]pyridinyl, imidazo[1,2-c]pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridinyl, thienopyridinyl, benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl, imidazo(2,1-b)(1,3)thiazole, and benzo-1,3-dioxolyl, phenyl, indenyl, and naphthyl.

In one embodiment, A is selected from phenyl, pyridinyl, pyrazinyl, pyridazinyl, pyrimidinyl, 2-3 dihydro-1H-isoindolyl, quinolinyl, isoquinolinyl, indolyl, and isoindolyl.

In one embodiment, A is selected from phenyl, pyridinyl, pyrazinyl, pyridazinyl, pyrimidinyl, and 2-3 dihydro-1H-isoindolyl.

In one embodiment, X is selected from N and C. In another embodiment, X is selected from O and S.

In one embodiment, $R^{5a}$ is selected from: halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, $C_{2-10}$ alkenyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, aryl $C_{2-10}$ alkenyl(oxy)$_{0-1}$(carbonyl)$_{0-1}C_{0-10}$ alkyl, aryl $C_{2-10}$ alkynyl(oxy)$_{0-1}$(carbonyl)$_{0-1}C_{0-10}$ alkyl, $C_{3-8}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$(carbonyl)$_{0-1}C_{0-10}$ alkyl, $(C_{3-8})$heterocycloalkyl $C_{0-10}$ alkyl(oxy)$_{0-1}$(carbonyl)$_{0-1}C_{0-10}$ alkyl, $C_{1-10}$ alkyl(carbonyl)$_{0-1}$oxy$C_{0-10}$ alkyl, $C_{1-10}$ heteroalkyl(carbonyl)$_{0-1}$oxy$C_{0-10}$ alkyl, $((C_{0-10})$alkyl)$_{1-2}$aminocarbonyloxy, $(C_{0-10})$heteroalkylaminocarbonyloxy, $C_{0-10}$ alkylamino(oxy)$_{0-1}$carbonyl$C_{0-10}$ alkyl, $(C_{0-10})$heteroalkylamino(oxy)$_{0-1}$carbonyl$C_{0-10}$ alkyl, $C_{3-8}$ cycloalkyl $C_{0-10}$ alkylamino(oxy)$_{0-1}$carbonyl$C_{0-10}$ alkyl, aryl $C_{0-10}$alkylamino(oxy)$_{0-1}$carbonyl$C_{0-10}$ alkyl, heteroaryl$C_{0-10}$alkylamino(oxy)$_{0-1}$carbonyl$C_{0-10}$ alkyl, $(C_{3-8})$heterocycloalkyl$C_{0-10}$ alkylamino(oxy)$_{0-1}$carbonyl $C_{0-10}$ alkyl, $C_{1-10}$ alkyl(oxy)$_{0-1}$(carbonyl)$_{0-1}$amino$C_{0-10}$ alkyl, $C_{1-10}$ heteroalkyl(oxy)$_{0-1}$(carbonyl)$_{0-1}$amino$C_{0-10}$ alkyl, —$CO_2(C_{0-10}$ alkyl), —$(C_{0-10}$ alkyl)$CO_2H$, Oxo (=O); $C_{1-10}$ alkylsulfonyl, $C_{1-10}$ heteroalkylsulfonyl, $(C_{3-8})$ cycloalkylsulfonyl, $(C_{3-8})$ cycloheteroalkylsulfonyl, heteroarylsulfonyl, arylsulfonyl, aminosulfonyl, —$SO_2N(C_{1-6}$alkyl)$_{1-2}$, —$SO_2C_{1-6}$alkyl, —$SO_2CF_3$, —$SO_2CF_2H$, —$Si(CH_3)_3$, $(C_{0-10}$ alkyl)$_{1-2}$ amino, hydroxy, $(C_{1-10}$ alkyl)OH, $C_{0-10}$ alkylalkoxy, cyano, $(C_{1-6}$alkyl)cyano, and $C_{1-6}$haloalkyl; wherein two $R^{5a}$ and the atom to which they are attached may optionally form a −4, −5, or −6 member saturated ring system and wherein $R^{5a}$ is each optionally substituted with 1, 2, 3, or 4 $R^6$ substituents.

In another embodiment, $R^{5a}$ is selected from: halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, $C_{2-10}$ alkenyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, aryl $C_{2-10}$ alkenyl(oxy)$_{0-1}$(carbonyl)$_{0-1}C_{0-10}$ alkyl, aryl $C_{2-10}$ alkynyl(oxy)$_{0-1}$(carbonyl)$_{0-1}C_{0-10}$ alkyl, $C_{3-8}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$(carbonyl)$_{0-1}C_{0-10}$ alkyl, $(C_{3-8})$heterocycloalkyl $C_{0-10}$ alkyl(oxy)$_{0-1}$(carbonyl)$_{0-1}C_{0-10}$ alkyl, $C_{1-10}$ alkyl(carbonyl)$_{0-1}$oxy$C_{0-10}$ alkyl, $C_{1-10}$ heteroalkyl(carbonyl)$_{0-1}$oxy$C_{0-10}$ alkyl, $C_{0-10}$ alkylamino(oxy)$_{0-1}$carbonyl$C_{0-10}$ alkyl, $(C_{0-10})$heteroalkylamino(oxy)$_{0-1}$carbonyl $C_{0-10}$ alkyl, $C_{3-8}$cycloalkyl $C_{0-10}$ alkylamino(oxy)$_{0-1}$carbonyl$C_{0-10}$ alkyl, aryl $C_{0-10}$alkylamino(oxy)$_{0-1}$carbonyl$C_{0-10}$ alkyl, heteroaryl$C_{0-10}$alkylamino(oxy)$_{0-1}$carbonyl$C_{0-10}$ alkyl, $(C_{3-8})$heterocycloalkyl$C_{0-10}$alkylamino(oxy)$_{0-1}$carbonyl$C_{0-10}$ alkyl, —$(C_{0-10}$ alkyl)$CO_2H$, Oxo (=O); $C_{1-10}$ alkylsulfonyl, $C_{1-10}$ heteroalkylsulfonyl, $(C_{3-8})$ cycloalkylsulfonyl, $(C_{3-8})$ cycloheteroalkylsulfonyl, heteroarylsulfonyl, arylsulfonyl, aminosulfonyl, —$SO_2N(C_{1-6}$alkyl)$_{1-2}$, —$SO_2C_{1-6}$alkyl, —$SO_2CF_3$, —$SO_2CF_2H$, $(C_{0-10}$ alkyl)$_{1-2}$ amino, hydroxy, $(C_{1-10}$ alkyl)OH, $C_{0-10}$ alkylalkoxy, cyano, $(C_{1-6}$alkyl)cyano, and $C_{1-6}$haloalkyl; wherein two $R^{5a}$ and the atom to which they are attached may optionally form a −4, −5, or −6 member saturated and wherein $R^{5a}$ is each optionally substituted with 1, 2, 3, or 4 $R^6$ substituents In one embodiment, $R^{5a}$ is independently selected from: tert-butyloxycarbonyl, fluoro, ethoxy, methoxy, methylsulfonyl, oxo, methoxycarbonyl, (methylamino)carbonyl, cyano, 2-hydroxypropanyl, hydroxyethyl, acetyl, methylcarbonyl, trifluoromethylcabonyl, methyl, pyrazolyl, amino, (trifluoromethyl)sulfonyl, (difluoromethyl)sulfonyl, hydroxymethyl, sulfamoyl, dimethylsulfamoyl, dimethylaminocarbonyl, trifluoromethyl, morpholinylcarbonyl, aminocarbonyl, chloro, 1,2,4-oxadiazolyl, cyclobutyloxy, ethoxycarbonyl, cyclopropyl, hydroxypropanyl, trifluoroethyl, bromo, methoxyoxoethyl, morpholinyl, isoxazolyl, phenyl, naphthalenyl, methylCOOH, trifluoroethyl, pyridinylmethyl, benzyl, cyanopropyl, napthalenylmethyl, cyclohexylmethyl, 1,3-benzodioxolylmethyl, propyl, methylsulfonyl, (2E)-3-phenylprop-2-enyl, benzofuranylmethyl, phenylprop-2-ynyl, imidazolylmethyl, pyrazolylmethyl, imidazo[I,2-a]pyridinylmethyl, pyrazinylmethyl, thiazoylmethyl, 1,3-thiazoylmethyl, tetrahydro-2H-pyranylmethyl, pyrazolo[1,5-a]pyridinylmethyl, pyrrolo[2,3-b]pyridinylmethyl, furanylmethyl, indolylmethyl, cyclobutylmethyl, 1,3-oxazolylmethyl, isoxazolymethyl, benzimidazolylmethyl, 4,5-dyhydroisoxazolylmethyl, phenylethyl, 1-phenylethyl, 2-fluoroethyl, methylsulfonyl, benzyloxycarbonyl, propyloxycarbonyl, cyclobutyloxycarbonyl, cyclobutylmethyloxycarbonyl, isopropyloxycarbonyl, tetrahydrofuranyloxycarbonyl, tetrahydropyranyloxycarbonyl, oxetanyloxycarbonyl, oxetanylmethyloxycarbonyl, propyloxycarbonyl, cyclopentyloxycarbonyl, cyclopropyloxycarbonyl, cyclohexyloxycarbonyl, 2,3-dihydro-1H-indenyloxycarbonyl, pyridinylmethyloxycarbonyl, morpholinylethyloxycarbonyl, piperidinyloxycarbonyl, piperazinylethyloxycarbonyl, piperidinylmethyloxycarbonyl, ethyloxycarbonyl, cyclopropylmethyloxycarbonyl, naphthalenylethyloxycarbonyl, phenylethyloxycarbonyl, ethyloxycarbonyl, pyrrolidinylethyloxycarbonyl, pyridinylethyloxycarbonyl, pyridinylpropyloxycarbonyl, cyclopropylethyloxycarbonyl, ethylcarbonyl, (2E)-prop-2-enylcarbonyl methylcarbonyl, tert-butylcarbonyl, butylcarbonyl, methylcarbonyl, tetrahydrofuranylcarbonyl, pyridinylcarbonyl, pyrazinylcarbonyl, isoxazolylcarbonyl, cyclohexylcarbonyl, thiophenylcarbonyl, pyrrolidinylmethylcarbonyl, (1E)-ethylenylcarbonyl, phenylcarbonyl, indolylcarbonyl, benzylcarbonyl, naphthalenylcarbonyl, quinolinylcarbonyl, methylcarbonyl, tetrahydrofuranylmethylcarbonyl, methylethylcarbonyl, pyrazolylcarbonyl, cyclobutylcarbonyl, dimethylpropylcarbonyl, isopropylsulfonyl, furanylsulfonyl, tert-butylsulfonyl, phenylsulfonyl, imidazolylsulfonyl, cyclopropylsulfonyl, naphthalenylsulfonyl, trifluoromethylsulfonyl, phenylaminocarbonyl, cyclohexylaminocarbonyl, methylethylaminocarbonyl, butylaminocarbonyl, ethylaminocarbonyl, (1,1,3,3,-tetramethylbutyl)aminocarbonyl, phenylethylaminocarbonyl, azetidinyl, cyclohexylamino; phenylamino, pyridinylamino, tetrahydro-2H-pyranylamino, difluoromethylsulfonyl, ethylamino, cyclopropylmethylamino, methylamino, benzylamino, amino, tert-butylcarbonyl, 1,2,3,-tiazolyl, and tetrahydrofuranyloxycarbonyl; wherein two $R^{5a}$ and the atom to which they are attached may optionally form a −4, −5, or −6 member saturated and wherein $R^{5a}$ is each optionally substituted with 1, 2, 3, or 4 $R^6$ substituents.

In one embodiment, $R^6$ is independently selected from: halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, $C_{2-10}$ alkenyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$alkyl, aryl $C_{2-10}$ alkenyl(oxy)$_{0-1}$(carbonyl)$_{0-1}C_{0-10}$ alkyl, aryl $C_{2-10}$ alkynyl(oxy)$_{0-1}$(carbonyl)$_{0-1}C_{0-10}$ alkyl, $C_{3-8}$ cycloalkyl $C_{0-10}$ alkyl(oxy)$_{0-1}$(carbonyl)$_{0-1}$C$_{0-10}$ alkyl, heteroaryl C$_{0-10}$ alkyl(oxy)$_{0-1}$(carbonyl)$_{0-1}$C$_{0-10}$ alkyl, (C$_{3-8}$)heterocycloalkyl C$_{0-10}$ alkyl (oxy)$_{0-1}$(carbonyl)$_{0-1}$C$_{0-10}$ alkyl, C$_{1-10}$ alkyl (carbonyl)$_{0-1}$oxyC$_{0-10}$ alkyl, C$_{2-10}$ alkenyl (carbonyl)$_{0-1}$oxyC$_{0-10}$ alkyl, C$_{1-10}$ heteroalkyl (carbonyl)$_{0-1}$oxyC$_{0-10}$ alkyl, ((C$_{0-10}$)alkyl)$_{1-2}$aminocarbonyloxy, C$_{1-10}$ alkylamino(oxy)$_{0-1}$ carbonylC$_{0-10}$ alkyl, C$_{1-10}$ alkyl(oxy)$_{0-1}$(carbonyl)$_{0-1}$aminoC$_{0-10}$ alkyl, —CO$_2$(C$_{0-10}$ alkyl), (C$_{3-8}$)heterocycloalkyl C$_{0-10}$ alkyl(oxy)$_{0-1}$ (carbonyl)$_{0-1}$aminoC$_{0-10}$ alkyl, —(C$_{0-10}$ alkyl)CO$_2$H, Oxo (═O), Sulfonyl, C$_{1-10}$ alkylsulfonyl, C$_{1-10}$ heteroalkylsulfonyl, (C$_{3-8}$)cycloalkylsulfonyl, (C$_{3-8}$)cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —SO$_2$CF$_2$H, C$_{1-10}$ alkylsulfinyl, amino, (C$_{0-10}$ alkyl)$_{1-2}$ amino, -(oxy)$_{0-1}$(carbonyl)$_{0-1}$N(C$_{0-10}$ alkyl)$_{1-2}$ C$_{1-4}$acylaminoC$_{0-10}$ alkyl, —Si(CH$_3$)$_3$, hydroxy, (C$_{1-10}$ alkyl)OH, C$_{1-10}$ alkoxy, cyano, and C$_{1-6}$ haloalkyl; wherein two R$^6$ and the atoms to which they are attached may optionally form a 3-, 4-, 5-, or 6-membered saturated ring system and R$^6$ is optionally substituted with 1, 2, or 3 substituents selected from hydrogen, hydroxy, (C$_{1-6}$)alkyl, (C$_{1-6}$)alkoxy, (C$_{1-10}$ alkyl)OH, halogen, CO$_2$H, —(C$_{0-6}$)alkylCN, —O(C═O)C$_1$-C$_6$ alkyl, NO$_2$, trifluoromethoxy, trifluoroethoxy, trifluoromethyl, trifluoroethyl, —N—C(O)O(C$_{0-6}$)alkyl, C$_{1-10}$ alkylsulfonyl, C$_{1-10}$ heteroalkylsulfonyl, oxo (O═), (C$_{3-8}$) cycloalkylsulfonyl, (C$_{3-8}$) cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —SO$_2$CF$_2$H, —C$_{1-10}$ alkylsulfinyl, —OSi(C$_{1-10}$alkyl)$_3$, —O$_{(0-1)}$(C$_{1-10}$)haloalkyl, amino(C$_{1-6}$alkyl)$_{0-2}$ and NH$_2$.

In another embodiment of the invention R$^6$ is independently selected from:

halogen, C$_{1-10}$ alkyl(oxy)$_{0-1}$(carbonyl)$_{0-1}$C$_{0-10}$ alkyl,

C$_{1-10}$ heteroalkyl(oxy)$_{0-1}$(carbonyl)$_{0-1}$C$_{0-10}$ alkyl, aryl C$_{0-10}$ alkyl(oxy)$_{0-1}$(carbonyl)$_{0-1}$C$_{0-10}$ alkyl, C$_{3-8}$ cycloalkyl C$_{0-10}$ alkyl(oxy)$_{0-1}$(carbonyl)$_{0-1}$C$_{0-10}$ alkyl, heteroaryl C$_{0-10}$ alkyl(oxy)$_{0-1}$(carbonyl)$_{0-1}$C$_{0-10}$ alkyl, (C$_{3-8}$)heterocycloalkyl C$_{0-10}$ alkyl(oxy)$_{0-1}$(carbonyl)$_{0-1}$C$_{0-10}$ alkyl, C$_{0-10}$ alkylamino(oxy)$_{0-1}$carbonylC$_{0-10}$ alkyl, C$_{1-10}$ alkyl(oxy)$_{0-1}$carbonylaminoC$_{0-10}$ alkyl, Oxo (═O), sulfonyl, arylsulfonyl, aminosulfonyl, —SO$_2$C$_{1-6}$alkyl, —SO$_2$CF$_3$, —SO$_2$CF$_2$H, —Si(CH$_3$)$_3$, (C$_{0-10}$ alkyl)$_{1-2}$ amino, hydroxy, C$_{1-10}$ alkoxy, (C$_{1-10}$ alkyl)cyano, cyano, and C$_{1-6}$haloalkyl; wherein two R$^6$ and the atoms to which they are attached may optionally form a 3-, 4-, 5-, or 6-membered saturated ring system, and R$^6$ is optionally substituted with 1, 2, or 3 substituents selected from hydrogen, hydroxy, (C$_{1-6}$)alkyl, (C$_{1-6}$)alkoxy, (C$_{1-10}$ alkyl)OH, halogen, CO$_2$H, —(C$_{0-6}$)alkylCN, —O(C═O)C$_1$-C$_6$ alkyl, NO$_2$, trifluoromethoxy, trifluoroethoxy, trifluoromethyl, trifluoroethyl, —N—C(O)O(C$_{0-6}$) alkyl, C$_{1-10}$ alkylsulfonyl, C$_{1-10}$ heteroalkylsulfonyl, oxo (O═), (C$_{3-8}$) cycloalkylsulfonyl, (C$_{3-8}$) cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —SO$_2$CF$_2$H, —C$_{1-10}$ alkylsulfinyl, —OSi(C$_{1-10}$alkyl)$_3$, —O$_{(0-1)}$(C$_{1-10}$)haloalkyl, amino(C$_{1-6}$alkyl)$_{0-2}$ and NH$_2$.

In one particular embodiment, R$^6$ is independently selected from: oxo, tert-butyloxycarbonyl, methoxy, methyl, 1-hydroxymethylethyl, trifluoromethyl, fluoro, hydroxy, trifluoroethyl, ethoxy, methylethoxy, cyano, methoxycarbonyl, chloro, hydroxymethyl, trimethylsilyl, trimethylsilyloxy, difluoromethyl, ethoxycarbonyl, dimethylamino, methylcarbonyl, acetylamino, propyl, isopropyl, pyridinyl, morpholinyl, phenyl, piperazinyl, methylsulfonyl, ethyl, acetyl, difluoromethylsulfonyl, methylsulfonyl, phenylsulfonyl, methylcarbonylamino, and R$^6$ is optionally substituted with 1, 2, or 3 substituents selected from hydrogen, hydroxy, (C$_{1-6}$)alkyl, (C$_{1-6}$)alkoxy, (C$_{1-10}$ alkyl)OH, halogen, CO$_2$H, —(C$_{0-6}$)alkylCN, —O(C═O)C$_1$-C$_6$ alkyl, NO$_2$, trifluoromethoxy, trifluoroethoxy, trifluoromethyl, trifluoroethyl, —N—C(O)O(C$_{0-6}$) alkyl, C$_{1-10}$ alkylsulfonyl, C$_{1-10}$ heteroalkylsulfonyl, oxo (O═), (C$_{3-8}$) cycloalkylsulfonyl, (C$_{3-8}$) cycloheteroalkylsulfonyl, heteroarylsulfonyl, arylsulfonyl, aminosulfonyl, —SO$_2$N(C$_{1-6}$ alkyl)$_{1-2}$, —SO$_2$C$_{1-6}$ alkyl, —SO$_2$CF$_3$, —SO$_2$CF$_2$H, —C$_{1-10}$ alkylsulfinyl, —OSi(C$_{1-10}$alkyl)$_3$, —O$_{(0-1)}$(C$_{1-10}$)haloalkyl, amino(C$_{1-6}$alkyl)$_{0-2}$ and NH$_2$.

In one embodiment, R$^6$ is optionally substituted with 1, 2, or 3 substituents selected from hydrogen, methyl, fluoro, trifluoromethyl, hydroxymethyl, oxo, hydroxy, and methoxy.

In one embodiment, the compounds of the instant invention are selective JAK1 inhibitors relative to JAK2. The determination of relative selectivity for a given compound of JAK1 inhibition is defined as the relative ratio of the (JAK2 IC$_{50}$ value/JAK1 IC$_{50}$ value) is at least 2. In yet another embodiment, for a given compound, the relative ratios of the (JAK2 IC$_{50}$ value/JAK1 IC$_{50}$ value) is at least 5.

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —(CR$^3$R$^3$)$_2$—, each occurrence of the two R$^3$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

Optical Isomers—Diastereomers—Geometric Isomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, 1-(2S,3S and 2R,3R)-3-cyclobutan-2-yl]-3-(phenylamino)-1H-pyrazole-4-carboxamide, the "and" indicates a racemic mixture of the enantiomers. That is, the individual enantiomers were not individually isolated.

When the stereomeric nomenclature includes "or", for example, 1-(2S,3S or 2R,3R)-3-cyclobutan-2-yl]-3-(phenylamino)-1H-pyrazole-4-carboxamide, the "or" indicates that chiral resolution of racemate into individual enantiomers was accomplished but the actual optical activity of the specific enantiomer was not determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, Ia, Ib, Ic, Id and Ie, subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compound of formula I or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as JAK1, JAK2, JAK3 or TYK2. Such conditions and diseases include, but are not limited to:

(1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK-mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a JAK-mediated diseases or disorder.

One aspect of the invention is the use of a compound of formula I or a pharmaceutically acceptable salt or a stereoisomer thereof in the manufacture of a medicament for the treatment of a disease or a disorder ameliorated by the selective inhibition of a Janus kinase JAK1 relative to JAK 2.

Another aspect of the invention is the use of a compound of Formula I or a pharmaceutically acceptable salt or a stereoisomer thereof and a second active agent in the manufacture of a medicament for the treatment of a disease or a disorder ameliorated by the selective inhibition of a Janus kinase JAK1 relative to JAK 2.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Dislchaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of JAK mediated diseases, compound of formula I may be co-administered with other therapeutic agents. Thus in another aspect the present invention provides pharmaceutical compositions for treating JAK mediated diseases comprising a therapeutically effective amount of a compound of formula I and one or more other therapeutic agents. In particular, for the treatment of the inflammatory diseases rheumatoid arthritis, psoriasis, inflammatory bowel disease, COPD, asthma and allergic rhinitis a compound of formula I may be combined with agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethyl-norepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

METHODS OF SYNTHESIS

Schemes and Examples

The abbreviations used herein have the following tabulated meanings. Abbreviations not tabulated below have their meanings as commonly used unless specifically stated otherwise.

| | |
|---|---|
| ACN | acetonitrile |
| MeCN | acetonitrile |
| BAST | bis(2-methoxyethyl)aminosulfur trifluoride |
| Chiral SFC | chiral super critical fluid chromatography |
| $CO_2$ | carbon dioxide |
| $Cs_2CO_3$ | cesium carbonate |
| DBU | 1,8-diazabicyclo[5.4.0]undec-7-ene |
| DCE | 1,2-dichloroethane |
| DCM | dichloromethane |
| DIPEA | N,N-diisopropylethylamine |
| DMF | N,N-dimethylformamide |
| DMSO | dimethyl sulfoxide |
| DSC | N,N-disuccinimidyl carbonate |
| EDC | 3-(ethyliminomethyleneamino)-N,N-dimethyl-propan-1-amine |
| EtOAc | ethyl acetate |
| HATU | O-(7-aza-1H-benzotriazol-1-yl)-N,N,N',N'-tetramethyluronium hexafluorophosphate |
| HCl | hydrogen chloride |
| HOBt | 1-hydroxybenzotriazole |
| HPLC | high pressure liquid chromatography |
| IPA | 2-propanol |
| LDA | lithium diisopropylamide |
| m-CPBA | meta-chloroperoxybenzoic acid |
| LRMS | low resolution mass spectrometry |
| MeI | iodomethane |
| Me—THF | 2-methyltetrahydrofuran |
| $MgSO_4$ | magnesium sulfate |
| $MP-(OAc)_3BH$ | solid supported (macro porous) triacetoxyborohydride |
| MPLC | medium pressure liquid chromatography |
| NaH | sodium hydride |
| $Na_2SO_4$ | sodium sulfate |
| NaBH4 | sodium borohydride |
| $NaHCO_3$ | sodium bicarbonate |
| NaOMe | sodium methoxide |
| $Pd_2(dba)_3$ | tris(dibenzylideneacetone)dipalladium(0) |
| $POCl_3$ | phosphorus (V) oxychloride |
| PyBOP | (7-azabenzotriazol-1-yloxy)tripyrrolidino-phosphonium hexafluorophosphate |
| SEM—Cl | 2-(trimethylsilyl)ethoxymethyl chloride |
| SiliaCat ® DPP—Pd | silica bound diphenylphosphine palladium (II) |
| TBAF | tetra-n-butylammonium fluoride |
| TBS—Cl | tert-butyldimethylsilyl chloride |
| t-BuOH | tert-butanol |
| TEA | triethylamine |
| TFA | trifluoroacetic acid |
| THF | tetrahydrofuran |
| X-Phos | 2-dicyclohexylphosphino-2',4',6'-triisopropylbiphenyl |
| $Me_4-^tBu$—X-Phos | di-tert-butyl[3,4,5,6-tetramethyl-2',4',6'-tri(propan-2-yl)biphenyl-2-yl]phosphane |
| NMO | 4-methylmorpholine N-oxide |
| TPAP | tetra-n-propylammonium perruthenate (VII) |
| HCOOH | formic acid |
| K$^t$OBu | potassium tert-butoxide |
| $Na_2S_2O_5$ | sodium metabisulfite |
| NMR | nuclear magnetic resonance |
| TLC | thin layer chromatography |
| $(EtO)_2P(O)CH_2CN$ | diethyl (cyanomethyl)phosphonate |
| MsCl | methanesulfonyl chloride |
| TsOH | p-toluenesulfonic acid |
| KCN | potassium cyanide |
| Si—DMT | silica supported Dimercaptotriazine |
| TMS | trimethylsilane |
| $CF_3TMS$ | (trifluoromethyl)trimethylsilane |

Alkyl Group Abbreviations

| | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |

| c-Pen | cyclopentyl |
| c-Hex | cyclohexyl |

METHODS OF SYNTHESIS

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:
All reactions were stirred (mechanically, stir bar/stir plate, or shaken) and conducted under an inert atmosphere of nitrogen or argon unless specifically stated otherwise.
All temperatures are degrees Celsius (° C.) unless otherwise noted.
Ambient temperature is 15-25° C.
Most compounds were purified by reverse-phase preparative HPLC, MPLC on silica gel, recrystallization and/or swish (suspension in a solvent followed by filtration of the solid).
The course of the reactions was followed by thin layer chromatography (TLC) and/or LCMS and/or NMR and reaction times are given for illustration only.
All end products were analyzed by NMR and LCMS.
Intermediates were analyzed by NMR and/or TLC and/or LCMS.

Method 1

General procedures to prepare intermediates of the instant invention are described in Scheme 1. Alkyl Grignard reagents are reacted with appropriately substituted (hetero)aryl carboxylates I at or around 0° C. in an appropriate solvent, such as THF, to afford intermediates II used in the synthesis of examples of the instant invention.

SCHEME 1

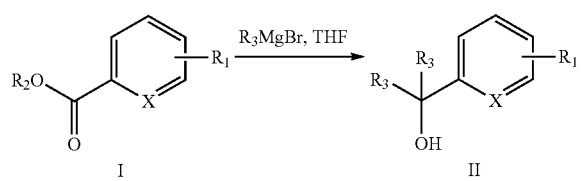

Method 2

General procedures to prepare intermediates of the instant invention are described in Scheme 2. A trifluoromethyl anion equivalent, such as $CF_3TMS$, is reacted with TBAF and an appropriately substituted (hetero)aryl aldehyde III in an appropriate solvent, such as THF, to yield intermediates IV used in the synthesis of examples of the instant invention.

SCHEME 2

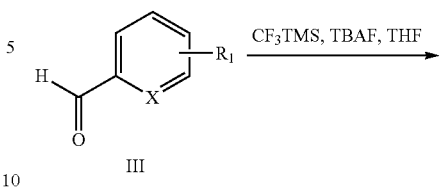

Method 3

General procedures to prepare intermediates of the instant invention are described in Scheme 3. Heteroaryl boronate esters or boronic acids VI are cross coupled to optionally substituted (hetero)aryl bromides V using a suitable palladium complex, such as $Pd(dppf)Cl_2$, and an appropriate base, such as $K_3PO_4$, in a compatible solvent or solvent mixture, such as 10:1 v:v dioxane:water, at or around 90° C. to yield intermediates VII in the synthesis of examples of the instant invention.

SCHEME 3

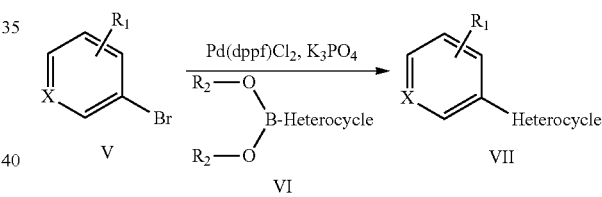

Method 4

General procedures to prepare intermediates of the instant invention are described in Scheme 4. Appropriately substituted benzyl bromides VIII can be reacted with aza heterocycles using a suitable base, such as potassium acetate, or be reacted with sodium azide followed by optionally substituted acetylenes and standard "Click chemistry" reagents to afford intermediates IX in the synthesis of examples of the instant invention.

SCHEME 4

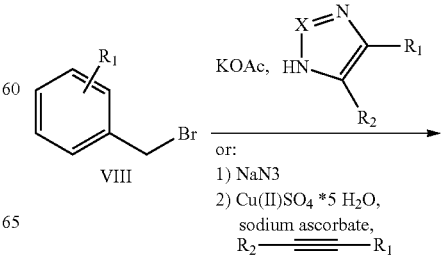

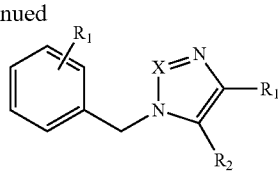

IX

Method 5

General procedures to prepare intermediates of the instant invention are described in Scheme 5. Appropriately substituted benzyl bromides X can be reacted with methyl hydroxy acetate in the presence of a suitable base, such as sodium hydride, and then further reacted with alkyl Grignard reagents to afford intermediates XI in the synthesis of examples of the instant invention.

SCHEME 5

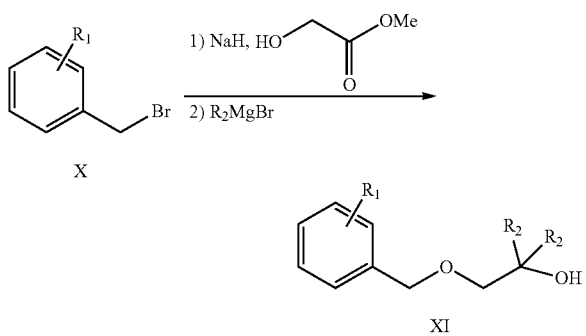

Method 6

General procedures to prepare intermediates of the instant invention are described in Scheme 6. Appropriately substituted thiophenols XII are reacted with a suitable base, such as sodium hydride, and a trifluoromethylating agent, such as 5-(trifluoromethyl)dibenzo[b,d]thiophenium trifluoromethanesulfonate at ambient temperature in an appropriate solvent, such as DMF. The resulting intermediate is oxidized to the corresponding sulfone XIII with a suitable oxidant, such as m-CPBA, to afford an intermediate used in the synthesis of examples of the instant invention.

SCHEME 6

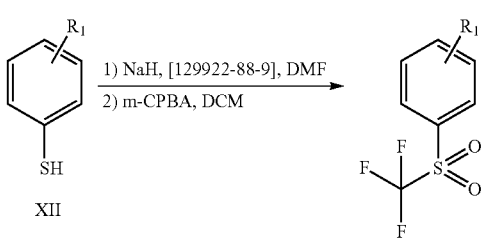

Method 7

General procedures to prepare intermediates of the instant invention are described in Scheme 7. Appropriately substituted thiophenols XII are reacted with a suitable base, such as potassium hydroxide, and a difluoromethylating agent, such as diethyl[bromo(difluoro)methyl]phosphonate, in an appropriate solvent or solvent mixture, such as 1:1 v:v MeCN:water. The resulting intermediate is oxidized to the corresponding sulfone XIV with a suitable oxidant, such as m-CPBA, to afford an intermediate used in the synthesis of examples of the instant invention.

SCHEME 7

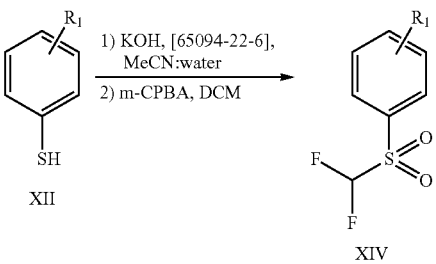

Method 8

General procedures to prepare intermediates of the instant invention are described in Scheme 8. Appropriately substituted aryl sulfoxides XV are reacted with a Lewis acid, such as zinc iodide, and a suitable nucleophilic fluorine source, such as BAST, in a solvent, such as 1,2-DCE, at or around 40° C. The resulting intermediate is oxidized to the corresponding sulfone XVI with a suitable oxidant, such as m-CPBA, to afford an intermediate used in the synthesis of examples of the instant invention.

SCHEME 8

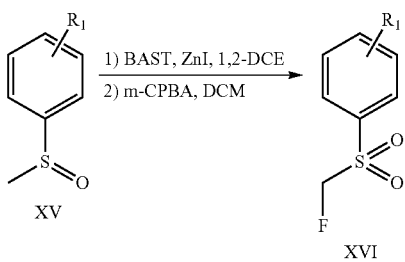

Method 9

General procedures to prepare intermediates of the instant invention are described in Scheme 9. Appropriately substituted benzothiophenes XVII are oxidized to the corresponding sulfones with a suitable oxidant, such as m-CPBA, and then hydroxylated upon stirring in aqueous sodium hydroxide at or around 100° C. to afford intermediates XVIII in the synthesis of examples of the instant invention.

SCHEME 9

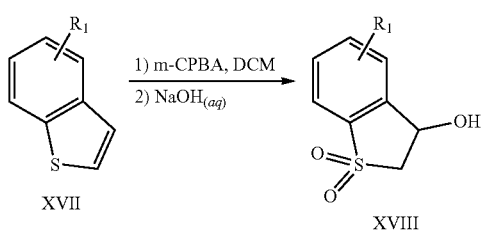

Method 10

General procedures to prepare intermediates of the instant invention are described in Scheme 10. Appropriately substituted 2,3-dihydro-1H-isoindol-ones XIX can be poly-methylated using a suitable base, such as sodium hydride, and methyl iodide to afford intermediates XX used in the synthesis of examples of the instant invention.

SCHEME 10

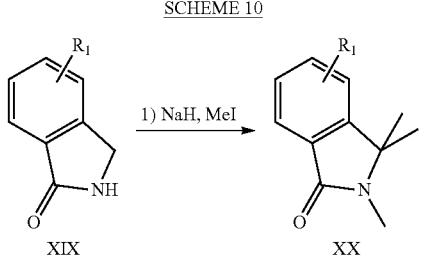

Method 11

General procedures to prepare intermediates of the instant invention are described in Scheme 11. Appropriately substituted 2,3-dihydro-1H-isoindol-ones XIX can be mono-alkylated using a suitable base, such as sodium hydride, and optionally substituted alkylating agents to afford intermediates XXI in the synthesis of examples of the instant invention.

SCHEME 11

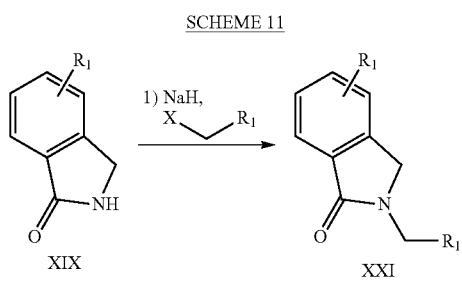

Method 12

General procedures to prepare intermediates of the instant invention are described in Scheme 12. Optionally substituted alkyl aldehydes XXII are condensed with diethyl (cyanomethyl)phosphonate in the presence of a suitable base, such as potassium tert-butoxide to yield substituted acrylonitriles XXIII used as intermediates in the synthesis of examples of the instant invention.

SCHEME 12

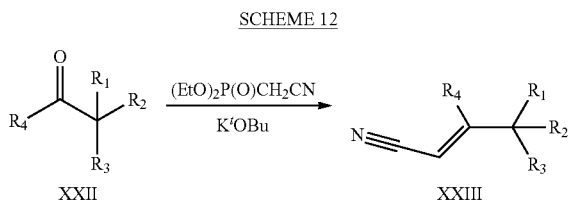

Method 13

General procedures to prepare intermediates of the instant invention are described in Scheme 13. Optionally substituted carbamate protected heterocyclic ketones XXIV are condensed with diethyl (cyanomethyl)phosphonate in the presence of a suitable base, such as potassium tert-butoxide, to yield optionally substituted acrylonitriles XXV used as intermediates in the synthesis of examples of the instant invention.

SCHEME 13

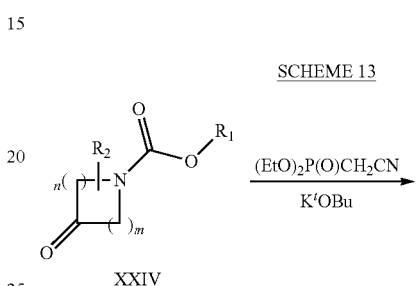

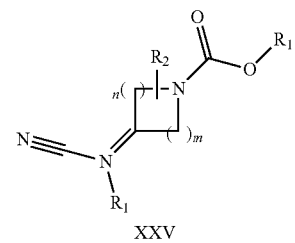

Method 14

General procedures to prepare intermediates of the instant invention are described in Scheme 14. Carbamate protected optionally substituted acrylonitriles XXV are deprotected in the presence of a suitable acid, such as TFA or HCl, to form amino intermediates XXVI that are further derivatized to form sulfonamide XXVII, urethane XXVIII, and N-arylated intermediates XXIX. Sulfonamide derivatives XXVII are formed by reacting deprotected optionally substituted acrylonitriles with optionally substituted sulfoyl chlorides in a suitable solvent, such as DCM, using an appropriate base, such as DIPEA. Urea derivatives XXVIII are formed by reacting deprotected optionally substituted acrylonitriles with a doubly activated carbonyl equivalent, such as DSC, and optionally substituted alcohols in the presence of a suitable base, such as TEA. N-arylated derivatives XXIX are formed by reacting deprotected optionally substituted acrylonitriles with optionally substituted aryl halides using a suitable palladium-ligand system, such as $Pd_2(dba)_3$ and X-Phos, an appropriate base, such as $Cs_2CO_3$, in a solvent, such as t-BuOH, at or around 90° C.

SCHEME 14

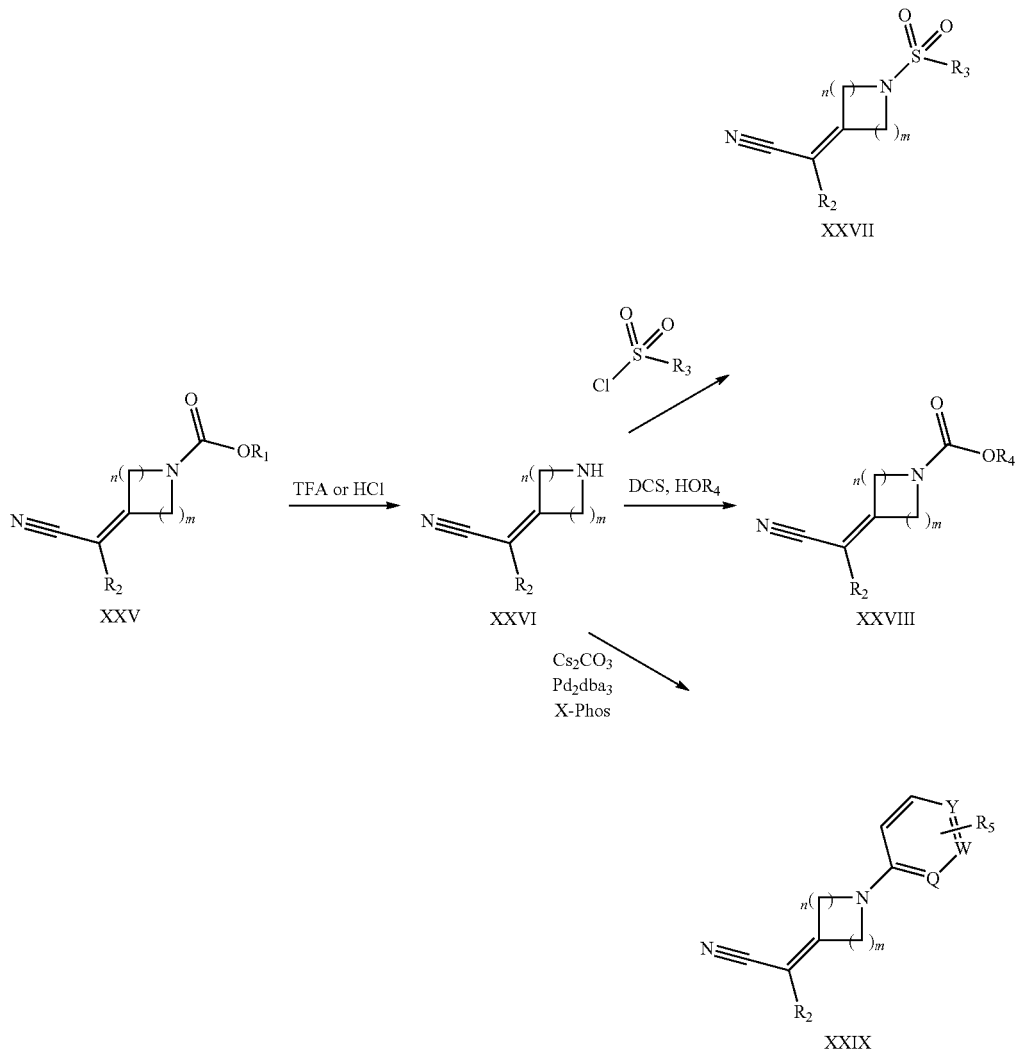

Method 15

General procedures to prepare intermediates of the instant invention are described in Scheme 15. Cyanohydrins XXXI of optionally substituted (hetero)cyclic ketones XXX are prepared using aqueous sodium metabisulfite, followed by the addition of a suitable cyanide source, such as potassium cyanide. Hydroxyl group activation with a suitable agent, such as mesyl chloride or $POCl_3$, followed by elimination under appropriate conditions, such as refluxing pyridine, yields substituted acrylonitriles XXXII used as intermediates in the synthesis of examples of the instant invention.

SCHEME 15

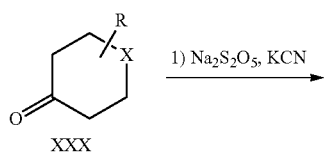

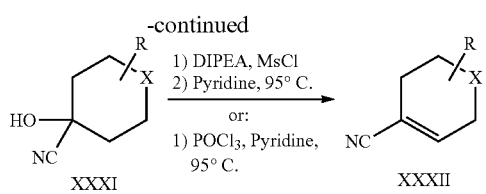

Method 16

General procedures to prepare intermediates of the instant invention are described in Scheme 16. Optionally substituted (hetero)cyclic ketones XXXIII are enolized with an appropriate base, such as LDA, and reacted with a suitable triflating agent, such as N-(5-chloropyridin-2-yl)-1,1,1-trifluoro-N-(trifluoromethylsulfonyl)methanesulfonamide. The resulting vinyl triflate XXXIV is reacted with a suitable palladium complex, such as tetrakis(triphenylphosphine) palladium (0), and an appropriate cyanide source, such as zinc cyanide, to afford substituted acrylonitriles XXXV used as intermediates in the synthesis of examples of the instant invention.

SCHEME 16

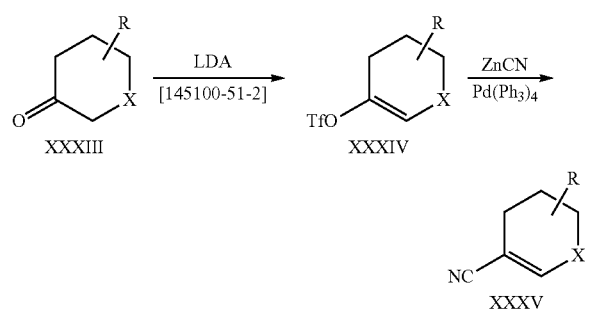

Method 17

General procedures to prepare intermediates of the instant invention are described in Scheme 17. Acrylonitrile is made to under go a Diels-Alder cyclization with an appropriately substituted butadiene using standard conditions, such as refluxing benzene. The cycloaddition product is deprotected with aqueous acid, such as 1N HCl, to provide substituted cyclohexenone XXXVI, which is then reacted with a suitable reductant, such as cerium (III) chloride and sodium borohydride, to afford intermediates XXXVII used in the synthesis of examples of the instant invention.

SCHEME 17

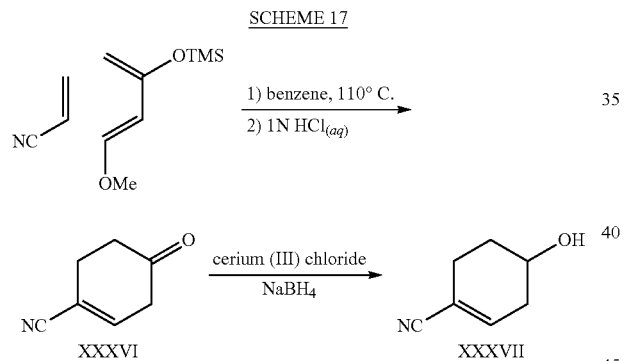

Method 18

General procedures to prepare intermediates of the instant invention are described in Scheme 18. 2-Chloroprop-2-enenitrile is reacted with benzene sulfinic acid sodium salt in aqueous acetic acid. The resulting olefin is regenerated by eliminating the chloro substituent with an appropriate base, such as TEA. The obtained acrylonitrile XXXVIII is made to undergo a Diels-Alder cyclization with an appropriately substituted butadiene using standard conditions, such as refluxing benzene, to yield a cyano benzosulfone substituted cyclohexanone XXXIX. This substituted cyclohexanone XXXIX is protected with ethylene glycol under acidic conditions, such as TsOH, in an appropriate solvent, such as benzene, at elevated temperatures, e.g. at or around 110° C. The acetal substituted acrylonitrile XL is obtained after elimination of the benzosulfone with an appropriate base, such as potassium tert-butoxide. This synthetic sequence affords intermediates used in the synthesis of examples of the instant invention.

SCHEME 18

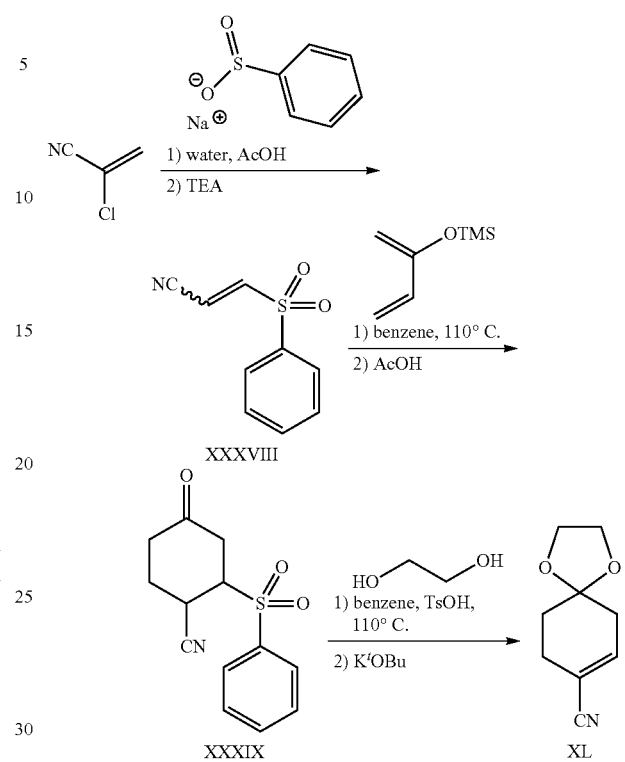

Method 19

General procedures to prepare intermediates of the instant invention are described in Scheme 19. 3-Amino pyrazole carboxamide XLI is cross coupled to (hetero)aryl halides XLII using a catalytic palladium-ligand system, such as $Pd_2(dba)_3$, and $Me_4$-$^tBu$-X-Phos, with a suitable base, such as $K_3PO_4$ or KOAc, in an appropriate solvent, such as 2-propanol, to yield pyrazole intermediates XLIII.

SCHEME 19

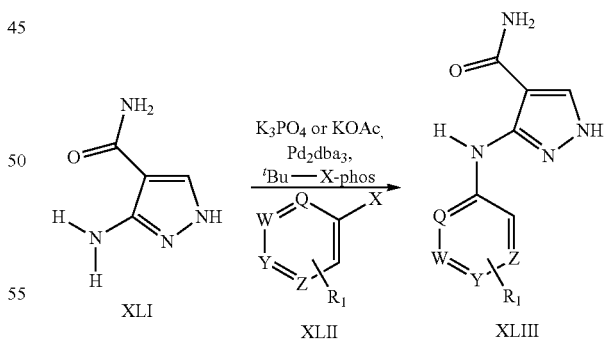

Method 20

General procedures to prepare intermediates of the instant invention are described in Scheme 20. 3-Amino-1H-pyrazole-4-carbonitrile XLIV is reacted with a suitable base, such as sodium hydride, and SEM-Cl to yield a mixture of 3-amino pyrazoles XLV and XLVI, which are arylated with an appropriately substituted halogenated (hetero)aromatic XLII using a suitable catalytic palladium-ligand system, such as $Pd_2(dba)_3$ and X-Phos, an appropriate base, such as $K_3PO_4$, in a suitable solvent, such as dioxane. The intermediate nitriles XLVII and XLVIII are oxidized to the corresponding amides using an appropriate oxidant, such as hydrogen peroxide mixed with sodium hydroxide, and the SEM group is then removed by acid hydrolysis to yield pyrazole XLIII, an intermediate in the synthesis of examples of the instant invention.

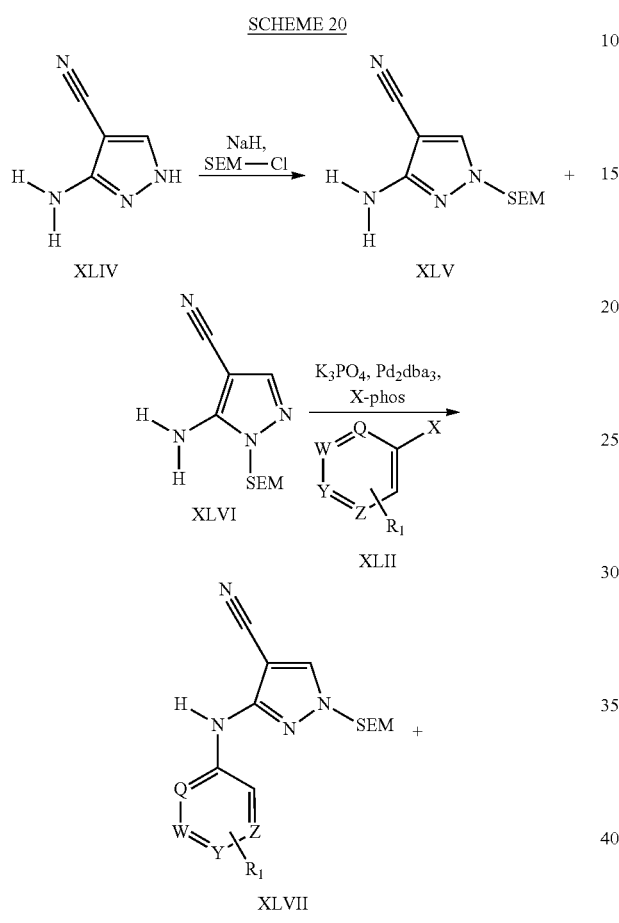

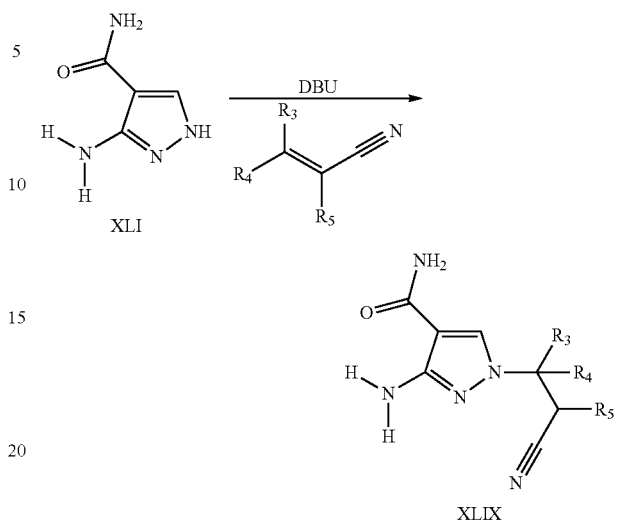

Method 21

General procedures to prepare intermediates of the instant invention are described in Scheme 21. Using an appropriate base, such as DBU, in a suitable solvent, such as MeCN, EtOH, or tert-BuOH, 3-amino pyrazole carboxamide XLI is conjugatively added to optionally substituted acrylonitriles, including but not limited to those illustrated in Schemes #12-18 to yield alkylated pyrazole carboxamide XLIX, an intermediate in the synthesis of examples of the instant invention.

Method 22

General procedures to prepare examples of the instant invention are described in Scheme 22. Methyl 5-amino-1H-pyrazole-4-carboxylate L is conjugatively added to substituted acrylonitriles including but not limited to those illustrated in Schemes #12-18 in the presence of a suitable base, such as catalytic sodium methoxide. The resulting intermediates LI are cross coupled to (hetero)aryl halides XLII using an appropriate catalytic palladium-ligand system, such as $Pd_2(dba)_3$ and X-Phos, and an appropriate base, such as $K_3PO_4$. Saponification of LII using aqueous hydroxide, such as LiOH, followed by amide formation using standard conditions, such as EDC, HOBT, and optionally substituted primary and secondary amines yields examples LIV of the instant invention.

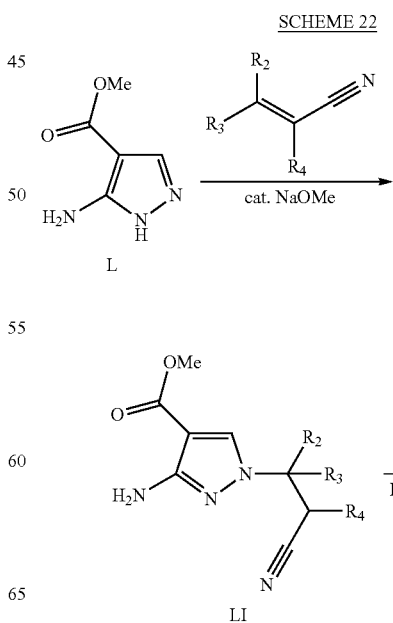

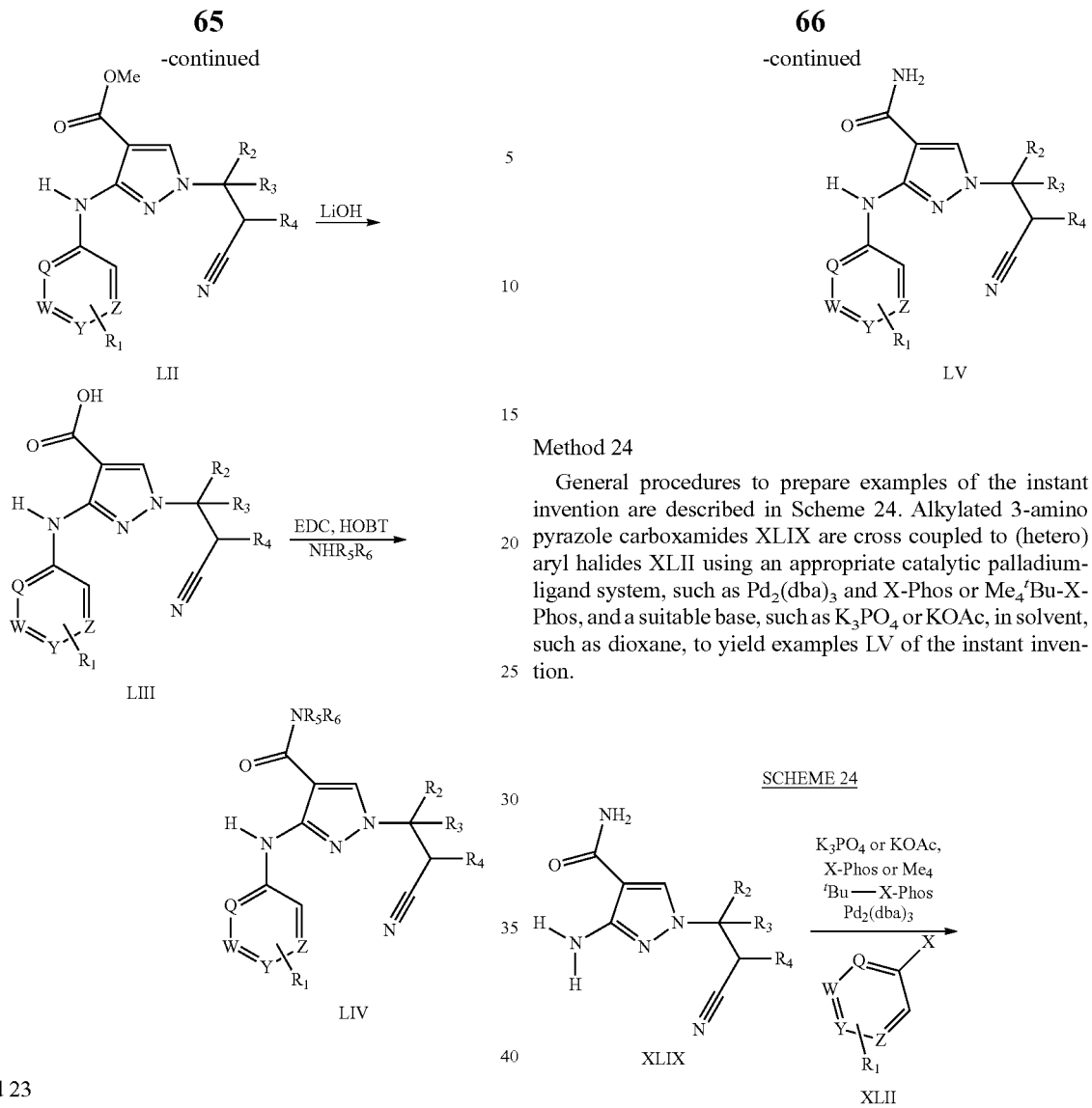

Method 24

General procedures to prepare examples of the instant invention are described in Scheme 24. Alkylated 3-amino pyrazole carboxamides XLIX are cross coupled to (hetero) aryl halides XLII using an appropriate catalytic palladium-ligand system, such as $Pd_2(dba)_3$ and X-Phos or $Me_4{}^tBu$-X-Phos, and a suitable base, such as $K_3PO_4$ or KOAc, in solvent, such as dioxane, to yield examples LV of the instant invention.

Method 23

General procedures to prepare examples of the instant invention are described in Scheme 23. Using an appropriate base, such as DBU, in a suitable solvent, such as MeCN, EtOH, or tert-BuOH, N-(hetero)arylated pyrazole carboxamides XLIII are conjugatively added to optionally substituted acrylonitriles, including but not limited to those illustrated in Schemes #12-18 to yield examples LV of the instant invention.

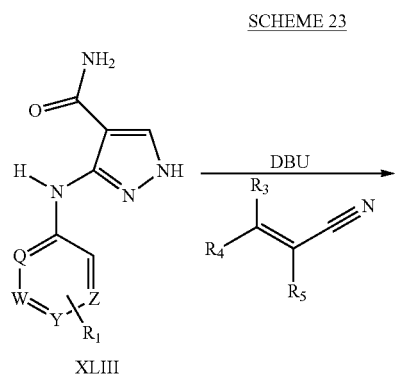

XLIII

Method 25

General procedures to prepare examples of the instant invention are described in Scheme 25. Using a solid supported palladium system, such as SiliaCat® DPP-Pd and a suitable base, such as, $K_2CO_3$, optionally substituted boronic acids LVII are cross coupled to bromophenyl substituted pyrazoles LVI to yield examples LVIII of the instant invention.

SCHEME 25

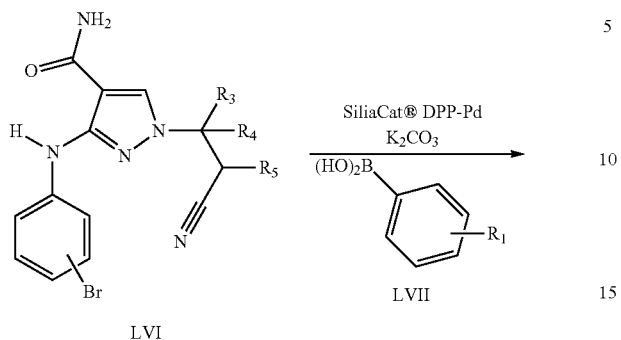

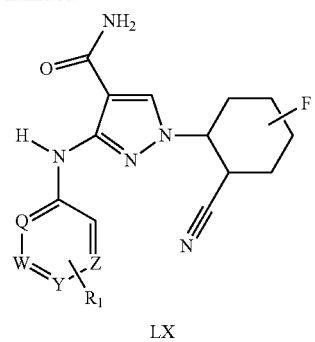

LX

Method 27

General procedures to prepare examples of the instant invention are described in Scheme 27. N-(hetero)arylated pyrazole carboxamides XLIII can be alkylated with optionally substituted alkyl halides LXI using heat and an appropriate base, such as $Cs_2CO_3$, to afford examples LXII of the instant invention.

SCHEME 27

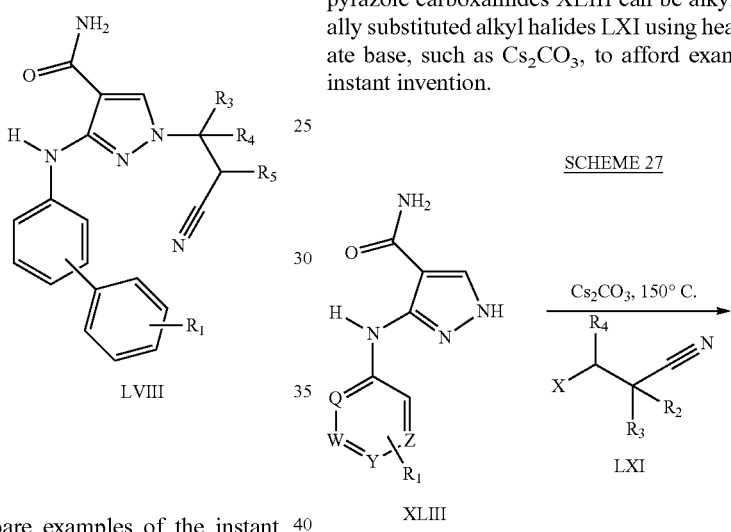

Method 26

General procedures to prepare examples of the instant invention are described in Scheme 26. Hydroxy substituted amino pyrazole carboxamides LIX can be fluorinated using a nucleophilic fluorine source, such as BAST, to afford examples LX of the instant invention.

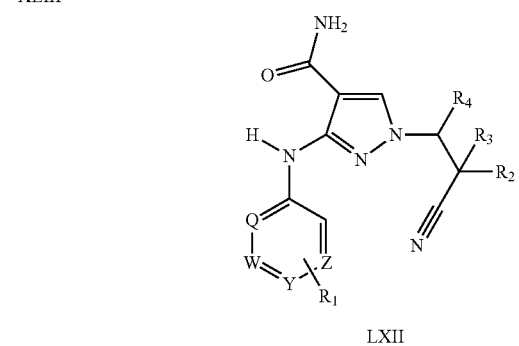

LXII

Method 28

General procedures to prepare examples of the instant invention are described in Scheme 28. Carbamate protected substituted amino pyrazole carboxamides LXII are deprotected in the presence of acid, such as TFA or HCl, to provide amino intermediates LXIV which are further derivatized using standard conditions known by those skilled in the art to yield examples of the instant invention. Examples include but are not limited to alkylated LXV, reductively aminated LXVI, and arylated LXVII derivatives, as well as carbamates LXVIII, ureas LXIX, amides LXX, and sulfonamides LXXI.

SCHEME 26

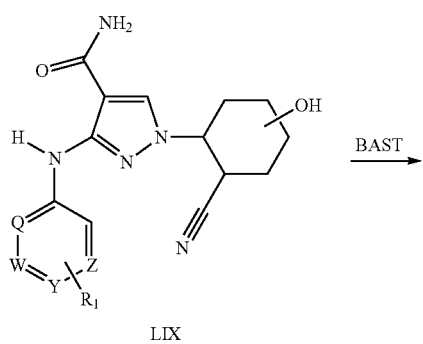

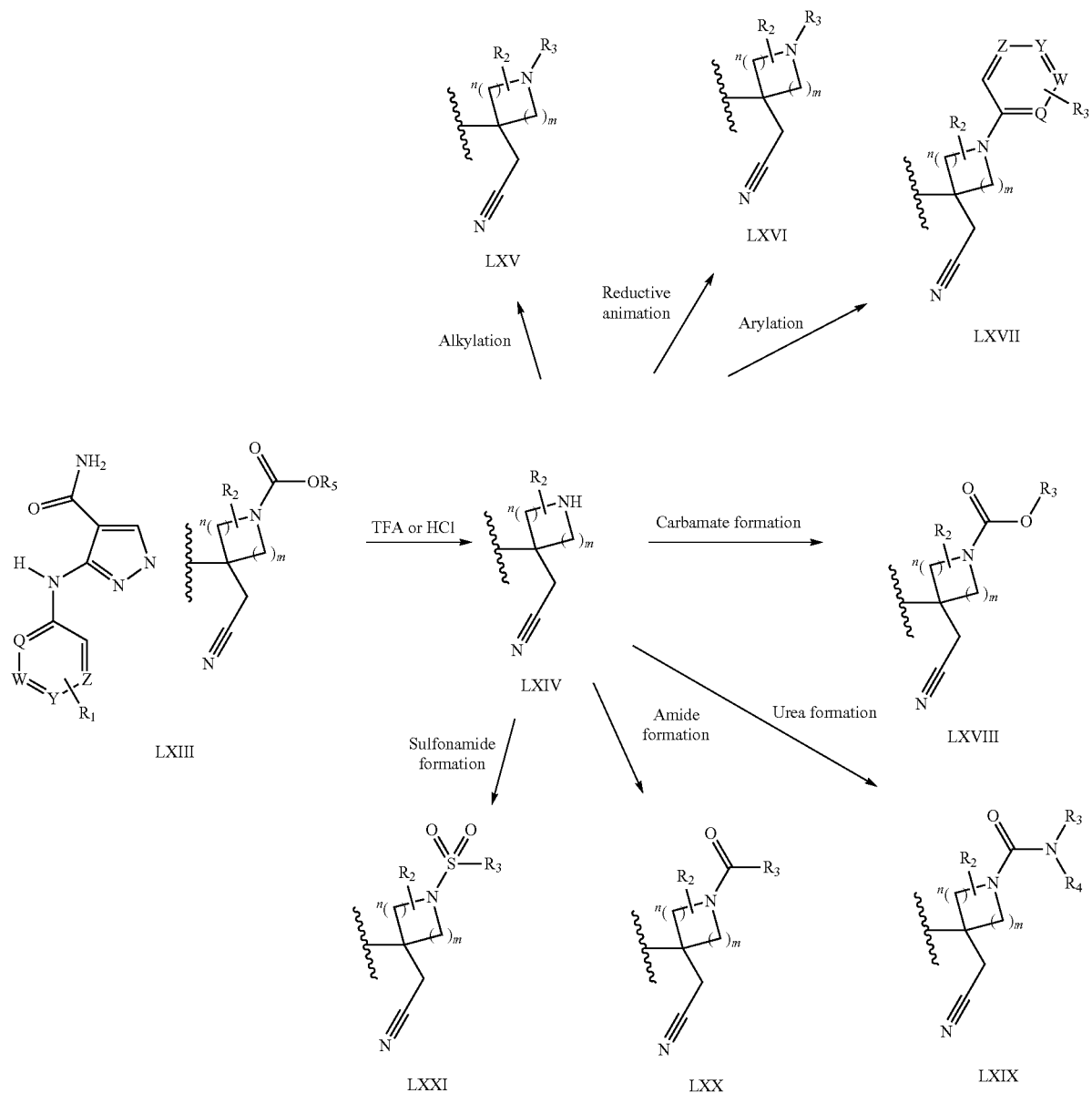

Method 29

General procedures to prepare examples of the instant invention are described in Scheme 29. Hydroxylated cyclohexyl pyrazole carboxamides LIX can be oxidized with an appropriate oxidant, such as TPAP and NMO, and then reductively aminated using standard conditions, such as AcOH, NACNBH$_3$, and optionally substituted primary and secondary amines, to afford examples LXXIII of the instant invention.

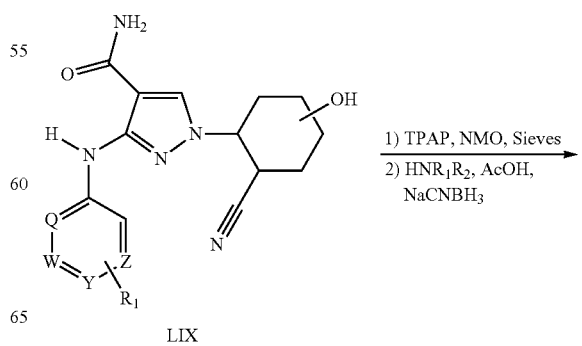

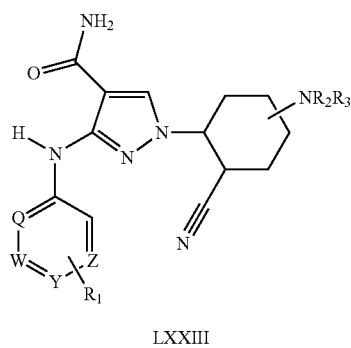

LXXIII

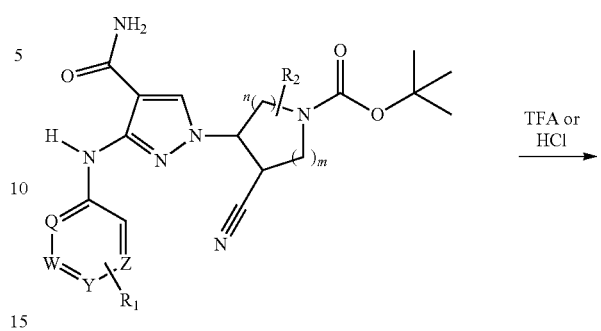

LXXV

Method 30

General procedures to prepare examples of the instant invention are described in Scheme 30. Hydroxylated cyclohexyl pyrazole carboxamides LIX can be reacted with optionally substituted isocyanates and DMAP to afford carbamate derivatives LXXIV of the instant invention.

SCHEME 30

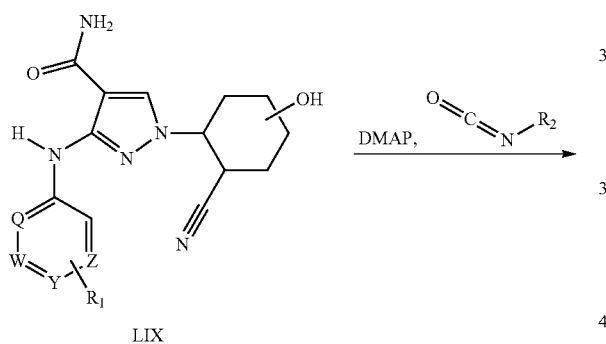

LXXVI

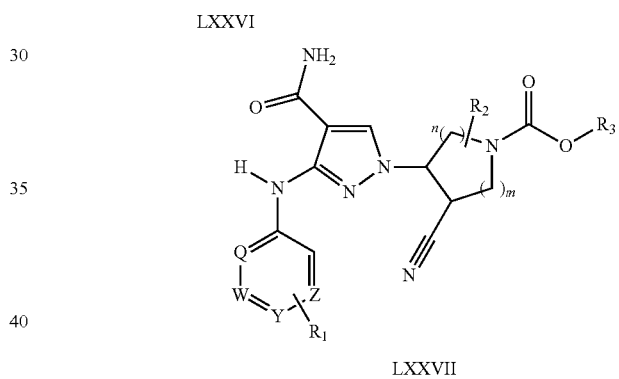

LXXVII

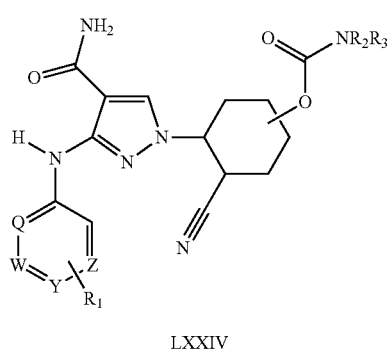

LXXIV

Method 31

General procedures to prepare examples of the instant invention are described in Scheme 31. Optionally substituted, carbamate protected pyrazole carboxamides LXXV are deprotected in the presence of acid, such as TFA or HCl, and then reacted with optionally substituted alcohols in the presence of a doubly activated carbonyl group, such as DSC or phosgene, to afford carbamate derivatives LXXVII of the instant invention.

Method 32

Cyclic sulfide-containing ketones such as LXXVIII are condensed with diethyl (cyanomethyl)phosphonate in the presence of a suitable base, such as potassium tert-butoxide, to yield optionally substituted unsaturated nitriles LXXIX used as intermediates in the synthesis of examples of the instant invention. Using an appropriate base, such as DBU, in a suitable solvent, such as MeCN, EtOH, or tert-BuOH, 3-amino pyrazole carboxamide XLIII is conjugatively added to optionally substituted acrylonitriles, including but not limited to LXXIX to yield alkylated pyrazole carboxamides such as LXXX as examples of the instant invention.

SCHEME 32

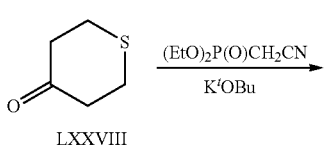

LXXVIII

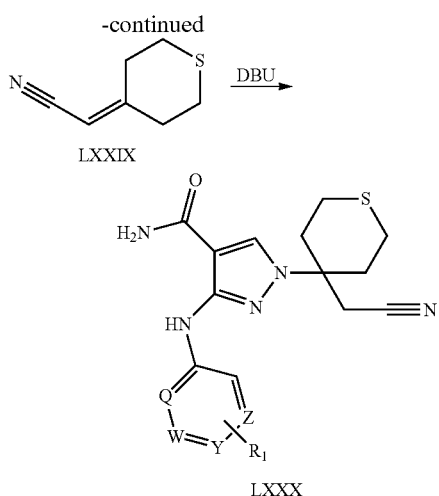

Method 33

Cyclic sulfone-containing ketones such as LXXXI are condensed with diethyl (cyanomethyl)phosphonate in the presence of a suitable base, such as potassium tert-butoxide, to yield optionally substituted unsaturated nitriles LXXXII used as intermediates in the synthesis of examples of the instant invention. Using an appropriate base, such as DBU, in a suitable solvent, such as MeCN, EtOH, or tert-BuOH, 3-amino pyrazole carboxamide XLIII is conjugatively added to optionally substituted acrylonitriles, including but not limited to LXXXII to yield alkylated pyrazole carboxamides such as LXXXIII as examples of the instant invention.

SCHEME 33

Method 34

Ketal protected pyrazole derivatives such as LXXXIV are deprotected using standard conditions, such as but not limited to aqueous hydrochloric acid solution in tetrahydrofuran at elevated temperature to yield intermediate ketones such as LXXXV. Ketone derivatives such as LXXXV are then reductively aminated with ammonium chloride, primary amines, or secondary amines to yield amine-substituted intermediates of the general structure LXXXVI. These pyrazole intermediates are then cross-coupled with aryl halides such as, but not limited to XLII to yield amine-containing pyrazole carboxamides such as LXXXVII as examples of the instant invention.

SCHEME 34

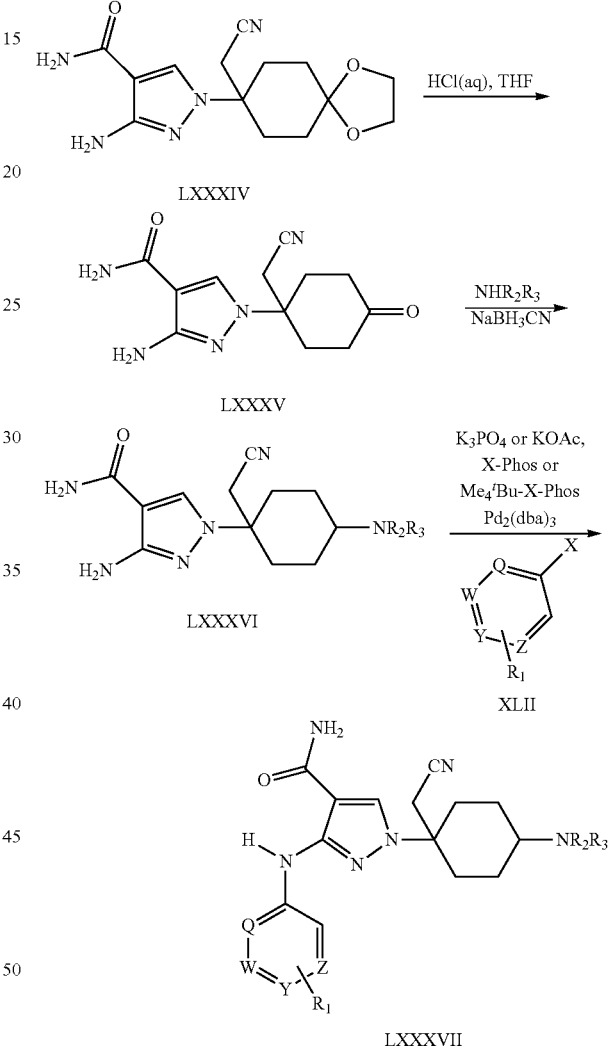

Method 35

As an alternative to Method 34 in the preparation of amine-containing pyrazole examples, optionally substituted ketones such as LXXXVIII are reductively aminated with ammonium acetate, using sodium cyanoborohydride or another appropriate reagent to yield primary amines such as LXXXIX, which are both examples and intermediates for use in the instant invention. Aldehydes of diverse structure can then be coupled to primary amine LXXXIX with a reductive amination reaction, such as with sodium cyanoborohydride and acetic acid to afford secondary amines such as XC as examples of the instant invention.

SCHEME 35

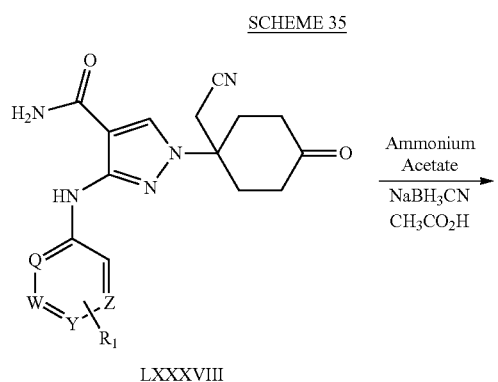

LXXXVIII

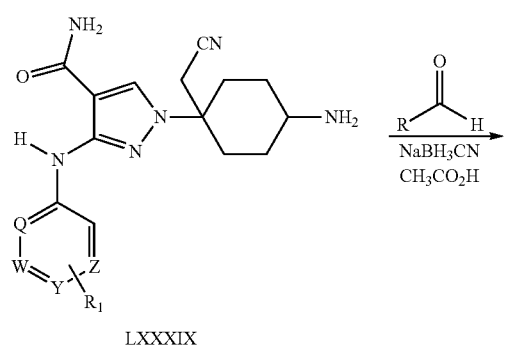

LXXXIX

XC

Method 36

As an alternative in the preparation of amine containing examples of the instant invention, ketal protected pyrazole derivative LXXXIV can be cross-coupled to XLII using an appropriate catalytic palladium-ligand system, such as $Pd_2(dba)_3$ and X-Phos or $Me_4{}^tBu$-X-Phos, and a suitable base, such as $K_3PO_4$ or KOAc, in solvent, such as dioxane, to yield arylated compounds such as XCI for use as intermediates in the instant invention. Arylated ketal derivatives such as XCI can then be deprotected using aqueous acidic conditions such as aqueous hydrochloric acid in tetrahydrofuran to give ketone derivatives such as LXXXVIII as intermediates which can then be reductively aminated with secondary or primary amines to give amine substituted compounds such as LXXXVII as examples of the instant invention.

SCHEME 36

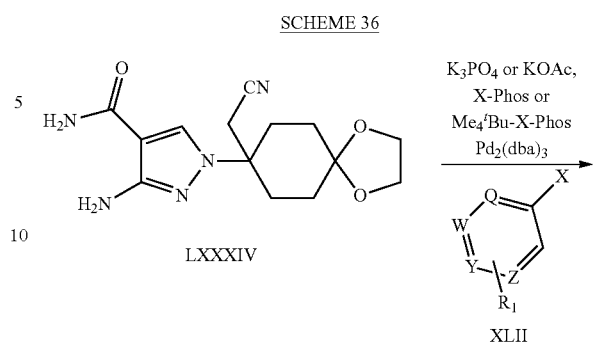

LXXXIV

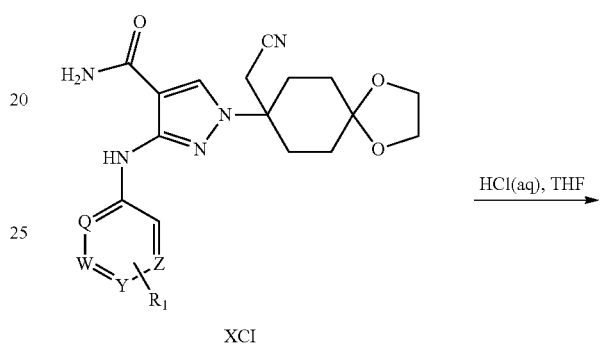

XCI

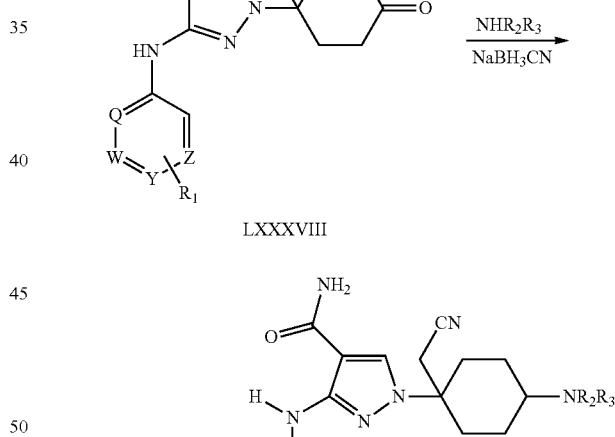

LXXXVIII

LXXXVII

Method 37

Piperidines such as XCII can be reductively aminated with optionally substituted aldehydes using an acid, such as trifluoroacetic acid or acetic acid, and a reducing reagent, such as sodium triacetoxy borohydride, to give tertiary amine substituted pyrazoles such as XCIII as examples of the instant invention.

SCHEME 37

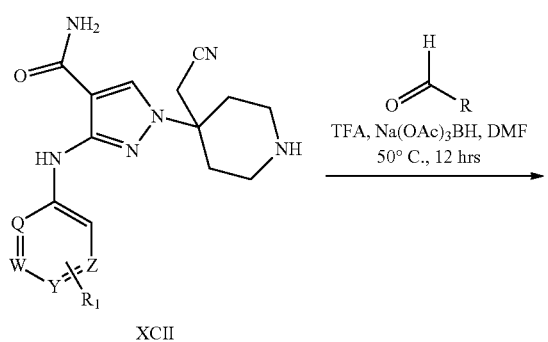

XCII

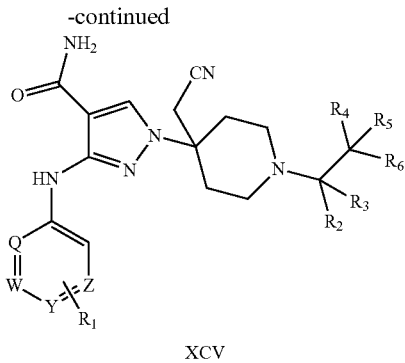

XCV

Method 39

Optionally substituted ketones such as LXXXVIII can be reduced with reagents such as sodium borohydride, the resulting alcohol can be activated as a leaving group with a reagent such as methanesulfonyl chloride, and the resulting mesylate or optionally activated alcohol derivative can be displaced with an azide source, such as sodium azide to give alkylated azide XCVI as intermediates for use in the instant invention. The azides can then be reacted with substituted alkynes in a 1,3-dipolar cycloaddition with copper II sulfate and sodium ascorbate in an appropriate solvent to afford triazole containing pyrazole carboxamides XCVII as examples of the instant invention.

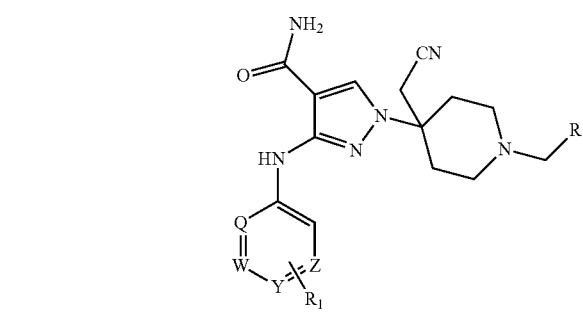

XCIII

Method 38

As an alternative to the preparation of tertiary amine containing examples, primary or secondary alcohols can be oxidized to the corresponding aldehydes or ketones with polystyrene-supported IBX, followed by reductive amination with secondary amines such as XCIV and appropriate reaction conditions, such as trifluoroacetic acid and sodium triacetoxyborohydride to give XCV as examples of the instant invention.

SCHEME 39

SCHEME 38

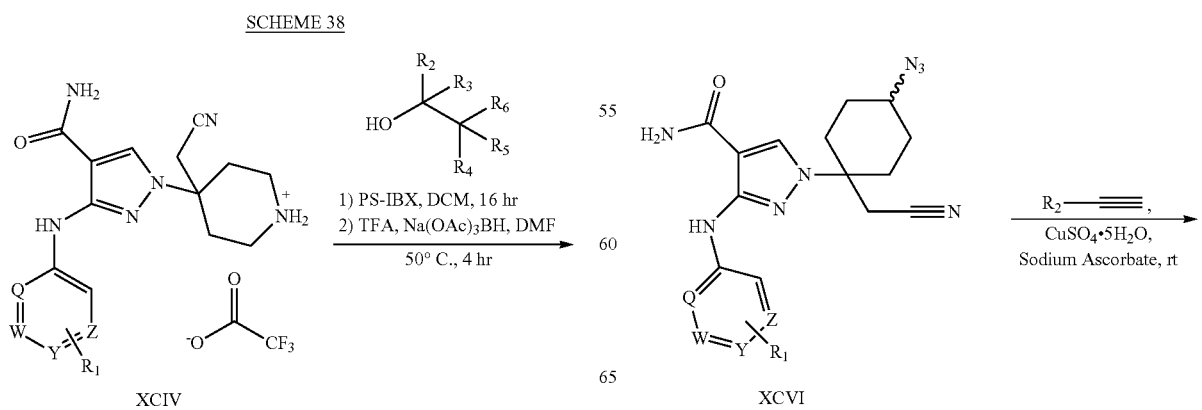

XCIV

LXXXVIII

XCVI

-continued

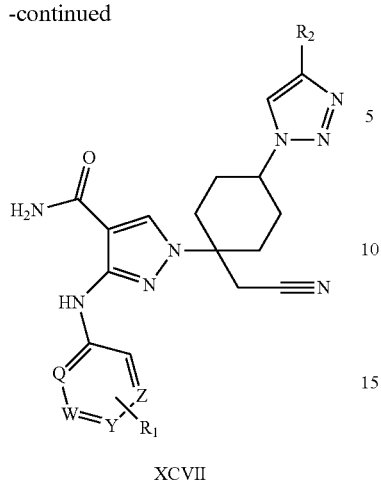

XCVII

-continued

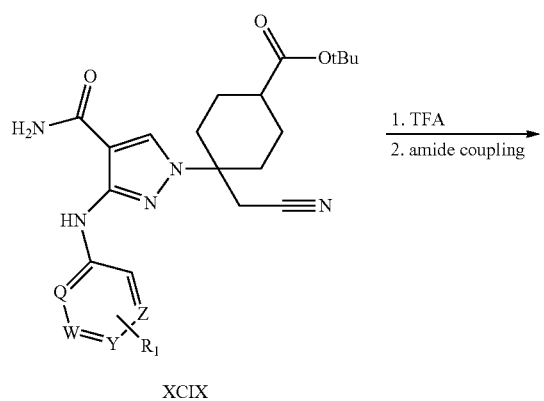

XCIX

Method 40

Using an appropriate base, such as DBU, in a suitable solvent, such as MeCN, EtOH, or tert-BuOH, 3-amino pyrazole carboxamide XLIII is conjugatively added to optionally substituted acrylonitriles, including but not limited to XCVIII to yield t-butyl ester substituted pyrazole carboxamides such as XCIX as intermediates for use in instant invention. The t-butyl esters such as XCIX can then be converted to carboxylic acids by treatment with trifluoroacetic acid (or another appropriate acid), and the carboxylic acid can be subjected to amide coupling conditions to give amide substituted pyrazole compounds such as C as examples of the instant invention.

SCHEME 40

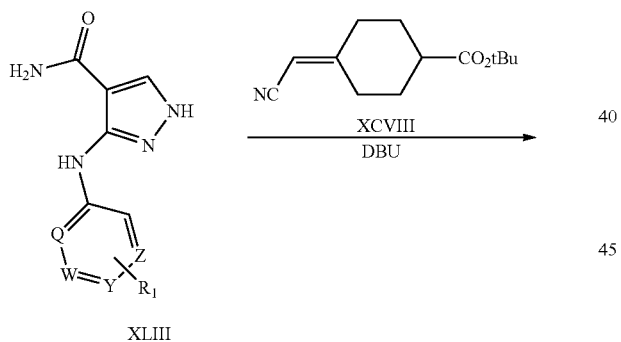

XLIII

C

COMMERCIALLY AVAILABLE/PREVIOUSLY DESCRIBED MATERIALS

The following table lists commercial sources, and previously disclosed synthetic routes for chemical materials employed in the synthesis of intermediates, and Examples of the instant invention. The list is not intended to be exhaustive, exclusive, or limiting in any way.

| Structure | Compound Name | Vendor |
|---|---|---|
| $F_3C$-CH=CH-CN | 4,4,4-trifluorobut-2-enenitrile | Oakwood |
| 4-Br-C6H4-C(O)-NH-CH3 | 4-bromo-N-methylbenzamide | Combi Blocks, Inc. |
| HO-cyclohexenyl-CN | 3-hydroxycyclohex-1-ene-1-carbonitrile | J. Org. Chem. 2001, 66, 2171-2174. |

-continued

| Structure | Compound Name | Vendor |
|---|---|---|
| 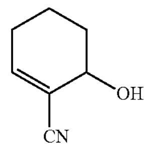 | 6-hydroxycyclohex-1-ene-1-carbonitrile | Tetrahedron Letters 1986, 27, 1577-1578. |
| 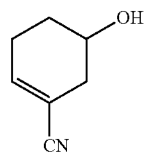 | 5-hydroxycyclohex-1-ene-1-carbonitrile | Canadian Journal of Chemistry 1984, 62, 1093-1098. |
| 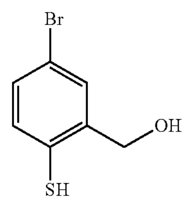 | (5-bromo-2-mercaptophenyl)methanol | Biogene Organics, Inc. |
| 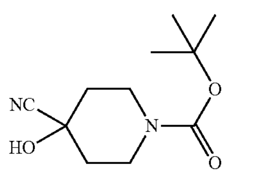 [SMILES: CC(C)(C)OC(=O)N1CCC(O)(C#N)CC1] | tert-butyl 4-cyano-4-hydroxypiperidine-1-carboxylate | Sinova, Inc. |
| 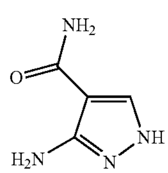 | 3-amino-1H-pyrazole-4-carboxamide | Enamine |
| 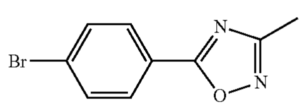 | 5-(4-bromophenyl)-3-methyl-1,2,4-oxadiazole | Maybridge |
| 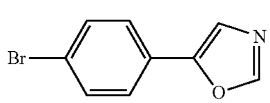 [SMILES: Brc1ccc(-c2cnco2)cc1] | 5-(4-bromophenyl)-1,3-oxazole | Maybridge |
| 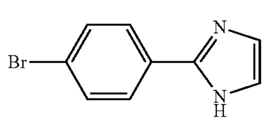 [SMILES: Brc1ccc(-c2ncc[nH]2)cc1] | 2-(4-bromophenyl)-1H-imidazole | J & W PharmLab LLC |
| 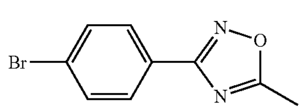 | 3-(4-bromophenyl)-5-methyl-1,2,4-oxadiazole | Maybridge |
| 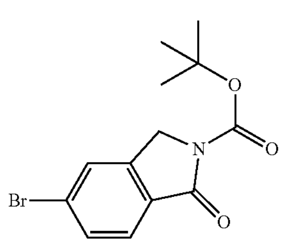 [SMILES: CC(C)(C)OC(=O)N1Cc2cc(Br)ccc2C1=O] | tert-butyl 5-bromo-1-oxo-1,3-dihydro-2H-isoindole-2-carboxylate | Ontario Chemical, Inc. |

-continued

| Structure | Compound Name | Vendor |
|---|---|---|
| 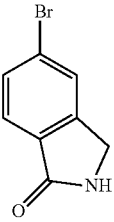 [SMILES: O=C1NCc2cc(Br)ccc21] | 5-bromo-2,3-dihydro-1H-isoindol-1-one | Atomole Scientific Co, ltd. |
| 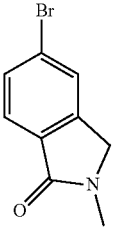 | 5-bromo-2-methyl-2,3-dihydro-1H-isoindol-1-one | J & W PharmLab LLC |
| 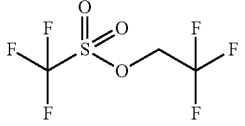 | 2,2,2-trifluoroethyl trifluoromethanesulfonate | Matrix Scientific |
| 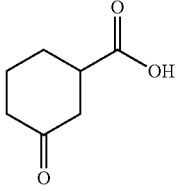 | 3-oxocyclohexanecarboxylic acid | Sigma Aldrich |
| 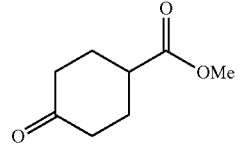 [SMILES: COC(=O)C1CCC(=O)CC1] | methyl 4-oxocyclohexanecarboxylate | Astatech Inc |
| 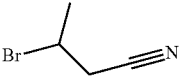 | 3-bromobutyronitrile | TCI America |
| 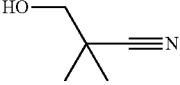 | 3-hydroxy-2,2-dimethylpropanenitrile | Matrix Scientific |
| 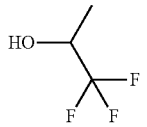 | 1,1,1-trifluoro-2-propanol | Sigma Aldrich |
| 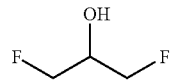 | 1,3-difluoro-2-propanol | Sigma Aldrich |
| 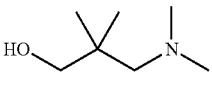 | 3-dimethylamino-2,2-dimethyl-1-propanol | TCI America |
| 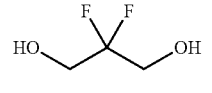 | 2,2-difluoropropane-1,3-diol | Chemstep |

-continued

| Structure | Compound Name | Vendor |
|---|---|---|
| HO-[cyclopropyl]-C≡N | [1-(hydroxymethyl)cyclopropyl]-acetonitrile | Matrix Scientific |
| oxetane with OH | oxetan-3-ol | Sigma Aldrich |
| methyl oxetane with CH2OH | (3-methyloxetan-3-yl)methanol | Sigma Aldrich |
| HO-CH2CH2-cyclopropyl | 2-cyclopropylethanol | Sigma Aldrich |
| Silica-S-(CH2)3-NH-triazine(SH)2 | Silica supported Dimercaptotriazine (Si—DMT) | Silicycle Inc. |
| Silica-S-(CH2)3-N=C=O | Silica supported Isocyanate | Silicycle Inc. |
| 4-Br, 2-F pyridine | 4-bromo-2-fluoropyridine | Synthonix |
| methyl 5-amino-1H-pyrazole-4-carboxylate structure | methyl 5-amino-1H-pyrazole-4-carboxylate | Chembridge Corporation |
| 5-Br, 2-F pyridine | 5-bromo-2-fluoropyridine | Matrix Scientific |
| 4-bromopyridazine | 4-bromopyridazine | Fisher Scientific |
| 4-Br-C6H4-C(O)NMe2 | 4-bromo-N,N-dimethylbenzamide | Chembridge Corporation |
| 4-Br-C6H4-SO2NH2 | 4-bromobenzenesulfonamide | Sigma Aldrich |

-continued

| Structure | Compound Name | Vendor |
|---|---|---|
| (4-bromophenyl trifluoromethyl sulfone structure) | 1-bromo-4-[(trifluoromethyl)sulfonyl]benzene | Sunshine ChemLab. Inc |
| (4-bromophenyl difluoromethyl sulfone structure) | 1-bromo-4-[(difluoromethyl)sulfonyl]benzene | WXAT |
| (5-bromo-2-cyanopyridine structure) | 5-bromopyridine-2-carbonitrile | Sigma Aldrich |
| (methyl 4-bromophenylacetate structure) | methyl (4-bromophenyl)acetate | Toyobo Co., Ltd. |
| (methyl 2-hydroxy-2-methylpropanoate structure) | methyl 2-hydroxy-2-methylpropanoate | Sigma Aldrich |
| (tert-butyl 3-methyl-4-oxopiperidine-1-carboxylate structure) | tert-butyl 3-methyl-4-oxopiperidine-1-carboxylate | Small Molecules Inc. |
| (tert-butyl 2-methyl-4-oxopiperidine-1-carboxylate structure) | tert-butyl 2-methyl-4-oxopiperidine-1-carboxylate | Small Molecules Inc. |
| (4-bromo-2-(trifluoromethyl)pyridine structure) | 4-bromo-2-(trifluoromethyl)pyridine | CombiPhos Catalysts, Inc. |
| (3-methylbut-2-enenitrile structure) | 3-methylbut-2-enenitrile | BePharm Ltd. |
| (cyclobutanecarbaldehyde structure) | cyclobutanecarbaldehyde | Beta Pharma Inc |
| (tetrahydro-2H-pyran-3-carbaldehyde structure) | tetrahydro-2H-pyran-3-carbaldehyde | J & W PharmLab LLC |

-continued

| Structure | Compound Name | Vendor |
|---|---|---|
| 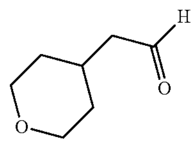 | tetrahydro-2H-pyran-4-ylacetaldehyde | Maybridge |
| 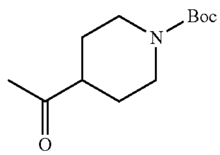 [SMILES: CC(=O)C1CCN(C(=O)OC(C)(C)C)CC1] | tert-butyl 4-acetylpiperidine-1-carboxylate | Syntech Development Company |
| 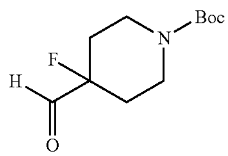 [SMILES: CC(C)(C)OC(=O)N1CCC(F)(C=O)CC1] | tert-butyl 4-fluoro-4-formylpiperidine-1-carboxylate | Ark Pharm, Inc. |
| 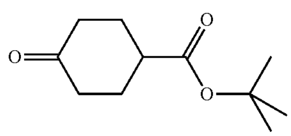 | tert-butyl 4-oxocyclohexanecarboxylate | Fisher Scientific |
| 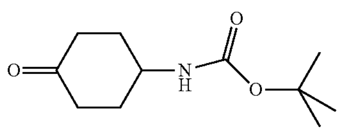 | tert-butyl (4-oxocyclohexyl)carbamate | Fisher Scientific |
| 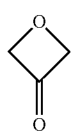 | oxetan-3-one | Synthonix |
| 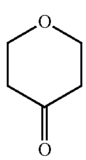 | tetrahydro-4H-pyran-4-one | Fisher Scientific |
| 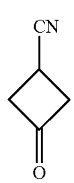 | 3-oxocyclobutanecarbonitrile | Fisher Scientific |
| 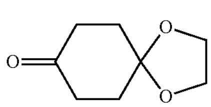 [SMILES: O=C1CCC2(CC1)OCCO2] | 1,4-dioxaspiro[4.5]decan-8-one | Sigma Aldrich |
| 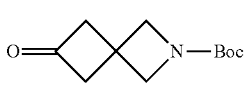 [SMILES: CC(C)(C)OC(=O)N1CC2(CC(=O)C2)C1] | tert-butyl 6-oxo-2-azaspiro[3.3]heptane-2-carboxylate | Org. Lett. 2009, 11, 3523-3525. |
| 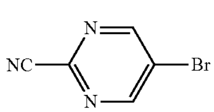 | 5-bromopyrimidine-2-carbonitrile | Fisher Scientific |

| Structure | Compound Name | Vendor |
|---|---|---|
| (structure) | 4-(5-BROMOPYRIDIN-2-YL)MORPHOLINE | Fisher Scientific |

INTERMEDIATES

The following experimental procedures detail the preparation of chemical materials used in the synthesis of Examples of the instant invention. The exemplified procedures are for illustrative purposes only, and are not intended to limit the scope f the instant invention in any way.

Intermediate #1

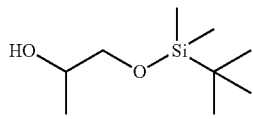

1-{[tert-Butyl(dimethyl)silyl]oxy}propan-2-ol

To a solution of propylene glycol (1.0 g, 13 mmol) in DCM (60.0 mL) was added tert-butyldimethylchlorosilane (2.0 g, 13 mmol) followed by DIPEA (3.2 mL, 18 mmol). The reaction mixture was stirred at ambient temperature for 18 hours. The solution was diluted with ether, washed with saturated aqueous $NaHCO_3$, brine, dried over anhydrous $MgSO_4$, filtered, and concentrated in vacuo to afford the title compound.
LRMS (ESI) calc'd for $C_9H_{22}O_2Si$ $[M+H]^+$: 191. Found: 191.

Intermediate #2

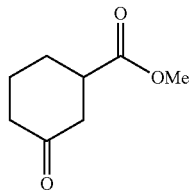

tert-Butyl 3-oxocyclohexanecarboxylate

Anhydrous $MgSO_4$ (3.4 g, 28 mmol) was suspended in DCM (28.1 mL) and to this vigorously stirred mixture was added concentrated sulfuric acid (0.7 g, 7 mmol). The resulting mixture was allowed to stir at ambient temperature for 30 minutes. 3-Oxocyclohexanecarboxylic acid (1.0 g, 7.0 mmol) was added followed by t-BuOH (2.6 g, 35 mmol). The resulting mixture was allowed to stir for 24 hours before it was filtered and flushed with DCM. The filtrate was washed with water, and the organic layer was again washed with water, brine, dried over anhydrous $MgSO_4$, filtered, and concentrated in vacuo to afford the title compound. The residue was used without further purification.

$^1$H NMR (500 MHz, $CDCl_3$): δ 2.72-2.64 (m, 1H), 2.47 (d, J=8.1 Hz, 2H), 2.36-2.24 (m, 2H), 2.08-1.98 (m, 2H), 1.84-1.66 (m, 2H), 1.44 (s, 9H).

Intermediate #3

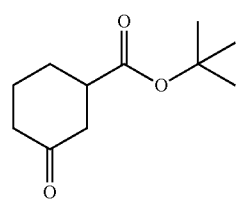

Methyl 3-oxocyclohexanecarboxylate

To a solution of 3-oxocyclohexanecarboxylic acid (1.0 g, 7.0 mmol) in diethyl ether (28 mL) was added dropwise TMS-diazomethane (3.5 mL, 7.0 mmol, 2.0 mL in diethyl ether). MeOH (30 mL) was added and the mixture was maintained at ambient temperature for 30 minutes. The mixture was concentrated in vacuo, and the residue was purified by MPLC on silica gel (using a gradient elution of 0-45% EtOAc/hexanes). Desired fractions were identified, combined, and concentrated in vacuo to afford the title compound.
$^1$H NMR (500 MHz, $CDCl_3$): δ 3.66 (s, 3H), 2.82-2.72 (m, 1H), 2.54-2.46 (m, 2H), 2.38-2.24 (m, 2H), 2.12-1.98 (m, 2H), 1.86-1.75 (m, 1H), 1.75-1.64 (m, 1H).

Intermediate #4

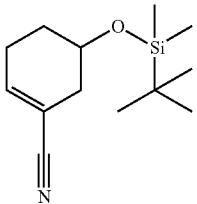

5-{[tert-Butyl(dimethyl)silyl]oxy}cyclohex-1-ene-1carbonitrile

5-Hydroxycyclohex-1-ene-1-carbonitrile (500 mg, 4.06 mmol) was dissolved in anhydrous DMF (5.1 mL) and then cooled to 0° C. Imidazole (276 mg, 4.06 mmol) and TBS-Cl (612 mg, 4.06 mmol) were added and the reaction mixture was allowed to stir at 0° C. for 2 hours. The reaction mixture was partitioned between water and DCM. The organic layer was collected and the aqueous layer was again extracted with DCM. The combined organic extracts were washed with brine, dried over anhydrous $Na_2SO_4$, filtered, and concentrated in vacuo. The residue was purified by MPLC on silica gel (using a gradient elution of 0-100%, EtOAc/hexanes) to afford the title compound.

LRMS (ESI) calc'd for $C_{13}H_{23}NOSi$ $[M+H]^+$: 238. Found: 238.

Scheme #1

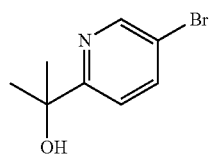

Intermediate #5

2-(5-Bromopyridin-2-yl)propan-2-ol

Methyl 5-bromopicolinate (500 mg, 2.31 mmol) was dissolved in THF (7.0 mL) and the flask was sealed with a septum and flushed with argon. The mixture was cooled to 0° C. and methylmagnesium bromide (3.1 mL, 9.3 mmol, 3M in THF) was added. The resulting mixture was allowed to stir at 0° C. for 1 hour before the reaction was quenched with saturated aqueous ammonium chloride and extracted with EtOAc. The organic layer was then washed with brine, dried over anhydrous $MgSO_4$, filtered, and concentrated in vacuo to afford the title compound, which was used without further purification. LRMS (ESI) calc'd for $C_8H_{10}BrNO$ $[M+H]^+$: 216. Found: 216.

Scheme #2

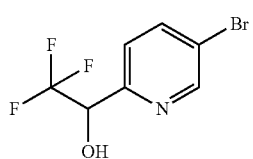

Intermediate #6

1-(5-Bromopyridin-2-yl)-2,2,2-trifluoroethanol

5-Bromopicolinaldehyde (500 mg, 2.70 mmol) was dissolved in THF (9.0 mL) and the flask was then sealed with a septum, flushed with argon, and cooled to 0° C. (Trifluoromethyl)trimethylsilane (0.44 mL, 3.0 mmol) was then added followed by TBAF (2.7 mL, 2.7 mmol, 1M in THF). The resulting mixture was allowed to warm to ambient temperature and was stirred for 2 hours. The reaction was then quenched with water and extracted with DCM (2×). The combined organic extracts were washed with brine, dried over anhydrous $MgSO_4$, and concentrated in vacuo. The residue was purified by MPLC on silica gel (using a gradient elution of 10-20% EtOAc/hexanes) to afford the title compound. LRMS (ESI) calc'd for $C_8H_6BrF_3O$ $[M+H]^+$: 256. Found: 256.

Scheme #3

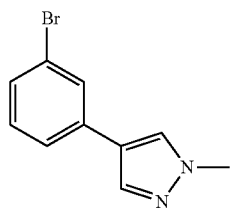

Intermediate #7-1

4-(3-Bromophenyl)-1-methyl-1H-pyrazole 1,3-Dibromobenzene (0.38 mL, 3.2 mmol), 1-methyl-4-(4,4,5,5-tetramethyl-1,3,2-dioxaborolan-2-yl)-1H-pyrazole (595 mg, 2.86 mmol), $Pd(dppf)Cl_2$ (260 mg, 0.320 mmol), and potassium phosphate (2.0 g, 9.5 mmol) were combined in a flask and dissolved in dioxane (16.0 mL) and water (1.6 mL). The flask was then sealed and flushed with argon. The reaction mixture was allowed to stir at 90° C. for 90 minutes. The mixture was then cooled to ambient temperature and diluted with EtOAc. The organic layer was washed with water, brine, dried over anhydrous $MgSO_4$, and concentrated in vacuo. The residue was purified by MPLC on silica gel (50% EtOAc/hexanes) to afford the title compound.

LRMS (ESI) calc'd for $C_{10}H_9BrN_2$ $[M+H]^+$: 237. Found: 237.

The following intermediates found in TABLE 1 were prepared according to Scheme #3 following similar procedures described for Intermediate #7-1, which can be achieved by those of ordinary skill in the art of organic synthesis.

TABLE 1

| Intermediate | Structure | Compound Name | Exact Mass $[M + H]^+$ |
| --- | --- | --- | --- |
| 7-2 | 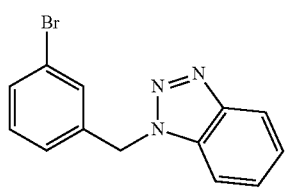 | 3-bromo-5-(1-methyl-1H-pyrazol-4-yl)pyridine | Calc'd 238, Found 238 |

Scheme #4

Intermediate #8-1

1-(3-Bromobenzyl)-1H-benzotriazole

To a solution of 1H-benzotriazole (0.52 g, 4.4 mmol) in THF (25 mL) was added potassium tert-butoxide (4.6 mL, 4.6 mmol, 1M in THF) followed by the addition of 1-bromo-3-

(bromomethyl)benzene (1.0 g, 4.0 mmol). The solution was allowed to stir for 4 hours before the reaction was quenched with saturated aqueous NaHCO$_3$ and diluted with EtOAc. The organic layer was separated and washed with brine, dried over anhydrous MgSO$_4$, filtered, and concentrated to dryness in vacuo. The residue was purified by MPLC on silica gel (using a gradient elution of 0-80% EtOAc/hexanes) to afford the title compound as a white solid.

LRMS (ESI) calc'd for C$_{13}$H$_{11}$BrN$_3$ [M+H]$^+$: 288. Found 288.

The following intermediates disclosed in TABLE 2 were prepared according to Scheme #4 following similar procedures described for Intermediate #8-1, which can be achieved by those of ordinary skill in the art of organic synthesis.

TABLE 2

| Intermediate | Structure | Compound Name | Exact Mass [M + H]$^+$ |
|---|---|---|---|
| 8-2 | 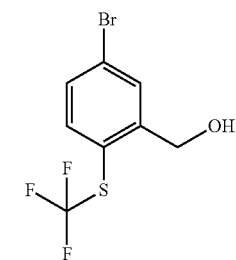 | 1-(3-bromo-benzyl)-1H-imidazole | Calc'd 237, Found 237 |

Scheme #6

Intermediate #9

{5-Bromo-2-[(trifluoromethyl)sulfanyl]phenyl}methanol

NaH (120 mg, 3.01 mmol, 60% dispersion in oil) and 5-(trifluoromethyl)dibenzo[b,d]thiophenium trifluoromethanesulfonate (808 mg, 2.01 mmol) were added sequentially to a solution of (5-bromo-2-sulfanylphenyl)methanol (440 mg, 2.01 mmol) in DMF (10 mL) at 23° C. The reaction mixture was stirred at 23° C. for 45 minutes, and was then partitioned between EtOAc and water. The organic layer was washed with brine, dried over anhydrous Na$_2$SO$_4$, filtered, and concentrated in vacuo. The residue was purified by MPLC on silica gel (using a gradient elution of 0-20%, EtOAc/hexanes) to afford the title compound.

$^1$H NMR (500 MHz, CDCl$_3$): δ 7.82 (d, J=1.8 Hz, 1H), 7.53-7.48 (m, 2H), 4.92 (s, 2H), 2.02 (s, 1H).

Scheme #7

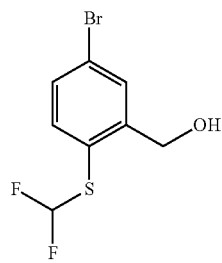

Intermediate #10

{5-Bromo-2-[(difluoromethyl)sulfanyl]phenyl}methanol (5-Bromo-2-sulfanylphenyl)methanol (0.50 g, 2.8 mmol) was dissolved in acetonitrile (11.4 mL) followed by the addition of water (11.4 mL) and solid potassium hydroxide (2.56 g, 45.6 mmol). The mixture was plunged into a −78° C. bath and when the mixture began to freeze diethyl [bromo(difluoro)methyl]phosphonate (1.22 g, 4.56 mmol) was added all at once and the cold bath was removed. The mixture was allowed to warm to ambient temperature and was stirred for 20 minutes. The mixture was then partitioned between EtOAc and water. The organic layer was washed with brine, dried over anhydrous MgSO$_4$ and concentrated in vacuo. The residue was purified by MPLC on silica gel (using a gradient elution of 0-25% EtOAc/hexanes). Desired fractions were identified, combined, and concentrated in vacuo to afford the title compound.

$^1$H NMR (500 MHz, CDCl$_3$): δ 7.76 (s, 1H), 7.47 (m, 2H), 6.80 (t, J=56.5 Hz, 1H), 4.87 (s, 2H), 1.96 (br s, 1H).

Scheme #8

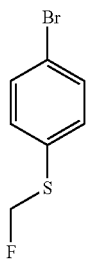

Intermediate #11

1-Bromo-4-[(fluoromethyl)sulfanyl]benzene

1-Bromo-4-(methylsulfinyl)benzene (1.50 g, 6.85 mmol) was dissolved in 1,2-DCE (13.7 mL) and stirred at ambient temperature. BAST (3.79 g, 17.1 mmol) was added dropwise followed by zinc iodide (0.07 g, 0.21 mmol). The reaction vessel was sealed and the mixture was heated to 40° C., allowed to stir for 24 hours, and then allowed to cool to ambient temperature. The mixture was partitioned between EtOAc and water, the layers were separated and the organic layer was dried over anhydrous MgSO$_4$, filtered, and concentrated in vacuo. The residue was purified by MPLC on silica gel (using a gradient elution of 0-20% EtOAc/hexanes). Desired fractions were identified, combined, and concentrated in vacuo to afford the title compound.

$^1$H NMR (500 MHz, CDCl$_3$): δ 7.49-7.44 (m, 2H), 7.38-7.33 (m, 2H), 5.69 (d, J=52.8 Hz, 2H).

Scheme #6

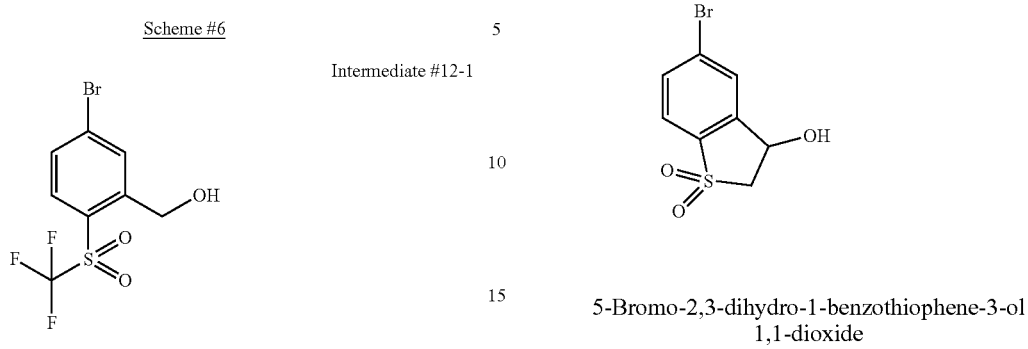

Intermediate #12-1

{5-Bromo-2-[(trifluoromethyl)sulfonyl]phenyl}methanol

A mixture of m-CPBA (452 mg, 2.62 mmol) and {5-bromo-2-[(trifluoromethyl)thio]phenyl}methanol (188 mg, 0.655 mmol) in DCM (6.6 mL) was heated to 40° C. and stirred in a microwave reaction vial for 30 hours. After cooling to 23° C., the reaction mixture was partitioned between EtOAc and aqueous potassium bisulfate solution (40% w/w). The organic layer was washed sequentially with saturated aqueous NaHCO$_3$, brine, dried over anhydrous Na$_2$SO$_4$, filtered, and concentrated in vacuo. The residue was purified by MPLC on silica gel (using a gradient elution of 0-30%, EtOAc/hexanes) to afford the title compound.

$^1$H NMR (500 MHz, CDCl$_3$): δ 8.06 (d, J=1.7 Hz, 1H), 7.91 (d, J=8.6 Hz, 1H), 7.73 (dd, J=8.6, 2.0 Hz, 1H), 5.01 (s, 2H), 2.56 (s, 1H).

TABLE 3 discloses intermediates 12-2 and 12-3 that were prepared according to Schemes #6-8 following similar procedures described for Intermediate #12-1, which can be achieved by those of ordinary skill in the art of organic synthesis.

Scheme #9

Intermediate #13

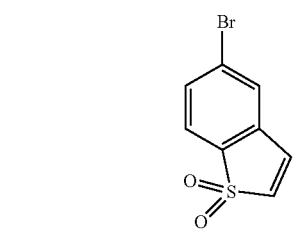 [SMILES: O=S1(=O)C=Cc2cc(Br)ccc21]

5-Bromo-2,3-dihydro-1-benzothiophene-3-ol 1,1-dioxide

Step A. 5-Bromo-1-benzothiophene 1,1-dioxide

5-Bromo-1-benzothiophene (1.50 g, 7.04 mmol) was dissolved in chloroform (47 mL) and allowed to stir vigorously at ambient temperature. m-CPBA (4.34 g, 17.6 mmol) was added in three portions and the resulting mixture was maintained at ambient temperature for 16 hours. The mixture was then diluted with 1M aqueous sodium thiosulfate and extracted with EtOAc. The organic layer was again washed with 1M aqueous sodium thiosulfate, saturated aqueous

TABLE 3

| Intermediate | Structure | Compound Name | $^1$H NMR δ (ppm) |
|---|---|---|---|
| 12-2 | ![structure] | {5-bromo-2-[(difluoromethyl)sulfonyl]phenyl}methanol | $^1$H NMR (500 MHz, CDCl$_3$): δ 7.93 (d, J = 1.9 Hz, 1H), 7.89 (d, J = 8.3 Hz, 1H), 7.72 (dd, J = 8.3, 1.9 Hz, 1H), 6.33 (t, J = 53.6 Hz, 1H), 4.98 (d, J = 6.4 Hz, 2H), 2.53 (t, J = 6.4 Hz, 1H). |
| 12-3 | ![structure] | 1-bromo-4-[(fluoromethyl)sulfonyl]benzene | $^1$H NMR (500 MHz, CDCl$_3$): δ 7.86-7.80 (m, 2H), 7.80-7.74 (m, 2H), 5.13 (d, J = 46.9 Hz, 2H). |

NaHCO₃, brine, dried over anhydrous MgSO₄, filtered, and concentrated in vacuo. The residue was purified by MPLC on silica gel (using a gradient elution of 0-30% EtOAc/hexanes). Desired fractions were identified, combined, and concentrated in vacuo to afford the title compound.

$^1$H NMR (600 MHz, CDCl₃): δ 7.65 (dd, J=7.9, 1.8 Hz, 1H), 7.55 (d, J=7.9 Hz, 1H), 7.50 (d, J=1.8 Hz, 1H), 7.15 (d, J=6.9 Hz, 1H), 6.74 (d, J=6.9 Hz, 1H).

Step B. 5-Bromo-2,3-dihydro-1-benzothiophene-3-ol 1,1-dioxide

5-Bromo-1-benzothiophene 1,1-dioxide (100 mg, 0.41 mmol) was suspended in 1N aqueous sodium hydroxide (2.0 mL), heated to 100° C. in a microwave, and allowed to stir for 15 minutes. The mixture was then allowed to cool to ambient temperature before the mixture was diluted with saturated aqueous ammonium chloride and extracted with EtOAc. The organic layer was washed with brine, dried over anhydrous MgSO₄, filtered, and concentrated in vacuo. The residue was used without further purification. LRMS (ESI) calc'd for C₈H₇BrO₃S [M+Na]⁺: 285. Found: 285.

Scheme #10

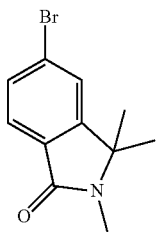

Intermediate #14

5-Bromo-2,3,3-trimethyl-2,3-dihydro-1H-isoindol-1-one

5-Bromo-2,3-dihydro-1H-isoindol-1-one (150 mg, 0.71 mmol) was dissolved in DMF (3.5 mL) and stirred at ambient temperature. NaH (85 mg, 2.12 mmol, 60% dispersion in oil) was carefully added in two portions, and the resulting mixture was allowed to stir for 15 minutes before MeI (151 mg, 1.06 mmol) was added. The mixture was allowed to stir at ambient temperature for 30 minutes before water (10 mL) was carefully added. The mixture was extracted with EtOAc, and the organic layer was washed with water, brine, dried over anhydrous MgSO₄, filtered, and concentrated in vacuo. The residue was purified by MPLC on silica gel (using a gradient elution of 0-20% EtOAc/hexanes). Desired fractions were identified, combined, and concentrated in vacuo to afford the title compound.

LRMS (ESI) calc'd for C₁₁H₁₂BrNO [M+H]⁺: 254. Found: 254.

Scheme #11

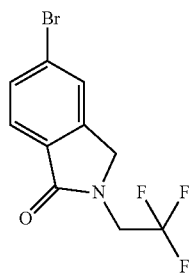

Intermediate #15

5-Bromo-2-(2,2,2-trifluoroethyl)-2,3-dihydro-1H-isoindol-1-one

5-Bromo-2,3-dihydro-1H-isoindol-1-one (100 mg, 0.47 mmol) was dissolved in DMF (4.7 mL) and stirred at 0° C. NaH (38 mg, 0.94 mmol, 60% dispersion in oil) was carefully added in two portions, and the resulting mixture was allowed to stir at 0° C. for 15 minutes before 2,2,2-trifluoroethyl trifluoromethanesulfonate (110 mg, 0.47 mmol) was added. The mixture was allowed to stir at 0° C. for 30 minutes before saturated aqueous NaHCO₃ (10 mL) was carefully added, and the mixture was extracted with EtOAc. The organic layer was washed with water, brine, dried over anhydrous MgSO₄, filtered, and concentrated in vacuo. The residue was purified by MPLC on silica gel (using a gradient elution of 0-20% EtOAc/hexanes). Desired fractions were identified, combined, and concentrated in vacuo to afford the title compound.
LRMS (ESI) calc'd for C₁₀H₇BrF₃NO [M+H]⁺: 294. Found: 294.

Scheme #11

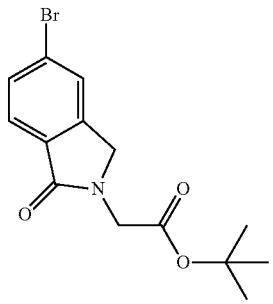

Intermediate #16 tert-Butyl (5-bromo-1-oxo-1,3-dihydro-2H-isoindol-2-yl)acetate

5-Bromo-2,3-dihydro-1H-isoindol-1-one (100 mg, 0.47 mmol) was dissolved in DMF (4.7 mL) and stirred at 0° C. NaH (38 mg, 0.94 mmol, 60% dispersion in oil) was carefully added in two portions, and the resulting mixture was allowed to stir at 0° C. for 15 minutes before tert-butyl bromoacetate (92 mg, 0.47 mmol) was added. The mixture was allowed to stir at 0° C. for 30 minutes before saturated aqueous NaHCO₃ (10 mL) was carefully added. The mixture was extracted with EtOAc, and the organic layer was washed with water, brine, dried over anhydrous MgSO₄, filtered, and concentrated in vacuo. The residue was purified by MPLC on silica gel (using a gradient elution of 0-20% EtOAc/hexanes). Desired fractions were identified, combined, and concentrated in vacuo to afford the title compound. LRMS (ESI) calc'd for $C_{14}H_{16}BrNO_3$ [M+Na]$^+$: 348. Found: 348.

Scheme #5

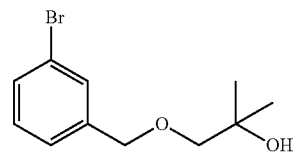

Intermediate #17

1-[(3-Bromobenzyl)oxy]-2-methylpropan-2-ol

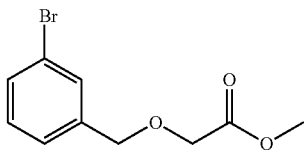

Step A. Methyl [(3-bromobenzyboxy]acetate

Methyl hydroxyacetate (0.80 g, 8.8 mmol) was dissolved in THF (10 mL) and allowed to stir at 0° C. under a nitrogen atmosphere. NaH (0.40 g, 9.6 mmol, 60% dispersion in oil) was added portionwise over approximately 5 minutes. The cooling bath was removed and the reaction mixture was allowed to warm to ambient temperature. 1-Bromo-3-(bromomethyl)benzene (2.0 g, 8.0 mmol) was added in a single portion and the resulting mixture was heated to 40° C. After 4 hours, the reaction mixture was allowed to cool to ambient temperature and partitioned between water and EtOAc. The layers were separated, and the organic layer was washed with saturated aqueous NaHCO$_3$, brine, dried over anhydrous Na$_2$SO$_4$, filtered, and concentrated in vacuo to afford the title compound, which was carried forward without further purification.
$^1$H NMR (600 MHz, CDCl$_3$): δ 7.53-7.50 (m, 1H), 7.42-7.38 (m, 1H), 7.30-7.17 (m, 2H), 4.57 (s, 2H), 4.09 (s, 2H), 3.74 (s, 3H).

Step B.
1-[(3-Bromobenzyl)oxy]-2-methylpropan-2-ol

Methyl [(3-bromobenzyl)oxy]acetate (2.0 g, 7.7 mmol) was dissolved in THF (10 mL) and was allowed to stir under a nitrogen atmosphere. Methylmagnesium bromide (7.7 mL, 23 mmol, 3.0 M in THF) was added dropwise. The reaction mixture was allowed to stir at ambient temperature for 4 hours before the reaction was quenched with water and the mixture was extracted with EtOAc. The organic layer was washed with saturated aqueous NaHCO$_3$, brine, dried over anhydrous Na$_2$SO$_4$, filtered, and concentrated in vacuo. The residue was purified by MPLC on silica gel (using a gradient elution of 2-70% EtOAc/hexanes). Desired fractions were identified, combined, and concentrated in vacuo to the title compound.
$^1$H NMR (600 MHz, CDCl$_3$): δ 7.46 (s, 1H), 7.40 (d, J=7.9 Hz, 1H), 7.25-7.18 (m, 2H), 4.52 (s, 2H), 3.29 (s, 2H), 1.21 (s, 6H).

Scheme #4

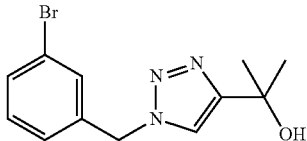

Intermediate #18

Step A-B. 2-[1-(3-Bromobenzyl)-1H-1,2,3-triazol-4-yl]propan-2-ol

To a solution of 1-bromo-3-(bromomethyl)benzene (5.0 g, 20 mmol) in DMSO (40 mL) was added sodium azide (1.3 g, 20 mmol). The resulting mixture was allowed to stir at ambient temperature for 18 hours before it was diluted with water and extracted with diethyl ether (2×). The combined organic extracts were washed with brine, dried over anhydrous Na$_2$SO$_4$, filtered, and concentrated in vacuo. The crude residue was dissolved in $^t$BuOH (65 mL and water (39 mL) and to this mixture was added 2-methylbut-3-yn-2-ol (2.3 g, 27 mmol), and then a solution of copper (II) sulfate pentahydrate (0.26 g, 1.0 mmol) in water (10 mL) followed by a solution of sodium ascorbate (0.83 g, 4.2 mmol) in water (8 mL). The resulting mixture was allowed to stir at ambient temperature for 2 hours before it was diluted with water and extracted with EtOAc (2×). The combined organic extracts were washed with brine, dried over anhydrous Na$_2$SO$_4$, filtered, and concentrated in vacuo. The residue was used without further purification.
LRMS (ESI) calc'd for $C_{12}H_{14}BrN_3O$ [M+H]$^+$: 296. Found: 296.

Scheme #13

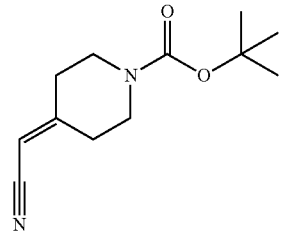

Intermediate #19-1 tert-Butyl 4-(cyanomethylidene)piperidine-1-carboxylate

To a three necked round bottom flask equipped with a mechanical stirring bar was added potassium tert-butoxide (263 mL, 263 mmol, 1.0 M in THF) and THF (200 mL). The mixture was cooled to 0° C., followed by the addition of diethyl (cyanomethyl)phosphonate (43.7 mL, 276 mmol) slowly by syringe. The reaction mixture was maintained at 0° C. for 10 minutes, then warmed to ambient temperature and maintained for 1 hour. The mixture was cooled to 0° C. and treated with the dropwise addition of tert-butyl 4-oxopiperidine-1-carboxylate (50.0 g, 251 mmol) in THF (150 mL) over 30 minutes. After addition, the mixture was maintained at 0° C. for 20 minutes, then warmed to ambient temperature and maintained for 18 hours. The reaction mixture was then diluted with water (800 mL) and extracted with EtOAc (700 mL×2). The combined organic extracts were washed with water, brine, dried over anhydrous $Na_2SO_4$, filtered, and concentrated in vacuo to afford the title compound as a light pink solid.

$^1$H-NMR (600 MHz, $CDCl_3$) δ 5.19 (S, 1H), 3.48-3.53 (m, 4H), 2.56 (t, J=5.4 Hz, 2H), 2.33 (t, J=5.4 Hz, 2H), 1.47 (s, 9H).

TABLE 4 discloses Intermediates 19-2 through 19-24 that were prepared according to Scheme #12 and 13 following similar procedures described for Intermediate #19-1, which can be achieved by those of ordinary skill in the art of organic synthesis.

TABLE 4

| Intermediate | Structure | Compound Name | Exact Mass [M + H]$^+$ or $^1$H NMR δ (ppm) |
|---|---|---|---|
| 19-2 | 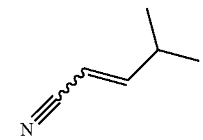 | (2E and Z)-4-methylpent-2-enenitrile | $^1$H NMR (600 MHz, $CDCl_3$): 1:1 E:Z δ 6.68 (dd, J = 16.4, 6.6, 1H), 5.27-5.23 (m, 1H), 1.96-1.82 (m, 1H), 1.04 (d, J = 6.8, 6H); $^1$H NMR (600 MHz, $CDCl_3$): δ 6.31-6.24 (m, 1H), 5.18 (d, J = 10.9, 1H), 1.77-1.64 (m, 1H), 1.06 (d, J = 6.6, 6H). |
| 19-3 | 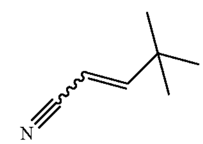 | (2E and Z)-4,4-dimethylpent-2-enenitrile | $^1$H NMR (600 MHz, $CDCl_3$): 1:1 E:Z δ 6.70 (d, J = 16.6, 1H), 5.20 (d, J = 12.3, 5.20, 1H), 1.22 (s, 9H); $^1$H NMR (600 MHz, $CDCl_3$): δ 6.32 (d, J = 12.3, 1H), 5.22 (d, J = 16.6, 1H), 1.05 (s, 9H). |
| 19-4 | 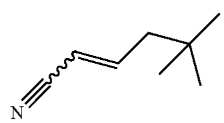 | (2E and Z)-5,5-dimethylhex-2-enenitrile | $^1$H NMR (600 MHz, $CDCl_3$): 1:1 E:Z δ 6.72 (dt, J = 15.9, 7.9, 1H), 5.30 (dt, J = 15.2, 1.49, 1H), 2.08 (dd, J = 7.9, 1.3, 2H), 0.91 (s, 9H). $^1$H NMR (600 MHz, $CDCl_3$) δ 6.53 (dt, J = 11.0, 8.0, 1H), 5.37 (dt, J = 11.0, 1.1, 1H), 2.30 (d, J = 8.0, 2H), 2, 0.95 (s, 9H). |
| 19-5 | 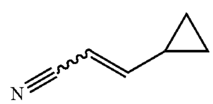 | (2E and 2Z)-3-cyclopropylprop-2-enenitrile | $^1$H NMR (600 MHz, $CDCl_3$): 5:3 E:Z δ 6.10-6.04 (m, 1H), 5.30 (d, J = 16.1 Hz, 1H), 1.58-1.50 (m, 1H), 1.04-0.92 (m, 4H); $^1$H NMR (600 MHz, $CDCl_3$): δ 5.74 (t, J = 10.6, 1H), 5.12 (d, J = 10.6 Hz, 1H), 1.98-1.90 (m, 1H), 0.65-0.58 (m, 4H). |
| 19-6 | 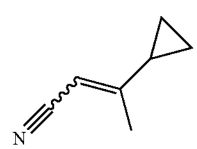 | (2E and Z)-3-cyclopropylbut-2-enenitrile | $^1$H NMR (600 MHz, $CDCl_3$): 3:1 E:Z δ 5.09-5.07 (m, 1H), 1.82-1.81 (m, 3H), 1.53 (t, J = 1.1, 1H), 0.87-0.81 (m, 2H), 0.70-0.65 (m, 2H); $^1$H NMR (600 MHz, $CDCl_3$): δ 5.07-5.06 (m, 1H), 2.17-2.11 (m, 1H), 1.59-1.54 (m, 3H), 0.94-0.88 (m, 2H), 0.78-0.74 (m, 2H). |
| 19-7 | 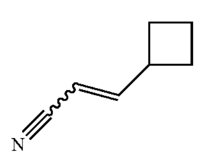 | (2E and Z)-3-cyclobutylprop-2-enenitrile | $^1$H NMR (600 MHz, $CDCl_3$): 1:1 E:Z δ 6.78 (dd, J = 16.3, 6.8, 1H), 5.21 (dd, J = 16.3, 1.5, 1H), 2.30-1.85 (m, 7H); $^1$H NMR (600 MHz, $CDCl_3$): δ 6.53 (dd, J = 10.8, 9.4, 1H), 5.12 (dd, J = 10.9, 0.8, 1H), 2.30-1.85 (m, 7H). |
| 19-8 | 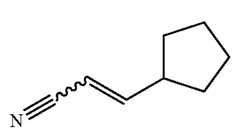 | (2E and 2Z)-3-cyclopentylprop-2-enenitrile | $^1$H NMR (600 MHz, $CDCl_3$): 4:5 E:Z δ 6.68-6.64 (m, 1H), 5.26 (d, J = 17.6 Hz, 1H), 2.60-2.50 (m, 1H), 1.96-1.28 (m, 8H); $^1$H NMR (600 MHz, $CDCl_3$): δ 6.34 (t, J = 10.6, 1H), 5.18 (d, J = 10.9 Hz, 1H), 3.04-2.94 (m, 1H), 1.96- |

TABLE 4-continued

| Intermediate | Structure | Compound Name | Exact Mass [M + H]⁺ or ¹H NMR δ (ppm) |
|---|---|---|---|
| | | | 1.28 (m, 8H). |
| 19-9 | 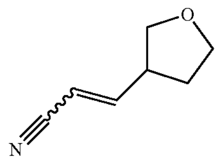 | (2E and 2Z)-3-(tetrahydrofuran-3-yl)prop-2-enenitrile | ¹H NMR (600 MHz, CDCl$_3$): 1:1 E:Z δ 6.63 (dd, J = 16.3, 8.8, 1H), 6.39 (t, J = 10.5, 1H), 5.40-5.35 (m, 1H), 5.31 (d, J = 10.8, 1H), 3.97-3.87 (m, 4H), 3.82-3.77 (m, 2H), 3.56-3.50 (m, 2H), 3.46-3.39 (m, 1H), 3.02-2.92 (m, 1H), 2.27-2.27 (m, 1H), 2.19-2.13 (m, 1H), 1.79-1.67 (m, 2H). |
| 19-10 | 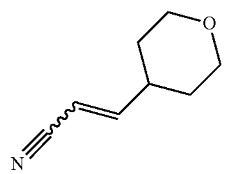 | (2E and 2Z)-3-(tetrahydro-2H-pyran-4-yl)prop-2-enenitrile | ¹H NMR (600 MHz, CDCl$_3$): 1:1 E:Z δ 6.64 (dd, J = 16.5, 6.6, 1H), 5.29 (dd, J = 16.5, 1.6, 1H), 1.77-1.66 (m, 1H), 1.65-1.59 (m, 4H), 1.56-1.43 (m, 4H); ¹H NMR (600 MHz, CDCl$_3$): 6.28 (dd, J = 10.8, 9.8, 1H), 5.27-5.25 (m, 1H), 3.99-3.93 (m, 4H), 3.42 (dtd, J = 34.3, 11.8, 2.2, 4H), 2.43-2.33 (m, 1H). |
| 19-11 | 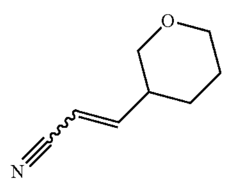 | (2E and 2Z)-3-(tetrahydro-2H-pyran-3-yl)prop-2-enenitrile | ¹H NMR (600 MHz, CDCl$_3$): 3:5 E:Z δ 6.58 (dd, J = 16.5, 7.3, 1H), 5.36 (dd, J = 16.5, 1.4, 1H), 3.88-1.44 (m, 9H); ¹H NMR (600 MHz, CDCl$_3$): δ 6.37 (t, J = 10.5 1H), 5.33 (dd, J = 11.0, 0.6, 1H), 3.88-1.44 (m, 9H). |
| 19-12 | 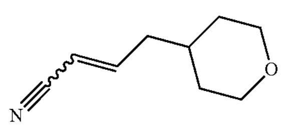 [SMILES: N#CC=CCC1CCOCC1] | (2E and 2Z)-4-(tetrahydro-2H-pyran-4-yl)but-2-enenitrile | ¹H NMR (600 MHz, CDCl$_3$): 1:1 E:Z δ 6.66 (dt, J = 16.2, 7.6, 1H), 5.33 (dt, J = 16.3, 1.5, 1H), 3.97-3.89 (m, 8H), 2.18-2.14 (m, 2H), 1.78-1.54 (m, 1H); ¹H NMR (600 MHz, CDCl$_3$): 6.48 (dt, J = 10.9, 7.8, 1H), 5.37 (dt, J = 10.9, 1.2, 1H), 3.38-3.31 (m, 8H), 2.37 (t, J = 7.3, 2H), 1.78-1.54 (m, 1H). |
| 19-13 | 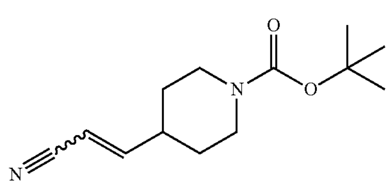 [SMILES: CC(C)(C)OC(=O)N1CCC(C=CC#N)CC1] | tert-butyl 4-[(E and Z)-2-cyanoethenyl]piperidine-1-carboxylate | ¹H NMR (500 MHz, CDCl$_3$): 18:5 E:Z δ 6.70-6.62 (m, 1H), 5.36-5.28 (m, 1H), 4.25-4.05 (m, 2H), 2.85-2.65 (m, 2H), 2.35-2.25 (m, 1H), 1.75-1.68 (m, 2H), 1.46 (s, 9H), 1.38-1.20 (m, 2H); ¹H NMR (500 MHz, CDCl$_3$): δ 6.28 (t, J = 10.4, 1H), 5.29 (d, J = 10.9 Hz, 1H), 4.25-4.00 (m, 2H), 2.90-2.70 (m, 3H), 1.75-1.65 (m, 2H), 1.46 (s, 9H), 1.43-1.30 (m, 2H). |
| 19-14 | 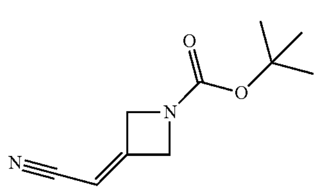 | tert-butyl 3-(cyanomethylidene)azetidine-1-carboxylate | ¹H NMR (600 MHz, CDCl$_3$): δ 5.38-5.35 (m, 1H), 4.69 (m, 2H), 4.61-4.58 (m, 2H), 1.44 (s, 9H). |

TABLE 4-continued

| Intermediate | Structure | Compound Name | Exact Mass [M + H]+ or 1H NMR δ (ppm) |
|---|---|---|---|
| 19-15 | 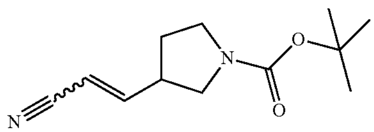 [SMILES: CC(C)(C)OC(=O)N1CCC(C=CC#N)C1] | tert-butyl 3-[(E and Z)-2-cyanoethenyl]pyrrolidine 1-carboxylate | 1H NMR (600 MHz, CDCl3): 4:1 E:Z δ 6.37 (t, J = 10.6 Hz, 1H), 5.35 (d, J = 10.6 Hz, 1H), 3.70-2.86 (m, 5H), 2.20-2.00 (m, 1H), 1.84-1.70 (m, 1H), 1.43 (s, 9H); 1H NMR (600 MHz, CDCl3): δ 6.68-6.60 (m, 1H), 5.35 (dd, J = 16.4, 1.2 Hz, 1H), 3.70-2.86 (m, 5H), 2.20-2.00 (m, 1H), 1.84-1.70 (m, 1H), 1.43 (s, 9H). |
| 19-16 | 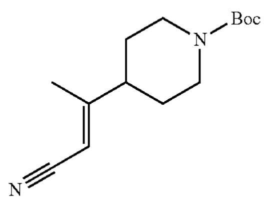 [SMILES: C/C(=C\C#N)C1CCN(C(=O)OC(C)(C)C)CC1] | tert-butyl 4-[(1E and Z)-1-cyanoprop-1-en-2-yl]piperidine-1-carboxylate | Calc'd 251, Found 195 (M + H—C4H8) |
| 19-17 | 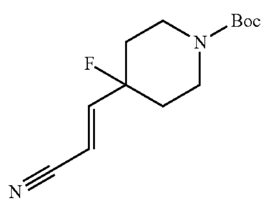 [SMILES: CC(C)(C)OC(=O)N1CCC(F)(/C=C/C#N)CC1] | tert-butyl 4-[(E and Z)-2-cyanoethenyl]-4-fluoropiperidine-1-carboxylate | Calc'd 255, Found 199 (M + H—C4H8) |
| 19-18 | 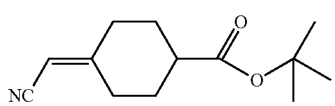 [SMILES: CC(C)(C)OC(=O)C1CCC(=CC#N)CC1] | tert-butyl 4-(cyanomethylidene)cyclohexanecarboxylate | 1H NMR (600 MHz, CDCl3): 5.07 (s, 1H), 2.82 (dt, J = 14.4 and 4.8 Hz, 1H), 2.38-2.46 (m, 2H), 2.16-2.26 (m, 2H), 1.95-2.06 (m, 2H), 1.61-1.71 (m, 2H). |
| 19-19 | 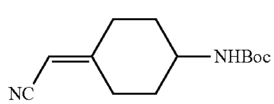 [SMILES: CC(C)(C)OC(=O)NC1CCC(=CC#N)CC1] | tert-butyl [4-(cyanomethylidene)cyclohexyl]carbamate | used as crude |
| 19-20 | 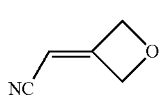 | oxetan-3-ylideneacetonitrile | 1H NMR (600 MHz, CDCl3): 5.33-5.35 (m, 2H), 5.24-5.26 (m, 2H), 5.21-5.22 (m, 1H). |
| 19-21 | 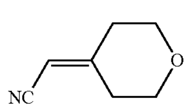 | tetrahydro-4H-pyran-4-ylideneacetonitrile | used as crude |
| 19-22 | 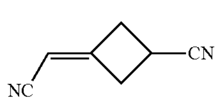 | 3-(cyanomethylidene)cyclobutanecarbonitrile | 1H NMR (600 MHz, CDCl3): 5.27-5.29 (m, 1H), 3.32-3.43 (m, 2H), 3.25-3.41 (m, 3H). |
| 19-23 | 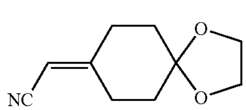 [SMILES: N#CC=C1CCC2(CC1)OCCO2] | 1,4-dioxaspiro[4.5]dec-8-ylideneacetonitrile | used as crude |
| 19-24 | 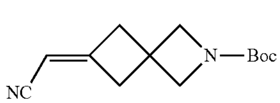 [SMILES: CC(C)(C)OC(=O)N1CC2(CC(=CC#N)C2)C1] | tert-butyl 6-(cyanomethylidene)-2-azaspiro[3.3]heptane-2-carboxylate | 1H NMR (600 MHz, CDCl3): 5.18 (s, 1H), 3.93-3.98 (m, 4H), 3.11 (s, 2H), 3.01 (s, 2H). |

Scheme #13

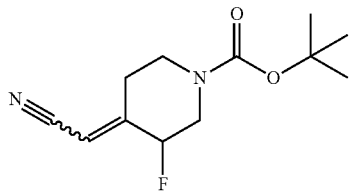

Intermediate #20 tert-Butyl (4E and 4Z)-4-(cyanomethylidene)-3-fluoropiperidine-1-carboxylate

To a solution of NaH (0.27 g, 6.6 mmol, 60% in mineral oil) in DMF (10 mL) was added diethyl (cyanomethyl)phosphonate (1.5 g, 6.6 mmol). The mixture was stirred at ambient temperature for 30 minutes before tert-butyl 3-fluoro-4-oxopiperidine-1-carboxylate (0.70 g, 3.3 mmol) was added. The resulting mixture was stirred for 1 hour before the reaction was quenched with water and the mixture was concentrated in vacuo. The crude residue was purified by MPLC on silica gel to afford the title compound. LRMS (ESI) calc'd for $(C_{12}H_{18}FN_2O_2)$ $[M+H]^+$: 241. Found 241.

Scheme #13

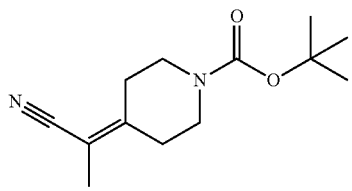

Intermediate #21 tert-Butyl 4-(1-cyanoethylidene)piperidine-1-carboxylate

To a solution of MeI (1.4 g, 10 mmol) in DMF was added NaH (0.40 g, 10 mmol, 60% in mineral oil), followed by diethyl (cyanomethyl)phosphonate (2.3 g, 10 mmol). The mixture was stirred at ambient temperature. After 30 minutes another batch of NaH (0.40 g, 10 mmol, 60% in mineral oil) was added, followed by tert-butyl 4-oxopiperidine-1-carboxylate (2.0 g, 10 mmol). The resulting mixture was stirred for 30 minutes before the reaction was quenched with water and the mixture was concentrated in vacuo. The crude residue was purified by MPLC on silica gel to afford the title compound. LRMS (ESI) calc'd for $C_{13}H_{21}N_2O_2$ $[M+H]^+$ 237. Found 237.

Scheme #13

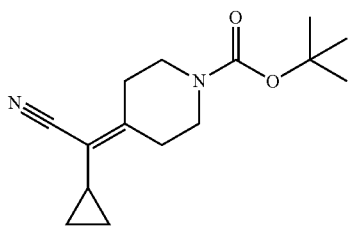

Intermediate #22 tert-Butyl 4-[cyano(cyclopropyl)methylidene]piperidine-1-carboxylate tert-Butyl 4-oxopiperidine-1-carboxylate (2.0 g, 10 mmol) and cyclopropylacetonitrile (0.97 g, 12 mmol) were dissolved in THF (20 mL), heated to reflux, and allowed to stir for 3 hours. The mixture was then cooled to ambient temperature and concentrated in vacuo. The residue was purified by MPLC on silica gel to afford the title compound as a white solid.

LRMS (ESI) calc'd for $C_{15}H_{23}N_2O_2$ $[M+H]^+$263. Found 263.

Scheme #14

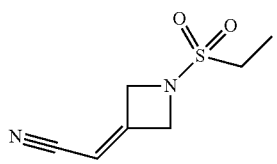

Intermediate #23

Step A-B.
[1-(Ethylsulfonyl)azetidin-3-ylidene]acetonitrile tert-Butyl 3-(cyanomethylidene)azetidine-1-carboxylate (5.0 g, 26 mmol) was dissolved in 4M HCl in dioxane (25.7 mL) and allowed to stir at ambient temperature for 16 hours. The mixture was concentrated to dryness in vacuo, then dissolved in DCM (30.0 mL) and cooled to −10° C. DIPEA (11.6 g, 90.0 mmol) was added followed by ethanesulfonyl chloride (5.0 g, 39 mmol). The resulting mixture was allowed to stir for 7 hours before the mixture was diluted with water and extracted with DCM. The organic layer was dried over anhydrous $Na_2SO_4$, filtered and concentrated in vacuo. The residue was purified by MPLC on silica gel (using a gradient elution of 5-70% EtOAc/heptane). Desired fractions were identified, combined, and concentrated in vacuo to afford the title compound.

LRMS (ESI) calc'd for $C_7H_{10}N_2O_2S$ $[M+H]^+$: 187. Found: 187.

Scheme #14

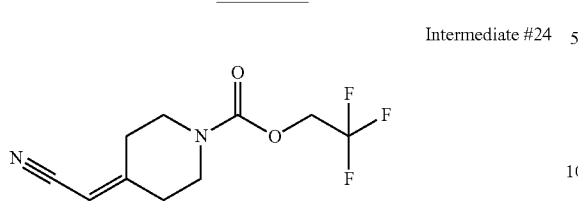

Intermediate #24

2,2,2-Trifluoroethyl 4-(cyanomethylene)piperidine-1-carboxylate

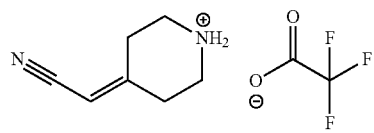 [SMILES: N#CC=C1CC[NH2+]CC1 ; O=C([O-])C(F)(F)F]

Step A. 4-(Cyanomethylidene)piperidinium trifluoroacetate tert-Butyl 4-(cyanomethylene)piperidine-1-carboxylate (5.0 g, 22 mmol) was dissolved in DCM (75.0 mL). TFA (8.7 mL, 112 mmol) was added, and the resulting mixture was allowed to stir at ambient temperature for 2 hours. The mixture was concentrated in vacuo to afford the title compound.

LRMS (ESI) calc'd for $C_7H_{10}N_2$ [M+H]$^+$: 123. Found: 123.

Step B. 2,2,2-Trifluoroethyl 4-(cyanomethylene)piperidine-1-carboxylate 2,2,2-Trifluoroethanol (1.6 mL, 22 mmol) and TEA (6.2 mL, 45 mmol) were dissolved in acetonitrile (200 mL). N,N-disuccinimidyl carbonate (8.6 g, 34 mmol) was added and the resulting mixture was stirred at ambient temperature for 90 minutes. 4-(Cyanomethylidene)piperidinium trifluoroacetate (5.3 g, 23 mmol) in DMSO (10 mL) was then added, followed by TEA (6.2 mL, 45 mmol). The resulting mixture was stirred at 50° C. for 16 hours. The reaction mixture was cooled to ambient temperature, diluted with EtOAc and washed sequentially with saturated NaHCO$_3$ (aq) and water. The organic layer was dried over anhydrous MgSO$_4$, filtered, and concentrated in vacuo. The residue was purified by MPLC on silica gel (using a gradient elution of 0-5% MeOH in DCM) to afford the title compound. LRMS (ESI) calc'd for $C_{10}H_{11}F_3N_2O_2$ [M+H]$^+$: 249. Found: 249.

Scheme #14

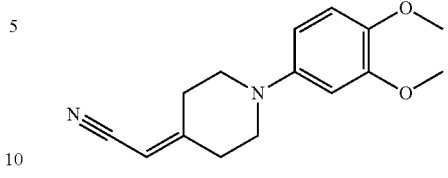

Intermediate #25-1

[1-(3,4-Dimethoxyphenyl)piperidin-4-ylidene]aceto-nitrile

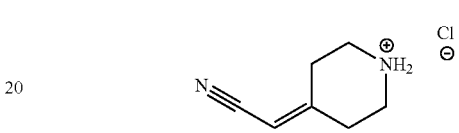

Step A. 4-(Cyanomethylidene)piperidinium chloride tert-Butyl 4-(cyanomethylidene)piperidine-1-carboxylate (20 g, 90 mmol) was dissolved in 4M HCl in dioxane and allowed to stir at ambient temperature for 2 hours. The mixture was then concentrated in vacuo to afford the title compound.

LRMS (ESI) calc'd for $C_7H_{10}N_2$ [M+H]$^+$: 123. Found: 123.

Step B. [1-(3,4-Dimethoxyphenyl)piperidin-4-ylidene]acetonitrile

In a sealed tube, 4-(cyanomethylidene)piperidinium chloride (16 mg, 0.10 mmol), Pd$_2$(dba)$_3$ (14 mg, 0.015 mmol), X-Phos (20 mg, 0.020 mmol), 4-bromo-1,2-dimethoxybenzene (33 mg, 0.15 mmol), and Cs$_2$CO$_3$ (98 mg, 0.30 mmol) were suspended in t-BuOH (0.5 mL). The reaction mixture was purged with argon for 5 minutes, the reaction flask was capped, and heated to 90° C. for 12 hours. The reaction was then cooled to ambient temperature and diluted with DMF:MeCN (1.0 mL, 50:50). To this mixture, Silica Supported-DMT (0.50 mmol, 0.57 mmol/g) followed by Silica Supported-Isocyanate (0.15 mmol, 1.33 mmol/g) was added. The resulting mixture was then shaken at 50° C. for 4 hours. The mixture was then passed through a nylon syringe filter (0.45 µm), and the filtrate was concentrated in vacuo to afford the title compound. The crude residue was used without further purification.

LRMS (ESI) calc'd for $C_{15}H_{18}N_2O_2$ [M+H]$^+$: 259. Found: 259.

TABLE 5 depicts intermediates 25-2 through 25-55 that were prepared according to Scheme #14 following similar procedures described for Intermediates #25-1, which can be achieved by those of ordinary skill in the art of organic synthesis.

TABLE 5

| Intermediate | Structure | Compound Name | Exact Mass [M+ H]+ |
|---|---|---|---|
| 25-2 | 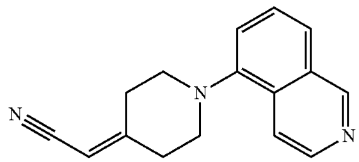 [SMILES: N#CC=C1CCN(c2cccc3cnccc23)CC1] | [1-(isoquinolin-5-yl)piperidin-4-ylidene]acetonitrile | Calc'd 250, Found 250 |
| 25-3 | 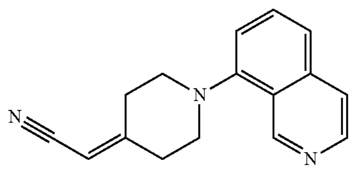 [SMILES: N#CC=C1CCN(c2cccc3ccncc23)CC1] | [1-(isoquinolin-8-yl)piperidin-4-ylidene]acetonitrile | Calc'd 250, Found 250 |
| 25-4 | 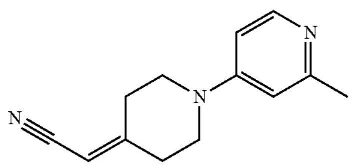 [SMILES: Cc1cc(N2CCC(=CC#N)CC2)ccn1] | 2-(1-(2-methylpyridin-4-yl)piperidin-4-ylidene)acetonitrile | Calc'd 214, Found 214 |
| 25-5 | 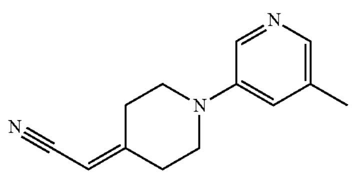 [SMILES: Cc1cncc(N2CCC(=CC#N)CC2)c1] | 2-(1-(5-methylpyridin-3-yl)piperidin-4-ylidene)acetonitrile | Calc'd 214, Found 214 |
| 25-6 | 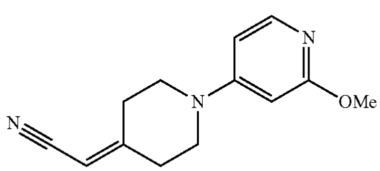 [SMILES: COc1cc(N2CCC(=CC#N)CC2)ccn1] | 2-(1-(2-methoxypyridin-4-yl)piperidin-4-ylidene)acetonitrile | Calc'd 230, Found 230 |
| 25-7 | 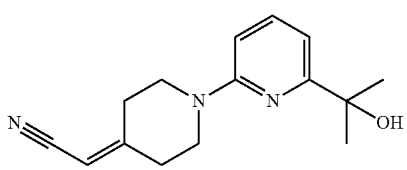 [SMILES: CC(C)(O)c1cccc(N2CCC(=CC#N)CC2)n1] | 2-(1-(6-(2-hydroxypropan-2-yl)pyridin-2-yl)piperidin-4-ylidene)acetonitrile | Calc'd 258, Found 258 |
| 25-8 | 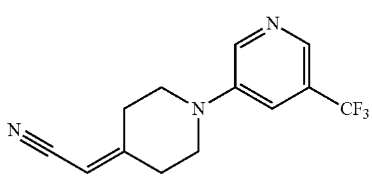 [SMILES: N#CC=C1CCN(c2cncc(C(F)(F)F)c2)CC1] | 2-(1-(5-(trifluoromethyl)pyridin-3-yl)piperidin-4-ylidene)acetonitrile | Calc'd 268, Found 268 |
| 25-9 | 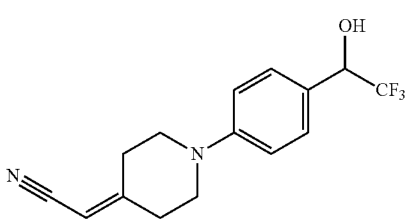 [SMILES: N#CC=C1CCN(c2ccc(C(O)C(F)(F)F)cc2)CC1] | 2-(1-(4-(2,2,2-trifluoro-1-hydroxyethyl)phenyl)piperidin-4-ylidene)acetonitrile | Calc'd 297, Found 297 |

TABLE 5-continued

| Intermediate | Structure | Compound Name | Exact Mass [M+ H]⁺ |
|---|---|---|---|
| 25-10 | 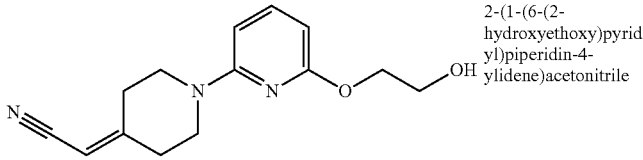 | 2-(1-(6-(2-hydroxyethoxy)pyridin-2-yl)piperidin-4-ylidene)acetonitrile | Calc'd 260, Found 260 |
| 25-11 | 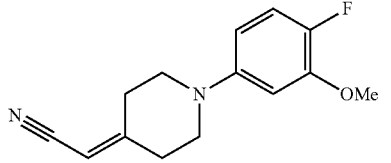 [SMILES: COc1cc(N2CCC(=CC#N)CC2)ccc1F] | 2-(1-(4-fluoro-3-methoxyphenyl)piperidin-4-ylidene)acetonitrile | Calc'd 247, Found 247 |
| 25-12 | 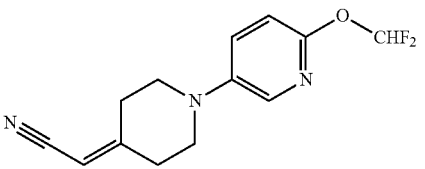 [SMILES: N#CC=C1CCN(c2ccc(OC(F)F)nc2)CC1] | 2-(1-(6-(difluoromethoxy)pyridin-3-yl)piperidin-4-ylidene)acetonitrile | Calc'd 266, Found 266 |
| 25-13 | 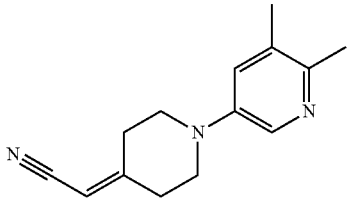 [SMILES: Cc1cc(N2CCC(=CC#N)CC2)cnc1C] | 2-(1-(5,6-dimethylpyridin-3-yl)piperidin-4-ylidene)acetonitrile | Calc'd 228, Found 228 |
| 25-14 | 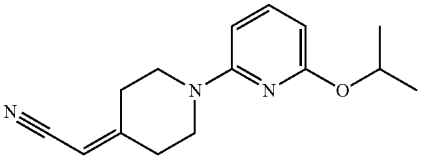 [SMILES: CC(C)Oc1cccc(N2CCC(=CC#N)CC2)n1] | 2-(1-(6-isopropoxypyridin-2-yl)piperidin-4-ylidene)acetonitrile | Calc'd 258, Found 258 |
| 25-15 | 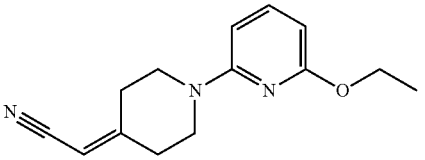 [SMILES: CCOc1cccc(N2CCC(=CC#N)CC2)n1] | 2-(1-(6-ethoxypyridin-2-yl)piperidin-4-ylidene)acetonitrile | Calc'd 244, Found 244 |
| 25-16 | 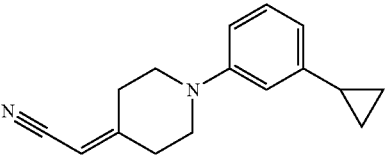 [SMILES: N#CC=C1CCN(c2cccc(C3CC3)c2)CC1] | 2-(1-(3-cyclopropylphenyl)piperidin-4-ylidene)acetonitrile | Calc'd 239, Found 239 |
| 25-17 | 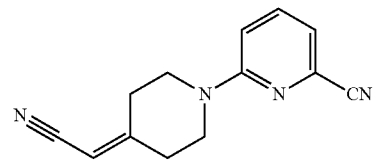 [SMILES: N#CC=C1CCN(c2cccc(C#N)n2)CC1] | 6-(4-(cyanomethylene)piperidin-1-yl)picolinonitrile | Calc'd 225, Found 225 |

TABLE 5-continued

| Intermediate | Structure | Compound Name | Exact Mass [M+ H]+ |
|---|---|---|---|
| 25-18 | 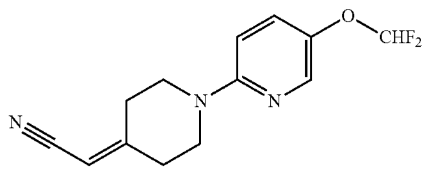 [SMILES: N#CC=C1CCN(c2ccc(OC(F)F)cn2)CC1] | 2-(1-(5-(difluoromethoxy)pyridin-2-yl)piperidin-4-ylidene)acetonitrile | Calc'd 266, Found 266 |
| 25-19 | 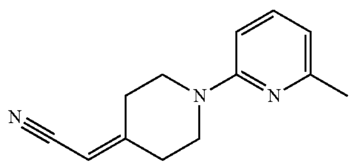 [SMILES: Cc1cccc(N2CCC(=CC#N)CC2)n1] | 2-(1-(6-methylpyridin-2-yl)piperidin-4-ylidene)acetonitrile | Calc'd 214, Found 214 |
| 25-20 | 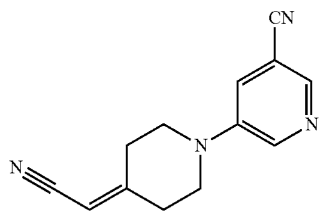 [SMILES: N#CC=C1CCN(c2cncc(C#N)c2)CC1] | 5-(4-(cyanomethylene)piperidin-1-yl)nicotinonitrile | Calc'd 225, Found 225 |
| 25-21 | 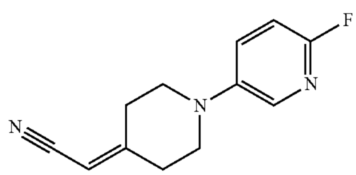 [SMILES: N#CC=C1CCN(c2ccc(F)nc2)CC1] | 2-(1-(6-fluoropyridin-3-yl)piperidin-4-ylidene)acetonitrile | Calc'd 218, Found 218 |
| 25-22 | 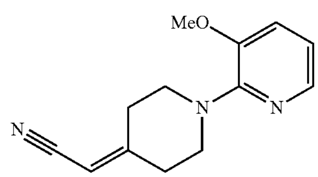 [SMILES: COc1cccnc1N1CCC(=CC#N)CC1] | 2-(1-(3-methoxypyridin-2-yl)piperidin-4-ylidene)acetonitrile | Calc'd 230, Found 230 |
| 25-23 | 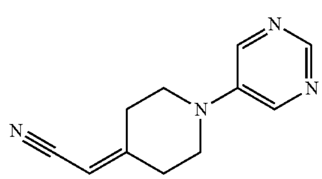 [SMILES: N#CC=C1CCN(c2cncnc2)CC1] | 2-(1-(pyrimidin-5-yl)piperidin-4-ylidene)acetonitrile | Calc'd 201, Found 201 |
| 25-24 | 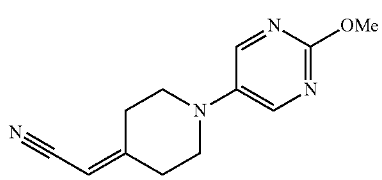 [SMILES: COc1ncc(N2CCC(=CC#N)CC2)cn1] | 2-(1-(2-methoxypyrimidin-5-yl)piperidin-4-ylidene)acetonitrile | Calc'd 231, Found 231 |
| 25-25 | 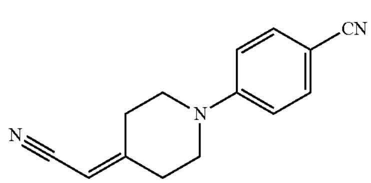 [SMILES: N#CC=C1CCN(c2ccc(C#N)cc2)CC1] | 4-(4-(cyanomethylene)piperidin-1-yl)benzonitrile | Calc'd 224, Found 224 |

TABLE 5-continued

| Intermediate | Structure | Compound Name | Exact Mass [M+ H]⁺ |
|---|---|---|---|
| 25-26 | 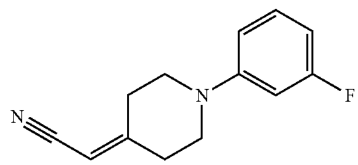 [SMILES: N#CC=C1CCN(c2cccc(F)c2)CC1] | 2-(1-(3-fluorophenyl)piperidin-4-ylidene)acetonitrile | Calc'd 217, Found 217 |
| 25-27 | 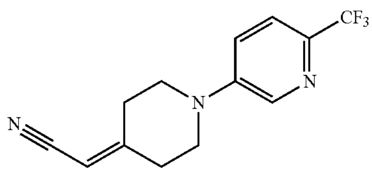 [SMILES: N#CC=C1CCN(c2ccc(C(F)(F)F)nc2)CC1] | 2-(1-(6-(trifluoromethyl)pyridin-3-yl)piperidin-4-ylidene)acetonitrile | Calc'd 268, Found 268 |
| 25-28 | 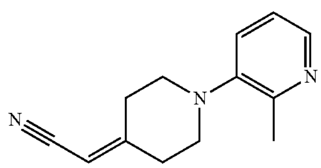 [SMILES: Cc1ncccc1N1CCC(=CC#N)CC1] | 2-(1-(2-methylpyridin-3-yl)piperidin-4-ylidene)acetonitrile | Calc'd 214, Found 214 |
| 25-29 | 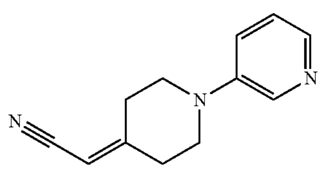 [SMILES: N#CC=C1CCN(c2cccnc2)CC1] | 2-(1-(pyridin-3-yl)piperidin-4-ylidene)acetonitrile | Calc'd 200, Found 200 |
| 25-30 | 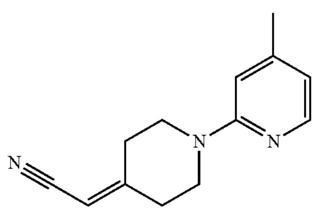 [SMILES: Cc1ccnc(N2CCC(=CC#N)CC2)c1] | 2-(1-(4-methylpyridin-2-yl)piperidin-4-ylidene)acetonitrile | Calc'd 214, Found 214 |
| 25-31 | 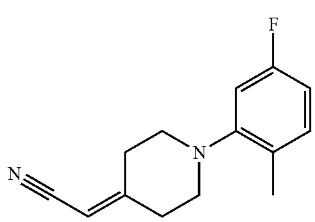 [SMILES: Cc1ccc(F)cc1N1CCC(=CC#N)CC1] | 2-(1-(5-fluoro-2-methylphenyl)piperidin-4-ylidene)acetonitrile | Calc'd 231, Found 231 |
| 25-32 | 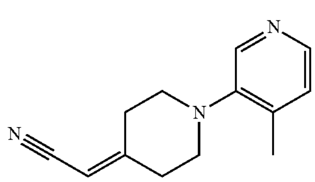 [SMILES: Cc1ccncc1N1CCC(=CC#N)CC1] | 2-(1-(4-methylpyridin-3-yl)piperidin-4-ylidene)acetonitrile | Calc'd 214, Found 214 |
| 25-33 | 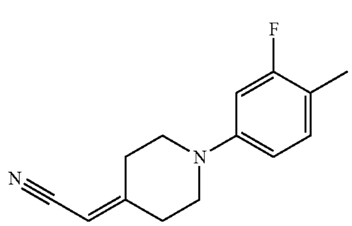 [SMILES: Cc1ccc(N2CCC(=CC#N)CC2)cc1F] | 2-(1-(3-fluoro-4-methylphenyl)piperidin-4-ylidene)acetonitrile | Calc'd 231, Found 231 |

TABLE 5-continued

| Intermediate | Compound Name | Exact Mass [M+ H]+ |
|---|---|---|
| 25-34 | methyl 6-(4-(cyanomethylene)piperidin-1-yl)picolinate | Calc'd 258, Found 258 |
| 25-35 | 2-(1-(6-ethoxypyridin-3-yl)piperidin-4-ylidene)acetonitrile | Calc'd 244, Found 244 |
| 25-36 | 2-(1-(5-methoxypyridin-3-yl)piperidin-4-ylidene)acetonitrile | Calc'd 230, Found 230 |
| 25-37 | 2-(1-(4-fluorophenyl)piperidin-4-ylidene)acetonitrile | Calc'd 217, Found 217 |
| 25-38 | 2-(1-(p-tolyl)piperidin-4-ylidene)acetonitrile | Calc'd 213, Found 213 |
| 25-39 | 2-(1-(3,5-difluorophenyl)piperidin-4-ylidene)acetonitrile | Calc'd 235, Found 235 |
| 25-40 | 2-(1-(2-methoxyphenyl)piperidin-4-ylidene)acetonitrile | Calc'd 229, Found 229 |
| 25-41 | 2-(1-(4-fluoro-3-methylphenyl)piperidin-4-ylidene)acetonitrile | Calc'd 231, Found 231 |

TABLE 5-continued

| Intermediate | Structure | Compound Name | Exact Mass [M+ H]+ |
|---|---|---|---|
| 25-42 | 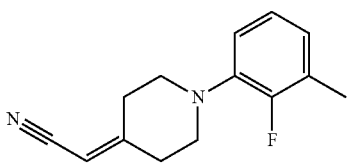 [SMILES: Cc1cccc(N2CCC(=CC#N)CC2)c1F] | 2-(1-(2-fluoro-3-methylphenyl)piperidin-4-ylidene)acetonitrile | Calc'd 231, Found 231 |
| 25-43 | 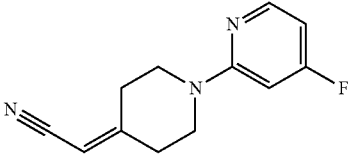 [SMILES: N#CC=C1CCN(c2cc(F)ccn2)CC1] | 2-(1-(4-fluoropyridin-2-yl)piperidin-4-ylidene)acetonitrile | Calc'd 218, Found 218 |
| 25-44 | 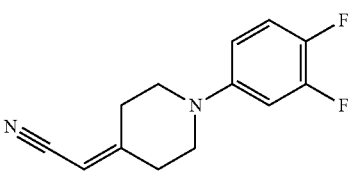 [SMILES: N#CC=C1CCN(c2ccc(F)c(F)c2)CC1] | 2-(1-(3,4-difluorophenyl)piperidin-4-ylidene)acetonitrile | Calc'd 235, Found 235 |
| 25-45 | 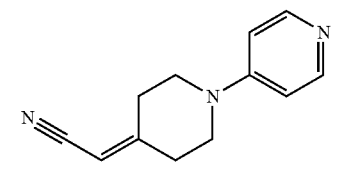 [SMILES: N#CC=C1CCN(c2ccncc2)CC1] | 2-(1-(pyridin-4-yl)piperidin-4-ylidene)acetonitrile | Calc'd 200, Found 200 |
| 25-46 | 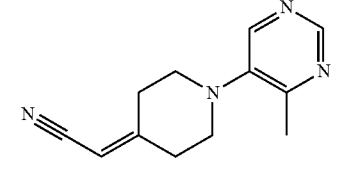 [SMILES: Cc1ncncc1N1CCC(=CC#N)CC1] | 2-(1-(4-methylpyrimidin-5-yl)piperidin-4-ylidene)acetonitrile | Calc'd 215, Found 215 |
| 25-47 | 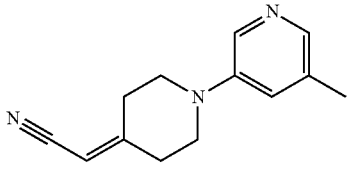 [SMILES: Cc1cncc(N2CCC(=CC#N)CC2)c1] | 2-(1-(5-methylpyridin-3-yl)piperidin-4-ylidene)acetonitrile | Calc'd 214, Found 214 |
| 25-48 | 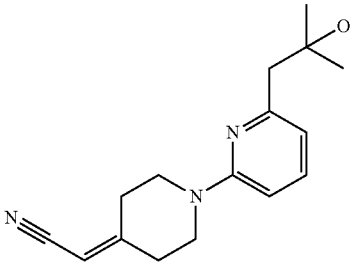 | 2-(1-(6-(2-hydroxy-2-methylpropyl)pyridin-2-yl)piperidin-4-ylidene)acetonitrile | Calc'd 272, Found 272 |
| 25-49 | 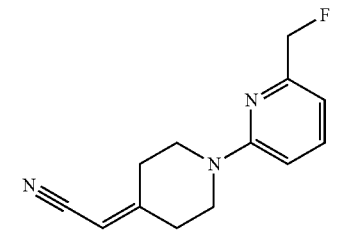 [SMILES: N#CC=C1CCN(c2cccc(CF)n2)CC1] | 2-(1-(6-(fluoromethyl)pyridin-2-yl)piperidin-4-ylidene)acetonitrile | Calc'd 232, Found 232 |

TABLE 5-continued

| Intermediate | Structure | Compound Name | Exact Mass [M+ H]+ |
|---|---|---|---|
| 25-50 | 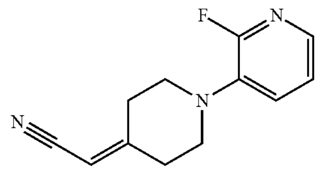 [SMILES: N#CC=C1CCN(c2cccnc2F)CC1] | 2-(1-(2-fluoropyridin-3-yl)piperidin-4-ylidene)acetonitrile | Calc'd 218, Found 218 |
| 25-51 | 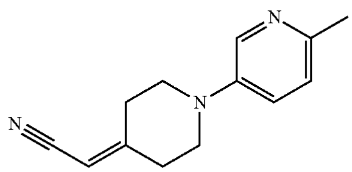 [SMILES: Cc1ccc(N2CCC(=CC#N)CC2)cn1] | 2-(1-(6-methylpyridin-3-yl)piperidin-4-ylidene)acetonitrile | Calc'd 214, Found 214 |
| 25-52 | 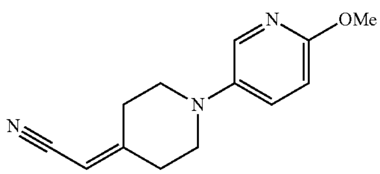 [SMILES: COc1ccc(N2CCC(=CC#N)CC2)cn1] | 2-(1-(6-methoxypyridin-3-yl)piperidin-4-ylidene)acetonitrile | Calc'd 230, Found 230 |
| 25-53 | 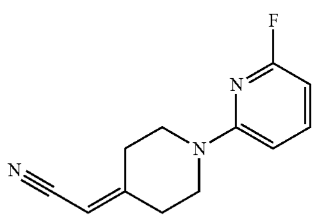 [SMILES: N#CC=C1CCN(c2cccc(F)n2)CC1] | 2-(1-(6-fluoropyridin-2-yl)piperidin-4-ylidene)acetonitrile | Calc'd 218, Found 218 |
| 25-54 | 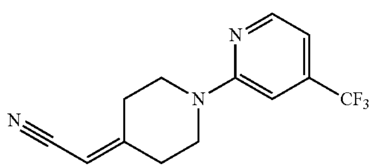 [SMILES: N#CC=C1CCN(c2cc(C(F)(F)F)ccn2)CC1] | 2-(1-(4-(trifluoromethyl)pyridin-2-yl)piperidin-4-ylidene)acetonitrile | Calc'd 268, Found 268 |
| 25-55 | 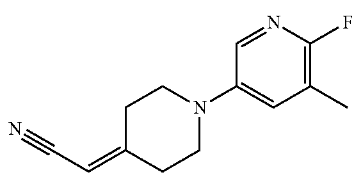 [SMILES: Cc1cc(N2CCC(=CC#N)CC2)cnc1F] | 2-(1-(6-fluoro-5-methylpyridin-3-yl)piperidin-4-ylidene)acetonitrile | Calc'd 232, Found 232 |

Scheme #15

Intermediate #26-1

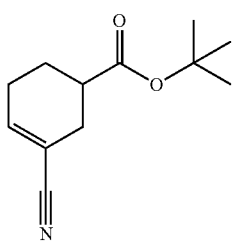

Step A-C. tert-Butyl 3-cyanocyclohex-3-ene-1-carboxylate tert-Butyl 3-oxocyclohexanecarboxylate (1.35 g, 6.81 mmol) was taken up in water (11.4 mL) and stirred at ambient temperature. Sodium metabisulfite (0.75 g, 3.9 mmol) was added and the mixture was allowed to stir for 40 minutes. Diethyl ether (11.4 mL) was added, followed by potassium cyanide (0.70 g, 11 mmol). The resulting mixture was allowed to stir vigorously for 1 hour before it was partitioned between diethyl ether and water. The organic layer was washed with water, brine, dried over anhydrous MgSO4, filtered, and concentrated in vacuo. The residue, used without further purification, was dissolved in DCM (22.0 mL). DIPEA (1.07 g, 8.26 mmol) was added and the resulting mixture was cooled to 0° C. Methanesulfonyl chloride (0.69 g, 6.1 mmol) was added dropwise and the resulting mixture was maintained at 0° C. for 20 minutes then allowed to warm to ambient temperature. The mixture was partitioned between DCM and water. The organic layer was dried over anhydrous Na$_2$SO$_4$, filtered, and concentrated in vacuo. The residue, used without further purification, was dissolved in pyridine (13.6 mL) and heated to 95° C. for 20 hours. The mixture was then allowed to cool to ambient temperature and was concentrated in vacuo. The residue was purified by MPLC on silica gel (using a gradient elution of 0-45% EtOAc/hexanes). Desired fractions were identified, combined, and concentrated in vacuo to afford the title compound.

$^1$H NMR (500 MHz, CDCl$_3$): δ 6.63-6.58 (m, 1H), 2.54-2.48 (m, 1H), 2.44-2.40 (m, 2H), 2.36-2.16 (m, 2H), 2.02-1.94 (m, 1H), 1.71-1.63 (m, 1H), 1.44 (s, 9H).

TABLE 6 depicts intermediates 26-2 through 26-4 that were prepared according to Scheme #15 following similar procedures described for Intermediate #26-1, which can be achieved by those of ordinary skill in the art of organic synthesis.

abisulfite (0.98 g, 5.2 mmol). The resulting mixture was allowed to stir at ambient temperature for 15-30 minutes before diethyl ether (8.9 mL) was added followed by potassium cyanide (0.91 g, 14 mmol). The biphasic mixture was stirred vigorously for at least 30 minutes before the layers were partitioned and the organic layer was washed with water, followed by brine. The organic layer was dried over anhydrous Na$_2$SO$_4$, filtered, and concentrated in vacuo (23° C. water bath) to afford 4-methyl-1-hydroxycyclohexanecarbonitrile as a crude residue, which was carried forward without further purification. The crude residue (0.50 g, 3.6 mmol) was combined with pyridine (18.3 mL, 226 mmol), and POCl$_3$ (1.34 mL, 14.4 mmol) in a microwave vial and sealed. The reaction mixture was heated to reflux for 16 hours. The reaction mixture was then cooled to ambient temperature, diluted with diethyl ether, and washed with 2N aqueous HCl saturated with sodium chloride (3×). The organic layer was washed with brine, dried over anhydrous MgSO$_4$, filtered,

TABLE 6

| Intermediate | Structure | Compound Name | $^1$H NMR δ (ppm) |
|---|---|---|---|
| 26-2 | 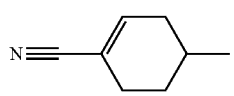 | methyl 3-cyanocyclohex-3-ene-1-carboxylate | $^1$H NMR (500 MHz, CDCl$_3$): δ 6.66-6.60 (m, 1H), 3.70 (s, 3H), 2.68-2.60 (m, 1H), 2.52-2.44 (m, 2H), 2.40-2.18 (m, 2H), 2.10-2.00 (m, 1H), 1.80-1.66 (m, 1H). |
| 26-3 | 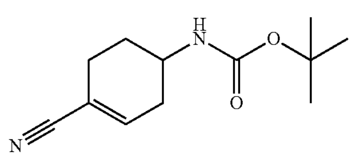 [SMILES: CC(C)(C)OC(=O)NC1CC=C(C#N)CC1] | 4-tert-butyl (4-cyanocyclohex-3-en-1-yl)carbamate | $^1$H NMR (600 MHz, CDCl$_3$): δ 6.53-6.50 (m, 1H), 4.46 (s, 1H), 3.77 (s, 1H), 2.58 (br d, J = 19.9 Hz, 1H), 2.48-2.27 (br d, J = 19.2 Hz, 2H), 2.03 (ddq, J = 19.3, 8.0, 3.6, 1H), 1.96-1.91 (m, 1H), 1.63-1.56 (m, 1H), 1.42 (s, 9H). |
| 26-4 | 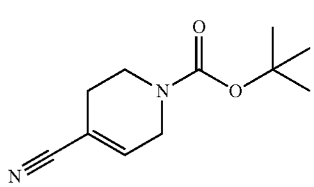 | tert-butyl 4-cyano-3,6-dihydropyridine-1(2H)-carboxylate | $^1$H NMR (500 MHz, CDCl$_3$): δ 6.55 (br s, 1H), 4.05 (m, 2H), 3.55 (t, J = 5.6 Hz, 2H), 2.34 (br s, 2H), 1.46 (s, 9H). |

Scheme #15

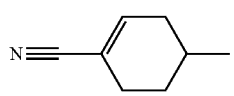

Intermediate #27-1

Step A-B. 4-Methylcyclohex-1-ene-1-carbonitrile

4-Methylcyclohexanone (1.0 g, 8.9 mmol) was added to a stirred solution of water (8.9 mL) containing sodium metand concentrated in vacuo (23° C. water bath) to afford the title compound as an oil.

$^1$H NMR (600 MHz, CDCl$_3$): δ 6.59-6.56 (m, 1H), 2.28-2.20 (m, 3H), 1.80-1.71 (m, 2H), 1.71-1.59 (m, 1H), 1.28-1.21 (m, 1H), 0.96 (d, J=6.6, 3H).

TABLE 7 depicts intermediates 27-2 and 27-3 were prepared according to Scheme #15 following similar procedures described for Intermediate #27-1, which can be achieved by those of ordinary skill in the art of organic synthesis.

TABLE 7

| Intermediate | Structure | Compound Name | $^1$H NMR δ (ppm) |
|---|---|---|---|
| 27-2 | ![structure] | methyl 4-cyanocyclohex-3-ene-1-carboxylate | $^1$H NMR (600 MHz, CDCl$_3$): δ 6.61-6.57 (m, 1H), 3.68 (s, 3H), 2.62-2.54 (m, 1H), 2.48-2.40 (m 2H), 2.36-2.22 (m, 2H), 2.10-2.02 (m, 1H), 1.80-1.70 (m, 1H). |
| 27-3 | ![structure] | 4,4-dimethylcyclohex-1-ene-1-carbonitrile | $^1$H NMR (600 MHz, CDCl$_3$): δ 6.55-6.52 (m, 1H), 2.24-2.19 (m, 2H), 1.96-1.91 (m, 2H), 1.41 (t, J = 6.4, 2H), 0.91 (s, 6H). |

Scheme #16

Intermediate #28

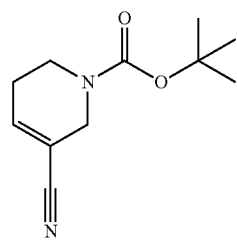

Steps A-B. tert-Butyl
5-cyano-3,6-dihydropyridine-1(2H)-carboxylate

A solution of n-butyllithium (2.8 mL, 7.0 mmol, 2.5 M in hexanes) was added to a solution of diisopropylamine (1.0 mL, 7.0 mmol) in THF (10.0 mL) at 78° C. The cooling bath was removed for 15 minutes, and then the reaction mixture was cooled back to 78° C. A solution of tert-butyl 3-oxopiperidine-1-carboxylate (1.0 g, 5.0 mmol) in THF (6 mL) was added to the cooled solution of LDA dropwise over 5 minutes, maintained for 15 minutes, and then N-(5-chloropyridin-2-yl)-1,1,1-trifluoro-N-[(trifluoromethyl)sulfonyl]methanesulfonamide (2.4 g, 6.0 mmol) was added in one portion. The reaction mixture was stirred at 78° C. for 15 minutes, and then the cooling bath was removed. The reaction mixture was stirred for 45 minutes after removal of the cooling bath, and was then partitioned between EtOAc and water. The organic layer was washed with brine, dried over anhydrous Na$_2$SO$_4$ and filtered. The filtrate was concentrated in vacuo and the residue was purified by MPLC on silica gel (using a gradient elution of 0-20%, diethyl ether/hexanes) to afford tert-butyl 5-{[(trifluoromethyl)sulfonyl]oxy}-3,6-dihydropyridine-1 (2H)-carboxylate as the second regioisomer to elute. A portion of the product (123 mg, 0.371 mmol) was combined with zinc cyanide (52 mg, 0.45 mmol), Pd(PPh$_3$)$_4$ (64 mg, 0.056 mmol) and DMF (1.9 mL) in a microwave tube. The reaction mixture was heated in the microwave at 100° C. for 20 minutes. After cooling to 23° C., the reaction mixture was partitioned between EtOAc and water. The organic layer was washed with brine, dried over anhydrous Na$_2$SO$_4$ and filtered. The filtrate was concentrated in vacuo and the residue was purified by MPLC on silica gel (using a gradient elution of 0-100%, EtOAc/hexanes) to afford the title compound.

$^1$H NMR (500 MHz, CDCl$_3$): δ 6.73 (br s, 1H), 4.02 (br s, 2H), 3.49 (t, J=5.6 Hz, 2H), 2.29 (br s, 2H), 1.47 (s, 9H).

Scheme #17

Intermediate #29

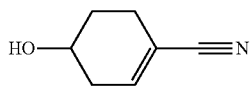

4-Hydroxycyclohex-1-ene-1-carbonitrile

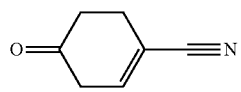

Step A. 4-Oxocyclohex-1-ene-1-carbonitrile

In a sealed tube, {[(3E)-4-methoxybuta-1,3-dien-2-yl]oxy}(trimethyl)silane (5.65 mL, 29.0 mmol) and acrylonitrile (1.91 mL, 29.0 mmol) were combined in benzene (9.67 mL), heated to reflux, and allowed to stir for 16 hours. The reaction mixture was then cooled to ambient temperature and the volatiles were removed in vacuo (23° C. water bath). The residue was stirred into a mixture of 1N aqueous HCl (29.0 mL, 29.0 mmol) and THF (9.67 mL). After being stirred at ambient temperature for 3 hours, the reaction mixture was extracted with diethyl ether. The organic layer was washed with de-ionized water (2×), brine, dried over anhydrous Na$_2$SO$_4$, filtered and concentrated in vacuo (23° C. water bath). The residue was purified by MPLC on silica gel (using a gradient elution of 0-50% hexanes/acetone). Desired fractions were identified, combined and concentrated in vacuo (23° C. water bath) to afford the title compound.

$^1$H NMR (600 MHz, CDCl$_3$): δ 6.68 (tt, J=4.0, 1.5, 1H), 3.05 (dt, J=4.3, 2.2, 2H), 2.71 (tq, J=6.9, 1.9, 2H), 2.61-2.53 (t, J=6.9 2H).

Step B. 4-Hydroxycyclohex-1-ene-1-carbonitrile

To a stirred solution of 4-oxocyclohex-1-ene-1-carbonitrile (170 mg, 1.40 mmol) in MeOH (2.3 mL) at −78° C. was added cerium (III) chloride (484 mg, 1.96 mmol) in MeOH (4.7 mL). The resulting mixture was allowed to stir for 5 minutes at −78° C. before NaBH$_4$ (48 mg, 1.26 mmol) was added in one portion. The mixture was stirred for 20 minutes and then allowed to warm to ambient temperature. After being stirred for 30 minutes, the reaction mixture was diluted with water and extracted with diethyl ether (3×). The combined organic extracts were washed with brine, dried over anhydrous Na₂SO₄, filtered, and concentrated in vacuo (23° C. water bath) to afford the title compound.

$^1$H NMR (600 MHz, CDCl₃): δ 6.50 (tt, J=3.9, 1.8, 1H), 4.03-3.98 (m, 1H), 3.50-3.42 (qd, J=11.4, 4.5, 1H), 2.50 (br d, J=19.2, 1H), 2.46-2.38 (m, 1H), 2.33-2.23 (m, 1H), 2.21-2.13 (m, 1H), 1.90-1.84 (m, 1H), 1.76-1.67 (m, 1H).

Scheme #18

Intermediate #30

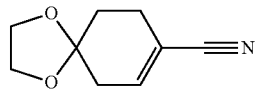

1,4-Dioxaspiro[4.5]dec-7-ene-8-carbonitrile

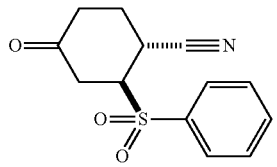 [SMILES: N#C[C@H]1CCC(=O)C[C@@H]1S(=O)(=O)c1ccccc1]

Step A-C. (1R,2S and 1S,2R)-4-Oxo-2-(phenylsulfonyl)cyclohexanecarbonitrile

Benzenesulfinic acid sodium salt (9.4 g, 57 mmol) was dissolved in a mixture of water (18.3 mL) and acetic acid (9.1 mL). 2-Chloroprop-2-enenitrile (4.6 mL, 57 mmol) was added, followed by MeOH (18.3 mL). The resulting mixture was allowed to stir for 10 minutes before the solid product was collected by filtration and rinsed with minimal water. The majority of the solid filtered through with the rinse and so all material was rinsed through the filter. The filtrate was extracted with DCM (2×) and the combined organic layers were washed with saturated aqueous NaHCO₃, brine, dried over anhydrous Na₂SO₄, filtered, and concentrated in vacuo to afford 2-chloro-3-(phenylsulfonyl)propanenitrile as a crude residue. Crude 2-chloro-3-(phenylsulfonyl)propanenitrile (6.1 g, 27 mmol) was dissolved in chloroform (41 mL) cooled in an ice-salt bath and stirred before adding TEA (3.7 mL, 27 mmol) dropwise. The mixture was allowed to stir at 0° C. for 20 minutes. The reaction mixture was then washed sequentially with dilute 1N aqueous HCl, followed by saturate aqueous NaHCO₃. The organic layer was dried over anhydrous Na₂SO₄, filtered, and concentrated in vacuo (23° C. water bath) to afford (2E and 2Z)-3-(phenylsulfonyl)prop-2-enenitrile as a crude residue. The crude residue (4.9 g, 25 mmol) and (buta-1,3-dien-2-yloxy)(trimethyl)silane (4.2 g, 29 mmol) were refluxed together in benzene (63.8 mL) under nitrogen for 16 hours. The reaction mixture was then concentrated in vacuo to afford an oily mixture of the intermediate adducts. The residue was dissolved in aqueous acetic acid (80%) and allowed to stir. After 1 hour at ambient temperature, the mixture was diluted with water and extracted with DCM (2×). The combined organic extracts were concentrated in vacuo and the residue was dissolved in DCM. A solid precipitated from the solution and was collected by filtration to afford the title compound.

$^1$H NMR (600 MHz, CDCl₃): δ 7.91 (d, J=7.7, 2H), 7.74 (t, J=7.4, 1H), 7.63 (t, J=7.8, 2H), 3.81 (q, J=4.4, 1H), 3.68 (q, J=4.8, 1H), 2.76 (dd, J=16.5, 6.3, 1H), 2.74-2.66 (m, 1H), 2.62 (dd, J=11.4, 4.5, 1H), 2.61-2.56 (m, 2H), 2.25 (dq, J=14.3, 4.9, 1H).

Step D-E.
1,4-Dioxaspiro[4.5]dec-7-ene-8-carbonitrile
(Intermediate #30)

To a pressure vessel was added (1R,2S and 1S,2R)-4-oxo-2-(phenylsulfonyl) cyclohexanecarbonitrile (100 mg, 0.380 mmol), benzene (19.0 mL), ethylene glycol (0.90 mL, 16 mmol), and p-toluenesulfonic acid monohydrate (14 mg, 0.076 mmol). The vessel was capped and the reaction mixture was heated to reflux and allowed to stir for 16 hours. The reaction mixture was allowed to cool to ambient temperature before it was diluted with EtOAc. The organic layer was washed with water (3×), brine, dried over anhydrous Na₂SO₄, filtered, and concentrated in vacuo (23° C. water bath) to afford (7S,8R and 7R,8S)-7-(phenylsulfonyl)-1,4-dioxaspiro[4.5]decane-8-carbonitrile as a crude residue. To the crude residue (110 mg, 0.358 mmol) was added THF (7.1 mL) and potassium tert-butoxide (137 mg, 1.22 mmol). The reaction mixture was allowed to stir at ambient temperature for 15 minutes before it was diluted with diethyl ether. The organic layer was washed with water, brine, dried over anhydrous MgSO₄, filtered, and concentrated in vacuo (23° C. water bath) to afford the title compound.

$^1$H NMR (600 MHz, CDCl₃): δ 6.48 (tt, J=4.0, 1.8, 1H), 3.96 (s, 4H), 2.45 (tq, J=6.6, 2.2, 2H), 2.39 (q, J=3.1, 2H), 1.78 (t, J=6.6, 2H).

Scheme #19

Intermediate #31-1

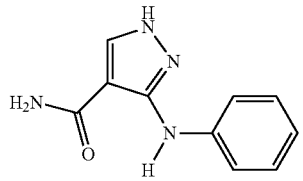

3-(Phenylamino)-1H pyrazole-4-carboxamide

3-Amino-1H-pyrazole-4-carboxamide (19.8 g, 157 mmol), K₃PO₄ (66.7 g, 314 mmol), bromobenzene (23.2 mL, 220 mmol) and 2-propanol (785 mL) were combined in a round bottom flask and purged with a stream of N₂ gas for 40 minutes. Pd₂(dba)₃ (1.80 g, 1.96 mmol) and 2-di-t-butylphosphino-3,4,5,6-tetramethyl-2',4',6'-tri-i-propylbiphenyl (3.77 g, 7.85 mmol) were added and the reaction was purged for an additional 5 minutes. The reaction mixture was then heated to 80° C. and allowed to stir under a N₂ atmosphere for 12 hours. The mixture was then allowed to cool to ambient temperature for an additional 16 hours. The reaction mixture was diluted with EtOAc (300 mL) and filtered through celite (slowly). The celite was washed with EtOAc (300 mL) and the combined filtrates were concentrated in vacuo to afford an oil which was purified by MPLC on silica gel (using a gradient elution of 0-10% MeOH/DCM). The major, low rf product, was isolated to afford a reddish-brown oily solid. The brown solid was suspended in 40 mL of warm MeOH, cooled to ambient temperature, and water (40 mL) was added. The mixture was stirred for 30 minutes and filtered. The solid was suction dried for 16 hours to afford the title compound as a peach-colored solid.

LRMS (ESI) calc'd for $C_{10}H_{10}N_4O$ $[M+H]^+$: 203. Found: 203.

The following intermediates shown in TABLE 8 were prepared according to Scheme #19 following similar procedures described for Intermediate #31-1, which can be achieved by those of ordinary skill in the art of organic synthesis.

TABLE 8

| Intermediate | Structure | Compound Name | Exact Mass $[M + H]^+$ |
|---|---|---|---|
| 31-2 | 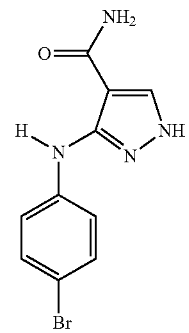 [SMILES: NC(=O)c1c[nH]nc1Nc1ccc(Br)cc1] | 3-[(4-bromophenyl)amino]-1H-pyrazole-4-carboxamide | Calc'd 280, Found 280 |
| 31-3 | 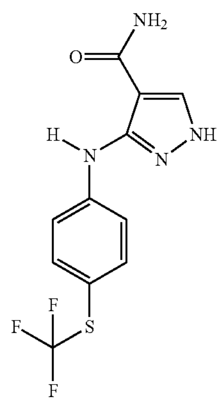 [SMILES: NC(=O)c1c[nH]nc1Nc1ccc(SC(F)(F)F)cc1] | 3-({4-[(trifluoromethyl)sulfanyl]-phenyl}amino)-1H-pyrazole-4-carboxamide | Calc'd 303, Found 303 |
| 31-4 | 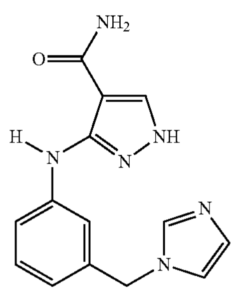 [SMILES: NC(=O)c1c[nH]nc1Nc1cccc(Cn2ccnc2)c1] | 3-{[3-(1H-imidazol-1-ylmethyl)phenyl]amino}-1H-pyrazole-4-carboxamide | Calc'd 283, Found 283 |
| 31-5 | 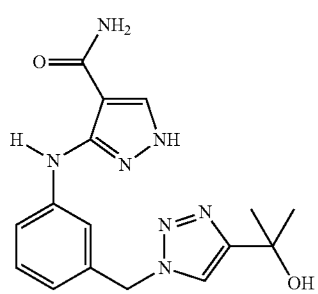 [SMILES: CC(C)(O)c1cn(Cc2cccc(Nc3n[nH]cc3C(N)=O)c2)nn1] | 3-[(3-{[4-(2-hydroxypropan-2-yl)-1H-1,2,3-triazol-1-yl]methyl}phenyl)amino]-1H-pyrazole-4-carboxamide | Calc'd 342, Found 342 |

TABLE 8-continued

| Intermediate | Structure | Compound Name | Exact Mass [M + H]+ |
|---|---|---|---|
| 31-6 | 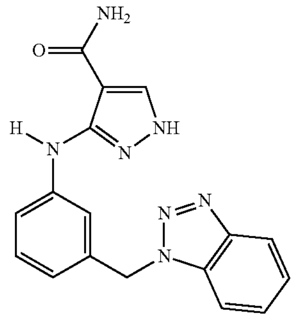 [SMILES: NC(=O)c1c[nH]nc1Nc1cccc(Cn2nnc3ccccc32)c1] | 3-{[3-(1H-benzotriazol-1-ylmethyl)phenyl]amino}-1H-pyrazole-4-carboxamide | Calc'd 334, Found 334 |
| 31-7 | 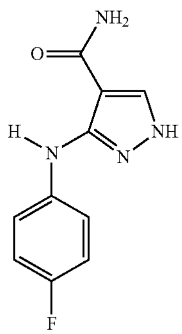 [SMILES: NC(=O)c1c[nH]nc1Nc1ccc(F)cc1] | 3-[(4-fluorophenyl)amino]-1H-pyrazole-4-carboxamide | Calc'd 221, Found 221 |
| 31-8 | 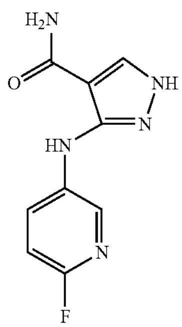 [SMILES: NC(=O)c1c[nH]nc1Nc1ccc(F)nc1] | 3-[(6-fluoropyridin-3-yl)amino]-1H-pyrazole-4-carboxamide | Calc'd 222, found 222 |

Intermediate #32

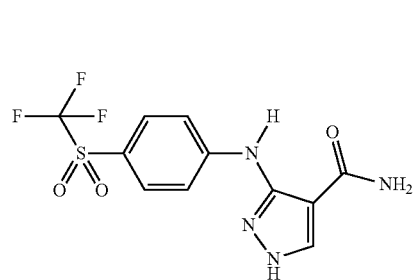

3-({4-[(trifluoromethyl)sulfonyl]phenyl}amino)-1H-pyrazole-4-carboxamide

The title compound, Intermediate #32, can be prepared according to the general procedure described for Intermediate #31-1 using 3-amino-1H-pyrazole-4-carboxamide (0.48 g, 3.8 mmol) and 1-bromo-4-[(trifluoromethyl)sulfonyl]benzene (1.0 g, 3.5 mmol) as starting materials.

LRMS (ESI) calc'd for $C_{17}H_{18}FN_5O_2$ [M+H]+: 335. Found: 335.

Alternatively, the title compound, Intermediate #32, can also be prepared by dissolving 3-({4-[(trifluoromethyl)sulfanyl]phenyl}amino)-1H-pyrazole-4-carboxamide (Intermediate 31-3) (0.50 g, 1.6 mmol) in acetic acid (5.0 mL) followed by the addition of hydrogen peroxide (0.87 mL, 9.9 mmol, 35 wt % in water). The resulting mixture was heated to 50° C. for 18 hours before additional hydrogen peroxide (0.87 mL, 9.9 mmol, 35 wt % in water) was added and the mixture was heated to 80° C. for 8 hours. The mixture was cooled to ambient temperature, concentrated in vacuo and diluted with EtOAc. The mixture was washed three times with aqueous sodium thiosulfate adjusted to pH>8 with saturated aqueous bicarbonate. The organic layer was collected, dried over anhydrous $Na_2SO_4$, filtered and concentrated in vacuo. The residue was purified by MPLC on silica gel (15% MeOH/DCM). Desired fractions were identified, combined, and concentrated in vacuo to afford the title compound.

LRMS (ESI) calc'd for $C_{11}H_9F_3N_4O_3S$ [M+H]+: 335. Found: 335.

Scheme #19

Intermediate #33

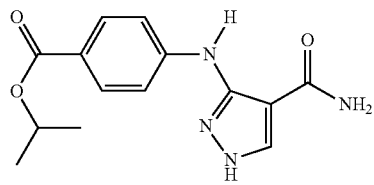

Propan-2-yl 4-[(4-carbamoyl-1H-pyrazol-3-yl)amino]benzoate

A round-bottomed flask was charged with 2-propanol (595 mL), and nitrogen was bubbled through the 2-propanol for 2 hours. Pd$_2$(dba)$_3$ (1.63 g, 1.78 mmol) and di-tert-butyl(2',4', 6'-triisopropyl-3,4,5,6-tetramethylbiphenyl-2-yl)phosphine (3.43 g, 7.14 mmol) were added, and the mixture was stirred for 20 minutes. Potassium acetate (17.5 g, 178 mmol), 3-amino-1H-pyrazole-4-carboxamide (15.0 g, 119 mmol), and isopropyl 4-bromobenzoate (34.7 g, 143 mmol) were then added, and the reaction mixture was heated to 75° C. for 6.5 hours. The reaction mixture was then cooled to 23° C., diluted with EtOAc (500 mL), and filtered through celite. The filtrate was adsorbed onto silica gel in vacuo and purified by MPLC on silica gel (using a gradient elution of 30-90%, EtOAc/hexanes) to afford the title compound.

LRMS (ESI) calc'd for C$_{14}$H$_{17}$N$_4$O$_3$ [M+H]$^+$: 289. Found: 289.

Scheme #20

Intermediate #34-1

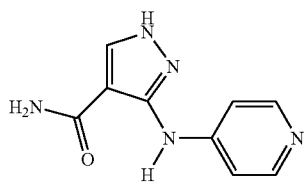

3-(Pyridin-4-ylamino)-1H-pyrazole-4-carboxamide

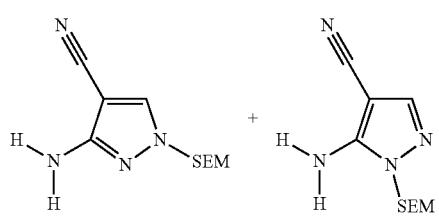 [SMILES: C[Si](C)(C)CCOCn1cc(C#N)c(N)n1 ; C[Si](C)(C)CCOCn1ncc(C#N)c1N]

Step A. 3-Amino-1-{[2-(trimethylsilyl)ethoxy]methyl}-1H-pyrazole-4-carbonitrile and 5-Amino-1-{[2-(trimethylsilyl)ethoxy]methyl}-1H-pyrazole-4-carbonitrile 3-Amino-1H-pyrazole-4-carbonitrile (10 g, 93 mmol) and NaH (4.0 g, 100 mmol, 60% dispersion in oil) were suspended in DMF (60 mL) at 0° C. SEMCl (19.7 mL, 111 mmol) was added dropwise and the resulting mixture was maintained at ambient temperature for 16 hours. Water was added and the mixture was extracted with EtOAc. The combined organic extracts were washed with brine, dried over anhydrous MgSO$_4$, filtered and concentrated in vacuo. Purification of the residue by MPLC on silica gel gave a mixture of two regioisomers as a yellow oily solid. 3-amino-1-{[2-(trimethylsilyl)ethoxy]methyl}-1H-pyrazole-4-carbonitrile and 5-amino-1-{[2-(trimethylsilyl)ethoxy]methyl}-1H-pyrazole-4-carbonitrile $^1$H NMR (600 MHz, DMSO-d$_6$): δ 7.54 (s, 1H), 6.77 (s, 2H), 5.21 (s, 2H), 3.49 (m, 2H), 0.78 (m, 2H), 0.08 (s, 9H). $^1$H NMR (600 MHz, DMSO-d$_6$): δ 8.24 (s, 1H), 5.60 (s, 2H), 5.11 (s, 2H), 3.47 (m, 2H), 0.79 (m, 2H), 0.07 (s, 9H).

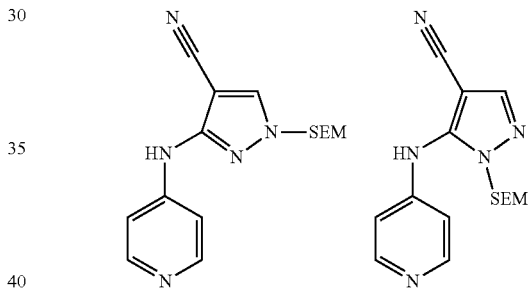

Step B. 3-(Pyridin-4-ylamino)-1-{[2-(trimethylsilyl)ethoxy]methyl}-1H-pyrazole-4-carbonitrile and 5-(pyridin-4-ylamino)-1-{[2-(trimethylsilyl)ethoxyl]methyl}-1H-pyrazole-4-carbonitrile To a microwave vessel was added a mixture of 3-amino-1-{[2-(trimethylsilyl) ethoxy]methyl}-1H-pyrazole-4-carbonitrile and 5-amino-1-{[2-(trimethylsilyl)ethoxy]methyl}-1H-pyrazole-4-carbonitrile (500 mg, 2.1 mmol), 4- iodopyridine (0.52 g, 2.5 mmol), dioxane (10.5 mL) and K$_3$PO$_4$ (0.89 g, 4.2 mmol). The mixture was degassed by bubbling nitrogen gas for 5 minutes. Pd$_2$(dba)$_3$ (0.19 mg, 0.21 mmol), and X-Phos (0.30 g, 0.63 mmol) were then added, and the mixture was heated to 100° C. and allowed to stir for 14 hours. The mixture was then allowed to cool to ambient temperature and was filtered through celite. The filtrate was adsorbed on silica gel in vacuo and the mixture was purified by MPLC on silica gel (using a gradient elution of 20-100% EtOAc/DCM) to afford the title compounds. LRMS (ESI) calc'd for C$_{15}$H$_{22}$N$_5$OSi [M+H]$^+$: 316. Found: 316.

Step C.
3-(Pyridin-4-ylamino)-1H-pyrazole-4-carboxamide

To a solution containing a mixture of 3-(pyridin-4-ylamino)-1-{[2-(trimethylsilyl)ethoxy]methyl}-1H-pyrazole-4-carbonitrile and 5-(pyridin-4-ylamino)-1-{[2-(trimethylsilyl)ethoxy]methyl}-1H-pyrazole-4-carbonitrile (150 mg, 0.5 mmol) in DMSO (1.2 mL) and EtOH (1.2 mL) was added 5M aqueous NaOH (0.7 mL, 3.3 mmol). The mixture was heated to 55° C., followed by the dropwise addition of 30% $H_2O_2$ (0.7 mL, 7.1 mmol). After 10 minutes, additional 30% $H_2O_2$ (0.30 mL, 3.4 mmol) was added dropwise. The mixture was maintained for 30 minutes before it was allowed to cool to ambient temperature. To the crude reaction mixture was added MeOH (1 mL) and 6N aqueous HCl (2 mL). The resulting mixture was heated at 55° C. for 1.5 hours. Additional 6N aqueous HCl (1 mL) was added and the mixture continued stirring for another 1 hour. The mixture was cooled to ambient temperature and carefully neutralized with 5N aqueous NaOH until pH 6-7. The mixture was then concentrated in vacuo to remove most of the solvent. To the slurry-like residue was added MeOH (20 mL), and the resulting mixture was sonicated for 5 minutes. The mixture was filtered to remove insoluble precipitate and the filtrate was concentrated in vacuo to afford crude residue containing the title compound, Intermediate #34-1, which was used without further purification.

LRMS (ESI) calc'd for $C_9H_9N_5O$ [M+H]$^+$: 204. Found: 204.

The following intermediates shown in TABLE 9 were prepared according to Scheme #20 following similar procedures described for Intermediate #34-1, which can be achieved by those of ordinary skill in the art of organic synthesis.

Scheme #21

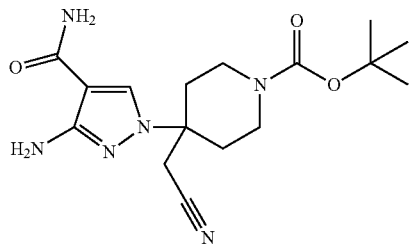

Intermediate #35-1 tert-Butyl 4-(3-amino-4-carbamoyl-1H-pyrazol-1-yl)-4-(cyanomethyl)piperidine-1-carboxylate 3-Amino-1H-pyrazole-4-carboxamide (0.80 g, 6.3 mmol) and tert-butyl 4-(cyanomethylene)piperidine-1-carboxylate (2.1 g, 9.5 mmol) were combined with acetonitrile (31 mL) in a pressure vessel. DBU (1.05 mL, 6.98 mmol) was then added at ambient temperature. The reaction vessel was sealed and the mixture was heated to 80° C. for 16 hours. The reaction mixture was then allowed to cool to ambient temperature before water (150 mL) was added. The aqueous mixture was extracted with EtOAc (2×). The organic layers were then combined and washed with brine, dried over anhydrous $MgSO_4$, filtered, and concentrated in vacuo. The crude residue was adsorbed on silica gel in vacuo and purified by MPLC on silica gel (using a gradient elution of 75-100% EtOAc/hexanes) to afford the title compound, Intermediate #35-1.

LRMS (ESI) calc'd for $C_{16}H_{24}N_6O_3$ [M+H]$^+$: 349. Found: 349

The following intermediates shown in TABLE 10 were prepared according to Scheme #21 following similar procedures described for Intermediate #35-1, which can be achieved by those of ordinary skill in the art of organic synthesis.

TABLE 9

| Intermediate | Structure | Compound Name | Exact Mass [M + H]$^+$ |
|---|---|---|---|
| 34-2 | 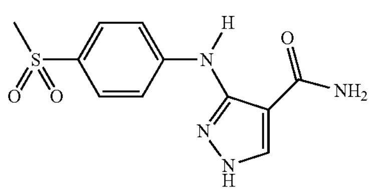 [SMILES: CS(=O)(=O)c1ccc(Nc2n[nH]cc2C(N)=O)cc1] | 3-{[4-(methylsulfonyl)phenyl]amino}-1H-pyrazole-4-carboxamide | Calc'd 281, Found 281 |
| 34-3 | 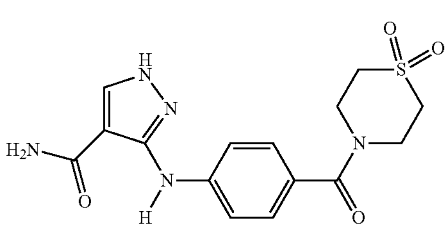 [SMILES: NC(=O)c1c[nH]nc1Nc1ccc(C(=O)N2CCS(=O)(=O)CC2)cc1] | 3-({4-[(1,1-dioxidothiomorpholin-4-yl)carbonyl]phenyl}amino)-1H-pyrazole-4-carboxamide | Calc'd 364, Found 364 |

…

TABLE 10

| Intermediate | Structure | Compound Name | Exact Mass [M + H]+ |
|---|---|---|---|
| 35-2 | 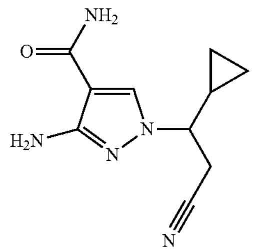 [SMILES: N#CCC(C1CC1)n1cc(C(N)=O)c(N)n1] | 3-amino-1-(2-cyano-1-cyclopropylethyl)-1H-pyrazole-4-carboxamide | Calc'd 220, Found 220 |
| 35-3 | 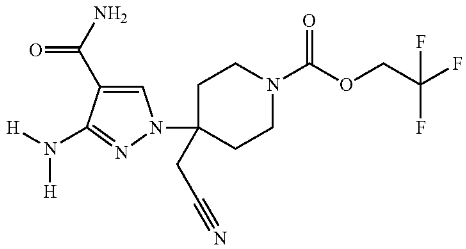 [SMILES: N#CCC1(n2cc(C(N)=O)c(N)n2)CCN(C(=O)OCC(F)(F)F)CC1] | 2,2,2-trifluoroethyl 4-(3-amino-4-carbamoyl-1H-pyrazol-1-yl)-4-(cyanomethyl)piperidine-1-carboxylate | Calc'd 375, Found 375 |
| 35-4 | 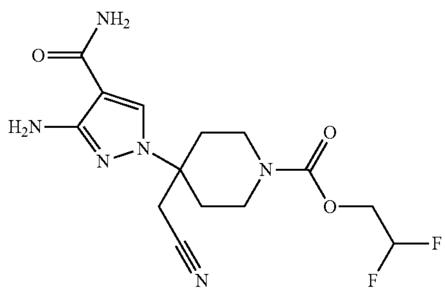 [SMILES: N#CCC1(n2cc(C(N)=O)c(N)n2)CCN(C(=O)OCC(F)F)CC1] | 2,2-difluoroethyl 4-(3-amino-4-carbamoyl-1H-pyrazol-1-yl)-4-(cyanomethyl)piperidine-1-carboxylate | Calc'd 357, Found 357 |
| 35-5 | 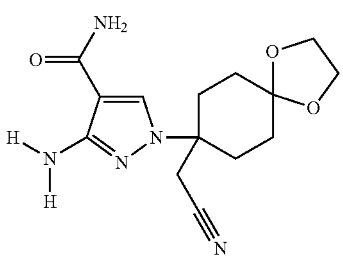 [SMILES: N#CCC1(n2cc(C(N)=O)c(N)n2)CCC2(CC1)OCCO2] | 3-amino-1-(8-(cyanomethyl)-1,4-dioxaspiro[4.5]decan-8-yl)-1H-pyrazole-4-carboxamide | Calc'd 306, Found 306 |

Scheme #21

Intermediate #36

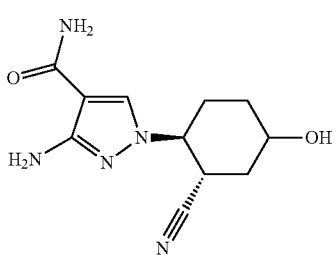

3-Amino-1-[(1S,2S and 1R,2R)-2-cyano-4-hydroxy-cyclohexyl]-1H-pyrazole-4-carboxamide DBU (1.20 mL, 7.93 mmol) was added to a mixture of 3-amino-1H-pyrazole-4-carboxamide (500 mg, 3.96 mmol) and 5-hydroxycyclohex-1-ene-1-carbonitrile (976 mg, 7.93 mmol) in ethanol (7.2 mL) at 23° C. The reaction mixture was then heated to 70° C. for 16 hours. The mixture was then cooled to ambient temperature, silica gel was added, and the mixture was concentrated in vacuo. The resulting powder was then purified by MPLC on silica gel (using a gradient elution of 0-15%, MeOH/EtOAc) to afford the title compound. The stereochemistry of the major isomer was 1,2-trans, 1,4-cis, and the minor isomer was 1,2-trans, 1,4-trans, with these two isomers constituting 90% of the product mixture. LRMS (ESI) calc'd for $C_7H_{16}N_5O_2$ [M+H]+: 250. Found: 250.

Scheme #21

Intermediates #37-1 & #37-2

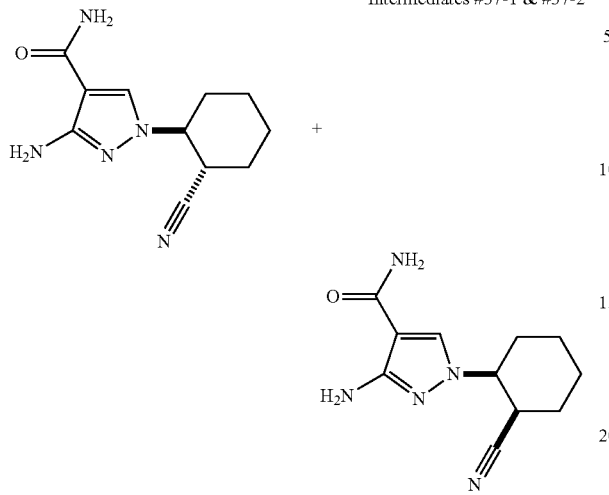

3-Amino-1-[(1S,2S and 1R,2R)-2-cyanocyclohexyl]-1H-pyrazole-4-carboxamide and 3-amino-1-[(1S,2R and 1R,2S)-2-cyanocyclohexyl]-1H-pyrazole-4-carboxamide The title compounds were prepared according to the general procedure in
Intermediate 36 using 3-amino-1H-pyrazole-4-carboxamide (10 g, 79 mmol) and cyclohex-1-ene-1-carbonitrile (17 g, 160 mmol) as starting materials.
Intermediate #37-1: 3-Amino-1-[(1S,2S and 1R,2R)-2-cyanocyclohexyl]-1H-pyrazole-4-carboxamide
LRMS (ESI) calc'd for $C_{11}H_{16}N_5O$ $[M+H]^+$: 234. Found: 234.
Intermediate #37-2: 3-Amino-1-[(1S,2R and 1R,2S)-2-cyanocyclohexyl]-1H-pyrazole-4-carboxamide
LRMS (ESI) calc'd for $C_{11}H_{16}N_5O$ $[M+H]^+$: 234. Found: 234.

EXAMPLES OF THE INSTANT INVENTION

The following experimental procedures detail the preparation of specific examples of the instant invention. The examples are for illustrative purposes only and are not intended to limit the scope of the instant invention in any way.

Scheme #22

Example #1

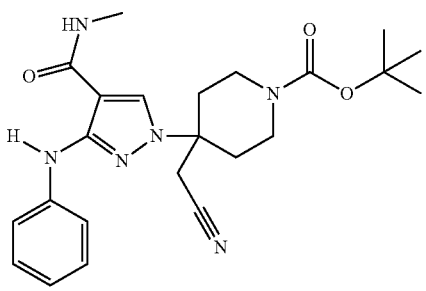

tert-Butyl 4-(cyanomethyl)-4-[4-(methylcarbamoyl)-3-(phenylamino)-1H-pyrazol-1-yl]piperidine-1-carboxylate

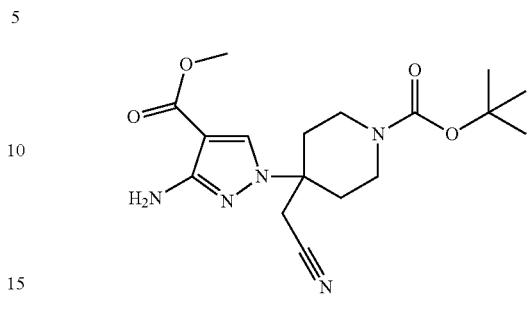

Step A. tert-Butyl 4-[3-amino-4-(methoxycarbonyl)-1H-pyrazol-1-yl]-4-(cyanomethyl)piperidine-1-carboxylate (Step A Intermediate)

To a flask containing 5-amino-1H-pyrazole-4-carboxylic acid methyl ester (2.0 g, 14 mmol) was added tert-butyl 4-(cyanomethylidene)piperidine-1-carboxylate (6.3 g, 28 mmol), acetonitrile (57 mL), and DMF (25 mL), followed by the addition of catalytic NaOMe (0.10 g, 2.1 mmol). The mixture was heated to 70° C. and allowed to stir for 18 hours. The mixture was then allowed to cool to ambient temperature, diluted with water and extracted with EtOAc (2×). The combined organic extracts were washed with brine, dried over anhydrous $Na_2SO_4$, filtered, and concentrated in vacuo. The residue was purified by MPLC on silica gel (using a gradient elution of 0-10% MeOH/DCM) to afford the title compound. LRMS (ESI) calc'd for $C_{17}H_{26}N_5O_4$ $[M+H]^+$: 364. Found: 364.

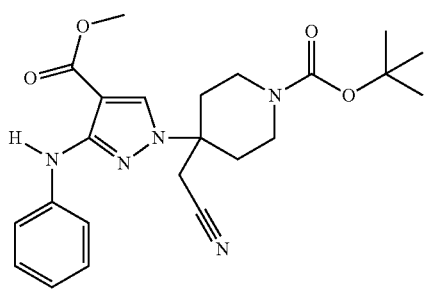 [SMILES: COC(=O)c1cn(C2(CC#N)CCN(C(=O)OC(C)(C)C)CC2)nc1Nc1ccccc1]

Step B. tert-Butyl 4-(cyanomethyl)-4-[4-(methoxycarbonyl)-3-(phenylamino)-1H-pyrazol-1-yl]piperidine-1-carboxylate (Step B Intermediate)

To a microwave vessel was added tert-butyl 4-[3-amino-4-(methoxycarbonyl)-1H-pyrazol-1-yl]-4-(cyanomethyl)piperidine-1-carboxylate (0.400 g, 1.10 mmol), $K_3PO_4$ (467 mg, 2.20 mmol), bromobenzene (0.13 mL, 1.2 mmol), and dioxane (5.5 mL). The mixture was degassed by bubbling argon for 5 minutes. $Pd_2(dba)_3$ (50 mg, 0.05 mmol) and X-Phos (79 mg, 0.16 mmol) were added, and the vial was sealed and heated to 95° C. for 3 hours. The reaction was then cooled to ambient temperature, diluted with EtOAc, filtered through celite, and rinsed with EtOAc. The filtrate was concentrated in vacuo, and the residue was purified by MPLC on silica gel (using a gradient elution of 0-50% EtOAc/hexanes) to afford the title compound.

LRMS (ESI) calc'd for $C_{23}H_{30}N_5O_4$ [M+H]$^+$: 440. Found: 440.

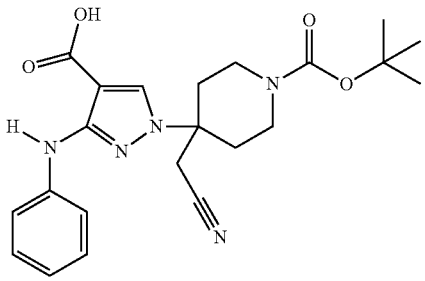 [SMILES: CC(C)(C)OC(=O)N1CCC(CC#N)(n2cc(C(=O)O)c(Nc3ccccc3)n2)CC1]

Step C. 1-[1-(tert-Butoxycarbonyl)-4-(cyanomethyl)piperidin-4-yl]-3-(phenylamino)-1H-pyrazole-4-carboxylic acid To a solution of tert-butyl 4-(cyanomethyl)-4-[4-(methoxycarbonyl)-3-(phenylamino)-1H-pyrazol-1-yl]piperidine-1-carboxylate (0.12 g, 0.27 mmol) in THF (1.8 mL) was added MeOH (1 mL), and 1M aqueous NaOH (0.82 mL, 0.82 mmol). The mixture was heated to 50° C. for 2 hours. The mixture was then cooled to ambient temperature and acidified to pH 3-4 with 1N aqueous HCl. The mixture was extracted with EtOAc (2×). The combined organic extracts were washed with brine, dried over anhydrous MgSO$_4$, filtered, and concentrated in vacuo. The residue was purified by MPLC on silica gel (using a gradient elution of 0-10% MeOH/DCM) to afford the title compound.

LRMS (ESI) calc'd for $C_{22}H_{28}N_5O_4$[M+H]$^+$: 426. Found: 426.

Step D. Tert-Butyl 4-(cyanomethyl)-4-[4-(methylcarbamoyl)-3-(phenylamino)-1H-pyrazol-1-yl]piperidine-1-carboxylate To a solution of 1-[1-(tert-butoxycarbonyl)-4-(cyanomethyl)piperidin-4-yl]-3-(phenylamino)-1H-pyrazole-4-carboxylic acid (25 mg, 0.059 mmol) in DCM (0.6 mL) was added DIPEA (0.030 mL, 0.18 mmol), methylamine (0.040 mL, 0.082 mmol, 2.0 M in THF), HOBT (13 mg, 0.082 mmol), and EDC (16 mg, 0.082 mmol). The resulting mixture was maintained at ambient temperature for 18 hours, then purified directly by MPLC on silica gel (using a gradient elution of 0-10% MeOH/DCM) to afford the title compound.

$^1$H NMR (600 MHz, acetone-d$_6$): δ 9.19 (s, 1H), 8.33 (s, 1H), 7.54 (d, J=7.2 Hz, 2H), 7.35 (br s, 1H), 7.21 (t, J=7.2 Hz, 2H), 6.79 (t, J=7.2 Hz, 1H), 3.80-3.84 (m, 2H), 3.11 (s, 2H), 3.05 (br s, 2H), 2.83 (s, 3H), 2.52-2.57 (m, 2H), 2.00-2.06 (m, 2H), 1.38 (s, 9H).

LRMS (ESI) calc'd for $C_{23}H_{31}N_6O_3$ [M+H]$^+$: 439. Found: 439.

Scheme #23

Example #2-1

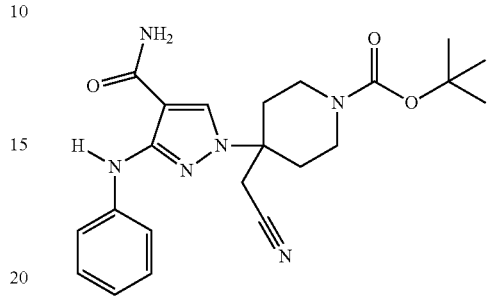

tert-Butyl 4-[4-carbamoyl-3-(phenylamino)-1H-pyrazol-1-yl]-4-(cyanomethyl)piperidine-1-carboxylate To a mixture of 3-(phenylamino)-1H-pyrazole-4-carboxamide, Intermediate 31-1, (1.4 g, 6.9 mmol) and tert-butyl 4-(cyanomethylidene)piperidine-1-carboxylate, Intermediate 19-1 (3.1 g, 13.8 mmol) in acetonitrile (23 mL) was added DBU (1.0 mL, 6.9 mmol), and maintained at ambient temperature for 18 hours. The mixture was diluted with water, extracted with EtOAc, and the combined organics were washed with brine, dried over anhydrous MgSO$_4$, and filtered. The filtrate was adsorbed onto silica gel in vacuo and then purified by MPLC on silica gel (using a gradient elution of 0-80% EtOAc/DCM) to afford the title compound, Example #2-1.

LRMS (ESI) calc'd for $C_{22}H_{28}N_6O_3$ [M+H]$^+$: 425. Found: 425.

$^1$H NMR (600 MHz, CDCl3): δ 8.78 (s, 1H), 7.76 (s, 1H), 7.51 (d, J=7.2 Hz, 2H), 7.29 (t, J=7.2 Hz, 2H), 6.91 (t, J=7.2 Hz, 1H), 5.48 (br s, 2H), 3.89 (br s, 2H), 3.09-3.14 (m, 2H), 2.90 (s, 2H), 2.59-2.63 (m, 2H), 1.98-2.04 (m, 2H), 1.45 (s, 9H).

The following examples shown in TABLE 11 were prepared according to Scheme #23 following similar procedures described for Example #2-1, which can be achieved by those of ordinary skill in the art of organic synthesis.

TABLE 11

| Example | Structure | Compound Name | Exact Mass [M + H]$^+$ |
|---|---|---|---|
| 2-2 | 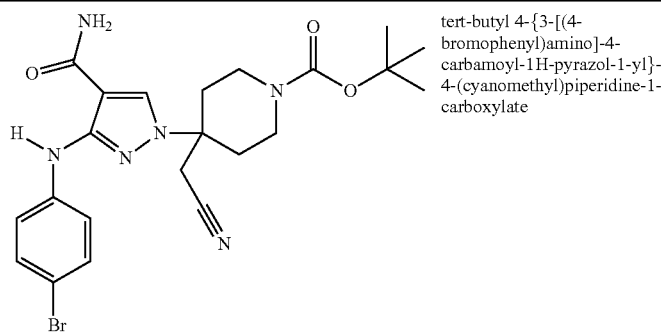 | tert-butyl 4-{3-[(4-bromophenyl)amino]-4-carbamoyl-1H-pyrazol-1-yl}-4-(cyanomethyl)piperidine-1-carboxylate | Calc'd 503, Found 503 |

TABLE 11-continued

| Example | Structure | Compound Name | Exact Mass [M + H]+ |
|---|---|---|---|
| 2-3 | 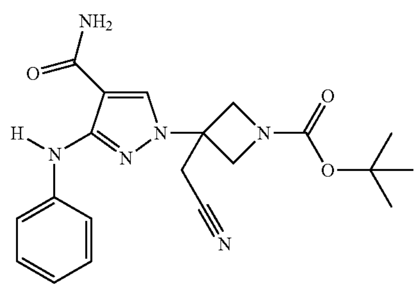 [SMILES: CC(C)(C)OC(=O)N1CC(CC#N)(n2cc(C(N)=O)c(Nc3ccccc3)n2)C1] | tert-butyl 3-[4-carbamoyl-3-(phenylamino)-1H-pyrazol-1-yl]-3-(cyanomethyl)azetidine-1-carboxylate | Calc'd 397, Found 397 |
| 2-4 | 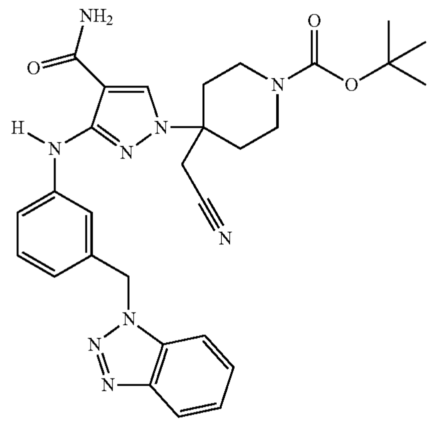 [SMILES: CC(C)(C)OC(=O)N1CCC(CC#N)(n2cc(C(N)=O)c(Nc3cccc(Cn4nnc5ccccc54)c3)n2)CC1] | tert-butyl 4-(3-{[3-(1H-benzotriazol-1-ylmethyl)phenyl]amino}-4-carbamoyl-1H-pyrazol-1-yl)-4-(cyanomethyl)piperidine-1-carboxylate | Calc'd 556, Found 556 |
| 2-5 | 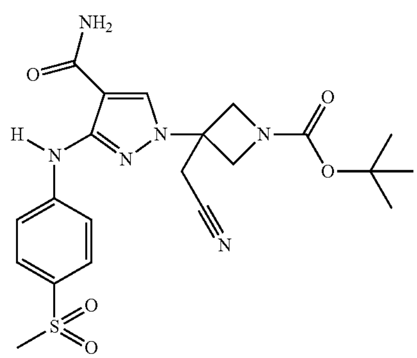 [SMILES: CC(C)(C)OC(=O)N1CC(CC#N)(n2cc(C(N)=O)c(Nc3ccc(S(C)(=O)=O)cc3)n2)C1] | tert-butyl 3-(4-carbamoyl-3-{[4-(methylsulfonyl)phenyl]amino}-1H-pyrazol-1-yl)-3-(cyanomethyl)azetidine-1-carboxylate | Calc'd 475, Found 375 (M + H-Boc) |
| 2-6 | 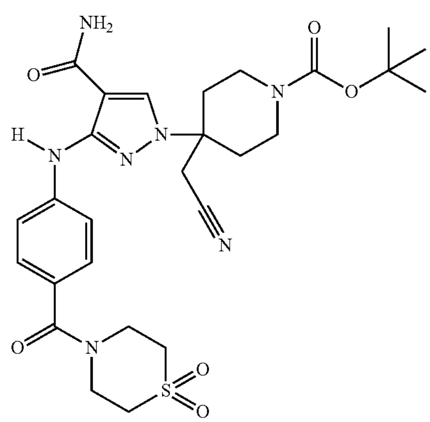 [SMILES: CC(C)(C)OC(=O)N1CCC(CC#N)(n2cc(C(N)=O)c(Nc3ccc(C(=O)N4CCS(=O)(=O)CC4)cc3)n2)CC1] | tert-butyl 4-[4-carbamoyl-3-({4-[(1,1-dioxidothiomorpholin-4-yl)carbonyl]phenyl}amino)-1H-pyrazol-1-yl]-4-(cyanomethyl)piperidine-1-carboxylate | Calc'd 586, Found 486 (M + H-Boc) |

TABLE 11-continued

| Example | Structure | Compound Name | Exact Mass [M + H]+ |
|---|---|---|---|
| 2-7 | 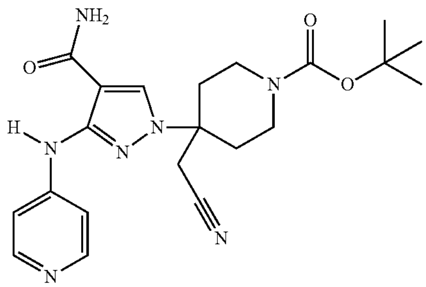 [SMILES: CC(C)(C)OC(=O)N1CCC(CC#N)(n2cc(C(N)=O)c(Nc3ccncc3)n2)CC1] | tert-butyl 4-[4-carbamoyl-3-(pyridin-4-ylamino)-1H-pyrazol-1-yl]-4-(cyanomethyl)piperidine-1-carboxylate | Calc'd 426, Found 426 |
| 2-8 | 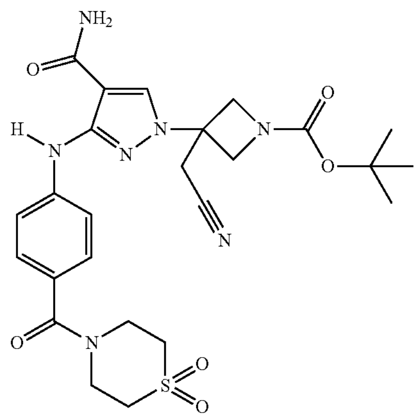 [SMILES: CC(C)(C)OC(=O)N1CC(CC#N)(n2cc(C(N)=O)c(Nc3ccc(C(=O)N4CCS(=O)(=O)CC4)cc3)n2)C1] | tert-butyl 3-[4-carbamoyl-3-({4-[(1,1-dioxidothiomorpholin-4-yl)carbonyl]phenyl}amino)-1H-pyrazol-1-yl]-3-(cyanomethyl)azetidine-1-carboxylate | Calc'd 558, Found 458 (M + H-Boc) |
| 2-9 | 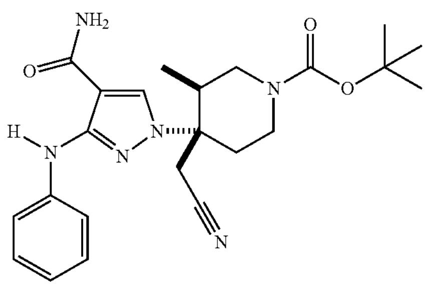 | tert-Butyl (3S,4R and 3R,4S)-4-[4-carbamoyl-3-(phenylamino)-1H-pyrazol-1-yl]-4-(cyanomethyl)-3-methylpiperidine-1-carboxylate | Calc'd 439, Found 439 |
| 2-10 | 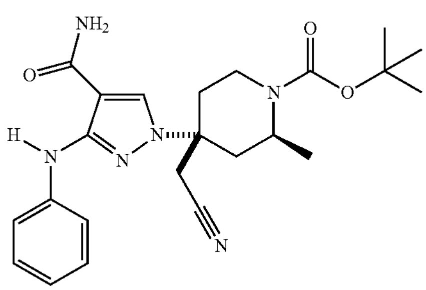 | tert-Butyl (2S,4R and 2R,4S)-4-[4-carbamoyl-3-(phenylamino)-1H-pyrazol-1-yl]-4-(cyanomethyl)-2-methylpiperidine-1-carboxylate | Calc'd 439, Found 439 |
| 2-11 | 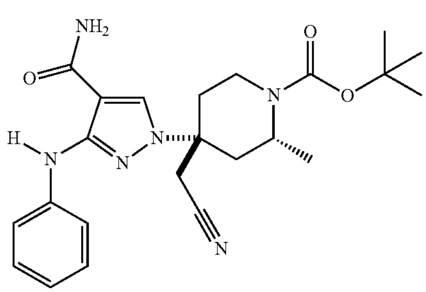 | tert-butyl (2R,4R and 2S,4S)-4-[4-carbamoyl-3-(phenylamino)-1H-pyrazol-1-yl]-4-(cyanomethyl)-2-methylpiperidine-1-carboxylate | Calc'd 439, Found 439 |

TABLE 11-continued

| Example | Structure | Compound Name | Exact Mass [M + H]+ |
|---|---|---|---|
| 2-12 | 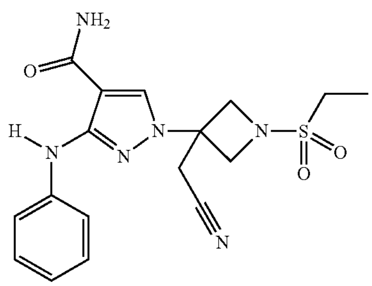 [SMILES: CCS(=O)(=O)N1CC(CC#N)(n2cc(C(N)=O)c(Nc3ccccc3)n2)C1] | 1-[3-(cyanomethyl)-1-(ethylsulfonyl)azetidin-3-yl]-3-(phenylamino)-1H-pyrazole-4-carboxamide | Calc'd 389, Found 389 |
| 2-13 | 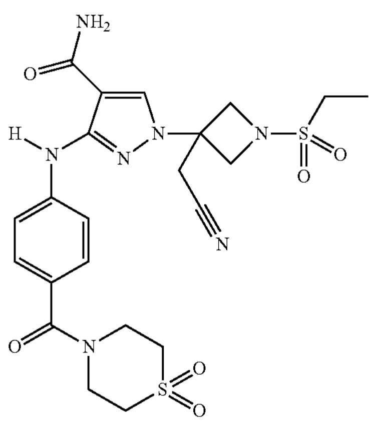 [SMILES: CCS(=O)(=O)N1CC(CC#N)(n2cc(C(N)=O)c(Nc3ccc(C(=O)N4CCS(=O)(=O)CC4)cc3)n2)C1] | 1-[3-(cyanomethyl)-1-(ethylsulfonyl)azetidin-3-yl]-3-({4-[(1,1-dioxidothiomorpholin-4-yl)carbonyl]phenyl}amino)-1H-pyrazole-4-carboxamide | Calc'd 550, Found 550 |
| 2-14 | 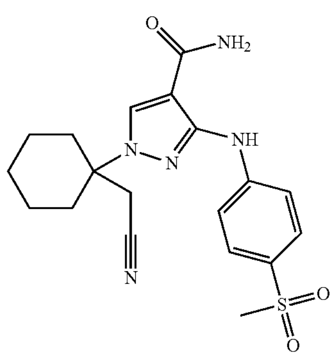 [SMILES: CS(=O)(=O)c1ccc(Nc2nn(C3(CC#N)CCCCC3)cc2C(N)=O)cc1] | 1-[1-(cyanomethyl)cyclohexyl]-3-{[4-(methylsulfonyl)phenyl]amino}-1H-pyrazole-4-carboxamide | Calc'd 402.0, found 402 |
| 2-15 | 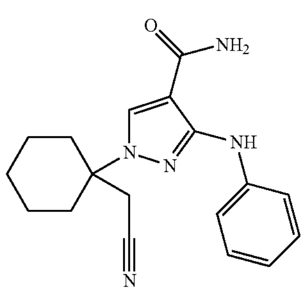 [SMILES: N#CCC1(n2cc(C(N)=O)c(Nc3ccccc3)n2)CCCCC1] | 1-[1-(cyanomethyl)cyclohexyl]-3-(phenylamino)-1H-pyrazole-4-carboxamide | Calc'd 324, found 324 |

TABLE 11-continued

| Example | Structure | Compound Name | Exact Mass [M + H]+ |
|---|---|---|---|
| 2-16 | 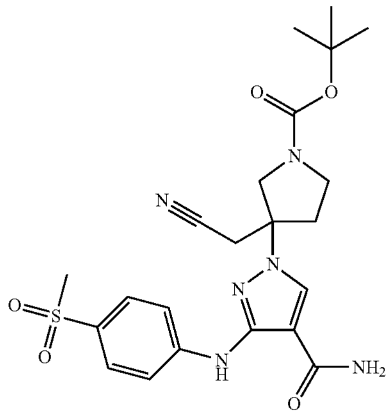 [SMILES: CC(C)(C)OC(=O)N1CCC(CC#N)(n2cc(C(N)=O)c(Nc3ccc(S(C)(=O)=O)cc3)n2)C1] | tert-butyl 3-(4-carbamoyl-3-{[4-(methylsulfonyl)phenyl]amino}-1H-pyrazol-1-yl)-3-(cyanomethyl)pyrrolidine-1-carboxylate | Calc'd 489, found 389 (M + H-Boc) |
| 2-17 | 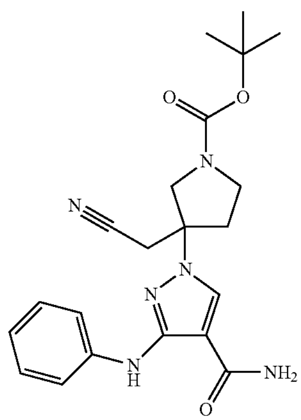 [SMILES: CC(C)(C)OC(=O)N1CCC(CC#N)(n2cc(C(N)=O)c(Nc3ccccc3)n2)C1] | tert-butyl 3-[4-carbamoyl-3-(phenylamino)-1H-pyrazol-1-yl]-3-(cyanomethyl)pyrrolidine-1-carboxylate | Calc'd 411, found 411 |
| 2-18 | 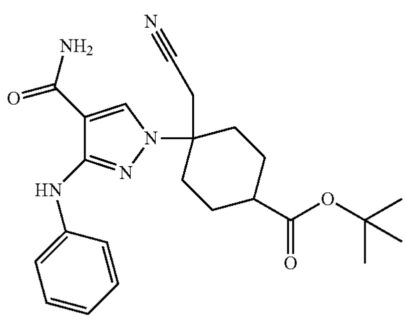 [SMILES: CC(C)(C)OC(=O)C1CCC(CC#N)(n2cc(C(N)=O)c(Nc3ccccc3)n2)CC1] | tert-butyl 4-[4-carbamoyl-3-(phenylamino)-1H-pyrazol-1-yl]-4-(cyanomethyl)cyclohexanecarboxylate | Calc'd 424, found 424 |
| 2-19 | 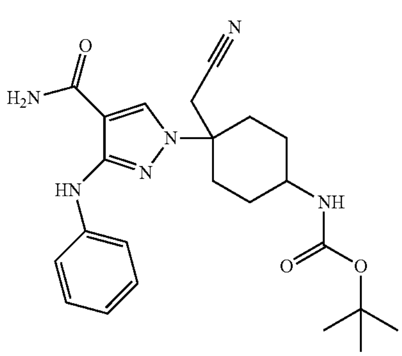 [SMILES: CC(C)(C)OC(=O)NC1CCC(CC#N)(n2cc(C(N)=O)c(Nc3ccccc3)n2)CC1] | (1s,3s or 1r,3r) tert-butyl {4-[4-carbamoyl-3-(phenylamino)-1H-pyrazol-1-yl]-4-(cyanomethyl)cyclohexyl}carbamate | Calc'd 439, found 439 |

TABLE 11-continued

| Example | Compound Name | Exact Mass [M + H]⁺ |
|---|---|---|
| 2-20 | 1-[3-(cyanomethyl)oxetan-3-yl]-3-(phenylamino)-1H-pyrazole-4-carboxamide | Calc'd 298, found 298 |
| 2-21 | 1-((1s,3s)-3-cyano-1-(cyanomethyl)cyclobutyl)-3-(phenylamino)-1H-pyrazole-4-carboxamide | Calc'd 321, found 321 |
| 2-22 | 1-((1r,3r)-3-cyano-1-(cyanomethyl)cyclobutyl)-3-((4-(methylsulfonyl)phenyl)amino)-1H-pyrazole-4-carboxamide | Calc'd 399, found 399 |
| 2-23 | tert-butyl 6-[4-carbamoyl-3-(phenylamino)-1H-pyrazol-1-yl]-6-(cyanomethyl)-2-azaspiro[3.3]heptane-2-carboxylate | Calc'd 437, found 437 |

Scheme #23

Example #3-1

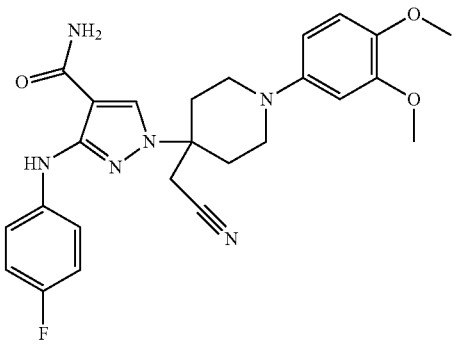

1-[4-(Cyanomethyl)-1-(3,4-dimethoxyphenyl)piperidin-4-yl]-3-[(4-fluorophenyl)amino]-1H-pyrazole-4-carboxamide

[1-(3,4-Dimethoxyphenyl)piperidin-4-ylidene]acetonitrile (Intermediate 25-1) (0.026 g, 0.10 mmol), acetonitrile (0.4 mL), DMF (0.4 mL), 3-[(4-fluorophenyl)amino]-1H-pyrazole-4-carboxamide (Intermediate 31-7) (0.022 g, 0.10 mmol), and DBU (0.045 mL, 0.30 mmol) were combined, heated to 50° C., and allowed to stir for 16 hours. The reaction mixture was directly purified by reverse phase preparative HPLC (using a gradient elution of 0-95% MeCN/water, with 0.1% v/v TFA modifier) to afford the title compound, Example #3-1.

LRMS (ESI) calc'd for $C_{25}H_{27}FN_6O_3$ [M+H]$^+$: 479. Found: 479.

$^1$H NMR (500 MHz, DMSO-d$_6$): δ 9.05 (s, 1H), 8.52 (s, 1H), 7.62-7.52 (m, 3H), 7.17 (br s, 1H), 7.06 (t, J=8.8 Hz, 2H), 6.81 (d, J=8.8 Hz, 1H), 6.74-6.68 (m, 1H), 6.58-6.50 (m, 1H), 3.72 (s, 3H), 3.66 (s, 3H), 3.50-3.42 (m, 2H), 3.23 (s, 2H), 2.96-2.82 (m, 2H), 2.58-2.46 (m, 2H), 2.28-2.18 (m, 2H).

The following examples shown in TABLE 12 were prepared according to Scheme #23 following similar procedures described for Example #3-1, which can be achieved by those of ordinary skill in the art of organic synthesis utilizing Intermediate 31-7, and intermediates including but not limited to intermediates described in Table 5.

TABLE 12

| Example | Structure | Compound Name | Exact Mass [M + H]$^+$ |
| --- | --- | --- | --- |
| 3-2 | 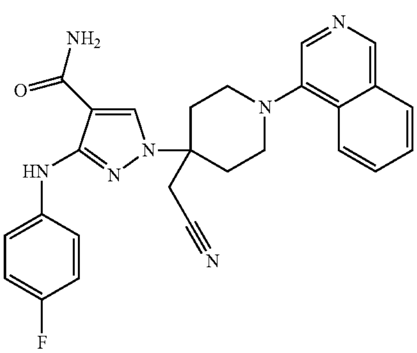 [SMILES: N#CCC1(n2cc(C(N)=O)c(Nc3ccc(F)cc3)n2)CCN(c2cncc3ccccc23)CC1] | 1-[4-(cyanomethyl)-1-isoquinolin-4-ylpiperidin-4-yl]-3-[(4-fluorophenyl)amino]-1H-pyrazole-4-carboxamide | Calc'd 470, Found 470 |
| 3-3 | 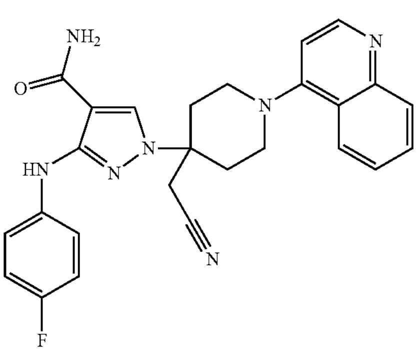 [SMILES: N#CCC1(n2cc(C(N)=O)c(Nc3ccc(F)cc3)n2)CCN(c2ccnc3ccccc23)CC1] | 1-[4-(cyanomethyl)-1-quinolin-4-ylpiperidin-4-yl]-3-[(4-fluorophenyl)amino]-1H-pyrazole-4-carboxamide | Calc'd 470, Found 470 |

TABLE 12-continued

| Example | Structure | Compound Name | Exact Mass [M + H]+ |
|---|---|---|---|
| 3-4 | 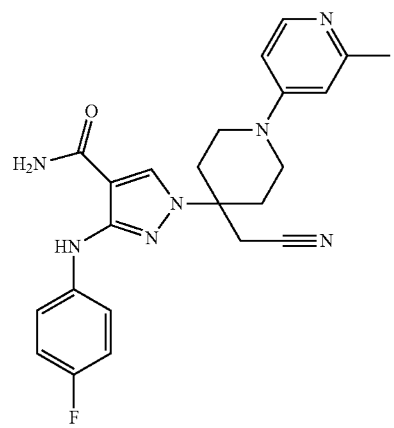 [SMILES: Cc1cc(N2CCC(CC#N)(n3cc(C(N)=O)c(Nc4ccc(F)cc4)n3)CC2)ccn1] | 1-[4-(cyanomethyl)-1-(2-methylpyridin-4-yl)piperidin-4-yl]-3-[(4-fluorophenyl)amino]-1H-pyrazole-4-carboxamide | Calc'd 434, found 434 |
| 3-5 | 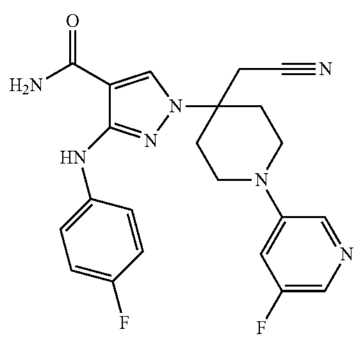 [SMILES: N#CCC1(n2cc(C(N)=O)c(Nc3ccc(F)cc3)n2)CCN(c2cncc(F)c2)CC1] | 1-[4-(cyanomethyl)-1-(5-fluoropyridin-3-yl)piperidin-4-yl]-3-[(4-fluorophenyl)amino]-1H-pyrazole-4-carboxamide | Calc'd 438, found 438 |
| 3-6 | 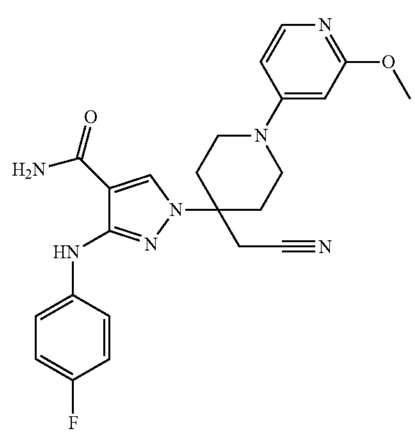 [SMILES: COc1cc(N2CCC(CC#N)(n3cc(C(N)=O)c(Nc4ccc(F)cc4)n3)CC2)ccn1] | 1-[4-(cyanomethyl)-1-(2-methoxypyridin-4-yl)piperidin-4-yl]-3-[(4-fluorophenyl)amino]-1H-pyrazole-4-carboxamide | Calc'd 450, found 450 |

TABLE 12-continued

| Example | Structure | Compound Name | Exact Mass [M + H]+ |
|---------|-----------|---------------|---------------------|
| 3-7 | 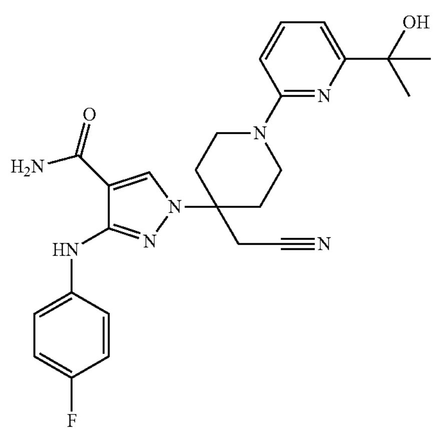 [SMILES: CC(C)(O)c1cccc(N2CCC(CC#N)(n3cc(C(N)=O)c(Nc4ccc(F)cc4)n3)CC2)n1] | 1-{4-(cyanomethyl)-1-[6-(1-hydroxy-1-methylethyl)pyridin-2-yl]piperidin-4-yl}-3-[(4-fluorophenyl)amino]-1H-pyrazole-4-carboxamide | Calc'd 478, found 478 |
| 3-8 | 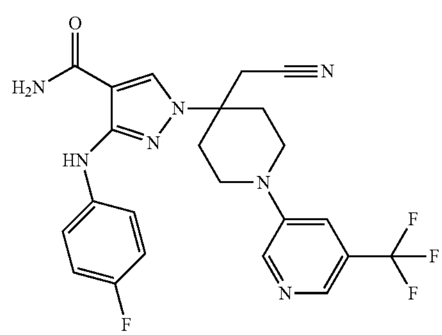 [SMILES: N#CCC1(n2cc(C(N)=O)c(Nc3ccc(F)cc3)n2)CCN(c2cncc(C(F)(F)F)c2)CC1] | 1-{4-(cyanomethyl)-1-[5-(trifluoromethyl)pyridin-3-yl]piperidin-4-yl}-3-[(4-fluorophenyl)amino]-1H-pyrazole-4-carboxamide | Calc'd 488, found 488 |
| 3-9 | 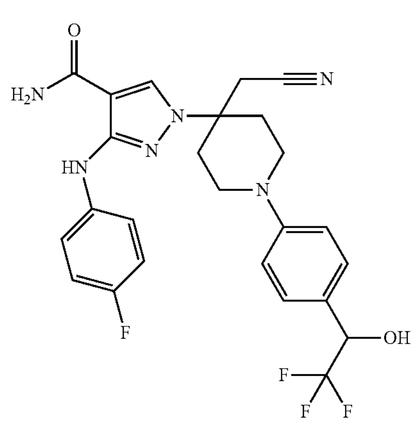 [SMILES: N#CCC1(n2cc(C(N)=O)c(Nc3ccc(F)cc3)n2)CCN(c2ccc(C(O)C(F)(F)F)cc2)CC1] | 1-{4-(cyanomethyl)-1-[4-(2,2,2-trifluoro-1-hydroxyethyl)phenyl]piperidin-4-yl}-3-[(4-fluorophenyl)amino]-1H-pyrazole-4-carboxamide | Calc'd 517, found 517 |

TABLE 12-continued

| Example | Structure | Compound Name | Exact Mass [M + H]+ |
|---------|-----------|---------------|---------------------|
| 3-10 | 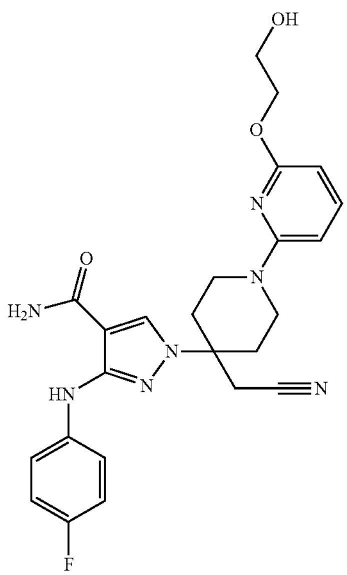 [SMILES: N#CCC1(n2cc(C(N)=O)c(Nc3ccc(F)cc3)n2)CCN(c2cccc(OCCO)n2)CC1] | 1-{4-(cyanomethyl)-1-[6-(2-hydroxyethoxy)pyridin-2-yl]piperidin-4-yl}-3-[(4-fluorophenyl)amino]-1H-pyrazole-4-carboxamide | Calc'd 480, found 480 |
| 3-11 | 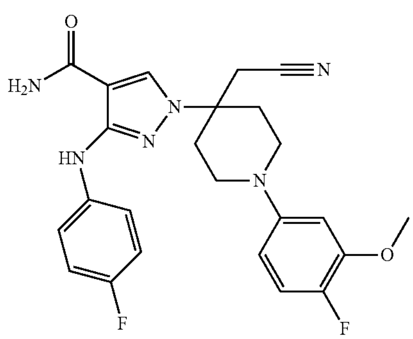 [SMILES: COc1cc(N2CCC(CC#N)(n3cc(C(N)=O)c(Nc4ccc(F)cc4)n3)CC2)ccc1F] | 1-[4-(cyanomethyl)-1-(4-fluoro-3-methoxyphenyl)piperidin-4-yl]-3-[(4-fluorophenyl)amino]-1H-pyrazole-4-carboxamide | Calc'd 467, found 467 |
| 3-12 | 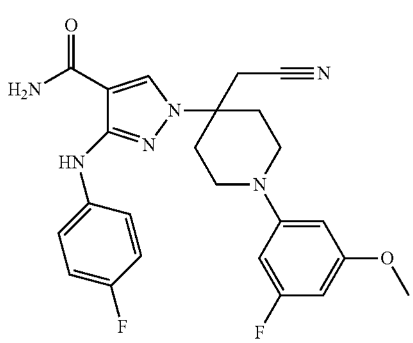 [SMILES: COc1cc(F)cc(N2CCC(CC#N)(n3cc(C(N)=O)c(Nc4ccc(F)cc4)n3)CC2)c1] | 1-[4-(cyanomethyl)-1-(3-fluoro-5-methoxyphenyl)piperidin-4-yl]-3-[(4-fluorophenyl)amino]-1H-pyrazole-4-carboxamide | Calc'd 467, found 467 |

TABLE 12-continued

| Example | Structure | Compound Name | Exact Mass [M + H]+ |
|---|---|---|---|
| 3-13 | 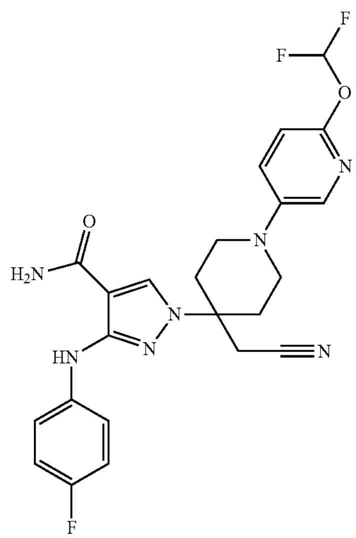 [SMILES: N#CCC1(n2cc(C(N)=O)c(Nc3ccc(F)cc3)n2)CCN(c2ccc(OC(F)F)nc2)CC1] | 1-{4-(cyanomethyl)-1-[6-(difluoromethoxy)pyridin-3-yl]piperidin-4-yl}-3-[(4-fluorophenyl)amino]-1H-pyrazole-4-carboxamide | Calc'd 486, found 486 |
| 3-14 | 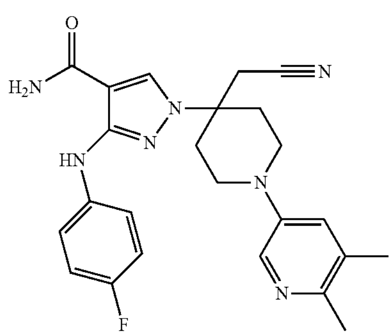 [SMILES: Cc1cc(N2CCC(CC#N)(n3cc(C(N)=O)c(Nc4ccc(F)cc4)n3)CC2)cnc1C] | 1-[4-(cyanomethyl)-1-(5,6-dimethylpyridin-3-yl)piperidin-4-yl]-3-[(4-fluorophenyl)amino]-1H-pyrazole-4-carboxamide | Calc'd 448, found 488 |
| 3-15 | 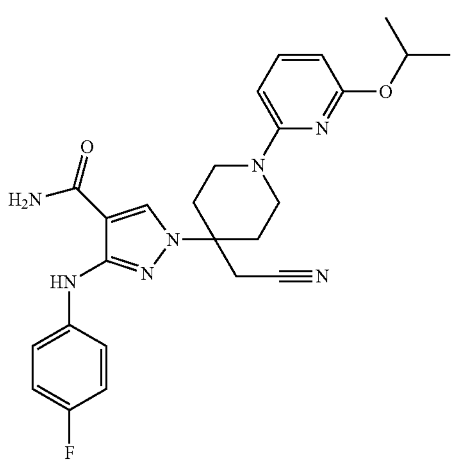 [SMILES: CC(C)Oc1cccc(N2CCC(CC#N)(n3cc(C(N)=O)c(Nc4ccc(F)cc4)n3)CC2)n1] | 1-{4-(cyanomethyl)-1-[6-(1-methylethoxy)pyridin-2-yl]piperidin-4-yl}-3-[(4-fluorophenyl)amino]-1H-pyrazole-4-carboxamide | Calc'd 478, found 478 |

TABLE 12-continued

| Example | Structure | Compound Name | Exact Mass [M + H]+ |
|---|---|---|---|
| 3-16 | 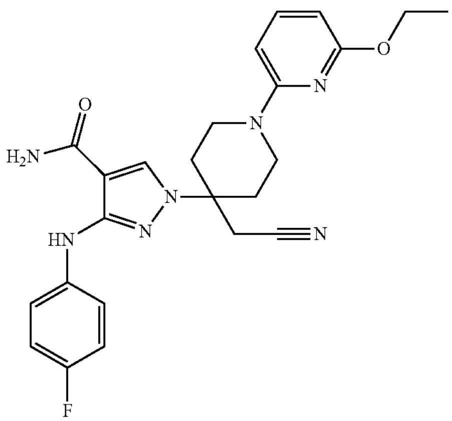 [SMILES: CCOc1cccc(N2CCC(CC#N)(n3cc(C(N)=O)c(Nc4ccc(F)cc4)n3)CC2)n1] | 1-[4-(cyanomethyl)-1-(6-ethoxypyridin-2-yl)piperidin-4-yl]-3-[(4-fluorophenyl)amino]-1H-pyrazole-4-carboxamide | Calc'd 464, found 464 |
| 3-17 | 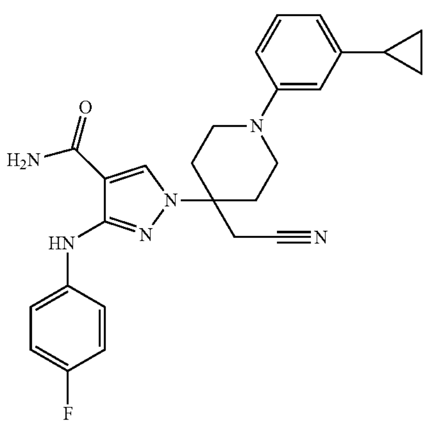 [SMILES: N#CCC1(n2cc(C(N)=O)c(Nc3ccc(F)cc3)n2)CCN(c2cccc(C3CC3)c2)CC1] | 1-[4-(cyanomethyl)-1-(3-cyclopropylphenyl)piperidin-4-yl]-3-[(4-fluorophenyl)amino]-1H-pyrazole-4-carboxamide | Calc'd 459, found 459 |
| 3-18 | 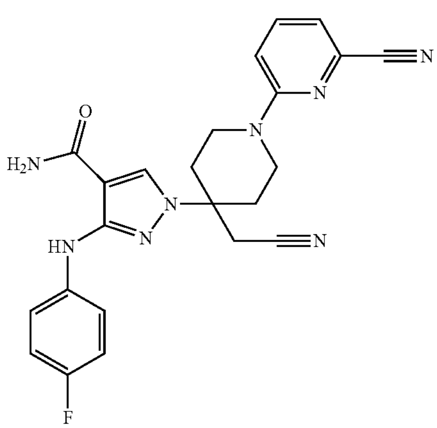 [SMILES: N#CCC1(n2cc(C(N)=O)c(Nc3ccc(F)cc3)n2)CCN(c2cccc(C#N)n2)CC1] | 1-[4-(cyanomethyl)-1-(6-cyanopyridin-2-yl)piperidin-4-yl]-3-[(4-fluorophenyl)amino]-1H-pyrazole-4-carboxamide | Calc'd 445, found 445 |

TABLE 12-continued

| Example | Structure | Compound Name | Exact Mass [M + H]+ |
|---|---|---|---|
| 3-19 | 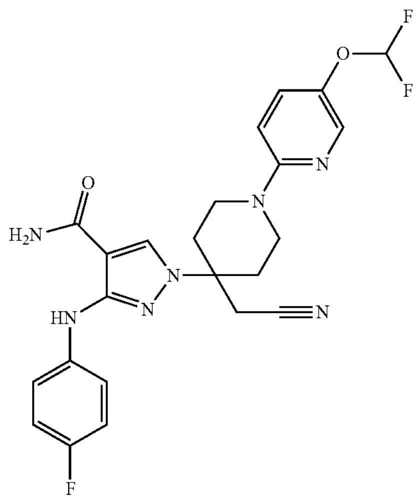 [SMILES: N#CCC1(n2cc(C(N)=O)c(Nc3ccc(F)cc3)n2)CCN(c2ccc(OC(F)F)cn2)CC1] | 1-{4-(cyanomethyl)-1-[5-(difluoromethoxy)pyridin-2-yl]piperidin-4-yl}-3-[(4-fluorophenyl)amino]-1H-pyrazole-4-carboxamide | Calc'd 486, found 486 |
| 3-20 | 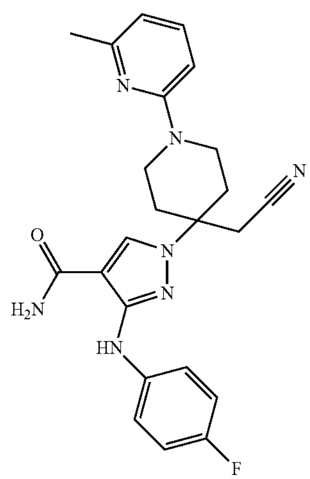 [SMILES: Cc1cccc(N2CCC(CC#N)(n3cc(C(N)=O)c(Nc4ccc(F)cc4)n3)CC2)n1] | 1-[4-(cyanomethyl)-1-(6-methylpyridin-2-yl)piperidin-4-yl]-3-[(4-fluorophenyl)amino]-1H-pyrazole-4-carboxamide | Calc'd 434, found 434 |
| 3-21 | 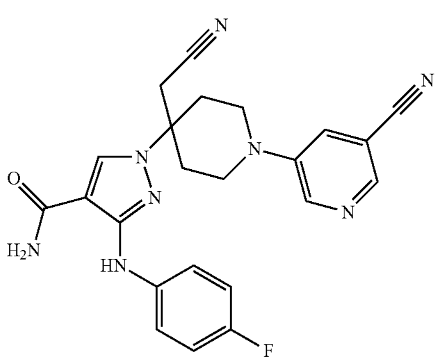 [SMILES: N#CCC1(n2cc(C(N)=O)c(Nc3ccc(F)cc3)n2)CCN(c2cncc(C#N)c2)CC1] | 1-[4-(cyanomethyl)-1-(5-cyanopyridin-3-yl)piperidin-4-yl]-3-[(4-fluorophenyl)amino]-1H-pyrazole-4-carboxamide | Calc'd 445, found 445 |

TABLE 12-continued

| Example | Structure | Compound Name | Exact Mass [M + H]+ |
|---|---|---|---|
| 3-22 | 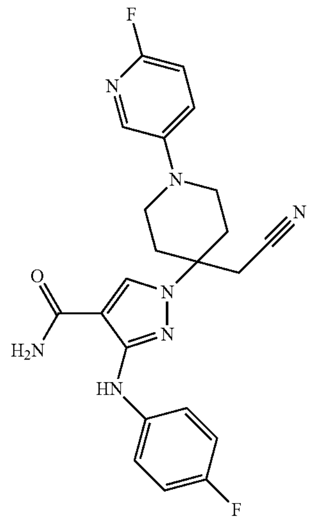 [SMILES: N#CCC1(n2cc(C(N)=O)c(Nc3ccc(F)cc3)n2)CCN(c2ccc(F)nc2)CC1] | 1-[4-(cyanomethyl)-1-(6-fluoropyridin-3-yl)piperidin-4-yl]-3-[(4-fluorophenyl)amino]-1H-pyrazole-4-carboxamide | Calc'd 438, found 438 |
| 3-23 | 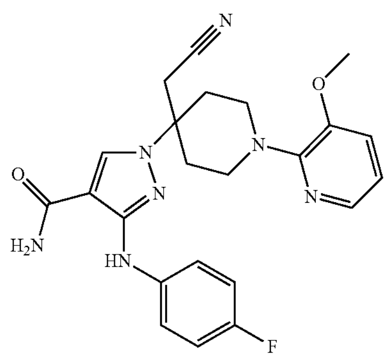 [SMILES: COc1cccnc1N1CCC(CC#N)(n2cc(C(N)=O)c(Nc3ccc(F)cc3)n2)CC1] | 1-[4-(cyanomethyl)-1-(3-methoxypyridin-2-yl)piperidin-4-yl]-3-[(4-fluorophenyl)amino]-1H-pyrazole-4-carboxamide | Calc'd 450, found 450 |
| 3-24 | 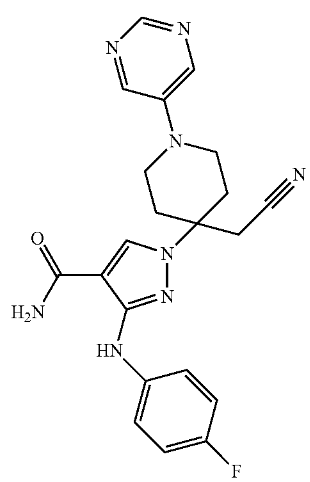 [SMILES: N#CCC1(n2cc(C(N)=O)c(Nc3ccc(F)cc3)n2)CCN(c2cncnc2)CC1] | 1-[4-(cyanomethyl)-1-pyrimidin-5-ylpiperidin-4-yl]-3-[(4-fluorophenyl)amino]-1H-pyrazole-4-carboxamide | Calc'd 421, found 421 |

TABLE 12-continued

| Example | Structure | Compound Name | Exact Mass [M + H]+ |
|---|---|---|---|
| 3-25 | 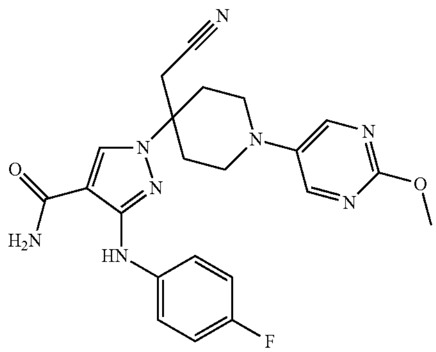 [SMILES: COc1ncc(N2CCC(CC#N)(n3cc(C(N)=O)c(Nc4ccc(F)cc4)n3)CC2)cn1] | 1-[4-(cyanomethyl)-1-(2-methoxypyrimidin-5-yl)piperidin-4-yl]-3-[(4-fluorophenyl)amino]-1H-pyrazole-4-carboxamide | Calc'd 451, found 451 |
| 3-26 | 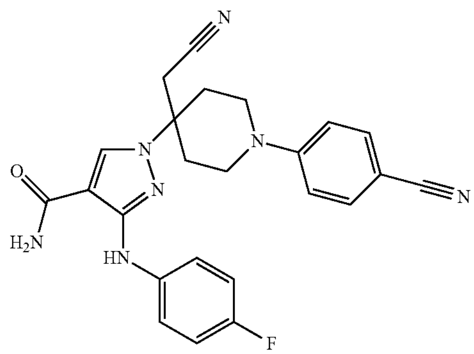 [SMILES: N#CCC1(n2cc(C(N)=O)c(Nc3ccc(F)cc3)n2)CCN(c2ccc(C#N)cc2)CC1] | 1-[4-(cyanomethyl)-1-(4-cyanophenyl)piperidin-4-yl]-3-[(4-fluorophenyl)amino]-1H-pyrazole-4-carboxamide | Calc'd 444, found 444 |
| 3-27 | 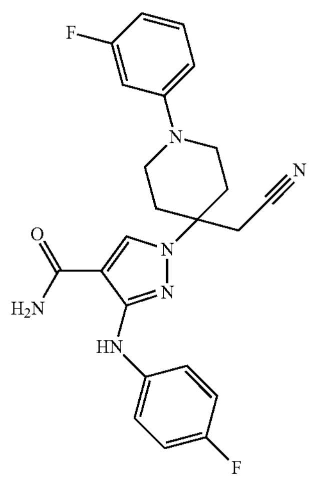 [SMILES: N#CCC1(n2cc(C(N)=O)c(Nc3ccc(F)cc3)n2)CCN(c2cccc(F)c2)CC1] | 1-[4-(cyanomethyl)-1-(3-fluorophenyl)piperidin-4-yl]-3-[(4-fluorophenyl)amino]-1H-pyrazole-4-carboxamide | Calc'd 437, found 437 |
| 3-28 | 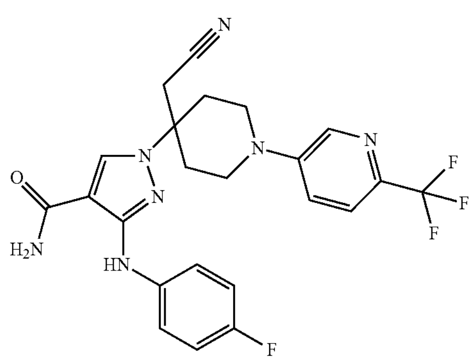 [SMILES: N#CCC1(n2cc(C(N)=O)c(Nc3ccc(F)cc3)n2)CCN(c2ccc(C(F)(F)F)nc2)CC1] | 1-{4-(cyanomethyl)-1-[6-(trifluoromethyl)pyridin-3-yl]piperidin-4-yl}-3-[(4-fluorophenyl)amino]-1H-pyrazole-4-carboxamide | Calc'd 488, found 488 |

TABLE 12-continued

| Example | Structure | Compound Name | Exact Mass [M + H]$^+$ |
|---------|-----------|---------------|------------------------|
| 3-29 | 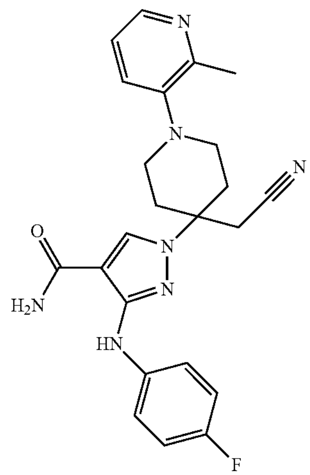 [SMILES: Cc1ncccc1N1CCC(CC#N)(n2cc(C(N)=O)c(Nc3ccc(F)cc3)n2)CC1] | 1-[4-(cyanomethyl)-1-(2-methylpyridin-3-yl)piperidin-4-yl]-3-[(4-fluorophenyl)amino]-1H-pyrazole-4-carboxamide | Calc'd 434, found 434 |
| 3-30 | 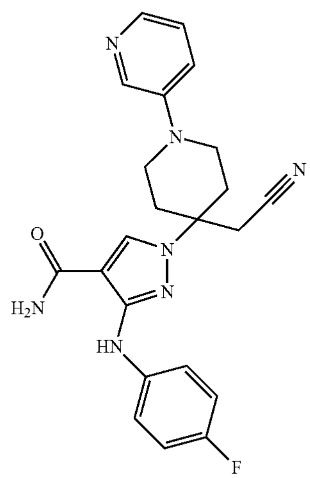 [SMILES: N#CCC1(n2cc(C(N)=O)c(Nc3ccc(F)cc3)n2)CCN(c2cccnc2)CC1] | 1-[4-(cyanomethyl)-1-pyridin-3-ylpiperidin-4-yl]-3-[(4-fluorophenyl)amino]-1H-pyrazole-4-carboxamide | Calc'd 420, found 420 |
| 3-31 | 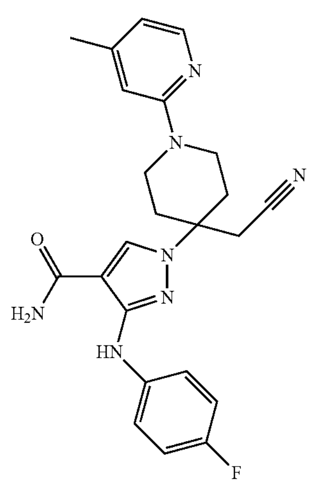 [SMILES: Cc1ccnc(N2CCC(CC#N)(n3cc(C(N)=O)c(Nc4ccc(F)cc4)n3)CC2)c1] | 1-[4-(cyanomethyl)-1-(4-methylpyridin-2-yl)piperidin-4-yl]-3-[(4-fluorophenyl)amino]-1H-pyrazole-4-carboxamide | Calc'd 434, found 434 |

TABLE 12-continued

| Example | Structure | Compound Name | Exact Mass [M + H]+ |
|---|---|---|---|
| 3-32 | 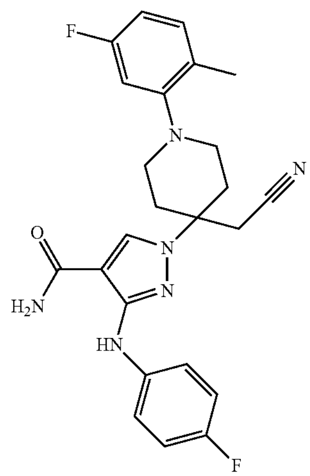 [SMILES: Cc1ccc(F)cc1N1CCC(CC#N)(n2cc(C(N)=O)c(Nc3ccc(F)cc3)n2)CC1] | 1-[4-(cyanomethyl)-1-(5-fluoro-2-methylphenyl)piperidin-4-yl]-3-[(4-fluorophenyl)amino]-1H-pyrazole-4-carboxamide | Calc'd 451, found 451 |
| 3-33 | 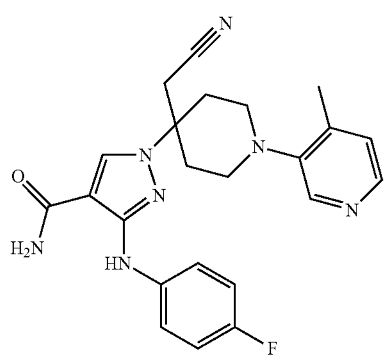 [SMILES: Cc1ccncc1N1CCC(CC#N)(n2cc(C(N)=O)c(Nc3ccc(F)cc3)n2)CC1] | 1-[4-(cyanomethyl)-1-(4-methylpyridin-3-yl)piperidin-4-yl]-3-[(4-fluorophenyl)amino]-1H-pyrazole-4-carboxamide | Calc'd 434, found 434 |
| 3-34 | 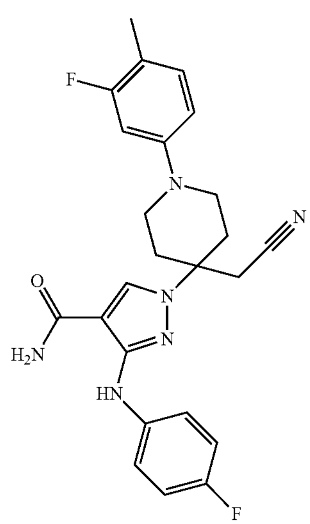 [SMILES: Cc1ccc(N2CCC(CC#N)(n3cc(C(N)=O)c(Nc4ccc(F)cc4)n3)CC2)cc1F] | 1-[4-(cyanomethyl)-1-(3-fluoro-4-methylphenyl)piperidin-4-yl]-3-[(4-fluorophenyl)amino]-1H-pyrazole-4-carboxamide | Calc'd 451, found 451 |

TABLE 12-continued

| Example | Structure | Compound Name | Exact Mass [M + H]+ |
|---|---|---|---|
| 3-35 | 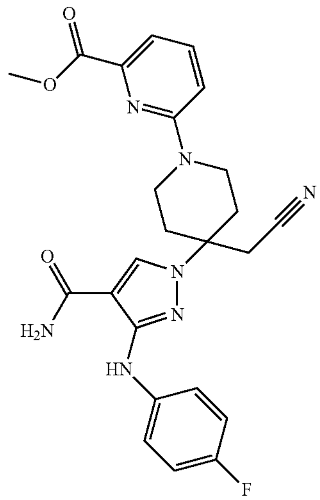 [SMILES: COC(=O)c1cccc(N2CCC(CC#N)(n3cc(C(N)=O)c(Nc4ccc(F)cc4)n3)CC2)n1] | methyl 6-[4-{4-carbamoyl-3-[(4-fluorophenyl)amino]-1H-pyrazol-1-yl}-4-(cyanomethyl)piperidin-1-yl]pyridine-2-carboxylate | Calc'd 478, found 478 |
| 3-36 | 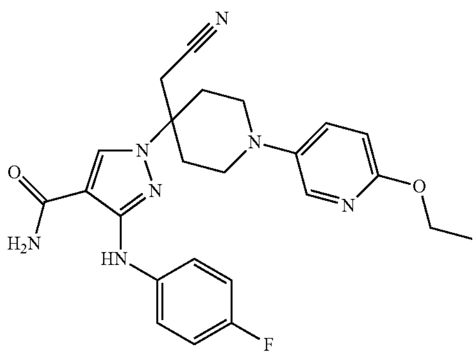 [SMILES: CCOc1ccc(N2CCC(CC#N)(n3cc(C(N)=O)c(Nc4ccc(F)cc4)n3)CC2)cn1] | 1-[4-(cyanomethyl)-1-(6-ethoxypyridin-3-yl)piperidin-4-yl]-3-[(4-fluorophenyl)amino]-1H-pyrazole-4-carboxamide | Calc'd 464, found 464 |
| 3-37 | 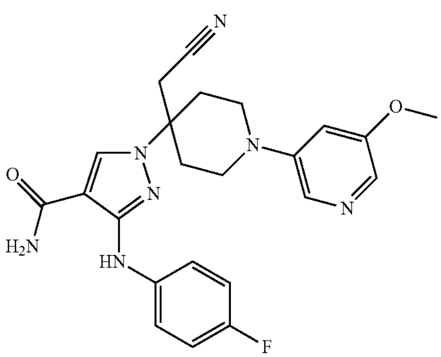 [SMILES: COc1cncc(N2CCC(CC#N)(n3cc(C(N)=O)c(Nc4ccc(F)cc4)n3)CC2)c1] | 1-[4-(cyanomethyl)-1-(5-methoxypyridin-3-yl)piperidin-4-yl]-3-[(4-fluorophenyl)amino]-1H-pyrazole-4-carboxamide | Calc'd 450, found 450 |
| 3-38 | 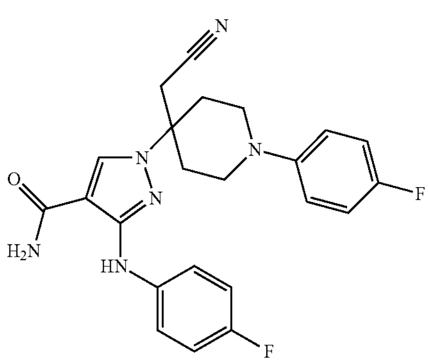 [SMILES: N#CCC1(n2cc(C(N)=O)c(Nc3ccc(F)cc3)n2)CCN(c2ccc(F)cc2)CC1] | 1-[4-(cyanomethyl)-1-(4-fluorophenyl)piperidin-4-yl]-3-[(4-fluorophenyl)amino]-1H-pyrazole-4-carboxamide | Calc'd 437, found 437 |

TABLE 12-continued

| Example | Structure | Compound Name | Exact Mass [M + H]⁺ |
|---|---|---|---|
| 3-39 | 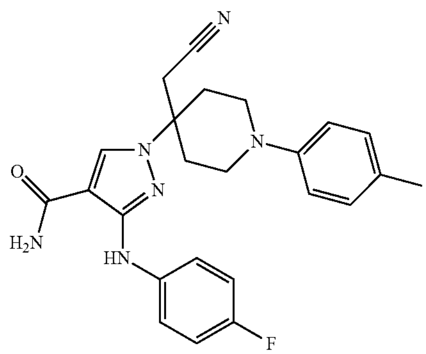 [SMILES: Cc1ccc(N2CCC(CC#N)(n3cc(C(N)=O)c(Nc4ccc(F)cc4)n3)CC2)cc1] | 1-[4-(cyanomethyl)-1-(4-methylphenyl)piperidin-4-yl]-3-[(4-fluorophenyl)amino]-1H-pyrazole-4-carboxamide | Calc'd 433, found 433 |
| 3-40 | 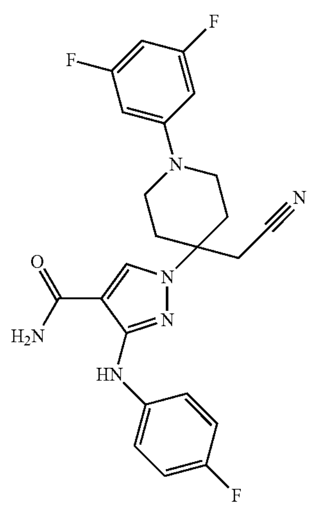 [SMILES: N#CCC1(n2cc(C(N)=O)c(Nc3ccc(F)cc3)n2)CCN(c2cc(F)cc(F)c2)CC1] | 1-[4-(cyanomethyl)-1-(3,5-difluorophenyl)piperidin-4-yl]-3-[(4-fluorophenyl)amino]-1H-pyrazole-4-carboxamide | Calc'd 455, found 455 |
| 3-41 | 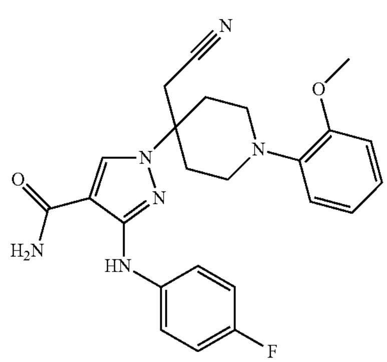 [SMILES: COc1ccccc1N1CCC(CC#N)(n2cc(C(N)=O)c(Nc3ccc(F)cc3)n2)CC1] | 1-[4-(cyanomethyl)-1-(2-methoxyphenyl)piperidin-4-yl]-3-[(4-fluorophenyl)amino]-1H-pyrazole-4-carboxamide | Calc'd 449, found 449 |

TABLE 12-continued

| Example | Structure | Compound Name | Exact Mass [M + H]+ |
|---|---|---|---|
| 3-42 | 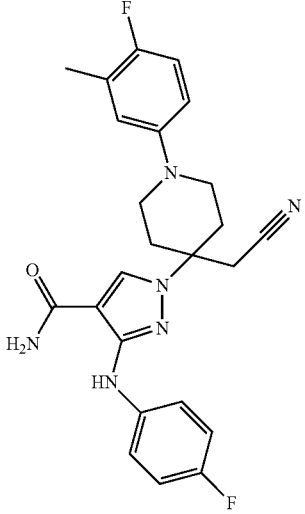 | 1-[4-(cyanomethyl)-1-(4-fluoro-3-methylphenyl)piperidin-4-yl]-3-[(4-fluorophenyl)amino]-1H-pyrazole-4-carboxamide | Calc'd 451, found 451 |
| 3-43 | 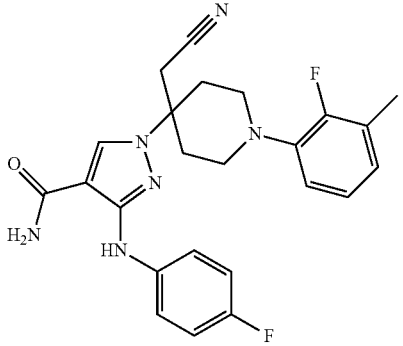 [SMILES: Cc1cccc(N2CCC(CC#N)(n3cc(C(N)=O)c(Nc4ccc(F)cc4)n3)CC2)c1F] | 1-[4-(cyanomethyl)-1-(2-fluoro-3-methylphenyl)piperidin-4-yl]-3-[(4-fluorophenyl)amino]-1H-pyrazole-4-carboxamide | Calc'd 451, found 451 |
| 3-44 | 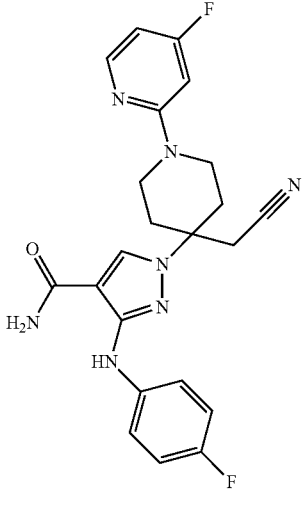 [SMILES: N#CCC1(n2cc(C(N)=O)c(Nc3ccc(F)cc3)n2)CCN(c2cc(F)ccn2)CC1] | 1-[4-(cyanomethyl)-1-(4-fluoropyridin-2-yl)piperidin-4-yl]-3-[(4-fluorophenyl)amino]-1H-pyrazole-4-carboxamide | Calc'd 438, found 438 |

TABLE 12-continued

| Example | Structure | Compound Name | Exact Mass [M + H]+ |
|---|---|---|---|
| 3-45 | 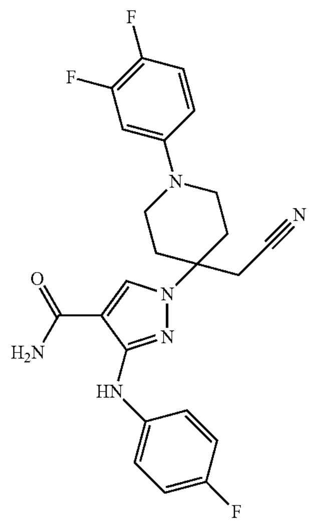 [SMILES: N#CCC1(n2cc(C(N)=O)c(Nc3ccc(F)cc3)n2)CCN(c2ccc(F)c(F)c2)CC1] | 1-[4-(cyanomethyl)-1-(3,4-difluorophenyl)piperidin-4-yl]-3-[(4-fluorophenyl)amino]-1H-pyrazole-4-carboxamide | Calc'd 455, found 455 |
| 3-46 | 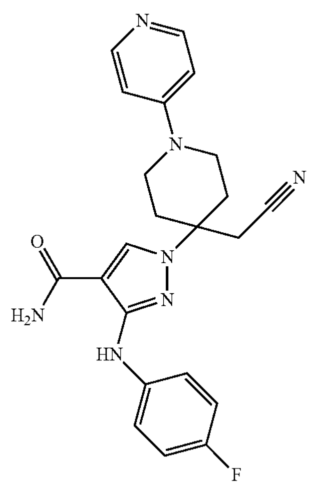 [SMILES: N#CCC1(n2cc(C(N)=O)c(Nc3ccc(F)cc3)n2)CCN(c2ccncc2)CC1] | 1-[4-(cyanomethyl)-1-pyridin-4-ylpiperidin-4-yl]-3-[(4-fluorophenyl)amino]-1H-pyrazole-4-carboxamide | Calc'd 420, found 420 |
| 3-47 | 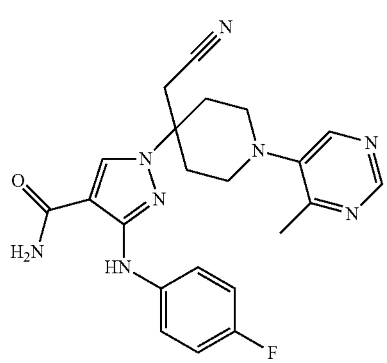 [SMILES: Cc1ncncc1N1CCC(CC#N)(n2cc(C(N)=O)c(Nc3ccc(F)cc3)n2)CC1] | 1-[4-(cyanomethyl)-1-(4-methylpyrimidin-5-yl)piperidin-4-yl]-3-[(4-fluorophenyl)amino]-1H-pyrazole-4-carboxamide | Calc'd 435, found 435 |

TABLE 12-continued

| Example | Structure | Compound Name | Exact Mass [M + H]+ |
|---|---|---|---|
| 3-48 | 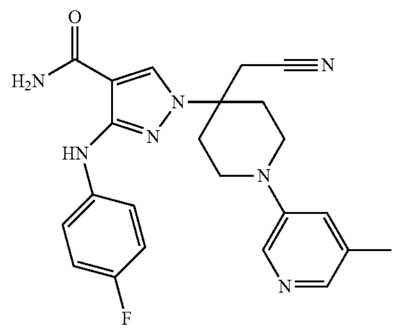 [SMILES: Cc1cncc(N2CCC(CC#N)(n3cc(C(N)=O)c(Nc4ccc(F)cc4)n3)CC2)c1] | 1-[4-(cyanomethyl)-1-(5-methylpyridin-3-yl)piperidin-4-yl]-3-[(4-fluorophenyl)amino]-1H-pyrazole-4-carboxamide | Calc'd 434, found 434 |
| 3-49 | 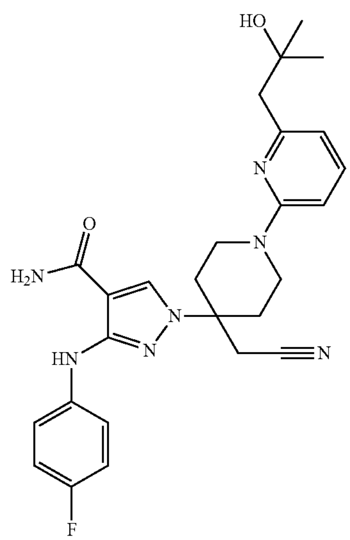 [SMILES: CC(C)(O)Cc1cccc(N2CCC(CC#N)(n3cc(C(N)=O)c(Nc4ccc(F)cc4)n3)CC2)n1] | 1-{4-(cyanomethyl)-1-[6-(2-hydroxy-2-methylpropyl)pyridin-2-yl]piperidin-4-yl}-3-[(4-fluorophenyl)amino]-1H-pyrazole-4-carboxamide | Calc'd 492, found 492 |
| 3-50 | 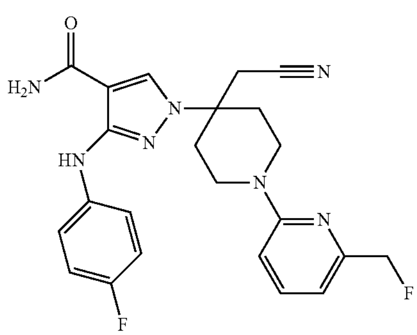 [SMILES: N#CCC1(n2cc(C(N)=O)c(Nc3ccc(F)cc3)n2)CCN(c2cccc(CF)n2)CC1] | 1-{4-(cyanomethyl)-1-[6-(fluoromethyl)pyridin-2-yl]piperidin-4-yl}-3-[(4-fluorophenyl)amino]-1H-pyrazole-4-carboxamide | Calc'd 452, found 452 |
| 3-51 | 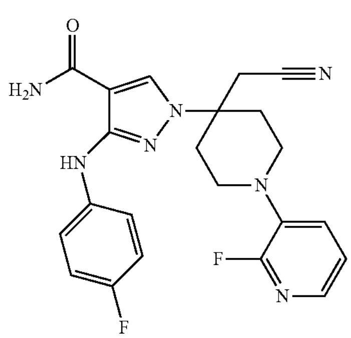 [SMILES: N#CCC1(n2cc(C(N)=O)c(Nc3ccc(F)cc3)n2)CCN(c2cccnc2F)CC1] | 1-[4-(cyanomethyl)-1-(2-fluoropyridin-3-yl)piperidin-4-yl]-3-[(4-fluorophenyl)amino]-1H-pyrazole-4-carboxamide | Calc'd 438, found 438 |

TABLE 12-continued

| Example | Structure | Compound Name | Exact Mass [M + H]+ |
|---|---|---|---|
| 3-52 | 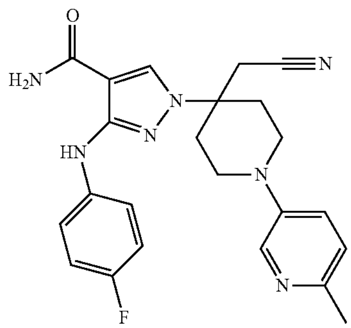 [SMILES: Cc1ccc(N2CCC(CC#N)(n3cc(C(N)=O)c(Nc4ccc(F)cc4)n3)CC2)cn1] | 1-[4-(cyanomethyl)-1-(6-methylpyridin-3-yl)piperidin-4-yl]-3-[(4-fluorophenyl)amino]-1H-pyrazole-4-carboxamide | Calc'd 434, found 434 |
| 3-53 | 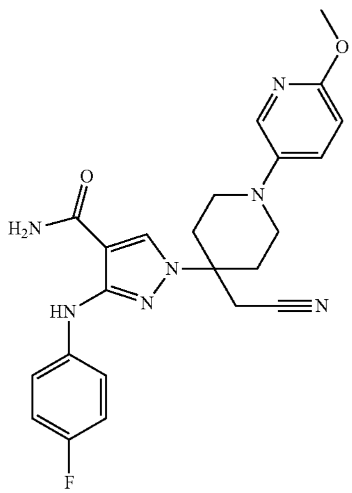 [SMILES: COc1ccc(N2CCC(CC#N)(n3cc(C(N)=O)c(Nc4ccc(F)cc4)n3)CC2)cn1] | 1-[4-(cyanomethyl)-1-(6-methoxypyridin-3-yl)piperidin-4-yl]-3-[(4-fluorophenyl)amino]-1H-pyrazole-4-carboxamide | Calc'd 450, found 450 |
| 3-54 | 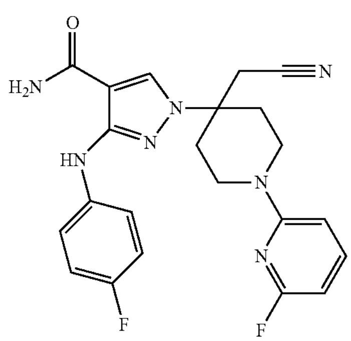 [SMILES: N#CCC1(n2cc(C(N)=O)c(Nc3ccc(F)cc3)n2)CCN(c2cccc(F)n2)CC1] | 1-[4-(cyanomethyl)-1-(6-fluoropyridin-2-yl)piperidin-4-yl]-3-[(4-fluorophenyl)amino]-1H-pyrazole-4-carboxamide | Calc'd 438, found 438 |
| 3-55 | 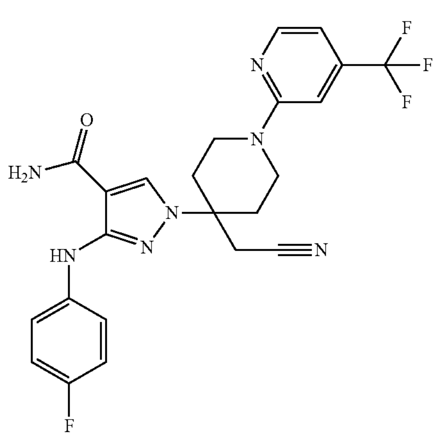 [SMILES: N#CCC1(n2cc(C(N)=O)c(Nc3ccc(F)cc3)n2)CCN(c2cc(C(F)(F)F)ccn2)CC1] | 1-{4-(cyanomethyl)-1-[4-(trifluoromethyl)pyridin-2-yl]piperidin-4-yl}-3-[(4-fluorophenyl)amino]-1H-pyrazole-4-carboxamide | Calc'd 488, found 488 |

TABLE 12-continued

| Example | Structure | Compound Name | Exact Mass [M + H]+ |
|---|---|---|---|
| 3-56 | 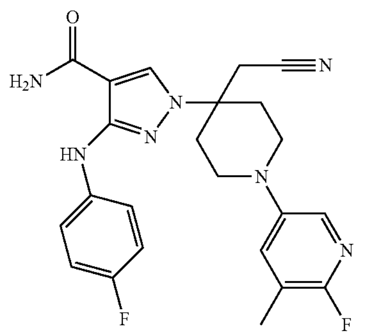 [SMILES: Cc1cc(N2CCC(CC#N)(n3cc(C(N)=O)c(Nc4ccc(F)cc4)n3)CC2)cnc1F] | 1-[4-(cyanomethyl)-1-(6-fluoro-5-methylpyridin-3-yl)piperidin-4-yl]-3-[(4-fluorophenyl)amino]-1H-pyrazole-4-carboxamide | Calc'd 452, found 452 |

Scheme #23

Example #4-1

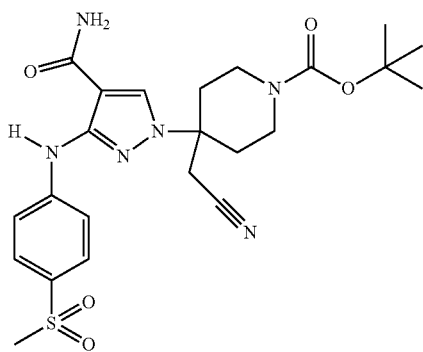

tert-Butyl 4-(4-carbamoyl-3-{[4-(methylsulfonyl)phenyl]amino}-1H-pyrazol-1-yl)-4-(cyanomethyl)piperidine-1-carboxylate DBU (0.118 mL, 0.785 mmol) was added 3-((4-(methylsulfonyl)phenyl)amino)-1H-pyrazole-4-carboxamide (Intermediate 34-2) (200 mg, 0.714 mmol) and tert-butyl 4-(cyanomethylidene)piperidine-1-carboxylate (Intermediate 19-1) (317 mg, 1.43 mmol) stirred in DMF (3 mL) and the mixture was heated to 50° C. for 5 h. The reaction mixture was cooled to 23° C., water was added to the reaction mixture and the mixture was extracted with ethyl acetate. The combined organic fractions were dried ($Na_2SO_4$), filtered and the solvent was evaporated under reduced pressure. The residue was purified by column chromatography on silica gel eluting with EtOAc/hexanes to afford the title compound.

LRMS (ESI) calc'd for $C_{23}H_{30}N_6O_5S$ [M+H]+: 503. Found: 403 [M+H-Boc].

$^1$H NMR (600 MHz, DMSO-$d_6$): δ 9.51 (s, 1H), 8.51 (s, 1H), 7.72 (s, 4H), 7.61 (s, 1H), 7.26 (s, 1H), 3.70-3.64 (m, 2H), 3.19 (s, 2H), 3.09 (s, 3H), 3.04-2.94 (m, 2H), 2.37-2.32 (m, 2H), 1.99-1.95 (m, 2H), 1.36 (s, 9H).

The following examples shown in TABLE 13 were prepared according to Scheme #23 following similar procedures described for Examples #4-1, which can be achieved by those of ordinary skill in the art of organic synthesis utilizing, among others, Intermediates 19-1, 19-23, 24, 31-4, 31-6, 33, and 34-2.

TABLE 13

| Example | Structure | Compound Name | Exact Mass [M + H]+ |
|---|---|---|---|
| 4-2 | 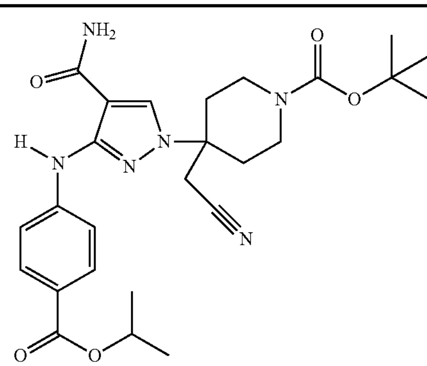 | tert-butyl 4-[4-carbamoyl-3-({4-[(1-methylethoxy)carbonyl]phenyl}amino)-1H-pyrazol-1-yl]-4-(cyanomethyl)piperidine-1-carboxylate | Calc'd 511, Found 511 |

TABLE 13-continued

| Example | Structure | Compound Name | Exact Mass [M + H]⁺ |
|---------|-----------|---------------|---------------------|
| 4-3 | 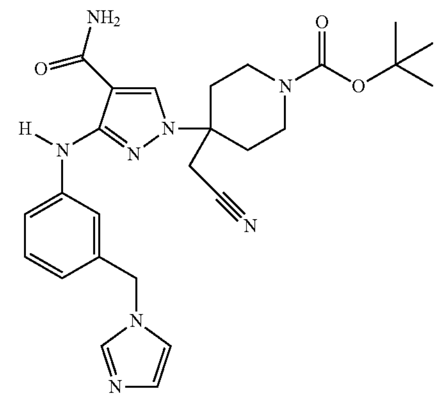 [SMILES: CC(C)(C)OC(=O)N1CCC(CC#N)(n2cc(C(N)=O)c(Nc3cccc(Cn4ccnc4)c3)n2)CC1] | tert-butyl 4-(4-carbamoyl-3-{[3-(1H-imidazol-1-ylmethyl)phenyl]amino}-1H-pyrazol-1-yl)-4-(cyanomethyl)piperidine-1-carboxylate | Calc'd 505, Found 505 |
| 4-4 | 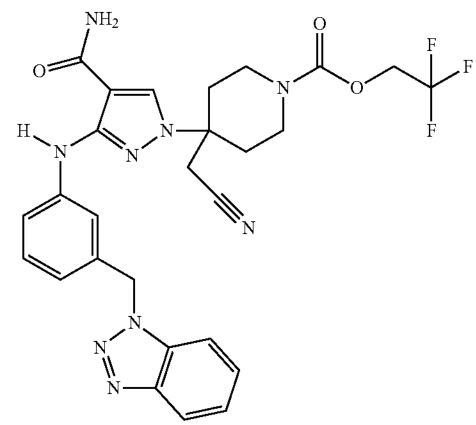 [SMILES: N#CCC1(n2cc(C(N)=O)c(Nc3cccc(Cn4nnc5ccccc54)c3)n2)CCN(C(=O)OCC(F)(F)F)CC1] | 2,2,2-trifluoroethyl 4-(3-{[3-(1H-benzotriazol-1-ylmethyl)phenyl]amino}-4-carbamoyl-1H-pyrazol-1-yl)-4-(cyanomethyl)piperidine-1-carboxylate | Calc'd 582, Found 582 |
| 4-5 | 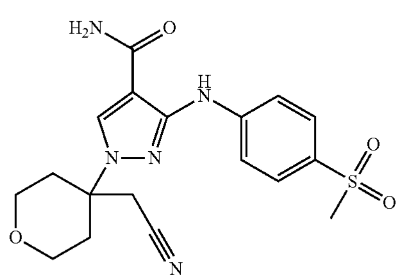 [SMILES: CS(=O)(=O)c1ccc(Nc2nn(C3(CC#N)CCOCC3)cc2C(N)=O)cc1] | 1-[4-(cyanomethyl)tetrahydro-2H-pyran-4-yl]-3-{[4-(methylsulfonyl)phenyl]amino}-1H-pyrazole-4-carboxamide | Calc'd 404, found 404 |
| 4-6 | 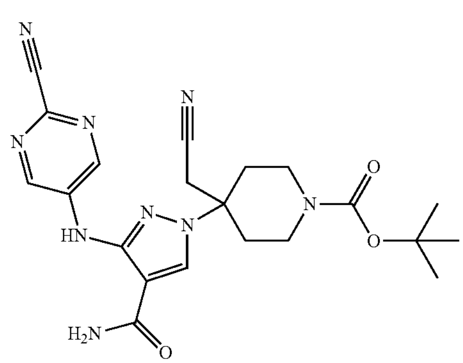 [SMILES: CC(C)(C)OC(=O)N1CCC(CC#N)(n2cc(C(N)=O)c(Nc3cnc(C#N)nc3)n2)CC1] | tert-butyl 4-{4-carbamoyl-3-[(2-cyanopyrimidin-5-yl)amino]-1H-pyrazol-1-yl}-4-(cyanomethyl)piperidine-1-carboxylate | Calc'd 452, found 396 (loss of t-butyl) |

Scheme #23

Example #5-1

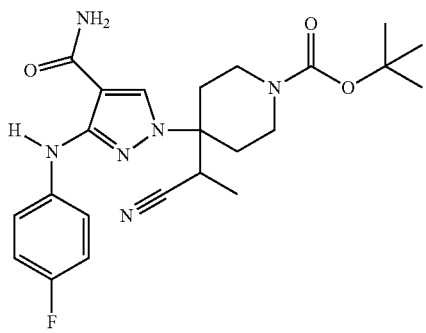 [SMILES: CC(C)(C)OC(=O)N1CCC(C(C#N)C2CC2)(n2cc(C(N)=O)c(Nc3ccc(F)cc3)n2)CC1]

tert-Butyl 4-(4-carbamoyl-3-((4-fluorophenyl)
amino)-1H-pyrazol-1-yl)-4-(1-cyanoethyl)piperi-
dine-1-carboxylate A mixture of tert-butyl 4-(1-cyanoethylidene)piperidine-1-carboxylate (Intermediate 21) (440 mg, 0.020 mol), DBU (0.9 g, 0.006 mol) and 3-((4-fluorophenyl)amino)-1H-pyrazole-4-carboxamide (Intermediate 31-7) (0.5 g, 0.002 mol) in 10 mL of MeCN was stirred under reflux overnight. After the conversion was stable, the mixture was concentrated and purified by reverse phase preparative HPLC (using a gradient elution of 0-95% MeCN/water, with 0.1% v/v TFA modifier) to afford the title compound.

$^1$H NMR (300 MHz, CDCl$_3$): δ 6.99-6.93 (m, 2H), 5.69 (s, 2H), 4.08 (s, 2H), 2.86-2.58 (m, 5H), 2.16-2.04 (m, 2H), 1.42 (s, 5H), 0.77 (s, 2H), 0.58 (s, 2H), 0.30 (s, 1H), 0.17 (s, 1H).

The following examples shown in TABLE 14 were prepared according to Scheme #23 following similar procedures described for Example #5-1, which can be achieved by those of ordinary skill in the art of organic synthesis utilizing, among others, Intermediates 19-23, 20, 22, 30, 31-1, 31-7, 31-8, and 34-2.

TABLE 14

| Example | Structure | Compound Name | Exact Mass [M + H]$^+$ |
|---|---|---|---|
| 5-2 | 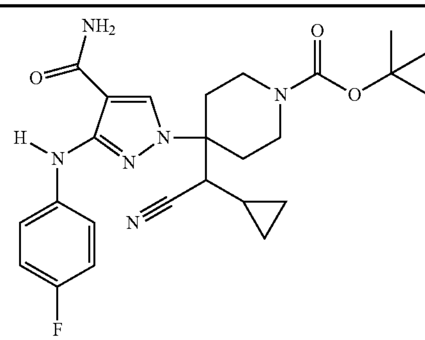 | tert-butyl 4-{4-carbamoyl-3-[(4-fluorophenyl)amino]-1H-pyrazol-1-yl}-4-[cyano(cyclopropyl)methyl]piperidine-1-carboxylate | Calc'd 483, Found 483 |
| 6-3 | 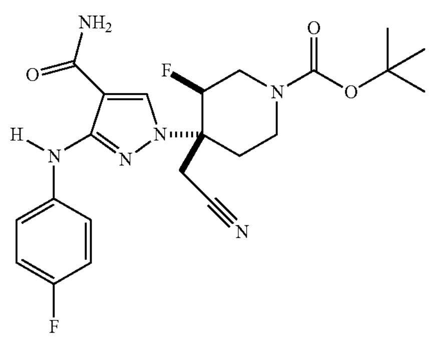 | tert-butyl (3S,4R and 3R,4S)-4-{4-carbamoyl-3-[(4-fluorophenyl)amino]-1H-pyrazol-1-yl}-4-(cyanomethyl)-3-fluoropiperidine-1-carboxylate | Calc'd 461, Found 461 |
| 6-4 | 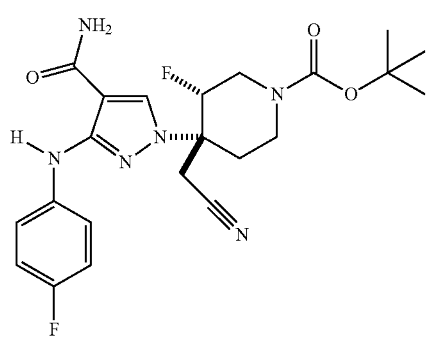 | tert-butyl (3S,4S and 3R,4R)-4-{4-carbamoyl-3-[(4-fluorophenyl)amino]-1H-pyrazol-1-yl}-4-(cyanomethyl)-3-fluoropiperidine-1-carboxylate | Calc'd 461, Found 461 |

TABLE 14-continued

| Example | Structure | Compound Name | Exact Mass [M + H]+ |
|---|---|---|---|
| 6-5 | 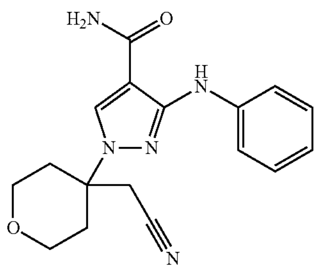 [SMILES: N#CCC1(n2cc(C(N)=O)c(Nc3ccccc3)n2)CCOCC1] | 1-[4-(cyanomethyl)tetrahydro-2H-pyran-4-yl]-3-(phenylamino)-1H-pyrazole-4-carboxamide | Calc'd 326, found 326 |
| 6-6 | 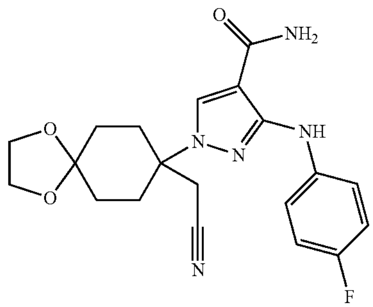 [SMILES: N#CCC1(n2cc(C(N)=O)c(Nc3ccc(F)cc3)n2)CCC2(CC1)OCCO2] | 1-[8-(cyanomethyl)-1,4-dioxaspiro[4.5]dec-8-yl]-3-[(4-fluorophenyl)amino]-1H-pyrazole-4-carboxamide | Calc'd 400, found 400 |
| 6-7 | 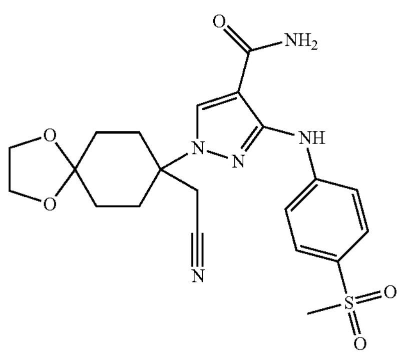 [SMILES: CS(=O)(=O)c1ccc(Nc2nn(C3(CC#N)CCC4(CC3)OCCO4)cc2C(N)=O)cc1] | 1-[8-(cyanomethyl)-1,4-dioxaspiro[4.5]dec-8-yl]-3-{[4-(methylsulfonyl)phenyl]amino}-1H-pyrazole-4-carboxamide | Calc'd 460, found 460 |

Scheme #32

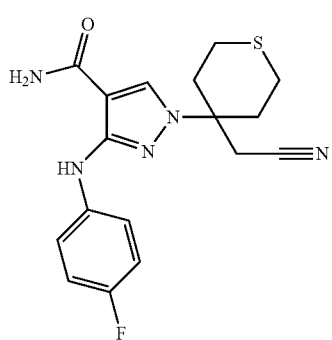

Example #7

1-(4-(Cyanomethyl)tetrahydro-2H-thiopyran-4-yl)-3-((4-fluorophenyl)amino)-1H-pyrazole-4-carboxamide

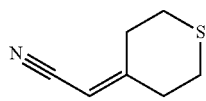

Step A
2-(Dihydro-2H-thiopyran-4(3H)-ylidene)acetonitrile

Potassium tert-butoxide (4.5 mL, 4.5 mmol, 1.0 M in THF) was stirred at 0° C. and THF (10 mL) was added. Diethyl (cyanomethyl)phosphonate (0.72 mL, 4.5 mmol) was added slowly by syringe. The reaction mixture was maintained at 0° C. for 10 minutes, then warmed to ambient temperature and maintained for 1 hour. The mixture was cooled to 0° C. and treated with the dropwise addition of dihydro-2H-thiopyran-4(3H)-one (0.50 g, 4.3 mmol) in THF (7 mL). After addition, the mixture was maintained at 0° C. for 20 minutes, then warmed to ambient temperature and maintained for 18 hours. The reaction mixture was then diluted with water and extracted with EtOAc. The combined organic extracts were washed with water, brine, dried over anhydrous Na$_2$SO$_4$, filtered, and concentrated in vacuo. The residue was purified MPLC on silica gel (using a gradient elution of 0-50% EtOAc/hexanes). Desired fractions were identified, combined, and concentrated in vacuo to the title compound.

$^1$H NMR (500 MHz, CDCl$_3$): δ 5.15 (s, 1H), 2.83-2.84 (m, 2H), 2.74-2.75 (m, 4H), 2.59 (t, J=5.8 Hz, 2H).

Step B: 1-(4-(Cyanomethyl)tetrahydro-2H-thiopyran-4-yl)-3-((4-fluorophenyl)amino)-1H-pyrazole-4-carboxamide 3-[(4-Fluorophenyl)amino]-1H-pyrazole-4-carboxamide (Intermediate 31-7) (100 mg, 0.45 mmol) was added to a mixture of 2-(1,1-dioxidodihydro-2H-thiopyran-4(3H)-ylidene)acetonitrile (160 mg, 0.91 mmol) in MeCN (1.51 mL). DBU (0.068 mL, 0.45 mmol) was then added, the reaction vessel was capped and the reaction mixture was heated to 80° C. for 4 hours. The reaction mixture was cooled to ambient temperature, and purified by reverse phase preparative HPLC (using a gradient elution of MeCN/water, with 0.1% v/v TFA modifier). Desired fractions were combined, basified with saturated aqueous NaHCO$_3$, and extracted with EtOAc. The organic layer was dried over anhydrous NaSO$_4$, filtered, and concentrated in vacuo to afford the title compound, Example #7.

LRMS (ESI) calc'd for C$_{17}$H$_{18}$FN$_5$OS [M+H]$^+$: 360. Found: 360.

$^1$H NMR (500 MHz, 10:1 CDCl$_3$:CD$_3$OD): δ 8.09 (s, 1H), 7.37-7.38 (m, 2H), 6.89 (t, J=8.7 Hz, 2H), 2.76-2.85 (m, 4H), 2.67-2.70 (m, 2H), 2.53 (d, J=14.4 Hz, 2H), 2.13 (ddd, J=14.2, 11.0, 3.3 Hz, 2H).

Scheme #33

Example #8

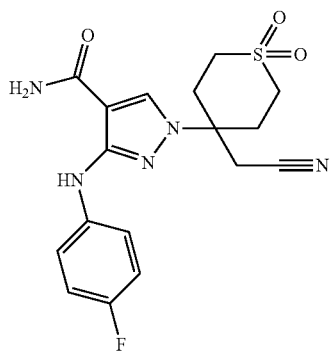

1-(4-(Cyanomethyl)-1,1-dioxidotetrahydro-2H-thiopyran-4-yl)-3-((4-fluorophenyl)amino)-1H-pyrazole-4-carboxamide

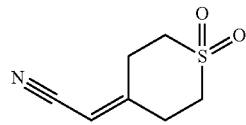 [SMILES: N#CC=C1CCS(=O)(=O)CC1]

Step A: 2-(1,1-Dioxidodihydro-2H-thiopyran-4(3H)-ylidene)acetonitrile

Potassium tert-butoxide (3.5 mL, 3.5 mmol, 1.0 M in THF) was stirred at 0° C. and THF (8 mL) was added. Diethyl (cyanomethyl)phosphonate (0.56 mL, 3.5 mmol) was added slowly by syringe. The reaction mixture was maintained at 0° C. for 10 minutes, then warmed to ambient temperature and maintained for 1 hour. The mixture was cooled to 0° C. and treated with the dropwise addition of dihydro-2H-thiopyran-4(3H)-one 1,1-dioxide (0.50 g, 3.4 mmol) in THF (5 mL). After addition, the mixture was maintained at 0° C. for 20 minutes, then warmed to ambient temperature and maintained for 18 hours. The reaction mixture was then diluted with water and extracted with EtOAc. The combined organic extracts were washed with water, brine, dried over anhydrous Na$_2$SO$_4$, filtered, and concentrated in vacuo. The residue was purified MPLC on silica gel (using a gradient elution of 0-50% EtOAc/hexanes). Desired fractions were identified, combined, and concentrated in vacuo to the title compound.

Step B: 1-(4-(Cyanomethyl)-1,1-dioxidotetrahydro-2H-thiopyran-4-yl)-3-((4-fluorophenyl)amino)-1H-pyrazole-4-carboxamide 3-[(4-Fluorophenyl)amino]-1H-pyrazole-4-carboxamide (Intermediate 31-7) (100 mg, 0.45 mmol) was added to a mixture of 2-(dihydro-2H-thiopyran-4(3H)-ylidene)acetonitrile (130 mg, 0.91 mmol) in MeCN (1.51 mL). DBU (0.068 mL, 0.45 mmol) was then added, the reaction vessel was capped and the reaction mixture was heated to 80° C. for 4 hours. The reaction mixture was cooled to ambient temperature, and purified by reverse phase preparative HPLC (using a gradient elution of MeCN/water, with 0.1% v/v TFA modifier). Desired fractions were combined, basified with saturated aqueous NaHCO$_3$, and extracted with EtOAc. The organic layer was dried over anhydrous NaSO$_4$, filtered, and concentrated in vacuo to afford the title compound, Example #8.

LRMS (ESI) calc'd for C$_{17}$H$_{18}$FN$_5$O$_3$S [M+H]$^+$: 392. Found: 392.

$^1$H NMR (500 MHz, 10:1 CDCl$_3$:CD$_3$OD): δ 8.24 (s, 1H), 7.33-7.34 (m, 2H), 6.89 (t, J=8.6 Hz, 2H), 2.97-3.10 (m, 6H), 2.86 (s, 2H), 2.53-2.56 (m, 2H).

Scheme #24

Example #9-1

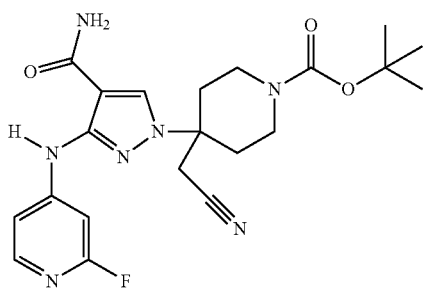

tert-Butyl 4-{4-carbamoyl-3-[(2-fluoropyridin-4-yl)amino]-1H-pyrazol-1-yl}-4-(cyanomethyl)piperidine-1-carboxylate To a microwave vial was added tert-butyl 4-(3-amino-4-carbamoyl-1H-pyrazol-1-yl)-4-(cyanomethyl)piperidine-1-carboxylate (Intermediate 35-1) (5.0 g, 14 mmol), 4-bromo-2-fluoropyridine (2.5 g, 14 mmol), $K_3PO_4$ (6.1 g, 29 mmol), and dioxane (72 mL). The mixture was degassed with bubbling argon for 5 minutes. $Pd_2(dba)_3$ (0.7 g, 0.7 mmol) and X-Phos (1.0 g, 2.2 mmol) were then added, and the vial was sealed and heated to 95° C. for 5 hours. The mixture was then cooled to ambient temperature, diluted with EtOAc, filtered through celite, and eluted with EtOAc. The filtrate was concentrated in vacuo, and the resulting yellow oil was purified by MPLC on silica gel (using a gradient elution of 50-100% EtOAc/hexanes) to afford the title compound, Example #9-1.

LRMS (ESI) calc'd for $C_{21}H_{26}FN_7O_3$ $[M+H]^+$: 444. Found: 444.

$^1$H NMR (500 MHz, acetone-$d_6$): δ 9.78 (s, 1H), 8.56 (s, 1H), 7.95 (d, J=5.6 Hz, 1H), 7.41 (d, J=1.5 Hz, 1H), 7.38-7.24 (m, 2H), 6.69 (br s, 1H), 3.92-3.84 (m, 2H), 3.23 (s, 2H), 3.15 (br s, 2H), 2.61 (d, J=14.2 Hz, 2H), 2.20-2.10 (m, 2H), 1.44 (s, 9H).

The following examples, disclosed in TABLE 15 were prepared according to Scheme #24 following similar procedures described for Example #9-1, which can be achieved by those of ordinary skill in the art of organic synthesis.

TABLE 15

| Example | Structure | Compound Name | Exact Mass $[M + H]^+$ |
|---|---|---|---|
| 9-2 | 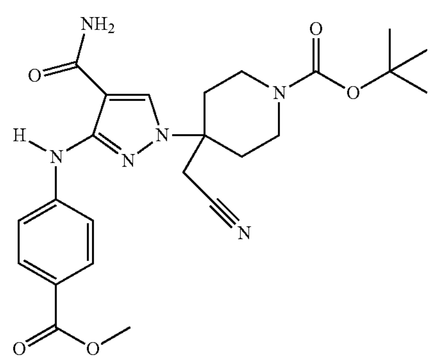 [SMILES: COC(=O)c1ccc(Nc2nn(C3(CC#N)CCN(C(=O)OC(C)(C)C)CC3)cc2C(N)=O)cc1] | tert-butyl 4-(4-carbamoyl-3-{[4-(methoxycarbonyl)phenyl]amino}-1H-pyrazol-1-yl)-4-(cyanomethyl)piperidine-1-carboxylate | Calc'd 483, Found 483 |
| 9-3 | 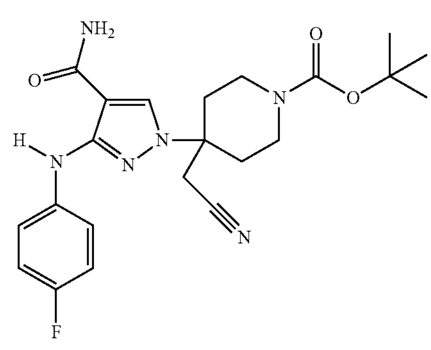 [SMILES: CC(C)(C)OC(=O)N1CCC(CC#N)(n2cc(C(N)=O)c(Nc3ccc(F)cc3)n2)CC1] | tert-butyl 4-{4-carbamoyl-3-[(4-fluorophenyl)amino]-1H-pyrazol-1-yl}-4-(cyanomethyl)piperidine-1-carboxylate | Calc'd 443, Found 443 |

TABLE 15-continued

| Example | Structure | Compound Name | Exact Mass [M + H]⁺ |
|---|---|---|---|
| 9-4 | 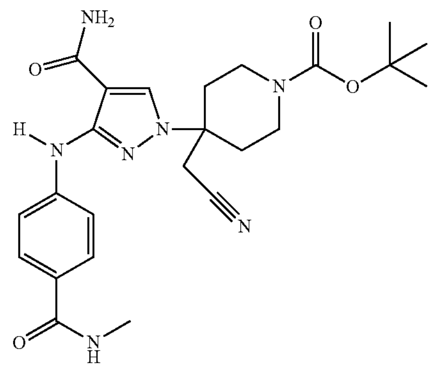 [SMILES: CNC(=O)c1ccc(Nc2nn(C3(CC#N)CCN(C(=O)OC(C)(C)C)CC3)cc2C(N)=O)cc1] | tert-Butyl 4-[4-(aminocarbonyl)-3-({4-[(methylamino)carbonyl]phenyl}amino)-1H-pyrazol-1-yl]-4-(cyanomethyl)piperidine-1-carboxylate | Calc'd 482, Found 482 |
| 9-5 | 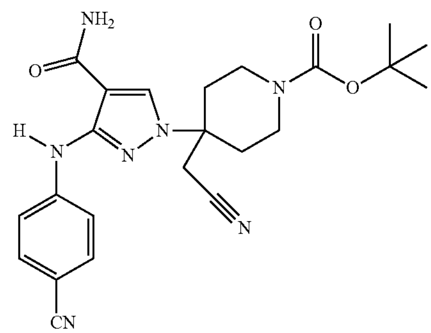 [SMILES: CC(C)(C)OC(=O)N1CCC(CC#N)(n2cc(C(N)=O)c(Nc3ccc(C#N)cc3)n2)CC1] | tert-butyl 4-{4-carbamoyl-3-[(4-cyanophenyl)amino]-1H-pyrazol-1-yl}-4-(cyanomethyl)piperidine-1-carboxylate | Calc'd 450, Found 450 |
| 9-6 | 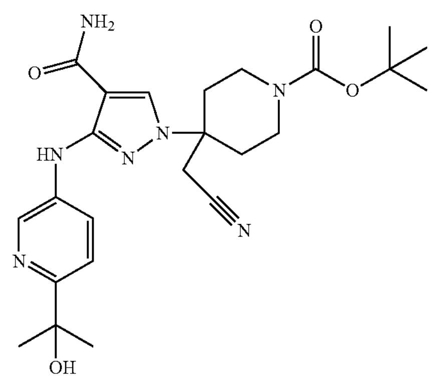 [SMILES: CC(C)(C)OC(=O)N1CCC(CC#N)(n2cc(C(N)=O)c(Nc3ccc(C(C)(C)O)nc3)n2)CC1] | tert-butyl 4-(4-carbamoyl-3-(6-(2-hydroxypropan-2-yl)pyridin-3-ylamino)-1H-pyrazol-1-yl)-4-(cyanomethyl)piperidine-1-carboxylate | Calc'd 484, Found 484 |
| 9-7 | 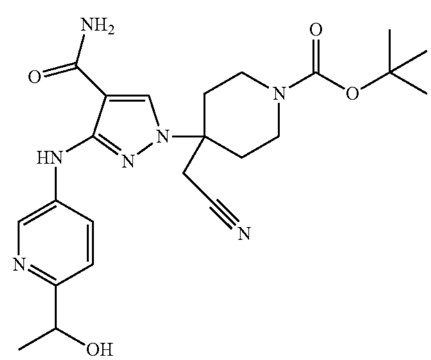 [SMILES: CC(O)c1ccc(Nc2nn(C3(CC#N)CCN(C(=O)OC(C)(C)C)CC3)cc2C(N)=O)cn1] | tert-butyl 4-(4-carbamoyl-3-(6-(1-hydroxyethyl)pyridin-3-ylamino)-1H-pyrazol-1-yl)-4-(cyanomethyl)piperidine-1-carboxylate | Calc'd 470, Found 470 |

TABLE 15-continued

| Example | Structure | Compound Name | Exact Mass [M + H]+ |
|---|---|---|---|
| 9-8 | 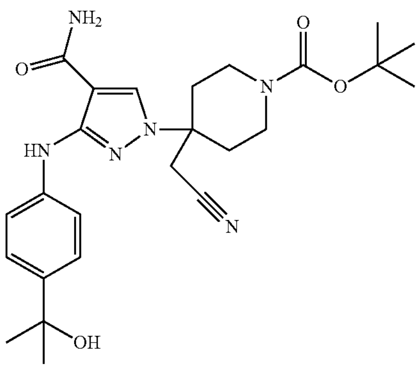 [SMILES: CC(C)(C)OC(=O)N1CCC(CC#N)(n2cc(C(N)=O)c(Nc3ccc(C(C)(C)O)cc3)n2)CC1] | tert-butyl 4-(4-carbamoyl-3-(4-(2-hydroxypropan-2-yl)phenylamino)-1H-pyrazol-1-yl)-4-(cyanomethyl)piperidine-1-carboxylate | Calc'd 483, Found 465 (M—OH) |
| 9-9 | 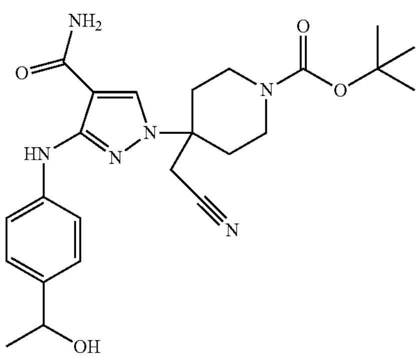 [SMILES: CC(O)c1ccc(Nc2nn(C3(CC#N)CCN(C(=O)OC(C)(C)C)CC3)cc2C(N)=O)cc1] | tert-butyl 4-(4-carbamoyl-3-(4-(1-hydroxyethyl)phenylamino)-1H-pyrazol-1-yl)-4-(cyanomethyl)piperidine-1-carboxylate | Calc'd 469, Found 451 (M—OH) |
| 9-10 | 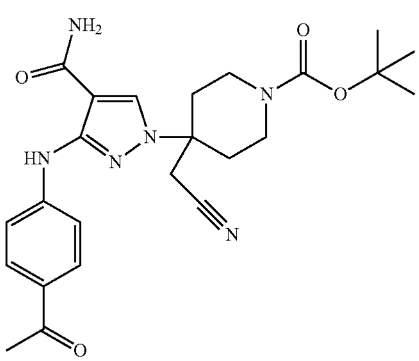 [SMILES: CC(=O)c1ccc(Nc2nn(C3(CC#N)CCN(C(=O)OC(C)(C)C)CC3)cc2C(N)=O)cc1] | tert-butyl 4-(3-(4-acetylphenylamino)-4-carbamoyl-1H-pyrazol-1-yl)-4-(cyanomethyl)piperidine-1-carboxylate | Calc'd 467, Found 467 |
| 9-11 | 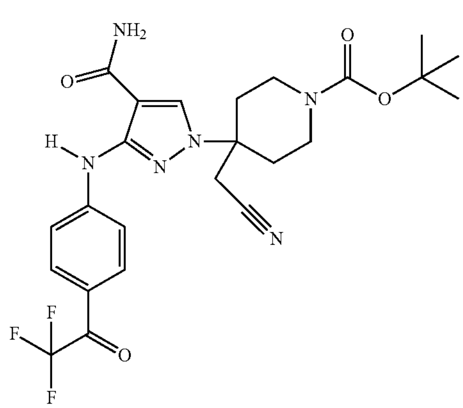 [SMILES: CC(C)(C)OC(=O)N1CCC(CC#N)(n2cc(C(N)=O)c(Nc3ccc(C(=O)C(F)(F)F)cc3)n2)CC1] | tert-butyl 4-(4-carbamoyl-3-{[4-(trifluoroacetyl)phenyl]amino}-1H-pyrazol-1-yl)-4-(cyanomethyl)piperidine-1-carboxylate | Calc'd 521, Found 521 |

TABLE 15-continued

| Example | Structure | Compound Name | Exact Mass [M + H]+ |
|---|---|---|---|
| 9-12 | 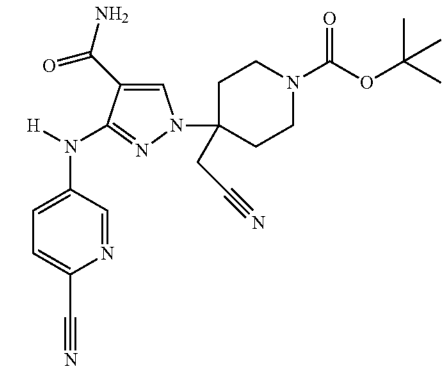 [SMILES: CC(C)(C)OC(=O)N1CCC(CC#N)(n2cc(C(N)=O)c(Nc3ccc(C#N)nc3)n2)CC1] | tert-butyl 4-{4-carbamoyl-3-[(6-cyanopyridin-3-yl)amino]-1H-pyrazol-1-yl}-4-(cyanomethyl)piperidine-1-carboxylate | Calc'd 451, Found 451 |
| 9-13 | 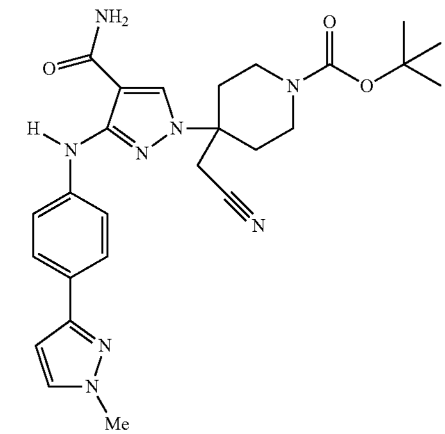 [SMILES: Cn1ccc(-c2ccc(Nc3nn(C4(CC#N)CCN(C(=O)OC(C)(C)C)CC4)cc3C(N)=O)cc2)n1] | tert-butyl 4-(4-carbamoyl-3-{[4-(1-methyl-1H-pyrazol-3-yl)phenyl]amino}-1H-pyrazol-1-yl)-4-(cyanomethyl)piperidine-1-carboxylate | Calc'd 505, Found 505 |
| 9-14 | 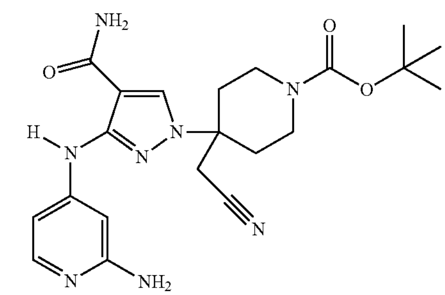 [SMILES: CC(C)(C)OC(=O)N1CCC(CC#N)(n2cc(C(N)=O)c(Nc3ccnc(N)c3)n2)CC1] | tert-butyl 4-{3-[(2-aminopyridin-4-yl)amino]-4-carbamoyl-1H-pyrazol-1-yl}-4-(cyanomethyl)piperidine-1-carboxylate | Calc'd 441, Found 441 |
| 9-15 | 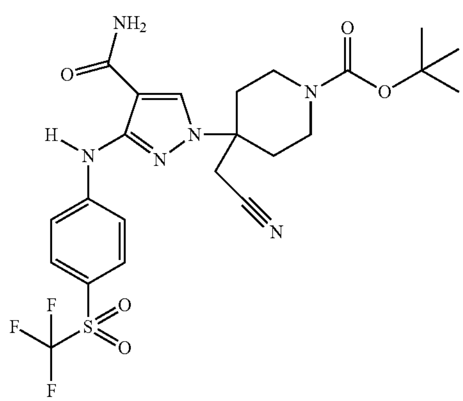 [SMILES: CC(C)(C)OC(=O)N1CCC(CC#N)(n2cc(C(N)=O)c(Nc3ccc(S(=O)(=O)C(F)(F)F)cc3)n2)CC1] | tert-butyl 4-[4-carbamoyl-3-({4-[(trifluoromethyl)sulfonyl]phenyl}amino)-1H-pyrazol-1-yl]-4-(cyanomethyl)piperidine-1-carboxylate | Calc'd 557, Found 501 (M + H—C$_4$H$_8$) |

TABLE 15-continued

| Example | Structure | Compound Name | Exact Mass [M + H]+ |
|---|---|---|---|
| 9-16 | 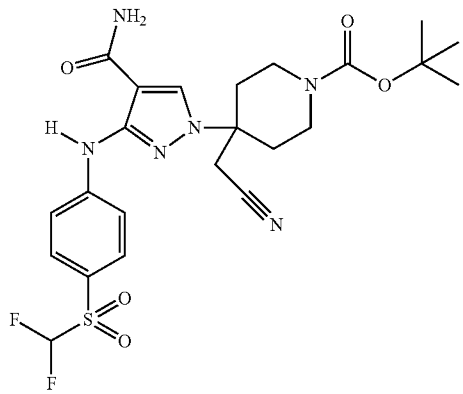 [SMILES: CC(C)(C)OC(=O)N1CCC(CC#N)(n2cc(C(N)=O)c(Nc3ccc(S(=O)(=O)C(F)F)cc3)n2)CC1] | tert-butyl 4-[4-carbamoyl-3-({4-[(difluoromethyl)sulfonyl]phenyl}amino)-1H-pyrazol-1-yl]-4-(cyanomethyl)piperidine-1-carboxylate | Calc'd 539, Found 483 (M + H—C$_4$H$_8$) |
| 9-17 | 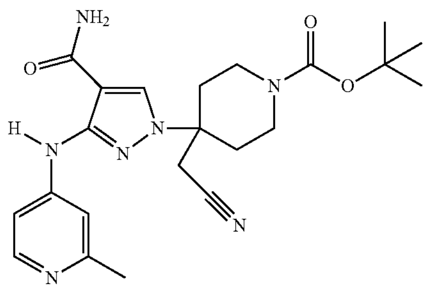 [SMILES: Cc1cc(Nc2nn(C3(CC#N)CCN(C(=O)OC(C)(C)C)CC3)cc2C(N)=O)ccn1] | tert-butyl 4-{4-carbamoyl-3-[(2-methylpyridin-4-yl)amino]-1H-pyrazol-1-yl}-4-(cyanomethyl)piperidine-1-carboxylate | Calc'd 440, Found 440 |
| 9-18 | 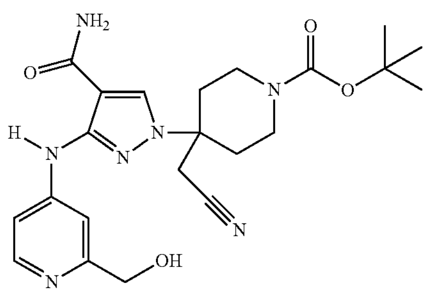 [SMILES: CC(C)(C)OC(=O)N1CCC(CC#N)(n2cc(C(N)=O)c(Nc3ccnc(CO)c3)n2)CC1] | tert-butyl 4-(4-carbamoyl-3-{[2-(hydroxymethyl)pyridin-4-yl]amino}-1H-pyrazol-1-yl)-4-(cyanomethyl)piperidine-1-carboxylate | Calc'd 456, Found 456 |
| 9-19 | 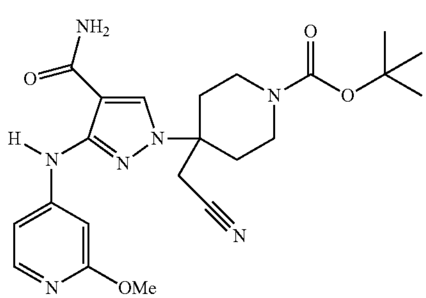 [SMILES: COc1cc(Nc2nn(C3(CC#N)CCN(C(=O)OC(C)(C)C)CC3)cc2C(N)=O)ccn1] | tert-butyl 4-{4-carbamoyl-3-[(2-methoxypyridin-4-yl)amino]-1H-pyrazol-1-yl}-4-(cyanomethyl)piperidine-1-carboxylate | Calc'd 456, Found 456 |

TABLE 15-continued

| Example | Structure | Compound Name | Exact Mass [M + H]⁺ |
|---|---|---|---|
| 9-20 | 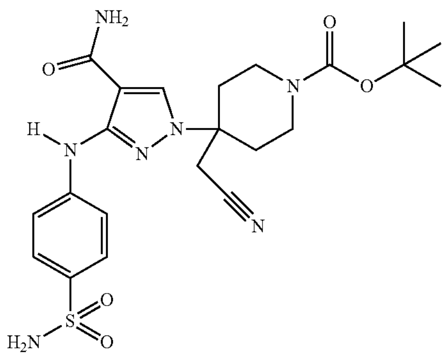 [SMILES: CC(C)(C)OC(=O)N1CCC(CC#N)(n2cc(C(N)=O)c(Nc3ccc(S(N)(=O)=O)cc3)n2)CC1] | tert-butyl 4-{4-carbamoyl-3-[(4-sulfamoylphenyl)amino]-1H-pyrazol-1-yl}-4-(cyanomethyl)piperidine-1-carboxylate | Calc'd 504, Found 404 (M + H—Boc) |
| 9-21 | 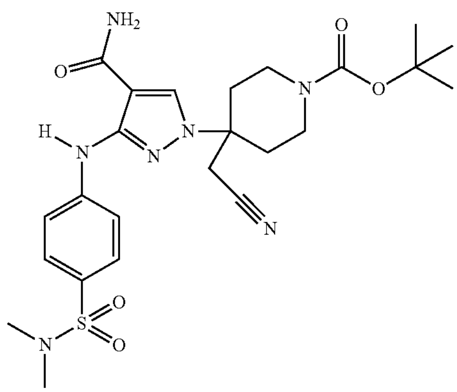 [SMILES: CN(C)S(=O)(=O)c1ccc(Nc2nn(C3(CC#N)CCN(C(=O)OC(C)(C)C)CC3)cc2C(N)=O)cc1] | tert-butyl 4-(4-carbamoyl-3-{[4-(dimethylsulfamoyl)phenyl]amino}-1H-pyrazol-1-yl)-4-(cyanomethyl)piperidine-1-carboxylate | Calc'd 532, Found 432 (M + H—Boc) |
| 9-22 | 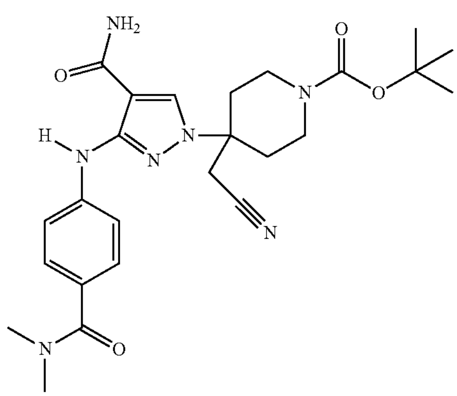 [SMILES: CN(C)C(=O)c1ccc(Nc2nn(C3(CC#N)CCN(C(=O)OC(C)(C)C)CC3)cc2C(N)=O)cc1] | tert-butyl 4-(4-carbamoyl-3-{[4-(dimethylcarbamoyl)phenyl]amino}-1H-pyrazol-1-yl)-4-(cyanomethyl)piperidine-1-carboxylate | Calc'd 443, Found 443 |
| 9-23 | 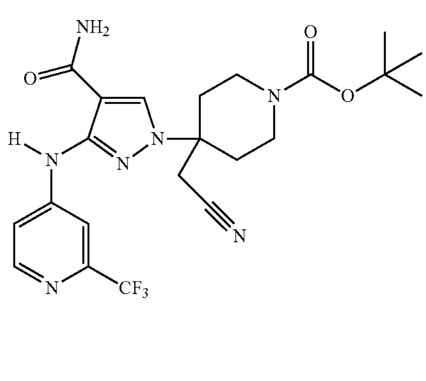 | tert-butyl 4-(4-carbamoyl-3-{[2-(trifluoromethyl)pyridin-4-yl]amino}-1H-pyrazol-1-yl)-4-(cyanomethyl)piperidine-1-carboxylate | Calc'd 494, Found 494 |

TABLE 15-continued

| Example | Structure | Compound Name | Exact Mass [M + H]+ |
|---|---|---|---|
| 9-24 | 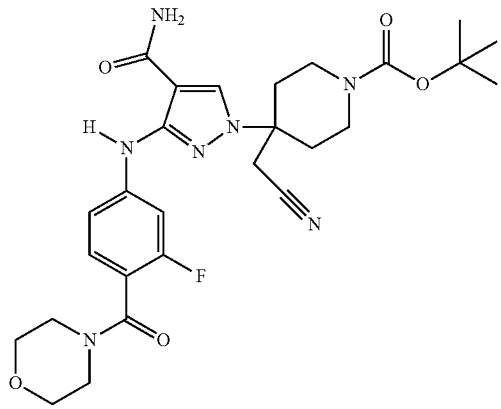 [SMILES: CC(C)(C)OC(=O)N1CCC(CC#N)(n2cc(C(N)=O)c(Nc3ccc(C(=O)N4CCOCC4)c(F)c3)n2)CC1] | tert-butyl 4-(4-carbamoyl-3-{[3-fluoro-4-(morpholin-4-ylcarbonyl)phenyl]amino}-1H-pyrazol-1-yl)-4-(cyanomethyl)piperidine-1-carboxylate | Calc'd 556, Found 556 |
| 9-25 | 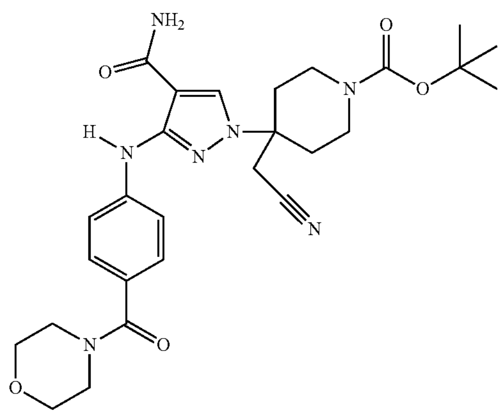 [SMILES: CC(C)(C)OC(=O)N1CCC(CC#N)(n2cc(C(N)=O)c(Nc3ccc(C(=O)N4CCOCC4)cc3)n2)CC1] | tert-butyl 4-(4-carbamoyl-3-{[4-(morpholin-4-ylcarbonyl)phenyl]amino}-1H-pyrazol-1-yl)-4-(cyanomethyl)piperidine-1-carboxylate | Calc'd 538, Found 538 |
| 9-26 | 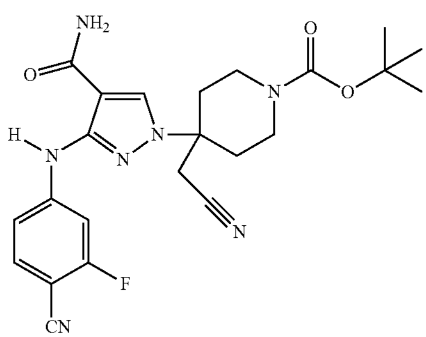 [SMILES: CC(C)(C)OC(=O)N1CCC(CC#N)(n2cc(C(N)=O)c(Nc3ccc(C#N)c(F)c3)n2)CC1] | tert-butyl 4-{4-carbamoyl-3-[(4-cyano-3-fluorophenyl)amino]-1H-pyrazol-1-yl}-4-(cyanomethyl)piperidine-1-carboxylate | Calc'd 468, Found 468 |
| 9-27 | 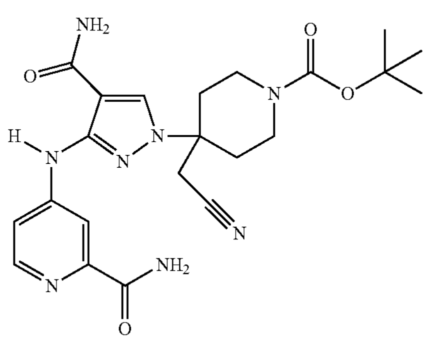 [SMILES: CC(C)(C)OC(=O)N1CCC(CC#N)(n2cc(C(N)=O)c(Nc3ccnc(C(N)=O)c3)n2)CC1] | tert-butyl 4-{4-carbamoyl-3-[(2-carbamoylpyridin-4-yl)amino]-1H-pyrazol-1-yl}-4-(cyanomethyl)piperidine-1-carboxylate | Calc'd 469, Found 469 |

TABLE 15-continued

| Example | Structure | Compound Name | Exact Mass [M + H]+ |
|---|---|---|---|
| 9-28 | 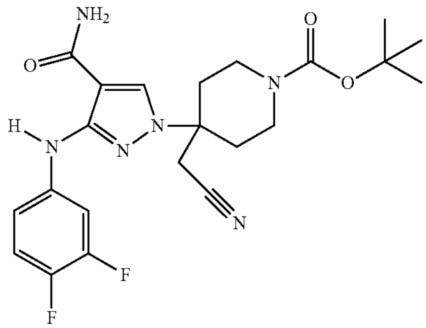 [SMILES: CC(C)(C)OC(=O)N1CCC(CC#N)(n2cc(C(N)=O)c(Nc3ccc(F)c(F)c3)n2)CC1] | tert-butyl 4-{4-carbamoyl-3-[(3,4-difluorophenyl)amino]-1H-pyrazol-1-yl}-4-(cyanomethyl)piperidine-1-carboxylate | Calc'd 461, Found 461 |
| 9-29 | 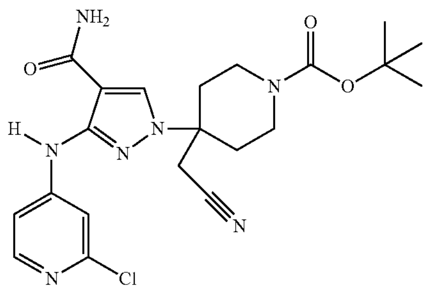 [SMILES: CC(C)(C)OC(=O)N1CCC(CC#N)(n2cc(C(N)=O)c(Nc3ccnc(Cl)c3)n2)CC1] | tert-butyl 4-{4-carbamoyl-3-[(2-chloropyridin-4-yl)amino]-1H-pyrazol-1-yl}-4-(cyanomethyl)piperidine-1-carboxylate | Calc'd 460, Found 460 |
| 9-30 | 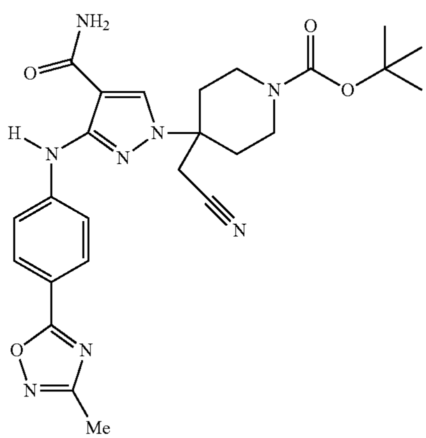 [SMILES: Cc1noc(-c2ccc(Nc3nn(C4(CC#N)CCN(C(=O)OC(C)(C)C)CC4)cc3C(N)=O)cc2)n1] | tert-butyl 4-(4-carbamoyl-3-{[4-(3-methyl-1,2,4-oxadiazol-5-yl)phenyl]amino}-1H-pyrazol-1-yl)-4-(cyanomethyl)piperidine-1-carboxylate | Calc'd 507, Found 507 |
| 9-31 | 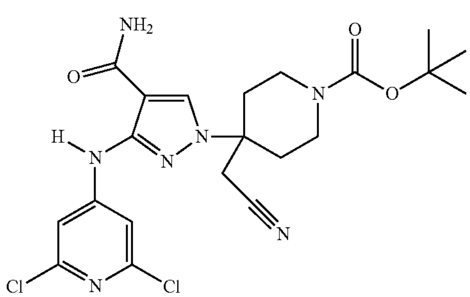 [SMILES: CC(C)(C)OC(=O)N1CCC(CC#N)(n2cc(C(N)=O)c(Nc3cc(Cl)nc(Cl)c3)n2)CC1] | tert-butyl 4-{4-carbamoyl-3-[(2,6-dichloropyridin-4-yl)amino]-1H-pyrazol-1-yl}-4-(cyanomethyl)piperidine-1-carboxylate | Calc'd 495, Found 495 |

TABLE 15-continued

| Example | Structure | Compound Name | Exact Mass [M + H]+ |
|---|---|---|---|
| 9-32 | 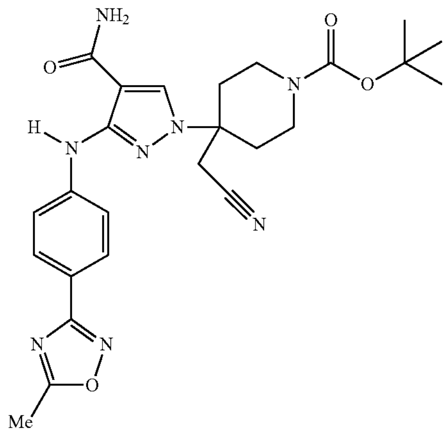 [SMILES: Cc1nc(-c2ccc(Nc3nn(C4(CC#N)CCN(C(=O)OC(C)(C)C)CC4)cc3C(N)=O)cc2)no1] | tert-butyl 4-(4-carbamoyl-3-{[4-(5-methyl-1,2,4-oxadiazol-3-yl)phenyl]amino}-1H-pyrazol-1-yl)-4-(cyanomethyl)piperidine-1-carboxylate | Calc'd 507, Found 507 |
| 9-33 | 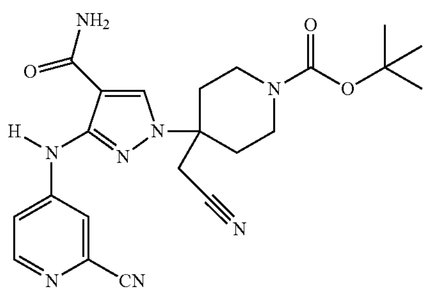 [SMILES: CC(C)(C)OC(=O)N1CCC(CC#N)(n2cc(C(N)=O)c(Nc3ccnc(C#N)c3)n2)CC1] | tert-butyl 4-{4-carbamoyl-3-[(2-cyanopyridin-4-yl)amino]-1H-pyrazol-1-yl}-4-(cyanomethyl)piperidine-1-carboxylate | Calc'd 451, Found 451 |
| 9-34 | 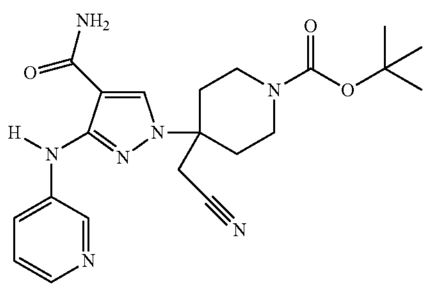 [SMILES: CC(C)(C)OC(=O)N1CCC(CC#N)(n2cc(C(N)=O)c(Nc3cccnc3)n2)CC1] | tert-butyl 4-[4-carbamoyl-3-(pyridin-3-ylamino)-1H-pyrazol-1-yl]-4-(cyanomethyl)piperidine-1-carboxylate | Calc'd 426, Found 426 |
| 9-35 | 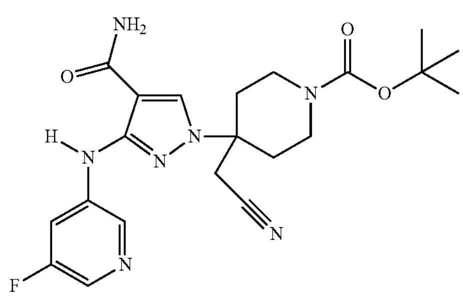 [SMILES: CC(C)(C)OC(=O)N1CCC(CC#N)(n2cc(C(N)=O)c(Nc3cncc(F)c3)n2)CC1] | tert-butyl 4-{4-carbamoyl-3-[(5-fluoropyridin-3-yl)amino]-1H-pyrazol-1-yl}-4-(cyanomethyl)piperidine-1-carboxylate | Calc'd 444, Found 444 |

TABLE 15-continued

| Example | Compound Name | Exact Mass [M + H]+ |
|---|---|---|
| 9-36 | tert-butyl 4-{4-carbamoyl-3-[(5-chloropyridin-3-yl)amino]-1H-pyrazol-1-yl}-4-(cyanomethyl)piperidine-1-carboxylate | Calc'd 460, Found 460 |
| 9-37 | 2,2-difluoroethyl 4-(4-carbamoyl-3-{[6-(cyclobutyloxy)pyridin-3-yl]amino}-1H-pyrazol-1-yl)-4-(cyanomethyl)piperidine-1-carboxylate | Calc'd 504, found 504 |
| 9-38 | 2,2-difluoroethyl 4-{4-carbamoyl-3-[(6-cyclobutylpyridin-3-yl)amino]-1H-pyrazol-1-yl}-4-(cyanomethyl)piperidine-1-carboxylate | Calc'd 488, found 488 |
| 9-39 | 2,2-difluoroethyl 4-{4-carbamoyl-3-[(2-methoxypyridin-4-yl)amino]-1H-pyrazol-1-yl}-4-(cyanomethyl)piperidine-1-carboxylate | Calc'd 464, found 464 |

TABLE 15-continued

| Example | Structure | Compound Name | Exact Mass [M + H]+ |
|---|---|---|---|
| 9-40 | 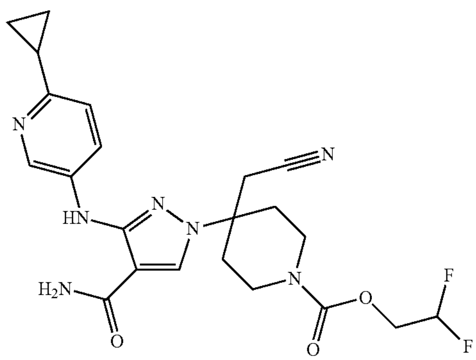 [SMILES: N#CCC1(n2cc(C(N)=O)c(Nc3ccc(C4CC4)nc3)n2)CCN(C(=O)OCC(F)F)CC1] | 2,2-difluoroethyl 4-{4-carbamoyl-3-[(6-cyclopropylpyridin-3-yl)amino]-1H-pyrazol-1-yl}-4-(cyanomethyl)piperidine-1-carboxylate | Calc'd 474, found 474 |
| 9-41 | 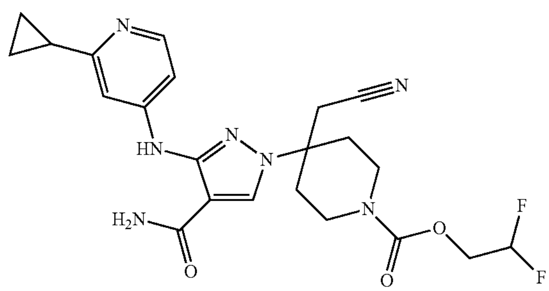 [SMILES: N#CCC1(n2cc(C(N)=O)c(Nc3ccnc(C4CC4)c3)n2)CCN(C(=O)OCC(F)F)CC1] | 2,2-difluoroethyl 4-{4-carbamoyl-3-[(2-cyclopropylpyridin-4-yl)amino]-1H-pyrazol-1-yl}-4-(cyanomethyl)piperidine-1-carboxylate | Calc'd 474, found 474 |

Scheme #24

Example #10-1

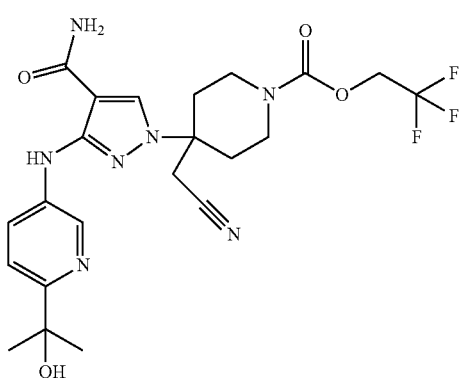

2,2,2-Trifluoroethyl 4-(4-carbamoyl-3-(6-(2-hydroxypropan-2-yl)pyridin-3-ylamino)-1H-pyrazol-1-yl)-4-(cyanomethyl)piperidine-1-carboxylate 2-(5-Bromopyridin-2-yl)propan-2-ol (Intermediate 5) (23 mg, 0.11 mmol), 2,2,2-trifluoroethyl 4-(3-amino-4-carbamoyl-1H-pyrazol-1-yl)-4-(cyanomethyl)piperidine-1-carboxylate (Intermediate 35-3) 40 mg, 0.11 mmol), Pd$_2$(dba)$_3$ (10 mg, 0.011 mmol), 2-di-t-butylphosphino-3,4,5,6-teramethyl-2',4',6'-triisopropylbiphenyl (15 mg, 0.032 mmol), potassium phosphate (45 mg, 0.21 mmol), and 1,4-dioxane (1.0 mL) were combined in a 4 mL vial. The vial was capped and flushed with argon. The mixture was heated to 90° C. and allowed to stir for 2 hours. The mixture was then cooled to ambient temperature, diluted with EtOAc, and washed sequentially with water and brine. The organic layer was dried over anhydrous MgSO$_4$, filtered, and concentrated in vacuo. The residue was purified by MPLC on silica gel (using a gradient elution of 0-10% MeOH/DCM) to afford the title compound, Example #10-1.

$^1$H NMR (500 MHz, CDCl3): δ 8.9 (s, 1H), δ 8.8 (d, J=2.4 Hz, 1H), 8.0 (s, 1H), 7.8 (dd, J=2.4 Hz, J=6.4 Hz, 1H), 7.3 (d, J=8.3 Hz, 1H), 5.9 (br s, 2H), 4.9 (s, 1H), 4.5 (m, 2H), 4.02-3.94 (m, 2H), 3.18-3.11 (m, 2H), 2.9 (s, 2H), 2.72-2.64 (m, 2H), 2.05-1.98 (m, 2H), 1.5 (s, 6H).

LRMS (ESI) calc'd for C$_{22}$H$_{26}$F$_3$N$_7$O$_4$ [M+H]$^+$: 510. Found: 510

The following compounds disclosed in TABLE 16 were prepared according to Scheme #24 following similar procedures described for Example #10-1, which can be achieved by those of ordinary skill in the art of organic synthesis.

TABLE 16

| Example | Structure | Compound Name | Exact Mass [M + H]+ |
|---|---|---|---|
| 10-2 | 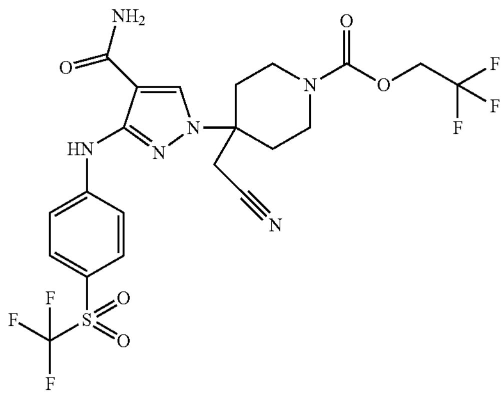 [SMILES: N#CCC1(n2cc(C(N)=O)c(Nc3ccc(S(=O)(=O)C(F)(F)F)cc3)n2)CCN(C(=O)OCC(F)(F)F)CC1] | 2,2,2-trifluoroethyl 4-(4-carbamoyl-3-(4-(trifluoromethylsulfonyl)phenylamino)-1H-pyrazol-1-yl)-4-(cyanomethyl)piperidine-1-carboxylate | Calc'd 583, Found 583 |
| 10-3 | 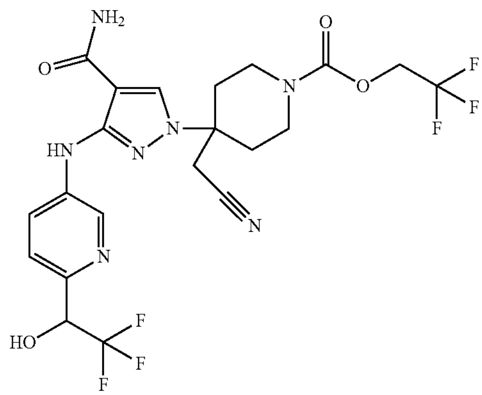 [SMILES: N#CCC1(n2cc(C(N)=O)c(Nc3ccc(C(O)C(F)(F)F)nc3)n2)CCN(C(=O)OCC(F)(F)F)CC1] | 2,2,2-trifluoroethyl 4-(4-carbamoyl-3-(6-(2,2,2-trifluoro-1-hydroxyethyl)pyridin-3-ylamino)-1H-pyrazol-1-yl)-4-(cyanomethyl)piperidine-1-carboxylate | Calc'd 550, Found 550 |
| 10-4 | 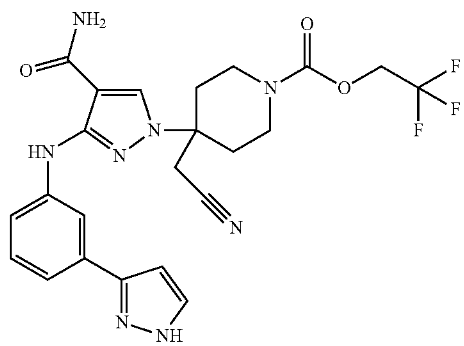 [SMILES: N#CCC1(n2cc(C(N)=O)c(Nc3cccc(-c4cc[nH]n4)c3)n2)CCN(C(=O)OCC(F)(F)F)CC1] | 2,2,2-trifluoroethyl 4-(3-(3-(1H-pyrazol-3-yl)phenylamino)-4-carbamoyl-1H-pyrazol-1-yl)-4-(cyanomethyl)piperidine-1-carboxylate | Calc'd 517, Found 517 |
| 10-5 | 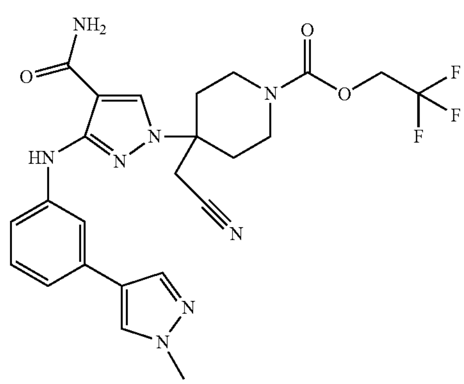 [SMILES: Cn1cc(-c2cccc(Nc3nn(C4(CC#N)CCN(C(=O)OCC(F)(F)F)CC4)cc3C(N)=O)c2)cn1] | 2,2,2-trifluoroethyl 4-(4-carbamoyl-3-(3-(1-methyl-1H-pyrazol-4-yl)phenylamino)-1H-pyrazol-1-yl)-4-(cyanomethyl)piperidine-1-carboxylate | Calc'd 531, Found 531 |

TABLE 16-continued

| Example | Compound Name | Exact Mass [M + H]+ |
|---|---|---|
| 10-6 | 2,2,2-trifluoroethyl 4-(4-carbamoyl-3-(5-(1-methyl-1H-pyrazol-4-yl)pyridinl-3-ylamino)-1H-pyrazol-1-yl)-4-(cyanomethyl)piperidine-1-carboxylate | Calc'd 532, Found 532 |
| 10-7 | 2,2,2-trifluoroethyl 4-(4-carbamoyl-3-(pyridin-3-ylamino)-1H-pyrazol-1-yl)-4-(cyanomethyl)piperidine-1-carboxylate | Calc'd 452, Found 452 |
| 10-8 | 2,2,2-trifluoroethyl 4-(4-carbamoyl-3-(5-fluoropyridin-3-ylamino)-1H-pyrazol-1-yl)-4-(cyanomethyl)piperidine-1-carboxylate | Calc'd 470, Found 470 |
| 10-9 | 2,2,2-trifluoroethyl 4-{4-carbamoyl-3-[(5-chloropyridin-3-yl)amino]-1H-pyrazol-1-yl}-4-(cyanomethyl)piperidine-1-carboxylate | Calc'd 486, Found 486 |

Example #11-1

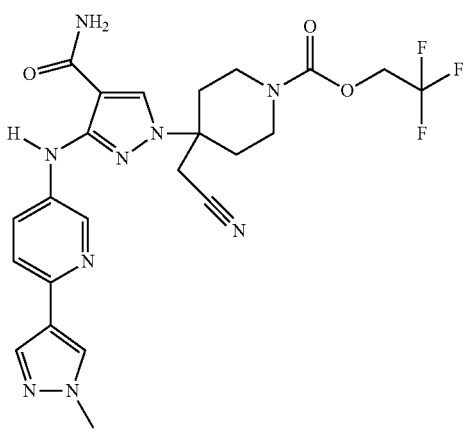

2,2,2-Trifluoroethyl 4-(4-carbamoyl-3-{[6-(1-methyl-1H-pyrazol-4-yl)pyridin-3-yl]amino}-1H-pyrazol-1-yl)-4-(cyanomethyl)piperidine-1-carboxylate

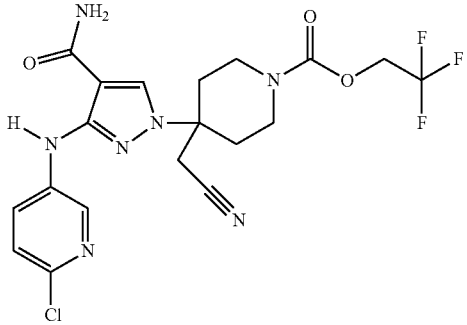

Step A: 2,2,2-Trifluoroethyl 4-(4-carbamoyl-3-((6-chloropyridin-3-yl)amino)-1H-pyrazol-1-yl)-4-(cyanomethyl)piperidine-1-carboxylate 5-Bromo-2-chloropyridine (206 mg, 1.07 mmol), 2,2,2-trifluoroethyl 4-(3-amino-4-carbamoyl-1H-pyrazol-1-yl)-4-(cyanomethyl)piperidine-1-carboxylate (400 mg, 1.07 mmol), $Pd_2(dba)_3$ (98 mg, 0.11 mmol), 2-di-t-butylphosphino-3,4,5,6-teramethyl-2',4',6'-triisopropylbiphenyl (154 mg, 0.321 mmol), and potassium phosphate (454 mg, 2.14 mmol) were combined in a 40 mL vial and dissolved in 1,4-dioxane (5.3 mL). The vial was capped, flushed with argon, and stirred at 90° C. for 2 hours. The mixture was cooled to ambient temperature and diluted with ethyl acetate. The organic layer was then washed with water and brine, dried over anhydrous magnesium sulfate, filtered, and concentrated in vacuo. The residue was purified by MPLC on silica gel (using a gradient elution of 0-5% MeOH/DCM) to afford 2,2,2-trifluoroethyl 4-(4-carbamoyl-3-((6-chloropyridin-3-yl)amino)-1H-pyrazol-1-yl)-4-(cyanomethyl)piperidine-1-carboxylate.

$^1$H NMR (500 MHz, Acetone-$d_6$) δ 9.34 (s, 1H), 8.67-8.67 (d, J=2.9 Hz, 1H), 8.55 (s, 1H), 8.17-8.15 (dd, J=2.9, 8.8 Hz, 1H), 7.31-7.29 (d, J=8.8 Hz, 1H), 7.25 (br, 1H), 6.64 (br, 1H), 4.68-4.63 (m, 2H), 3.98-3.96 (m, 2H), 3.32-3.28 (m, 2H), 3.23 (s, 2H), 2.71-2.69 (m, 2H), 2.23-2.17 (m, 2H).

LRMS (ESI) calc'd for $C_{19}H_{19}ClF_3N_7O_3$ $[M+H]^+$: 486. Found: 486.

Step B: 2,2,2-Trifluoroethyl 4-(4-carbamoyl-3-{[6-(1-methyl-1H-pyrazol-4-yl)pyridin-3-yl]amino}-1H-pyrazol-1-yl)-4-(cyanomethyl)piperidine-1-carboxylate 2,2,2-Trifluoroethyl 4-(4-carbamoyl-3-(6-chloropyridin-3-ylamino)-1H-pyrazol-1-yl)-4-(cyanomethyl)piperidine-1-carboxylate (45 mg, 0.093 mmol), 1-methyl-4-(4,4,5,5-tetramethyl-1,3,2-dioxaborolan-2-yl)-1H-pyrazole (23 mg, 0.11 mmol), $Pd(dppf)Cl_2$ (8 mg, 0.009 mmol), potassium phosphate (59 mg, 0.28 mmol), 1,4-dioxane (0.25 mL), and water (0.03 mL) were combined in a 4 mL vial. The vial was then sealed and flushed with argon. The mixture was heated to 90° C. and was allowed to stir for 90 minutes. The mixture was cooled to ambient temperature, diluted with EtOAc and washed sequentially with water and brine. The organic layer was dried with anhydrous $MgSO_4$, and concentrated in vacuo. The residue was purified by MPLC on silica gel (using a gradient elution of 0-10% MeOH/DCM) to afford the title compound, Example #11-1.

$^1$H NMR (500 MHz, CDCl3): δ 8.89 (s, 1H), δ 8.86 (d, J=2.4 Hz, 1H), 7.89 (s, 1H), 7.85 (s, 2H), 7.78 (dd, J=2.4 Hz, J=6.4 Hz, 1H), 7.4 (d, J=8.3 Hz, 1H), 5.7 (br s, 2H), 4.5 (m, 2H), 4.02-3.94 (m, 2H), 3.9 (s, 3H), 3.18-3.11 (m, 2H), 2.9 (s, 2H), 2.72-2.64 (m, 2H), 2.05-1.98 (m, 2H).

LRMS (ESI) calc'd for $C_{23}H_{24}F_3N_9O_3$ $[M+H]^+$: 532. Found: 532.

The following compounds shown in TABLE 17 were prepared following similar procedures described for Example #11-1, which can be achieved by those of ordinary skill in the art of organic synthesis.

TABLE 17

| Example | Structure | Compound Name | Exact Mass $[M + H]^+$ |
|---|---|---|---|
| 11-2 | ![structure] | 2,2,2-trifluoroethyl 4-(4-carbamoyl-3-{[6-(1H-pyrazol-4-yl)pyridin-3-yl]amino}-1H-pyrazol-1-yl)-4-(cyanomethyl)piperidine-1-carboxylate | Calc'd 518, found 518 |

Scheme #24

Example #12-1

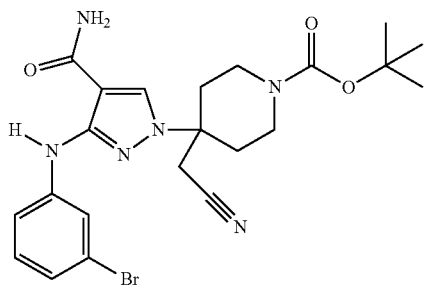

tert-Butyl 4-{3-[(3-bromophenyl)amino]-4-carbamoyl-1H-pyrazol-1-yl}-4-(cyanomethyl)piperidine-1-carboxylate tert-Butyl 4-(3-amino-4-carbamoyl-1H-pyrazol-1-yl)-4-(cyanomethyl)piperidine-1-carboxylate (Intermediate 35-1) (500 mg, 1.44 mmol), potassium acetate (211 mg, 2.15 mmol), 1,3-dibromobenzene (0.69 mL, 5.74 mmol) and 2-propanol (7.2 mL) were combined in a vial and purged with a stream of $N_2$ gas for 10 minutes. $Pd_2(dba)_3$ (52 mg, 0.060 mmol) and 2-di-t-butylphosphino-3,4,5,6-tetramethyl-2',4',6'-tri-i-propylbiphenyl (103 mg, 0.220 mmol) were then added. The reaction vessel was capped and the reaction mixture was heated to 85° C. and allowed to stir for 16 hours. The mixture was then cooled to ambient temperature, filtered through celite, eluting with EtOAc. The filtrate was concentrated in vacuo and the residue was purified by MPLC on silica gel (using a gradient elution of 0-10% MeOH/DCM) to afford the title compound, Example #12-1.

$^1$H NMR (600 MHz, DMSO-$d_6$): δ 9.16 (s, 1H), 8.52-8.44 (m, 1H), 7.80 (s, 1H), 7.55 (s, 1H), 7.42 (d, J=10.0 Hz, 1H), 7.20 (s, 1H), 7.16 (dd, J=13.7, 21.7 Hz, 1H), 6.97 (d, 1H), 3.67 (d, J=14.0 Hz, 2H), 3.15 (s, 2H), 2.98 (s, 2H), 2.39-2.25 (m, 2H), 1.95 (s, 2H), 1.36 (s, 9H).

LRMS (ESI) calc'd for $C_{22}H_{27}BrN_6O_3$ [M+H− tert-butyl]$^+$: 448. Found: 448.

The following compounds shown in TABLE 18 were prepared according to Scheme #24 following similar procedures described for Example #12-1, which can be achieved by those of ordinary skill in the art of organic synthesis utilizing but not limited to Intermediate 35-1.

TABLE 18

| Example | Structure | Compound Name | Exact Mass [M + H]$^+$ |
|---|---|---|---|
| 12-2 | 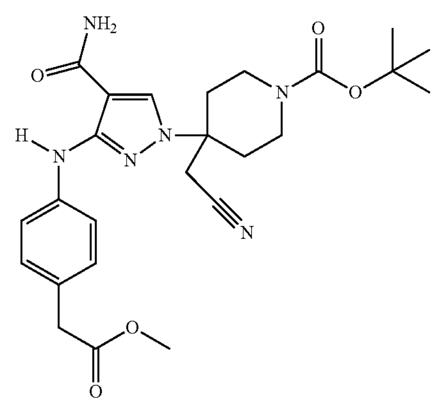 [SMILES: COC(=O)Cc1ccc(Nc2nn(C3(CC#N)CCN(C(=O)OC(C)(C)C)CC3)cc2C(N)=O)cc1] | tert-butyl 4-(4-carbamoyl-3-{[4-(2-methoxy-2-oxoethyl)phenyl]amino}-1H-pyrazol-1-yl)-4-(cyanomethyl)piperidine-1-carboxylate | Calc'd 497, Found 497 |
| 12-3 | 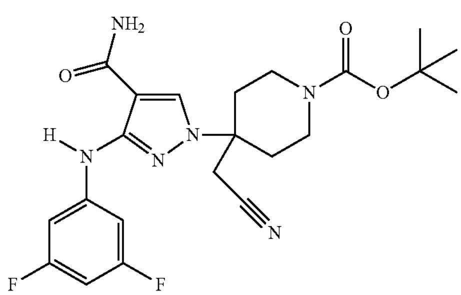 [SMILES: CC(C)(C)OC(=O)N1CCC(CC#N)(n2cc(C(N)=O)c(Nc3cc(F)cc(F)c3)n2)CC1] | tert-butyl 4-{4-carbamoyl-3-[(3,5-difluorophenyl)amino]-1H-pyrazol-1-yl}-4-(cyanomethyl)piperidine-1-carboxylate | Calc'd 461, Found 461 |

TABLE 18-continued

| Example | Structure | Compound Name | Exact Mass [M + H]+ |
|---------|-----------|---------------|---------------------|
| 12-4 | 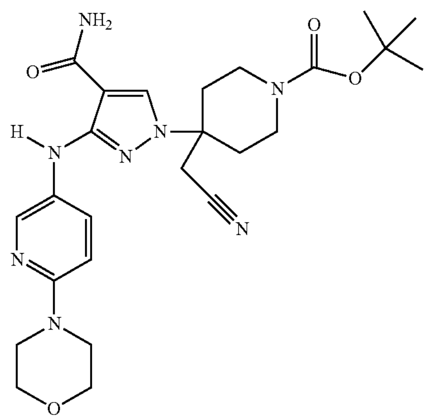 [SMILES: CC(C)(C)OC(=O)N1CCC(CC#N)(n2cc(C(N)=O)c(Nc3ccc(N4CCOCC4)nc3)n2)CC1] | tert-butyl 4-(4-carbamoyl-3-{[6-(morpholin-4-yl) aphthal-3-yl]amino}-1H-pyrazol-1-yl)-4-(cyanomethyl)piperidine-1-carboxylate | Calc'd 511, Found 511 |
| 12-5 | 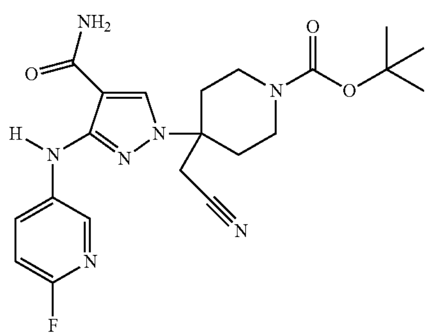 | tert-butyl 4-{4-carbamoyl-3-[(6-fluoropyridin-3-yl)amino]-1H-pyrazol-1-yl}-4-(cyanomethyl)piperidine-1-carboxylate | Calc'd 444, Found 444 |
| 12-6 | 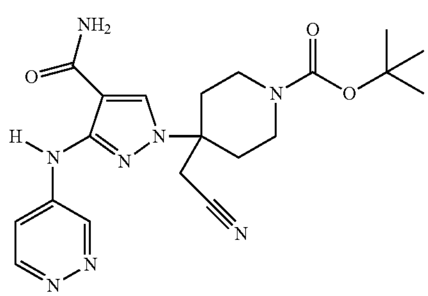 [SMILES: CC(C)(C)OC(=O)N1CCC(CC#N)(n2cc(C(N)=O)c(Nc3ccnnc3)n2)CC1] | tert-butyl 4-[4-carbamoyl-3-(pyridazin-4-ylamino)-1H-pyrazol-1-yl]-4-(cyanomethyl)piperidine-1-carboxylate | Calc'd 427, Found 427 |
| 12-7 | 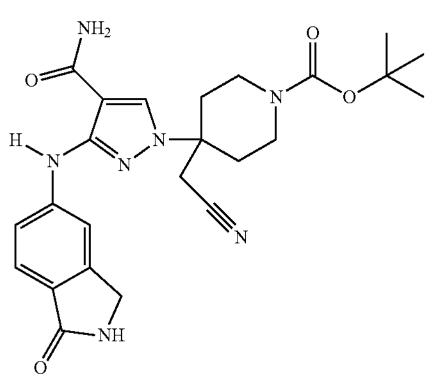 [SMILES: CC(C)(C)OC(=O)N1CCC(CC#N)(n2cc(C(N)=O)c(Nc3ccc4c(c3)CNC4=O)n2)CC1] | tert-butyl 4-{4-carbamoyl-3-[(1-oxo-2,3-dihydro-1H-isoindol-5-yl)amino]-1H-pyrazol-1-yl}-4-(cyanomethyl)piperidine-1-carboxylate | Calc'd 480, Found 480 |

Scheme #24

Example #13-1

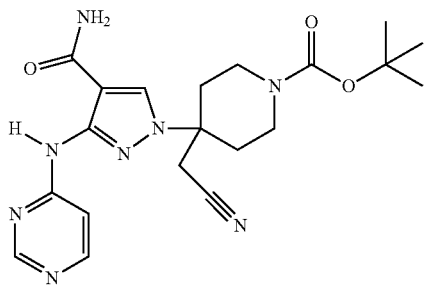

tert-Butyl 4-(4-carbamoyl-3-(pyrimidin-4-ylamino)-1H-pyrazol-1-yl)-4-(cyanomethyl)piperidine-1-carboxylate $K_3PO_4$ (75 mg, 0.35 mmol), X-Phos (21 mg, 0.043 mmol), 4-bromopyrimidine (34 mg, 0.22 mmol) and tert-butyl 4-(3-amino-4-carbamoyl-1H-pyrazol-1-yl)-4-(cyanomethyl)piperidine-1-carboxylate (Intermediate 35-1) (50 mg, 0.14 mmol) were suspended in t-BuOH (3 mL) and degassed with argon for 5 minutes in a microwave vial. The catalyst, $Pd_2(dba)_3$ (20 mg, 0.022 mmol), was added and then the mixture was heated at 80° C. for 2 hours. The mixture was then cooled to ambient temperature, Si-DMT (0.10 g) was added and the resulting mixture was allowed to stir for 1 hour. The mixture was filtered and passed through a C18 silica plug. The column was washed with acetonitrile (4 mL) and then the column eluent was evaporated to dryness in vacuo. The crude material was purified by reverse-phase preparative HPLC (MeCN/water, with 0.1% v/v TFA modifier). Desired fractions were identified, combined, passed through a 6 mL Silicycle Carbonate cartridge, and lyophilized to afford the title compound, Example #13-1, as a white solid.

$^1$H NMR (500 MHz, DMSO-$d_6$): δ 10.40 (s, 1H), 8.83 (br s, 1H), 8.58 (s, 1H), 8.55 (d, J=7.2 Hz, 1H), 8.02 (d, J=7.2 Hz, 1H), 7.78 (br s, 1H), 7.47 (br s, 1H), 3.61-3.75 (m, 2H), 3.25 (br s, 2H), 2.90-3.15 (m, 2H), 2.30-2.54 (m, 2H), 1.94-2.04 (m, 2H), 1.38 (s, 9H).

LRMS (ESI) calc'd for $C_{20}H_{26}N_8O_3$ [M+H]$^+$: 427. Found: 427.

The following compounds, shown in TABLE 19 were prepared according to Scheme #24 following similar procedures described for Example #13-1, which can be achieved by those of ordinary skill in the art of organic synthesis.

TABLE 19

| Example | Structure | Compound Name | Exact Mass [M + H]$^+$ |
| --- | --- | --- | --- |
| 13-2 | 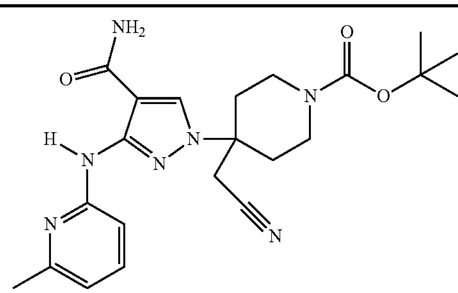 | tert-butyl 4-(4-carbamoyl-3-(6-methylpyridin-2-ylamino)-1H-pyrazol-1-yl)-4-(cyanomethyl)piperidine-1-carboxylate | Calc'd 440, Found 440 |
| 13-3 | 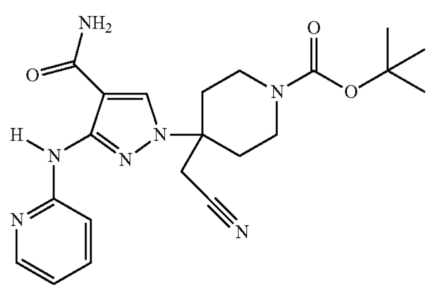 [SMILES: CC(C)(C)OC(=O)N1CCC(CC#N)(n2cc(C(N)=O)c(Nc3ccccn3)n2)CC1] | tert-butyl 4-(4-carbamoyl-3-(pyridin-2-ylamino)-1H-pyrazol-1-yl)-4-(cyanomethyl)piperidine-1-carboxylate | Calc'd 426, Found 426 |
| 13-4 | 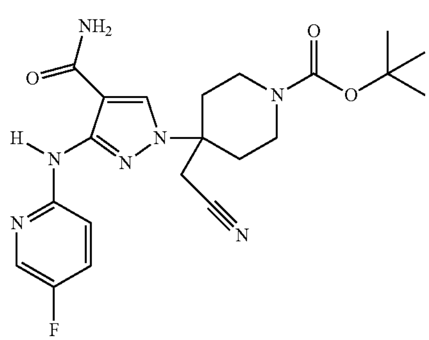 | tert-butyl 4-(4-carbamoyl-3-(5-fluoropyridin-2-ylamino)-1H-pyrazol-1-yl)-4-(cyanomethyl)piperidine-1-carboxylate | Calc'd 444, Found 444 |

TABLE 19-continued

| Example | Structure | Compound Name | Exact Mass [M + H]+ |
|---|---|---|---|
| 13-5 | 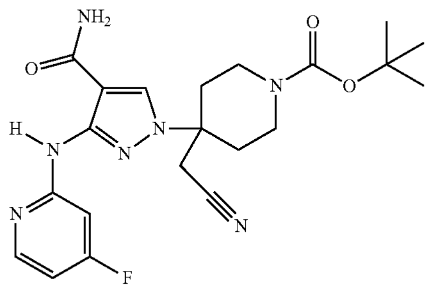 [SMILES: CC(C)(C)OC(=O)N1CCC(CC#N)(n2cc(C(N)=O)c(Nc3cc(F)ccn3)n2)CC1] | tert-butyl 4-(4-carbamoyl-3-(4-fluoropyridin-2-ylamino)-1H-pyrazol-1-yl)-4-(cyanomethyl)piperidine-1-carboxylate | Calc'd 444, Found 444 |
| 13-6 | 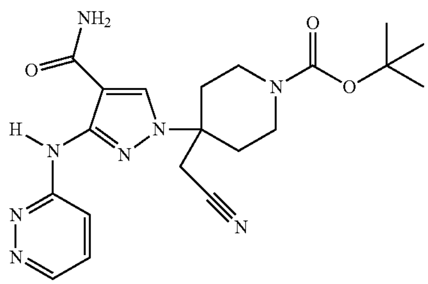 [SMILES: CC(C)(C)OC(=O)N1CCC(CC#N)(n2cc(C(N)=O)c(Nc3cccnn3)n2)CC1] | tert-butyl 4-(4-carbamoyl-3-(pyridazin-3-ylamino)-1H-pyrazol-1-yl)-4-(cyanomethyl)piperidine-1-carboxylate | Calc'd 427, Found 427 |
| 13-7 | 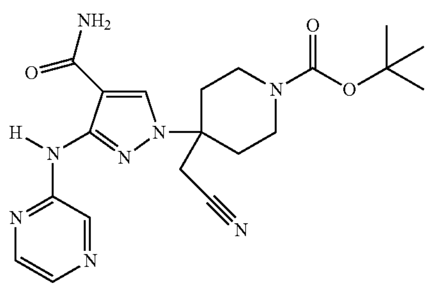 [SMILES: CC(C)(C)OC(=O)N1CCC(CC#N)(n2cc(C(N)=O)c(Nc3cnccn3)n2)CC1] | tert-butyl 4-(4-carbamoyl-3-(pyrazine-2-ylamino)-1H-pyrazol-1-yl)-4-(cyanomethyl)piperidine-1-carboxylate | Calc'd 427, Found 427 |
| 13-8 | 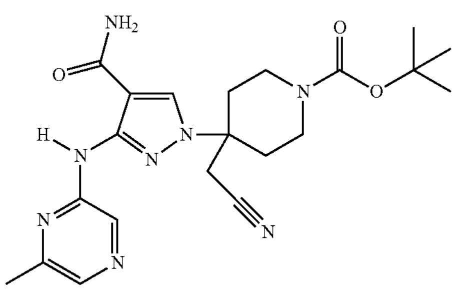 [SMILES: Cc1cncc(Nc2nn(C3(CC#N)CCN(C(=O)OC(C)(C)C)CC3)cc2C(N)=O)n1] | tert-butyl 4-(4-carbamoyl-3-(6-methylpyrazine-2-ylamino)-1H-pyrazol-1-yl)-4-(cyanomethyl)piperidine-1-carboxylate | Calc'd 441, Found 441 |
| 13-9 | 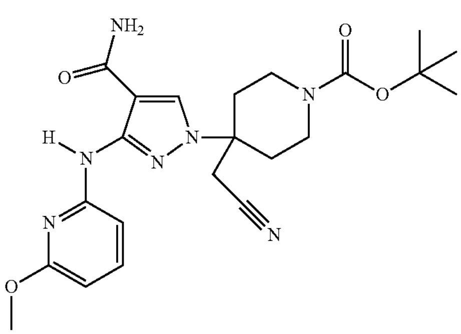 [SMILES: COc1cccc(Nc2nn(C3(CC#N)CCN(C(=O)OC(C)(C)C)CC3)cc2C(N)=O)n1] | tert-butyl 4-(4-carbamoyl-3-(6-methoxypyridin-2-ylamino)-1H-pyrazol-1-yl)-4-(cyanomethyl)piperidine-1-carboxylate | Calc'd 456, Found 456 |

TABLE 19-continued

| Example | Structure | Compound Name | Exact Mass [M + H]+ |
|---|---|---|---|
| 13-10 | 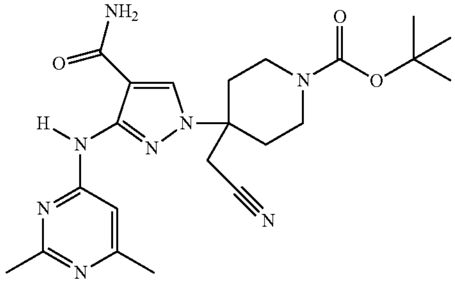 [SMILES: Cc1cc(Nc2nn(C3(CC#N)CCN(C(=O)OC(C)(C)C)CC3)cc2C(N)=O)nc(C)n1] | tert-butyl 4-(4-carbamoyl-3-(2,6-dimethylpyrimidin-4-ylamino)-1H-pyrazol-1-yl)-4-(cyanomethyl)piperidine-1-carboxylate | Calc'd 455, Found 455 |
| 13-11 | 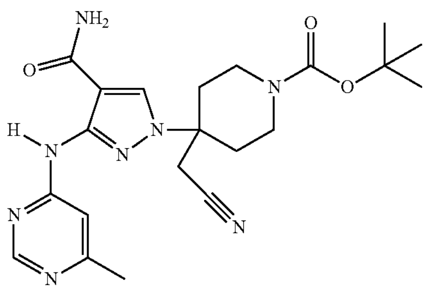 | tert-butyl 4-(4-carbamoyl-3-(6-methylpyrimidin-4-ylamino)-1H-pyrazol-1-yl)-4-(cyanomethyl)piperidine-1-carboxylate | Calc'd 441, Found 441 |
| 13-12 | 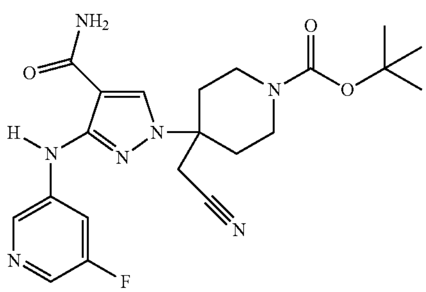 [SMILES: CC(C)(C)OC(=O)N1CCC(CC#N)(n2cc(C(N)=O)c(Nc3cncc(F)c3)n2)CC1] | tert-butyl 4-(4-carbamoyl-3-((5-fluoropyridin-3-yl)amino)-1H-pyrazol-1-yl)-4-(cyanomethyl)piperidine-1-carboxylate | Calc'd 444, Found 444 |

Scheme #25

Example #14

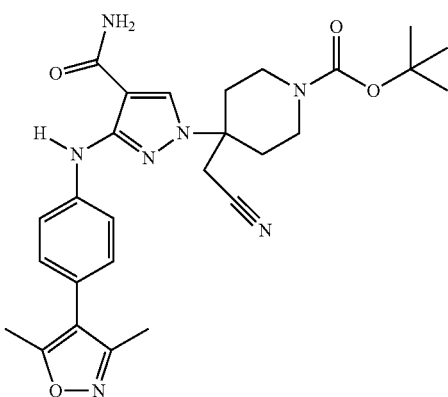

tert-Butyl 4-(4-carbamoyl-3-{[4-(3,5-dimethylisoxazol-4-yl)phenyl]amino}-1H-pyrazol-1-yl)-4-(cyanomethyl)piperidine-1-carboxylate tert-Butyl 4-{3-[(4-bromophenyl)amino]-4-carbamoyl-1H pyrazol-1-yl}-4-(cyanomethyl)piperidine-1-carboxylate (Example #2-2) (50 mg, 0.10 mmol), 3,5-dimethyl-4-(4,4,5,5-tetramethyl-1,3,2-dioxaborolan-2-yl)isoxazole (22 mg, 0.10 mmol), potassium carbonate (55 mg, 0.40 mmol), and tetrakis(triphenylphosphine)palladium (0) (6 mg, 0.005 mmol) was suspended in 2:1 THF:water (1.2 mL) and heated to 100° C. for 16 hours. The mixture was then cooled to ambient temperature, diluted with MeOH, and filtered through a 0.45 micron nylon syringe filter. The filtrate was concentrated in vacuo and the residue was purified by reverse-phase preparative HPLC (using a gradient elution of 35-70% MeCN/water, with 0.1% v/v TFA modifier). Desired fractions were identified, combined, and lyophilized to afford the title compound, Example #14.

$^1$H NMR (600 MHz, DMSO-d$_6$) δ 9.15 (s, 1H), 8.48 (s, 1H), 7.62-7.44 (m, 3H), 7.36-7.30 (m, 1H), (7.21 (d, J=8.5

Hz, 1H), 7.16 (br s, 1H), 3.72-3.62 (m, 2H), 3.17 (s, 2H), 2.98 (br s, 2H), 2.38-2.30 (m, 5H), 2.17 (s, 3H), 2.00-1.90 (m, 2H), 1.36 (s, 9H).

LRMS (ESI) calc'd for $C_{27}H_{33}N_7O_4$ [M+H]$^+$: 520. Found: 520.

Scheme #25

Example #15-1

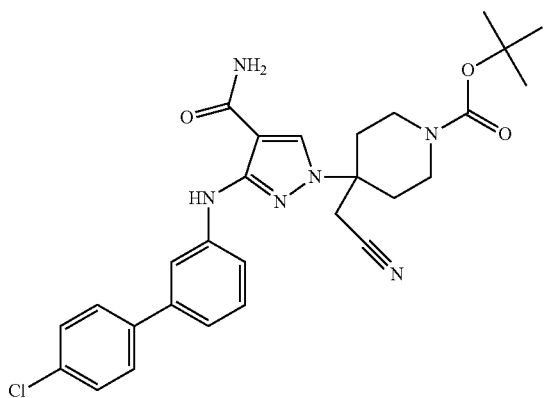

tert-Butyl 4-{4-carbamoyl-3-[(4'-chlorobiphenyl-3-yl)amino]-1H-pyrazol-1-yl}-4-(cyanomethyl)piperidine-1-carboxylate tert-Butyl 4-{3-[(3-bromophenyl)amino]-4-carbamoyl-1H-pyrazol-1-yl}-4-(cyanomethyl)piperidine-1-carboxylate (Example 12-1) (20 mg, 0.040 mmol) was combined with 4-chlorophenylboronic acid (12 mg, 0.080 mmol), SiliaCat® DPP-Pd (28 mg, 0.0080 mmol) and potassium carbonate (16 mg, 0.12 mmol) and then diluted with THF (0.8 mL). The reaction mixture was heated to 65° C. for 16 hours. After cooling to ambient temperature the mixture was filtered through celite and the filtrate was diluted with 1.0 mL DMSO. This mixture was purified by reverse-phase preparative HPLC (MeCN/water, with 0.1% v/v TFA modifier) to afford the title compound, Example #15-1.

$^1$H NMR (600 MHz, DMSO-d$_6$): δ 9.13 (s, 1H), 8.48 (s, 1H), 7.85 (s, 1H), 7.67 (d, J=8.6, 2H), 7.55 (s, 1H), 7.53-7.42 (m, 3H), 7.31 (t, J=7.9, 1H), 7.17 (s, 1H), 7.11 (d, J=7.7, 1H), 3.69 (d, J=13.7, 2H), 3.16 (s, 2H), 2.49-2.44 (m, 2H), 2.40-2.32 (m, 2H), 2.00-1.90 (m, 2H), 1.36 (s, 9H). LRMS (ESI) calc'd for $C_{28}H_{32}ClN_6O_3$ [M+H]$^+$: 535. Found: 535.

The following compounds shown in TABLE 20 were prepared according to Scheme #25 following similar procedures described for Example #15-1, which can be achieved by those of ordinary skill in the art of organic synthesis utilizing but not limited Example 12-1 as an intermediate.

TABLE 20

| Example | Structure | Compound Name | Exact Mass [M + H]$^+$ |
|---|---|---|---|
| 15-2 | 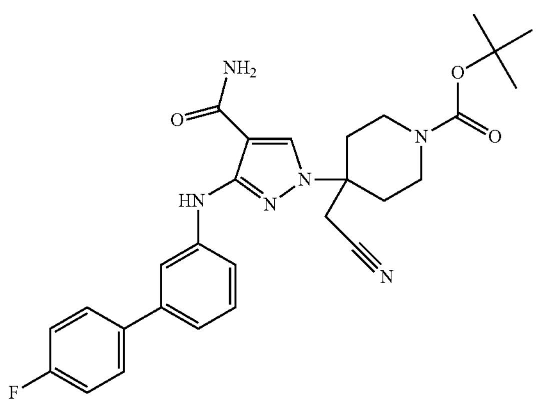 [SMILES: CC(C)(C)OC(=O)N1CCC(CC#N)(n2cc(C(N)=O)c(Nc3cccc(-c4ccc(F)cc4)c3)n2)CC1] | tert-butyl 4-{4-carbamoyl-3-[(4'-fluorobiphenyl-3-yl)amino]-1H-pyrazol-1-yl}-4-(cyanomethyl)piperidine-1-carboxylate | Calc'd 519, Found 519 |
| 15-3 | 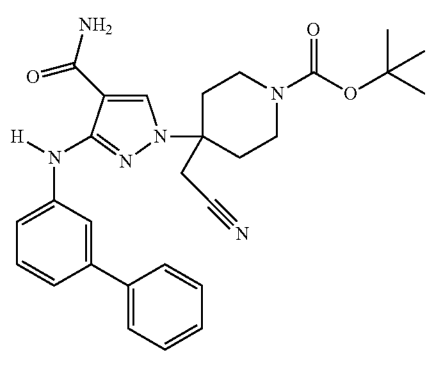 [SMILES: CC(C)(C)OC(=O)N1CCC(CC#N)(n2cc(C(N)=O)c(Nc3cccc(-c4ccccc4)c3)n2)CC1] | tert-butyl 4-[3-(biphenyl-3-ylamino)-4-carbamoyl-1H-pyrazol-1-yl]-4-(cyanomethyl)piperidine-1-carboxylate | Calc'd 501, Found 501 |

TABLE 20-continued

| Example | Structure | Compound Name | Exact Mass [M + H]+ |
|---|---|---|---|
| 15-4 | 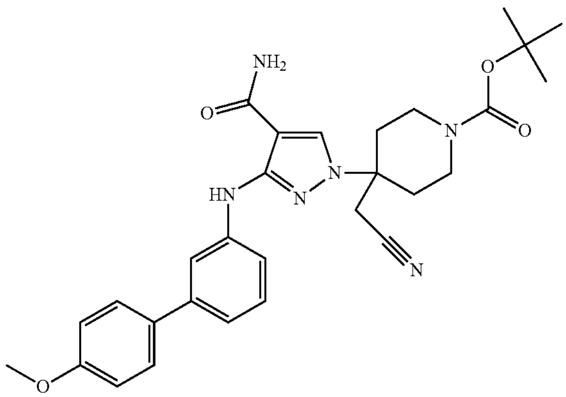 [SMILES: COc1ccc(-c2cccc(Nc3nn(C4(CC#N)CCN(C(=O)OC(C)(C)C)CC4)cc3C(N)=O)c2)cc1] | tert-butyl 4-{4-carbamoyl-3-[(4'-methoxybiphenyl-3-yl)amino]-1H-pyrazol-1-yl}-4-(cyanomethyl)piperidine-1-carboxylate | Calc'd 531, Found 531 |
| 15-5 | 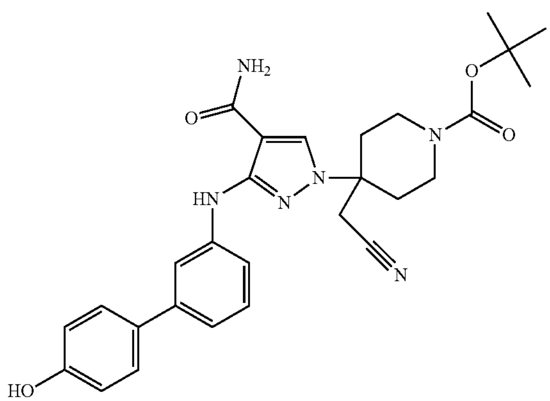 [SMILES: CC(C)(C)OC(=O)N1CCC(CC#N)(n2cc(C(N)=O)c(Nc3cccc(-c4ccc(O)cc4)c3)n2)CC1] | tert-butyl 4-{4-carbamoyl-3-[(4'-hydroxybiphenyl-3-yl)amino]-1H-pyrazol-1-yl}-4-(cyanomethyl)piperidine-1-carboxylate | Calc'd 517, Found 517 |
| 15-6 | 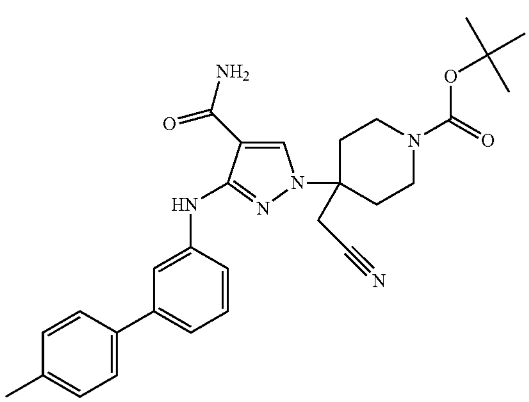 [SMILES: Cc1ccc(-c2cccc(Nc3nn(C4(CC#N)CCN(C(=O)OC(C)(C)C)CC4)cc3C(N)=O)c2)cc1] | tert-butyl 4-{4-carbamoyl-3-[(4'-methylbiphenyl-3-yl)amino]-1H-pyrazol-1-yl}-4-(cyanomethyl)piperidine-1-carboxylate | Calc'd 515, Found 515 |

TABLE 20-continued

| Example | Structure | Compound Name | Exact Mass [M + H]+ |
|---|---|---|---|
| 15-7 | 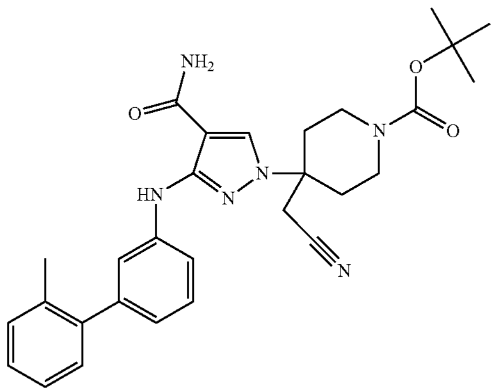 [SMILES: Cc1ccccc1-c1cccc(Nc2nn(C3(CC#N)CCN(C(=O)OC(C)(C)C)CC3)cc2C(N)=O)c1] | tert-butyl 4-{4-carbamoyl-3-[(2'-methylbiphenyl-3-yl)amino]-1H-pyrazol-1-yl}-4-(cyanomethyl)piperidine-1-carboxylate | Calc'd 515, Found 515 |
| 15-8 | 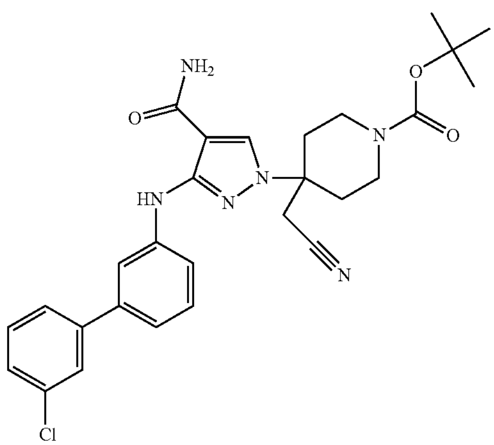 [SMILES: CC(C)(C)OC(=O)N1CCC(CC#N)(n2cc(C(N)=O)c(Nc3cccc(-c4cccc(Cl)c4)c3)n2)CC1] | tert-butyl 4-{4-carbamoyl-3-[(3'-chlorobiphenyl-3-yl)amino]-1H-pyrazol-1-yl}-4-(cyanomethyl)piperidine-1-carboxylate | Calc'd 535, Found 535 |
| 15-9 | 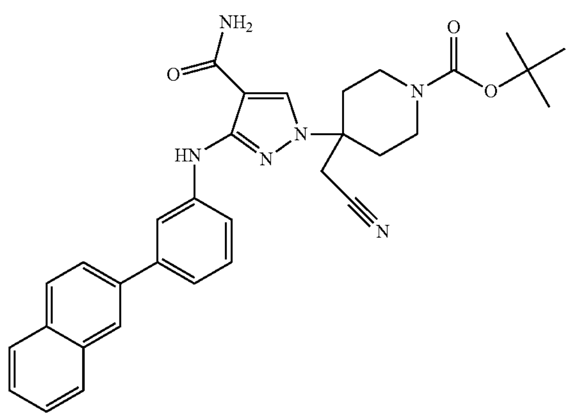 [SMILES: CC(C)(C)OC(=O)N1CCC(CC#N)(n2cc(C(N)=O)c(Nc3cccc(-c4ccc5ccccc5c4)c3)n2)CC1] | tert-butyl 4-{4-carbamoyl-3-[(3-naphthalen-2-ylphenyl)amino]-1H-pyrazol-1-yl}-4-(cyanomethyl)piperidine-1-carboxylate | Calc'd 551, Found 551 |

TABLE 20-continued

| Example | Structure | Compound Name | Exact Mass [M + H]+ |
|---|---|---|---|
| 15-10 | 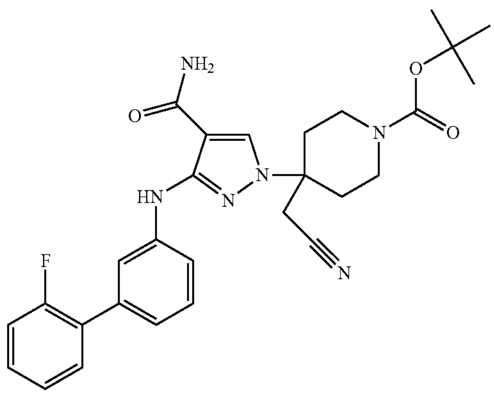 [SMILES: CC(C)(C)OC(=O)N1CCC(CC#N)(n2cc(C(N)=O)c(Nc3cccc(-c4ccccc4F)c3)n2)CC1] | tert-butyl 4-{4-carbamoyl-3-[(2'-fluorobiphenyl-3-yl)amino]-1H-pyrazol-1-yl}-4-(cyanomethyl)piperidine-1-carboxylate | Calc'd 519, Found 519 |
| 15-11 | 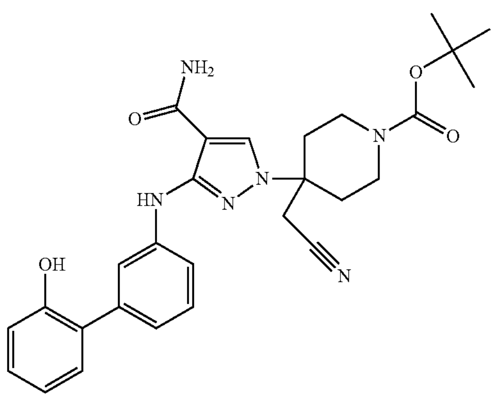 [SMILES: CC(C)(C)OC(=O)N1CCC(CC#N)(n2cc(C(N)=O)c(Nc3cccc(-c4ccccc4O)c3)n2)CC1] | tert-butyl 4-{4-carbamoyl-3-[(2'-hydroxybiphenyl-3-yl)amino]-1H-pyrazol-1-yl}-4-(cyanomethyl)piperidine-1-carboxylate | Calc'd 517, Found 517 |

Scheme #28 and 31

Intermediate #38-1

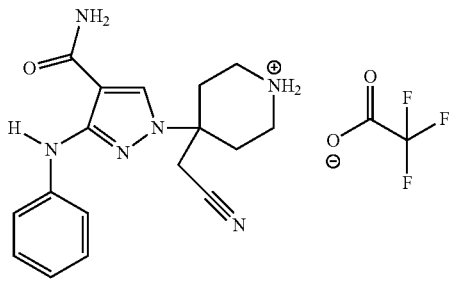

4-[4-Carbamoyl-3-(phenylamino)-1H-pyrazol-1-yl]-4-(cyanomethyl)piperidinium trifluoroacetate To a suspension of tert-butyl 4-[4-carbamoyl-3-(phenylamino)-1H-pyrazol-1-yl]-4-(cyanomethyl)piperidine-1-carboxylate (2.0 g, 4.7 mmol) in DCM (20 mL) was added TFA (5.0 mL) dropwise. The resultant clear solution was maintained at ambient temperature for 1.5 hours. The mixture was then concentrated in vacuo, and the residue was dissolved in a mixture of MeCN/water (35 mL:15 mL) and lyophilized to afford the title compound, Example #38-1.

LRMS (ESI) acid for $C_{17}H_{20}N_6O$ [M+H]+: 325. Found: 325.

The following compounds shown in TABLE 21 were prepared according to Scheme #28 and #31 following similar procedures described for Intermediate #38-1, which can be achieved by those of ordinary skill in the art of organic synthesis.

TABLE 21

| Intermediate | Structure | Compound Name | Exact Mass [M + H]+ |
|---|---|---|---|
| 38-2 | 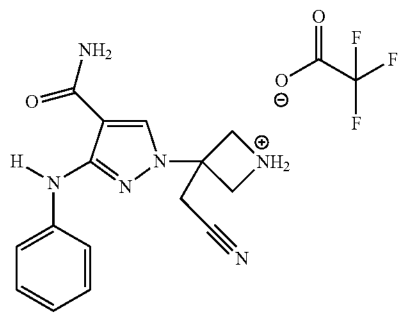 [SMILES: N#CCC1(n2cc(C(N)=O)c(Nc3ccccc3)n2)C[NH2+]C1 ; O=C([O-])C(F)(F)F] | 3-[4-carbamoyl-3-(phenylamino)-1H-pyrazol-1-yl]-3-(cyanomethyl)azetidinium trifluoroacetate | Calc'd 297, Found 297 |
| 38-3 | 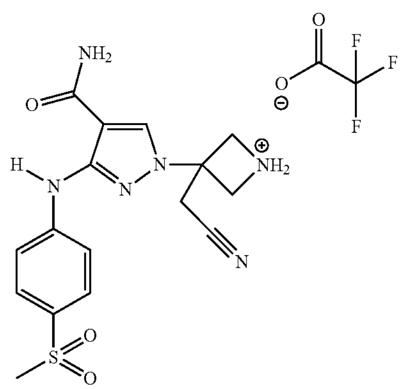 [SMILES: CS(=O)(=O)c1ccc(Nc2nn(C3(CC#N)C[NH2+]C3)cc2C(N)=O)cc1 ; O=C([O-])C(F)(F)F] | 3-(4-carbamoyl-3-{[4-(methylsulfonyl)phenyl]amino}-1H-pyrazol-1-yl)-3-(cyanomethyl)azetidinium trifluoroacetate | Calc'd 375, Found 375 |
| 38-4 | 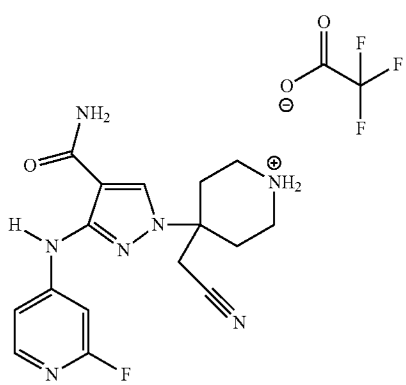 [SMILES: N#CCC1(n2cc(C(N)=O)c(Nc3ccnc(F)c3)n2)CC[NH2+]CC1 ; O=C([O-])C(F)(F)F] | 4-{4-carbamoyl-3-[(2-fluoropyridin-4-yl)amino]-1H-pyrazol-1-yl}-4-(cyanomethyl)piperidinium trifluoroacetate | Calc'd 344, Found 344 |
| 38-5 | 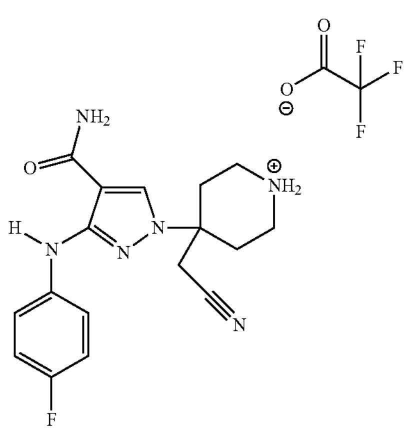 [SMILES: N#CCC1(n2cc(C(N)=O)c(Nc3ccc(F)cc3)n2)CC[NH2+]CC1 ; O=C([O-])C(F)(F)F] | 4-{4-carbamoyl-3-[(4-fluorophenyl)amino]-1H-pyrazol-1-yl}-4-(cyanomethyl)piperidinium trifluoroacetate | Calc'd 343, Found 343 |

TABLE 21-continued

| Intermediate | Structure | Compound Name | Exact Mass [M + H]⁺ |
|---|---|---|---|
| 38-6 | 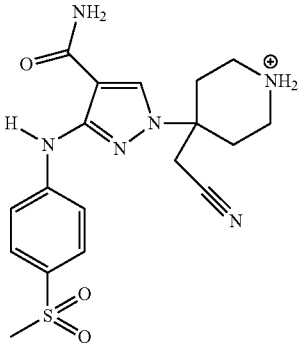 | 4-(4-carbamoyl-3-{[4-(methylsulfonyl)phenyl]amino}-1H-pyrazol-1-yl)-4-(cyanomethyl)piperidinium trifluoroacetate | Calc'd 403, Found 403 |
| 38-7 | 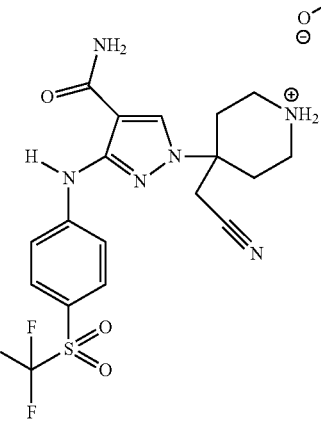 | 4-[4-carbamoyl-3-({4-[(trifluoromethyl)sulfonyl]phenyl}amino)-1H-pyrazol-1-yl]-4-(cyanomethyl)piperidinium trifluoroacetate | Calc'd 457, Found 457 |
| 38-8 | 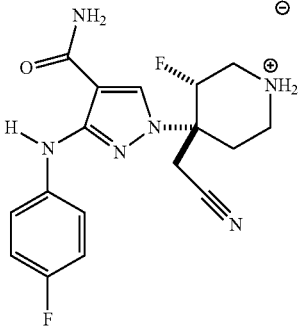 | 1-[(3S,4S and 3R,4R)-4-{4-carbamoyl-3-[(4-fluorophenyl)amino]-1H-pyrazol-1-yl}-4-(cyanomethyl)-3-fluoropiperidinium trifluoroacetate | Calc'd 361, Found 361 |

Scheme #28 and #31

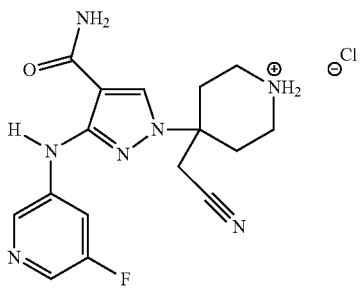

Intermediate #39

4-{4-Carbamoyl-3-[(5-fluoropyridin-3-yl)amino]-1H-pyrazol-1-yl}-4-(cyanomethyl)piperidinium chloride tert-Butyl 4-(4-carbamoyl-3-(5-fluoropyridin-3-ylamino)-1H-pyrazol-1-yl)-4-(cyanomethyl)piperidine-1-carboxylate (Example 13-14) (305 mg, 0.688 mmol) was dissolved in 4 M HCl in 1,4-dioxane (7 mL). The resulting solution was maintained at ambient temperature for 2 hours. The mixture was then concentrated in vacuo to afford the title compound, Intermediate #39.
LRMS (ESI) calc'd for $C_{16}H_{18}FN_7O$ [M+H]$^+$: 344. Found: 344.

Example #18

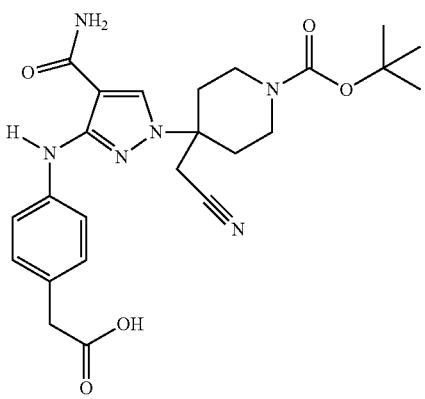

[4-({1-[1-(tert-Butoxycarbonyl)-4-(cyanomethyl)piperidin-4-yl]-4-carbamoyl-1H-pyrazol-3-yl}amino)phenyl]acetic acid To a solution of tert-butyl 4-(4-carbamoyl-3-{[4-(2-methoxy-2-oxoethyl)phenyl]amino}-1H-pyrazol-1-yl)-4-(cyanomethyl)piperidine-1-carboxylate (Example 12-2) (0.10 g, 0.20 mmol) in THF (1.0 mL) was added a solution of LiOH (19 mg, 0.81 mmol) in water (0.8 mL). The mixture was stirred at ambient temperature for 2 hours. The mixture was then neutralized with 1N aqueous HCl to pH 3-4, diluted with water, and extracted with EtOAc. The organic layer was separated, washed with brine, dried over anhydrous MgSO$_4$, and concentrated in vacuo. The residue was purified by MPLC on silica gel (using a gradient elution of 0-10% MeOH/EtOAc) to afford the title compound, Example #18.

$^1$H NMR (600 MHz, DMSO-d$_6$): δ 11.3 (br s, 1H), 9.70 (s, 1H), 9.01 (s, 1H), 8.09 (d, J=8.4 Hz, 2H), 7.75 (d, J=8.4 Hz, 2H), 7.72 (br s, 1H), 7.09 (br s, 1H), 4.38-4.43 (m, 2H), 4.08 (s, 2H), 3.71 (s, 2H), 3.65 (br s, 2H), 3.10-3.16 (m, 2H), 2.59-2.65 (m, 2H), 1.97 (s, 9H).
LRMS (ESI) calc'd for $C_{24}H_{31}N_6O_5$ [M+H]$^+$: 483. Found: 483.

Scheme #28

Example #19

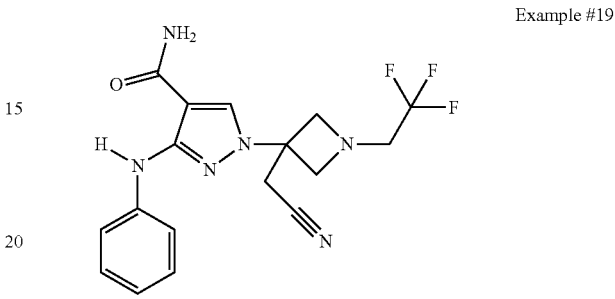

1-[3-(Cyanomethyl)-1-(2,2,2-trifluoroethyl)azetidin-3-yl]-3-(phenylamino)-1H-pyrazole-4-carboxamide To a suspension of 3-[4-carbamoyl-3-(phenylamino)-1H-pyrazol-1-yl]-3-(cyanomethyl)azetidinium trifluoroacetate (Intermediate #38-2) (23 mg, 0.078 mmol) in dioxane (2 mL) was added 2,2,2-trifluoroethyl trifluoromethanesulfonate (36 mg, 0.15 mmol), followed by K$_2$CO$_3$ (23 mg, 0.078 mmol). The resulting mixture was heated to 110° C. and allowed to stir for 2 hours. The reaction was then cooled to ambient temperature, water was added and the reaction mixture was extracted with EtOAc (3×). The combined organic extracts were dried over anhydrous Na$_2$SO$_4$, filtered, and concentrated in vacuo. The residue was purified by MPLC on silica gel (using a gradient elution of 0-100%, EtOAc/hexanes) to afford the title compound, Example #19. $^1$H NMR (600 MHz, CDCl$_3$): δ 8.78 (s, 1H), 7.75 (s, 1H), 7.48 (d, J=7.7 Hz, 2H), 7.26 (t, J=7.9 Hz, 2H), 6.90 (t, J=7.3 Hz, 1H), 5.62 (s, 2H), 3.81 (d, J=8.6 Hz, 2H), 3.74 (d, J=8.6 Hz, 2H), 3.34 (s, 2H), 3.09 (q, J=9.1 Hz, 2H). LRMS (ESI) calc'd for $C_{17}H_{17}F_3N_6O$ [M+H]$^+$: 379. Found: 379.

Scheme #28

Example #20

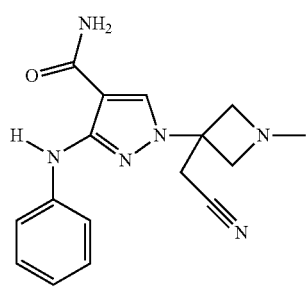

1-[3-(Cyanomethyl)-1-methylazetidin-3-yl]-3-(phenylamino)-1H-pyrazole-4-carboxamide To a suspension of 3-[4-carbamoyl-3-(phenylamino)-1H-pyrazol-1-yl]-3-(cyanomethyl)azetidinium trifluoroacetate (Intermediate #38-2) (50 mg, 0.17 mmol) in DCE (2.0 mL) was added sodium triacetoxyborohydride (79 mg, 0.37 mmol), followed by formaldehyde (0.050 mL, 0.67 mmol, 37 wt % in water). The resulting mixture was allowed to stir for 1 hour before saturated aqueous NaHCO₃ solution was added and the resulting mixture was extracted with EtOAc (3×). The combined organic layers were dried over anhydrous Na₂SO₄, filtered, and concentrated in vacuo. The residue was purified by MPLC on silica gel (using a gradient elution of 0-100%, EtOAc/hexanes) to afford the title compound, Example #20.

¹H NMR (600 MHz, CDCl₃): δ 8.76 (s, 1H), 7.81 (s, 1H), 7.49 (d, J=7.9 Hz, 2H), 7.28-7.24 (m, 2H), 6.89 (t, J=7.3 Hz, 1H), 5.74 (s, 2H), 3.66 (d, J=8.6 Hz, 2H), 3.53 (d, J=8.6 Hz, 2H), 3.32 (s, 2H), 2.39 (d, J=27.6 Hz, 3H). LRMS (ESI) calc'd for $C_{16}H_{18}N_6O$ [M+H]⁺: 311. Found: 311.

Scheme #28

Example #21-1

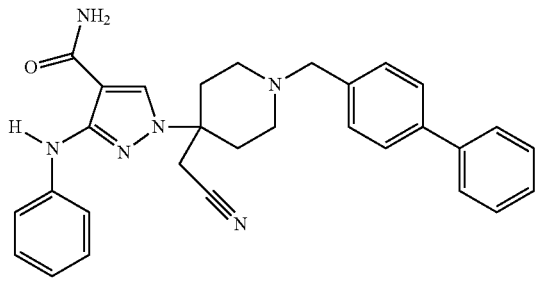

1-[1-(Biphenyl-4-ylmethyl)-4-(cyanomethyl)piperidin-4-yl]-3-(phenylamino)-1H-pyrazole-4-carboxamide Biphenyl-4-carbaldehyde (12 mg, 0.070 mmol) was treated with a solution of 4-[4-carbamoyl-3-(phenylamino)-1H-pyrazol-1-yl]-4-(cyanomethyl)piperidinium trifluoroacetate (Intermediate #38-2) (20 mg, 0.050 mmol) and TFA (0.020 mL, 0.23 mmol) in DMF (0.65 mL). The resulting solution was then treated with MP-(OAc)₃BH (80 mg, 0.16 mmol). The resulting mixture was shaken at ambient temperature for 16 hours on an orbital shaker. The mixture was then filtered through a 0.45 micron frit and the frit was washed with DMSO (1.0 mL). The filtrate was then purified directly by reverse-phase preparative HPLC (using a gradient elution of 5-95% MeCN/water, with 0.1% v/v NH₄OH modifier). Desired fractions were identified, combined, and concentrated in vacuo to afford the title compound, Example #21-1.

LRMS (ESI) calc'd for $C_{30}H_{31}N_6O$ [M+H]⁺: 491. Found: 491.

The following compounds shown in TABLE 22 were prepared according to Scheme #28 following similar procedures described for Example #21-1, which can be achieved by those of ordinary skill in the art of organic synthesis.

TABLE 22

| Example | Structure | Compound Name | Exact Mass [M + H]⁺ |
|---|---|---|---|
| 21-2 | 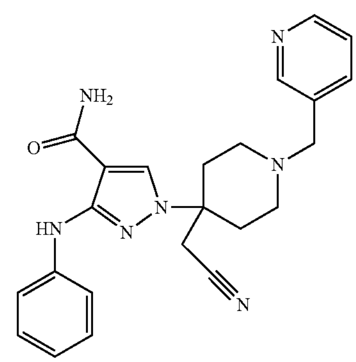 [SMILES: N#CCC1(n2cc(C(N)=O)c(Nc3ccccc3)n2)CCN(Cc2cccnc2)CC1] | 1-[4-(cyanomethyl)-1-(pyridin-3-ylmethyl)piperidin-4-yl]-3-(phenylamino)-1H-pyrazole-4-carboxamide | Calc'd 416, Found 416 |
| 21-3 | 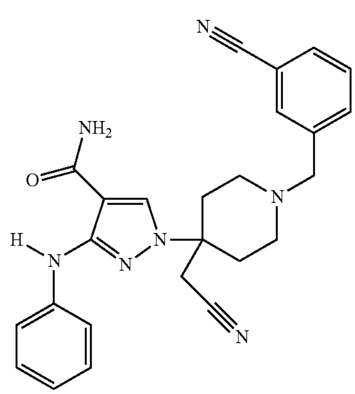 [SMILES: N#CCC1(n2cc(C(N)=O)c(Nc3ccccc3)n2)CCN(Cc2cccc(C#N)c2)CC1] | 1-[1-(3-cyanobenzyl)-4-(cyanomethyl)piperidin-4-yl]-3-(phenylamino)-1H-pyrazole-4-carboxamide | Calc'd 440, Found 440 |

TABLE 22-continued

| Example | Structure | Compound Name | Exact Mass [M + H]+ |
|---------|-----------|---------------|---------------------|
| 21-4 | 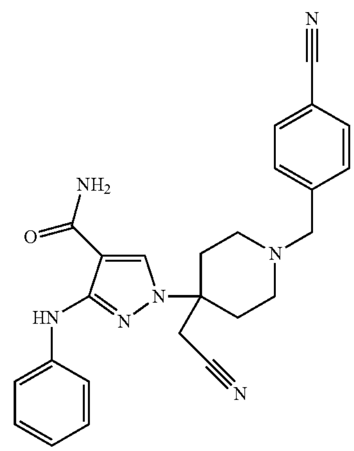 [SMILES: N#CCC1(n2cc(C(N)=O)c(Nc3ccccc3)n2)CCN(Cc2ccc(C#N)cc2)CC1] | 1-[1-(4-cyanobenzyl)-4-(cyanomethyl)piperidin-4-yl]-3-(phenylamino)-1H-pyrazole-4-carboxamide | Calc'd 440, Found 440 |
| 21-5 | 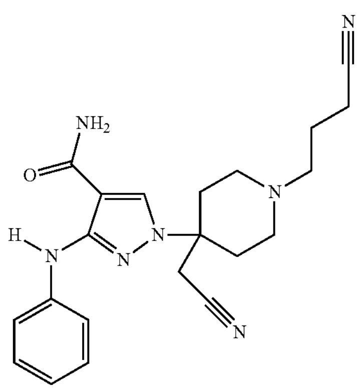 [SMILES: N#CCCCN1CCC(CC#N)(n2cc(C(N)=O)c(Nc3ccccc3)n2)CC1] | 1-[4-(cyanomethyl)-1-(3-cyanopropyl)piperidin-4-yl]-3-(phenylamino)-1H-pyrazole-4-carboxamide | Calc'd 392, Found 392 |
| 21-6 | 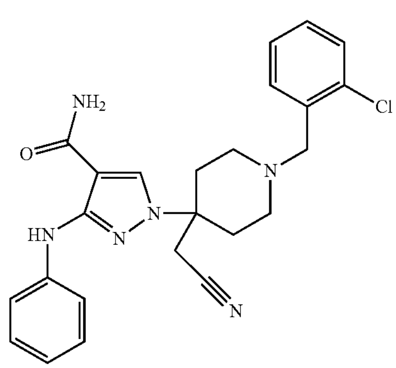 [SMILES: N#CCC1(n2cc(C(N)=O)c(Nc3ccccc3)n2)CCN(Cc2ccccc2Cl)CC1] | 1-[1-(2-chlorobenzyl)-4-(cyanomethyl)piperidin-4-yl]-3-(phenylamino)-1H-pyrazole-4-carboxamide | Calc'd 449, Found 449 |

TABLE 22-continued

| Example | Structure | Compound Name | Exact Mass [M + H]+ |
|---|---|---|---|
| 21-7 | 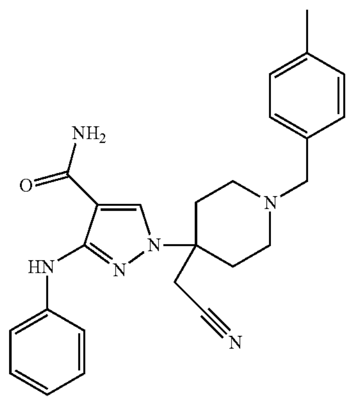 [SMILES: Cc1ccc(CN2CCC(CC#N)(n3cc(C(N)=O)c(Nc4ccccc4)n3)CC2)cc1] | 1-[4-(cyanomethyl)-1-(4-methylbenzyl)piperidin-4-yl]-3-(phenylamino)-1H-pyrazole-4-carboxamide | Calc'd 429, Found 429 |
| 21-8 | 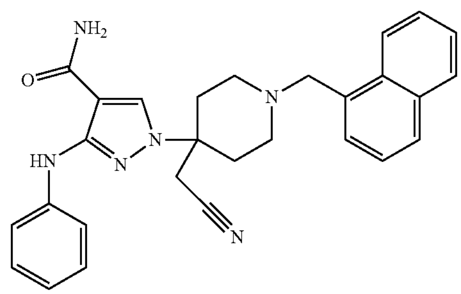 [SMILES: N#CCC1(n2cc(C(N)=O)c(Nc3ccccc3)n2)CCN(Cc2cccc3ccccc23)CC1] | 1-[4-(cyanomethyl)-1-(naphthalene-1-ylmethyl)piperidin-4-yl]-3-(phenylamino)-1H-pyrazole-4-carboxamide | Calc'd 465, Found 465 |
| 21-9 | 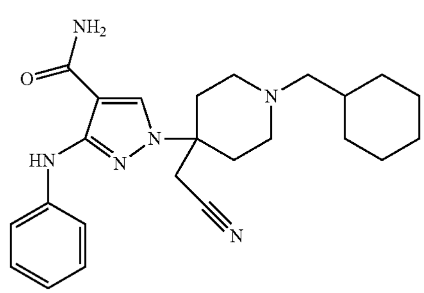 [SMILES: N#CCC1(n2cc(C(N)=O)c(Nc3ccccc3)n2)CCN(CC2CCCCC2)CC1] | 1-[4-(cyanomethyl)-1-(cyclohexylmethyl)piperidin-4-yl]-3-(phenylamino)-1H-pyrazole-4-carboxamide | Calc'd 421, Found 421 |
| 21-10 | 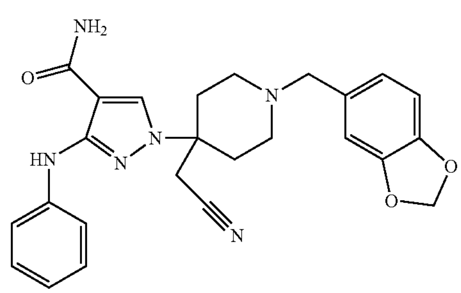 [SMILES: N#CCC1(n2cc(C(N)=O)c(Nc3ccccc3)n2)CCN(Cc2ccc3c(c2)OCO3)CC1] | 1-[1-(1,3-benzodioxol-5-ylmethyl)-4-(cyanomethyl)piperidin-4-yl]-3-(phenylamino)-1H-pyrazole-4-carboxamide | Calc'd 459, Found 459 |

TABLE 22-continued

| Example | Structure | Compound Name | Exact Mass [M + H]+ |
|---|---|---|---|
| 21-11 | 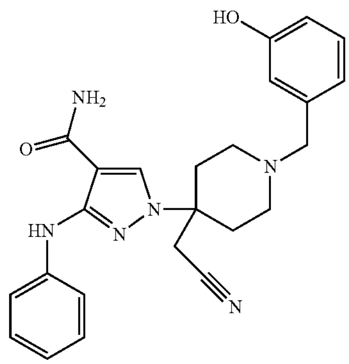 [SMILES: N#CCC1(n2cc(C(N)=O)c(Nc3ccccc3)n2)CCN(Cc2cccc(O)c2)CC1] | 1-[4-(cyanomethyl)-1-(3-hydroxybenzyl)piperidin-4-yl]-3-(phenylamino)-1H-pyrazole-4-carboxamide | Calc'd 431, Found 431 |
| 21-12 | 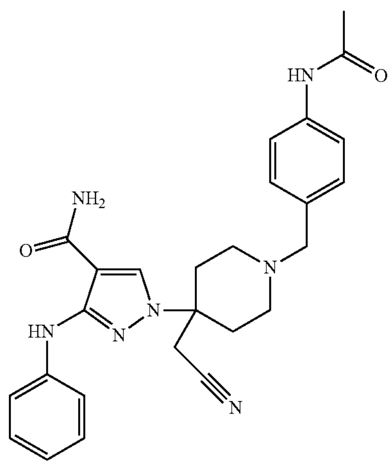 [SMILES: CC(=O)Nc1ccc(CN2CCC(CC#N)(n3cc(C(N)=O)c(Nc4ccccc4)n3)CC2)cc1] | 1-{1-[4-(acetylamino)benzyl]-4-(cyanomethyl)piperidin-4-yl}-3-(phenylamino)-1H-pyrazole-4-carboxamide | Calc'd 472, Found 472 |
| 21-13 | 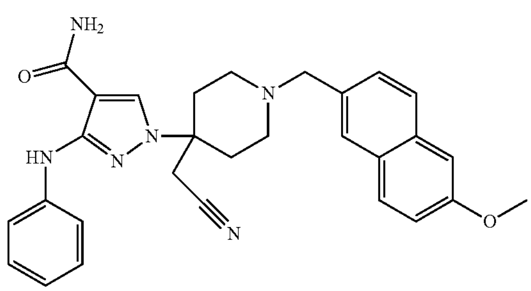 [SMILES: COc1ccc2cc(CN3CCC(CC#N)(n4cc(C(N)=O)c(Nc5ccccc5)n4)CC3)ccc2c1] | 1-{4-(cyanomethyl)-1-[(6-methoxynaphthalen-2-yl)methyl]piperidin-4-yl}-3-(phenylamino)-1H-pyrazole-4-carboxamide | Calc'd 495, Found 495 |
| 21-14 | 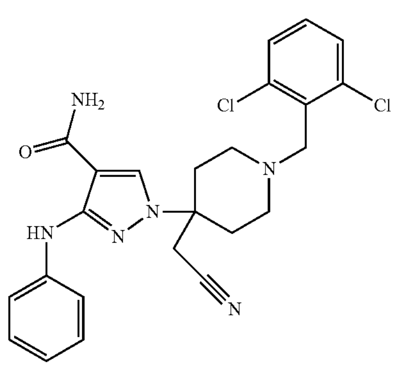 [SMILES: N#CCC1(n2cc(C(N)=O)c(Nc3ccccc3)n2)CCN(Cc2c(Cl)cccc2Cl)CC1] | 1-[4-(cyanomethyl)-1-(2,6-dichlorobenzyl)piperidin-4-yl]-3-(phenylamino)-1H-pyrazole-4-carboxamide | Calc'd 483, Found 483 |

TABLE 22-continued

| Example | Structure | Compound Name | Exact Mass [M + H]+ |
|---|---|---|---|
| 21-15 | 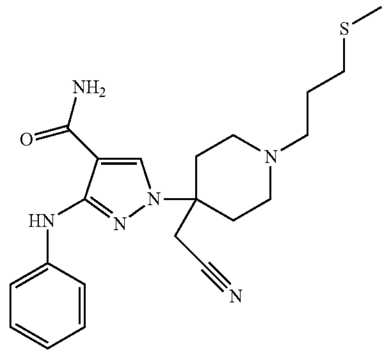 [SMILES: CSCCCN1CCC(CC#N)(n2cc(C(N)=O)c(Nc3ccccc3)n2)CC1] | 1-{4-(cyanomethyl)-1-[3-(methylsulfanyl)propyl]piperidin-4-yl}-3-(phenylamino)-1H-pyrazole-4-carboxamide | Calc'd 413, Found 413 |
| 21-16 | 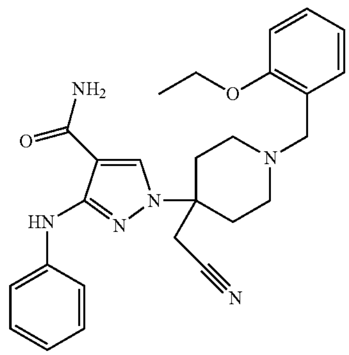 [SMILES: CCOc1ccccc1CN1CCC(CC#N)(n2cc(C(N)=O)c(Nc3ccccc3)n2)CC1] | 1-[4-(cyanomethyl)-1-(2-ethoxybenzyl)piperidin-4-yl]-3-(phenylamino)-1H-pyrazole-4-carboxamide | Calc'd 459, Found 459 |
| 21-17 | 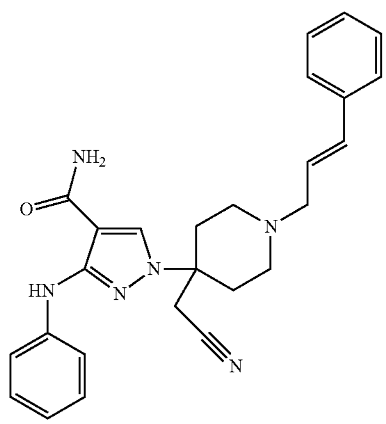 [SMILES: N#CCC1(n2cc(C(N)=O)c(Nc3ccccc3)n2)CCN(C/C=C/c2ccccc2)CC1] | 1-{4-(cyanomethyl)-1-[(2E)-3-phenylprop-2-en-1-yl]piperidin-4-yl}-3-(phenylamino)-1H-pyrazole-4-carboxamide | Calc'd 441, Found 441 |
| 21-18 | 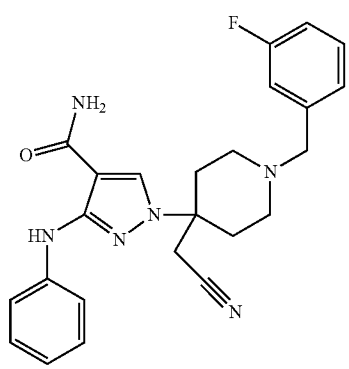 [SMILES: N#CCC1(n2cc(C(N)=O)c(Nc3ccccc3)n2)CCN(Cc2cccc(F)c2)CC1] | 1-[4-(cyanomethyl)-1-(3-fluorobenzyl)piperidin-4-yl]-3-(phenylamino)-1H-pyrazole-4-carboxamide | Calc'd 433, Found 433 |

TABLE 22-continued

| Example | Structure | Compound Name | Exact Mass [M + H]+ |
|---|---|---|---|
| 21-19 | 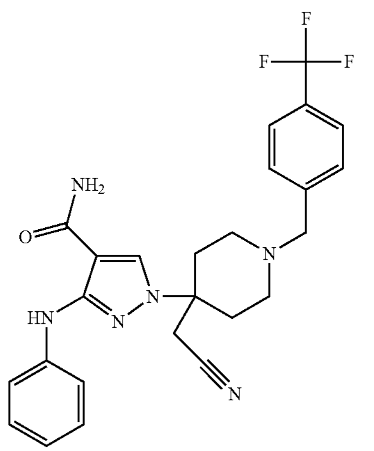 [SMILES: N#CCC1(n2cc(C(N)=O)c(Nc3ccccc3)n2)CCN(Cc2ccc(C(F)(F)F)cc2)CC1] | 1-{4-(cyanomethyl)-1-[4-(trifluoromethyl)benzyl]piperidin-4-yl}-3-(phenylamino)-1H-pyrazole-4-carboxamide | Calc'd 483, Found 483 |
| 21-20 | 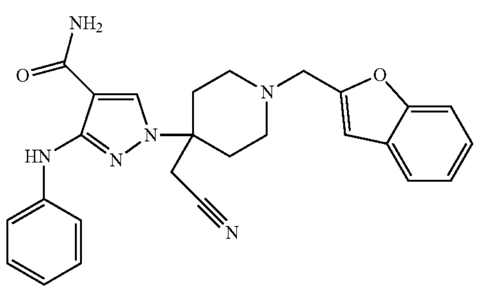 [SMILES: N#CCC1(n2cc(C(N)=O)c(Nc3ccccc3)n2)CCN(Cc2cc3ccccc3o2)CC1] | 1-[1-(1-benzofuran-2-ylmethyl)-4-(cyanomethyl)piperidin-4-yl]-3-(phenylamino)-1H-pyrazole-4-carboxamide | Calc'd 455, Found 455 |
| 21-21 | 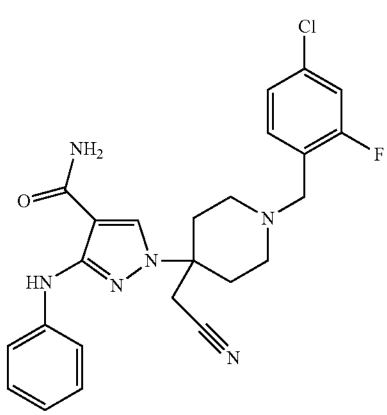 [SMILES: N#CCC1(n2cc(C(N)=O)c(Nc3ccccc3)n2)CCN(Cc2ccc(Cl)cc2F)CC1] | 1-[1-(4-chloro-2-fluorobenzyl)-4-(cyanomethyl)piperidin-4-yl]-3-(phenylamino)-1H-pyrazole-4-carboxamide | Calc'd 467, Found 467 |

TABLE 22-continued

| Example | Structure | Compound Name | Exact Mass [M + H]+ |
|---|---|---|---|
| 21-22 | 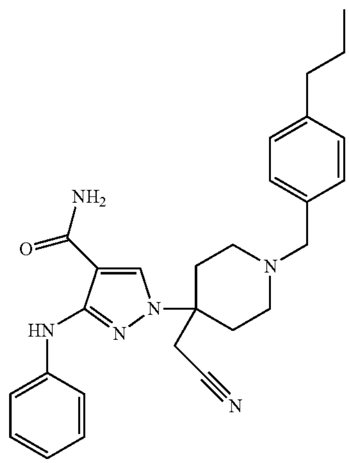 [SMILES: CCCc1ccc(CN2CCC(CC#N)(n3cc(C(N)=O)c(Nc4ccccc4)n3)CC2)cc1] | 1-[4-(cyanomethyl)-1-(4-propylbenzyl)piperidin-4-yl]-3-(phenylamino)-1H-pyrazole-4-carboxamide | Calc'd 457, Found 457 |
| 21-23 | 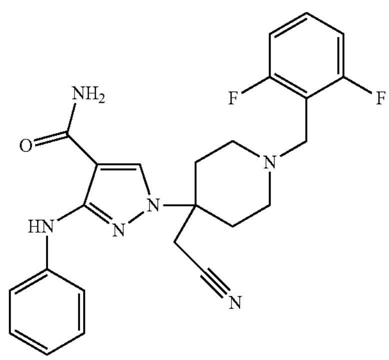 [SMILES: N#CCC1(n2cc(C(N)=O)c(Nc3ccccc3)n2)CCN(Cc2c(F)cccc2F)CC1] | 1-[4-(cyanomethyl)-1-(2,6-difluorobenzyl)piperidin-4-yl]-3-(phenylamino)-1H-pyrazole-4-carboxamide | Calc'd 451, Found 451 |
| 21-24 | 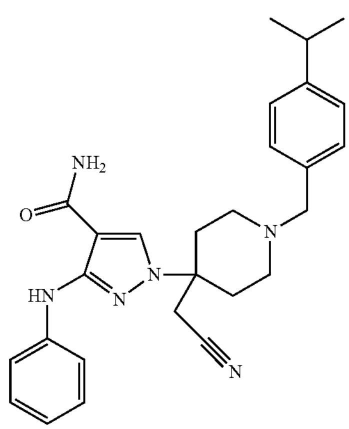 [SMILES: CC(C)c1ccc(CN2CCC(CC#N)(n3cc(C(N)=O)c(Nc4ccccc4)n3)CC2)cc1] | 1-{4-(cyanomethyl)-1-[4-(1-methylethyl)benzyl]piperidin-4-yl}-3-(phenylamino)-1H-pyrazole-4-carboxamide | Calc'd 457, Found 457 |

TABLE 22-continued

| Example | Structure | Compound Name | Exact Mass [M + H]+ |
|---|---|---|---|
| 21-25 | 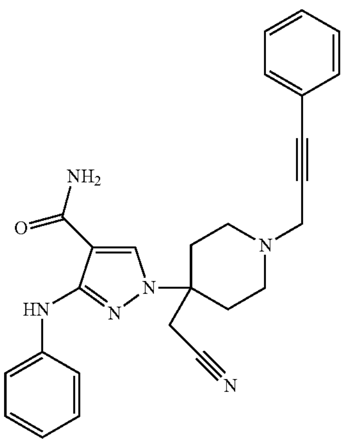 [SMILES: N#CCC1(n2cc(C(N)=O)c(Nc3ccccc3)n2)CCN(CC#Cc2ccccc2)CC1] | 1-[4-(cyanomethyl)-1-(3-phenylprop-2-yn-1-yl)piperidin-4-yl]-3-(phenylamino)-1H-pyrazole-4-carboxamide | Calc'd 439, Found 439 |
| 21-26 | 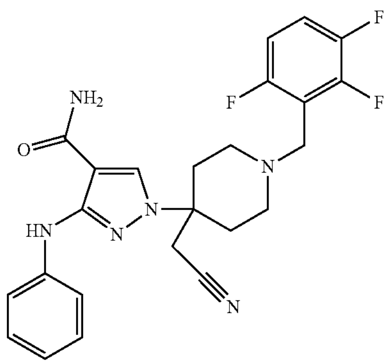 [SMILES: N#CCC1(n2cc(C(N)=O)c(Nc3ccccc3)n2)CCN(Cc2c(F)ccc(F)c2F)CC1] | 1-[4-(cyanomethyl)-1-(2,3,6-trifluorobenzyl)piperidin-4-yl]-3-(phenylamino)-1H-pyrazole-4-carboxamide | Calc'd 469, Found 469 |
| 21-27 | 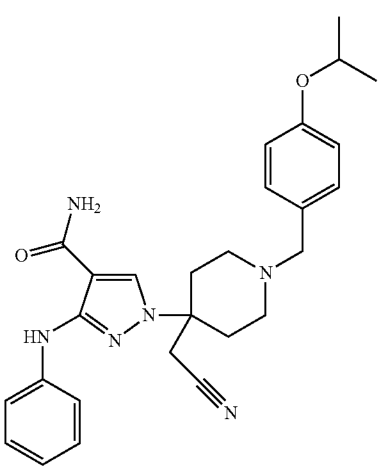 [SMILES: CC(C)Oc1ccc(CN2CCC(CC#N)(n3cc(C(N)=O)c(Nc4ccccc4)n3)CC2)cc1] | 1-{4-(cyanomethyl)-1-[4-(1-methylethoxy)benzyl]piperidin-4-yl}-3-(phenylamino)-1H-pyrazole-4-carboxamide | Calc'd 473, Found 473 |

TABLE 22-continued

| Example | Structure | Compound Name | Exact Mass [M + H]+ |
|---|---|---|---|
| 21-28 | 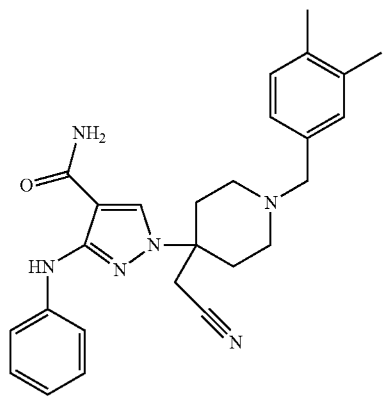 [SMILES: Cc1ccc(CN2CCC(CC#N)(n3cc(C(N)=O)c(Nc4ccccc4)n3)CC2)cc1C] | 1-[4-(cyanomethyl)-1-(3,4-dimethylbenzyl)piperidin-4-yl]-3-(phenylamino)-1H-pyrazole-4-carboxamide | Calc'd 443, Found 443 |
| 21-29 | 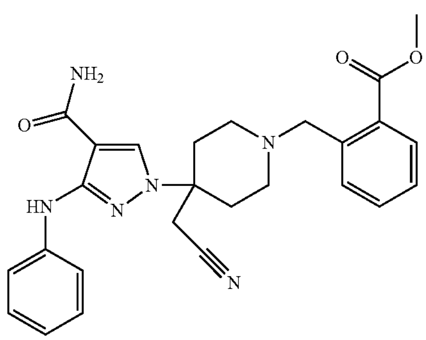 [SMILES: COC(=O)c1ccccc1CN1CCC(CC#N)(n2cc(C(N)=O)c(Nc3ccccc3)n2)CC1] | methyl 2-({4-[4-carbamoyl-3-(phenylamino)-1H-pyrazol-1-yl]-4-(cyanomethyl)piperidin-1-yl}methyl)benzoate | Calc'd 473, Found 473 |

Scheme #37

Example #22-1

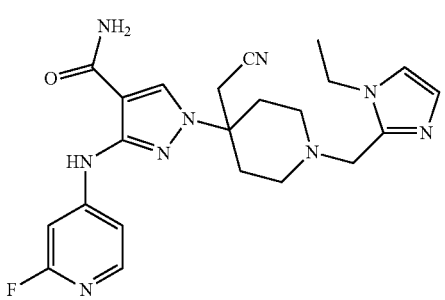

1-(4-(Cyanomethyl)-1-((1-ethyl-1H-imidazol-2-yl)methyl)piperidin-4-yl)-3-((2-fluoropyridin-4-yl)amino)-1H-pyrazole-4-carboxamide To a reaction vial was added 4-{4-carbamoyl-3-[(2-fluoropyridin-4-yl)amino]-1H-pyrazol-1-yl}-4-(cyanomethyl)piperidinium trifluoroacetate (Intermediate #38-4) (0.020 g, 0.058 mmol), 1-ethyl-1H-imidazole-2-carbaldehyde (0.0072 g, 0.058 mmol), Na(OAc)₃BH (0.062 g, 0.29 mmol), TFA (0.030 g, 0.26 mmol) suspended in DMF (0.97 mL). The reaction vessel was sealed and heated to 50° C. with stirring for 12 hours. The completed reaction was directly purified by reverse phase preparative HPLC (using a gradient elution of 0-95% ACN/water with 0.1% v/v NH₄OH modifier) to afford the title compound, Example #22-1.

LRMS (ESI) calc'd for $C_{22}H_{26}FN_9O$ [M+H]+: 452. Found: 452.

The following compounds shown in TABLE 23 were prepared according to Scheme #37 following similar procedures described for Example #22-1, which can be achieved by those of ordinary skill in the art of organic synthesis utilizing but not limited to Intermediates #38-4 and 38-5 as intermediates.

TABLE 23

| Example | Structure | Compound Name | Exact Mass [M + H]+ |
|---|---|---|---|
| 22-2 | 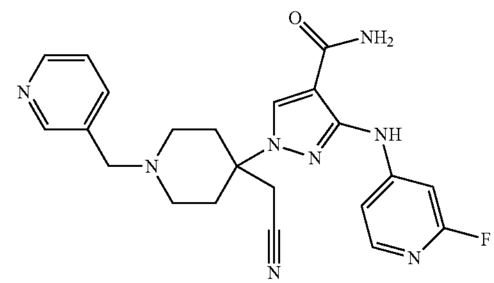 [SMILES: N#CCC1(n2cc(C(N)=O)c(Nc3ccnc(F)c3)n2)CCN(Cc2cccnc2)CC1] | 1-[4-(cyanomethyl)-1-(pyridin-3-ylmethyl)piperidin-4-yl]-3-[(2-fluoropyridin-4-yl)amino]-1H-pyrazole-4-carboxamide | Calc'd 435, found 435 |
| 22-3 | 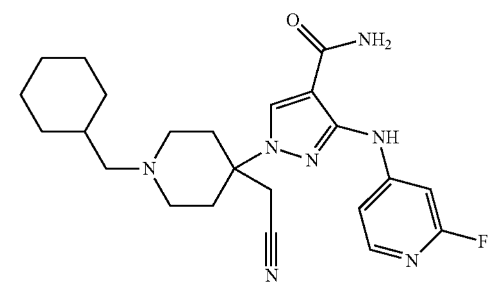 [SMILES: N#CCC1(n2cc(C(N)=O)c(Nc3ccnc(F)c3)n2)CCN(CC2CCCCC2)CC1] | 1-[4-(cyanomethyl)-1-(cyclohexylmethyl)piperidin-4-yl]-3-[(2-fluoropyridin-4-yl)amino]-1H-pyrazole-4-carboxamide | Calc'd 440, found 440 |
| 22-4 | 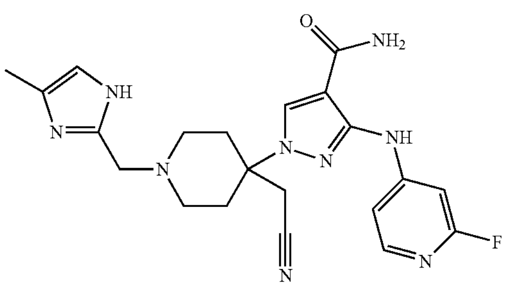 [SMILES: Cc1c[nH]c(CN2CCC(CC#N)(n3cc(C(N)=O)c(Nc4ccnc(F)c4)n3)CC2)n1] | 1-{4-(cyanomethyl)-1-[(4-methyl-1H-imidazol-2-yl)methyl]piperidin-4-yl}-3-[(2-fluoropyridin-4-yl)amino]-1H-pyrazole-4-carboxamide | Calc'd 438, found 438 |
| 22-5 | 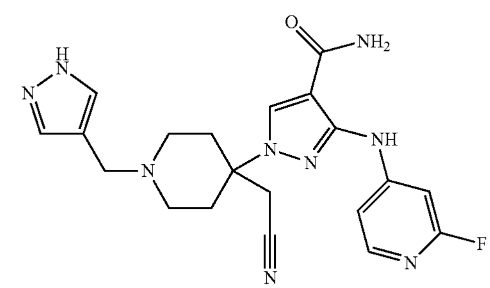 [SMILES: N#CCC1(n2cc(C(N)=O)c(Nc3ccnc(F)c3)n2)CCN(Cc2cn[nH]c2)CC1] | 1-[4-(cyanomethyl)-1-(1H-pyrazol-4-ylmethyl)piperidin-4-yl]-3-[(2-fluoropyridin-4-yl)amino]-1H-pyrazole-4-carboxamide | Calc'd 424, found 424 |
| 22-6 | 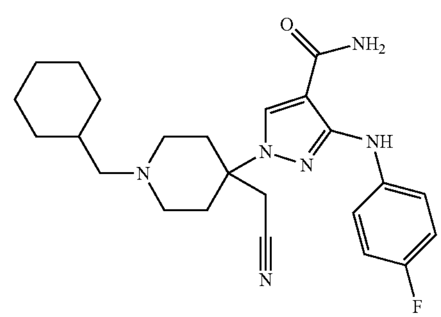 [SMILES: N#CCC1(n2cc(C(N)=O)c(Nc3ccc(F)cc3)n2)CCN(CC2CCCCC2)CC1] | 1-[4-(cyanomethyl)-1-(cyclohexylmethyl)piperidin-4-yl]-3-[(4-fluorophenyl)amino]-1H-pyrazole-4-carboxamide | Calc'd 439, found 439 |

TABLE 23-continued

| Example | Structure | Compound Name | Exact Mass [M + H]+ |
|---|---|---|---|
| 22-7 | 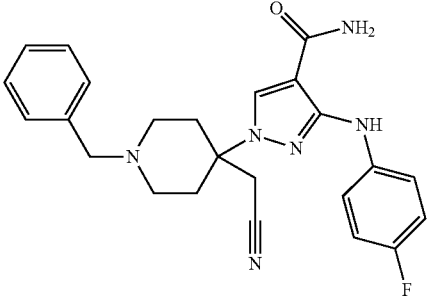 [SMILES: N#CCC1(n2cc(C(N)=O)c(Nc3ccc(F)cc3)n2)CCN(Cc2ccccc2)CC1] | 1-[1-benzyl-4-(cyanomethyl)piperidin-4-yl]-3-[(4-fluorophenyl)amino]-1H-pyrazole-4-carboxamide | Calc'd 433, found 433 |
| 22-8 | 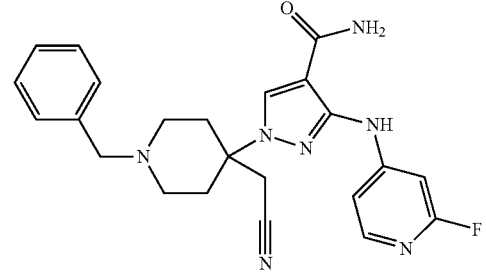 [SMILES: N#CCC1(n2cc(C(N)=O)c(Nc3ccnc(F)c3)n2)CCN(Cc2ccccc2)CC1] | 1-[1-benzyl-4-(cyanomethyl)piperidin-4-yl]-3-[(2-fluoropyridin-4-yl)amino]-1H-pyrazole-4-carboxamide | Calc'd 434, found 434 |
| 22-9 | 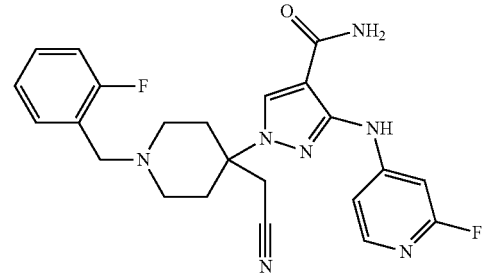 [SMILES: N#CCC1(n2cc(C(N)=O)c(Nc3ccnc(F)c3)n2)CCN(Cc2ccccc2F)CC1] | 1-[4-(cyanomethyl)-1-(2-fluorobenzyl)piperidin-4-yl]-3-[(2-fluoropyridin-4-yl)amino]-1H-pyrazole-4-carboxamide | Calc'd 452, found 452 |
| 22-10 | 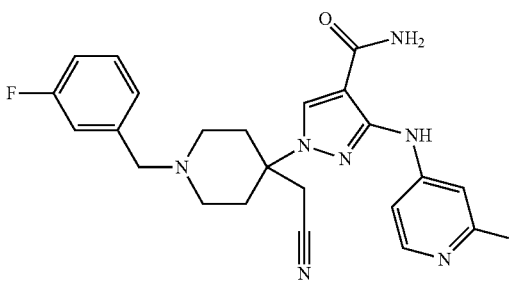 | 1-[4-(cyanomethyl)-1-(3-fluorobenzyl)piperidin-4-yl]-3-[(2-fluoropyridin-4-yl)amino]-1H-pyrazole-4-carboxamide | Calc'd 452, found 452 |
| 22-11 | 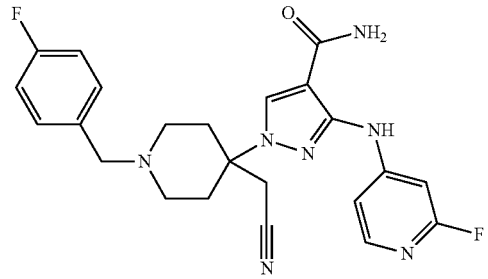 [SMILES: N#CCC1(n2cc(C(N)=O)c(Nc3ccnc(F)c3)n2)CCN(Cc2ccc(F)cc2)CC1] | 1-[4-(cyanomethyl)-1-(4-fluorobenzyl)piperidin-4-yl]-3-[(2-fluoropyridin-4-yl)amino]-1H-pyrazole-4-carboxamide | Calc'd 452, found 452 |

TABLE 23-continued

| Example | Structure | Compound Name | Exact Mass [M + H]+ |
|---|---|---|---|
| 22-12 | 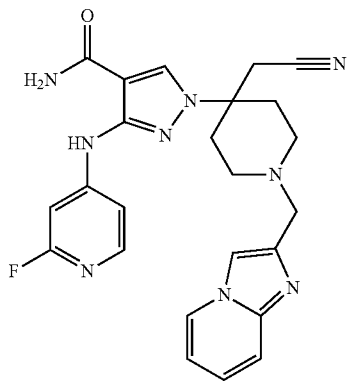 [SMILES: N#CCC1(n2cc(C(N)=O)c(Nc3ccnc(F)c3)n2)CCN(Cc2cn3ccccc3n2)CC1] | 1-[4-(cyanomethyl)-1-(imidazo[1,2-a]pyridin-2-ylmethyl)piperidin-4-yl]-3-[(2-fluoropyridin-4-yl)amino]-1H-pyrazole-4-carboxamide | Calc'd 474, found 474 |
| 22-13 | 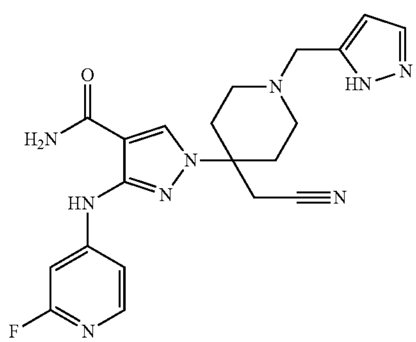 [SMILES: N#CCC1(n2cc(C(N)=O)c(Nc3ccnc(F)c3)n2)CCN(Cc2ccn[nH]2)CC1] | 1-[4-(cyanomethyl)-1-(1H-pyrazol-5-ylmethyl)piperidin-4-yl]-3-[(2-fluoropyridin-4-yl)amino]-1H-pyrazole-4-carboxamide | Calc'd 424, found 424 |
| 22-14 | 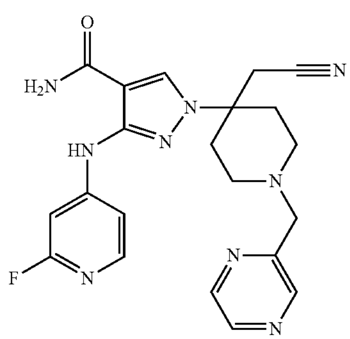 [SMILES: N#CCC1(n2cc(C(N)=O)c(Nc3ccnc(F)c3)n2)CCN(Cc2cnccn2)CC1] | 1-[4-(cyanomethyl)-1-(pyrazin-2-ylmethyl)piperidin-4-yl]-3-[(2-fluoropyridin-4-yl)amino]-1H-pyrazole-4-carboxamide | Calc'd 436, found 436 |
| 22-15 | 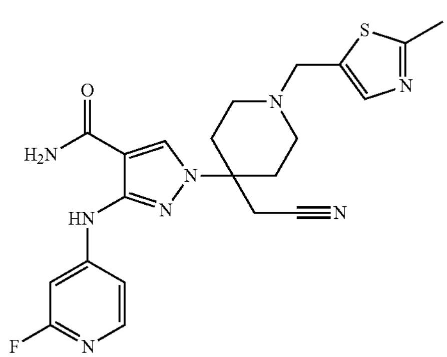 [SMILES: Cc1ncc(CN2CCC(CC#N)(n3cc(C(N)=O)c(Nc4ccnc(F)c4)n3)CC2)s1] | 1-{4-(cyanomethyl)-1-[(2-methyl-1,3-thiazol-5-yl)methyl]piperidin-4-yl}-3-[(2-fluoropyridin-4-yl)amino]-1H-pyrazole-4-carboxamide | Calc'd 455, found 455 |

TABLE 23-continued

| Example | Structure | Compound Name | Exact Mass [M + H]$^+$ |
|---|---|---|---|
| 22-16 | 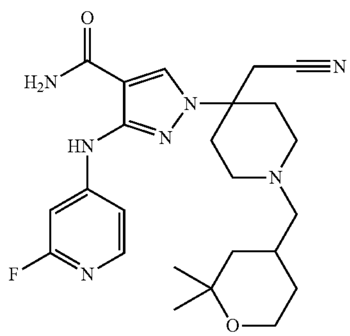 [SMILES: CC1(C)CC(CN2CCC(CC#N)(n3cc(C(N)=O)c(Nc4ccnc(F)c4)n3)CC2)CCO1] | 1-{4-(cyanomethyl)-1-[(2,2-dimethyltetrahydro-2H-pyran-4-yl)methyl]piperidin-4-yl}-3-[(2-fluoropyridin-4-yl)amino]-1H-pyrazole-4-carboxamide | Calc'd 470, found 470 |
| 22-17 | 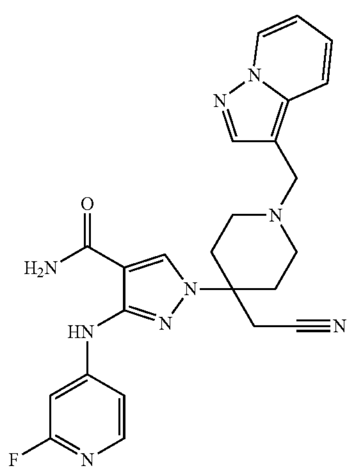 [SMILES: N#CCC1(n2cc(C(N)=O)c(Nc3ccnc(F)c3)n2)CCN(Cc2cnn3ccccc23)CC1] | 1-[4-(cyanomethyl)-1-(pyrazolo[1,5-a]pyridin-3-ylmethyl)piperidin-4-yl]-3-[(2-fluoropyridin-4-yl)amino]-1H-pyrazole-4-carboxamide | Calc'd 474, found 474 |
| 22-18 | 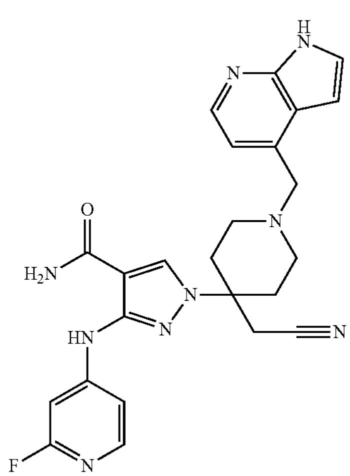 [SMILES: N#CCC1(n2cc(C(N)=O)c(Nc3ccnc(F)c3)n2)CCN(Cc2ccnc3[nH]ccc23)CC1] | 1-[4-(cyanomethyl)-1-(1H-pyrrolo[2,3-b]pyridin-4-ylmethyl)piperidin-4-yl]-3-[(2-fluoropyridin-4-yl)amino]-1H-pyrazole-4-carboxamide | Calc'd 474, found 474 |

TABLE 23-continued

| Example | Structure | Compound Name | Exact Mass [M + H]+ |
|---|---|---|---|
| 22-19 | 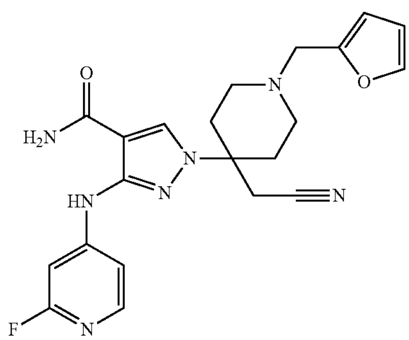 [SMILES: N#CCC1(n2cc(C(N)=O)c(Nc3ccnc(F)c3)n2)CCN(Cc2ccco2)CC1] | 1-[4-(cyanomethyl)-1-(furan-2-ylmethyl)piperidin-4-yl]-3-[(2-fluoropyridin-4-yl)amino]-1H-pyrazole-4-carboxamide | Calc'd 424, found 424 |
| 22-20 | 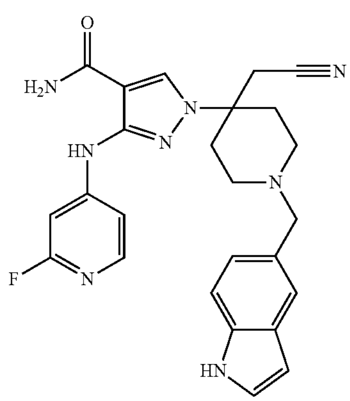 [SMILES: N#CCC1(n2cc(C(N)=O)c(Nc3ccnc(F)c3)n2)CCN(Cc2ccc3[nH]ccc3c2)CC1] | 1-[4-(cyanomethyl)-1-(1H-indol-5-ylmethyl)piperidin-4-yl]-3-[(2-fluoropyridin-4-yl)amino]-1H-pyrazole-4-carboxamide | Calc'd 473, found 473 |
| 22-21 | 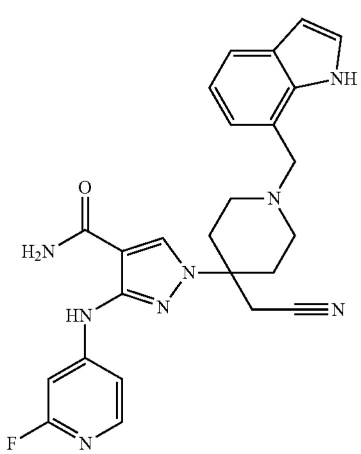 [SMILES: N#CCC1(n2cc(C(N)=O)c(Nc3ccnc(F)c3)n2)CCN(Cc2cccc3cc[nH]c23)CC1] | 1-[4-(cyanomethyl)-1-(1H-indol-7-ylmethyl)piperidin-4-yl]-3-[(2-fluoropyridin-4-yl)amino]-1H-pyrazole-4-carboxamide | Calc'd 473, found 473 |

TABLE 23-continued

| Example | Structure | Compound Name | Exact Mass [M + H]+ |
|---|---|---|---|
| 22-22 | 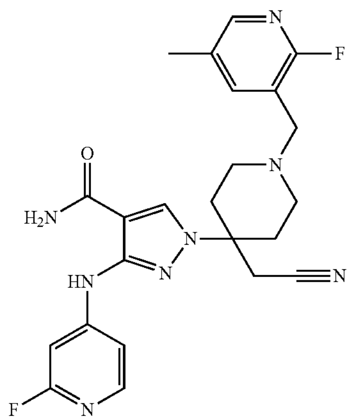 [SMILES: Cc1cnc(F)c(CN2CCC(CC#N)(n3cc(C(N)=O)c(Nc4ccnc(F)c4)n3)CC2)c1] | 1-{4-(cyanomethyl)-1-[(2-fluoro-5-methylpyridin-3-yl)methyl]piperidin-4-yl}-3-[(2-fluoropyridin-4-yl)amino]-1H-pyrazole-4-carboxamide | Calc'd 467, found 467 |
| 22-23 | 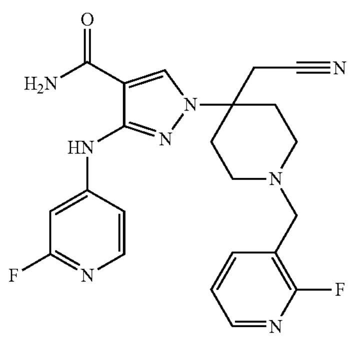 [SMILES: N#CCC1(n2cc(C(N)=O)c(Nc3ccnc(F)c3)n2)CCN(Cc2cccnc2F)CC1] | 1-{4-(cyanomethyl)-1-[(2-fluoropyridin-3-yl)methyl]piperidin-4-yl}-3-[(2-fluoropyridin-4-yl)amino]-1H-pyrazole-4-carboxamide | Calc'd 453, found 453 |
| 22-24 | 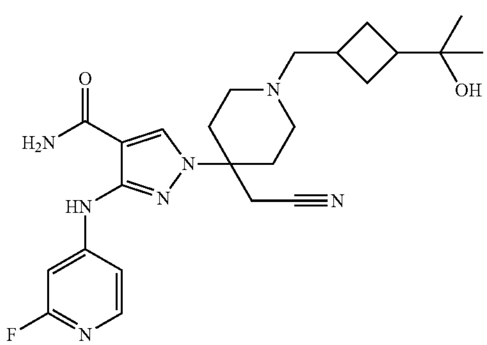 [SMILES: CC(C)(O)C1CC(CN2CCC(CC#N)(n3cc(C(N)=O)c(Nc4ccnc(F)c4)n3)CC2)C1] | 1-[4-(cyanomethyl)-1-{[3-(1-hydroxy-1-methylethyl)cyclobutyl]methyl}piperidin-4-yl]-3-[(2-fluoropyridin-4-yl)amino]-1H-pyrazole-4-carboxamide | Calc'd 470, found 470 |
| 22-25 | 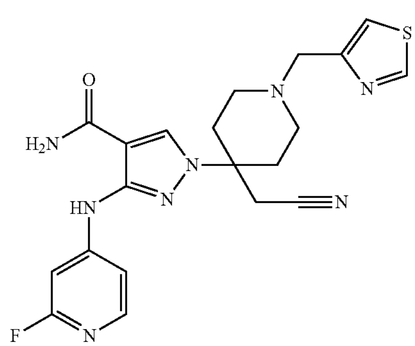 [SMILES: N#CCC1(n2cc(C(N)=O)c(Nc3ccnc(F)c3)n2)CCN(Cc2cscn2)CC1] | 1-[4-(cyanomethyl)-1-(1,3-thiazol-4-ylmethyl)piperidin-4-yl]-3-[(2-fluoropyridin-4-yl)amino]-1H-pyrazole-4-carboxamide | Calc'd 441, found 441 |

TABLE 23-continued

| Example | Structure | Compound Name | Exact Mass [M + H]+ |
|---|---|---|---|
| 22-26 | 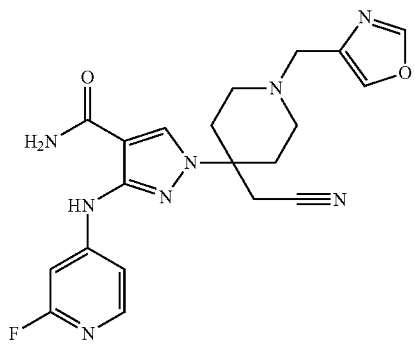 [SMILES: N#CCC1(n2cc(C(N)=O)c(Nc3ccnc(F)c3)n2)CCN(Cc2cocn2)CC1] | 1-[4-(cyanomethyl)-1-(1,3-oxazol-4-ylmethyl)piperidin-4-yl]-3-[(2-fluoropyridin-4-yl)amino]-1H-pyrazole-4-carboxamide | Calc'd 425, found 425 |
| 22-27 | 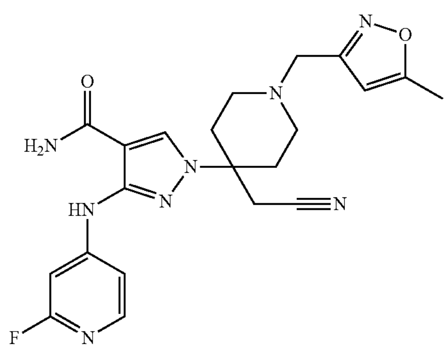 [SMILES: Cc1cc(CN2CCC(CC#N)(n3cc(C(N)=O)c(Nc4ccnc(F)c4)n3)CC2)no1] | 1-{4-(cyanomethyl)-1-[(5-methylisoxazol-3-yl)methyl]piperidin-4-yl}-3-[(2-fluoropyridin-4-yl)amino]-1H-pyrazole-4-carboxamide | Calc'd 439, found 439 |
| 22-28 | 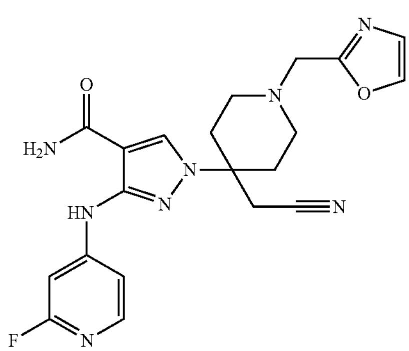 [SMILES: N#CCC1(n2cc(C(N)=O)c(Nc3ccnc(F)c3)n2)CCN(Cc2ncco2)CC1] | 1-[4-(cyanomethyl)-1-(1,3-oxazol-2-ylmethyl)piperidin-4-yl]-3-[(2-fluoropyridin-4-yl)amino]-1H-pyrazole-4-carboxamide | Calc'd 425, found 425 |
| 22-29 | 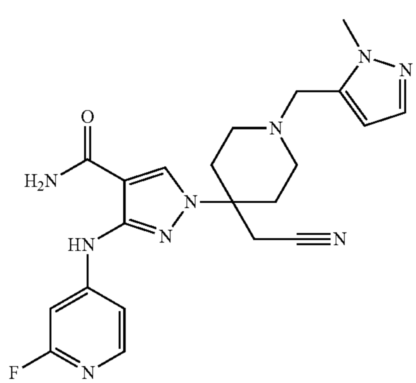 [SMILES: Cn1nccc1CN1CCC(CC#N)(n2cc(C(N)=O)c(Nc3ccnc(F)c3)n2)CC1] | 1-{4-(cyanomethyl)-1-[(1-methyl-1H-pyrazol-5-yl)methyl]piperidin-4-yl}-3-[(2-fluoropyridin-4-yl)amino]-1H-pyrazole-4-carboxamide | Calc'd 438, found 438 |

TABLE 23-continued

| Example | Structure | Compound Name | Exact Mass [M + H]+ |
|---|---|---|---|
| 22-30 | 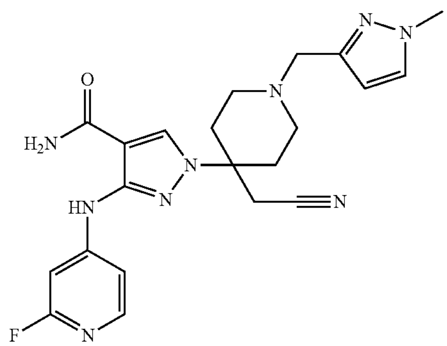 [SMILES: Cn1ccc(CN2CCC(CC#N)(n3cc(C(N)=O)c(Nc4ccnc(F)c4)n3)CC2)n1] | 1-{4-(cyanomethyl)-1-[(1-methyl-1H-pyrazol-3-yl)methyl]piperidin-4-yl}-3-[(2-fluoropyridin-4-yl)amino]-1H-pyrazole-4-carboxamide | Calc'd 438, found 438 |
| 22-31 | 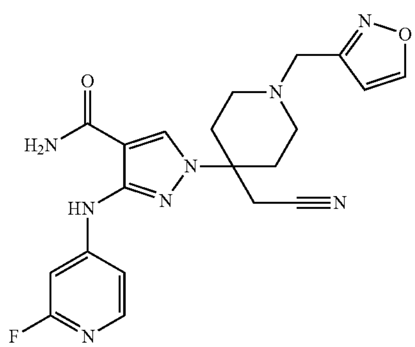 [SMILES: N#CCC1(n2cc(C(N)=O)c(Nc3ccnc(F)c3)n2)CCN(Cc2ccon2)CC1] | 1-[4-(cyanomethyl)-1-(isoxazol-3-ylmethyl)piperidin-4-yl]-3-[(2-fluoropyridin-4-yl)amino]-1H-pyrazole-4-carboxamide | Calc'd 425, found 425 |
| 22-32 | 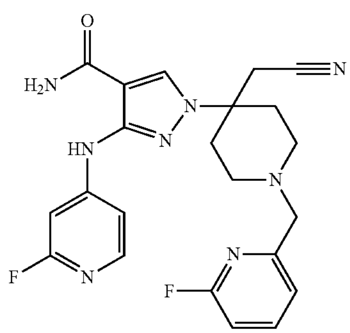 [SMILES: N#CCC1(n2cc(C(N)=O)c(Nc3ccnc(F)c3)n2)CCN(Cc2cccc(F)n2)CC1] | 1-{4-(cyanomethyl)-1-[(6-fluoropyridin-2-yl)methyl]piperidin-4-yl}-3-[(2-fluoropyridin-4-yl)amino]-1H-pyrazole-4-carboxamide | Calc'd 453, found 453 |
| 22-33 | 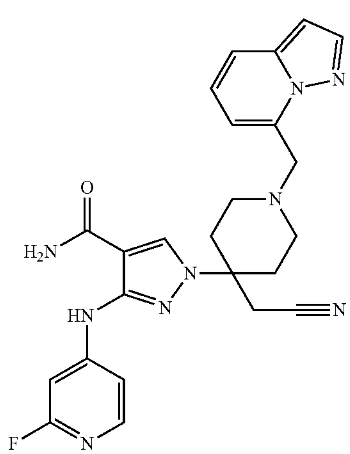 [SMILES: N#CCC1(n2cc(C(N)=O)c(Nc3ccnc(F)c3)n2)CCN(Cc2cccc3ccnn23)CC1] | 1-[4-(cyanomethyl)-1-(pyrazolo[1,5-a]pyridin-7-ylmethyl)piperidin-4-yl]-3-[(2-fluoropyridin-4-yl)amino]-1H-pyrazole-4-carboxamide | Calc'd 474, found 474 |

TABLE 23-continued

| Example | Structure | Compound Name | Exact Mass [M + H]+ |
|---|---|---|---|
| 22-34 | 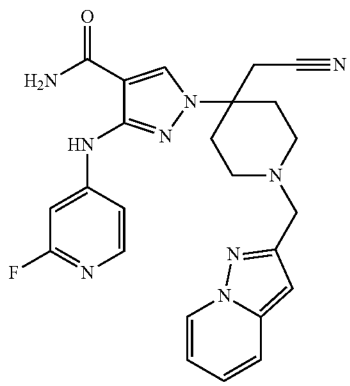 [SMILES: N#CCC1(n2cc(C(N)=O)c(Nc3ccnc(F)c3)n2)CCN(Cc2cc3ccccn3n2)CC1] | 1-[4-(cyanomethyl)-1-(pyrazolo[1,5-a]pyridin-2-ylmethyl)piperidin-4-yl]-3-[(2-fluoropyridin-4-yl)amino]-1H-pyrazole-4-carboxamide | Calc'd 474, found 474 |
| 22-35 | 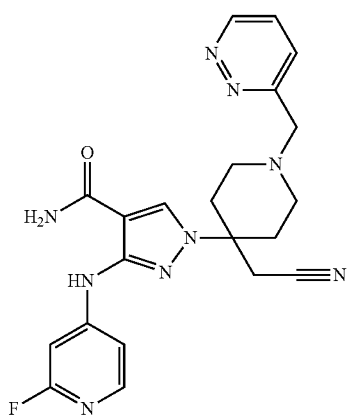 [SMILES: N#CCC1(n2cc(C(N)=O)c(Nc3ccnc(F)c3)n2)CCN(Cc2cccnn2)CC1] | 1-[4-(cyanomethyl)-1-(pyridazin-3-ylmethyl)piperidin-4-yl]-3-[(2-fluoropyridin-4-yl)amino]-1H-pyrazole-4-carboxamide | Calc'd 436, found 436 |
| 22-36 | 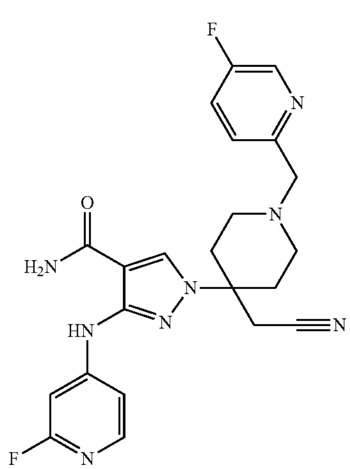 [SMILES: N#CCC1(n2cc(C(N)=O)c(Nc3ccnc(F)c3)n2)CCN(Cc2ccc(F)cn2)CC1] | 1-{4-(cyanomethyl)-1-[(5-fluoropyridin-2-yl)methyl]piperidin-4-yl}-3-[(2-fluoropyridin-4-yl)amino]-1H-pyrazole-4-carboxamide | Calc'd 453, found 453 |

TABLE 23-continued

| Example | Structure | Compound Name | Exact Mass [M + H]+ |
|---|---|---|---|
| 22-37 | 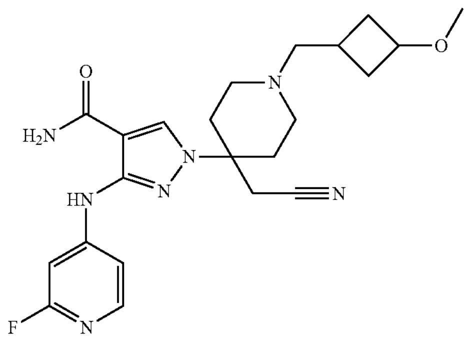 [SMILES: COC1CC(CN2CCC(CC#N)(n3cc(C(N)=O)c(Nc4ccnc(F)c4)n3)CC2)C1] | 1-{4-(cyanomethyl)-1-[(3-methoxycyclobutyl)methyl]piperidin-4-yl}-3-[(2-fluoropyridin-4-yl)amino]-1H-pyrazole-4-carboxamide | Calc'd 442, found 442 |
| 22-38 | 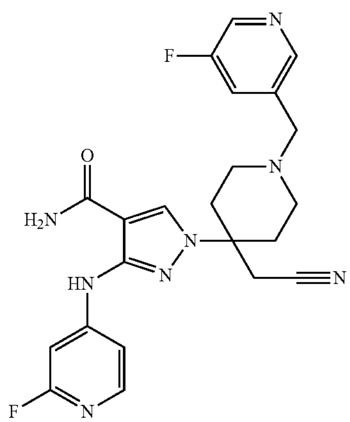 [SMILES: N#CCC1(n2cc(C(N)=O)c(Nc3ccnc(F)c3)n2)CCN(Cc2cncc(F)c2)CC1] | 1-{4-(cyanomethyl)-1-[(5-fluoropyridin-3-yl)methyl]piperidin-4-yl}-3-[(2-fluoropyridin-4-yl)amino]-1H-pyrazole-4-carboxamide | Calc'd 453, found 453 |
| 22-39 | 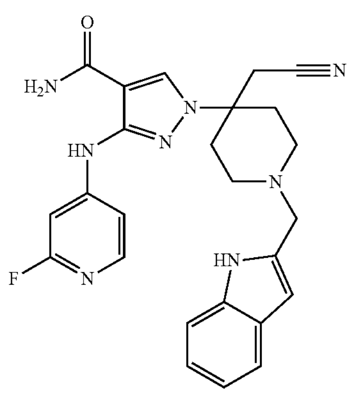 [SMILES: N#CCC1(n2cc(C(N)=O)c(Nc3ccnc(F)c3)n2)CCN(Cc2cc3ccccc3[nH]2)CC1] | 1-[4-(cyanomethyl)-1-(1H-indol-2-ylmethyl)piperidin-4-yl]-3-[(2-fluoropyridin-4-yl)amino]-1H-pyrazole-4-carboxamide | Calc'd 473, found 473 |
| 22-40 | 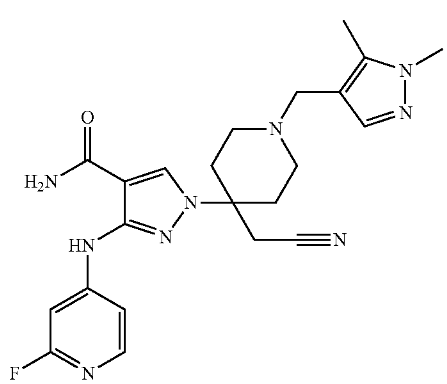 [SMILES: Cc1c(CN2CCC(CC#N)(n3cc(C(N)=O)c(Nc4ccnc(F)c4)n3)CC2)cnn1C] | 1-{4-(cyanomethyl)-1-[(1,5-dimethyl-1H-pyrazol-4-yl)methyl]piperidin-4-yl}-3-[(2-fluoropyridin-4-yl)amino]-1H-pyrazole-4-carboxamide | Calc'd 452, found 452 |

TABLE 23-continued

| Example | Structure | Compound Name | Exact Mass [M + H]+ |
|---|---|---|---|
| 22-41 | 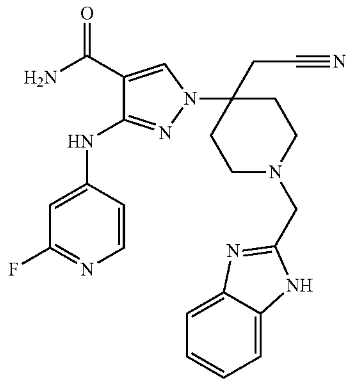 [SMILES: N#CCC1(n2cc(C(N)=O)c(Nc3ccnc(F)c3)n2)CCN(Cc2nc3ccccc3[nH]2)CC1] | 1-[1-(1H-benzimidazol-2-ylmethyl)-4-(cyanomethyl)piperidin-4-yl]-3-[(2-fluoropyridin-4-yl)amino]-1H-pyrazole-4-carboxamide | Calc'd 474, found 474 |
| 22-42 | 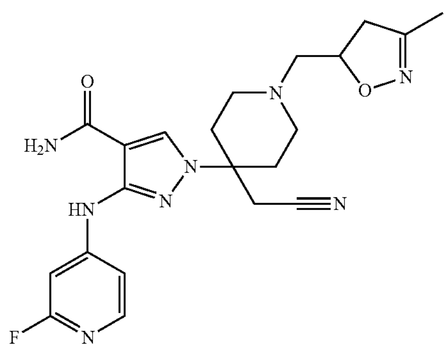 [SMILES: CC1=NOC(CN2CCC(CC#N)(n3cc(C(N)=O)c(Nc4ccnc(F)c4)n3)CC2)C1] | 1-{4-(cyanomethyl)-1-[(3-methyl-4,5-dihydroisoxazol-5-yl)methyl]piperidin-4-yl}-3-[(2-fluoropyridin-4-yl)amino]-1H-pyrazole-4-carboxamide | Calc'd 441, found 441 |
| 22-43 | 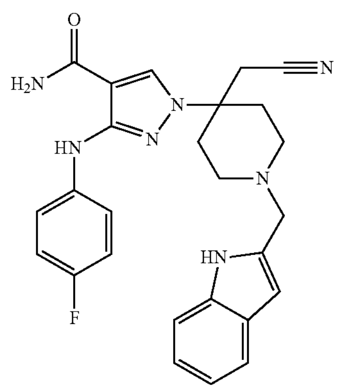 [SMILES: N#CCC1(n2cc(C(N)=O)c(Nc3ccc(F)cc3)n2)CCN(Cc2cc3ccccc3[nH]2)CC1] | 1-[4-(cyanomethyl)-1-(1H-indol-2-ylmethyl)piperidin-4-yl]-3-[(4-fluorophenyl)amino]-1H-pyrazole-4-carboxamide | Calc'd 472, found 472 |
| 22-44 | 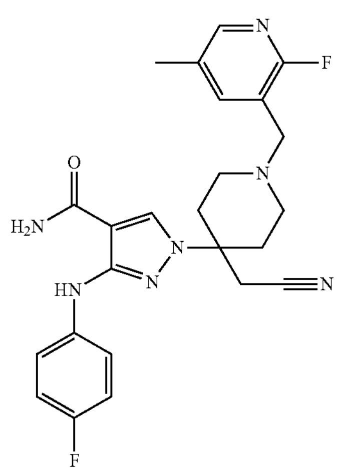 [SMILES: Cc1cnc(F)c(CN2CCC(CC#N)(n3cc(C(N)=O)c(Nc4ccc(F)cc4)n3)CC2)c1] | 1-{4-(cyanomethyl)-1-[(2-fluoro-5-methylpyridin-3-yl)methyl]piperidin-4-yl}-3-[(4-fluorophenyl)amino]-1H-pyrazole-4-carboxamide | Calc'd 466, found 466 |

TABLE 23-continued

| Example | Structure | Compound Name | Exact Mass [M + H]+ |
|---|---|---|---|
| 22-45 | 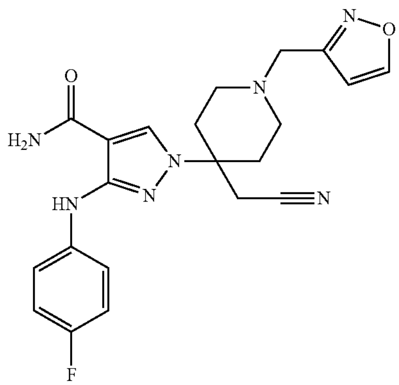 [SMILES: N#CCC1(n2cc(C(N)=O)c(Nc3ccc(F)cc3)n2)CCN(Cc2ccon2)CC1] | 1-[4-(cyanomethyl)-1-(isoxazol-3-ylmethyl)piperidin-4-yl]-3-[(4-fluorophenyl)amino]-1H-pyrazole-4-carboxamide | Calc'd 424, found 424 |
| 22-46 | 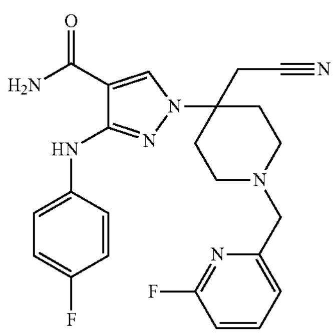 [SMILES: N#CCC1(n2cc(C(N)=O)c(Nc3ccc(F)cc3)n2)CCN(Cc2cccc(F)n2)CC1] | 1-{4-(cyanomethyl)-1-[(6-fluoropyridin-2-yl)methyl]piperidin-4-yl}-3-[(4-fluorophenyl)amino]-1H-pyrazole-4-carboxamide | Calc'd 452, found 452 |
| 22-47 | 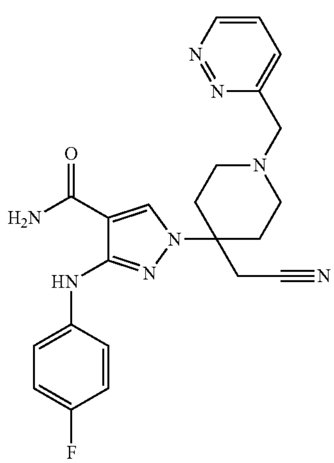 [SMILES: N#CCC1(n2cc(C(N)=O)c(Nc3ccc(F)cc3)n2)CCN(Cc2cccnn2)CC1] | 1-[4-(cyanomethyl)-1-(pyridazin-3-ylmethyl)piperidin-4-yl]-3-[(4-fluorophenyl)amino]-1H-pyrazole-4-carboxamide | Calc'd 435, found 435 |

TABLE 23-continued

| Example | Structure | Compound Name | Exact Mass [M + H]+ |
|---|---|---|---|
| 22-48 | 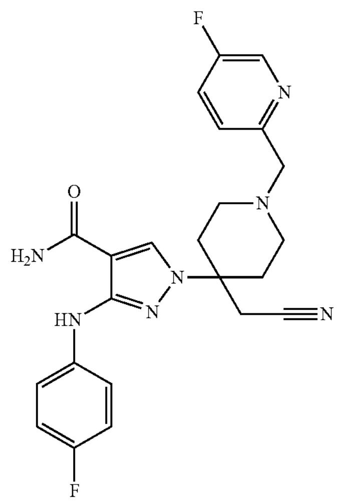 [SMILES: N#CCC1(n2cc(C(N)=O)c(Nc3ccc(F)cc3)n2)CCN(Cc2ccc(F)cn2)CC1] | 1-{4-(cyanomethyl)-1-[(5-fluoropyridin-2-yl)methyl]piperidin-4-yl}-3-[(4-fluorophenyl)amino]-1H-pyrazole-4-carboxamide | Calc'd 452, found 452 |
| 22-49 | 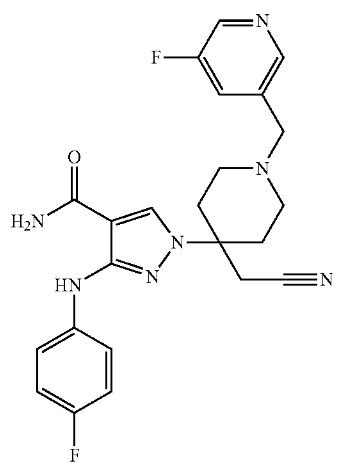 [SMILES: N#CCC1(n2cc(C(N)=O)c(Nc3ccc(F)cc3)n2)CCN(Cc2cncc(F)c2)CC1] | 1-{4-(cyanomethyl)-1-[(5-fluoropyridin-3-yl)methyl]piperidin-4-yl}-3-[(4-fluorophenyl)amino]-1H-pyrazole-4-carboxamide | Calc'd 452, found 452 |
| 22-50 | 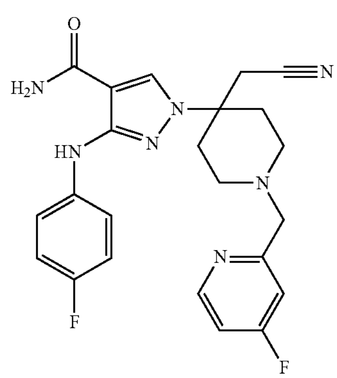 [SMILES: N#CCC1(n2cc(C(N)=O)c(Nc3ccc(F)cc3)n2)CCN(Cc2cc(F)ccn2)CC1] | 1-{4-(cyanomethyl)-1-[(4-fluoropyridin-2-yl)methyl]piperidin-4-yl}-3-[(4-fluorophenyl)amino]-1H-pyrazole-4-carboxamide | Calc'd 452, found 452 |

TABLE 23-continued

| Example | Structure | Compound Name | Exact Mass [M + H]+ |
|---|---|---|---|
| 22-51 | 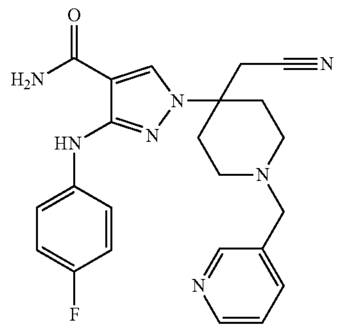 [SMILES: N#CCC1(n2cc(C(N)=O)c(Nc3ccc(F)cc3)n2)CCN(Cc2cccnc2)CC1] | 1-[4-(cyanomethyl)-1-(pyridin-3-ylmethyl)piperidin-4-yl]-3-[(4-fluorophenyl)amino]-1H-pyrazole-4-carboxamide | Calc'd 434, found 434 |
| 22-52 | 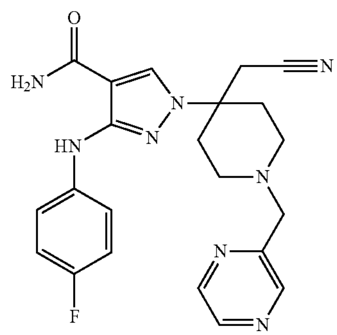 [SMILES: N#CCC1(n2cc(C(N)=O)c(Nc3ccc(F)cc3)n2)CCN(Cc2cnccn2)CC1] | 1-[4-(cyanomethyl)-1-(pyrazin-2-ylmethyl)piperidin-4-yl]-3-[(4-fluorophenyl)amino]-1H-pyrazole-4-carboxamide | Calc'd 435, found 435 |
| 22-53 | 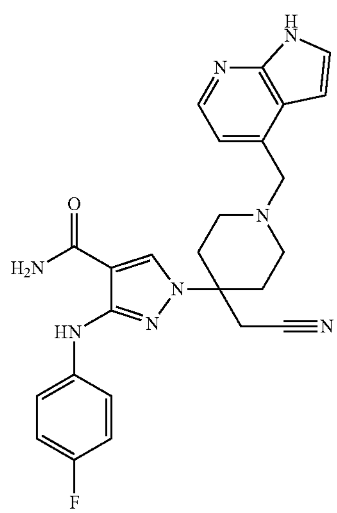 [SMILES: N#CCC1(n2cc(C(N)=O)c(Nc3ccc(F)cc3)n2)CCN(Cc2ccnc3[nH]ccc23)CC1] | 1-[4-(cyanomethyl)-1-(1H-pyrrolo[2,3-b]pyridin-4-ylmethyl)piperidin-4-yl]-3-[(4-fluorophenyl)amino]-1H-pyrazole-4-carboxamide | Calc'd 473, found 473 |
| 22-54 | 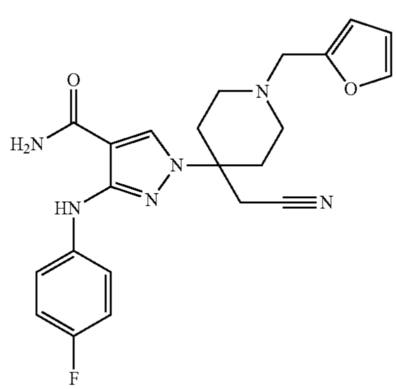 [SMILES: N#CCC1(n2cc(C(N)=O)c(Nc3ccc(F)cc3)n2)CCN(Cc2ccco2)CC1] | 1-[4-(cyanomethyl)-1-(furan-2-ylmethyl)piperidin-4-yl]-3-[(4-fluorophenyl)amino]-1H-pyrazole-4-carboxamide | Calc'd 423, found 423 |

TABLE 23-continued

| Example | Structure | Compound Name | Exact Mass [M + H]+ |
|---|---|---|---|
| 22-55 | 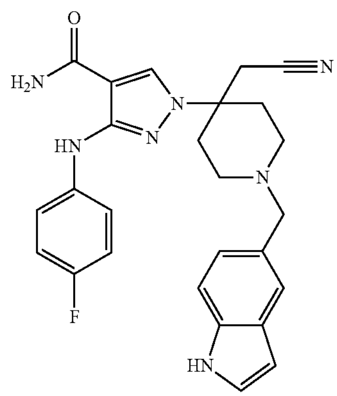 [SMILES: N#CCC1(n2cc(C(N)=O)c(Nc3ccc(F)cc3)n2)CCN(Cc2ccc3[nH]ccc3c2)CC1] | 1-[4-(cyanomethyl)-1-(1H-indol-5-ylmethyl)piperidin-4-yl]-3-[(4-fluorophenyl)amino]-1H-pyrazole-4-carboxamide | Calc'd 472, found 472 |
| 22-56 | 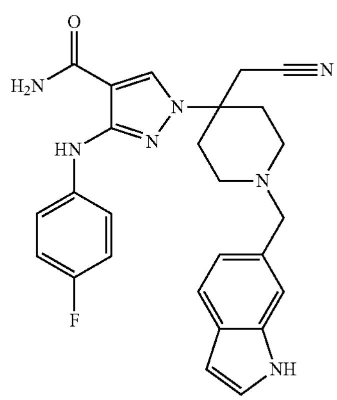 [SMILES: N#CCC1(n2cc(C(N)=O)c(Nc3ccc(F)cc3)n2)CCN(Cc2ccc3cc[nH]c3c2)CC1] | 1-[4-(cyanomethyl)-1-(1H-indol-6-ylmethyl)piperidin-4-yl]-3-[(4-fluorophenyl)amino]-1H-pyrazole-4-carboxamide | Calc'd 472, found 472 |
| 22-57 | 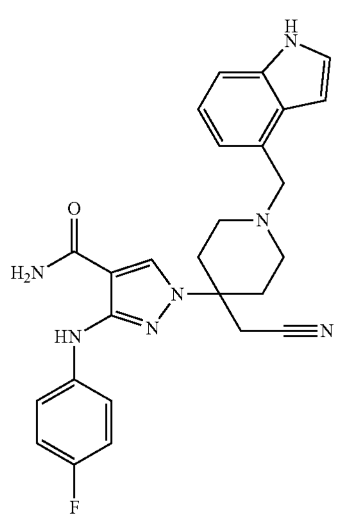 [SMILES: N#CCC1(n2cc(C(N)=O)c(Nc3ccc(F)cc3)n2)CCN(Cc2cccc3[nH]ccc23)CC1] | 1-[4-(cyanomethyl)-1-(1H-indol-4-ylmethyl)piperidin-4-yl]-3-[(4-fluorophenyl)amino]-1H-pyrazole-4-carboxamide | Calc'd 472, found 472 |

TABLE 23-continued

| Example | Structure | Compound Name | Exact Mass [M + H]+ |
|---|---|---|---|
| 22-58 | 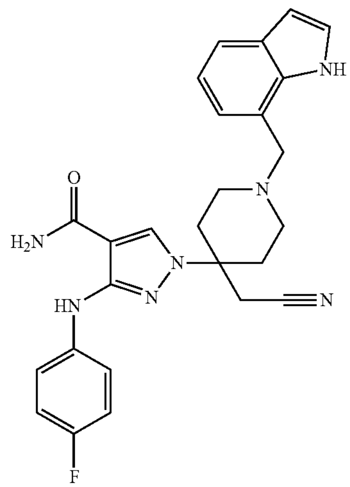 [SMILES: N#CCC1(n2cc(C(N)=O)c(Nc3ccc(F)cc3)n2)CCN(Cc2cccc3cc[nH]c23)CC1] | 1-[4-(cyanomethyl)-1-(1H-indol-7-ylmethyl)piperidin-4-yl]-3-[(4-fluorophenyl)amino]-1H-pyrazole-4-carboxamide | Calc'd 472, found 472 |
| 22-59 | 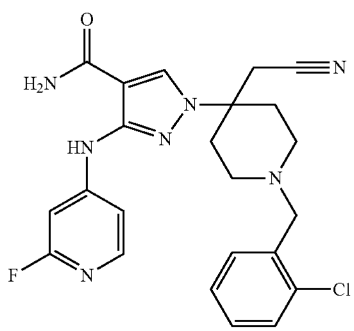 [SMILES: N#CCC1(n2cc(C(N)=O)c(Nc3ccnc(F)c3)n2)CCN(Cc2ccccc2Cl)CC1] | 1-[1-(2-chlorobenzyl)-4-(cyanomethyl)piperidin-4-yl]-3-[(2-fluoropyridin-4-yl)amino]-1H-pyrazole-4-carboxamide | Calc'd 468, found 468 |
| 22-60 | 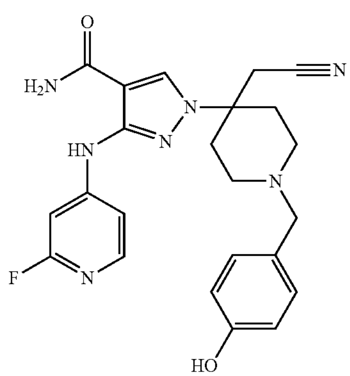 [SMILES: N#CCC1(n2cc(C(N)=O)c(Nc3ccnc(F)c3)n2)CCN(Cc2ccc(O)cc2)CC1] | 1-[4-(cyanomethyl)-1-(4-hydroxybenzyl)piperidin-4-yl]-3-[(2-fluoropyridin-4-yl)amino]-1H-pyrazole-4-carboxamide | Calc'd 450, found 450 |
| 22-61 | 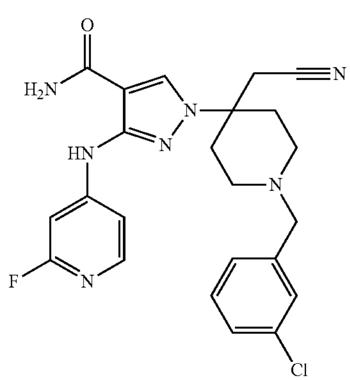 [SMILES: N#CCC1(n2cc(C(N)=O)c(Nc3ccnc(F)c3)n2)CCN(Cc2cccc(Cl)c2)CC1] | 1-[1-(3-chlorobenzyl)-4-(cyanomethyl)piperidin-4-yl]-3-[(2-fluoropyridin-4-yl)amino]-1H-pyrazole-4-carboxamide | Calc'd 468, found 468 |

TABLE 23-continued

| Example | Structure | Compound Name | Exact Mass [M + H]+ |
|---|---|---|---|
| 22-62 | 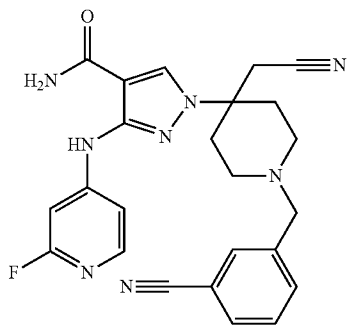 [SMILES: N#CCC1(n2cc(C(N)=O)c(Nc3ccnc(F)c3)n2)CCN(Cc2cccc(C#N)c2)CC1] | 1-[1-(3-cyanobenzyl)-4-(cyanomethyl)piperidin-4-yl]-3-[(2-fluoropyridin-4-yl)amino]-1H-pyrazole-4-carboxamide | Calc'd 459, found 459 |
| 22-63 | 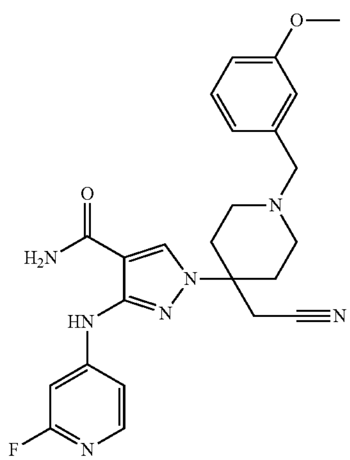 [SMILES: COc1cccc(CN2CCC(CC#N)(n3cc(C(N)=O)c(Nc4ccnc(F)c4)n3)CC2)c1] | 1-[4-(cyanomethyl)-1-(3-methoxybenzyl)piperidin-4-yl]-3-[(2-fluoropyridin-4-yl)amino]-1H-pyrazole-4-carboxamide | Calc'd 464, found 464 |
| 22-64 | 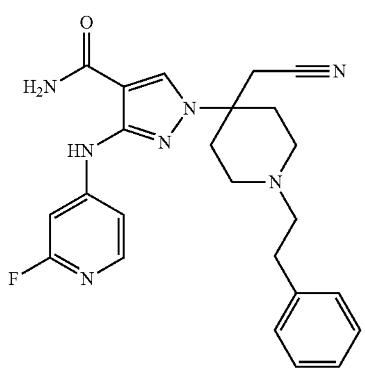 [SMILES: N#CCC1(n2cc(C(N)=O)c(Nc3ccnc(F)c3)n2)CCN(CCc2ccccc2)CC1] | 1-[4-(cyanomethyl)-1-(2-phenylethyl)piperidin-4-yl]-3-[(2-fluoropyridin-4-yl)amino]-1H-pyrazole-4-carboxamide | Calc'd 448, found 448 |
| 22-65 | 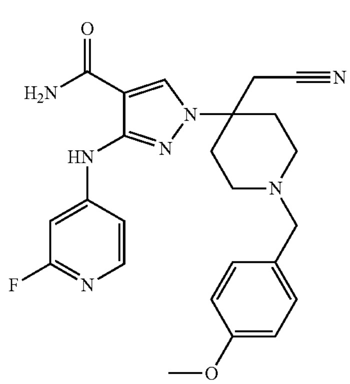 [SMILES: COc1ccc(CN2CCC(CC#N)(n3cc(C(N)=O)c(Nc4ccnc(F)c4)n3)CC2)cc1] | 1-[4-(cyanomethyl)-1-(4-methoxybenzyl)piperidin-4-yl]-3-[(2-fluoropyridin-4-yl)amino]-1H-pyrazole-4-carboxamide | Calc'd 464, found 464 |

TABLE 23-continued

| Example | Structure | Compound Name | Exact Mass [M + H]+ |
|---|---|---|---|
| 22-66 | 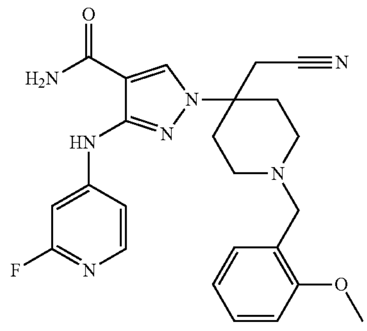 [SMILES: COc1ccccc1CN1CCC(CC#N)(n2cc(C(N)=O)c(Nc3ccnc(F)c3)n2)CC1] | 1-[4-(cyanomethyl)-1-(2-methoxybenzyl)piperidin-4-yl]-3-[(2-fluoropyridin-4-yl)amino]-1H-pyrazole-4-carboxamide | Calc'd 464, found 464 |
| 22-67 | 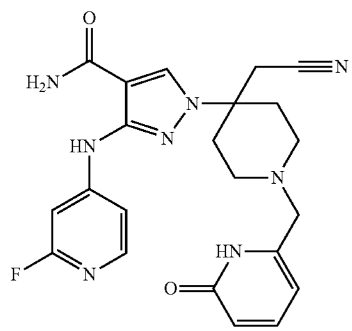 [SMILES: N#CCC1(n2cc(C(N)=O)c(Nc3ccnc(F)c3)n2)CCN(Cc2cccc(=O)[nH]2)CC1] | 1-{4-(cyanomethyl)-1-[(6-oxo-1,6-dihydropyridin-2-yl)methyl]piperidin-4-yl}-3-[(2-fluoropyridin-4-yl)amino]-1H-pyrazole-4-carboxamide | Calc'd 451, found 451 |
| 22-68 | 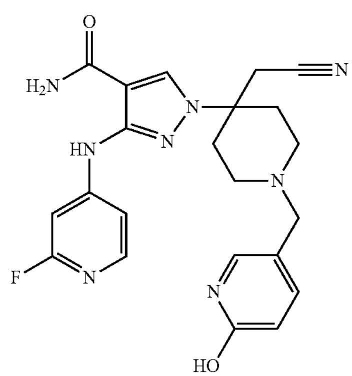 [SMILES: N#CCC1(n2cc(C(N)=O)c(Nc3ccnc(F)c3)n2)CCN(Cc2ccc(O)nc2)CC1] | 1-{4-(cyanomethyl)-1-[(6-hydroxypyridin-3-yl)methyl]piperidin-4-yl}-3-[(2-fluoropyridin-4-yl)amino]-1H-pyrazole-4-carboxamide | Calc'd 451, found 451 |
| 22-69 | 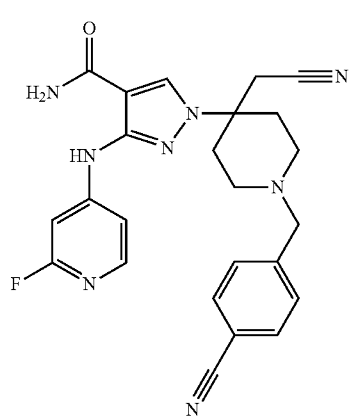 [SMILES: N#CCC1(n2cc(C(N)=O)c(Nc3ccnc(F)c3)n2)CCN(Cc2ccc(C#N)cc2)CC1] | 1-[1-(4-cyanobenzyl)-4-(cyanomethyl)piperidin-4-yl]-3-[(2-fluoropyridin-4-yl)amino]-1H-pyrazole-4-carboxamide | Calc'd 459, found 459 |

TABLE 23-continued

| Example | Structure | Compound Name | Exact Mass [M + H]+ |
|---|---|---|---|
| 22-70 | 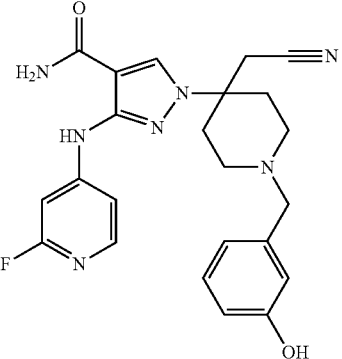 [SMILES: N#CCC1(n2cc(C(N)=O)c(Nc3ccnc(F)c3)n2)CCN(Cc2cccc(O)c2)CC1] | 1-[4-(cyanomethyl)-1-(3-hydroxybenzyl)piperidin-4-yl]-3-[(2-fluoropyridin-4-yl)amino]-1H-pyrazole-4-carboxamide | Calc'd 450, found 450 |
| 22-71 | 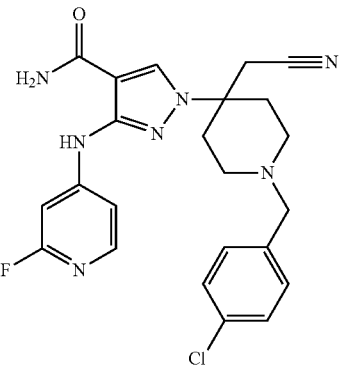 [SMILES: N#CCC1(n2cc(C(N)=O)c(Nc3ccnc(F)c3)n2)CCN(Cc2ccc(Cl)cc2)CC1] | 1-[1-(4-chlorobenzyl)-4-(cyanomethyl)piperidin-4-yl]-3-[(2-fluoropyridin-4-yl)amino]-1H-pyrazole-4-carboxamide | Calc'd 468, found 468 |
| 22-72 | 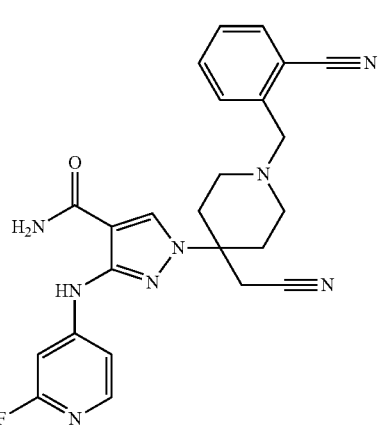 | 1-[1-(2-cyanobenzyl)-4-(cyanomethyl)piperidin-4-yl]-3-[(2-fluoropyridin-4-yl)amino]-1H-pyrazole-4-carboxamide | Calc'd 459, found 459 |

Scheme #28

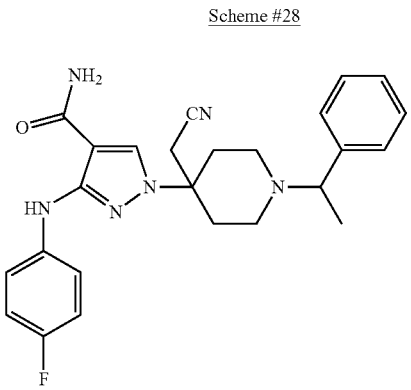

Example #23

1-(4-(Cyanomethyl)-1-(1-phenylethyl)piperidin-4-yl)-3-((4-fluorophenyl)amino)-1H-pyrazole-4-carboxamide To a solution of 1-(4-(cyanomethyl)piperidin-4-yl)-3-((4-fluorophenyl)amino)-1H-pyrazole-4-carboxamide (Intermediate #38-5) (50 mg, 0.11 mmol) in MeOH (0.32 mL) and DMF (0.063 mL) was added acetophenone (41 mg, 0.34 mmol) and acetic acid (0.065 mL, 1.1 mmol). The reaction mixture was allowed to stir at room temperature for 15 minutes. Sodium cyanoborohydride (7 mg, 0.1 mmol) was added and the reaction mixture was allowed to stir for 24 hours at ambient temperature. The mixture was then purified directly by mass-triggered reverse-phase preparative HPLC (MeCN/water, with 0.1% v/v TFA modifier). Desired fractions were identified, combined, and concentrated in vacuo. The residue was dissolved in MeOH and passed through a Si-Carbonate cartridge to afford the title compound as a free base.

$^1$H NMR (500 MHz, DMSO-$d_6$): δ 9.57 (br s, 1H), 9.02 (s, 1H), 8.46 (s, 1H), 7.52-7.49 (m, 4H), 7.43 (s, 4H), 7.23 (br s, 1H), 7.04 (t, J=8.5 Hz, 2H), 4.47 (m, 1H), 3.91-3.88 (m, 1H), 3.12 (s, 2H), 3.02-3.00 (m, 1H), 2.86-2.80 (m, 2H), 2.68-2.66 (m, 2H), 2.31-2.26 (m, 1H), 2.16-2.12 (m, 1H), 1.59 (m, d, J=7 Hz, 2H).

LRMS (ESI) calc'd for $C_{25}H_{27}FN_6O$ [M+H]$^+$: 447. Found: 447.

Scheme #38

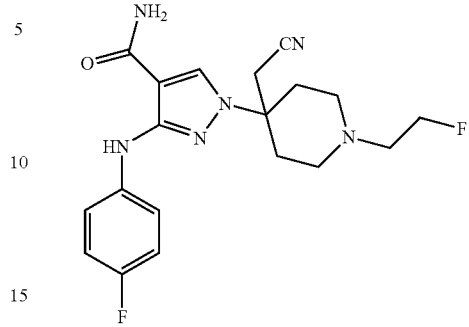

Example #24-1

1-(4-(Cyanomethyl)-1-(2-fluoroethyl)piperidin-4-yl)-3-((4-fluorophenyl)amino)-1H-pyrazole-4-carboxamide To a sealed vial was added 2-fluoroethanol (0.0090 g, 0.14 mmol), PS-IBX (0.28 g, 0.28 mmol, 1.0 mmol/g) suspended in DCE (1.0 mL). The vial was capped and shaken at RT for 16 hours. The reaction was passed though a syringe filter and the eluent was collected into a reaction vial. To the reaction vial was added 4-(4-carbamoyl-3-((4-fluorophenyl)amino)-1H-pyrazol-1-yl)-4-(cyanomethyl)piperidin-1-ium 2,2,2-trifluoroacetate (Intermediate #38-5) (0.020 g, 0.058 mmol), TFA (0.020 mL, 0.26 mmol), Na(OAc)$_3$BH (0.037 g, 0.18 mmol) suspended in DMF (0.50 mL). The reaction vial was capped and heated to 50° C. for 4 hours. The completed reaction was concentrated in vacuo and the residue taken up in DMF (1.0 mL). The crude reaction was passed through a syringe filter and the eluent was directly purified by reverse phase preparative HPLC (using a gradient elution of 0-95% ACN/water with 0.1% v/v TFA modifier). The collected HPLC fraction was concentrated in vacuo and the residue was taken up in MeOH and passed through a Si-Carbonate SPE cartridge. The eluent was collected and evaporated to afford the title compound.

LRMS (ESI) calc'd for $C_{19}H_{22}F_2N_6O$ [M+H]$^+$: 389. Found: 389.

The following compounds shown in TABLE 24 were prepared according to Scheme #38 following similar procedures described for Example #24-1, which can be achieved by those of ordinary skill in the art of organic synthesis.

TABLE 24

| Example | Structure | Compound Name | Exact Mass [M + H]$^+$ |
|---------|-----------|---------------|------------------------|
| 24-2 | ![structure] | 1-[4-(cyanomethyl)-1-(cyclopropylmethyl) piperidin-4-yl]-3-[(4-fluorophenyl)amino]-1H-pyrazole-4-carboxamide | Calc'd 397, found 397 |

Scheme #28

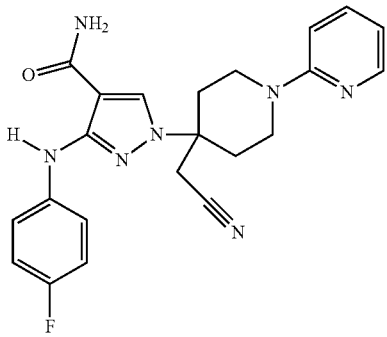

Example #25

1-(4-(Cyanomethyl)-1-(pyridin-2-yl)piperidin-4-yl)-3-(4-fluorophenylamino)-1H-pyrazole-4-carboxamide A mixture of 4-{4-carbamoyl-3-[(4-fluorophenyl)amino]-1H-pyrazol-1-yl}-4-(cyanomethyl)piperidinium trifluoroacetate (Intermediate #38-5) (52 mg, 0.11 mmol), copper (I) iodide (2 mg, 0.01 mmol), L-proline (3 mg, 0.02 mmol) and $K_3PO_4$ (48 mg, 0.23 mmol) was dissolved in DMSO (0.16 mL). 2-Bromopyridine (0.011 mL, 0.11 mmol) was added, and the resulting mixture was heated to 90° C. and allowed to stir for 72 hours. The reaction mixture was then allowed to cool to ambient temperature and was filtered. The filtrate was purified by reverse-phase preparative HPLC (MeCN/water, with 0.1% v/v TFA modifier). Desired fractions were identified, combined, and concentrated in vacuo to afford the title compound as a solid.

$^1$H NMR (600 MHz, DMSO-$d_6$): δ 9.02 (br s, 1H), 8.51 (s, 1H), 8.06 (dd, J=5.3, 1.4 Hz, 1H), 7.78 (br s, 1H), 7.60-7.45 (m, 3H), 7.25-7.10 (m, 2H), 7.10-7.00 (m, 2H), 6.85-6.75 (m, 1H), 4.00-3.92 (m, 2H), 3.32-3.20 (m, 2H), 3.18 (s, 2H), 2.51-2.44 (m, 2H), 2.11 (ddd, J=14.1, 10.1, 4.0 Hz, 2H).

LRMS (ESI) calc'd for $C_{22}H_{22}FN_7O$ [M+H]$^+$: 420. Found: 420.

Scheme #28

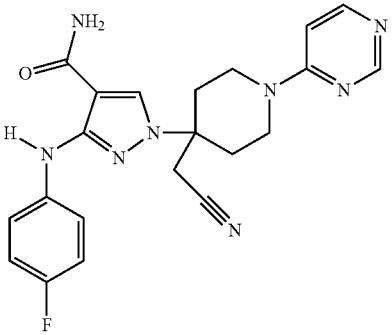

Example #26

1-[4-(Cyanomethyl)-1-pyrimidin-4-ylpiperidin-4-yl]-3-[(4-fluorophenyl)amino]-1H-pyrazole-4-carboxamide To a solution of 4-{4-carbamoyl-3-[(4-fluorophenyl)amino]-1H-pyrazol-1-yl}-4-(cyanomethyl)piperidinium trifluoroacetate (Intermediate #38-5) (50 mg, 0.11 mmol) in DCE (1.0 mL) was added DIPEA (0.096 mL, 0.55 mmol) followed by 4-bromopyrimidine (32 mg, 0.16 mmol). The reaction mixture was heated under microwave irradiation to 130° C. and allowed to stir for 15 minutes. The reaction mixture was then cooled to ambient temperature and diluted with a mixture of DCM and IPA. The resulting mixture was sequentially washed with water, brine, dried over anhydrous $Na_2SO_4$, filtered, and concentrated in vacuo. The resulting residue was purified by reverse-phase preparative HPLC (MeCN/water, with 0.1% v/v TFA modifier). Desired fractions were identified, combined, and concentrated in vacuo to afford the title compound, Example #26, as a solid.

LRMS (ESI) calc'd for $C_{21}H_{21}FN_8O$ [M+H]$^+$: 421. Found: 421.

Scheme #28

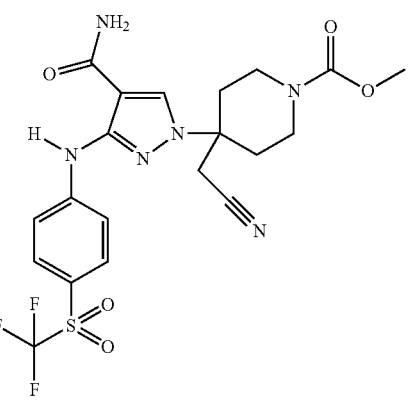

Example #27-1

Methyl 4-(4-carbamoyl-3-(4-(trifluoromethylsulfonyl)phenylamino)-1H-pyrazol-1-yl)-4-(cyanomethyl)piperidine-1-carboxylate 4-[4-Carbamoyl-3-({4-[(trifluoromethyl)sulfonyl]phenyl}amino)-1H-pyrazol-1-yl]-4-(cyanomethyl)piperidinium trifluoroacetate (Intermediate #38-7) (30 mg, 0.053 mmol) was dissolved in DCM (1.0 mL). DIPEA (0.055 mL, 0.32 mmol) was added, followed by methyl chloroformate (0.024 mL, 0.32 mmol). The resulting mixture was allowed to stir at ambient temperature for 30 minutes. The solvent was removed in vacuo and the crude residue was purified by reverse-phase preparative HPLC (MeCN/water, with 0.1% v/v TFA modifier). Desired fractions were identified, combined, and concentrated in vacuo to afford the title compound, Example #27-1, as a solid.

$^1$H NMR (600 MHz, DMSO-$d_6$): δ 9.87 (s, 1H), 8.57 (s, 1H), 7.93-7.84 (m, 4H), 7.68 (s, 1H), 7.34 (s, 1H), 3.72 (d, J=14.1 Hz, 2H), 3.57 (s, 3H), 3.22 (s, 2H), 3.12-3.02 (m, 2H), 2.37 (d, J=14.5 Hz, 2H), 2.01 (ddd, J=13.9, 9.9, 4.2 Hz, 2H).

LRMS (ESI) calc'd for $C_{20}H_{21}F_3N_6O_5S$ [M+H]$^+$: 515. Found: 515.

The following compounds shown in TABLE 25 were prepared according to Scheme #28 following similar procedures described for Example #27-1, which can be achieved by those of ordinary skill in the art of organic synthesis utilizing but not limited to Intermediates #38-1, 38-6, and 38-7.

TABLE 25

| Example | Structure | Compound Name | Exact Mass [M + H]+ |
|---|---|---|---|
| 27-2 | 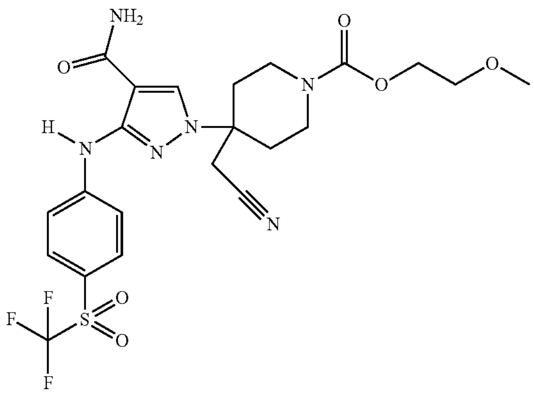 [SMILES: COCCOC(=O)N1CCC(CC#N)(n2cc(C(N)=O)c(Nc3ccc(S(=O)(=O)C(F)(F)F)cc3)n2)CC1] | 2-methoxyethyl 4-(4-carbamoyl-3-(4-(trifluoromethylsulfonyl)phenylamino)-1H-pyrazol-1-yl)-4-(cyanomethyl)piperidine-1-carboxylate | Calc'd 559, Found 559 |
| 27-3 | 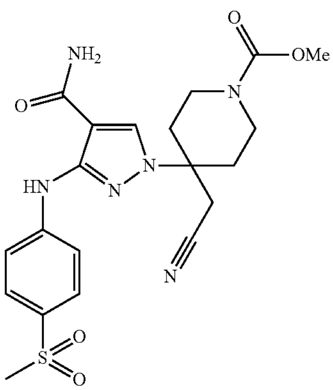 [SMILES: COC(=O)N1CCC(CC#N)(n2cc(C(N)=O)c(Nc3ccc(S(C)(=O)=O)cc3)n2)CC1] | methyl 4-(4-carbamoyl-3-{[4-(methylsulfonyl)phenyl]amino}-1H-pyrazol-1-yl)-4-(cyanomethyl)piperidine-1-carboxylate | Calc'd 461, Found 461 |
| 27-4 | 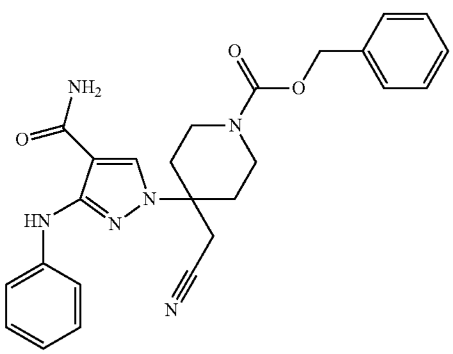 [SMILES: N#CCC1(n2cc(C(N)=O)c(Nc3ccccc3)n2)CCN(C(=O)OCc2ccccc2)CC1] | benzyl 4-[4-carbamoyl-3-(phenylamino)-1H-pyrazol-1-yl]-4-(cyanomethyl)piperidine-1-carboxylate | Calc'd 459, Found 459 |
| 27-5 | 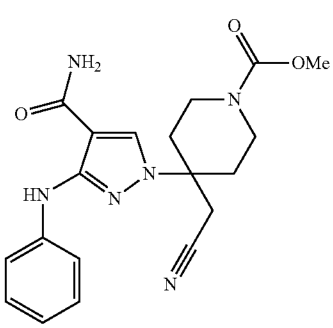 [SMILES: COC(=O)N1CCC(CC#N)(n2cc(C(N)=O)c(Nc3ccccc3)n2)CC1] | methyl 4-[4-carbamoyl-3-(phenylamino)-1H-pyrazol-1-yl]-4-(cyanomethyl)piperidine-1-carboxylate | Calc'd 383, Found 383 |

Scheme #28

Example #28

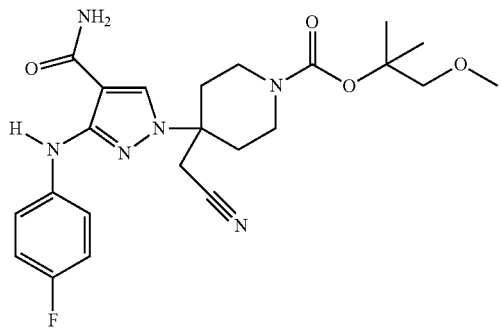 [SMILES: COCC(C)(C)OC(=O)N1CCC(CC#N)(n2cc(C(N)=O)c(Nc3ccc(F)cc3)n2)CC1]

2-Methoxy-1,1-dimethylethyl 4-{4-carbamoyl-3-[(4-fluorophenyl)amino]-1H-pyrazol-1-yl}-4-(cyanomethyl)piperidine-1-carboxylate A solution of 1-methoxy-2-methyl-2-propanol (91 mg, 0.88 mmol) in THF (1.5 mL) and TEA (0.20 mL, 1.4 mmol) was cooled to 0° C. and allowed to stir. Triphosgene (260 mg, 0.876 mmol) was added and the resulting mixture was allowed to warm to ambient temperature and was stirred for 15 minutes. A solution of 4-{4-carbamoyl-3-[(4-fluorophenyl)amino]-1H-pyrazol-1-yl}-4-(cyanomethyl)piperidinium trifluoroacetate (Intermediate #38-5) (80 mg, 0.18 mmol) and TEA (0.061 mL, 0.44 mmol) in DCM (1.0 mL) was then added to the reaction mixture dropwise. The resulting mixture was heated to 50° C. and allowed to stir for 16 hours. The solution was cooled to ambient temperature, diluted with DCM, washed with water, dried over anhydrous $MgSO_4$, and concentrated in vacuo. The resulting residue was purified by MPLC on silica gel (using a gradient elution of 0-10% MeOH/DCM) to afford the title compound, Example #28.

$^1$H NMR (600 MHz, acetone-$d_6$): δ 9.16 (s, 1H), 8.45 (s, 1H), 7.65-7.56 (m, 2H), 7.15 (br s, 1H), 7.03-6.98 (m, 2H), 6.47 (br s, 1H), 3.85 (dt, J=13.9, 4.3 Hz, 2H), 3.49 (s, 2H), 3.30 (s, 3H), 3.16 (s, 2H), 3.15-3.02 (m, 2H), 2.62-2.54 (m, 2H), 2.11-2.04 (m, 2H), 1.39 (s, 6H).

LRMS (ESI) calc'd for $C_{23}H_{29}FN_6O_4$ [M+H]$^+$: 473. Found: 473.

Scheme #28

Example #29

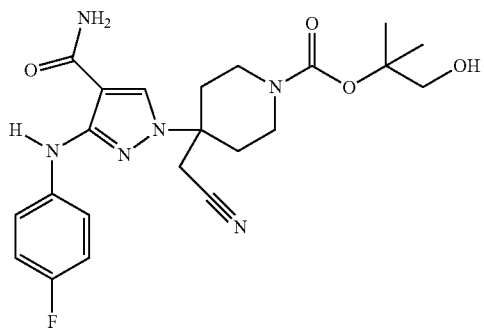

1-Hydroxy-2-methylpropan-2-yl 4-{4-carbamoyl-3-[(4-fluorophenyl)amino]-1H-pyrazol-1-yl}-4-(cyanomethyl)piperidine-1-carboxylate

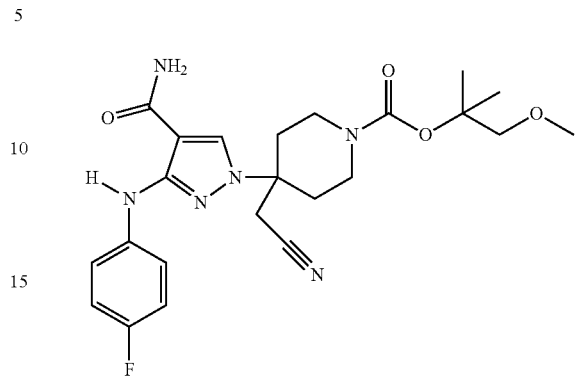

Step A: 1-Methoxy-2-methyl-1-oxopropan-2-yl 4-{4-carbamoyl-3-[(4-fluorophenyl)amino]-1H-pyrazol-1-yl}-4-(cyanomethyl)piperidine-1-carboxylate (Example 29-A)

To a solution of methyl 2-hydroxyisobutyrate (0.20 mL, 1.8 mmol) in THF (4 mL) was added TEA (0.49 mL, 3.5 mmol). The mixture was cooled to 0° C. and allowed to stir. Phosgene (1.70 g, 3.51 mmol, 20 w % in toluene) was added and the resulting mixture was allowed to stir at 0° C. for 3 hours. The mixture was then concentrated in vacuo. The residue was diluted with THF (5 mL) and concentrated in vacuo again. To the resulting residue was added DCM (3 mL), followed by TEA (0.49 mL, 3.5 mmol). The mixture was cooled to 0° C., and allowed to stir. 4-{4-Carbamoyl-3-[(4-fluorophenyl)amino]-1H-pyrazol-1-yl}-4-(cyanomethyl)piperidinium trifluoroacetate (Intermediate #38-5) (0.20 g, 0.44 mmol) was added and the resulting mixture was allowed to stir at 0° C. for 30 minutes. The reaction mixture was diluted with saturated aqueous $NaHCO_3$ and extracted with EtOAc. The organic layer was separated, washed with brine, dried over anhydrous $MgSO_4$, filtered, and concentrated in vacuo. The residue was purified by MPLC on silica gel (using a gradient elution of 50-100% EtOAc/hexanes) to afford the title compound, Example 29-A.

$^1$H NMR (600 MHz, acetone-$d_6$): δ 9.13 (s, 1H), 8.44 (s, 1H), 7.57 (dd, J=8.4, 3.6 Hz, 2H), 7.13 (br s, 1H), 6.98 (t, J=8.4 Hz, 2H) 6.52 (br s, 1H), 3.76-3.90 (m, 2H), 3.60 (s, 3H), 3.04-3.17 (m, 4H), 2.50-2.64 (m, 2H), 2.00-2.12 (m, 2H), 1.47 (s, 6H).

LRMS (ESI) calc'd for $C_{23}H_{28}FN_6O_5$ [M+H]$^+$: 487. Found: 487.

Step B. 1-Hydroxy-2-methylpropan-2-yl 4-{4-carbamoyl-3-[(4-fluorophenyl)amino]-1H-pyrazol-1-yl}-4-(cyanomethyl)piperidine-1-carboxylate To a solution of 1-methoxy-2-methyl-1-oxopropan-2-yl 4-{4-carbamoyl-3-[(4-fluorophenyl)amino]-1H-pyrazol-1-yl}-4-(cyanomethyl)piperidine-1-carboxylate (70 mg, 0.14 mmol) in THF (1.9 mL) at ambient temperature was added $LiBH_4$ (25 mg, 1.2 mmol). The mixture was allowed to stir at ambient temperature for 3 hours. The mixture was then diluted with EtOAc and saturated aqueous ammonium chloride. The organic layer was separated, washed with water, brine, dried over anhydrous $MgSO_4$, filtered, and concentrated in vacuo. The residue was purified by MPLC on silica gel (using a gradient elution of 0-10% MeOH/EtOAc) to afford the title compound, Example 29.

$^1$H NMR (600 MHz, acetone-$d_6$): δ 9.13 (s, 1H), 8.41 (s, 1H), 7.54-7.60 (m, 2H), 7.13 (br s, 1H), 6.95-6.99 (m, 2H), 6.45 (br s, 1H), 3.84-4.00 (m, 2H), 3.85 (s, 2H), 3.06-3.21 (m, 4H), 2.80 (s, 1H), 2.50-2.64 (m, 2H), 2.04-2.12 (m, 2H), 1.14 (s, 6H).

LRMS (ESI) calc'd for $C_{22}H_{28}FN_6O_4$ [M+H]$^+$: 459. Found: 459.

Scheme #28

Example #30-1

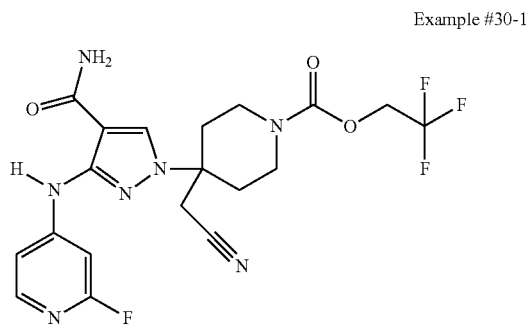

2,2,2-Trifluoroethyl 4-{4-carbamoyl-3-[(2-fluoropy-ridin-4-yl)amino]-1H-pyrazol-1-yl}-4-(cyanomethyl)piperidine-1-carboxylate To a solution of 2,2,2-trifluoroethanol (15 mg, 0.15 mmol) in acetonitrile (1.0 mL) was added TEA (0.043 mL, 0.31 mmol) followed by N,N'-disuccinimidyl carbonate (59 mg, 0.23 mmol). The resulting mixture was allowed to stir at ambient temperature for 4 hours. A solution of 4-{4-carbamoyl-3-[(2-fluoropyridin-4-yl)amino]-1H-pyrazol-1-yl}-4-(cyanomethyl)piperidinium trifluoroacetate (Intermediate #38-4) (70 mg, 0.15 mmol) and TEA (0.043 mL, 0.31 mmol) in DMSO (1.0 mL) was then added to the reaction mixture dropwise. The resulting mixture was heated to 50° C. and allowed to stir for 16 hours. The crude reaction mixture was cooled to ambient temperature and purified directly by reverse-phase preparative HPLC (MeCN/water, with 0.1% v/v TFA modifier). Desired fractions were identified, combined, and concentrated in vacuo to afford the title compound, Example #30-1.

$^1$H NMR (600 MHz, acetone-$d_6$): δ 9.76 (s, 1H), 8.57 (s, 1H), 7.93 (d, J=5.7 Hz, 1H), 7.39 (s, 1H), 7.28-7.20 (br m, 2H), 6.66 (br s, 1H), 4.64 (q, J=8.9 Hz, 2H), 3.95 (d, J=14.0 Hz, 2H), 3.39-3.15 (m, 4H), 2.74-2.63 (m, 2H), 2.21 (ddd, J=14.6, 10.6, 4.2 Hz, 2H).

LRMS (ESI) calc'd for $C_{19}H_{19}F_4N_7O_3$ [M+H]$^+$: 470. Found: 470.

The following compounds shown in TABLE 26 were prepared according to Scheme #28 following similar procedures described for Example #30-1, which can be achieved by those of ordinary skill in the art of organic synthesis utilizing but not limited to Intermediates #38-1, 38-2, 38-3, 38-4, 38-5, 38-7, and 38-8.

TABLE 26

| Example | Structure | Compound Name | Exact Mass [M + H]$^+$ |
|---|---|---|---|
| 30-2 | 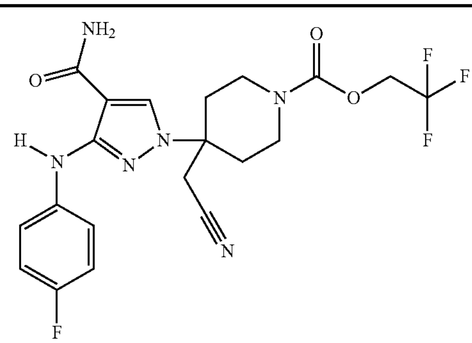 | 2,2,2-trifluoroethyl 4-(4-carbamoyl-3-(4-fluorophenylamino)-1H-pyrazol-1-yl)-4-(cyanomethyl)piperidine-1-carboxylate | Calc'd 469, Found 469 |
| 30-3 | 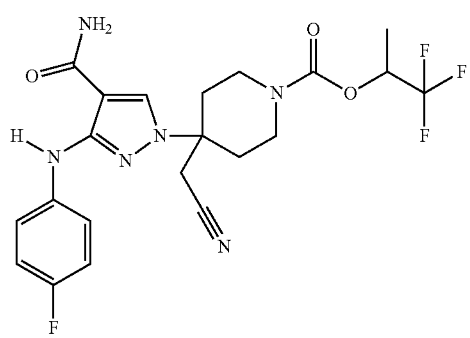 [SMILES: CC(OC(=O)N1CCC(CC#N)(n2cc(C(N)=O)c(Nc3ccc(F)cc3)n2)CC1)C(F)(F)F] | 1,1,1-trifluoropropan-2-yl 4-(4-carbamoyl-3-(4-fluorophenylamino)-1H-pyrazol-1-yl)-4-(cyanomethyl)piperidine-1-carboxylate | Calc'd 483, Found 483 |

TABLE 26-continued

| Example | Structure | Compound Name | Exact Mass [M + H]+ |
|---|---|---|---|
| 30-4 | 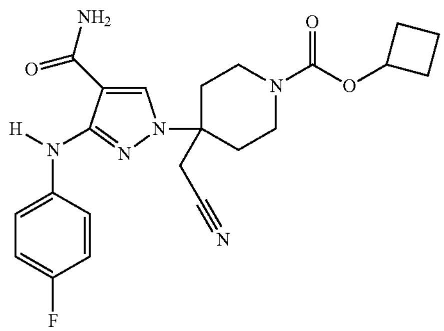 [SMILES: N#CCC1(n2cc(C(N)=O)c(Nc3ccc(F)cc3)n2)CCN(C(=O)OC2CCC2)CC1] | cyclobutyl 4-(4-carbamoyl-3-(4-fluorophenylamino)-1H-pyrazol-1-yl)-4-(cyanomethyl)piperidine-1-carboxylate | Calc'd 441, Found 441 |
| 30-5 | 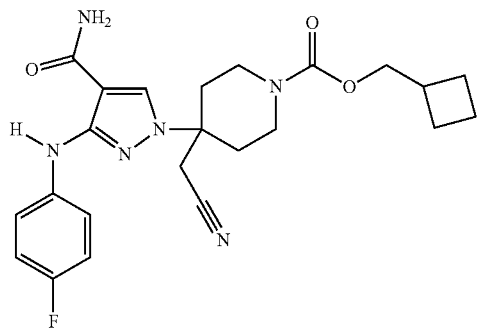 [SMILES: N#CCC1(n2cc(C(N)=O)c(Nc3ccc(F)cc3)n2)CCN(C(=O)OCC2CCC2)CC1] | cyclobutylmethyl 4-(4-carbamoyl-3-(4-fluorophenylamino)-1H-pyrazol-1-yl)-4-(cyanomethyl)piperidine-1-carboxylate | Calc'd 455, Found 455 |
| 30-6 | 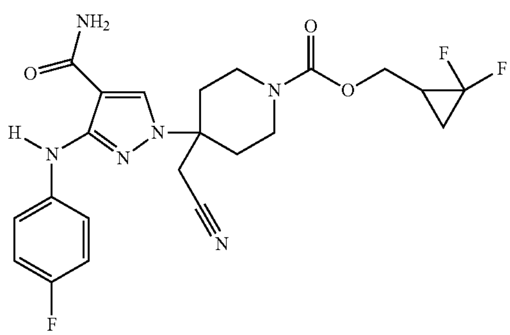 [SMILES: N#CCC1(n2cc(C(N)=O)c(Nc3ccc(F)cc3)n2)CCN(C(=O)OCC2CC2(F)F)CC1] | (2,2-difluorocyclopropyl)methyl 4-(4-carbamoyl-3-(4-fluorophenylamino)-1H-pyrazol-1-yl)-4-(cyanomethyl)piperidine-1-carboxylate | Calc'd 477, Found 477 |
| 30-7 | 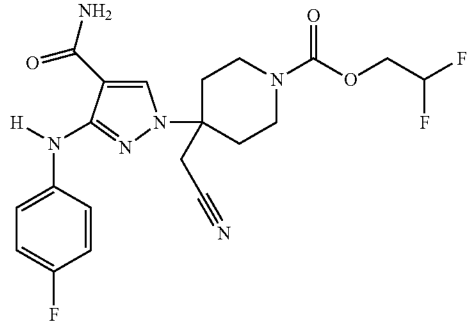 [SMILES: N#CCC1(n2cc(C(N)=O)c(Nc3ccc(F)cc3)n2)CCN(C(=O)OCC(F)F)CC1] | 2,2-difluoroethyl 4-(4-carbamoyl-3-(4-fluorophenylamino)-1H-pyrazol-1-yl)-4-(cyanomethyl)piperidine-1-carboxylate | Calc'd 451, Found 451 |

TABLE 26-continued

| Example | Structure | Compound Name | Exact Mass [M + H]+ |
|---|---|---|---|
| 30-8 | 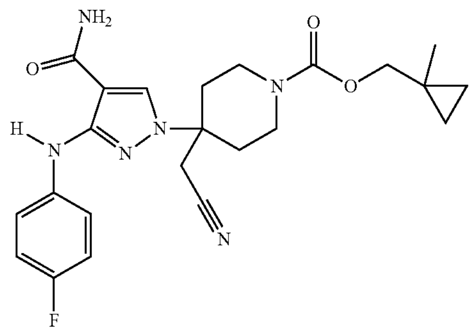 [SMILES: CC1(COC(=O)N2CCC(CC#N)(n3cc(C(N)=O)c(Nc4ccc(F)cc4)n3)CC2)CC1] | (1-methylcyclopropyl)methyl 4-(4-carbamoyl-3-(4-fluorophenylamino)-1H-pyrazol-1-yl)-4-(cyanomethyl)piperidine-1-carboxylate | Calc'd 455, Found 455 |
| 30-9 | 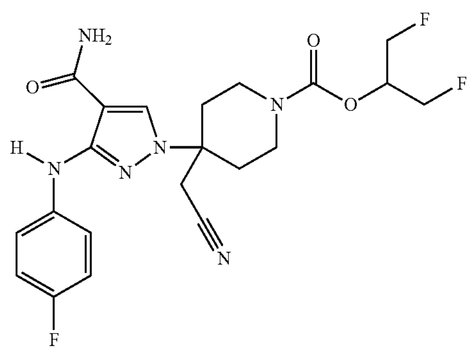 [SMILES: N#CCC1(n2cc(C(N)=O)c(Nc3ccc(F)cc3)n2)CCN(C(=O)OC(CF)CF)CC1] | 1,3-difluoropropan-2-yl 4-(4-carbamoyl-3-(4-fluorophenylamino)-1H-pyrazol-1-yl)-4-(cyanomethyl)piperidine-1-carboxylate | Calc'd 465, Found 465 |
| 30-10 | 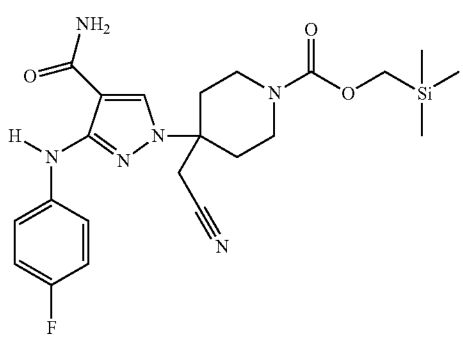 [SMILES: C[Si](C)(C)COC(=O)N1CCC(CC#N)(n2cc(C(N)=O)c(Nc3ccc(F)cc3)n2)CC1] | (trimethylsilyl)methyl 4-(4-carbamoyl-3-(4-fluorophenylamino)-1H-pyrazol-1-yl)-4-(cyanomethyl)piperidine-1-carboxylate | Calc'd 473, Found 473 |
| 30-11 | 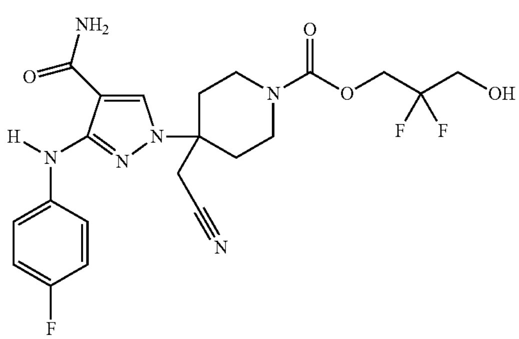 [SMILES: N#CCC1(n2cc(C(N)=O)c(Nc3ccc(F)cc3)n2)CCN(C(=O)OCC(F)(F)CO)CC1] | 2,2-difluoro-3-hydroxypropyl 4-(4-carbamoyl-3-(4-fluorophenylamino)-1H-pyrazol-1-yl)-4-(cyanomethyl)piperidine-1-carboxylate | Calc'd 481, Found 481 |

TABLE 26-continued

| Example | Structure | Compound Name | Exact Mass [M + H]+ |
|---|---|---|---|
| 30-12 | 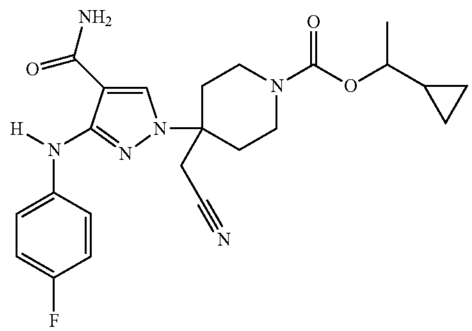 [SMILES: CC(OC(=O)N1CCC(CC#N)(n2cc(C(N)=O)c(Nc3ccc(F)cc3)n2)CC1)C1CC1] | 1-cyclopropylethyl 4-(4-carbamoyl-3-(4-fluorophenylamino)-1H-pyrazol-1-yl)-4-(cyanomethyl)piperidine-1-carboxylate | Calc'd 455, Found 455 |
| 30-13 | 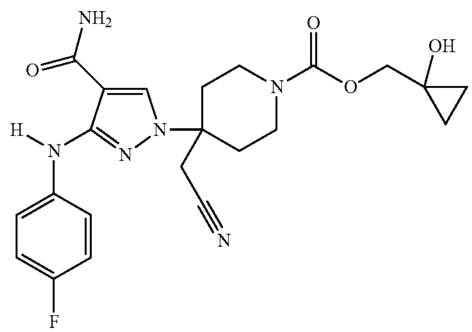 [SMILES: N#CCC1(n2cc(C(N)=O)c(Nc3ccc(F)cc3)n2)CCN(C(=O)OCC2(O)CC2)CC1] | (1-hydroxycyclopropyl)methyl 4-(4-carbamoyl-3-(4-fluorophenylamino)-1H-pyrazol-1-yl)-4-(cyanomethyl)piperidine-1-carboxylate | Calc'd 457, Found 457 |
| 30-14 | 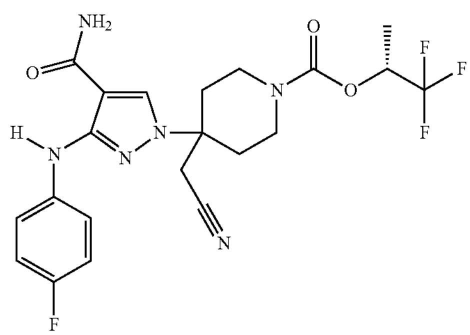 [SMILES: C[C@@H](OC(=O)N1CCC(CC#N)(n2cc(C(N)=O)c(Nc3ccc(F)cc3)n2)CC1)C(F)(F)F] | (R)-1,1,1-trifluoropropan-2-yl 4-(4-carbamoyl-3-(4-fluorophenylamino)-1H-pyrazol-1-yl)-4-(cyanomethyl)piperidine-1-carboxylate | Calc'd 483, Found 483 |
| 30-15 | 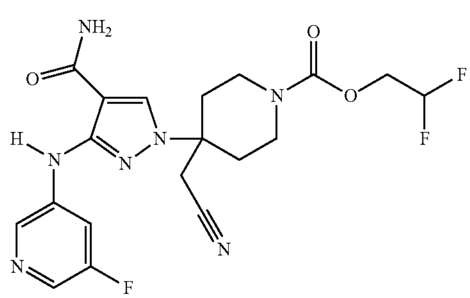 [SMILES: N#CCC1(n2cc(C(N)=O)c(Nc3cncc(F)c3)n2)CCN(C(=O)OCC(F)F)CC1] | 2,2-difluoroethyl 4-(4-carbamoyl-3-(5-fluoropyridin-3-ylamino)-1H-pyrazol-1-yl)-4-(cyanomethyl)piperidine-1-carboxylate | Calc'd 452, Found 452 |

TABLE 26-continued

| Example | Structure | Compound Name | Exact Mass [M + H]+ |
|---|---|---|---|
| 30-16 | 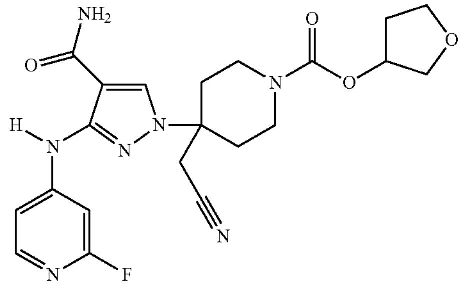 [SMILES: N#CCC1(n2cc(C(N)=O)c(Nc3ccnc(F)c3)n2)CCN(C(=O)OC2CCOC2)CC1] | tetrahydrofuran-3-yl 4-{4-carbamoyl-3-[(2-fluoropyridin-4-yl)amino]-1H-pyrazol-1-yl}-4-(cyanomethyl)piperidine-1-carboxylate | Calc'd 458, Found 458 |
| 30-17 | 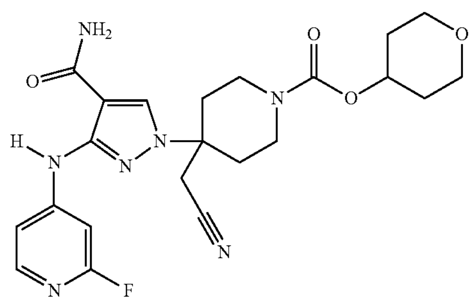 [SMILES: N#CCC1(n2cc(C(N)=O)c(Nc3ccnc(F)c3)n2)CCN(C(=O)OC2CCOCC2)CC1] | tetrahydro-2H-pyran-4-yl 4-{4-carbamoyl-3-[(2-fluoropyridin-4-yl)amino]-1H-pyrazol-1-yl}-4-(cyanomethyl)piperidine-1-carboxylate | Calc'd 472, Found 472 |
| 30-18 | 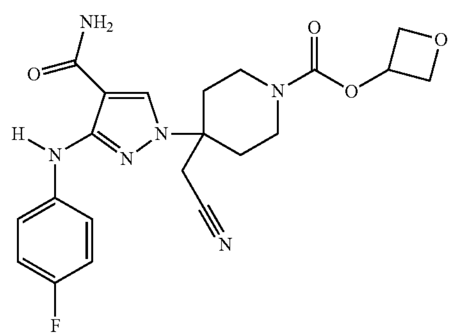 [SMILES: N#CCC1(n2cc(C(N)=O)c(Nc3ccc(F)cc3)n2)CCN(C(=O)OC2COC2)CC1] | oxetan-3-yl 4-{4-carbamoyl-3-[(4-fluorophenyl)amino]-1H-pyrazol-1-yl}-4-(cyanomethyl)piperidine-1-carboxylate | Calc'd 443, Found 443 |
| 30-19 | 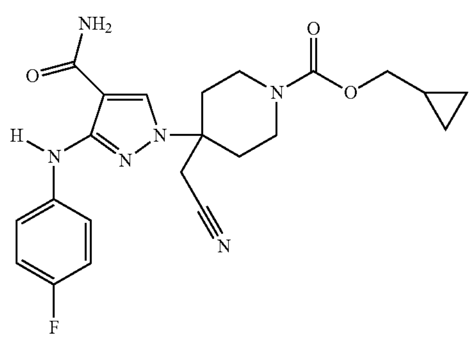 [SMILES: N#CCC1(n2cc(C(N)=O)c(Nc3ccc(F)cc3)n2)CCN(C(=O)OCC2CC2)CC1] | cyclopropylmethyl 4-{4-carbamoyl-3-[(4-fluorophenyl)amino]-1H-pyrazol-1-yl}-4-(cyanomethyl)piperidine-1-carboxylate | Calc'd 441, Found 441 |

TABLE 26-continued

| Example | Structure | Compound Name | Exact Mass [M + H]+ |
|---|---|---|---|
| 30-20 | 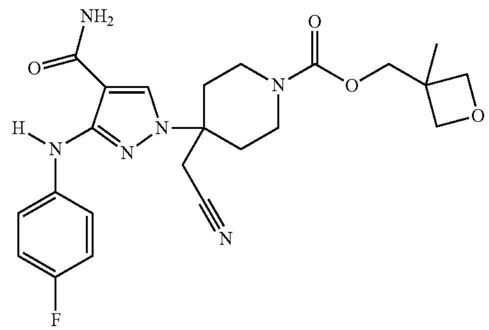 [SMILES: CC1(COC(=O)N2CCC(CC#N)(n3cc(C(N)=O)c(Nc4ccc(F)cc4)n3)CC2)COC1] | (3-methyloxetan-3-yl)methyl 4-{4-carbamoyl-3-[(4-fluorophenyl)amino]-1H-pyrazol-1-yl}-4-(cyanomethyl)piperidine-1-carboxylate | Calc'd 471, Found 471 |
| 30-21 | 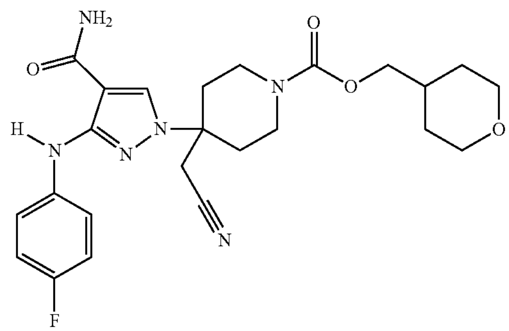 [SMILES: N#CCC1(n2cc(C(N)=O)c(Nc3ccc(F)cc3)n2)CCN(C(=O)OCC2CCOCC2)CC1] | tetrahydro-2H-pyran-4-ylmethyl 4-{4-carbamoyl-3-[(4-fluorophenyl)amino]-1H-pyrazol-1-yl}-4-(cyanomethyl)piperidine-1-carboxylate | Calc'd 485, Found 485 |
| 30-22 | 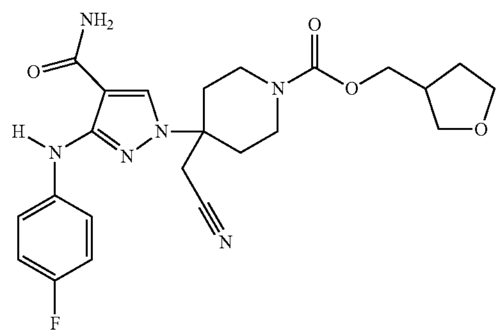 [SMILES: N#CCC1(n2cc(C(N)=O)c(Nc3ccc(F)cc3)n2)CCN(C(=O)OCC2CCOC2)CC1] | tetrahydrofuran-3-ylmethyl 4-{4-carbamoyl-3-[(4-fluorophenyl)amino]-1H-pyrazol-1-yl}-4-(cyanomethyl)piperidine-1-carboxylate | Calc'd 471, Found 471 |
| 30-23 | 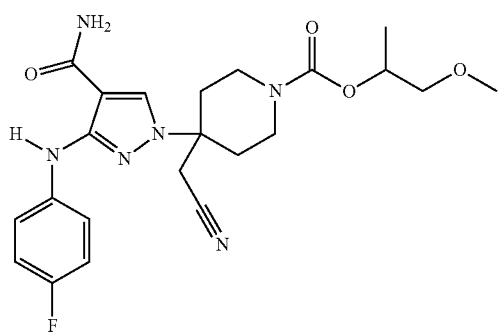 [SMILES: COCC(C)OC(=O)N1CCC(CC#N)(n2cc(C(N)=O)c(Nc3ccc(F)cc3)n2)CC1] | 1-methoxypropan-2-yl 4-{4-carbamoyl-3-[(4-fluorophenyl)amino]-1H-pyrazol-1-yl}-4-(cyanomethyl)piperidine-1-carboxylate | Calc'd 459, Found 459 |

TABLE 26-continued

| Example | Structure | Compound Name | Exact Mass [M + H]+ |
|---|---|---|---|
| 30-24 | 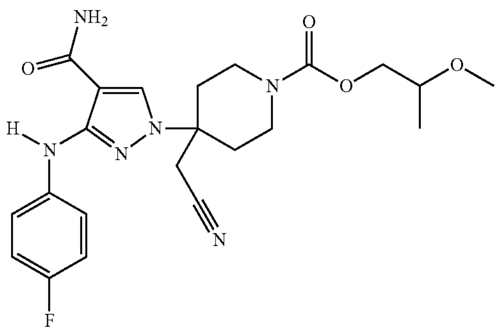 [SMILES: COC(C)COC(=O)N1CCC(CC#N)(n2cc(C(N)=O)c(Nc3ccc(F)cc3)n2)CC1] | 2-methoxypropyl 4-{4-carbamoyl-3-[(4-fluorophenyl)amino]-1H-pyrazol-1-yl}-4-(cyanomethyl)piperidine-1-carboxylate | Calc'd 459, Found 459 |
| 30-25 | 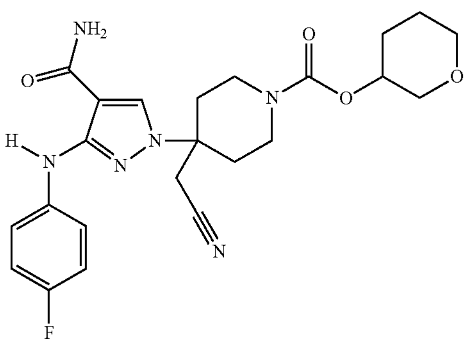 [SMILES: N#CCC1(n2cc(C(N)=O)c(Nc3ccc(F)cc3)n2)CCN(C(=O)OC2CCCOC2)CC1] | tetrahydro-2H-pyran-3-yl 4-{4-carbamoyl-3-[(4-fluorophenyl)amino]-1H-pyrazol-1-yl}-4-(cyanomethyl)piperidine-1-carboxylate | Calc'd 471, Found 471 |
| 30-26 | 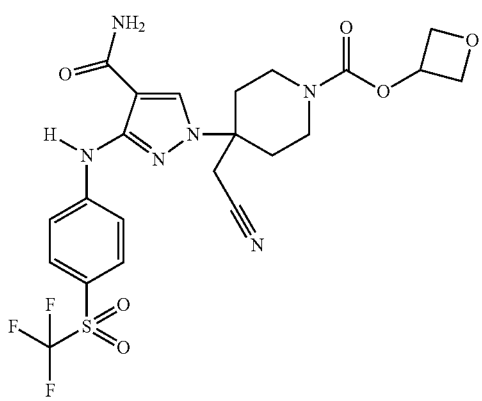 [SMILES: N#CCC1(n2cc(C(N)=O)c(Nc3ccc(S(=O)(=O)C(F)(F)F)cc3)n2)CCN(C(=O)OC2COC2)CC1] | oxetan-3-yl 4-(4-carbamoyl-3-(4-(trifluoromethylsulfonyl)phenylamino)-1H-pyrazol-1-yl)-4-(cyanomethyl)piperidine-1-carboxylate | Calc'd 557, Found 557 |
| 30-27 | 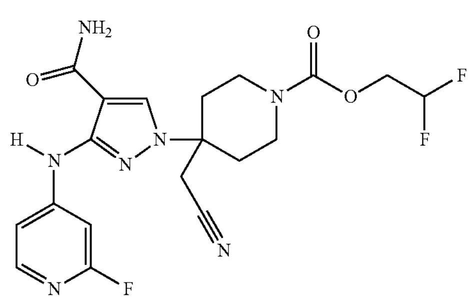 | 2,2-difluoroethyl 4-(4-carbamoyl-3-(2-fluoropyridin-4-ylamino)-1H-pyrazol-1-yl)-4-(cyanomethyl)piperidine-1-carboxylate | Calc'd 452, Found 452 |

TABLE 26-continued

| Example | Structure | Compound Name | Exact Mass [M + H]+ |
|---|---|---|---|
| 30-28 | 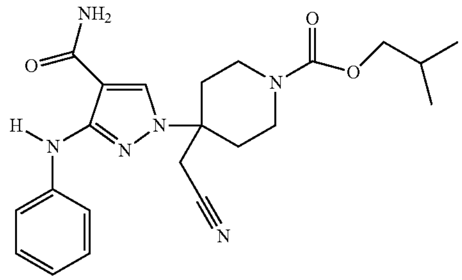 [SMILES: CC(C)COC(=O)N1CCC(CC#N)(n2cc(C(N)=O)c(Nc3ccccc3)n2)CC1] | 2-methylpropyl 4-[4-carbamoyl-3-(phenylamino)-1H-pyrazol-1-yl]-4-(cyanomethyl)piperidine-1-carboxylate | Calc'd 425, Found 425 |
| 30-29 | 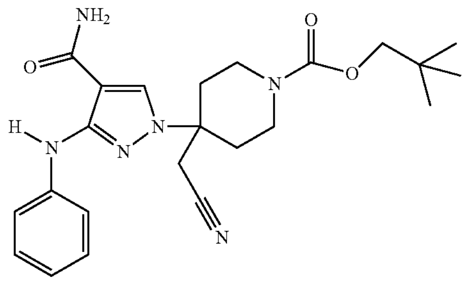 [SMILES: CC(C)(C)COC(=O)N1CCC(CC#N)(n2cc(C(N)=O)c(Nc3ccccc3)n2)CC1] | 2,2-dimethylpropyl 4-[4-carbamoyl-3-(phenylamino)-1H-pyrazol-1-yl]-4-(cyanomethyl)piperidine-1-carboxylate | Calc'd 439, Found 439 |
| 30-30 | 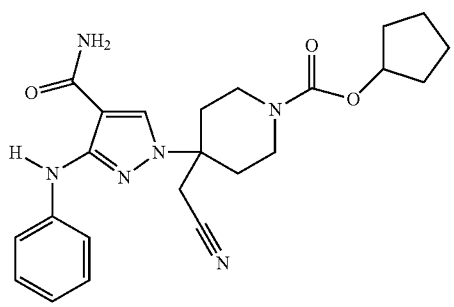 [SMILES: N#CCC1(n2cc(C(N)=O)c(Nc3ccccc3)n2)CCN(C(=O)OC2CCCC2)CC1] | cyclopentyl 4-[4-carbamoyl-3-(phenylamino)-1H-pyrazol-1-yl]-4-(cyanomethyl)piperidine-1-carboxylate | Calc'd 437, Found 437 |
| 30-31 | 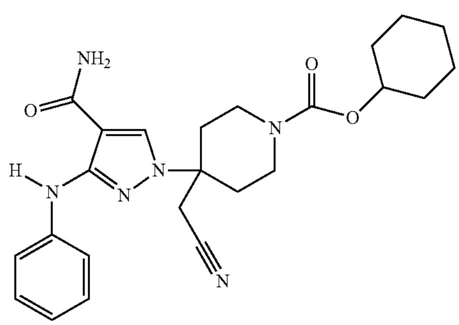 | cyclohexyl 4-[4-carbamoyl-3-(phenylamino)-1H-pyrazol-1-yl]-4-(cyanomethyl)piperidine-1-carboxylate | Calc'd 451, Found 451 |
| 30-32 | 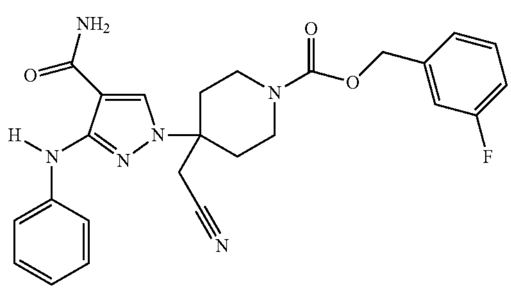 [SMILES: N#CCC1(n2cc(C(N)=O)c(Nc3ccccc3)n2)CCN(C(=O)OCc2cccc(F)c2)CC1] | 3-fluorobenzyl 4-[4-carbamoyl-3-(phenylamino)-1H-pyrazol-1-yl]-4-(cyanomethyl)piperidine-1-carboxylate | Calc'd 477, Found 477 |

TABLE 26-continued

| Example | Structure | Compound Name | Exact Mass [M + H]⁺ |
|---------|-----------|---------------|---------------------|
| 30-33 | 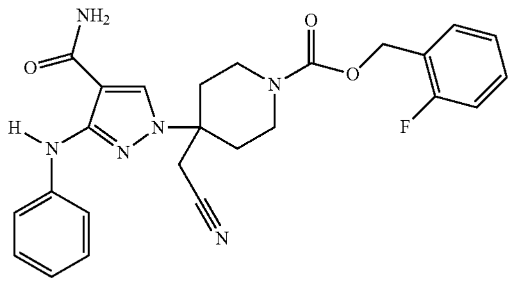 [SMILES: N#CCC1(n2cc(C(N)=O)c(Nc3ccccc3)n2)CCN(C(=O)OCc2ccccc2F)CC1] | 2-fluorobenzyl 4-[4-carbamoyl-3-(phenylamino)-1H-pyrazol-1-yl]-4-(cyanomethyl)piperidine-1-carboxylate | Calc'd 477, Found 477 |
| 30-34 | 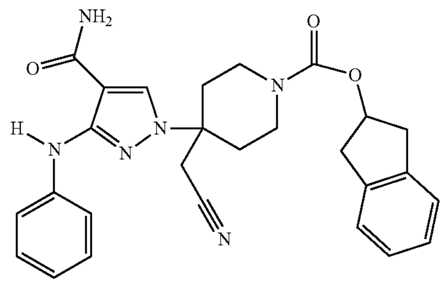 [SMILES: N#CCC1(n2cc(C(N)=O)c(Nc3ccccc3)n2)CCN(C(=O)OC2Cc3ccccc3C2)CC1] | 2,3-dihydro-1H-inden-2-yl 4-[4-carbamoyl-3-(phenylamino)-1H-pyrazol-1-yl]-4-(cyanomethyl)piperidine-1-carboxylate | Calc'd 485, Found 485 |
| 30-35 | 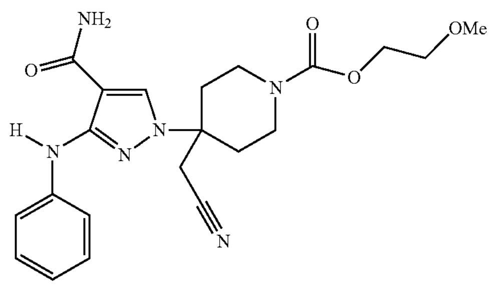 [SMILES: COCCOC(=O)N1CCC(CC#N)(n2cc(C(N)=O)c(Nc3ccccc3)n2)CC1] | 2-methoxyethyl 4-[4-carbamoyl-3-(phenylamino)-1H-pyrazol-1-yl]-4-(cyanomethyl)piperidine-1-carboxylate | Calc'd 427, Found 427 |
| 30-36 | 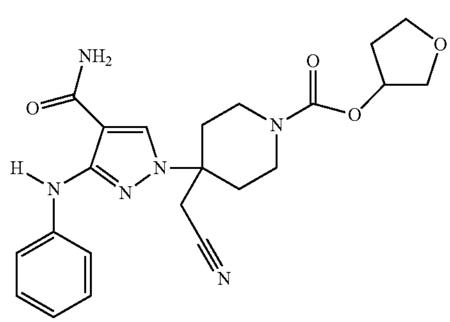 [SMILES: N#CCC1(n2cc(C(N)=O)c(Nc3ccccc3)n2)CCN(C(=O)OC2CCOC2)CC1] | 4-carbamoyl-1-[4-(cyanomethyl)-1-{[(3R and 3S)-tetrahydrofuran-3-yloxy]carbonyl}piperidin-4-yl]-3-(phenylamino)-1H-pyrazol-2-ium | Calc'd 439, Found 439 |
| 30-37 | 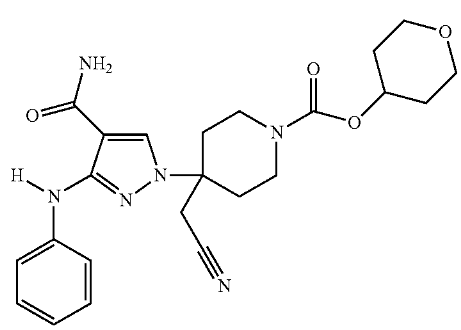 | tetrahydro-2H-pyran-4-yl 4-[4-carbamoyl-3-(phenylamino)-1H-pyrazol-1-yl]-4-(cyanomethyl)piperidine-1-carboxylate | Calc'd 453, Found 453 |

TABLE 26-continued

| Example | Structure | Compound Name | Exact Mass [M + H]+ |
|---|---|---|---|
| 30-38 | 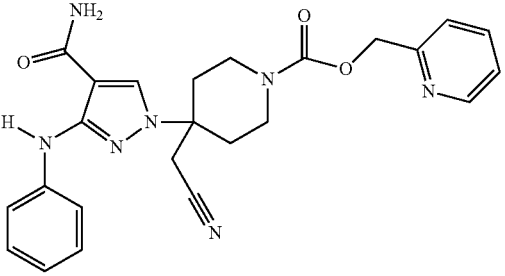 [SMILES: N#CCC1(n2cc(C(N)=O)c(Nc3ccccc3)n2)CCN(C(=O)OCc2ccccn2)CC1] | pyridin-3-ylmethyl 4-[4-carbamoyl-3-(phenylamino)-1H-pyrazol-1-yl]-4-(cyanomethyl)piperidine-1-carboxylate | Calc'd 460, Found 460 |
| 30-39 | 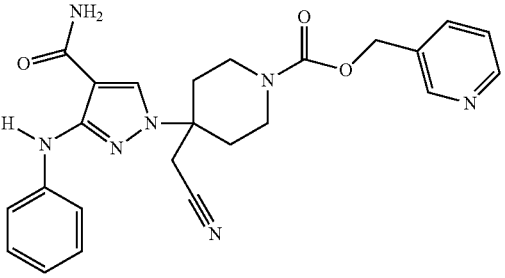 [SMILES: N#CCC1(n2cc(C(N)=O)c(Nc3ccccc3)n2)CCN(C(=O)OCc2cccnc2)CC1] | pyridin-3-ylmethyl 4-[4-carbamoyl-3-(phenylamino)-1H-pyrazol-1-yl]-4-(cyanomethyl)piperidine-1-carboxylate | Calc'd 460, Found 460 |
| 30-40 | 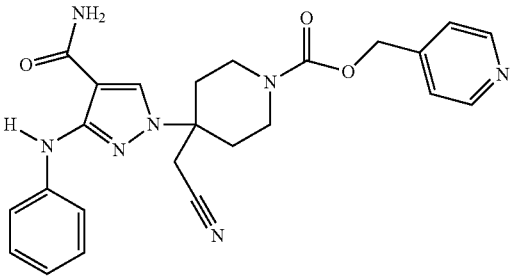 [SMILES: N#CCC1(n2cc(C(N)=O)c(Nc3ccccc3)n2)CCN(C(=O)OCc2ccncc2)CC1] | pyridin-4-ylmethyl 4-[4-carbamoyl-3-(phenylamino)-1H-pyrazol-1-yl]-4-(cyanomethyl)piperidine-1-carboxylate | Calc'd 460, Found 460 |
| 30-41 | 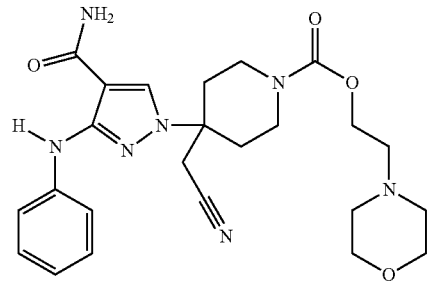 [SMILES: N#CCC1(n2cc(C(N)=O)c(Nc3ccccc3)n2)CCN(C(=O)OCCN2CCOCC2)CC1] | 2-morpholin-4-ylethyl 4-[4-carbamoyl-3-(phenylamino)-1H-pyrazol-1-yl]-4-(cyanomethyl)piperidine-1-carboxylate | Calc'd 482, Found 482 |
| 30-42 | 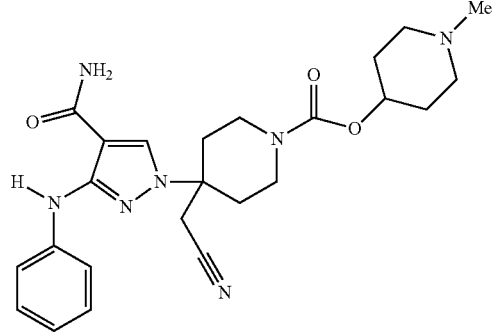 [SMILES: CN1CCC(OC(=O)N2CCC(CC#N)(n3cc(C(N)=O)c(Nc4ccccc4)n3)CC2)CC1] | 1-methylpiperidin-4-yl 4-[4-carbamoyl-3-(phenylamino)-1H-pyrazol-1-yl]-4-(cyanomethyl)piperidine-1-carboxylate | Calc'd 466, Found 466 |

TABLE 26-continued

| Example | Structure | Compound Name | Exact Mass [M + H]+ |
|---|---|---|---|
| 30-43 | 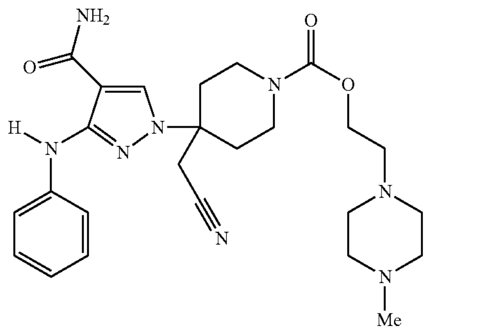 [SMILES: CN1CCN(CCOC(=O)N2CCC(CC#N)(n3cc(C(N)=O)c(Nc4ccccc4)n3)CC2)CC1] | 2-(4-methylpiperazin-1-yl)ethyl 4-[4-carbamoyl-3-(phenylamino)-1H-pyrazol-1-yl]-4-(cyanomethyl)piperidine-1-carboxylate | Calc'd 495, Found 495 |
| 30-44 | 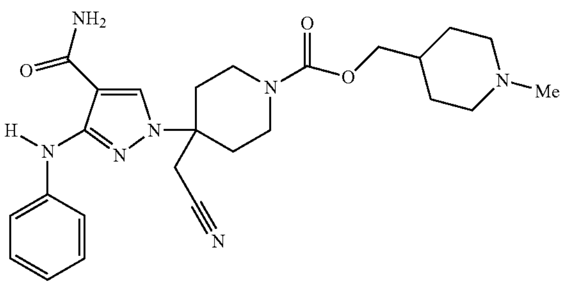 [SMILES: CN1CCC(COC(=O)N2CCC(CC#N)(n3cc(C(N)=O)c(Nc4ccccc4)n3)CC2)CC1] | (1-methylpiperidin-4-yl)methyl 4-[4-carbamoyl-3-(phenylamino)-1H-pyrazol-1-yl]-4-(cyanomethyl)piperidine-1-carboxylate | Calc'd 480, Found 480 |
| 30-45 | 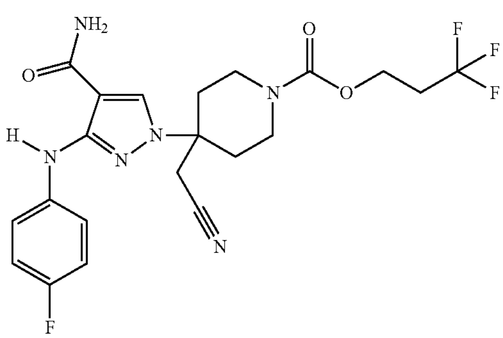 [SMILES: N#CCC1(n2cc(C(N)=O)c(Nc3ccc(F)cc3)n2)CCN(C(=O)OCCC(F)(F)F)CC1] | 3,3,3-Trifluoropropyl 4-{4-carbamoyl-3-[(4-fluorophenyl)amino]-1H-pyrazol-1-yl}-4-(cyanomethyl)piperidine-1-carboxylate | Calc'd 483, Found 483 |
| 30-46 | 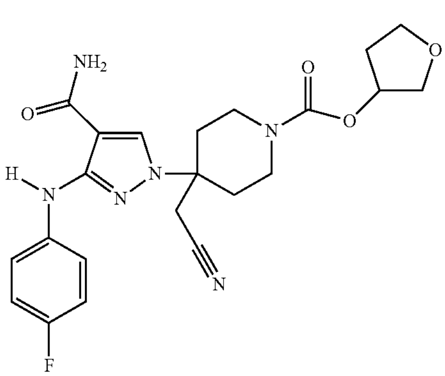 [SMILES: N#CCC1(n2cc(C(N)=O)c(Nc3ccc(F)cc3)n2)CCN(C(=O)OC2CCOC2)CC1] | tetrahydrofuran-3-yl 4-{4-carbamoyl-3-[(4-fluorophenyl)amino]-1H-pyrazol-1-yl}-4-(cyanomethyl)piperidine-1-carboxylate | Calc'd 457, Found 457 |

TABLE 26-continued

| Example | Structure | Compound Name | Exact Mass [M + H]+ |
|---|---|---|---|
| 30-47 | 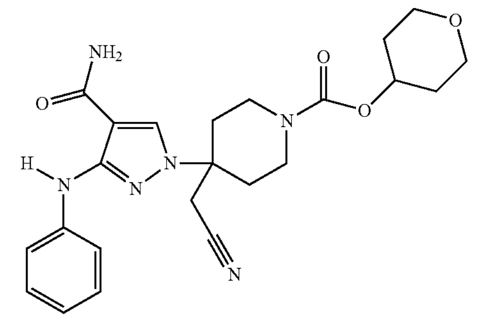 [SMILES: N#CCC1(n2cc(C(N)=O)c(Nc3ccccc3)n2)CCN(C(=O)OC2CCOCC2)CC1] | tetrahydro-2H-pyran-4-yl 4-{4-carbamoyl-3-[(4-fluorophenyl)amino]-1H-pyrazol-1-yl}-4-(cyanomethyl)piperidine-1-carboxylate | Calc'd 471, Found 471 |
| 30-48 | 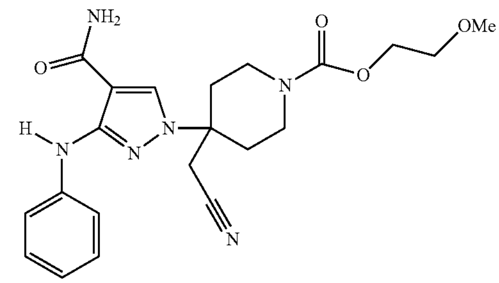 [SMILES: COCCOC(=O)N1CCC(CC#N)(n2cc(C(N)=O)c(Nc3ccccc3)n2)CC1] | 2-methoxyethyl 4-{4-carbamoyl-3-[(4-fluorophenyl)amino]-1H-pyrazol-1-yl}-4-(cyanomethyl)piperidine-1-carboxylate | Calc'd 445, Found 445 |
| 30-49 | 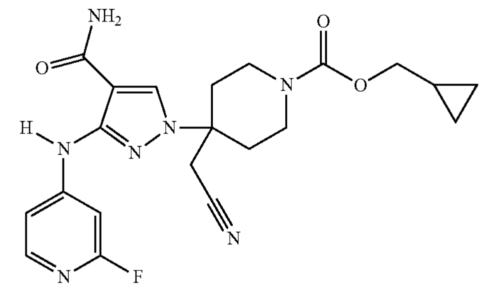 [SMILES: N#CCC1(n2cc(C(N)=O)c(Nc3ccnc(F)c3)n2)CCN(C(=O)OCC2CC2)CC1] | Cyclopropylmethyl 4-{4-carbamoyl-3-[(2-fluoropyridin-4-yl)amino]-1H-pyrazol-1-yl}-4-(cyanomethyl)piperidine-1-carboxylate | Calc'd 442, Found 442 |
| 30-50 | 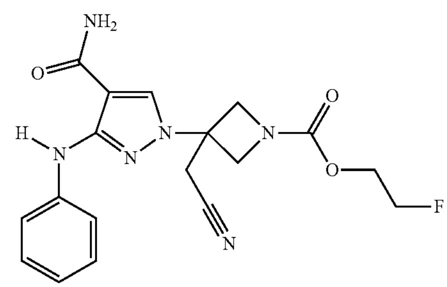 [SMILES: N#CCC1(n2cc(C(N)=O)c(Nc3ccccc3)n2)CN(C(=O)OCCF)C1] | 2-fluoroethyl 3-[4-carbamoyl-3-(phenylamino)-1H-pyrazol-1-yl]-3-(cyanomethyl)azetidine-1-carboxylate | Calc'd 387, Found 387 |
| 30-51 | 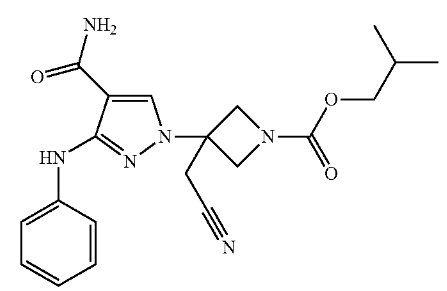 [SMILES: CC(C)COC(=O)N1CC(CC#N)(n2cc(C(N)=O)c(Nc3ccccc3)n2)C1] | 2-methylpropyl 3-[4-carbamoyl-3-(phenylamino)-1H-pyrazol-1-yl]-3-(cyanomethyl)azetidine-1-carboxylate | Calc'd 397, Found 397 |

341
342

TABLE 26-continued

| Example | Structure | Compound Name | Exact Mass [M + H]+ |
|---|---|---|---|
| 30-52 | 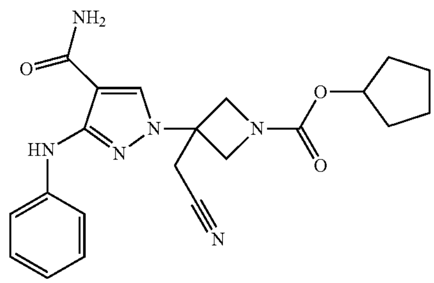 [SMILES: N#CCC1(n2cc(C(N)=O)c(Nc3ccccc3)n2)CN(C(=O)OC2CCCC2)C1] | cyclopentyl 3-[4-carbamoyl-3-(phenylamino)-1H-pyrazol-1-yl]-3-(cyanomethyl)azetidine-1-carboxylate | Calc'd 409, Found 409 |
| 30-53 | 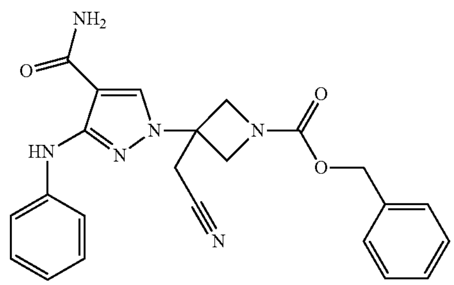 [SMILES: N#CCC1(n2cc(C(N)=O)c(Nc3ccccc3)n2)CN(C(=O)OCc2ccccc2)C1] | benzyl 3-[4-carbamoyl-3-(phenylamino)1H-pyrazol-1-yl]-3-(cyanomethyl)azetidine-1-carboxylate | Calc'd 431, Found 431 |
| 30-54 | 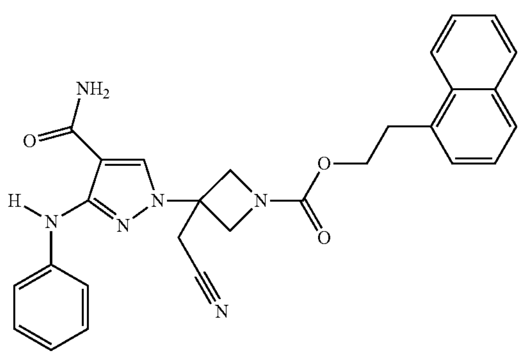 [SMILES: N#CCC1(n2cc(C(N)=O)c(Nc3ccccc3)n2)CN(C(=O)OCCc2cccc3ccccc23)C1] | 2-naphthalen-1-ylethyl 3-[4-carbamoyl-3-(phenylamino)-1H-pyrazol-1-yl]-3-(cyanomethyl)azetidine-1-carboxylate | Calc'd 495, Found 495 |
| 30-55 | 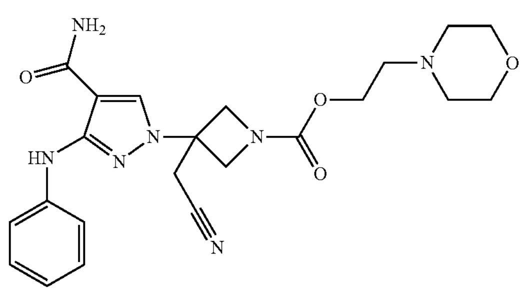 [SMILES: N#CCC1(n2cc(C(N)=O)c(Nc3ccccc3)n2)CN(C(=O)OCCN2CCOCC2)C1] | 2-morpholin-4-ylethyl 3-[4-carbamoyl-3-(phenylamino)-1H-pyrazol-1-yl]-3-(cyanomethyl)azetidine-1-carboxylate | Calc'd 454, Found 454 |
| 30-56 | 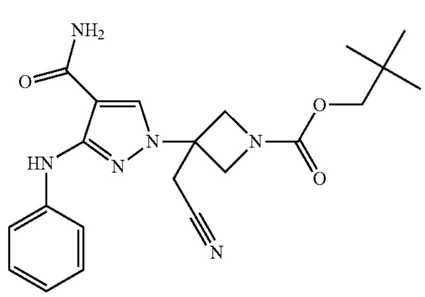 [SMILES: CC(C)(C)COC(=O)N1CC(CC#N)(n2cc(C(N)=O)c(Nc3ccccc3)n2)C1] | 2,2-dimethylpropyl 3-[4-carbamoyl-3-(phenylamino)-1H-pyrazol-1-yl]-3-(cyanomethyl)azetidine-1-carboxylate | Calc'd 411, Found 411 |

TABLE 26-continued

| Example | Structure | Compound Name | Exact Mass [M + H]+ |
|---|---|---|---|
| 30-57 | 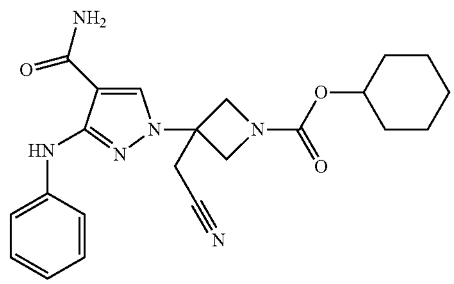 [SMILES: N#CCC1(n2cc(C(N)=O)c(Nc3ccccc3)n2)CN(C(=O)OC2CCCCC2)C1] | cyclohexyl 3-[4-carbamoyl-3-(phenylamino)-1H-pyrazol-1-yl]-3-(cyanomethyl)azetidine-1-carboxylate | Calc'd 423, Found 423 |
| 30-58 | 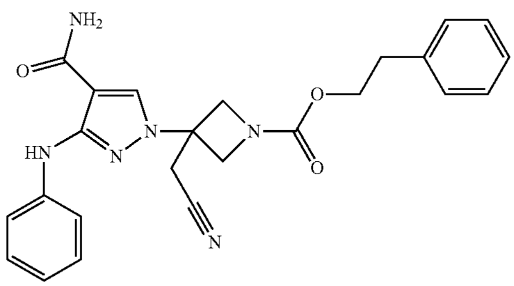 [SMILES: N#CCC1(n2cc(C(N)=O)c(Nc3ccccc3)n2)CN(C(=O)OCCc2ccccc2)C1] | 2-phenylethyl 3-[4-carbamoyl-3-(phenylamino)-1H-pyrazol-1-yl]-3-(cyanomethyl)azetidine-1-carboxylate | Calc'd 445, Found 445 |
| 30-59 | 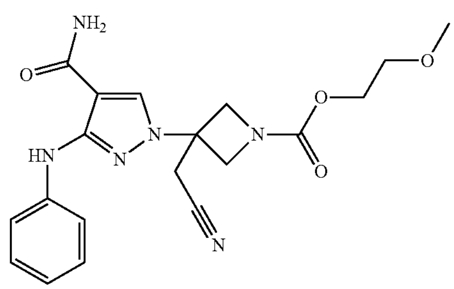 [SMILES: COCCOC(=O)N1CC(CC#N)(n2cc(C(N)=O)c(Nc3ccccc3)n2)C1] | 2-methoxyethyl 3-[4-carbamoyl-3-(phenylamino)-1H-pyrazol-1-yl]-3-(cyanomethyl)azetidine-1-carboxylate | Calc'd 399, Found 399 |
| 30-60 | 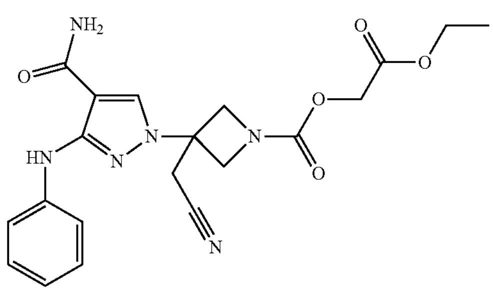 [SMILES: CCOC(=O)COC(=O)N1CC(CC#N)(n2cc(C(N)=O)c(Nc3ccccc3)n2)C1] | 2-ethoxy-2-oxoethyl 3-[4-carbamoyl-3-(phenylamino)-1H-pyrazol-1-yl]-3-(cyanomethyl)azetidine-1-carboxylate | Calc'd 427, Found 427 |
| 30-61 | 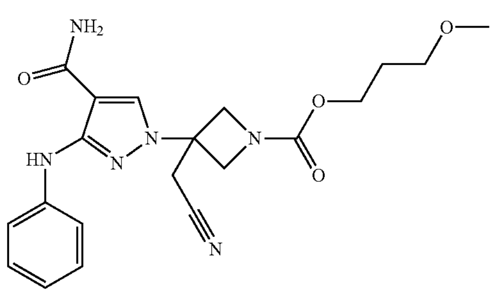 [SMILES: COCCCOC(=O)N1CC(CC#N)(n2cc(C(N)=O)c(Nc3ccccc3)n2)C1] | 3-methoxypropyl 3-[4-carbamoyl-3-(phenylamino)-1H-pyrazol-1-yl]-3-(cyanomethyl)azetidine-1-carboxylate | Calc'd 413, Found 413 |

TABLE 26-continued

| Example | Structure | Compound Name | Exact Mass [M + H]+ |
|---|---|---|---|
| 30-62 | 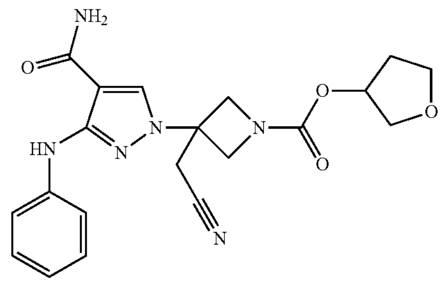 [SMILES: N#CCC1(n2cc(C(N)=O)c(Nc3ccccc3)n2)CN(C(=O)OC2CCOC2)C1] | tetrahydrofuran-3-yl 3-[4-carbamoyl-3-(phenylamino)-1H-pyrazol-1-yl]-3-(cyanomethyl)azetidine-1-carboxylate | Calc'd 411, Found 411 |
| 30-63 | 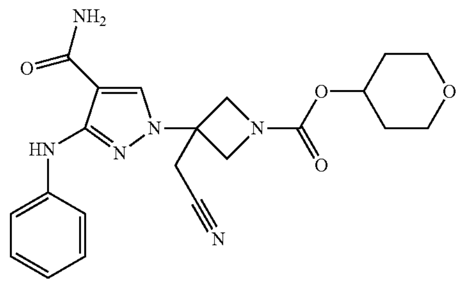 [SMILES: N#CCC1(n2cc(C(N)=O)c(Nc3ccccc3)n2)CN(C(=O)OC2CCOCC2)C1] | tetrahydro-2H-pyran-4-yl 3-[4-carbamoyl-3-(phenylamino)-1H-pyrazol-1-yl]-3-(cyanomethyl)azetidine-1-carboxylase | Calc'd 425, Found 425 |
| 30-64 | 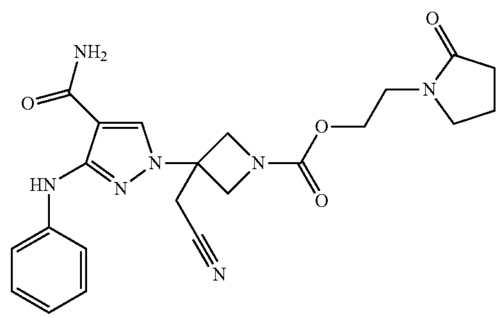 [SMILES: N#CCC1(n2cc(C(N)=O)c(Nc3ccccc3)n2)CN(C(=O)OCCN2CCCC2=O)C1] | 2-(2-oxopyrrolidin-1-yl)ethyl 3-[4-carbamoyl-3-(phenylamino)-1H-pyrazol-1-yl]-3-(cyanomethyl)azetidine-1-carboxylate | Calc'd 452, Found 452 |
| 30-65 | 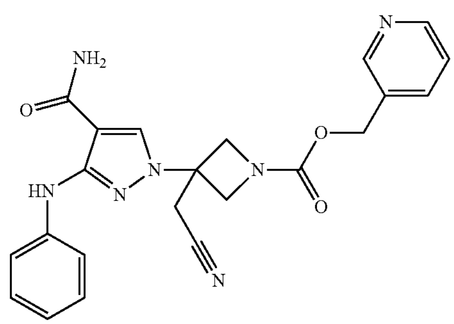 [SMILES: N#CCC1(n2cc(C(N)=O)c(Nc3ccccc3)n2)CN(C(=O)OCc2cccnc2)C1] | pyridin-3-ylmethyl 3-[4-carbamoyl-3-(phenylamino)-1H-pyrazol-1-yl]-3-(cyanomethyl)azetidine-1-carboxylate | Calc'd 432, Found 432 |
| 30-66 | 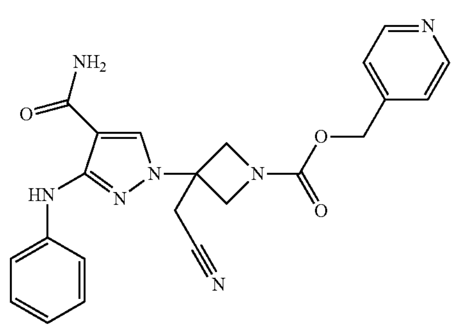 [SMILES: N#CCC1(n2cc(C(N)=O)c(Nc3ccccc3)n2)CN(C(=O)OCc2ccncc2)C1] | pyridin-4-ylmethyl 3-[4-carbamoyl-3-(phenylamino)-1H-pyrazol-1-yl]-3-(cyanomethyl)azetidine-1-carboxylate | Calc'd 432, Found 432 |

TABLE 26-continued

| Example | Structure | Compound Name | Exact Mass [M + H]+ |
|---|---|---|---|
| 30-67 | 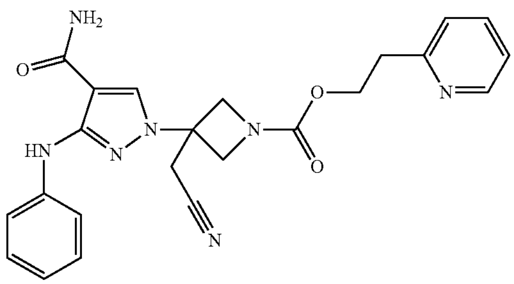 [SMILES: N#CCC1(n2cc(C(N)=O)c(Nc3ccccc3)n2)CN(C(=O)OCCc2ccccn2)C1] | 2-pyridin-2-ylethyl 3-[4-carbamoyl-3-(phenylamino)-1H-pyrazol-1-yl]-3-(cyanomethyl)azetidine-1-carboxylate | Calc'd 446, Found 446 |
| 30-68 | 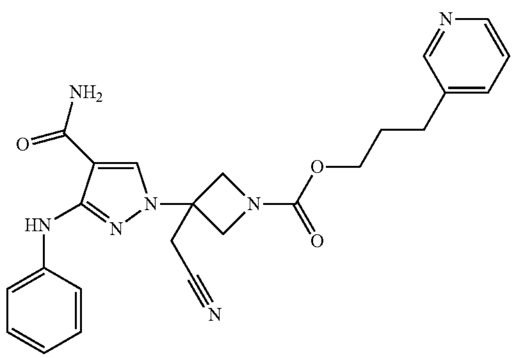 [SMILES: N#CCC1(n2cc(C(N)=O)c(Nc3ccccc3)n2)CN(C(=O)OCCCc2cccnc2)C1] | 3-pyridin-3-ylpropyl 3-[4-carbamoyl-3-(phenylamino)-1H-pyrazol-1-yl]-3-(cyanomethyl)azetidine-1-carboxylate | Calc'd 460, Found 460 |
| 30-69 | 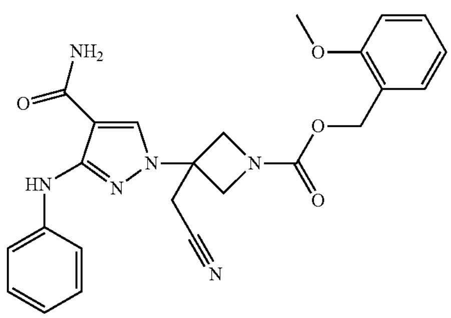 [SMILES: COc1ccccc1COC(=O)N1CC(CC#N)(n2cc(C(N)=O)c(Nc3ccccc3)n2)C1] | 2-methoxybenzyl 3-[4-carbamoyl-3-(phenylamino)-1H-pyrazol-1-yl]-3-(cyanomethyl)azetidine-1-carboxylate | Calc'd 461, Found 461 |
| 30-70 | 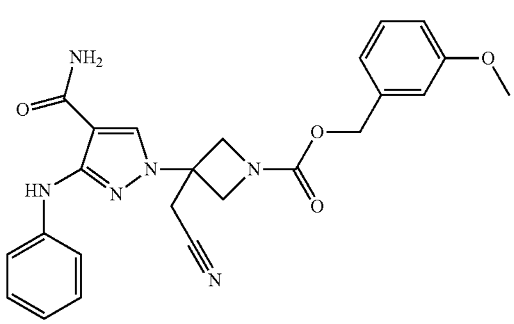 [SMILES: COc1cccc(COC(=O)N2CC(CC#N)(n3cc(C(N)=O)c(Nc4ccccc4)n3)C2)c1] | 3-methoxybenzyl 3-[4-carbamoyl-3-(phenylamino)-1H-pyrazol-1-yl]-3-(cyanomethyl)azetidine-1-carboxylate | Calc'd 461, Found 461 |

TABLE 26-continued

| Example | Structure | Compound Name | Exact Mass [M + H]+ |
|---|---|---|---|
| 30-71 | 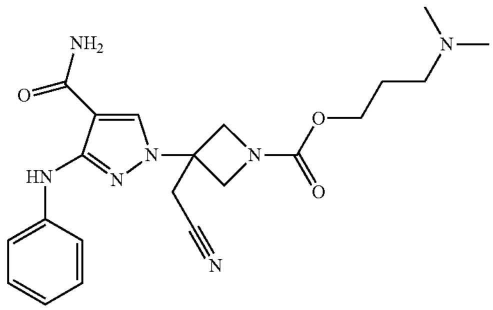 [SMILES: CN(C)CCCOC(=O)N1CC(CC#N)(n2cc(C(N)=O)c(Nc3ccccc3)n2)C1] | 3-(dimethylamino)propyl 3-[4-carbamoyl-3-(phenylamino)-1H-pyrazol-1-yl]-3-(cyanomethyl)azetidine-1-carboxylate | Calc'd 426, Found 426 |
| 30-72 | 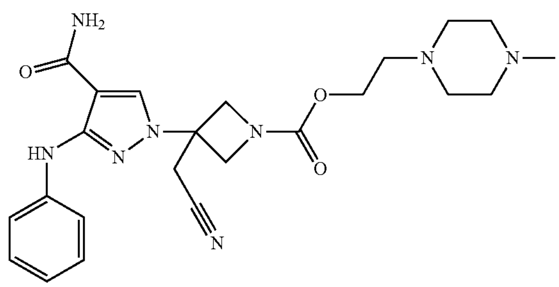 [SMILES: CN1CCN(CCOC(=O)N2CC(CC#N)(n3cc(C(N)=O)c(Nc4ccccc4)n3)C2)CC1] | 2-(4-methylpiperazin-1-yl)ethyl 3-[4-carbamoyl-3-(phenylamino)-1H-pyrazol-1-yl]-3-(cyanomethyl)azetidine-1-carboxylate | Calc'd 467, Found 467 |
| 30-73 | 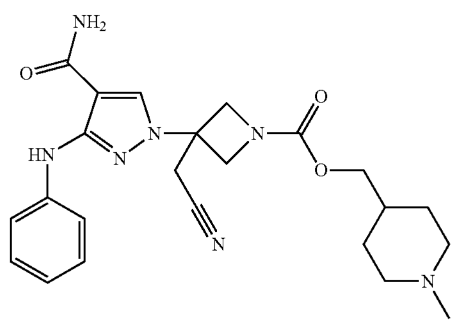 [SMILES: CN1CCC(COC(=O)N2CC(CC#N)(n3cc(C(N)=O)c(Nc4ccccc4)n3)C2)CC1] | (1-methylpiperidin-4-yl)methyl 3-[4-carbamoyl-3-(phenylamino)-1H-pyrazol-1-yl]-3-(cyanomethyl)azetidine-1-carboxylate | Calc'd 452, Found 452 |
| 30-74 | 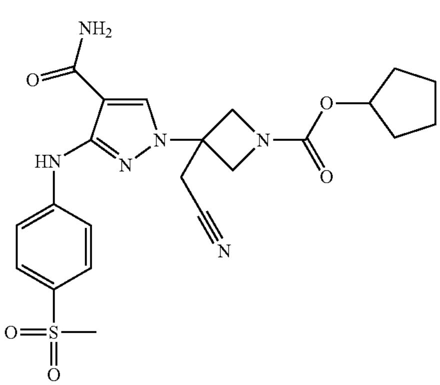 [SMILES: CS(=O)(=O)c1ccc(Nc2nn(C3(CC#N)CN(C(=O)OC4CCCC4)C3)cc2C(N)=O)cc1] | cyclopentyl 3-(4-carbamoyl-3-{[4-(methylsulfonyl)phenyl]amino}-1H-pyrazol-1-yl)-3-(cyanomethyl)azetidine-1-carboxylate | Calc'd 487, Found 973 (2M + H) |

TABLE 26-continued

| Example | Structure | Compound Name | Exact Mass [M + H]+ |
|---|---|---|---|
| 30-75 | 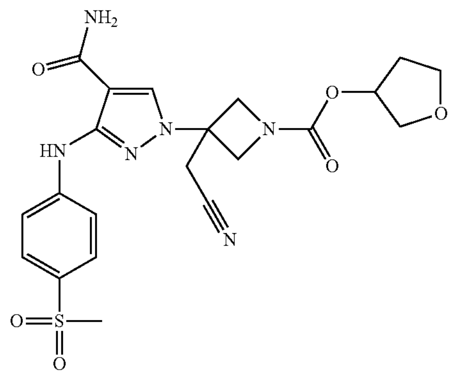 [SMILES: CS(=O)(=O)c1ccc(Nc2nn(C3(CC#N)CN(C(=O)OC4CCOC4)C3)cc2C(N)=O)cc1] | tetrahydrofuran-3-yl 3-(4-carbamoyl-3-{[4-(methylsulfonyl)phenyl]amino)-1H-pyrazol-1-yl)-3-(cyanomethyl)azetidine-1-carboxylate | Calc'd 489, Found 489 |
| 30-76 | 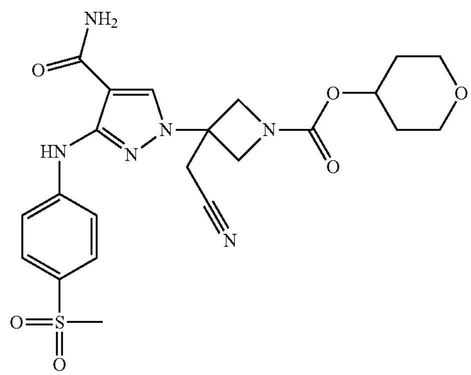 [SMILES: CS(=O)(=O)c1ccc(Nc2nn(C3(CC#N)CN(C(=O)OC4CCOCC4)C3)cc2C(N)=O)cc1] | tetrahydro-2H-pyran-4-yl 3-(4-carbamoyl-3-{[4-(methylsulfonyl)phenyl]amino}-1H-pyrazol-1-yl)-3-(cyanomethyl)azetidine-1-carboxylate | Calc'd 503, Found 503 |
| 30-77 | 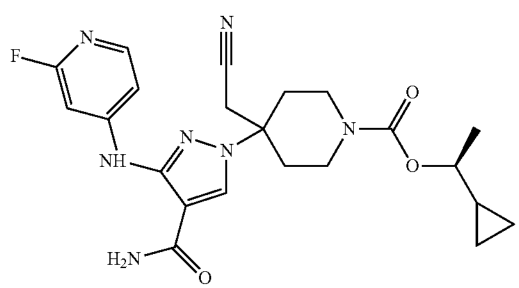 [SMILES: C[C@H](OC(=O)N1CCC(CC#N)(n2cc(C(N)=O)c(Nc3ccnc(F)c3)n2)CC1)C1CC1] | (1S)-1-cyclopropylethyl 4-{4-carbamoyl-3-[(2-fluoropyridin-4-yl)amino]-1H-pyrazol-1-yl}-4-(cyanomethyl)piperidine-1-carboxylate | Calc'd 456, Found 456 |
| 30-78 | 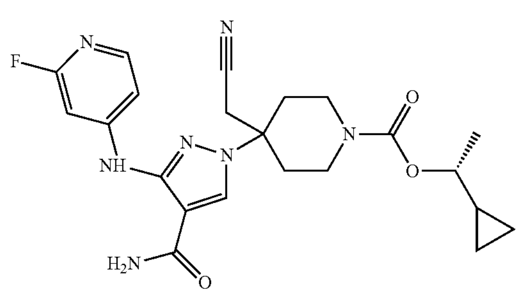 [SMILES: C[C@@H](OC(=O)N1CCC(CC#N)(n2cc(C(N)=O)c(Nc3ccnc(F)c3)n2)CC1)C1CC1] | (1R)-1-cyclopropylethyl 4-{4-carbamoyl-3-[(2-fluoropyridin-4-yl)amino]-1H-pyrazol-1-yl}-4-(cyanomethyl)piperidine-1-carboxylate | Calc'd 456, Found 456 |

Example #31

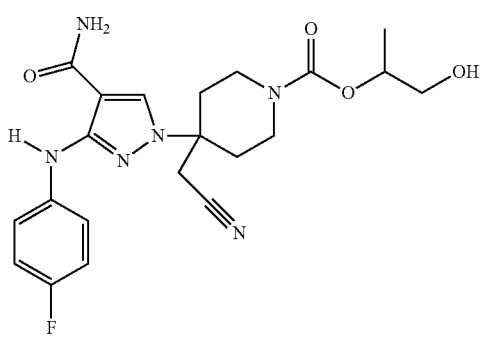

2-Hydroxy-1-methylethyl 4-{4-carbamoyl-3-[(4-fluorophenyl)amino]-1H-pyrazol-1-yl}-4-(cyanomethyl)piperidine-1-carboxylate To a solution of 1-{[tert-butyl(dimethyl)silyl]oxy}propan-2-yl4-{4-carbamoyl-3-[(4-fluorophenyl)amino]-1H-pyrazol-1-yl}-4-(cyanomethyl)piperidine-1-carboxylate (Example 30-51) (86 mg, 0.15 mmol) in THF (1.0 mL) was added a solution of TBAF.3H$_2$O (316 mg, 1.00 mmol) in THF (1.0 mL). The resulting mixture was allowed to stir at ambient temperature for 3 hours. The mixture was then diluted with DCM, washed with water, dried over anhydrous MgSO$_4$, filtered and concentrated in vacuo. The resulting residue was purified by MPLC on silica gel (using a gradient elution of 0-20% MeOH/DCM) to afford the title compound, Example #31.

$^1$H NMR (600 MHz, acetone-d$_6$): δ 9.16 (s, 1H), 8.47 (s, 1H), 7.67-7.55 (m, 2H), 7.16 (br s, 1H), 7.05-6.95 (m, 2H), 6.48 (br s, 1H), 4.86-4.69 (m, 1H), 4.02-3.80 (m, 3H), 3.57-3.50 (m, 2H), 3.16 (s, 2H), 3.14-3.08 (m, 2H), 2.70-2.50 (m, 2H), 2.16-2.05 (m, 2H), 1.21-1.12 (m, 3H).

LRMS (ESI) calcd for C$_{21}$H$_{25}$FN$_6$O$_4$ [M+H]$^+$: 445. Found: 445.

Scheme #28

Example #32

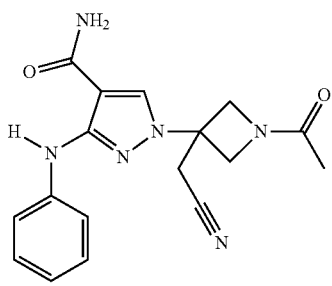

1-[1-Acetyl-3-(cyanomethyl)azetidin-3-yl]-3-(phenylamino)-1H-pyrazole-4-carboxamide To a suspension of 3-[4-carbamoyl-3-(phenylamino)-1H-pyrazol-1-yl]-3-(cyanomethyl)azetidinium trifluoroacetate (Intermediate #38-2) (50 mg, 0.17 mmol) in DCM (2 mL) was added pyridine (0.050 mL, 0.62 mmol), followed by acetic anhydride (0.030 mL, 0.32 mmol). The reaction mixture was allowed to stir for 30 minutes before the solvent was removed in vacuo. Saturated aqueous NaHCO$_3$ solution was added and the mixture was extracted with EtOAc (3×). The combined organic layers were dried over anhydrous Na$_2$SO$_4$, filtered, and concentrated in vacuo. The residue was purified by MPLC on silica gel (using a gradient elution of 50-100% EtOAc/hexanes followed by 10% MeOH/EtOAc) to afford the title compound, Example #32.

$^1$H NMR (600 MHz, CDCl$_3$): δ 8.86 (s, 1H), 8.17 (s, 1H), 7.47 (d, J=7.7 Hz, 2H), 7.33-7.19 (m, 2H), 6.90 (t, J=7.3 Hz, 1H), 5.8 (br s, 2H), 4.55 (dd, J=26.1, 10.1 Hz, 2H), 4.34 (dd, J=26.1, 10.1 Hz, 2H), 3.33-3.18 (m, 2H), 1.90 (s, 3H).

LRMS (ESI) calc'd for C$_{17}$H$_{18}$N$_6$O$_2$ [M+11]$^+$: 339. Found: 339.

Scheme #28

Example #33-1

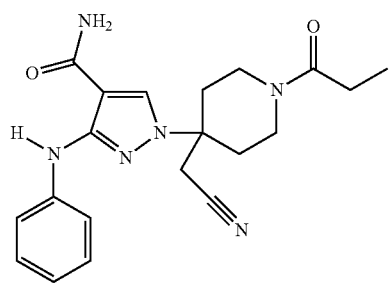

1-[4-(Cyanomethyl)-1-propanoylpiperidin-4-yl]-3-(phenylamino)-1H-pyrazole-4-carboxamide To a suspension of 4-[4-carbamoyl-3-(phenylamino)-1H-pyrazol-1-yl]-4-(cyanomethyl)piperidinium trifluoroacetate (Intermediate #38-1) (50 mg, 0.11 mmol) in THF (1 mL) was added DIPEA (0.060 mL, 0.34 mmol), followed by propanoyl chloride (0.020 mL, 0.18 mmol). The resulting mixture was allowed to stir for 18 hours before the reaction mixture was concentrated in vacuo to afford an orange oil. The residue was dissolved in DMSO (2 mL) and purified by mass-triggered reverse phase preparative HPLC (MeCN/water, with 0.1% v/v TFA modifier). Desired fractions were identified, combined, diluted with saturated aqueous NaHCO$_3$ and extracted with EtOAc (2×). The combined organic layers were washed with brine, dried over anhydrous Na$_2$SO$_4$, filtered and concentrated in vacuo to afford the title compound, Example #33-1, as a colorless solid.

$^1$H NMR (600 MHz, DMSO-d$_6$): δ 9.04 (s, 1H), 8.48 (s, 1H), 7.54 (br s, 1H), 7.47 (d, J=7.6 Hz, 2H), 7.21 (t, J=7.6 Hz, 2H), 7.14 (br s, 1H), 6.80 (t, J=7.3 Hz, 1H), 4.02-3.96 (m, 1H), 3.75-3.68 (m, 1H), 3.18-3.08 (m, 3H), 2.98-2.90 (m, 1H), 2.45-2.25 (m, 4H), 2.02-1.95 (m, 1H), 1.95-1.85 (m, 1H), 0.94 (t, J=7.3 Hz, 3H).

LRMS (ESI) calc'd for C$_{20}$H$_{24}$N$_6$O$_2$ [M+H]$^+$: 381. Found: 381.

The following compounds shown TABLE 27 were prepared according to Scheme #28 following similar procedures described for Example #33-1, which can be achieved by those of ordinary skill in the art of organic synthesis.

TABLE 27

| Example | Structure | Compound Name | Exact Mass [M + H]+ |
|---|---|---|---|
| 33-2 | 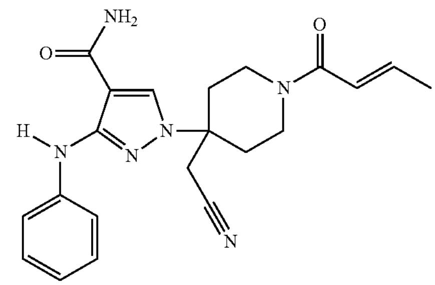 [SMILES: C/C=C/C(=O)N1CCC(CC#N)(n2cc(C(N)=O)c(Nc3ccccc3)n2)CC1] | 1-{1-[(2E)-but-2-enoyl]-4-(cyanomethyl)piperidin-4-yl}-3-(phenylamino)-1H-pyrazole-4-carboxamide | Calc'd 393, Found 393 |

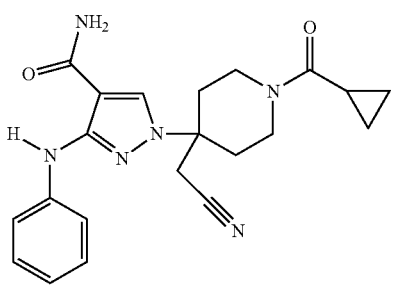

Scheme #28

Example #34-1

1-[4-(Cyanomethyl)-1-(cyclopropylcarbonyl)piperidin-4-yl]-3-(phenylamino)-1H-pyrazole-4-carboxamide 4-[4-Carbamoyl-3-(phenylamino)-1H-pyrazol-1-yl]-4-(cyanomethyl)piperidinium trifluoroacetate (Intermediate #38-1) (20 mg, 0.05 mmol) was diluted with DMF (0.5 mL) and treated with cyclopropanecarboxylic acid (5 mg, 0.06 mmol), DIPEA (0.020 mL, 0.12 mmol) and 1,3,5,2,4,6-trioxatriphosphorinane-2,4,6-trioxide (0.040 mL, 0.060 mmol). The reaction mixture was heated to 40° C. and allowed to stir for 16 hours. The mixture was then cooled to ambient temperature, diluted with DMSO (1.0 mL), and purified by reverse-phase preparative HPLC (using a gradient elution of 5-95% MeCN/water, with 0.1% v/v NH$_4$OH modifier). Desired fractions were identified, combined and concentrated in vacuo to afford the title compound, Example #34-1. $^1$H NMR (600 MHz, DMSO-d$_6$): δ 9.09-9.00 (m, 1H), 8.50 (s, 1H), 7.55 (s, 1H), 7.48 (d, J=7.7 Hz, 2H), 7.26-7.17 (m, 2H), 7.15 (s, 1H), 6.80 (m, 1H), 4.09-3.90 (m, 2H), 3.18 (s, 2H), 2.47 (s, 2H), 2.35 (s, 2H), 2.07-1.97 (m, 2H), 1.95-1.87 (m, 1H), 0.74-0.62 (m, 4H).

LRMS (ESI) calc'd for C$_{21}$H$_{24}$N$_6$O$_2$ [M+H]$^+$: 393. Found: 393.

The following compounds shown TABLE 28 were prepared according to Scheme #28 following similar procedures described for Example #34-1, which can be achieved by those of ordinary skill in the art of organic synthesis.

TABLE 28

| Example | Structure | Compound Name | Exact Mass [M + H]+ |
|---|---|---|---|
| 34-2 | 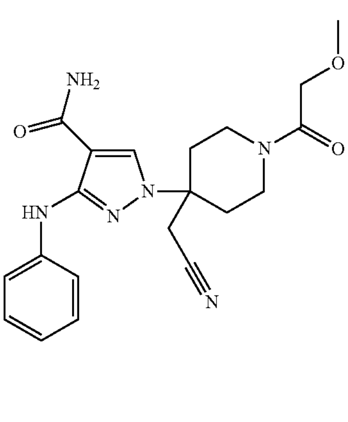 [SMILES: COCC(=O)N1CCC(CC#N)(n2cc(C(N)=O)c(Nc3ccccc3)n2)CC1] | 1-[4-(cyanomethyl)-1-(methoxyacetyl)piperidin-4-yl]-3-(phenylamino)-1H-pyrazole-4-carboxamide | Calc'd 397, Found 397 |

TABLE 28-continued

| Example | Structure | Compound Name | Exact Mass [M + H]+ |
|---|---|---|---|
| 34-3 | 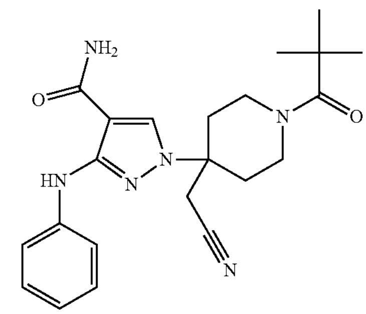 [SMILES: CC(C)(C)C(=O)N1CCC(CC#N)(n2cc(C(N)=O)c(Nc3ccccc3)n2)CC1] | 1-[4-(cyanomethyl)-1-(2,2-dimethylpropanoyl)piperidin-4-yl]-3-(phenylamino)-1H-pyrazole-4-carboxamide | Calc'd 409, Found 409 |
| 34-4 | 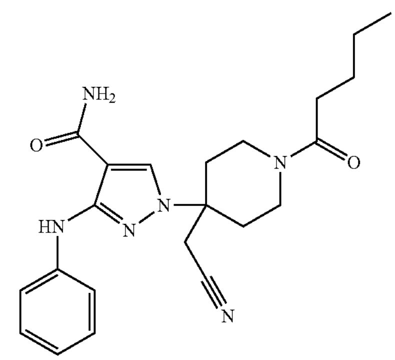 [SMILES: CCCCC(=O)N1CCC(CC#N)(n2cc(C(N)=O)c(Nc3ccccc3)n2)CC1] | 1-[4-(cyanomethyl)-1-pentanoylpiperidin-4-yl]-3-(phenylamino)-1H-pyrazole-4-carboxamide | Calc'd 409, Found 409 |
| 34-5 | 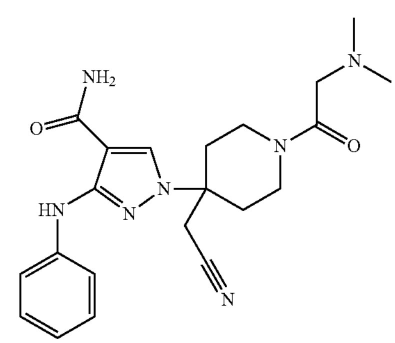 [SMILES: CN(C)CC(=O)N1CCC(CC#N)(n2cc(C(N)=O)c(Nc3ccccc3)n2)CC1] | 1-[4-(cyanomethyl)-1-(N,N-dimethylglycyl)piperidin-4-yl]-3-(phenylamino)-1H-pyrazole-4-carboxamide | Calc'd 410, Found 410 |
| 34-6 | 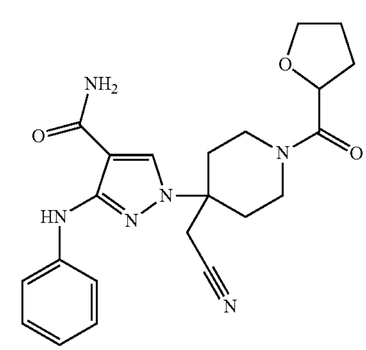 [SMILES: N#CCC1(n2cc(C(N)=O)c(Nc3ccccc3)n2)CCN(C(=O)C2CCCO2)CC1] | 1-[4-(cyanomethyl)-1-(tetrahydrofuran-2-ylcarbonyl)piperidin-4-yl]-3-(phenylamino)-1H-pyrazole-4-carboxamide | Calc'd 423, Found 423 |

TABLE 28-continued

| Example | Structure | Compound Name | Exact Mass [M + H]+ |
|---|---|---|---|
| 34-7 | 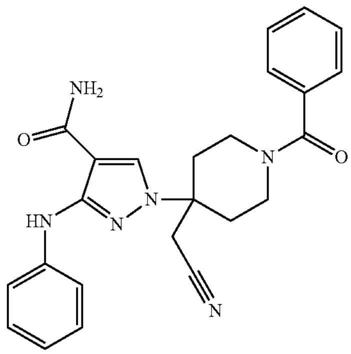 [SMILES: N#CCC1(n2cc(C(N)=O)c(Nc3ccccc3)n2)CCN(C(=O)c2ccccc2)CC1] | 1-[4-(cyanomethyl)-1-(phenylcarbonyl)piperidin-4-yl]-3-(phenylamino)-1H-pyrazole-4-carboxamide | Calc'd 429, Found 429 |
| 34-8 | 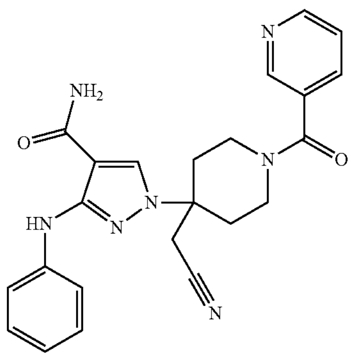 [SMILES: N#CCC1(n2cc(C(N)=O)c(Nc3ccccc3)n2)CCN(C(=O)c2cccnc2)CC1] | 1-[4-(cyanomethyl)-1-(pyridin-3-ylcarbonyl)piperidin-4-yl]-3-(phenylamino)-1H-pyrazole-4-carboxamide | Calc'd 430, Found 430 |
| 34-9 | 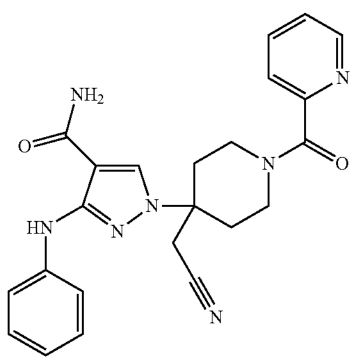 [SMILES: N#CCC1(n2cc(C(N)=O)c(Nc3ccccc3)n2)CCN(C(=O)c2ccccn2)CC1] | 1-[4-(cyanomethyl)-1-(pyridin-2-ylcarbonyl)piperidin-4-yl]-3-(phenylamino)-1H-pyrazole-4-carboxamide | Calc'd 430, Found 430 |
| 34-10 | 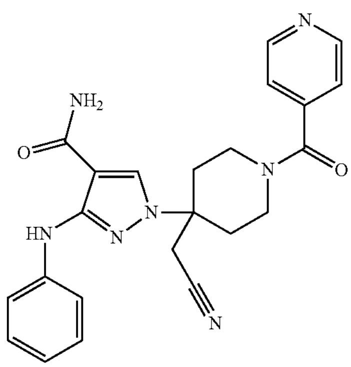 [SMILES: N#CCC1(n2cc(C(N)=O)c(Nc3ccccc3)n2)CCN(C(=O)c2ccncc2)CC1] | 1-[4-(cyanomethyl)-1-(pyridin-4-ylcarbonyl)piperidin-4-yl]-3-(phenylamino)-1H-pyrazole-4-carboxamide | Calc'd 430, Found 430 |

TABLE 28-continued

| Example | Structure | Compound Name | Exact Mass [M + H]+ |
|---|---|---|---|
| 34-11 | 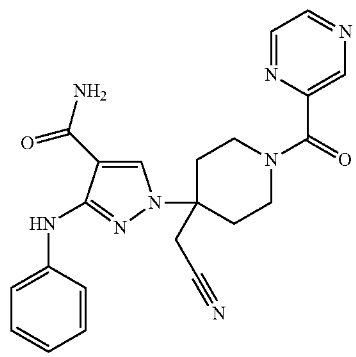 [SMILES: N#CCC1(n2cc(C(N)=O)c(Nc3ccccc3)n2)CCN(C(=O)c2cnccn2)CC1] | 1-[4-(cyanomethyl)-1-(pyrazin-2-ylcarbonyl)piperidin-4-yl]-3-(phenylamino)-1H-pyrazole-4-carboxamide | Calc'd 431, Found 431 |
| 34-12 | 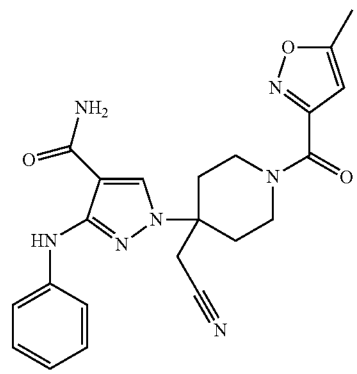 [SMILES: Cc1cc(C(=O)N2CCC(CC#N)(n3cc(C(N)=O)c(Nc4ccccc4)n3)CC2)no1] | 1-{4-(cyanomethyl)-1-[(5-methylisoxazol-3-yl)carbonyl]piperidin-4-yl}-3-(phenylamino)-1H-pyrazole-4-carboxamide | Calc'd 434, Found 434 |
| 34-13 | 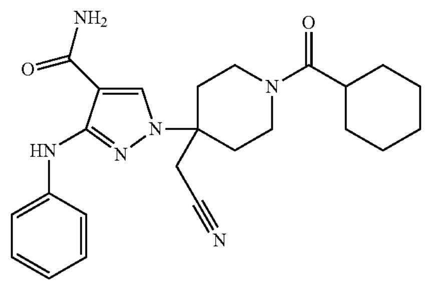 [SMILES: N#CCC1(n2cc(C(N)=O)c(Nc3ccccc3)n2)CCN(C(=O)C2CCCCC2)CC1] | 1-[4-(cyanomethyl)-1-(cyclohexylcarbonyl)piperidin-4-yl]-3-(phenylamino)-1H-pyrazole-4-carboxamide | Calc'd 435, Found 435 |
| 34-14 | 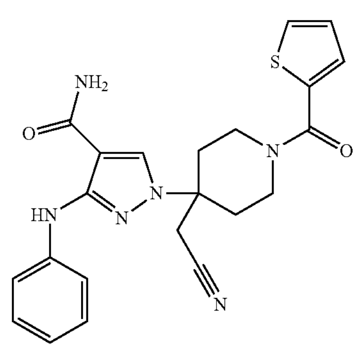 [SMILES: N#CCC1(n2cc(C(N)=O)c(Nc3ccccc3)n2)CCN(C(=O)c2cccs2)CC1] | 1-[4-(cyanomethyl)-1-(thiophen-2-ylcarbonyl)piperidin-4-yl]-3-(phenylamino)-1H-pyrazole-4-carboxamide | Calc'd 435, Found 435 |

TABLE 28-continued

| Example | Structure | Compound Name | Exact Mass [M + H]+ |
|---|---|---|---|
| 34-15 | 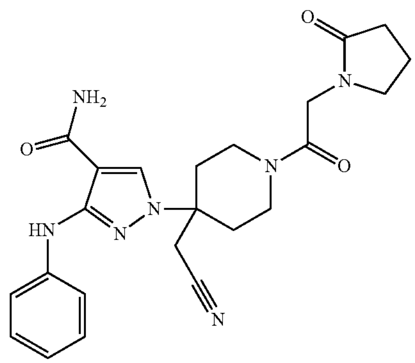 [SMILES: N#CCC1(n2cc(C(N)=O)c(Nc3ccccc3)n2)CCN(C(=O)CN2CCCC2=O)CC1] | 1-{4-(cyanomethyl)-1-[(2-oxopyrrolidin-1-yl)acetyl]piperidin-4-yl}-3-(phenylamino)-1H-pyrazole-4-carboxamide | Calc'd 450, Found 450 |
| 34-16 | 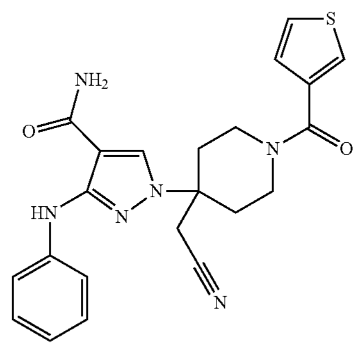 [SMILES: N#CCC1(n2cc(C(N)=O)c(Nc3ccccc3)n2)CCN(C(=O)c2ccsc2)CC1] | 1-[4-(cyanomethyl)-1-(thiophen-3-ylcarbonyl)piperidin-4-yl]-3-(phenylamino)-1H-pyrazole-4-carboxamide | Calc'd 435, Found 435 |
| 34-17 | 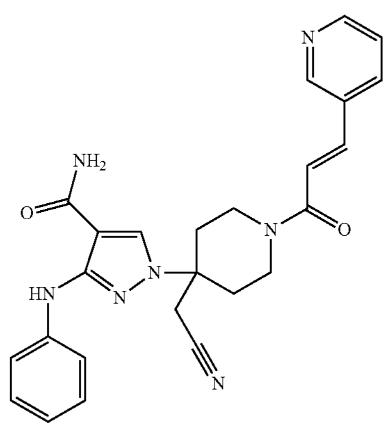 [SMILES: N#CCC1(n2cc(C(N)=O)c(Nc3ccccc3)n2)CCN(C(=O)/C=C/c2cccnc2)CC1] | 1-{4-(cyanomethyl)-1-[(2E)-3-pyridin-3-ylprop-2-enoyl]piperidin-4-yl}-3-(phenylamino)-1H-pyrazole-4-carboxamide | Calc'd 456, Found 456 |
| 34-18 | 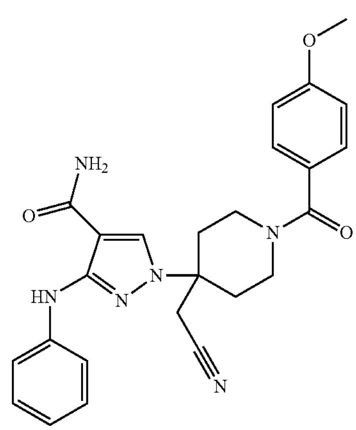 [SMILES: COc1ccc(C(=O)N2CCC(CC#N)(n3cc(C(N)=O)c(Nc4ccccc4)n3)CC2)cc1] | 1-{4-(cyanomethyl)-1-[(4-methoxyphenyl)carbonyl]piperidin-4-yl}-3-(phenylamino)-1H-pyrazole-4-carboxamide | Calc'd 459, Found 459 |

TABLE 28-continued

| Example | Structure | Compound Name | Exact Mass [M + H]+ |
|---|---|---|---|
| 34-19 | 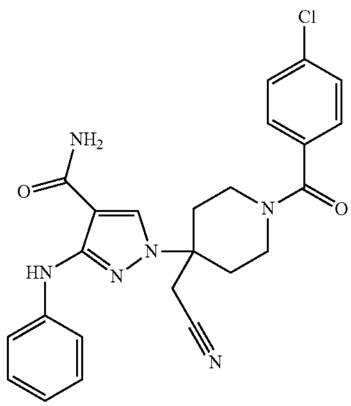 [SMILES: N#CCC1(n2cc(C(N)=O)c(Nc3ccccc3)n2)CCN(C(=O)c2ccc(Cl)cc2)CC1] | 1-{1-[(4-chlorophenyl)carbonyl]-4-(cyanomethyl)piperidin-4-yl}-3-(phenylamino)-1H-pyrazole-4-carboxamide | Calc'd 463, Found 463 |
| 34-20 | 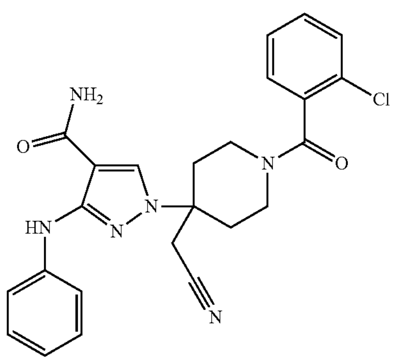 [SMILES: N#CCC1(n2cc(C(N)=O)c(Nc3ccccc3)n2)CCN(C(=O)c2ccccc2Cl)CC1] | 1-{1-[(2-chlorophenyl)carbonyl]-4-(cyanomethyl)piperidin-4-yl}-3-(phenylamino)-1H-pyrazole-4-carboxamide | Calc'd 463, Found 463 |
| 34-21 | 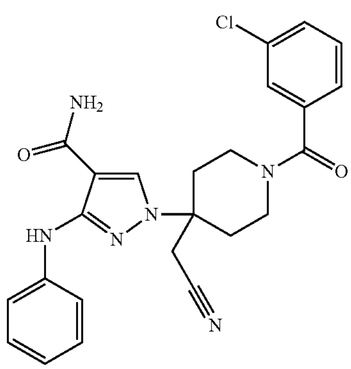 [SMILES: N#CCC1(n2cc(C(N)=O)c(Nc3ccccc3)n2)CCN(C(=O)c2cccc(Cl)c2)CC1] | 1-{1-[(3-chlorophenyl)carbonyl]-4-(cyanomethyl)piperidin-4-yl}-3-(phenylamino)-1H-pyrazole-4-carboxamide | Calc'd 463, Found 463 |
| 34-22 | 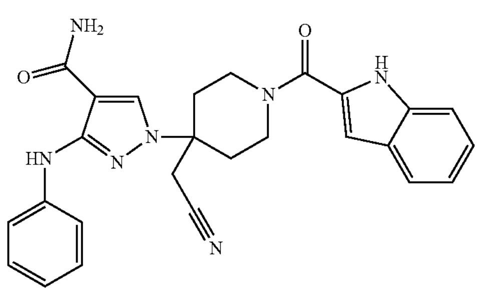 [SMILES: N#CCC1(n2cc(C(N)=O)c(Nc3ccccc3)n2)CCN(C(=O)c2cc3ccccc3[nH]2)CC1] | 1-[4-(cyanomethyl)-1-(1H-indol-2-ylcarbonyl)piperidin-4-yl]-3-(phenylamino)-1H-pyrazole-4-carboxamide | Calc'd 468, Found 468 |

TABLE 28-continued

| Example | Structure | Compound Name | Exact Mass [M + H]+ |
|---|---|---|---|
| 34-23 | 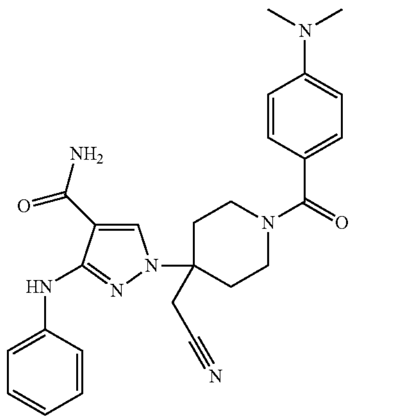 [SMILES: CN(C)c1ccc(C(=O)N2CCC(CC#N)(n3cc(C(N)=O)c(Nc4ccccc4)n3)CC2)cc1] | 1-[4-(cyanomethyl)-1-{[4-(dimethylamino)phenyl]carbonyl}piperidin-4-yl]-3-(phenylamino)-1H-pyrazole-4-carboxamide | Calc'd 472, Found 472 |
| 34-24 | 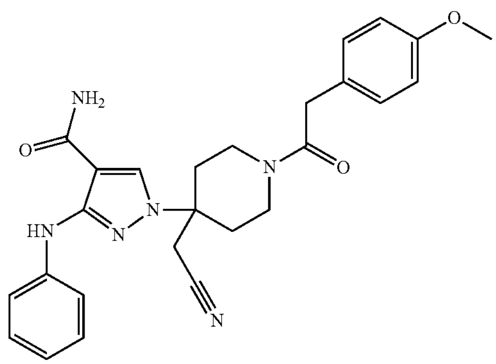 [SMILES: COc1ccc(CC(=O)N2CCC(CC#N)(n3cc(C(N)=O)c(Nc4ccccc4)n3)CC2)cc1] | 1-{4-(cyanomethyl)-1-[(4-methoxyphenyl)acetyl]piperidin-4-yl}-3-(phenylamino)-1H-pyrazole-4-carboxamide | Calc'd 473, Found 473 |
| 34-25 | 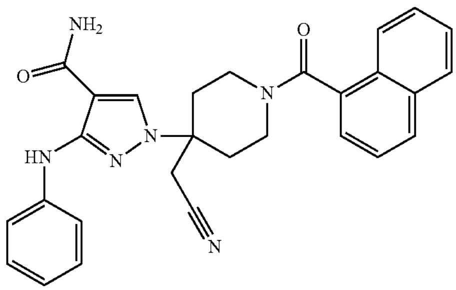 [SMILES: N#CCC1(n2cc(C(N)=O)c(Nc3ccccc3)n2)CCN(C(=O)c2cccc3ccccc23)CC1] | 1-[4-(cyanomethyl)-1-(naphthalene-1-ylcarbonyl)piperidin-4-yl]-3-(phenylamino)-1H-pyrazole-4-carboxamide | Calc'd 479, Found 479 |
| 34-26 | 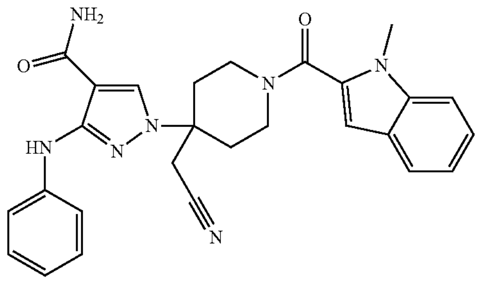 [SMILES: Cn1c(C(=O)N2CCC(CC#N)(n3cc(C(N)=O)c(Nc4ccccc4)n3)CC2)cc2ccccc21] | 1-{4-(cyanomethyl)-1-[(1-methyl-1H-indol-2-yl)carbonyl]piperidin-4-yl}-3-(phenylamino)-1H-pyrazole-4-carboxamide | Calc'd 482, Found 482 |

TABLE 28-continued

| Example | Structure | Compound Name | Exact Mass [M + H]+ |
|---------|-----------|---------------|---------------------|
| 34-27 | 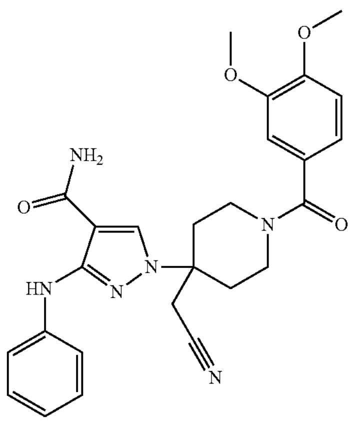 [SMILES: COc1ccc(C(=O)N2CCC(CC#N)(n3cc(C(N)=O)c(Nc4ccccc4)n3)CC2)cc1OC] | 1-{4-(cyanomethyl)-l-[(3,4-dimethoxyphenyl)carbonyl]piperidin-4-yl}-3-(phenylamino)-1H-pyrazole-4-carboxamide | Calc'd 489, Found 489 |
| 34-28 | 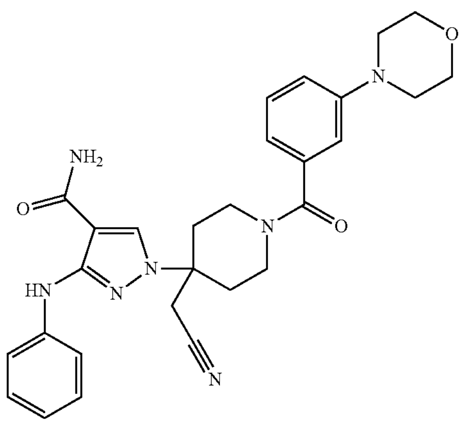 [SMILES: N#CCC1(n2cc(C(N)=O)c(Nc3ccccc3)n2)CCN(C(=O)c2cccc(N3CCOCC3)c2)CC1] | 1-(4-(cyanomethyl)-1-[(3-morpholin-4-ylphenyl)carbonyl]piperidin-4-yl}-3-(phenylamino)-1H-pyrazole-4-carboxamide | Calc'd 514, Found 514 |
| 34-29 | 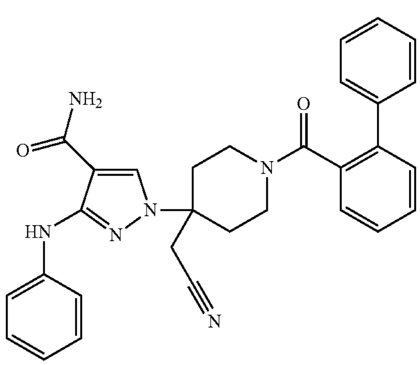 [SMILES: N#CCC1(n2cc(C(N)=O)c(Nc3ccccc3)n2)CCN(C(=O)c2ccccc2-c2ccccc2)CC1] | 1-[1-(biphenyl-2-ylcarbonyl)-4-(cyanomethyl)piperidin-4-yl]-3-(phenylamino)-1H-pyrazole-4-carboxamide | Calc'd 505, Found 505 |

TABLE 28-continued

| Example | Structure | Compound Name | Exact Mass [M + H]+ |
|---|---|---|---|
| 34-30 | 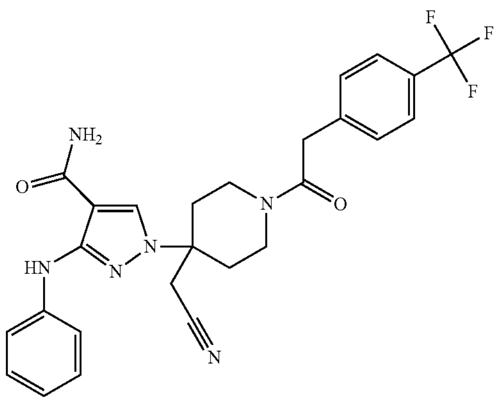 [SMILES: N#CCC1(n2cc(C(N)=O)c(Nc3ccccc3)n2)CCN(C(=O)Cc2ccc(C(F)(F)F)cc2)CC1] | 1-[4-(cyanomethyl)-1-{[4-(trifluoromethyl)phenyl]acetyl} piperidin-4-yl]-3-(phenylamino)-1H-pyrazole-4-carboxamide | Calc'd 511, Found 511 |
| 34-31 | 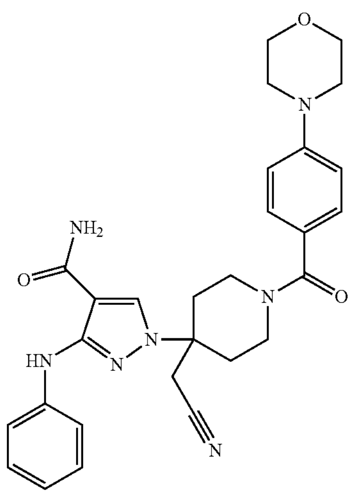 [SMILES: N#CCC1(n2cc(C(N)=O)c(Nc3ccccc3)n2)CCN(C(=O)c2ccc(N3CCOCC3)cc2)CC1] | 1-{4-(cyanomethyl)-1-[(4-morpholin-4-ylphenyl)carbonyl]piperidin-4-yl}-3-(phenylamino)-1H-pyrazole-4-carboxamide | Calc'd 514, Found 514 |
| 34-32 | 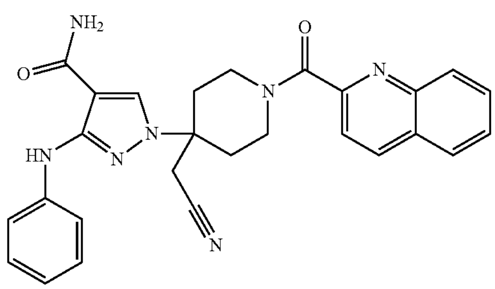 [SMILES: N#CCC1(n2cc(C(N)=O)c(Nc3ccccc3)n2)CCN(C(=O)c2ccc3ccccc3n2)CC1] | 1-[4-(cyanomethyl)-1-(quinolin-2-ylcarbonyl)piperidin-4-yl]-3-(phenylamino)-1H-pyrazole-4-carboxamide | Calc'd 480, Found 480 |
| 34-33 | 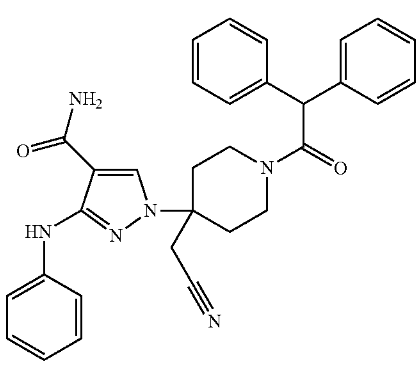 [SMILES: N#CCC1(n2cc(C(N)=O)c(Nc3ccccc3)n2)CCN(C(=O)C(c2ccccc2)c2ccccc2)CC1] | 1-[4-(cyanomethyl)-1-(diphenylacetyl)piperidin-4-yl]-3-(phenylamino)-1H-pyrazole-4-carboxamide | Calc'd 519, Found 519 |

TABLE 28-continued

| Example | Structure | Compound Name | Exact Mass [M + H]+ |
|---|---|---|---|
| 34-34 | 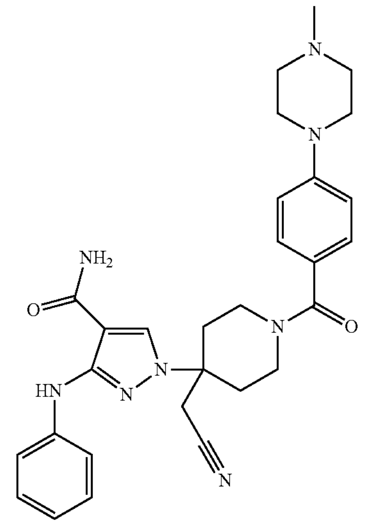 [SMILES: CN1CCN(c2ccc(C(=O)N3CCC(CC#N)(n4cc(C(N)=O)c(Nc5ccccc5)n4)CC3)cc2)CC1] | 1-[4-(cyanomethyl)-1-{[4-(4-methylpiperazin-1-yl)phenyl]carbonyl}piperidin-4-yl]3-(phenylamino)-1H-pyrazole-4-carboxamide | Calc'd 527, Found 527 |
| 34-35 | 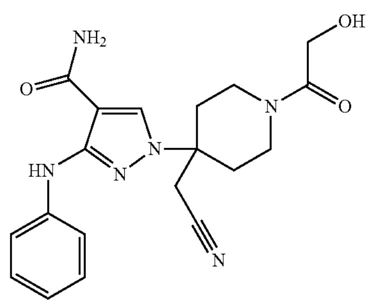 [SMILES: N#CCC1(n2cc(C(N)=O)c(Nc3ccccc3)n2)CCN(C(=O)CO)CC1] | 1-[4-(cyanomethyl)-1-(hydroxyacetyl)piperidin-4-yl]-3-(phenylamino)-1H-pyrazole-4-carboxamide | Calc'd 383, Found 383 |
| 34-36 | 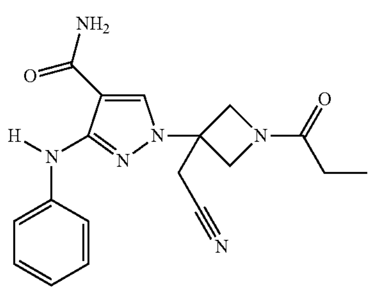 [SMILES: CCC(=O)N1CC(CC#N)(n2cc(C(N)=O)c(Nc3ccccc3)n2)C1] | 1-[3-(cyanomethyl)-1-propanoylazetidin-3-yl]-3-(phenylamino)-1H-pyrazole-4-carboxamide | Calc'd 353, Found 353 |
| 34-37 | 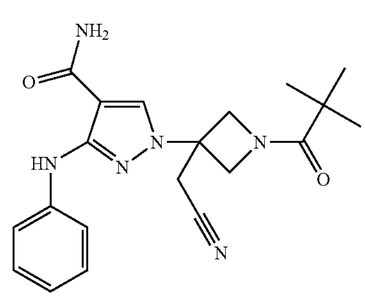 [SMILES: CC(C)(C)C(=O)N1CC(CC#N)(n2cc(C(N)=O)c(Nc3ccccc3)n2)C1] | 1-[3-(cyanomethyl)-1-(2,2-dimethylpropanoyl)azetidin-3-yl]-3-(phenylamino)-1H-pyrazole-4-carboxamide | Calc'd 381, Found 381 |

TABLE 28-continued

| Example | Structure | Compound Name | Exact Mass [M + H]+ |
|---|---|---|---|
| 34-38 | 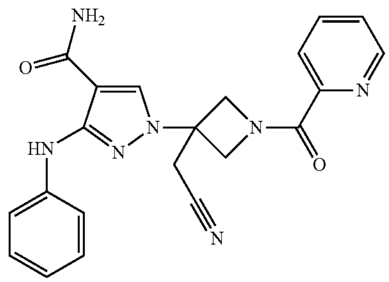 [SMILES: N#CCC1(n2cc(C(N)=O)c(Nc3ccccc3)n2)CN(C(=O)c2ccccn2)C1] | 1-[3-(cyanomethyl)-1-(pyridin-2-ylcarbonyl)azetidin-3-yl]-3-(phenylamino)-1H-pyrazole-4-carboxamide | Calc'd 402, Found 402 |
| 34-39 | 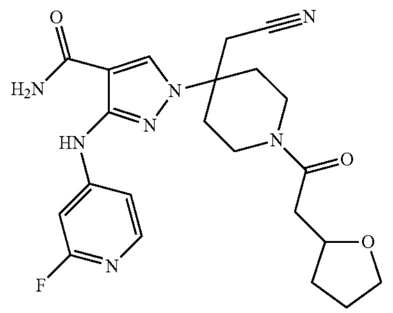 [SMILES: N#CCC1(n2cc(C(N)=O)c(Nc3ccnc(F)c3)n2)CCN(C(=O)CC2CCCO2)CC1] | 1-[4-(cyanomethyl)-1-(tetrahydrofuran-2-ylacetyl)piperidin-4-yl]-3-[(2-fluoropyridin-4-yl)amino]-1H-pyrazole-4-carboxamide | Calc'd 456, Found 456 |
| 34-40 | 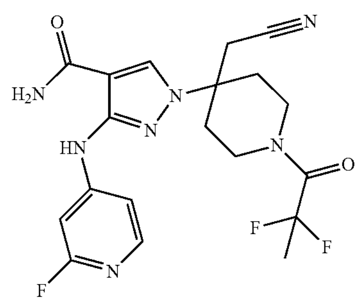 [SMILES: CC(F)(F)C(=O)N1CCC(CC#N)(n2cc(C(N)=O)c(Nc3ccnc(F)c3)n2)CC1] | 1-[4-(cyanomethyl)-1-(2,2-difluoropropanoyl)piperidin-4-yl]-3-[(2-fluoropyridin-4-yl)amino]-1H-pyrazole-4-carboxamide | Calc'd 436, Found 436 |
| 34-41 | 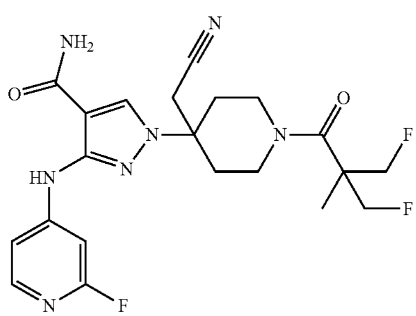 [SMILES: CC(CF)(CF)C(=O)N1CCC(CC#N)(n2cc(C(N)=O)c(Nc3ccnc(F)c3)n2)CC1] | 1-{4-(cyanomethyl)-1-[3-fluoro-2-(fluoromethyl)-2-methylpropanoyl]piperidin-4-yl}-3-[(2-fluoropyridin-4-yl)amino]-1H-pyrazole-4-carboxamide | Calc'd 464, Found 464 |
| 34-42 | 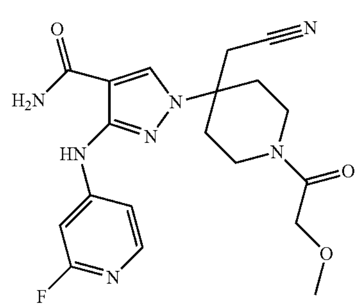 [SMILES: COCC(=O)N1CCC(CC#N)(n2cc(C(N)=O)c(Nc3ccnc(F)c3)n2)CC1] | 1-[4-(cyanomethyl)-1-(methoxyacetyl)piperidin-4-yl]-3-[(2-fluoropyridin-4-yl)amino]-1H-pyrazole-4-carboxamide | Calc'd 416, Found 416 |

TABLE 28-continued

| Example | Structure | Compound Name | Exact Mass [M + H]+ |
|---|---|---|---|
| 34-43 | 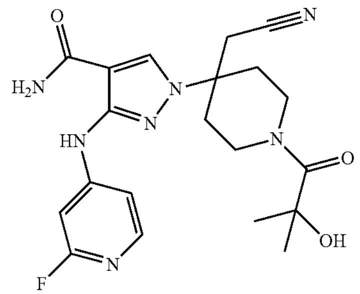 [SMILES: CC(C)(O)C(=O)N1CCC(CC#N)(n2cc(C(N)=O)c(Nc3ccnc(F)c3)n2)CC1] | 1-[4-(cyanomethyl)-1-(2-hydroxy-2-methylpropanoyl)piperidin-4-yl]-3-[(2-fluoropyridin-4-yl)amino]-1H-pyrazole-4-carboxamide | Calc'd 430, Found 430 |
| 34-44 | 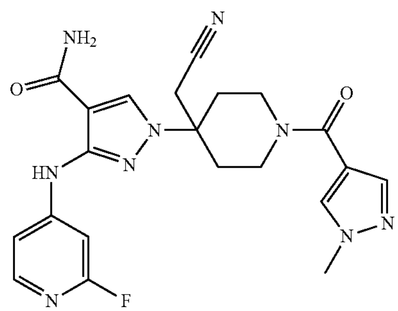 [SMILES: Cn1cc(C(=O)N2CCC(CC#N)(n3cc(C(N)=O)c(Nc4ccnc(F)c4)n3)CC2)cn1] | 1-{4-(cyanomethyl)-1-[(1-methyl-1H-pyrazol-4-yl)carbonyl]piperidin-4-yl}-3-[(2-fluoropyridin-4-yl)amino]-1H-pyrazole-4-carboxamide | Calc'd 452, Found 452 |
| 34-45 | 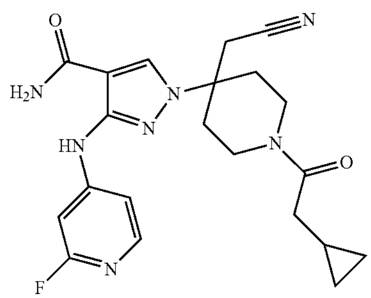 [SMILES: N#CCC1(n2cc(C(N)=O)c(Nc3ccnc(F)c3)n2)CCN(C(=O)CC2CC2)CC1] | 1-[4-(cyanomethyl)-1-(cyclopropylacetyl)piperidin-4-yl]-3-[(2-fluoropyridin-4-yl)amino]-1H-pyrazole-4-carboxamide | Calc'd 426, Found 426 |
| 34-46 | 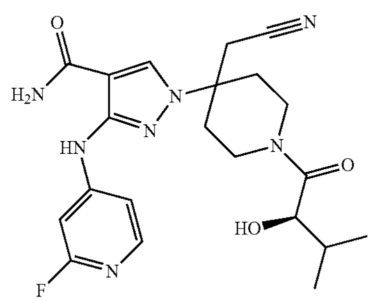 [SMILES: CC(C)[C@@H](O)C(=O)N1CCC(CC#N)(n2cc(C(N)=O)c(Nc3ccnc(F)c3)n2)CC1] | 1-{4-(cyanomethyl)-1-[(2R)-2-hydroxy-3-methylbutanoyl]piperidin-4-yl}-3-[(2-fluoropyridin-4-yl)amino]-1H-pyrazole-4-carboxamide | Calc'd 444, Found 444 |
| 34-47 | 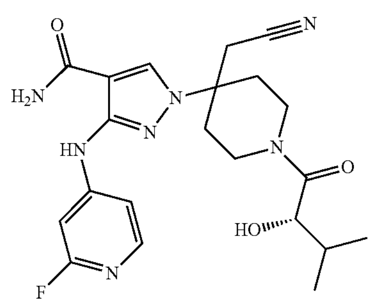 [SMILES: CC(C)[C@H](O)C(=O)N1CCC(CC#N)(n2cc(C(N)=O)c(Nc3ccnc(F)c3)n2)CC1] | 1-{4-(cyanomethyl)-1-[(2S)-2-hydroxy-3-methylbutanoyl]piperidin-4-yl}-3-[(2-fluoropyridin-4-yl)amino]-1H-pyrazole-4-carboxamide | Calc'd 444, Found 444 |

TABLE 28-continued

| Example | Compound Name | Exact Mass [M + H]+ |
|---|---|---|
| 34-48 | 1-[4-(cyanomethyl)-1-(3,3,3-trifluoro-2-methylpropanoyl)piperidin-4-yl]-3-[(2-fluoropyridin-4-yl)amino]-1H-pyrazole-4-carboxamide | Calc'd 468, Found 468 |
| 34-49 | 1-[1-(cyanoacetyl)-4-(cyanomethyl)piperidin-4-yl]-3-[(2-fluoropyridin-4-yl)amino]-1H-pyrazole-4-carboxamide | Calc'd 411, Found 411 |
| 34-50 | 1-[4-(cyanomethyl)-1-(3-hydroxy-3-methylbutanoyl)piperidin-4-yl]-3-[(2-fluoropyridin-4-yl)amino]-1H pyrazole-4-carboxamide | Calc'd 444, Found 444 |
| 34-51 | 1-[4-(cyanomethyl)-1-{[1-(trifluoromethyl)cyclobutyl]carbonyl}piperidin-4-yl]-3-[(2-fluoropyridin-4-yl)amino]-1H-pyrazole-4-carboxamide | Calc'd 494, Found 494 |
| 34-52 | 1-[4-(cyanomethyl)-1-(1H-imidazol-1-ylacetyl)piperidin-4-yl]-3-[(2-fluoropyridin-4-yl)amino]-1H-pyrazole-4-carboxamide | Calc'd 452, Found 452 |

TABLE 28-continued

| Example | Structure | Compound Name | Exact Mass [M + H]+ |
| --- | --- | --- | --- |
| 34-53 | 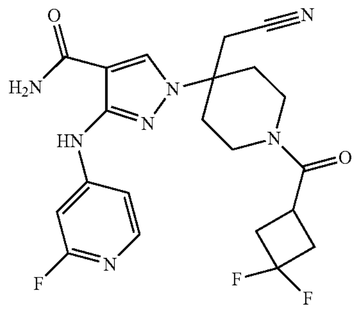 [SMILES: N#CCC1(n2cc(C(N)=O)c(Nc3ccnc(F)c3)n2)CCN(C(=O)C2CC(F)(F)C2)CC1] | 1-{4-(cyanomethyl)-1-[(3,3-difluorocyclobutyl)carbonyl]piperidin-4-yl}-3-[(2-fluoropyridin-4-yl)amino]-1H-pyrazole-4-carboxamide | Calc'd 462, Found 462 |
| 34-54 | 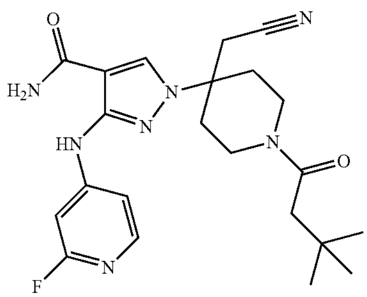 [SMILES: CC(C)(C)CC(=O)N1CCC(CC#N)(n2cc(C(N)=O)c(Nc3ccnc(F)c3)n2)CC1] | 1-[4-(cyanomethyl)-1-(3,3-dimethylbutanoyl)piperidin-4-yl]-3-[(2-fluoropyridin-4-yl)amino]-1H-pyrazole-4-carboxamide | Calc'd 442, Found 442 |
| 34-55 | 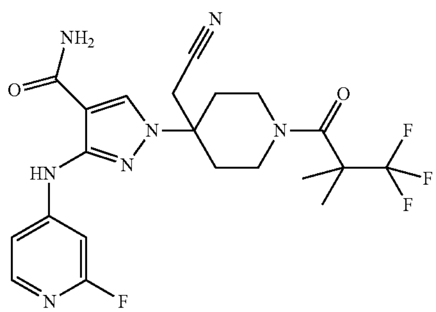 [SMILES: CC(C)(C(=O)N1CCC(CC#N)(n2cc(C(N)=O)c(Nc3ccnc(F)c3)n2)CC1)C(F)(F)F] | 1-[4-(cyanomethyl)-1-(3,3,3-trifluoro-2,2-dimethylpropanoyl)piperidin-4-yl]-3-[(2-fluoropyridin-4-yl)amino]-1H-pyrazole-4-carboxamide | Calc'd 482, Found 482 |
| 34-56 | 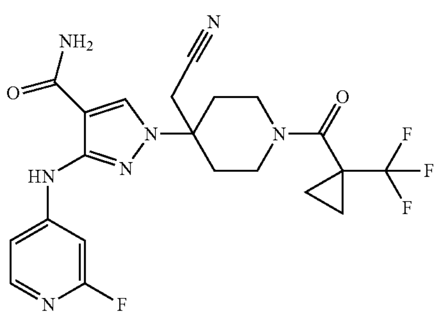 [SMILES: N#CCC1(n2cc(C(N)=O)c(Nc3ccnc(F)c3)n2)CCN(C(=O)C2(C(F)(F)F)CC2)CC1] | 1-[4-(cyanomethyl)-1-{[1-(trifluoromethyl)cyclopropyl]carbonyl}piperidin-4-yl]-3-[(2-fluoropyridin-4-yl)amino]-1H-pyrazole-4-carboxamide | Calc'd 480, Found 480 |
| 34-57 | 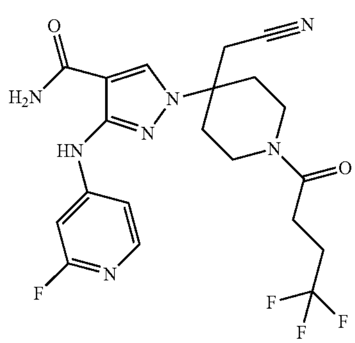 [SMILES: N#CCC1(n2cc(C(N)=O)c(Nc3ccnc(F)c3)n2)CCN(C(=O)CCC(F)(F)F)CC1] | 1-[4-(cyanomethyl)-1-(4,4,4-trifluorobutanoyl)piperidin-4-yl]-3-[(2-fluoropyridin-4-yl)amino]-1H-pyrazole-4-carboxamide | Calc'd 468, Found 468 |

TABLE 28-continued

| Example | Structure | Compound Name | Exact Mass [M + H]+ |
|---|---|---|---|
| 34-58 | 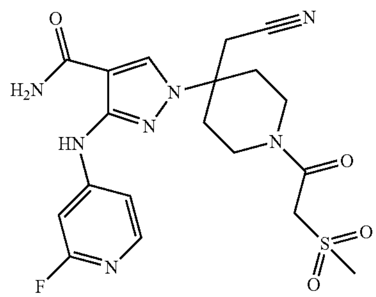 [SMILES: CS(=O)(=O)CC(=O)N1CCC(CC#N)(n2cc(C(N)=O)c(Nc3ccnc(F)c3)n2)CC1] | 1-{4-(cyanomethyl)-1-[(methylsulfonyl)acetyl]piperidin-4-yl}-3-[(2-fluoropyridin-4-yl)amino]-1H-pyrazole-4-carboxamide | Calc'd 464, Found 464 |
| 34-59 | 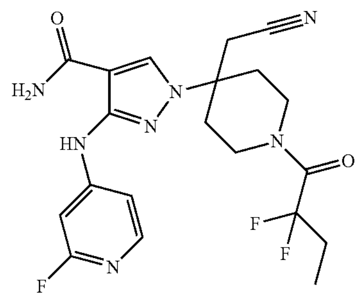 [SMILES: CCC(F)(F)C(=O)N1CCC(CC#N)(n2cc(C(N)=O)c(Nc3ccnc(F)c3)n2)CC1] | 1-[4-(cyanomethyl)-1-(2,2-difluorobutanoyl)piperidin-4-yl]-3-[(2-fluoropyridin-4-yl)amino]-1H-pyrazole-4-carboxamide | Calc'd 450, Found 450 |
| 34-60 | 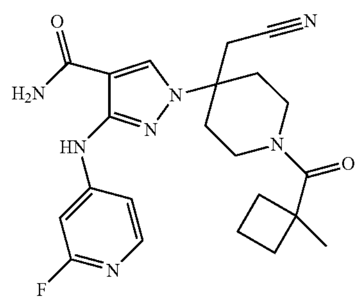 [SMILES: CC1(C(=O)N2CCC(CC#N)(n3cc(C(N)=O)c(Nc4ccnc(F)c4)n3)CC2)CCC1] | 1-{4-(cyanomethyl)-1-[(1-methylcyclobutyl)carbonyl]piperidin-4-yl}-3-[(2-fluoropyridin-4-yl)amino]-1H-pyrazole-4-carboxamide | Calc'd 440, Found 440 |
| 34-61 | 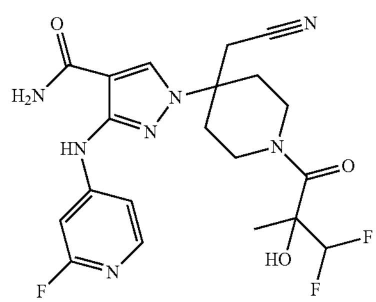 [SMILES: CC(O)(C(=O)N1CCC(CC#N)(n2cc(C(N)=O)c(Nc3ccnc(F)c3)n2)CC1)C(F)F] | 1-[4-(cyanomethyl)-1-(3,3-difluoro-2-hydroxy-2-methylpropanoyl)piperidin-4-yl]-3-[(2-fluoropyridin-4-yl)amino]-1H-pyrazole-4-carboxamide | Calc'd 466, Found 466 |
| 34-62 | 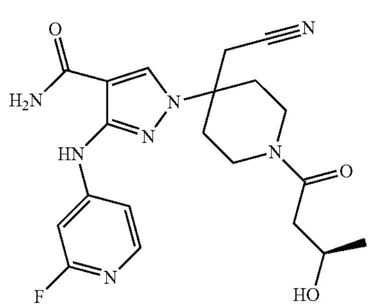 [SMILES: C[C@@H](O)CC(=O)N1CCC(CC#N)(n2cc(C(N)=O)c(Nc3ccnc(F)c3)n2)CC1] | 1-{4-(cyanomethyl)-1-[(3R)-3-hydroxybutanoyl]piperidin-4-yl}-3-[(2-fluoropyridin-4-yl)amino]-1H-pyrazole-4-carboxamide | Calc'd 430, Found 430 |

Scheme #28

Example #35-1

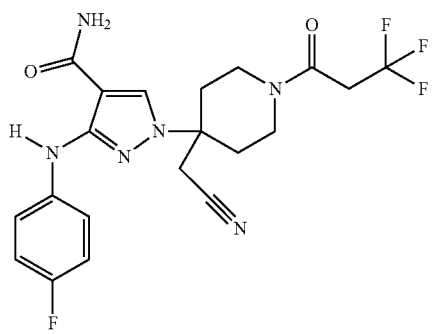

1-(4-(Cyanomethyl)-1-(3,3,3-trifluoropropanoyl)
piperidin-4-yl)-3-(4-fluorophenylamino)-1H-pyrazole-4-carboxamide 3,3,3-Trifluoropropanoic acid (0.009 mL, 0.1 mmol) and HATU (40 mg, 0.11 mmol) were combined in DMF (0.15 mL) and allowed to stir at ambient temperature for 5 minutes. A solution of 4-{4-carbamoyl-3-[(4-fluorophenyl)amino]-1H-pyrazol-1-yl}-4-(cyanomethyl)piperidinium trifluoroacetate (Intermediate #38-5) (30 mg, 0.066 mmol) in DMF (0.10 mL) was then added to the reaction mixture, followed by DIPEA (0.045 mL, 0.26 mmol). The resulting solution was allowed to stir at ambient temperature for 16 hours. The mixture was then purified directly by mass-triggered reverse-phase preparative HPLC (MeCN/water, with 0.1% v/v TFA modifier) to afford the title compound, Example #35-1.

$^1$H NMR (500 MHz, CDCl$_3$): δ 8.7 (s, 1H), 7.9 (s, 1H), 7.4 (m, J=4.4 Hz, 2H), 7.0 (t, J=8.8 Hz, 2H), 6.0 (br s, 2H), 4.4 (m, 1H), 3.7 (m, 1H), 3.18-3.11 (m, 3H), 3.0 (s, 1H), 2.9 (s, 2H), 2.72-2.64 (m, 2H), 2.05-1.98 (m, 2H).

LRMS (ESI) calc'd for $C_{20}H_{20}F_4N_6O_2$ [M+H]$^+$: 453. Found: 453

The following compounds shown TABLE 29 were prepared according to Scheme #28 following similar procedures described for Example #35-1, which can be achieved by those of ordinary skill in the art of organic synthesis utilizing but not limited to Intermediates #38-4 and 39 as an intermediate.

TABLE 29

| Example | Structure | Compound Name | Exact Mass [M + H]$^+$ |
|---|---|---|---|
| 35-2 | 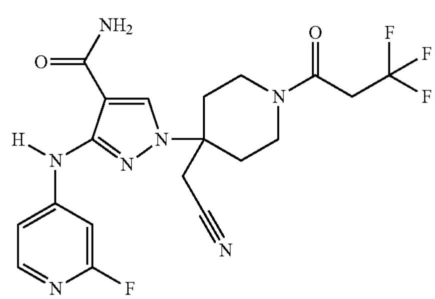 [SMILES: N#CCC1(n2cc(C(N)=O)c(Nc3ccnc(F)c3)n2)CCN(C(=O)CC(F)(F)F)CC1] | 1-(4-(cyanomethyl)-1-(3,3,3-trifluoropropanoyl)piperidin-4-yl)-3-(2-fluoropyridin-4-ylamino)-1H-pyrazole-4-carboxamide | Calc'd 454, Found 454 |
| 35-3 | 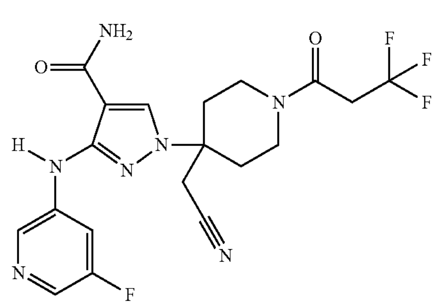 [SMILES: N#CCC1(n2cc(C(N)=O)c(Nc3cncc(F)c3)n2)CCN(C(=O)CC(F)(F)F)CC1] | 1-(4-(cyanomethyl)-1-(3,3,3-trifluoropropanoyl)piperidin-4-yl)-3-(5-fluoropyridin-3-ylamino)-1H-pyrazole-4-carboxamide | Calc'd 454, Found 454 |

Scheme #28

Example #36-1

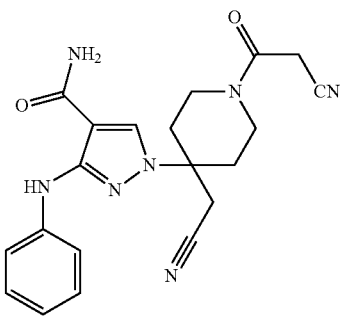

1-[1-(Cyanoacetyl)-4-(cyanomethyl)piperidin-4-yl]-
3-(phenylamino)-1H-pyrazole-4-carboxamide To a suspension of 4-[4-carbamoyl-3-(phenylamino)-1H-pyrazol-1-yl]-4-(cyanomethyl) piperidinium trifluoroacetate (60 mg, 0.14 mmol) in Me-THF (2.0 mL) was added DBU (0.065 mL, 0.43 mmol), followed by methyl cyanoacetate (28 mg, 0.29 mmol). The resulting mixture was allowed to stir for 1 hour before saturated aqueous NaHCO$_3$ solution was added and the resulting mixture was extracted with EtOAc (3×). The combined organic layers were dried over anhydrous Na$_2$SO$_4$, filtered, and concentrated in vacuo. The residue was purified by MPLC on silica gel (using a gradient elution of 50-100%, EtOAc/hexanes followed by elution with 10% MeOH/EtOAc) to afford the title compound, Example #36-1.

$^1$H NMR (600 MHz, DMSO-d$_6$): δ 9.04 (s, 1H), 8.49 (s, 1H), 7.50 (t, J=22.0 Hz, 3H), 7.20 (dd, J=26.7, 18.3 Hz, 3H), 6.80 (t, J=7.3 Hz, 1H), 4.15-3.91 (m, 3H), 3.57 (d, J=14.3 Hz, 1H), 3.16 (s, 2H), 3.14-3.05 (m, 1H), 3.02-2.92 (m, 1H), 2.40 (dd, J=28.1, 14.6 Hz, 2H), 2.05 (ddd, J=13.9, 10.2, 4.0 Hz, 1H), 2.00-1.88 (m, 1H).

LRMS (ESI) calc'd for C$_{20}$H$_{21}$N$_7$O$_2$ [M+H]$^+$: 392. Found: 392.

The following compounds shown in TABLE 30 were prepared according to Scheme #28 following similar procedures described for Example 36-1, which can be achieved by those of ordinary skill in the art of organic synthesis utilizing but not limited Intermediate #38-6 as an intermediate.

TABLE 30

| Example | Structure | Compound Name | Exact Mass [M + H]$^+$ |
|---|---|---|---|
| 36-2 | 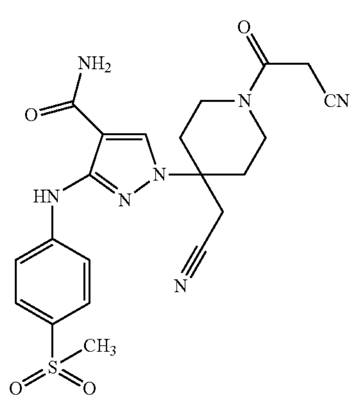 | 1-[1-(cyanoacetyl)-4-(cyanomethyl)piperidin-4-yl]-3-{[4-(methylsulfonyl)phenyl]amino}-1H-pyrazole-4-carboxamide | Calc'd 470, Found 470 |

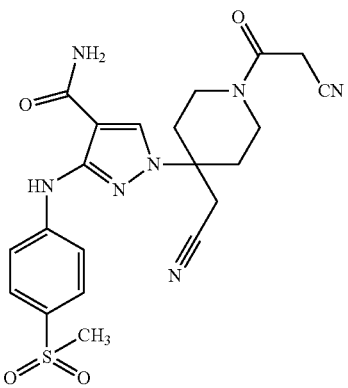 [SMILES: CS(=O)(=O)c1ccc(Nc2nn(C3(CC#N)CCN(C(=O)CC#N)CC3)cc2C(N)=O)cc1]

Scheme #28

Example #37-1

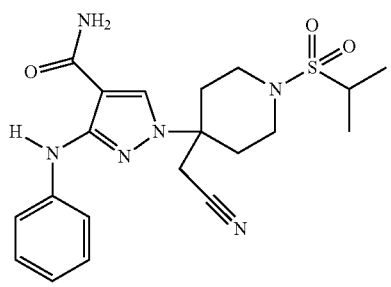

1-[4-(Cyanomethyl)-1-(isopropylsulfonyl)piperidin-4-yl]-3-(phenylamino)-1H-pyrazole-4-carboxamide To a suspension of 4-[4-carbamoyl-3-(phenylamino)-1H-pyrazol-1-yl]-4-(cyanomethyl)piperidinium trifluoroacetate (Intermediate #38-1) (30 mg, 0.068 mmol) in MeCN (0.50 mL) was added DIPEA (0.030 mL, 0.17 mmol) and DMAP (12 mg, 0.10 mmol). To this mixture was added isopropylsulfonyl chloride (0.008 mL, 0.1 mmol). The resulting mixture was allowed to stir at ambient temperature for 1 hour before it was diluted with DMSO (1.0 mL) and purified directly by reverse-phase preparative HPLC (using a gradient elution of 0-100% MeCN/water, with 0.1% v/v HCOOH modifier). Desired fractions were identified, combined and concentrated in vacuo to afford the title compound, Example #37-1. $^1$H NMR (600 MHz, DMSO-$d_6$): δ 9.03 (s, 1H), 8.47 (s, 1H), 7.54 (br s, 1H), 7.48 (d, J=7.8 Hz, 2H), 7.21 (t, J=7.8 Hz, 2H), 7.15 (br s, 1H), 6.80 (t, J=7.8 Hz, 1H), 3.50-3.56 (m, 2H), 3.19 (s, 2H), 2.98-3.10 (m, 2H), 2.38-2.49 (m, 3H), 2.02-2.08 (m, 2H), 1.15 (d, J=6.6 Hz, 6H). LRMS (ESI) calc'd for $C_{20}H_{26}N_6O_3S$ [M+H]+: 431. Found: 431.

The following compounds shown TABLE 31 were prepared according to Scheme #28 following similar procedures described for Example #37-1, which can be achieved by those of ordinary skill in the art of organic synthesis.

TABLE 31

| Example | Structure | Compound Name | Exact Mass [M + H]+ |
|---|---|---|---|
| 37-2 | 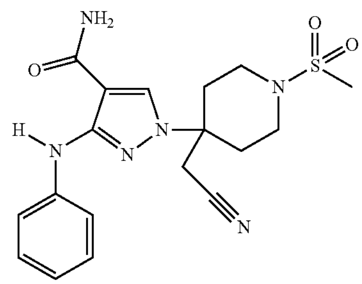 [SMILES: CS(=O)(=O)N1CCC(CC#N)(n2cc(C(N)=O)c(Nc3ccccc3)n2)CC1] | 1-[4-(cyanomethyl)-1-(methylsulfonyl)piperidin-4-yl]-3-(phenylamino)-1H-pyrazole-4-carboxamide | Calc'd 403, Found 403 |
| 37-3 | 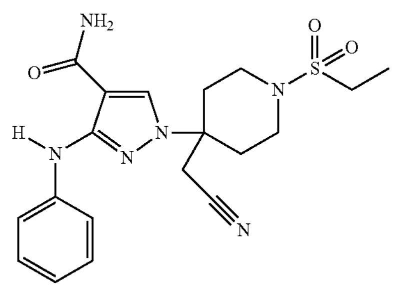 [SMILES: CCS(=O)(=O)N1CCC(CC#N)(n2cc(C(N)=O)c(Nc3ccccc3)n2)CC1] | 1-[4-(cyanomethyl)-1-(ethylsulfonyl)piperidin-4-yl]-3-(phenylamino)-1H-pyrazole-4-carboxamide | Calc'd 417, Found 417 |
| 37-4 | 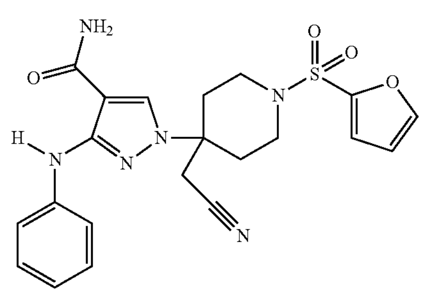 [SMILES: N#CCC1(n2cc(C(N)=O)c(Nc3ccccc3)n2)CCN(S(=O)(=O)c2ccco2)CC1] | 1-[4-(cyanomethyl)-1-(furan-2-ylsulfonyl)piperidin-4-yl]-3-(phenylamino)-1H-pyrazole-4-carboxamide | Calc'd 455, Found 455 |

TABLE 31-continued

| Example | Structure | Compound Name | Exact Mass [M + H]+ |
|---|---|---|---|
| 37-5 | 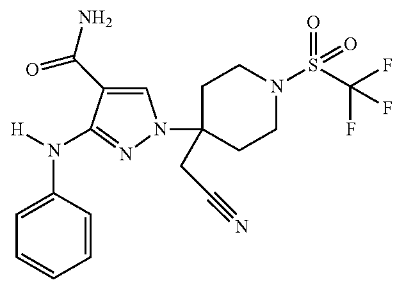 [SMILES: N#CCC1(n2cc(C(N)=O)c(Nc3ccccc3)n2)CCN(S(=O)(=O)C(F)(F)F)CC1] | 1-{4-(cyanomethyl)-1-[(trifluoromethyl)sulfonyl]piperidin-4-yl}-3-(phenylamino)-1H-pyrazole-4-carboxamide | Calc'd 457, Found 457 |
| 37-6 | 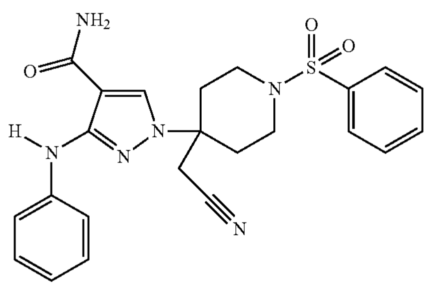 [SMILES: N#CCC1(n2cc(C(N)=O)c(Nc3ccccc3)n2)CCN(S(=O)(=O)c2ccccc2)CC1] | 1-[4-(cyanomethyl)-1-(phenylsulfonyl)piperidin-4-yl]-3-(phenylamino)-1H-pyrazole-4-carboxamide | Calc'd 465, Found 465 |
| 37-7 | 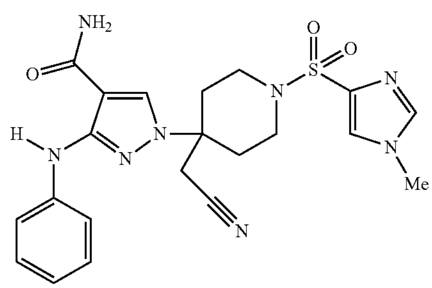 [SMILES: Cn1cnc(S(=O)(=O)N2CCC(CC#N)(n3cc(C(N)=O)c(Nc4ccccc4)n3)CC2)c1] | 1-{4-(cyanomethyl)-1-[(1-methyl-1H-imidazol-4-yl)sulfonyl]piperidin-4-yl}-3-(phenylamino)-1H-pyrazole-4-carboxamide | Calc'd 469, Found 469 |
| 37-8 | 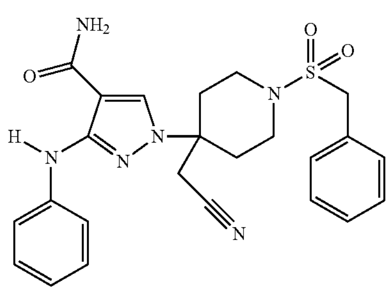 [SMILES: N#CCC1(n2cc(C(N)=O)c(Nc3ccccc3)n2)CCN(S(=O)(=O)Cc2ccccc2)CC1] | 1-[1-(benzylsulfonyl)-4-(cyanomethyl)piperidin-4-yl]-3-(phenylamino)-1H-pyrazole-4-carboxamide | Calc'd 479, Found 479 |
| 37-9 | 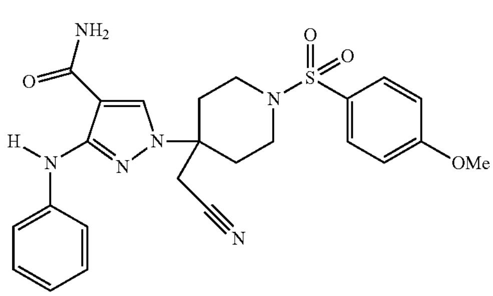 [SMILES: COc1ccc(S(=O)(=O)N2CCC(CC#N)(n3cc(C(N)=O)c(Nc4ccccc4)n3)CC2)cc1] | 1-{4-(cyanomethyl)-1-[(4-methoxyphenyl)sulfonyl]piperidin-4-yl}-3-(phenylamino)-1H-pyrazole-4-carboxamide | Calc'd 495, Found 495 |

TABLE 31-continued

| Example | Structure | Compound Name | Exact Mass [M + H]+ |
|---|---|---|---|
| 37-10 | 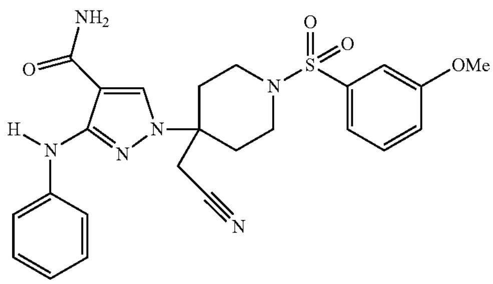 [SMILES: COc1cccc(S(=O)(=O)N2CCC(CC#N)(n3cc(C(N)=O)c(Nc4ccccc4)n3)CC2)c1] | 1-{4-(cyanomethyl)-1-[(3-methoxyphenyl)sulfonyl]piperidin-4-yl}-3-(phenylamino)-1H-pyrazole-4-carboxamide | Calc'd 495, Found 495 |
| 37-11 | 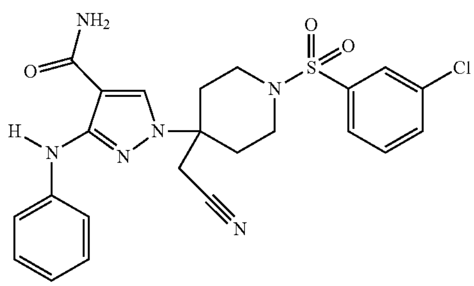 [SMILES: N#CCC1(n2cc(C(N)=O)c(Nc3ccccc3)n2)CCN(S(=O)(=O)c2cccc(Cl)c2)CC1] | 1-{1-[(3-chlorophenyl)sulfonyl]-4-(cyanomethyl)piperidin-4-yl}-3-(phenylamino)-1H-pyrazole-4-carboxamide | Calc'd 499, Found 499 |
| 37-12 | 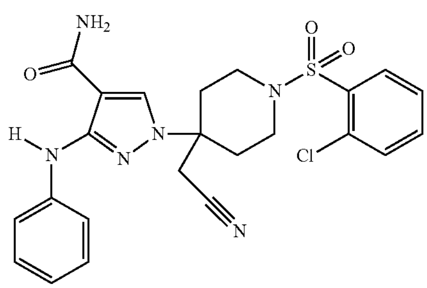 [SMILES: N#CCC1(n2cc(C(N)=O)c(Nc3ccccc3)n2)CCN(S(=O)(=O)c2ccccc2Cl)CC1] | 1-{1-[(2-chlorophenyl)sulfonyl]-4-(cyanomethyl)piperidin-4-yl}-3-(phenylamino)-1H-pyrazole-4-carboxamide | Calc'd 499, Found 499 |
| 37-13 | 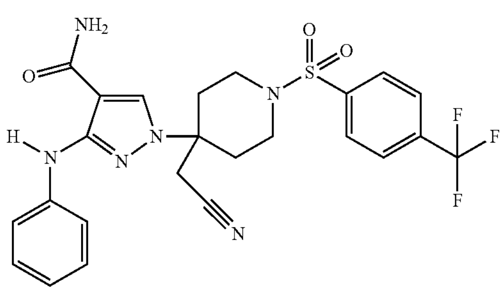 [SMILES: N#CCC1(n2cc(C(N)=O)c(Nc3ccccc3)n2)CCN(S(=O)(=O)c2ccc(C(F)(F)F)cc2)CC1] | 1-[4-(cyanomethyl)-1-{[4-(trifluoromethyl)phenyl]sulfonyl}piperidin-4-yl]-3-(phenylamino)-1H-pyrazole-4-carboxamide | Calc'd 533, Found 533 |
| 37-14 | 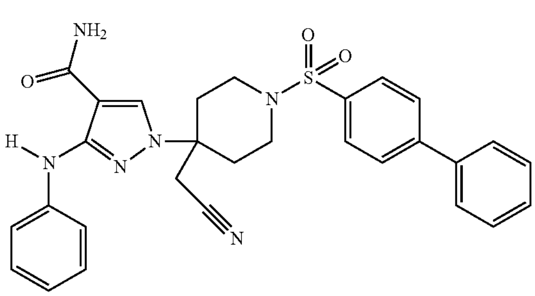 [SMILES: N#CCC1(n2cc(C(N)=O)c(Nc3ccccc3)n2)CCN(S(=O)(=O)c2ccc(-c3ccccc3)cc2)CC1] | 1-[1-(biphenyl-4-ylsulfonyl)-4-(cyanomethyl)piperidin-4-yl]-3-(phenylamino)-1H-pyrazole-4-carboxamide | Calc'd 541, Found 541 |

TABLE 31-continued

| Example | Compound Name | Exact Mass [M + H]+ |
|---|---|---|
| 37-15 | 1-[4-(cyanomethyl)-1-(cyclopropylsulfonyl)piperidin-4-yl]-3-(phenylamino)-1H-pyrazole-4-carboxamide | Calc'd 429, Found 429 |
| 37-16 | 1-[3-(cyanomethyl)-1-(methylsulfonyl)azetidin-3-yl]-3-(phenylamino)-1H-pyrazole-4-carboxamide | Calc'd 375, Found 375 |
| 37-17 | 1-[3-(cyanomethyl)-1-(furan-2-ylsulfonyl)azetidin-3-yl]-3-(phenylamino)-1H-pyrazole-4-carboxamide | Calc'd 427, Found 427 |
| 37-18 | 1-{3-(cyanomethyl)-1-[(trifluoromethyl)sulfonyl]azetidin-3-yl}-3-(phenylamino)-1H-pyrazole-4-carboxamide | Calc'd 429, Found 429 |
| 37-19 | 1-[3-(cyanomethyl)-1-(phenylsulfonyl)azetidin-3-yl]-3-(phenylamino)-1H-pyrazole-4-carboxamide | Calc'd 437, Found 437 |

TABLE 31-continued

| Example | Structure | Compound Name | Exact Mass [M + H]+ |
|---|---|---|---|
| 37-20 | 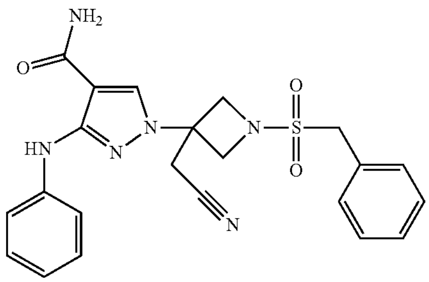 [SMILES: N#CCC1(n2cc(C(N)=O)c(Nc3ccccc3)n2)CN(S(=O)(=O)Cc2ccccc2)C1] | 1-[1-(benzylsulfonyl)-3-(cyanomethyl)azetidin-3-yl]-3-(phenylamino)-1H-pyrazole-4-carboxamide | Calc'd 451, Found 451 |

Scheme #28

Example #38-1

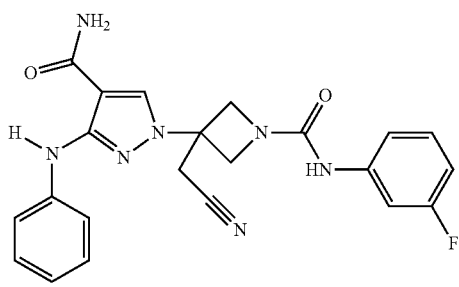

1-{3-(Cyanomethyl)-1-[(3-fluorophenyl)carbamoyl]azetidin-3-yl}-3-(phenylamino)-1H pyrazole-4-carboxamide 3-[4-Carbamoyl-3-(phenylamino)-1H-pyrazol-1-yl]-3-(cyanomethyl)azetidinium trifluoroacetate (Intermediate #38-2) (25 mg, 0.060 mmol) was dissolved in MeCN (0.50 mL) and treated with DIPEA (0.020 mL, 0.12 mmol) and 1-fluoro-3-isocyanatobenzene (0.010 mL, 0.090 mmol). The reaction mixture was stirred at ambient temperature for 2 hours and then diluted with DMSO (1.0 mL) and purified directly by reverse-phase preparative HPLC (using a gradient elution of 5-95% MeCN/water, with 0.1% v/v $NH_4OH$ modifier). Desired fractions were identified, combined, and concentrated in vacuo to afford the title compound, Example #38-1.

$^1$H NMR (600 MHz, DMSO-$d_6$) δ 9.09 (s, 1H), 8.92 (s, 1H), 8.55 (s, 1H), 7.62-7.56 (m, 1H), 7.50-7.46 (m, 3H), 7.25-7.18 (m, 5H), 6.81 (s, 1H), 6.73 (s, 1H), 4.36 (d, J=9.3, 2H), 4.30 (d, J=9.3, 2H), 3.59 (s, 2H). LRMS (ESI) calc'd for $C_{22}H_{20}FN_7O_2$ [M+H]+: 434. Found: 434.

The following compounds shown in TABLE 32 were prepared according to Scheme #28 following similar procedures described for Example #38-1, which can be achieved by those of ordinary skill in the art of organic synthesis utilizing but not limited to Intermediates #38-1, 38-2, 38-3, and 38-7 as intermediates.

TABLE 32

| Example | Structure | Compound Name | Exact Mass [M + H]+ |
|---|---|---|---|
| 38-2 | 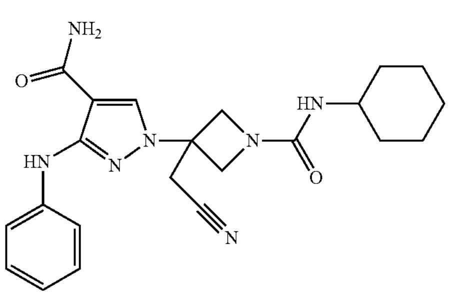 [SMILES: N#CCC1(n2cc(C(N)=O)c(Nc3ccccc3)n2)CN(C(=O)NC2CCCCC2)C1] | 1-[3-(cyanomethyl)-1-(cyclohexylcarbamoyl)azetidin-3-yl]-3-(phenylamino)-1H-pyrazole-4-carboxamide | Calc'd 422, Found 422 |

TABLE 32-continued

| Example | Structure | Compound Name | Exact Mass [M + H]+ |
|---|---|---|---|
| 38-3 | 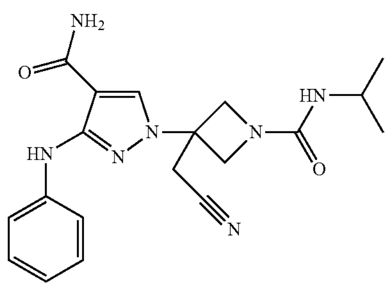 [SMILES: CC(C)NC(=O)N1CC(CC#N)(n2cc(C(N)=O)c(Nc3ccccc3)n2)C1] | 1-{3-(cyanomethyl)-1-[(1-methylethyl)carbamoyl]azetidin-3-yl}-3-(phenylamino)-1H-pyrazole-4-carboxamide | Calc'd 382, Found 382 |
| 38-4 | 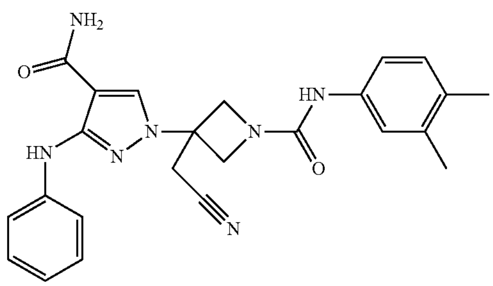 [SMILES: Cc1ccc(NC(=O)N2CC(CC#N)(n3cc(C(N)=O)c(Nc4ccccc4)n3)C2)cc1C] | 1-{3-(cyanomethyl)-1-[(3,4-dimethylphenyl)carbamoyl]azetidin-3-yl}-3-(phenylamino)-1H-pyrazole-4-carboxamide | Calc'd 444, Found 444 |
| 38-5 | 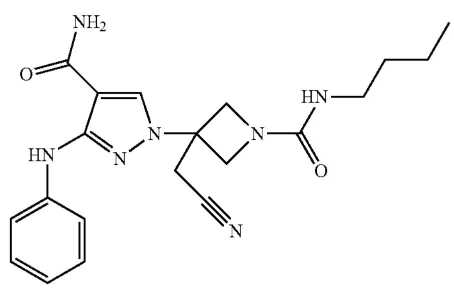 [SMILES: CCCCNC(=O)N1CC(CC#N)(n2cc(C(N)=O)c(Nc3ccccc3)n2)C1] | 1-[1-(butylcarbamoyl)-3-(cyanomethyl)azetidin-3-yl]-3-(phenylamino)-1H-pyrazole-4-carboxamide | Calc'd 396, Found 396 |
| 38-6 | 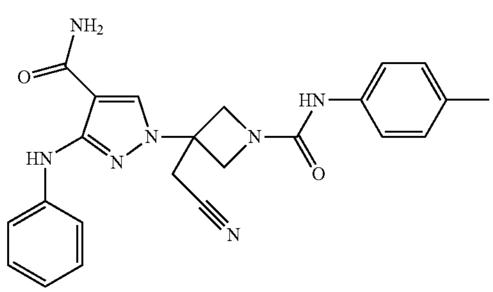 [SMILES: Cc1ccc(NC(=O)N2CC(CC#N)(n3cc(C(N)=O)c(Nc4ccccc4)n3)C2)cc1] | 1-{3-(cyanomethyl)-1-[(4-methylphenyl)carbamoyl]azetidin-3-yl}-3-(phenylamino)-1H-pyrazole-4-carboxamide | Calc'd 430, Found 430 |
| 38-7 | 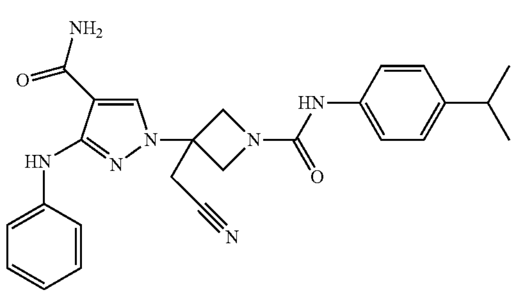 [SMILES: CC(C)c1ccc(NC(=O)N2CC(CC#N)(n3cc(C(N)=O)c(Nc4ccccc4)n3)C2)cc1] | 1-[3-(cyanomethyl)-1-{[4-(1-methylethyl)phenyl]carbamoyl}azetidin-3-yl-3-(phenylamino)-1H-pyrazole-4-carboxamide | Calc'd 458, Found 458 |

TABLE 32-continued

| Example | Structure | Compound Name | Exact Mass [M + H]⁺ |
|---|---|---|---|
| 38-8 | 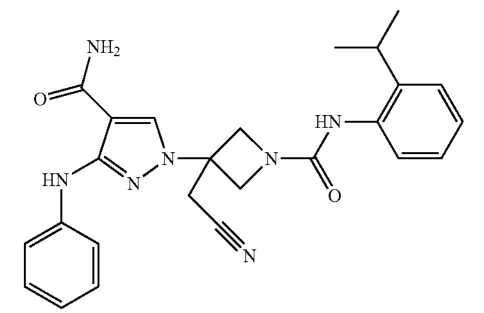 [SMILES: CC(C)c1ccccc1NC(=O)N1CC(CC#N)(n2cc(C(N)=O)c(Nc3ccccc3)n2)C1] | 1-[3-(cyanomethyl)-1-{[2-(1-methylethyl)phenyl]carbamoyl}azetidin-3-yl]-3-(phenylamino)-1H-pyrazole-4-carboxamide | Calc'd 458, Found 458 |
| 38-9 | 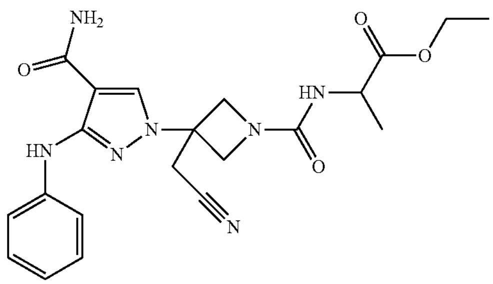 [SMILES: CCOC(=O)C(C)NC(=O)N1CC(CC#N)(n2cc(C(N)=O)c(Nc3ccccc3)n2)C1] | ethyl N-({3-[4-carbamoyl-3-(phenylamino)-1H-pyrazol-1-yl]-3-(cyanomethyl)azetidin-1-yl}carbonyl)alaninate | Calc'd 440, Found 440 |
| 38-10 | 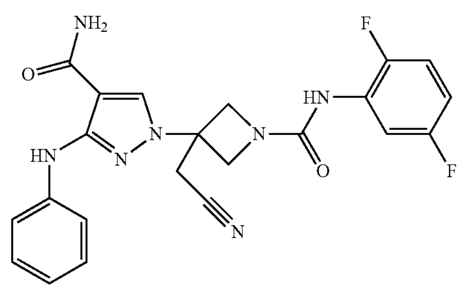 [SMILES: N#CCC1(n2cc(C(N)=O)c(Nc3ccccc3)n2)CN(C(=O)Nc2cc(F)ccc2F)C1] | 1-{3-(cyanomethyl)-1-[(2,5-difluorophenyl)carbamoyl]azetidin-3-yl}-3-(phenylamino)-1H-pyrazole-4-carboxamide | Calc'd 452, Found 452 |
| 38-11 | 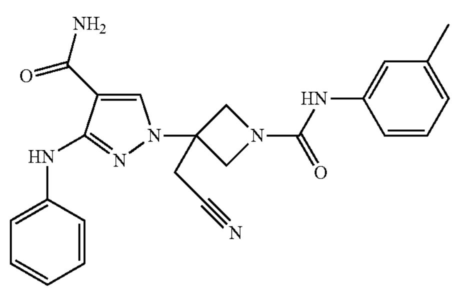 [SMILES: Cc1cccc(NC(=O)N2CC(CC#N)(n3cc(C(N)=O)c(Nc4ccccc4)n3)C2)c1] | 1-{3-(cyanomethyl)-1-[(3-methylphenyl)carbamoyl]azetidin-3-yl}-3-(phenylamino)-1H-pyrazole-4-carboxamide | Calc'd 430, Found 430 |
| 38-12 | 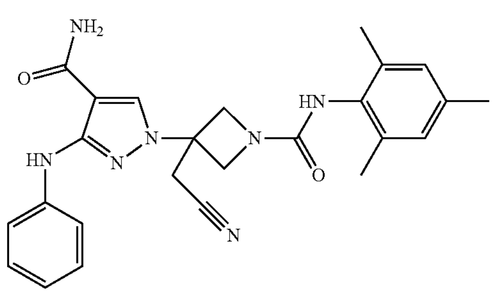 [SMILES: Cc1cc(C)c(NC(=O)N2CC(CC#N)(n3cc(C(N)=O)c(Nc4ccccc4)n3)C2)c(C)c1] | 1-{3-(cyanomethyl)-1-[(2,4,6-trimethylphenyl)carbamoyl]azetidin-3-yl}-3-(phenylamino)-1H-pyrazole-4-carboxamide | Calc'd 458, Found 458 |

TABLE 32-continued

| Example | Structure | Compound Name | Exact Mass [M + H]+ |
|---|---|---|---|
| 38-13 | 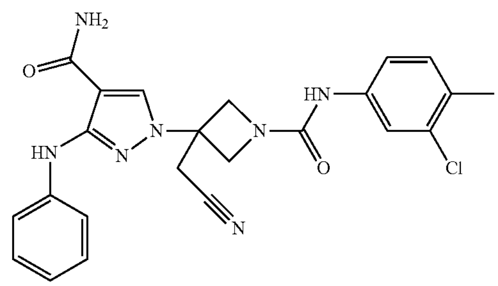 | 1-{1-[(3-chloro-4-methylphenyl)carbamoyl]-3-(cyanomethyl)azetidin-3-yl}-3-(phenylamino)-1H-pyrazole-4-carboxamide | Calc'd 464, Found 464 |
| 38-14 | 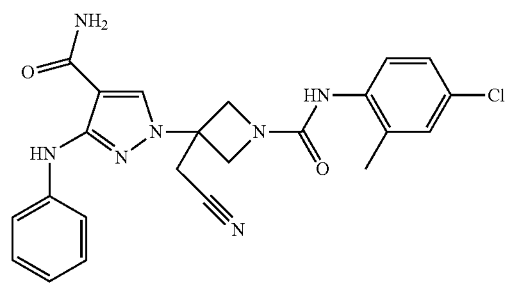 [SMILES: Cc1cc(Cl)ccc1NC(=O)N1CC(CC#N)(n2cc(C(N)=O)c(Nc3ccccc3)n2)C1] | 1-{1-[(4-chloro-2-methylphenyl)carbamoyl]-3-(cyanomethyl)azetidin-3-yl}-3-(phenylamino)-1H-pyrazole-4-carboxamide | Calc'd 464, Found 464 |
| 38-15 | 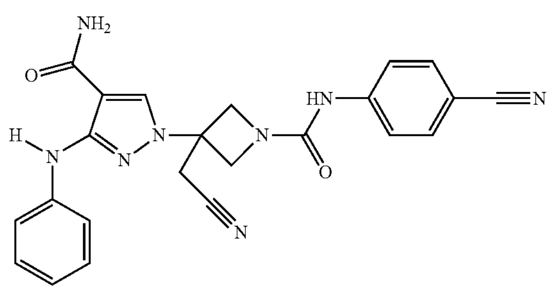 [SMILES: N#CCC1(n2cc(C(N)=O)c(Nc3ccccc3)n2)CN(C(=O)Nc2ccc(C#N)cc2)C1] | 1-{3-(cyanomethyl)-1-[(4-cyanophenyl)carbamoyl]azetidin-3-yl}-3-(phenylamino)-1H-pyrazole-4-carboxamide | Calc'd 441, Found 441 |
| 38-16 | 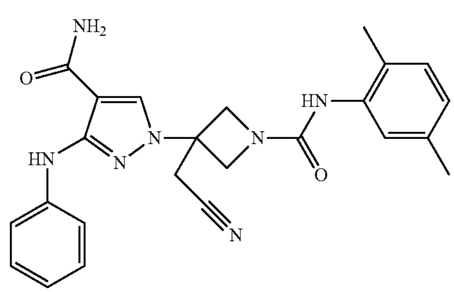 [SMILES: Cc1ccc(C)c(NC(=O)N2CC(CC#N)(n3cc(C(N)=O)c(Nc4ccccc4)n3)C2)c1] | 1-{3-(cyanomethyl)-1-[(2,5-dimethylphenyl)carbamoyl]azetidin-3-yl}-3-(phenylamino)-1H-pyrazole-4-carboxamide | Calc'd 444, Found 444 |
| 38-17 | 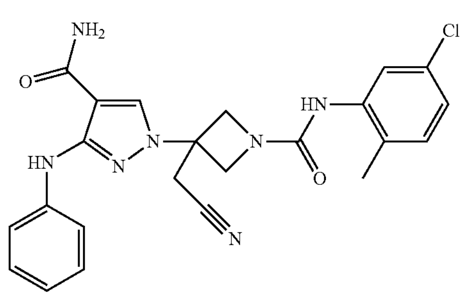 [SMILES: Cc1ccc(Cl)cc1NC(=O)N1CC(CC#N)(n2cc(C(N)=O)c(Nc3ccccc3)n2)C1] | 1-{1-[(5-chloro-2-methylphenyl)carbamoyl]-3-(cyanomethyl)azetidin-3-yl}-3-(phenylamino)-1H-pyrazole-4-carboxamide | Calc'd 464, Found 464 |

TABLE 32-continued

| Example | Structure | Compound Name | Exact Mass [M + H]+ |
|---|---|---|---|
| 38-18 | 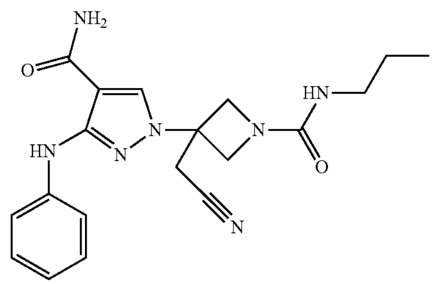 [SMILES: CCCNC(=O)N1CC(CC#N)(n2cc(C(N)=O)c(Nc3ccccc3)n2)C1] | 1-[3-(cyanomethyl)-1-(propylcarbamoyl)azetidin-3-yl]-3-(phenylamino)-1H-pyrazole-4-carboxamide | Calc'd 382, Found 382 |
| 38-19 | 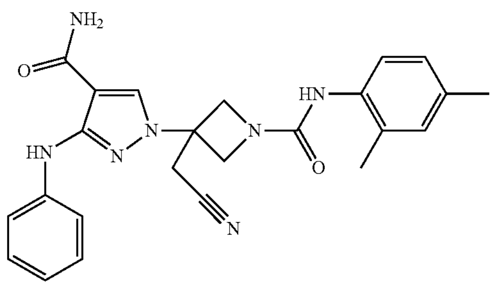 [SMILES: Cc1ccc(NC(=O)N2CC(CC#N)(n3cc(C(N)=O)c(Nc4ccccc4)n3)C2)c(C)c1] | 1-{3-(cyanomethyl)-1-[(2,4-dimethylphenyl)carbamoyl]azetidin-3-yl}-3-(phenylamino)-1H-pyrazole-4-carboxamide | Calc'd 444, Found 444 |
| 38-20 | 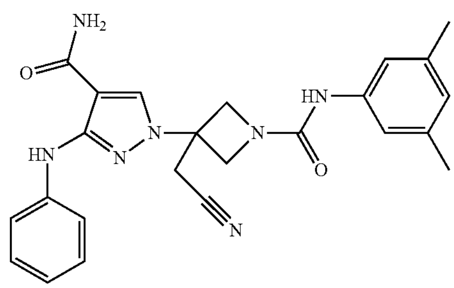 [SMILES: Cc1cc(C)cc(NC(=O)N2CC(CC#N)(n3cc(C(N)=O)c(Nc4ccccc4)n3)C2)c1] | 1-{3-(cyanomethyl)-1-[(3,5-dimethylphenyl)carbamoyl]azetidin-3-yl}-3-(phenylamino)-1H-pyrazole-4-carboxamide | Calc'd 444, Found 444 |
| 38-21 | 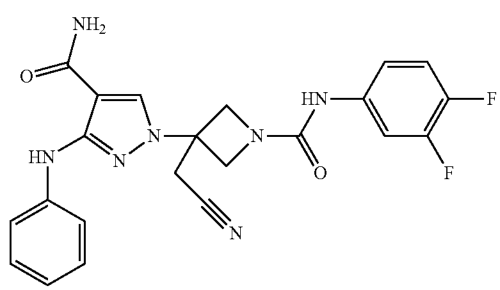 [SMILES: N#CCC1(n2cc(C(N)=O)c(Nc3ccccc3)n2)CN(C(=O)Nc2ccc(F)c(F)c2)C1] | 1-{3-(cyanomethyl)-1-[(3,4-difluorophenyl)carbamoyl]azetidin-3-yl}-3-(phenylamino)-1H-pyrazole-4-carboxamide | Calc'd 452, Found 452 |
| 38-22 | 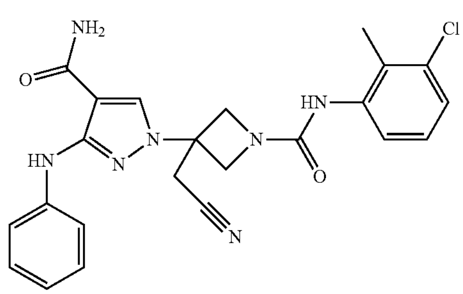 [SMILES: Cc1c(Cl)cccc1NC(=O)N1CC(CC#N)(n2cc(C(N)=O)c(Nc3ccccc3)n2)C1] | 1-{1-[(3-chloro-2-methylphenyl)carbamoyl]-3-(cyanomethyl)azetidin-3-yl}-3-(phenylamino)-1H-pyrazole-4-carboxamide | Calc'd 464, Found 464 |

TABLE 32-continued

| Example | Compound Name | Exact Mass [M + H]⁺ |
|---|---|---|
| 38-23 | 1-{3-(cyanomethyl)-1-[(2-ethyl-6-methylphenyl)carbamoyl]azetidin-3-yl}-3-(phenylamino)-1H-pyrazole-4-carboxamide | Calc'd 458, Found 458 |
| 38-24 | 1-{1-[(2-chloro-6-methylphenyl)carbamoyl]-3-(cyanomethyl)azetidin-3-yl}-3-(phenylamino)-1H-pyrazole-4-carboxamide | Calc'd 464, Found 464 |
| 38-25 | 1-{3-(cyanomethyl)-1-[(2-methoxy-5-methylphenyl)carbamoyl]azetidin-3-yl}-3-(phenylamino)-1H-pyrazole-4-carboxamide | Calc'd 460, Found 460 |
| 38-26 | 1-{3-(cyanomethyl)-1-[(4-ethoxyphenyl)carbamoyl]azetidin-3-yl}-3-(phenylamino)-1H-pyrazole-4-carboxamide | Calc'd 460, Found 460 |
| 38-27 | 1-{3-(cyanomethyl)-1-[(2-methylphenyl)carbamoyl]azetidin-3-yl}-3-(phenylamino)-1H-pyrazole-4-carboxamide | Calc'd 430, Found 430 |

TABLE 32-continued

| Example | Structure | Compound Name | Exact Mass [M + H]+ |
|---|---|---|---|
| 38-28 | 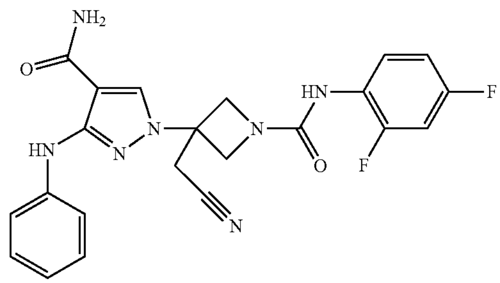 [SMILES: N#CCC1(n2cc(C(N)=O)c(Nc3ccccc3)n2)CN(C(=O)Nc2ccc(F)cc2F)C1] | 1-{3-(cyanomethyl)-1-[(2,4-difluorophenyl)carbamoyl]azetidin-3-yl}-3-(phenylamino)-1H-pyrazole-4-carboxamide | Calc'd 452, Found 452 |
| 38-29 | 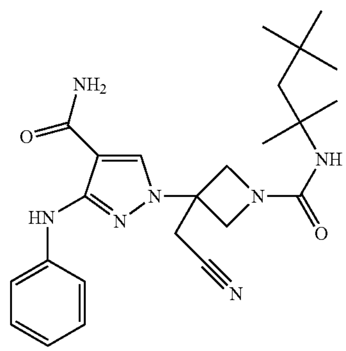 [SMILES: CC(C)(C)CC(C)(C)NC(=O)N1CC(CC#N)(n2cc(C(N)=O)c(Nc3ccccc3)n2)C1] | 1-{3-(cyanomethyl)-1-[(1,1,3,3-tetramethylbutyl)carbamoyl]azetidin-3-yl}-3-(phenylamino)-1H-pyrazole-4-carboxamide | Calc'd 452, Found 452 |
| 38-30 | 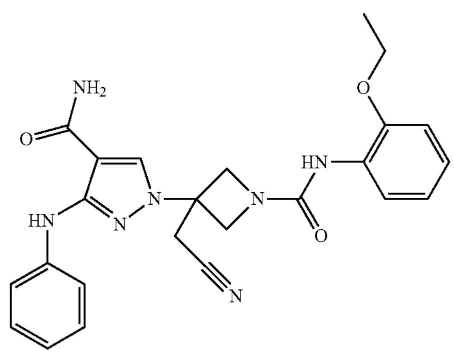 [SMILES: CCOc1ccccc1NC(=O)N1CC(CC#N)(n2cc(C(N)=O)c(Nc3ccccc3)n2)C1] | 1-{3-(cyanomethyl)-1-[(2-ethoxyphenyl)carbamoyl]azetidin-3-yl}-3-(phenylamino)-1H-pyrazole-4-carboxamide | Calc'd 460, Found 460 |
| 38-31 | 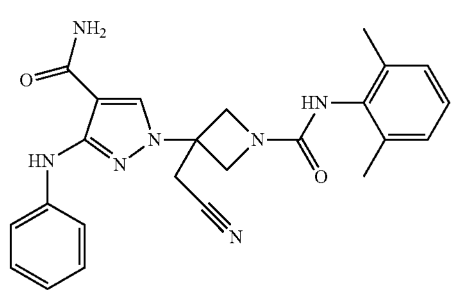 [SMILES: Cc1cccc(C)c1NC(=O)N1CC(CC#N)(n2cc(C(N)=O)c(Nc3ccccc3)n2)C1] | 1-{3-(cyanomethyl)-1-[(2,6-dimethylphenyl)carbamoyl]azetidin-3-yl}-3-(phenylamino)-1H-pyrazole-4-carboxamide | Calc'd 444, Found 444 |
| 38-32 | 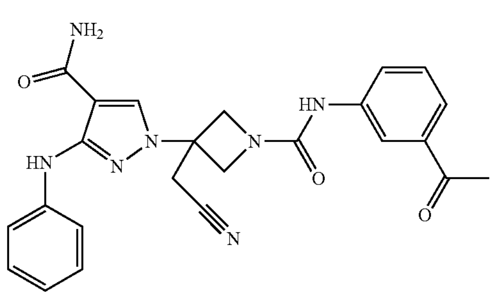 [SMILES: CC(=O)c1cccc(NC(=O)N2CC(CC#N)(n3cc(C(N)=O)c(Nc4ccccc4)n3)C2)c1] | 1-{1-[(3-acetylphenyl)carbamoyl]-3-(cyanomethyl)azetidin-3-yl}-3-(phenylamino)-1H-pyrazole-4-carboxamide | Calc'd 458, Found 458 |

TABLE 32-continued

| Example | Structure | Compound Name | Exact Mass [M + H]+ |
|---|---|---|---|
| 38-33 | 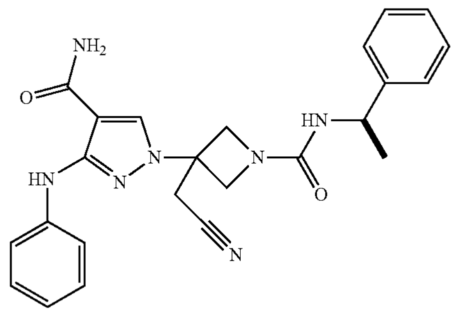 [SMILES: C[C@@H](NC(=O)N1CC(CC#N)(n2cc(C(N)=O)c(Nc3ccccc3)n2)C1)c1ccccc1] | 1-[3-(cyanomethyl)-1-{[(1R)-1-phenylethyl]carbamoyl}azetidin-3-yl]-3-(phenylamino)-1H-pyrazole-4-carboxamide | Calc'd 444, Found 444 |
| 38-34 | 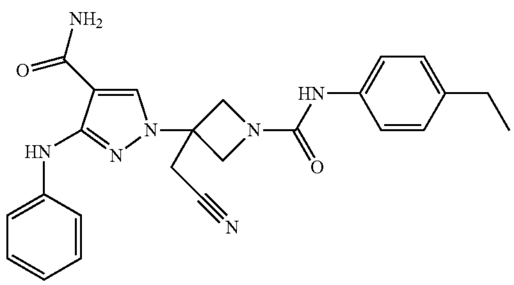 [SMILES: CCc1ccc(NC(=O)N2CC(CC#N)(n3cc(C(N)=O)c(Nc4ccccc4)n3)C2)cc1] | 1-{3-(cyanomethyl)-1-[(4-ethylphenyl)carbamoyl]azetidin-3-yl}-3-(phenylamino)-1H-pyrazole-4-carboxamide | Calc'd 444, Found 444 |
| 38-35 | 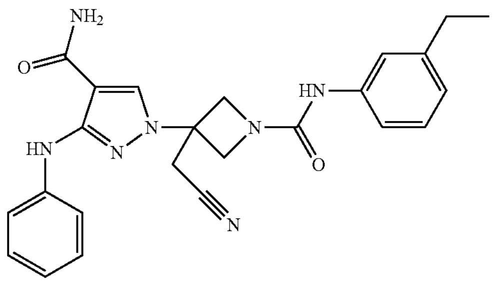 [SMILES: CCc1cccc(NC(=O)N2CC(CC#N)(n3cc(C(N)=O)c(Nc4ccccc4)n3)C2)c1] | 1-{3-(cyanomethyl)-1-[(3-ethylphenyl)carbamoyl]azetidin-3-yl}-3-(phenylamino)-1H-pyrazole-4-carboxamide | Calc'd 444, Found 444 |
| 38-36 | 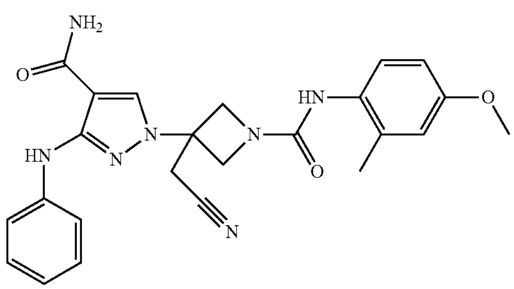 [SMILES: COc1ccc(NC(=O)N2CC(CC#N)(n3cc(C(N)=O)c(Nc4ccccc4)n3)C2)c(C)c1] | 1-{3-(cyanomethyl)-1-[(4-methoxy-2-methylphenyl)carbamoyl]azetidin-3-yl}-3-(phenylamino)-1H-pyrazole-4-carboxamide | Calc'd 460, Found 460 |
| 38-37 | 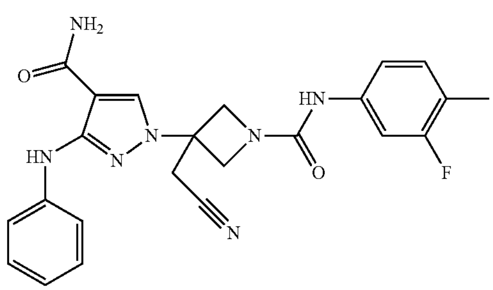 | 1-{3-(cyanomethyl)-1-[(3-fluoro-4-methylphenyl)carbamoyl]azetidin-3-yl}-3-(phenylamino)-1H-pyrazole-4-carboxamide | Calc'd 448, Found 448 |

TABLE 32-continued

| Example | Structure | Compound Name | Exact Mass [M + H]+ |
|---|---|---|---|
| 38-38 | 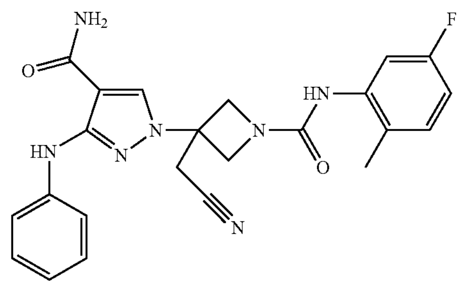 [SMILES: Cc1ccc(F)cc1NC(=O)N1CC(CC#N)(n2cc(C(N)=O)c(Nc3ccccc3)n2)C1] | 1-{3-(cyanomethyl)-1-[(5-fluoro-2-methylphenyl)carbamoyl]azetidin-3-yl}-3-(phenylamino)-1H-pyrazole-4-carboxamide | Calc'd 448, Found 448 |
| 38-39 | 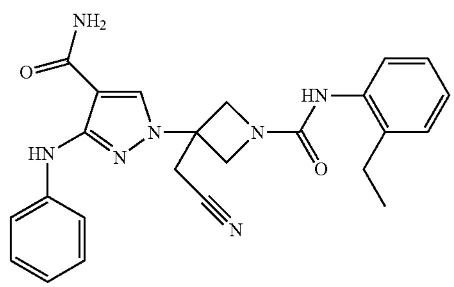 [SMILES: CCc1ccccc1NC(=O)N1CC(CC#N)(n2cc(C(N)=O)c(Nc3ccccc3)n2)C1] | 1-{3-(cyanomethyl)-1-[(2-ethylphenyl)carbamoyl]azetidin-3-yl}-3-(phenylamino)-1H-pyrazole-4-carboxamide | Calc'd 444, Found 444 |
| 38-40 | 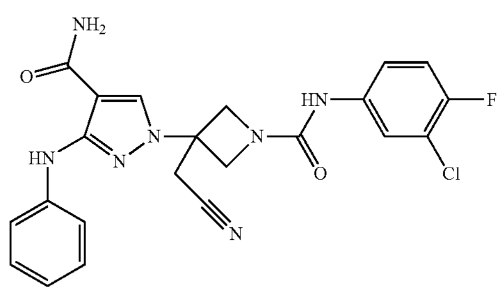 [SMILES: N#CCC1(n2cc(C(N)=O)c(Nc3ccccc3)n2)CN(C(=O)Nc2ccc(F)c(Cl)c2)C1] | 1-{1-[(3-chloro-4-fluorophenyl)carbamoyl]-3-(cyanomethyl)azetidin-3-yl}-3-(phenylamino)-1H-pyrazole-4-carboxamide | Calc'd 468, Found 468 |
| 38-41 | 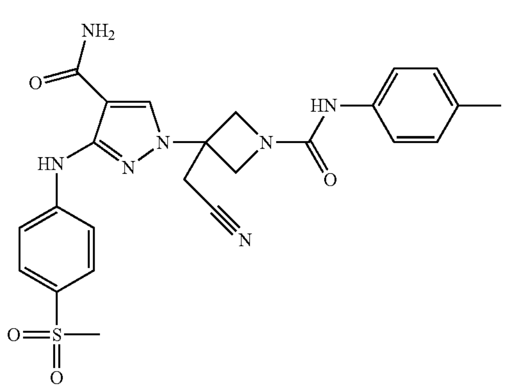 [SMILES: Cc1ccc(NC(=O)N2CC(CC#N)(n3cc(C(N)=O)c(Nc4ccc(S(C)(=O)=O)cc4)n3)C2)cc1] | 1-{3-(cyanomethyl)-1-[(4-methylphenyl)carbamoyl]azetidin-3-yl}-3-{[4-(methylsulfonyl)phenyl]amino}-1H-pyrazole-4-carboxamide | Calc'd 508, Found 508 |

TABLE 32-continued

| Example | Structure | Compound Name | Exact Mass [M + H]+ |
| --- | --- | --- | --- |
| 38-42 | 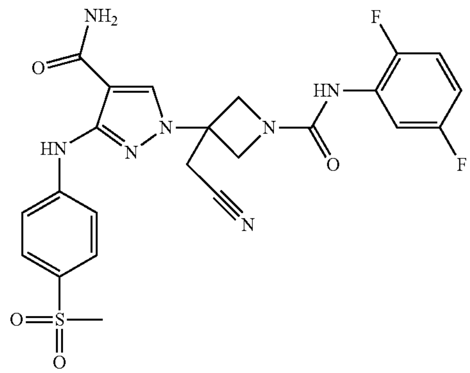 [SMILES: CS(=O)(=O)c1ccc(Nc2nn(C3(CC#N)CN(C(=O)Nc4cc(F)ccc4F)C3)cc2C(N)=O)cc1] | 1-{3-(cyanomethyl)-1-[(2,5-difluorophenyl)carbamoyl]azetidin-3-yl}-3-{[4-(methylsulfonyl)phenyl]amino}-1H-pyrazole-4-carboxamide | Calc'd 530, Found 530 |
| 38-43 | 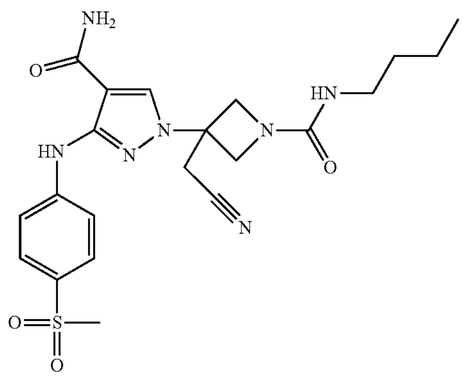 [SMILES: CCCCNC(=O)N1CC(CC#N)(n2cc(C(N)=O)c(Nc3ccc(S(C)(=O)=O)cc3)n2)C1] | 1-[1-(butylcarbamoyl)-3-(cyanomethyl)azetidin-3-yl]-3-{[4-(methylsulfonyl)phenyl]amino}-1H-pyrazole-4-carboxamide | Calc'd 474, Found 474 |
| 38-44 | 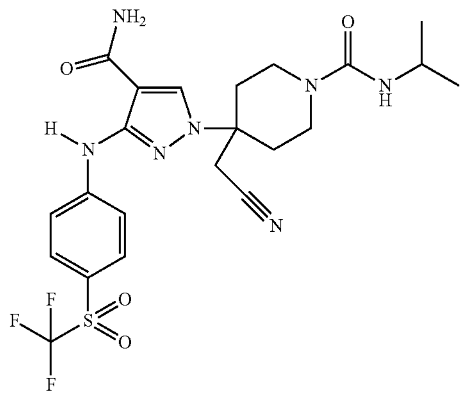 [SMILES: CC(C)NC(=O)N1CCC(CC#N)(n2cc(C(N)=O)c(Nc3ccc(S(=O)(=O)C(F)(F)F)cc3)n2)CC1] | 4-(4-carbamoyl-3-(4-(trifluoromethylsulfonyl)phenylamino)-1H-pyrazol-1-yl)-4-(cyanomethyl)-N-isopropylpiperidine-1-carboxamide | Calc'd 542, Found 542 |
| 38-45 | 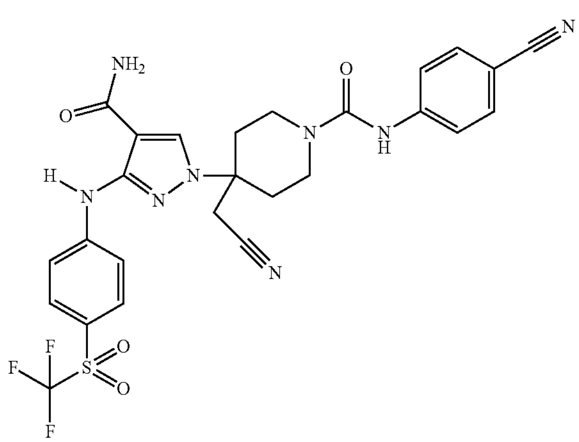 [SMILES: N#CCC1(n2cc(C(N)=O)c(Nc3ccc(S(=O)(=O)C(F)(F)F)cc3)n2)CCN(C(=O)Nc2ccc(C#N)cc2)CC1] | 4-(4-carbamoyl-3-(4-(trifluoromethylsulfonyl)phenylamino)-1H-pyrazol-1-yl)-4-(cyanomethyl)-N-(4-cyanophenyl)piperidine-1-carboxamide | Calc'd 601, Found 601 |

TABLE 32-continued

| Example | Structure | Compound Name | Exact Mass [M + H]+ |
|---|---|---|---|
| 38-46 | 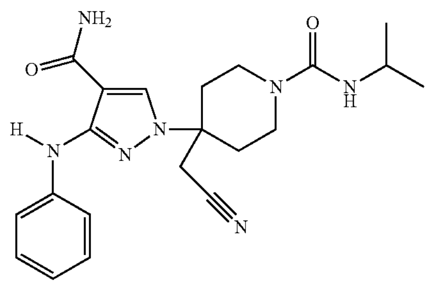 [SMILES: CC(C)NC(=O)N1CCC(CC#N)(n2cc(C(N)=O)c(Nc3ccccc3)n2)CC1] | 4-[4-Carbamoyl-3-(phenylamino)-1H-pyrazol-1-yl]-4-(cyanomethyl)-N-(1-methylethyl)piperidine-1-carboxamide | Calc'd 410, Found 410 |
| 38-47 | 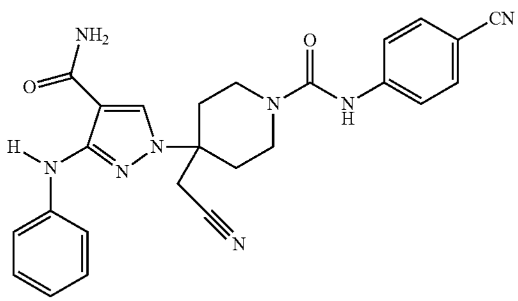 [SMILES: N#CCC1(n2cc(C(N)=O)c(Nc3ccccc3)n2)CCN(C(=O)Nc2ccc(C#N)cc2)CC1] | 4-[4-carbamoyl-3-(phenylamino)-1H-pyrazol-1-yl]-4-(cyanomethyl)-N-(4-cyanophenyl)piperidine-1-carboxamide | Calc'd 469, Found 469 |

Scheme #34

Example #39-1

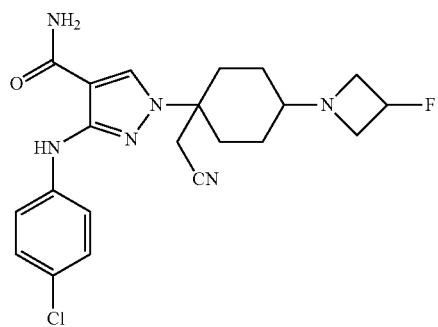

Cis or trans 3-((4-chlorophenyl)amino)-1-(1-(cyanomethyl)-4-(3-fluoroazetidin-1-yl)cyclohexyl)-1H-pyrazole-4-carboxamide

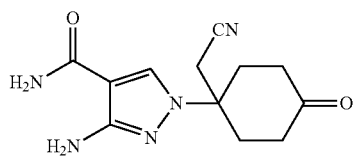

Step A. 3-Amino-1-(1-(cyanomethyl)-4-oxocyclohexyl)-1H-pyrazole-4-carboxamide

Aqueous hydrochloric acid (1 N, 36 mL, 36 mmol) was added to a solution of 3-amino-1-(8-(cyanomethyl)-1,4-dioxaspiro[4.5]decan-8-yl)-1H-pyrazole-4-carboxamide (Intermediate 35-5) (5.5 g, 18 mmol) in THF (106 mL). The reaction vessel was capped with a reflux condenser and heated to 80° C. for 2 hours. The reaction mixture was then cooled to ambient temperature, diluted with ethyl acetate, and neutralized with saturated aqueous sodium bicarbonate solution. The organic layer was separated and then washed with brine. The washed solution was dried over sodium sulfate, the dried solution was filtered, and the filtrate was concentrated to afford the title compound, which was used without further purification.

LRMS (ESI) calc'd for $C_{14}H_{29}N_5O_3$ [M+H]+: 262. Found: 262.

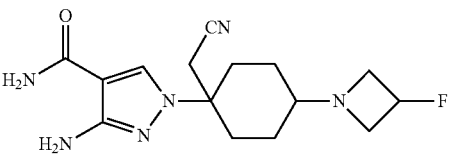

Step B. Cis or trans 3-amino-1-(1-(cyanomethyl)-4-(3-fluoroazetidin-1-yl)cyclohexyl)-1H-pyrazole-4-carboxamide Sodium cyanoborohydride (962 mg, 15.3 mmol) was added to a solution of 3-amino-1-(1-(cyanomethyl)-4-oxocyclohexyl)-1H-pyrazole-4-carboxamide (1.6 g, 6.1 mmol), 3-fluoroazetidine hydrochloride (1.71 g, 15.3 mmol), and triethylamine (2.13 mL, 15.3 mmol) in tetrahydrofuran (30 mL) and methanol (30 mL) at 23° C. The reaction mixture was stirred for 1 hour at 23° C., then was concentrated. The residue was partitioned between ethyl acetate and aqueous saturated sodium bicarbonate solution. The organic layer was washed with brine, and the washed solution was dried over anhydrous sodium sulfate. The dried solution was filtered, and the filtrate was concentrated in vacuo. The residue was purified by MPLC on silica gel (using a gradient elution of 5 to 15% MeOH/EtOAc) to afford the title compound.

LRMS (ESI) calc'd for $C_{15}H_{22}FN_6O$ [M+H]$^+$: 321. Found: 321.

Step C. Cis or trans 3-((4-chlorophenyl)amino)-1-(1-(cyanomethyl)-4-(3-fluoroazetidin-1-yl)cyclohexyl)-1H-pyrazole-4-carboxamide Nitrogen was sparged through a mixture of cis or trans 3-amino-1-(1-(cyanomethyl)-4-(3-fluoroazetidin-1-yl)cyclohexyl)-1H-pyrazole-4-carboxamide (50 mg, 0.16 mmol), 1-bromo-4-chlorobenzene (60 mg, 0.31 mmol), potassium acetate (31 mg, 0.31 mmol), and Me$_4$-$^t$Bu-X-Phos (30 mg, 0.062 mmol) in isopropanol (1.0 mL) in a reaction vessel for 5 minutes, and then Pd$_2$(dba)$_3$ (29 mg, 0.031 mmol) was added. The reaction vial was sealed, and heated to 85° C. After 2 hours, the reaction mixture was cooled to ambient temperature. The cooled reaction mixture was partitioned between ethyl acetate and water. The organic layer was washed with brine, the washed solution was dried over anhydrous sodium sulfate and then filtered. The filtrate was concentrated and the residue was purified by MPLC on silica gel (using a gradient elution of 80-100% EtOAc/hexanes) to afford the title compound, Example #39-1.

LRMS (ESI) calc'd for $C_{21}H_{25}ClFN_6O$ [M+H]$^+$: 431. Found: 431.

The following compound shown in TABLE 33 were prepared according to Scheme #34 following similar procedures described for Example #39-1, which can be achieved by those of ordinary skill in the art of organic synthesis.

Scheme #36

Examples #40-1 and 40-2

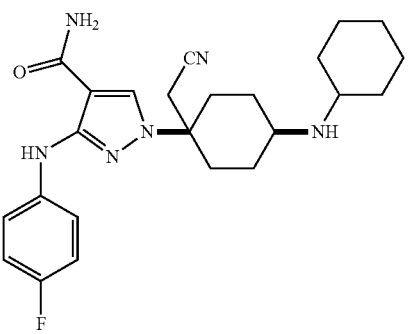

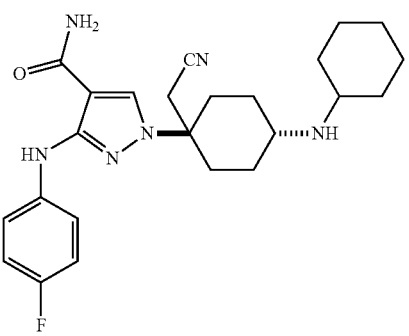

TABLE 33

| Example | Structure | Compound Name | Exact Mass [M + H]$^+$ |
|---------|-----------|---------------|------------------------|
| 39-2 | 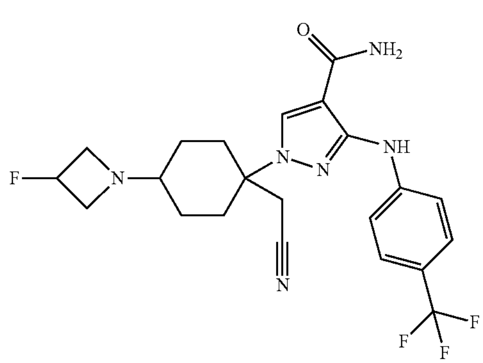 [SMILES: N#CCC1(n2cc(C(N)=O)c(Nc3ccc(C(F)(F)F)cc3)n2)CCC(N2CC(F)C2)CC1] | 1-[1-(cyanomethyl)-4-(3-fluoroazetidin-1-yl)cyclohexyl]-3-{[4-(trifluoromethyl)phenyl]amino}-1H-pyrazole-4-carboxamide | Calc'd 465, found 465 |

Cis or trans 1-(1-(cyanomethyl)-4-(cyclohexylamino)cyclohexyl)-3-((4-fluorophenyl)amino)-1H-pyrazole-4-carboxamide

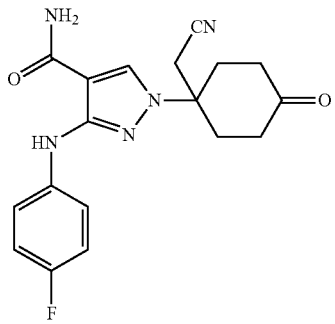 [SMILES: N#CCC1(n2cc(C(N)=O)c(Nc3ccc(F)cc3)n2)CCC(=O)CC1]

Step A: 1-(1-(Cyanomethyl)-4-oxocyclohexyl)-3-((4-fluorophenyl)amino)-1H-pyrazole-4-carboxamide (Example 40-1A)

A solution of 1-[8-(cyanomethyl)-1,4-dioxaspiro[4.5]dec-8-yl]-3-[(4-fluorophenyl)amino]-1H-pyrazole-4-carboxamide (Example 6-6) (150 mg, 0.376 mmol) in 1:3 ratio of 1N aqueous HCl/THF (0.6 mL/1.8 mL) was heated at 75° C. for 2 hours. The reaction mixture was cooled to ambient temperature, diluted with EtOAc and saturated aqueous NaHCO$_3$. The organic layer was separated, and the aqueous layer was extracted with EtOAc. The combined organic extracts were washed with brine, dried over anhydrous MgSO$_4$, and concentrated in vacuo. The residue was purified by MPLC on silica gel (using a gradient elution of 0-10% MeOH/DCM) to afford Intermediate 36-A. $^1$H NMR (600 MHz, acetone-d$_6$): δ 9.18 (s, 1H), 8.59 (s, 1H), 7.61-7.63 (m, 2H), 7.20 (brs, 1H), 7.01 (t, J=8.4 Hz, 2H), 6.54 (brs, 1H), 3.22 (s, 2H), 2.88-2.95 (m, 2H), 2.40-2.51 (m, 4H), 2.34-2.37 (m, 2H). LRMS (ESI) calc'd for C$_{18}$H$_{19}$FN$_5$O$_2$ [M+H]$^+$: 356. Found: 356.

Step B: Cis or trans 1-(1-(cyanomethyl)-4-(cyclohexylamino)cyclohexyl)-3-((4-fluorophenyl)amino)-1H-pyrazole-4-carboxamide Cyclohexanamine (0.026 mL, 0.22 mmol) was added to a mixture of 1-(1-(cyanomethyl)-4-oxocyclohexyl)-3-((4-fluorophenyl)amino)-1H-pyrazole-4-carboxamide (40 mg, 0.11 mmol) in MeOH (0.31 mL) and DMF (0.062 mL). The reaction mixture was allowed to stir at 60° C. for 15 minutes. Sodium cyanoborohydride (7 mg, 0.1 mmol) was added to the reaction mixture and allowed to stir at 60° C. for 24 hours. The mixture was then purified directly by mass-triggered reverse-phase preparative HPLC (MeCN/water, with 0.1% v/v TFA modifier) to afford a diastereometric mixture of the title compound. 1-(1-(cyanomethyl)-4-((2,4-difluorophenyl)amino)cyclohexyl)-3-((4-fluorophenyl)amino)-1H-pyrazole-4-carboxamide was chirally resolved to the constituent diastereomers by chiral SFC (Chiral Technology IB-H, 2.1× 25 cm, 30% MeOH/70% CO$_2$, 70 mL/min). Desired fractions were identified, combined, and concentrated in vacuo to afford diastereomerically pure samples of the title compounds:

Example #40-1

Cis or trans 1-(1-(cyanomethyl)-4-(cyclohexylamino)cyclohexyl)-3-((4-fluorophenyl)amino)-1H-pyrazole-4-carboxamide, first diastereomer to elute from column.
$^1$H NMR (600 MHz, DMSO-d$_6$): δ 9.02 (s, 1H), 8.49 (s, 1H), 7.58 (br s, 1H), 7.52-7.50 (m, 2H), 7.12 (br s, 1H), 7.04 (t, J=8.4 Hz, 2H), 3.32-3.31 (m, 114), 2.98 (s, 2H), 2.58-2.55 (m, 2H), 2.47-2.46 (m, 1H), 1.85-1.80 (m, 6H), 1.65-1.63 (m, 2H), 1.54-1.52 (m, 1H), 1.20-1.03 (m, 8H).
LRMS (ESI) calc'd for C$_{24}$H$_{31}$FN$_6$O [M+H]$^+$: 439. Found: 439.

Example #40-2

Cis or trans 1-(1-(cyanomethyl)-4-(cyclohexylamino)cyclohexyl)-3-((4-fluorophenyl)amino)-1H-pyrazole-4-carboxamide, second diastereomer to elute from column.
$^1$H NMR (600 MHz, DMSO-d$_6$): δ 9.02 (s, 1H), 8.40 (s, 1H), 7.57 (br s, 1H), 7.53-7.51 (m, 2H), 7.11 (br s, 1H), 7.03 (t, J=9 Hz, 2H), 3.32-3.31 (m, 1H), 3.17 (s, 2H), 2.47-2.46 (m, 1H), 2.25 (m, 2H), 1.99-1.96 (m, 2H), 1.87 (m, 4H), 1.69-1.67 (m, 2H), 1.56-1.54 (m, 3H), 1.23-1.20 (m, 3H), 1.10-1.02 (m, 3H).
LRMS (ESI) calc'd for C$_{24}$H$_{31}$FN$_6$O [M+H]$^+$: 439. Found: 439.

The following compounds shown in TABLE 34 were prepared according to Scheme #36 following similar procedures described for Example #40-1 and 40-2, which can be achieved by those of ordinary skill in the art of organic synthesis.

TABLE 34

| Example | Structure | Compound Name | Exact Mass [M + H]$^+$ |
|---|---|---|---|
| 40-3 | 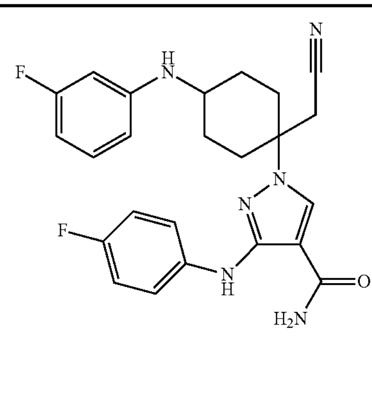 | Cis or trans 1-{1-(cyanomethyl)-4-[(3-fluorophenyl)amino]cyclohexyl}-3-[(4-fluorophenyl)amino]-1H-pyrazole-4-carboxamide | Calc'd 451, Found 451 |

TABLE 34-continued

| Example | Structure | Compound Name | Exact Mass [M + H]+ |
|---|---|---|---|
| 40-4 | 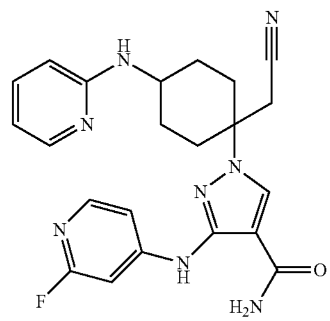 [SMILES: N#CCC1(n2cc(C(N)=O)c(Nc3ccnc(F)c3)n2)CCC(Nc2ccccn2)CC1] | Cis or trans 1-[1-(cyanomethyl)-4-(pyridin-2-ylamino)cyclohexyl]-3-[(2-fluoropyridin-4-yl)amino]-1H-pyrazole-4-carboxamide | Calc'd 435, Found 435 |
| 40-5 | 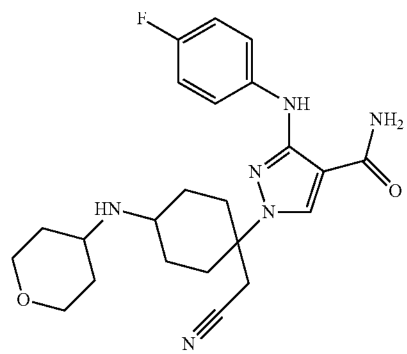 [SMILES: N#CCC1(n2cc(C(N)=O)c(Nc3ccc(F)cc3)n2)CCC(NC2CCOCC2)CC1] | Cis or trans 1-[1-(cyanomethyl)-4-(tetrahydro-2H-pyran-4-ylamino)cyclohexyl]-3-[(4-fluorophenyl)amino]-1H-pyrazole-4-carboxamide | Calc'd 441, Found 441 |
| 40-6 | 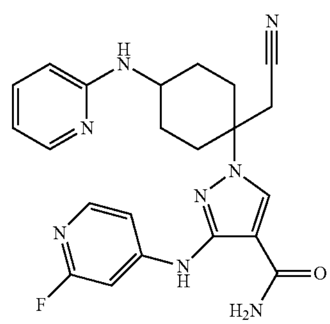 [SMILES: N#CCC1(n2cc(C(N)=O)c(Nc3ccnc(F)c3)n2)CCC(Nc2ccccn2)CC1] | Cis or trans 1-[1-(cyanomethyl)-4-(pyridin-3-ylamino)cyclohexyl]-3-[(2-fluoropyridin-4-yl)amino]-1H-pyrazole-4-carboxamide | Calc'd 435, Found 435 |
| 40-7 | 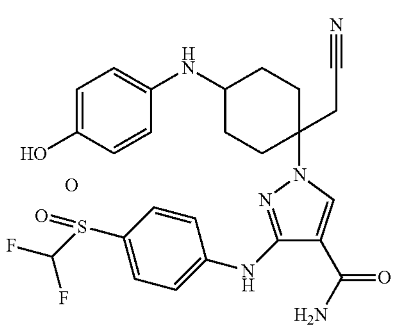 | Cis or trans 1-{1-(cyanomethyl)-4-[(4-hydroxyphenyl)amino]cyclohexyl}-3-({4-[(difluoromethyl)sulfonyl]phenyl}amino)-1H-pyrazole-4-carboxamide | Calc'd 545, Found 545 |

TABLE 34-continued

| Example | Structure | Compound Name | Exact Mass [M + H]+ |
|---|---|---|---|
| 40-8 | 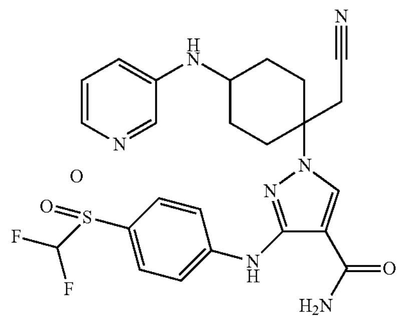 | Cis or trans 1-[1-(cyanomethyl)-4-(pyridin-3-ylamino)cyclohexyl]-3-({4-[(difluoromethyl)sulfonyl]phenyl}amino)-1H-pyrazole-4-carboxamide | Calc'd 530, Found 530 |
| 40-9 | 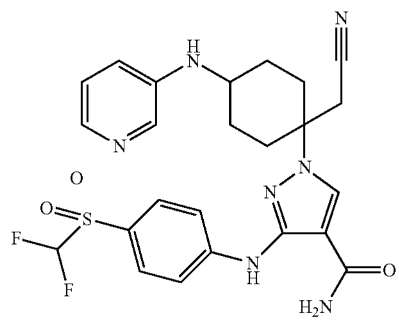 | Cis or trans 1-[1-(cyanomethyl)-4-(pyridin-3-ylamino)cyclohexyl]-3-({4-[(difluoromethyl)sulfonyl]phenyl}amino)-1H-pyrazole-4-carboxamide | Calc'd 530, Found 530 |
| 40-10 | 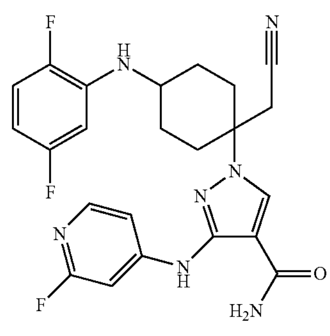 [SMILES: N#CCC1(n2cc(C(N)=O)c(Nc3ccnc(F)c3)n2)CCC(Nc2cc(F)ccc2F)CC1] | Cis or trans 1-{1-(cyanomethyl)-4-[(2,5-difluorophenyl)amino]cyclohexyl}-3-[(2-fluoropyridin-4-yl)amino]-1H-pyrazole-4-carboxamide | Calc'd 470, Found 470 |
| 40-11 | 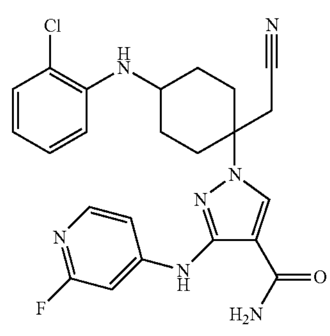 [SMILES: N#CCC1(n2cc(C(N)=O)c(Nc3ccnc(F)c3)n2)CCC(Nc2ccccc2Cl)CC1] | Cis or trans 1-{4-[(2-chlorophenyl)amino]-1-(cyanomethyl)cyclohexyl}-3-[(2-fluoropyridin-4-yl)amino]-1H-pyrazole-4-carboxamide | Calc'd 468, Found 468 |

TABLE 34-continued

| Example | Structure | Compound Name | Exact Mass [M + H]+ |
|---|---|---|---|
| 40-12 | 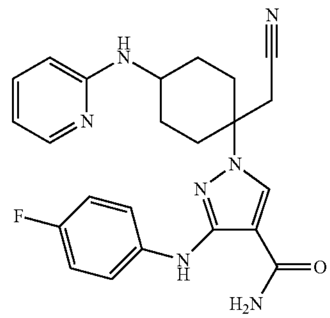 [SMILES: N#CCC1(n2cc(C(N)=O)c(Nc3ccc(F)cc3)n2)CCC(Nc2ccccn2)CC1] | Cis or trans 1-[1-(cyanomethyl)-4-(pyridin-2-ylamino)cyclohexyl]-3-[(4-fluorophenyl)amino]-1H-pyrazole-4-carboxamide | Calc'd 434, Found |
| 40-13 | 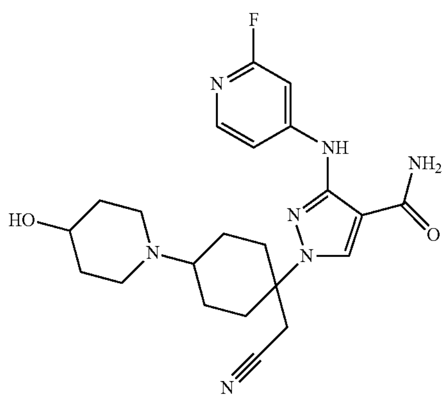 | Cis or trans 1-[1-(cyanomethyl)-4-(4-hydroxypiperidin-1-yl)cyclohexyl]-3-[(2-fluoropyridin-4-yl)amino]-1H-pyrazole-4-carboxamide | Calc'd 442, Found 442 |
| 40-14 | 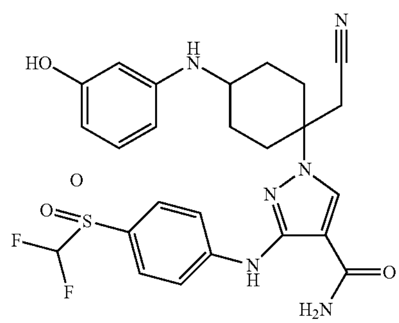 | Cis or trans 1-{1-(cyanomethyl)-4-[(3-hydroxyphenyl)amino]cyclohexyl}-3-({4-[(difluoromethyl)sulfonyl]phenyl}amino)-1H-pyrazole-4-carboxamide | Calc'd 545, Found 545 |
| 40-15 | 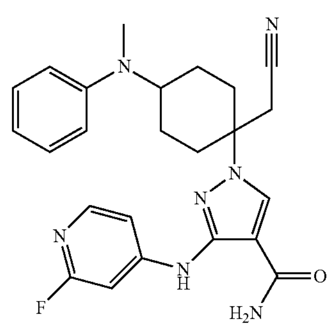 [SMILES: CN(c1ccccc1)C1CCC(CC#N)(n2cc(C(N)=O)c(Nc3ccnc(F)c3)n2)CC1] | Cis or trans 1-{1-(cyanomethyl)-4-[methyl(phenyl)amino]cyclohexyl}-3-[(2-fluoropyridin-4-yl)amino]-1H-pyrazole-4-carboxamide | Calc'd 448, Found 448 |

TABLE 34-continued

| Example | Structure | Compound Name | Exact Mass [M + H]+ |
|---|---|---|---|
| 40-16 | 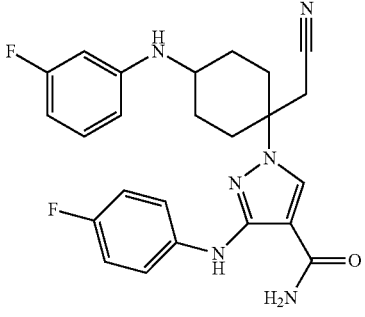 [SMILES: N#CCC1(n2cc(C(N)=O)c(Nc3ccc(F)cc3)n2)CCC(Nc2cccc(F)c2)CC1] | Cis or trans 1-{1-(cyanomethyl)-4-[(3-fluorophenyl)amino]cyclohexyl}-3-[(4-fluorophenyl)amino]-1H-pyrazole-4-carboxamide | Calc'd 451, Found 451 |
| 40-17 | 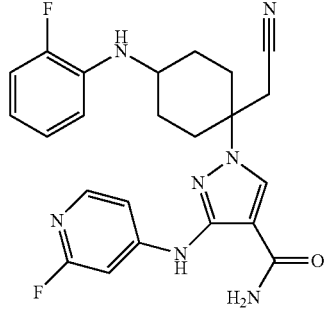 [SMILES: N#CCC1(n2cc(C(N)=O)c(Nc3ccnc(F)c3)n2)CCC(Nc2ccccc2F)CC1] | Cis or trans 1-{1-(cyanomethyl)-4-[(2-fluorophenyl)amino]cyclohexyl}-3-[(2-fluoropyridin-4-yl)amino]-1H-pyrazole-4-carboxamide | Calc'd 452, Found 452 |
| 40-18 | 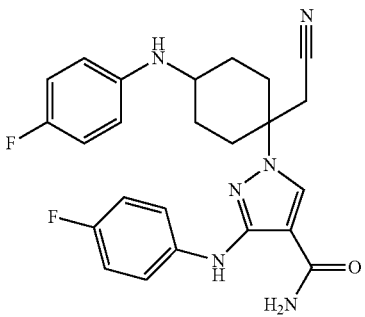 [SMILES: N#CCC1(n2cc(C(N)=O)c(Nc3ccc(F)cc3)n2)CCC(Nc2ccc(F)cc2)CC1] | Cis or trans 1-{1-(cyanomethyl)-4-[(4-fluorophenyl)amino]cyclohexyl}-3-[(4-fluorophenyl)amino]-1H-pyrazole-4-carboxamide | Calc'd 451, Found 451 |
| 40-19 | 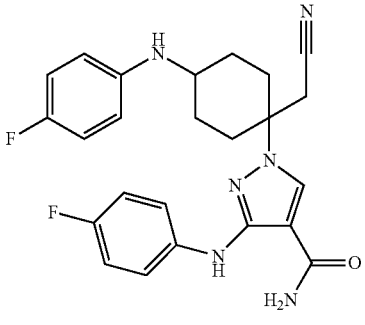 [SMILES: N#CCC1(n2cc(C(N)=O)c(Nc3ccc(F)cc3)n2)CCC(Nc2ccc(F)cc2)CC1] | Cis or trans 1-{1-(cyanomethyl)-4-[(4-fluorophenyl)amino]cyclohexyl}-3-[(4-fluorophenyl)amino]-1H-pyrazole-4-carboxamide | Calc'd 451, Found 451 |

TABLE 34-continued

| Example | Structure | Compound Name | Exact Mass [M + H]+ |
|---|---|---|---|
| 40-20 | 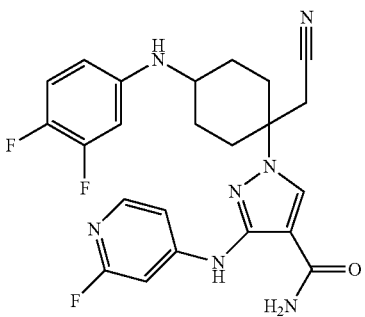 [SMILES: N#CCC1(n2cc(C(N)=O)c(Nc3ccnc(F)c3)n2)CCC(Nc2ccc(F)c(F)c2)CC1] | Cis or trans 1-{1-(cyanomethyl)-4-[(3,4-difluorophenyl)amino]cyclohexyl}-3-[(2-fluoropyridin-4-yl)amino]-1H-pyrazole-4-carboxamide | Calc'd 470, Found 470 |
| 40-21 | 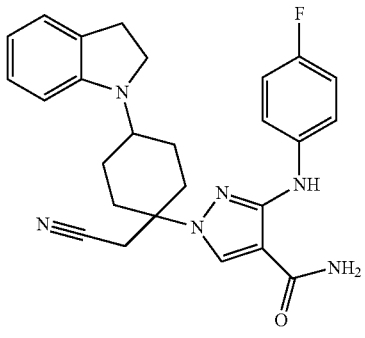 [SMILES: N#CCC1(n2cc(C(N)=O)c(Nc3ccc(F)cc3)n2)CCC(N2CCc3ccccc32)CC1] | Cis or trans 1-[1-(cyanomethyl)-4-(2,3-dihydro-1H-indol-1-yl)cyclohexyl]-3-[(4-fluorophenyl)amino]-1H-pyrazole-4-carboxamide | Calc'd 459, Found 459 |
| 40-22 | 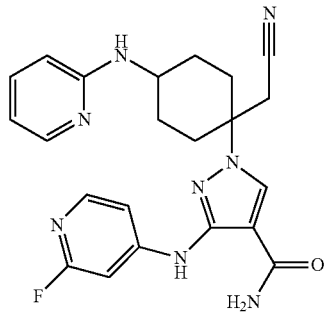 | Cis or trans 1-[1-(cyanomethyl)-4-(pyridin-2-ylamino)cyclohexyl]-3-[(2-fluoropyridin-4-yl)amino]-1H-pyrazole-4-carboxamide | Calc'd 435, Found 435 |
| 40-23 | 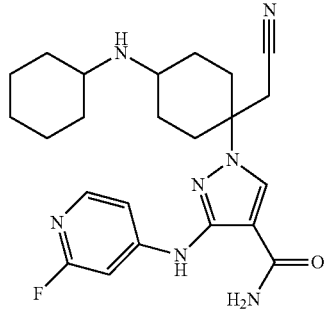 [SMILES: N#CCC1(n2cc(C(N)=O)c(Nc3ccnc(F)c3)n2)CCC(NC2CCCCC2)CC1] | Cis or trans 1-[1-(cyanomethyl)-4-(cyclohexylamino)cyclohexyl]-3-[(2-fluoropyridin-4-yl)amino]-1H-pyrazole-4-carboxamide | Calc'd 440, Found 440 |

TABLE 34-continued

| Example | Structure | Compound Name | Exact Mass [M + H]+ |
|---|---|---|---|
| 40-24 | 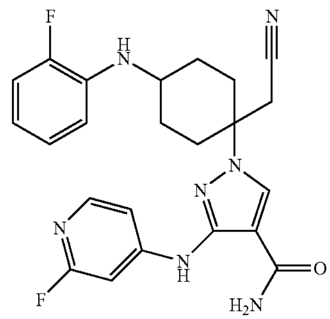 | Cis or trans 1-{1-(cyanomethyl)-4-[(2-fluorophenyl)amino]cyclohexyl}-3-[(2-fluoropyridin-4-yl)amino]-1H-pyrazole-4-carboxamide | Calc'd 452, Found 452 |
| 40-25 | 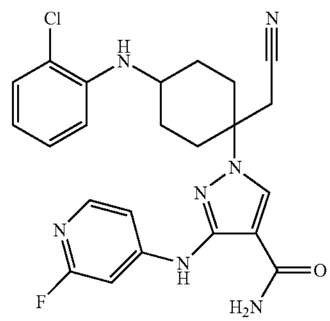 | Cis or trans 1-{4-[(2-chlorophenyl)amino]-1-(cyanomethyl)cyclohexyl}-3-[(2-fluoropyridin-4-yl)amino]-1H-pyrazole-4-carboxamide | Calc'd 468, Found 468 |
| 40-26 | 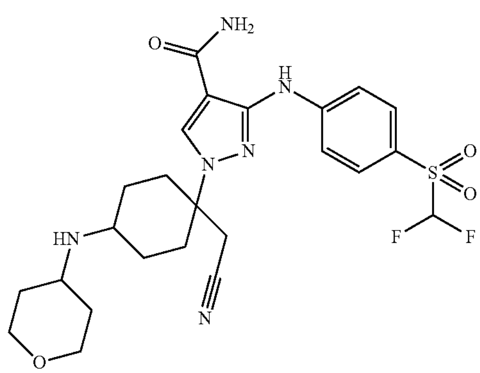 [SMILES: N#CCC1(n2cc(C(N)=O)c(Nc3ccc(S(=O)(=O)C(F)F)cc3)n2)CCC(NC2CCOCC2)CC1] | Cis or trans 1-[1-(cyanomethyl)-4-(tetrahydro-2H-pyran-4-ylamino)cyclohexyl]-3-({4-[(difluoromethyl)sulfonyl]phenyl}amino)-1H-pyrazole-4-carboxamide | Calc'd 537, Found 537 |
| 40-27 | 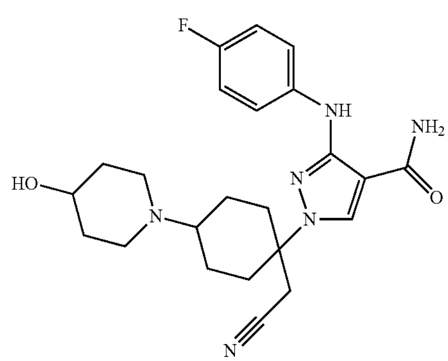 [SMILES: N#CCC1(n2cc(C(N)=O)c(Nc3ccc(F)cc3)n2)CCC(N2CCC(O)CC2)CC1] | Cis or trans 1-[1-(cyanomethyl)-4-(4-hydroxypiperidin-1-yl)cyclohexyl]-3-[(4-fluorophenyl)amino]-1H-pyrazole-4-carboxamide | Calc'd 441, Found 441 |

TABLE 34-continued

| Example | Structure | Compound Name | Exact Mass [M + H]+ |
|---|---|---|---|
| 40-28 | 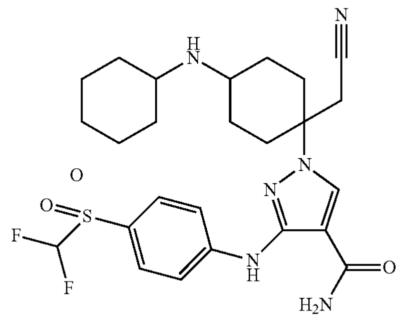 | Cis or trans 1-[1-(cyanomethyl)-4-(cyclohexylamino)cyclohexyl]-3-({4-[(difluoromethyl)sulfonyl]phenyl}amino)-1H-pyrazole-4-carboxamide | Calc'd 535, Found 535 |
| 40-29 | 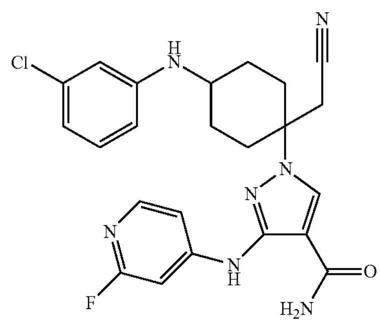 [SMILES: N#CCC1(n2cc(C(N)=O)c(Nc3ccnc(F)c3)n2)CCC(Nc2cccc(Cl)c2)CC1] | Cis or trans 1-{4-[(3-chlorophenyl)amino]-1-(cyanomethyl)cyclohexyl}-3-[(2-fluoropyridin-4-yl)amino]-1H-pyrazole-4-carboxamide | Calc'd 468, Found 468 |
| 40-30 | 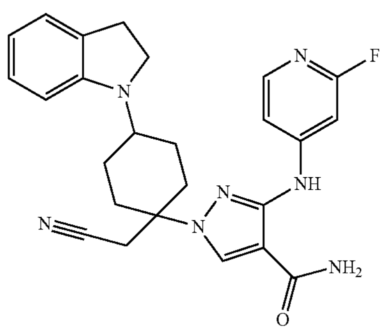 [SMILES: N#CCC1(n2cc(C(N)=O)c(Nc3ccnc(F)c3)n2)CCC(N2CCc3ccccc32)CC1] | Cis or trans 1-[1-(cyanomethyl)-4-(2,3-dihydro-1H-indol-1-yl)cyclohexyl]-3-[(2-fluoropyridin-4-yl)amino]-1H-pyrazole-4-carboxamide | Calc'd 460, Found 460 |
| 40-31 | 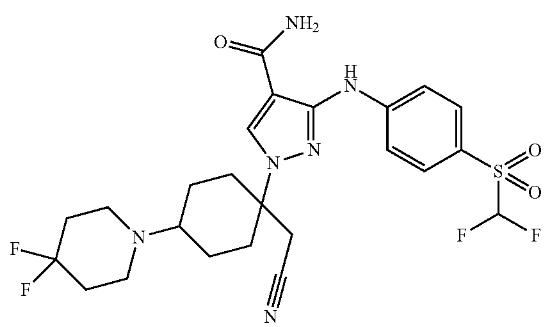 [SMILES: N#CCC1(n2cc(C(N)=O)c(Nc3ccc(S(=O)(=O)C(F)F)cc3)n2)CCC(N2CCC(F)(F)CC2)CC1] | Cis or trans 1-[1-(cyanomethyl)-4-(4,4-difluoropiperidin-1-yl)cyclohexyl]-3-({4-[(difluoromethyl)sulfonyl]phenyl}amino)-1H-pyrazole-4-carboxamide | Calc'd 557, Found 557 |

TABLE 34-continued

| Example | Structure | Compound Name | Exact Mass [M + H]+ |
|---|---|---|---|
| 40-32 | 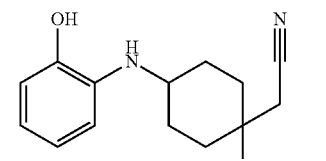 | Cis or trans 1-{1-(cyanomethyl)-4-[(2-hydroxyphenyl)amino]cyclohexyl}-3-({4-[(difluoromethyl)sulfonyl]phenyl}amino)-1H-pyrazole-4-carboxamide | Calc'd 545, Found 545 |
| 40-33 | 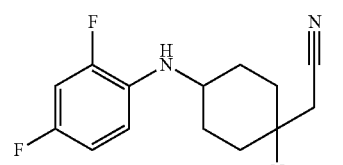 | Cis or trans 1-{1-(cyanomethyl)-4-[(2,4-difluorophenyl)amino]cyclohexyl}-3-[(2-fluoropyridin-4-yl)amino]-1H-pyrazole-4-carboxamide | Calc'd 470, Found 470 |
| 40-34 | 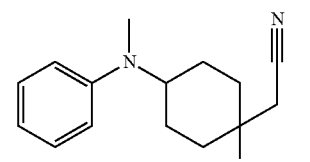 | Cis or trans 1-{1-(cyanomethyl)-4-[methyl(phenyl)amino]cyclohexyl}-3-[(2-fluoropyridin-4-yl)amino]-1H-pyrazole-4-carboxamide | Calc'd 448, Found 448 |
| 40-35 | 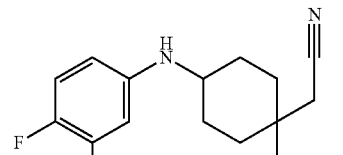 | Cis or trans 1-{1-(cyanomethyl)-4-[(3,4-difluorophenyl)amino]cyclohexyl}-3-[(4-fluorophenyl)amino]-1H-pyrazole-4-carboxamide | Calc'd 469, Found 469 |

TABLE 34-continued

| Example | Structure | Compound Name | Exact Mass [M + H]+ |
|---|---|---|---|
| 40-36 | 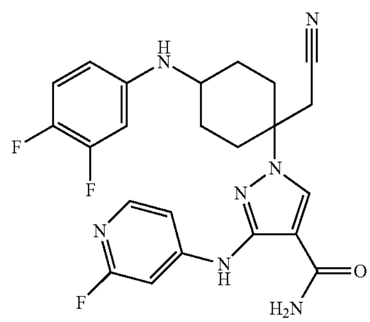 [SMILES: N#CCC1(n2cc(C(N)=O)c(Nc3ccnc(F)c3)n2)CCC(Nc2ccc(F)c(F)c2)CC1] | Cis or trans 1-{1-(cyanomethyl)-4-[(3,4-difluorophenyl)amino]cyclohexyl}-3-[(2-fluoropyridin-4-yl)amino]-1H-pyrazole-4-carboxamide | Calc'd 470, Found 470 |
| 40-37 | 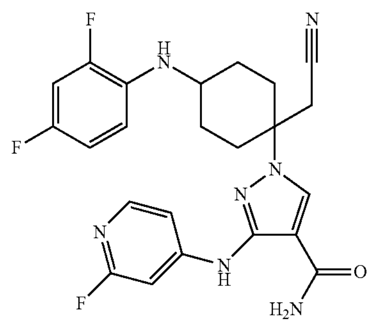 | Cis or trans 1-{1-(cyanomethyl)-4-[(2,4-difluorophenyl)amino]cyclohexyl}-3-[(2-fluoropyridin-4-yl)amino]-1H-pyrazole-4-carboxamide | Calc'd 470, Found 470 |
| 40-38 | 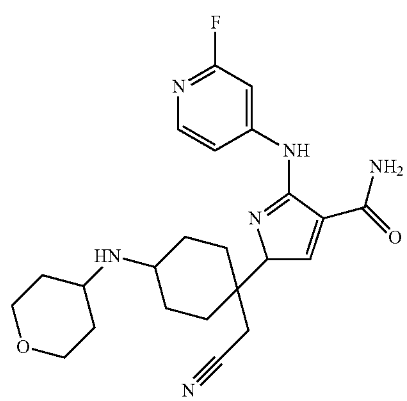 [SMILES: N#CCC1(C2C=C(C(N)=O)C(Nc3ccnc(F)c3)=N2)CCC(NC2CCOCC2)CC1] | Cis or trans 1-[1-(cyanomethyl)-4-(tetrahydro-2H-pyran-4-ylamino)cyclohexyl]-3-[(2-fluoropyridin-4-yl)amino]-1H-pyrazole-4-carboxamide | Calc'd 442, Found 442 |
| 40-39 | 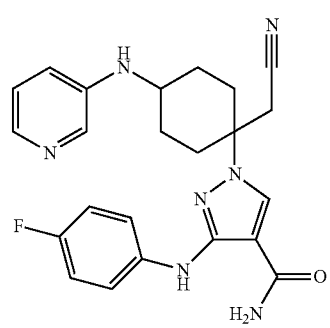 [SMILES: N#CCC1(n2cc(C(N)=O)c(Nc3ccc(F)cc3)n2)CCC(Nc2cccnc2)CC1] | Cis or trans 1-[1-(cyanomethyl)-4-(pyridin-3-ylamino)cyclohexyl]-3-[(4-fluorophenyl)amino]-1H-pyrazole-4-carboxamide | Calc'd 434, Found 434 |

TABLE 34-continued

| Example | Structure | Compound Name | Exact Mass [M + H]+ |
|---|---|---|---|
| 40-40 | 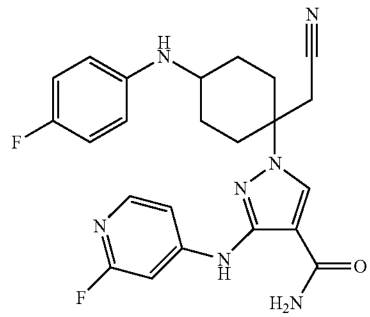 [SMILES: N#CCC1(n2cc(C(N)=O)c(Nc3ccnc(F)c3)n2)CCC(Nc2ccc(F)cc2)CC1] | Cis or trans 1-{1-(cyanomethyl)-4-[(4-fluorophenyl)amino]cyclohexyl}-3-[(2-fluoropyridin-4-yl)amino]-1H-pyrazole-4-carboxamide | Calc'd 452, Found 452 |
| 40-41 | 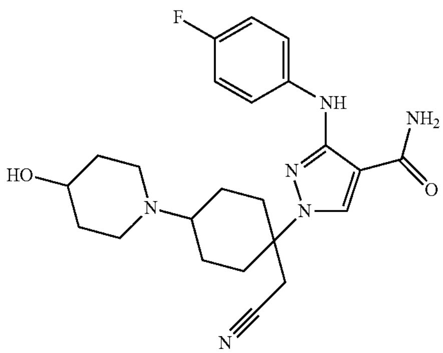 [SMILES: N#CCC1(n2cc(C(N)=O)c(Nc3ccc(F)cc3)n2)CCC(N2CCC(O)CC2)CC1] | Cis or trans 1-[1-(cyanomethyl)-4-(4-hydroxypiperidin-1-yl)cyclohexyl]-3-[(4-fluorophenyl)amino]-1H-pyrazole-4-carboxamide | Calc'd 441, Found 441 |
| 40-42 | 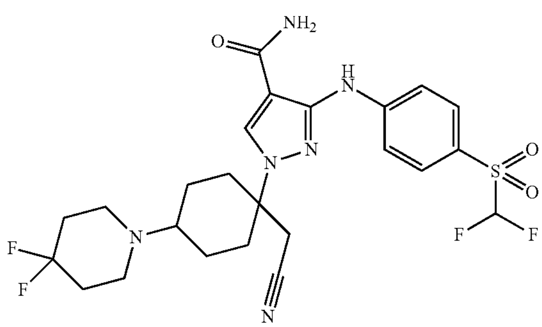 [SMILES: N#CCC1(n2cc(C(N)=O)c(Nc3ccc(S(=O)(=O)C(F)F)cc3)n2)CCC(N2CCC(F)(F)CC2)CC1] | Cis or trans 1-[1-(cyanomethyl)-4-(4,4-difluoropiperidin-1-yl)cyclohexyl]-3-({4-[(difluoromethyl)sulfonyl]phenyl}amino)-1H-pyrazole-4-carboxamide | Calc'd 557, Found 557 |
| 40-43 | 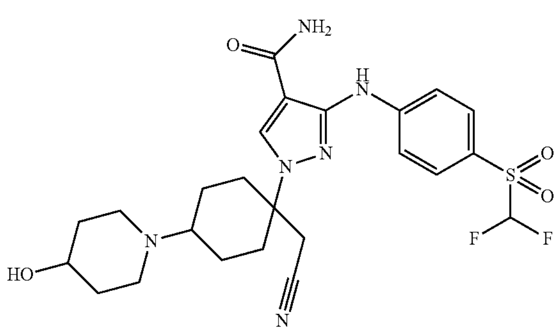 [SMILES: N#CCC1(n2cc(C(N)=O)c(Nc3ccc(S(=O)(=O)C(F)F)cc3)n2)CCC(N2CCC(O)CC2)CC1] | Cis or trans 1-[1-(cyanomethyl)-4-(4-hydroxypiperidin-1-yl)cyclohexyl]-3-({4-[(difluoromethyl)sulfonyl]phenyl}amino)-1H-pyrazole-4-carboxamide | Calc'd 537, Found 537 |

TABLE 34-continued

| Example | Structure | Compound Name | Exact Mass [M + H]+ |
|---|---|---|---|
| 40-44 | 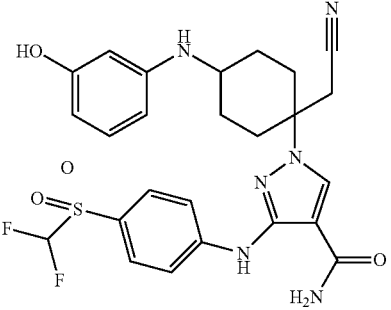 | Cis or trans 1-{1-(cyanomethyl)-4-[(3-hydroxyphenyl)amino]cyclohexyl}-3-({4-[(difluoromethyl)sulfonyl]phenyl}amino)-1H-pyrazole-4-carboxamide | Calc'd 545, Found 545 |
| 40-45 | 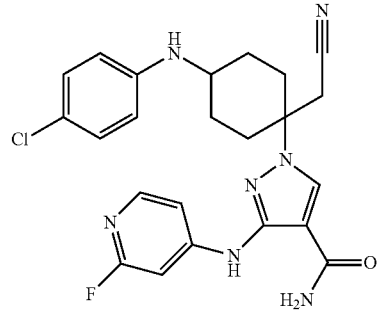 | Cis or trans 1-{4-[(4-chlorophenyl)amino]-1-(cyanomethyl)cyclohexyl}-3-[(2-fluoropyridin-4-yl)amino]-1H-pyrazole-4-carboxamide | Calc'd 468, Found 468 |
| 40-46 | 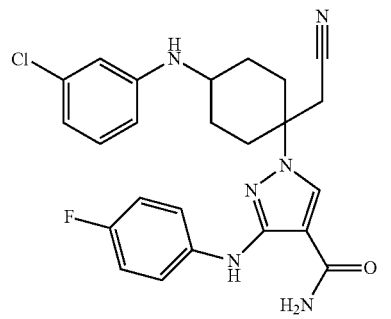 [SMILES: N#CCC1(n2cc(C(N)=O)c(Nc3ccc(F)cc3)n2)CCC(Nc2cccc(Cl)c2)CC1] | Cis or trans 1-{4-[(3-chlorophenyl)aminol-1-(cyanomethyl)cyclohexyl}-3-[(4-fluorophenyl)amino]-1H-pyrazole-4-carboxamide | Calc'd 467, Found 467 |
| 40-47 | 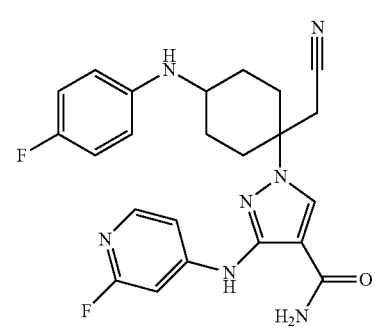 [SMILES: N#CCC1(n2cc(C(N)=O)c(Nc3ccnc(F)c3)n2)CCC(Nc2ccc(F)cc2)CC1] | Cis or trans 1-{1-(cyanomethyl)-4-[(4-fluorophenyl)amino]cyclohexyl}-3-[(2-fluoropyridin-4-yl)amino]-1H-pyrazole-4-carboxamide | Calc'd 452, Found 452 |

TABLE 34-continued

| Example | Structure | Compound Name | Exact Mass [M + H]+ |
|---|---|---|---|
| 40-48 | 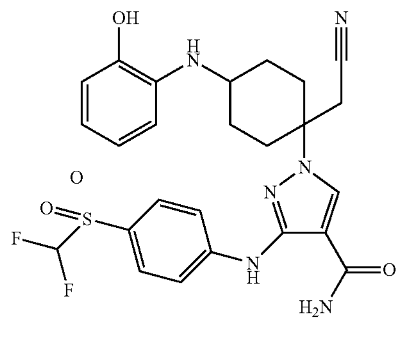 | Cis or trans 1-{1-(cyanomethyl)-4-[(2-hydroxyphenyl)amino]cyclohexyl}-3-({4-[(difluoromethyl)sulfonyl]phenyl}amino)-1H-pyrazole-4-carboxamide | Calc'd 545, Found 545 |
| 40-49 | 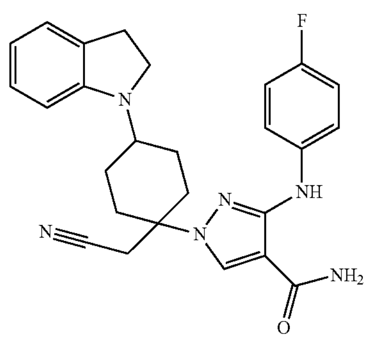 [SMILES: N#CCC1(n2cc(C(N)=O)c(Nc3ccc(F)cc3)n2)CCC(N2CCc3ccccc32)CC1] | Cis or trans 1-[1-(cyanomethyl)-4-(2,3-dihydro-1H-indol-1-yl)cyclohexyl]-3-[(4-fluorophenyl)amino]-1H-pyrazole-4-carboxamide | Calc'd 459, Found 459 |
| 40-50 | 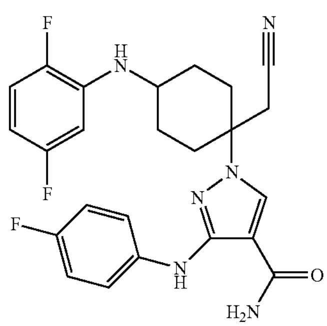 [SMILES: N#CCC1(n2cc(C(N)=O)c(Nc3ccc(F)cc3)n2)CCC(Nc2cc(F)ccc2F)CC1] | Cis and trans 1-{1-(cyanomethyl)-4-[(2,5-difluorophenyl)amino]cyclohexyl}-3-[(4-fluorophenyl)amino]-1H-pyrazole-4-carboxamide | Calc'd 469, Found 469 |
| 40-51 | 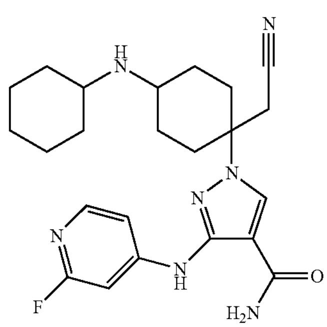 [SMILES: N#CCC1(n2cc(C(N)=O)c(Nc3ccnc(F)c3)n2)CCC(NC2CCCCC2)CC1] | Cis or trans 1-[1-(cyanomethyl)-4-(cyclohexylamino)cyclohexyl]-3-[(2-fluoropyridin-4-yl)amino]-1H-pyrazole-4-carboxamide | Calc'd 440, Found 440 |

TABLE 34-continued

| Example | Structure | Compound Name | Exact Mass [M + H]+ |
|---|---|---|---|
| 40-52 | 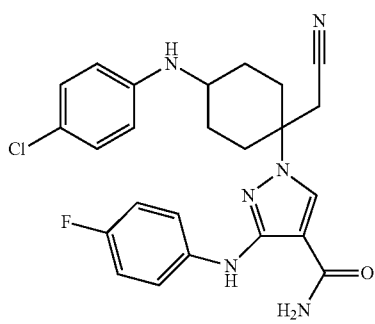 [SMILES: N#CCC1(n2cc(C(N)=O)c(Nc3ccc(F)cc3)n2)CCC(Nc2ccc(Cl)cc2)CC1] | Cis or trans 1-{4-[(4-chlorophenyl)amino]-1-(cyanomethyl)cyclohexyl}-3-[(4-fluorophenyl)amino]-1H-pyrazole-4-carboxamide | Calc'd 467, Found 467 |
| 40-53 | 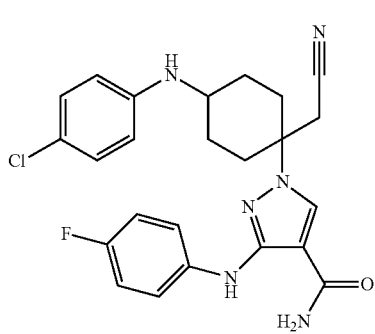 [SMILES: N#CCC1(n2cc(C(N)=O)c(Nc3ccc(F)cc3)n2)CCC(Nc2ccc(Cl)cc2)CC1] | Cis or trans 1-{4-[(4-chlorophenyl)amino]-1-(cyanomethyl)cyclohexyl}-3-[(4-fluorophenyl)amino]-1H-pyrazole-4-carboxamide | Calc'd 467, Found 467 |
| 40-54 | 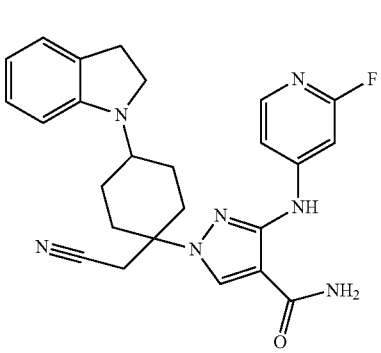 [SMILES: N#CCC1(n2cc(C(N)=O)c(Nc3ccnc(F)c3)n2)CCC(N2CCc3ccccc32)CC1] | Cis or trans 1-[1-(cyanomethyl)-4-(2,3-dihydro-1H-indol-1-yl)cyclohexyl]-3-[(2-fluoropyridin-4-yl)amino]-1H-pyrazole-4-carboxamide | Calc'd 460, Found 460 |
| 40-55 | 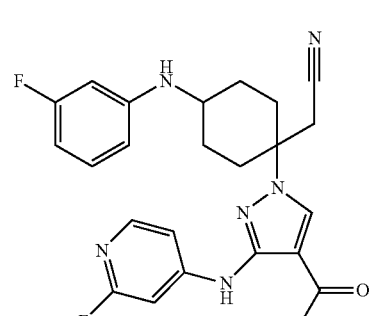 | Cis or trans 1-{1-(cyanomethyl)-4-[(3-fluorophenyl)amino]cyclohexyl}-3-[(2-fluoropyridin-4-yl)amino]-1H-pyrazole-4-carboxamide | Calc'd 452, Found 452 |

TABLE 34-continued

| Example | Structure | Compound Name | Exact Mass [M + H]+ |
|---|---|---|---|
| 40-56 | 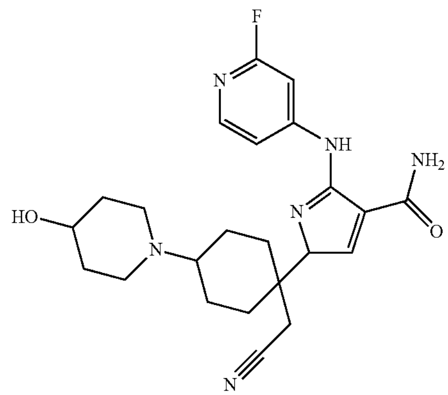 [SMILES: N#CCC1(C2C=C(C(N)=O)C(Nc3ccnc(F)c3)=N2)CCC(N2CCC(O)CC2)CC1] | Cis or trans 1-[1-(cyanomethyl)-4-(4-hydroxypiperidin-1-yl)cyclohexyl]-3-[(2-fluoropyridin-4-yl)amino]-1H-pyrazole-4-carboxamide | Calc'd 442, Found 442 |
| 40-57 | 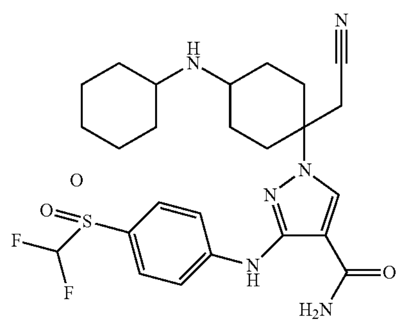 | Cis or trans 1-[1-(cyanomethyl)-4-(cyclohexylamino)cyclohexyl]-3-({4-[(difluoromethyl)sulfonyl]phenyl}amino)-1H-pyrazole-4-carboxamide | Calc'd 535, Found 535 |
| 40-58 | 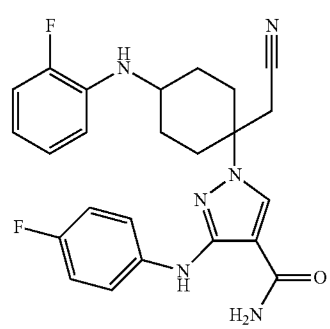 [SMILES: N#CCC1(n2cc(C(N)=O)c(Nc3ccc(F)cc3)n2)CCC(Nc2ccccc2F)CC1] | Cis or trans 1-{1-(cyanomethyl)-4-[(2-fluorophenyl)amino]cyclohexyl}-3-[(4-fluorophenyl)amino]-1H-pyrazole-4-carboxamide | Calc'd 451, Found 451 |
| 40-59 | 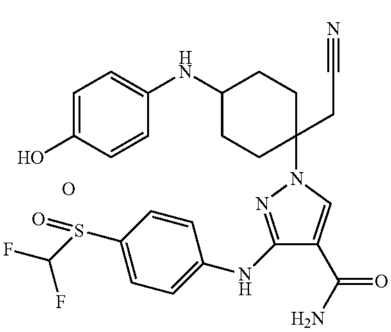 | Cis or trans 1-{1-(cyanomethyl)-4-[(4-hydroxyphenyl)amino]cyclohexyl}-3-({4-[(difluoromethyl)sulfonyl]phenyl}amino)-1H-pyrazole-4-carboxamide | Calc'd 545, Found 545 |

TABLE 34-continued

| Example | Structure | Compound Name | Exact Mass [M + H]+ |
|---|---|---|---|
| 40-60 | 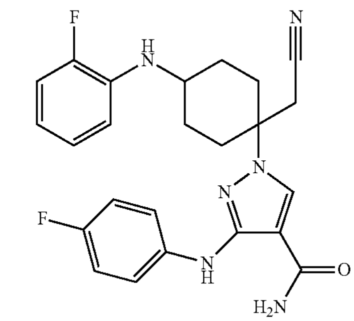 [SMILES: N#CCC1(n2cc(C(N)=O)c(Nc3ccc(F)cc3)n2)CCC(Nc2ccccc2F)CC1] | Cis or trans 1-{1-(cyanomethyl)-4-[(2-fluorophenyl)amino]cyclohexyl}-3-[(4-fluorophenyl)amino]-1H-pyrazole-4-carboxamide | Calc'd 451, Found 451 |
| 40-61 | 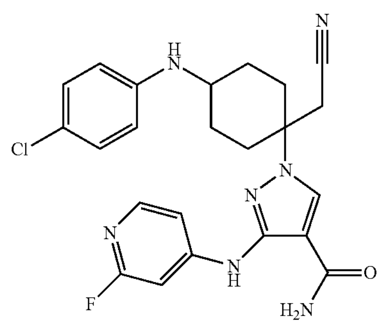 [SMILES: N#CCC1(n2cc(C(N)=O)c(Nc3ccnc(F)c3)n2)CCC(Nc2ccc(Cl)cc2)CC1] | Cis or trans 1-{4-[(4-chlorophenyl)amino]-1-(cyanomethyl)cyclohexyl}-3-[(2-fluoropyridin-4-yl)amino]-1H-pyrazole-4-carboxamide | Calc'd 468, Found 468 |
| 40-62 | 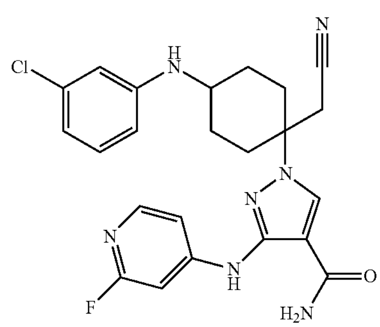 [SMILES: N#CCC1(n2cc(C(N)=O)c(Nc3ccnc(F)c3)n2)CCC(Nc2cccc(Cl)c2)CC1] | Cis or trans 1-{4-[(3-chlorophenyl)amino]-1-(cyanomethyl)cyclohexyl}-3-[(2-fluoropyridin-4-yl)amino]-1H-pyrazole-4-carboxamide | Calc'd 468, Found 468 |
| 40-63 | 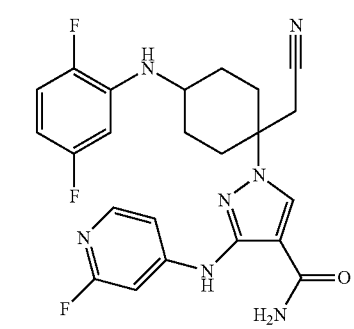 [SMILES: N#CCC1(n2cc(C(N)=O)c(Nc3ccnc(F)c3)n2)CCC(Nc2cc(F)ccc2F)CC1] | Cis or trans 1-{1-(cyanomethyl)-4-[(2,5-difluorophenyl)amino]cyclohexyl}-3-[(2-fluoropyridin-4-yl)amino]-1H-pyrazole-4-carboxamide | Calc'd 470, Found 470 |

TABLE 34-continued

| Example | Structure | Compound Name | Exact Mass [M + H]+ |
|---|---|---|---|
| 40-64 | 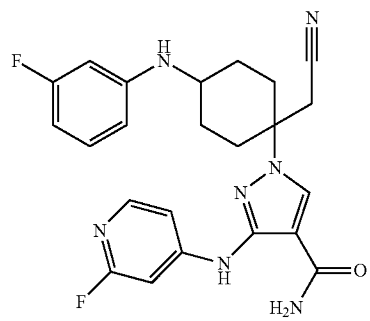 [SMILES: N#CCC1(n2cc(C(N)=O)c(Nc3ccnc(F)c3)n2)CCC(Nc2cccc(F)c2)CC1] | Cis or trans 1-{1-(cyanomethyl)-4-[(3-fluorophenyl)amino]cyclohexyl}-3-[(2-fluoropyridin-4-yl)amino]-1H-pyrazole-4-carboxamide | Calc'd 452, Found 452 |
| 40-65 | 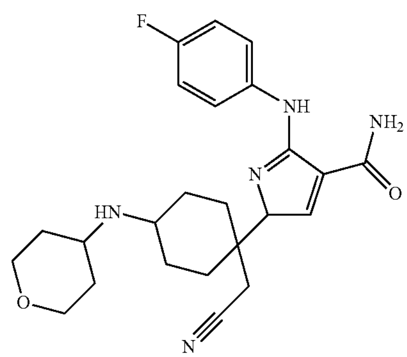 [SMILES: N#CCC1(C2C=C(C(N)=O)C(Nc3ccc(F)cc3)=N2)CCC(NC2CCOCC2)CC1] | Cis or trans 1-[1-(cyanomethyl)-4-(tetrahydro-2H-pyran-4-ylamino)cyclohexyl]-3-[(4-fluorophenyl)amino]-1H-pyrazole-4-carboxamide | Calc'd 441, Found 441 |
| 40-66 | 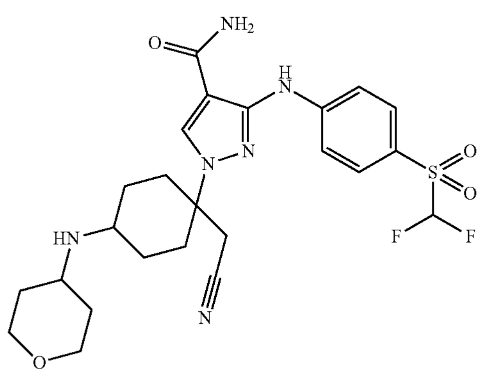 [SMILES: N#CCC1(n2cc(C(N)=O)c(Nc3ccc(S(=O)(=O)C(F)F)cc3)n2)CCC(NC2CCOCC2)CC1] | Cis or trans 1-[1-(cyanomethyl)-4-(tetrahydro-2H-pyran-4-ylamino)cyclohexyl]-3-({4-[(difluoromethyl)sulfonyl]phenyl}amino)-1H-pyrazole-4-carboxamide | Calc'd 537, Found 537 |
| 40-67 | 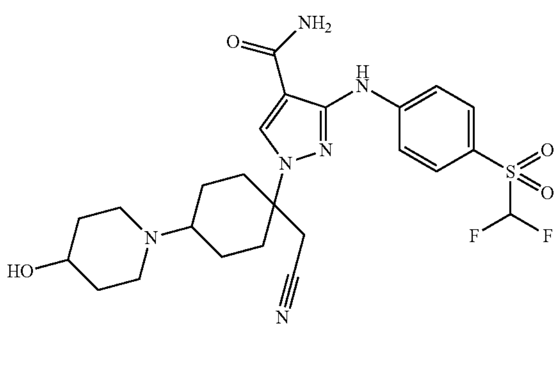 [SMILES: N#CCC1(n2cc(C(N)=O)c(Nc3ccc(S(=O)(=O)C(F)F)cc3)n2)CCC(N2CCC(O)CC2)CC1] | Cis or trans 1-[1-(cyanomethyl)-4-(4-hydroxypiperidin-1-yl)cyclohexyl]-3-({4-[(difluoromethyl)sulfonyl]phenyl}amino)-1H-pyrazole-4-carboxamide | Calc'd 537, Found 537 |

TABLE 34-continued

| Example | Structure | Compound Name | Exact Mass [M + H]+ |
|---|---|---|---|
| 40-68 | 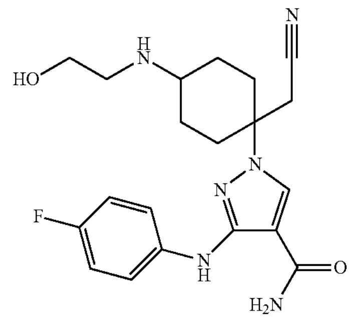 [SMILES: N#CCC1(n2cc(C(N)=O)c(Nc3ccc(F)cc3)n2)CCC(NCCO)CC1] | Cis or trans 1-{1-(cyanomethyl)-4-[(2-hydroxyethyl)amino]cyclohexyl}-3-[(4-fluorophenyl)amino]-1H-pyrazole-4-carboxamide | Calc'd 401, found 401 |
| 40-69 | 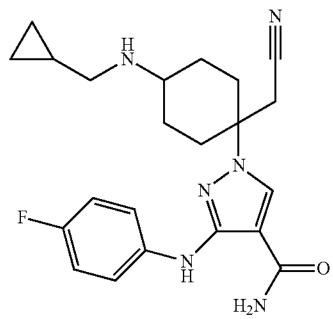 [SMILES: N#CCC1(n2cc(C(N)=O)c(Nc3ccc(F)cc3)n2)CCC(NCC2CC2)CC1] | Cis or trans 1-{1-(cyanomethyl)-4-[(cyclopropylmethyl)amino]cyclohexyl}-3-[(4-fluorophenyl)amino]-1H-pyrazole-4-carboxamide | Calc'd 411, found 411 |
| 40-70 | 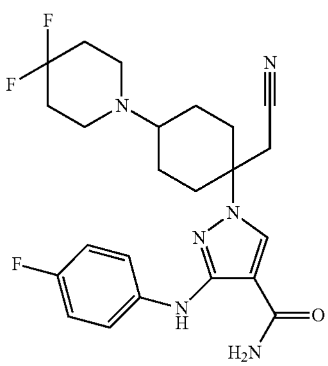 [SMILES: N#CCC1(n2cc(C(N)=O)c(Nc3ccc(F)cc3)n2)CCC(N2CCC(F)(F)CC2)CC1] | Cis or trans 1-[1-(cyanomethyl)-4-(4,4-difluoropiperidin-1-yl)cyclohexyl]-3-[(4-fluorophenyl)amino]-1H-pyrazole-4-carboxamide | Calc'd 461, found 461 |
| 40-71 | 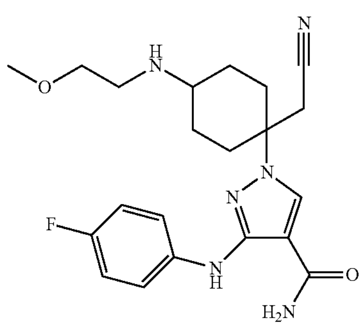 [SMILES: COCCNC1CCC(CC#N)(n2cc(C(N)=O)c(Nc3ccc(F)cc3)n2)CC1] | Cis or trans 1-{1-(cyanomethyl)-4-[(2-methoxyethyl)amino]cyclohexyl}-3-[(4-fluorophenyl)amino]-1H-pyrazole-4-carboxamide | Calc'd 415, found 415 |

TABLE 34-continued

| Example | Structure | Compound Name | Exact Mass [M + H]+ |
|---|---|---|---|
| 40-72 | 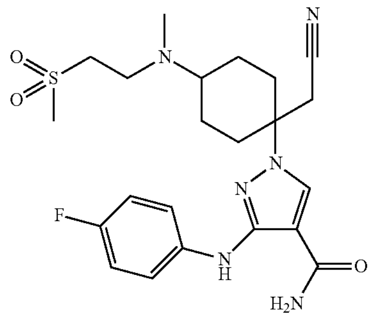 [SMILES: CN(CCS(C)(=O)=O)C1CCC(CC#N)(n2cc(C(N)=O)c(Nc3ccc(F)cc3)n2)CC1] | Cis or trans 1-[1-(cyanomethyl)-4-{methyl[2-(methylsulfonyl)ethyl]amino}cyclohexyl]-3-[(4-fluorophenyl)amino]-1H-pyrazole-4-carboxamide | Calc'd 477, found 477 |
| 40-73 | 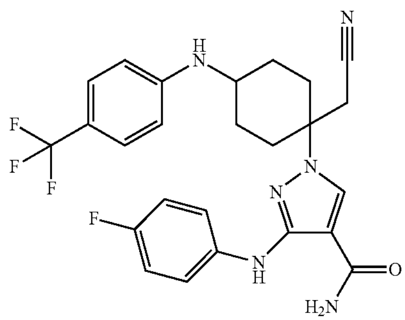 [SMILES: N#CCC1(n2cc(C(N)=O)c(Nc3ccc(F)cc3)n2)CCC(Nc2ccc(C(F)(F)F)cc2)CC1] | Cis or trans 1-[1-(cyanomethyl)-4-{[4-(trifluoromethyl)phenyl]amino}cyclohexyl]-3-[(4-fluorophenyl)amino]-1H-pyrazole-4-carboxamide | Calc'd 501, found 501 |
| 40-74 | 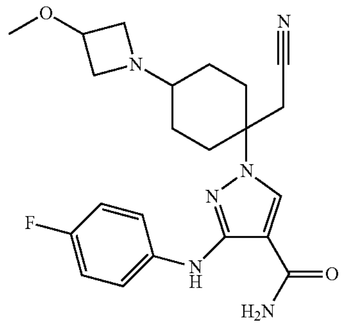 [SMILES: COC1CN(C2CCC(CC#N)(n3cc(C(N)=O)c(Nc4ccc(F)cc4)n3)CC2)C1] | Cis or trans 1-[1-(cyanomethyl)-4-(3-methoxyazetidin-1-yl)cyclohexyl]-3-[(4-fluorophenyl)amino]-1H-pyrazole-4-carboxamide | Calc'd 427, found 427 |
| 40-75 | 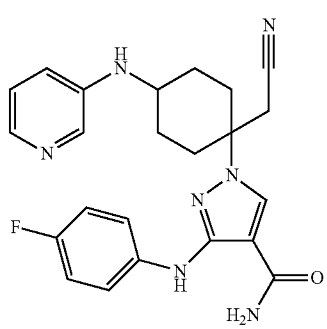 [SMILES: N#CCC1(n2cc(C(N)=O)c(Nc3ccc(F)cc3)n2)CCC(Nc2cccnc2)CC1] | Cis or trans 1-[1-(cyanomethyl)-4-(pyridin-3-ylamino)cyclohexyl]-3-[(4-fluorophenyl)amino]-1H-pyrazole-4-carboxamide | Calc'd 434, found 434 |

TABLE 34-continued

| Example | Structure | Compound Name | Exact Mass [M + H]+ |
|---|---|---|---|
| 40-76 | 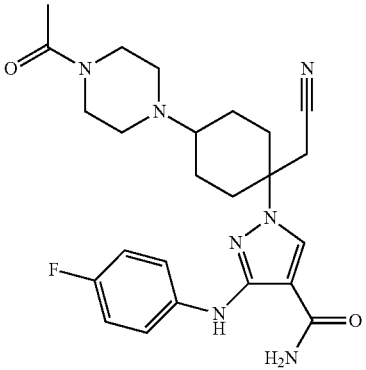 [SMILES: CC(=O)N1CCN(C2CCC(CC#N)(n3cc(C(N)=O)c(Nc4ccc(F)cc4)n3)CC2)CC1] | Cis or trans 1-[4-(4-acetylpiperazin-1-yl)-1-(cyanomethyl)cyclohexyl]-3-[(4-fluorophenyl)amino]-1H-pyrazole-4-carboxamide | Calc'd 468, found 468 |
| 40-77 | 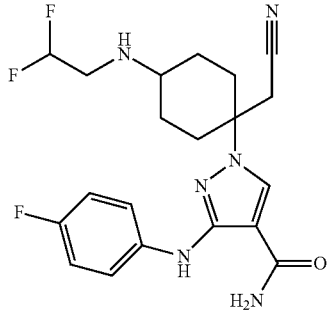 [SMILES: N#CCC1(n2cc(C(N)=O)c(Nc3ccc(F)cc3)n2)CCC(NCC(F)F)CC1] | Cis or trans 1-{1-(cyanomethyl)-4-[(2,2-difluoroethyl)amino]cyclohexyl}-3-[(4-fluorophenyl)amino]-1H-pyrazole-4-carboxamide | Calc'd 421, found 421 |
| 40-78 | 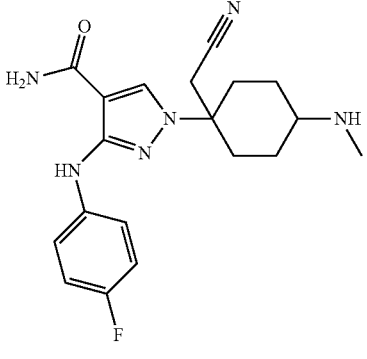 [SMILES: CNC1CCC(CC#N)(n2cc(C(N)=O)c(Nc3ccc(F)cc3)n2)CC1] | Cis or trans 1-[1-(cyanomethyl)-4-(methylamino)cyclohexyl]-3-[(4-fluorophenyl)amino]-1H-pyrazole-4-carboxamide | Calc'd 371, found 371 |
| 40-79 | 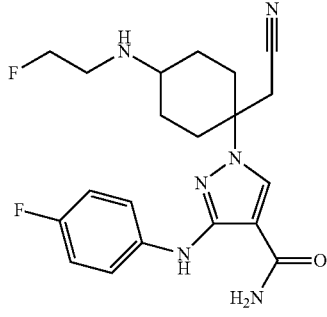 [SMILES: N#CCC1(n2cc(C(N)=O)c(Nc3ccc(F)cc3)n2)CCC(NCCF)CC1] | Cis or trans 1-{1-(cyanomethyl)-4-[(2-fluoroethyl)amino]cyclohexyl}-3-[(4-fluorophenyl)amino]-1H-pyrazole-4-carboxamide | Calc'd 403, found 403 |

TABLE 34-continued

| Example | Structure | Compound Name | Exact Mass [M + H]+ |
|---|---|---|---|
| 40-80 | 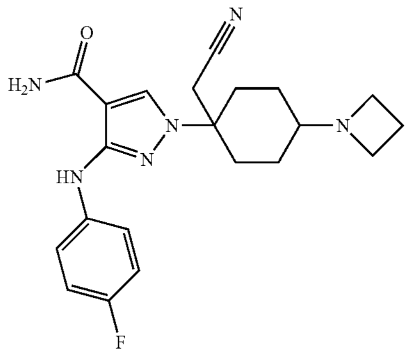 [SMILES: N#CCC1(n2cc(C(N)=O)c(Nc3ccc(F)cc3)n2)CCC(N2CCC2)CC1] | Cis or trans 1-[4-azetidin-1-yl-1-(cyanomethyl)cyclohexyl]-3-[(4-fluorophenyl)amino]-1H-pyrazole-4-carboxamide | Calc'd 397, found 397 |
| 40-81 | 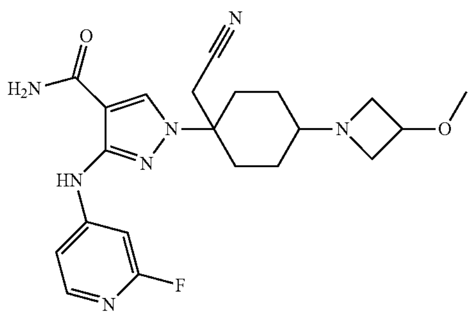 [SMILES: COC1CN(C2CCC(CC#N)(n3cc(C(N)=O)c(Nc4ccnc(F)c4)n3)CC2)C1] | Cis or trans 1-[1-(cyanomethyl)-4-(3-methoxyazetidin-1-yl)cyclohexyl]-3-[(2-fluoropyridin-4-yl)amino]-1H-pyrazole-4-carboxamide | Calc'd 428, found 428 |
| 40-82 | 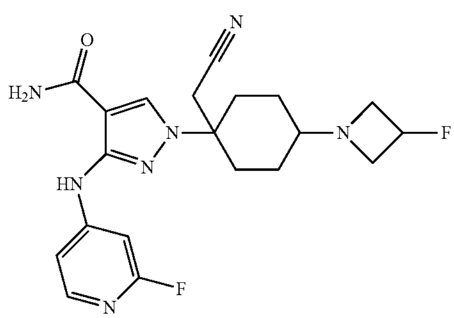 [SMILES: N#CCC1(n2cc(C(N)=O)c(Nc3ccnc(F)c3)n2)CCC(N2CC(F)C2)CC1] | Cis or trans 1-[1-(cyanomethyl)-4-(3-fluoroazetidin-1-yl)cyclohexyl]-3-[(2-fluoropyridin-4-yl)amino]-1H-pyrazole-4-carboxamide | Calc'd 416, found 416 |
| 40-83 | 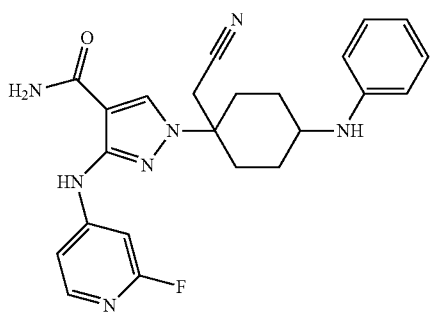 [SMILES: N#CCC1(n2cc(C(N)=O)c(Nc3ccnc(F)c3)n2)CCC(Nc2ccccc2)CC1] | Cis or trans 1-[1-(cyanomethyl)-4-(phenylamino)cyclohexyl]-3-[(2-fluoropyridin-4-yl)amino]-1H-pyrazole-4-carboxamide | Calc'd 434, found 434 |

TABLE 34-continued

| Example | Structure | Compound Name | Exact Mass [M + H]+ |
|---|---|---|---|
| 40-84 | 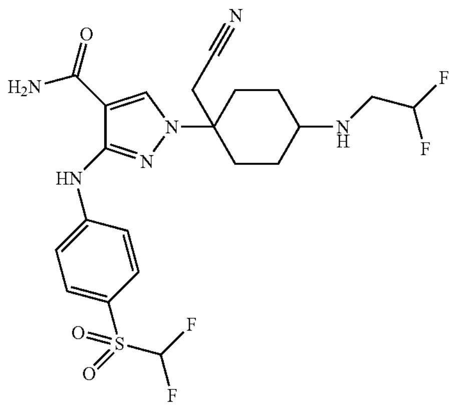 [SMILES: N#CCC1(n2cc(C(N)=O)c(Nc3ccc(S(=O)(=O)C(F)F)cc3)n2)CCC(NCC(F)F)CC1] | Cis or trans 1-{1-(cyanomethyl)-4-[(2,2-difluoroethyl)amino]cyclohexyl}-3-({4-[(difluoromethyl)sulfonyl]phenyl}amino)-1H-pyrazole-4-carboxamide | Calc'd 517, found 517 |
| 40-85 | 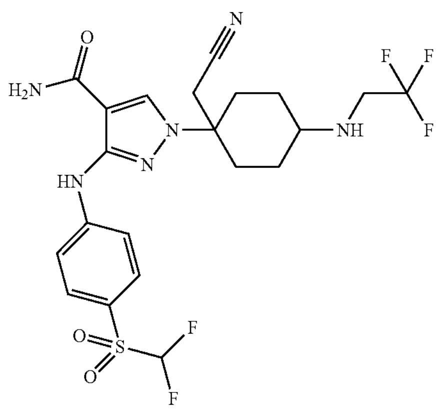 [SMILES: N#CCC1(n2cc(C(N)=O)c(Nc3ccc(S(=O)(=O)C(F)F)cc3)n2)CCC(NCC(F)(F)F)CC1] | Cis or trans 1-{1-(cyanomethyl)-4-[(2,2,2-trifluoroethyl)amino]cyclohexyl}-3-({4-[(difluoromethyl)sulfonyl]phenyl}amino)-1H-pyrazole-4-carboxamide | Calc'd 535, found 535 |
| 40-86 | 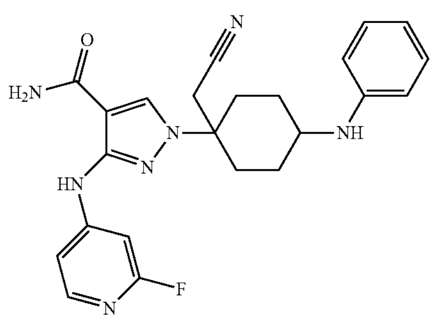 [SMILES: N#CCC1(n2cc(C(N)=O)c(Nc3ccnc(F)c3)n2)CCC(Nc2ccccc2)CC1] | Cis or trans 1-[1-(cyanomethyl)-4-(phenylamino)cyclohexyl]-3-[(2-fluoropyridin-4-yl)amino]-1H-pyrazole-4-carboxamide | Calc'd 434, found 434 |
| 40-87 | 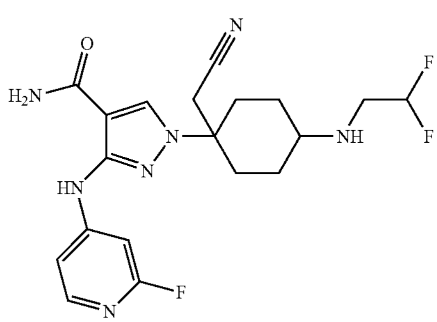 [SMILES: N#CCC1(n2cc(C(N)=O)c(Nc3ccnc(F)c3)n2)CCC(NCC(F)F)CC1] | Cis or trans 1-{1-(cyanomethyl)-4-[(2,2-difluoroethyl)amino]cyclohexyl}-3-[(2-fluoropyridin-4-yl)amino]-1H-pyrazole-4-carboxamide | Calc'd 422, found 422 |

TABLE 34-continued

| Example | Structure | Compound Name | Exact Mass [M + H]+ |
|---|---|---|---|
| 40-88 | 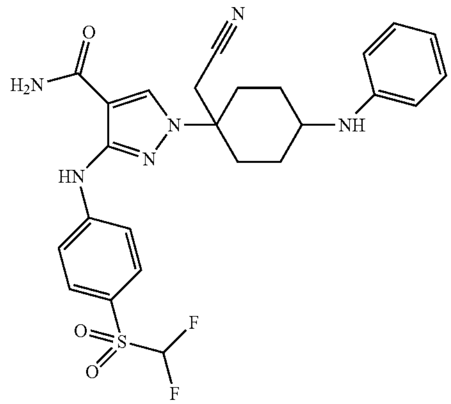 [SMILES: N#CCC1(n2cc(C(N)=O)c(Nc3ccc(S(=O)(=O)C(F)F)cc3)n2)CCC(Nc2ccccc2)CC1] | Cis or trans 1-[1-(cyanomethyl)-4-(phenylamino)cyclohexyl]-3-({4-[(difluoromethyl)sulfonyl]phenyl}amino)-1H-pyrazole-4-carboxamide | Calc'd 529, found 529 |
| 40-89 | 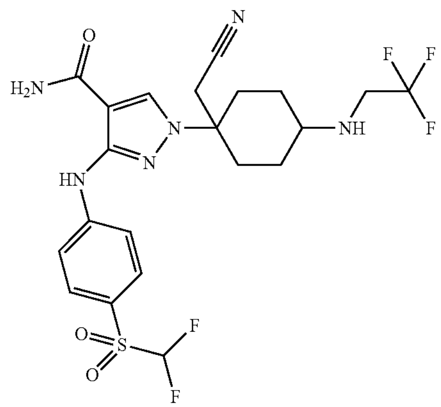 [SMILES: N#CCC1(n2cc(C(N)=O)c(Nc3ccc(S(=O)(=O)C(F)F)cc3)n2)CCC(NCC(F)(F)F)CC1] | Cis or trans 1-{1-(cyanomethyl)-4-[(2,2,2-trifluoroethyl)amino]cyclohexyl}-3-({4-[(difluoromethyl)sulfonyl]phenyl}amino)-1H-pyrazole-4-carboxamide | Calc'd 535, found 535 |
| 40-90 | 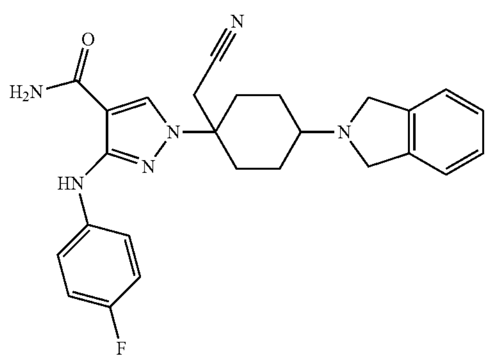 [SMILES: N#CCC1(n2cc(C(N)=O)c(Nc3ccc(F)cc3)n2)CCC(N2Cc3ccccc3C2)CC1] | Cis or trans 1-[1-(cyanomethyl)-4-(1,3-dihydro-2H-isoindol-2-yl)cyclohexyl]-3-[(4-fluorophenyl)amino]-1H-pyrazole-4-carboxamide | Calc'd 459, found 459 |
| 40-91 | 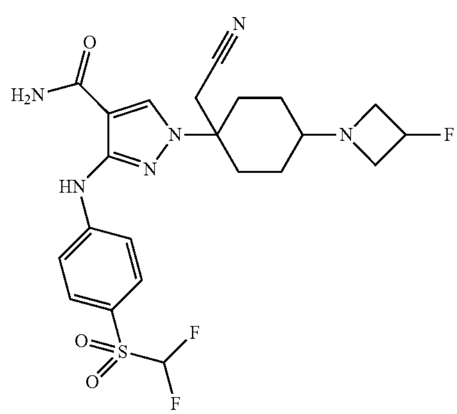 [SMILES: N#CCC1(n2cc(C(N)=O)c(Nc3ccc(S(=O)(=O)C(F)F)cc3)n2)CCC(N2CC(F)C2)CC1] | Cis or trans 1-[1-(cyanomethyl)-4-(3-fluoroazetidin-1-yl)cyclohexyl]-3-({4-[(difluoromethyl)sulfonyl]phenyl}amino)-1H-pyrazole-4-carboxamide | Calc'd 511, found 511 |

TABLE 34-continued

| Example | Compound Name | Exact Mass [M + H]+ |
|---|---|---|
| 40-92 | Cis or trans 1-[4-(benzylamino)-1-(cyanomethyl)cyclohexyl]-3-[(4-fluorophenyl)amino]-1H-pyrazole-4-carboxamide | Calc'd 447, found 447 |
| 40-93 | Cis or trans 1-{1-(cyanomethyl)-4-[(2,2,2-trifluoroethyl)amino]cyclohexyl}-3-[(2-fluoropyridin-4-yl)amino]-1H-pyrazole-4-carboxamide | Calc'd 440, found 440 |
| 40-94 | Cis or trans 1-[1-(cyanomethyl)-4-(3-methoxyazetidin-1-yl)cyclohexyl]-3-[(2-fluoropyridin-4-yl)amino]-1H-pyrazole-4-carboxamide | Calc'd 428, found 428 |
| 40-95 | Cis or trans 1-{1-(cyanomethyl)-4-[(2,2,2-trifluoroethyl)amino]cyclohexyl}-3-[(2-fluoropyridin-4-yl)amino]-1H-pyrazole-4-carboxamide | Calc'd 440, found 440 |

TABLE 34-continued

| Example | Structure | Compound Name | Exact Mass [M + H]+ |
|---|---|---|---|
| 40-96 | 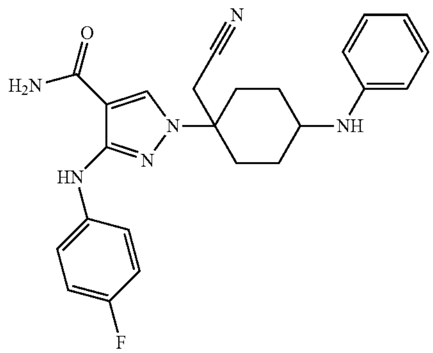 [SMILES: N#CCC1(n2cc(C(N)=O)c(Nc3ccc(F)cc3)n2)CCC(Nc2ccccc2)CC1] | Cis or trans 1-[1-(cyanomethyl)-4-(phenylamino)cyclohexyl]-3-[(4-fluorophenyl)amino]-1H-pyrazole-4-carboxamide | Calc'd 433, found 433 |
| 40-97 | 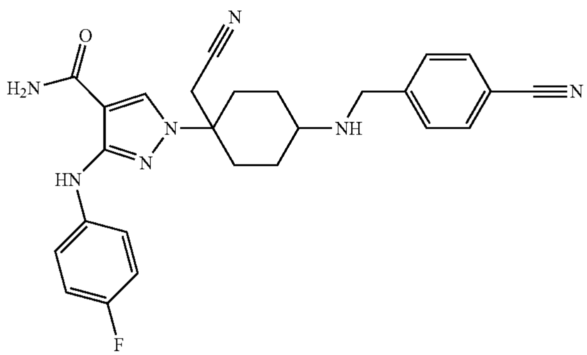 [SMILES: N#CCC1(n2cc(C(N)=O)c(Nc3ccc(F)cc3)n2)CCC(NCc2ccc(C#N)cc2)CC1] | Cis or trans 1-{4-[(4-cyanobenzyl)amino]-1-(cyanomethyl)cyclohexyl}-3-[(4-fluorophenyl)amino]-1H-pyrazole-4-carboxamide | Calc'd 472, found 472 |
| 40-98 | 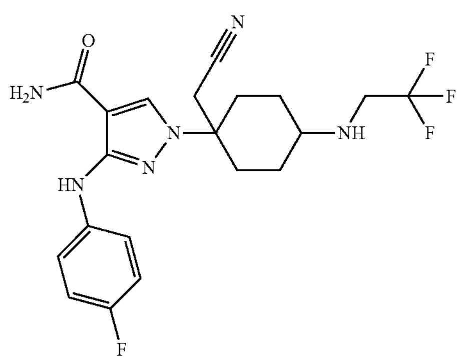 [SMILES: N#CCC1(n2cc(C(N)=O)c(Nc3ccc(F)cc3)n2)CCC(NCC(F)(F)F)CC1] | Cis or trans 1-{1-(cyanomethyl)-4-[(2,2,2-trifluoroethyl)amino]cyclohexyl}-3-[(4-fluorophenyl)amino]-1H-pyrazole-4-carboxamide | Calc'd 439, found 439 |
| 40-99 | 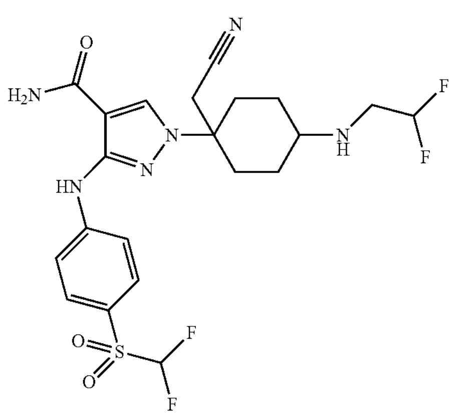 [SMILES: N#CCC1(n2cc(C(N)=O)c(Nc3ccc(S(=O)(=O)C(F)F)cc3)n2)CCC(NCC(F)F)CC1] | Cis or trans 1-{1-(cyanomethyl)-4-[(2,2-difluoroethyl)amino]cyclohexyl}-3-({4-[(difluoromethyl)sulfonyl]phenyl}amino)-1H-pyrazole-4-carboxamide | Calc'd 517, found 517 |

TABLE 34-continued

| Example | Structure | Compound Name | Exact Mass [M + H]+ |
|---|---|---|---|
| 40-100 | 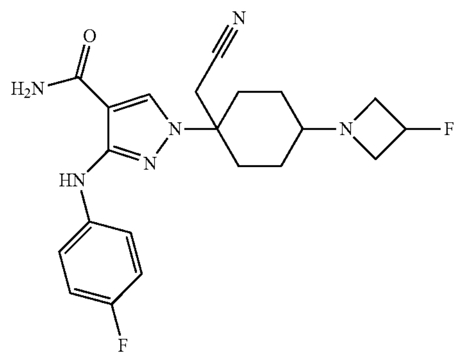 [SMILES: N#CCC1(n2cc(C(N)=O)c(Nc3ccc(F)cc3)n2)CCC(N2CC(F)C2)CC1] | Cis or trans 1-[1-(cyanomethyl)-4-(3-fluoroazetidin-1-yl)cyclohexyl]-3-[(4-fluorophenyl)amino]-1H-pyrazole-4-carboxamide | Calc'd 415, found 415 |
| 40-101 | 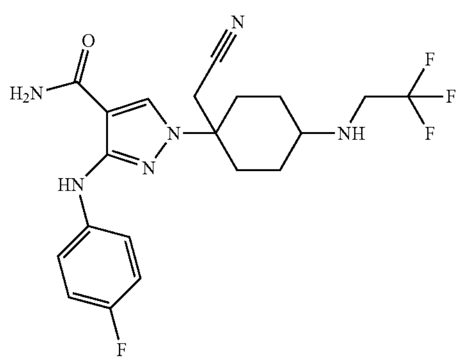 [SMILES: N#CCC1(n2cc(C(N)=O)c(Nc3ccc(F)cc3)n2)CCC(NCC(F)(F)F)CC1] | Cis or trans 1-{1-(cyanomethyl)-4-[(2,2,2-trifluoroethyl)amino]cyclohexyl}-3-[(4-fluorophenyl)amino]-1H-pyrazole-4-carboxamide | Calc'd 439, found 439 |
| 40-102 | 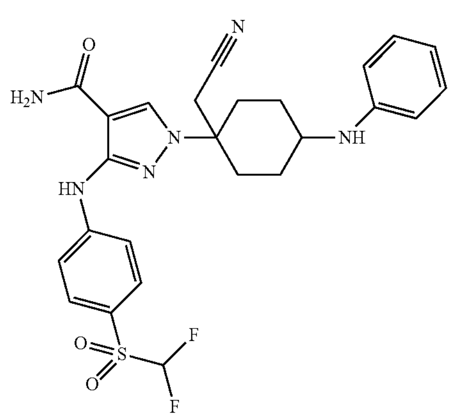 [SMILES: N#CCC1(n2cc(C(N)=O)c(Nc3ccc(S(=O)(=O)C(F)F)cc3)n2)CCC(Nc2ccccc2)CC1] | Cis or trans 1-[1-(cyanomethyl)-4-(phenylamino)cyclohexyl]-3-({4-[(difluoromethyl)sulfonyl]phenyl}amino)-1H-pyrazole-4-carboxamide | Calc'd 529, found 529 |
| 40-103 | 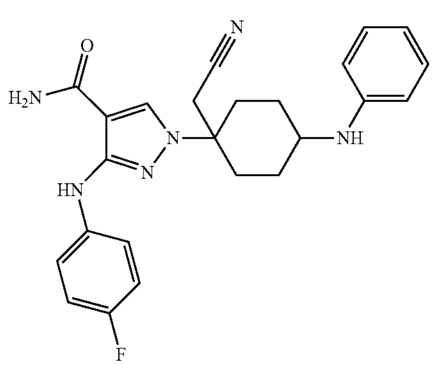 [SMILES: N#CCC1(n2cc(C(N)=O)c(Nc3ccc(F)cc3)n2)CCC(Nc2ccccc2)CC1] | Cis or trans 1-[1-(cyanomethyl)-4-(phenylamino)cyclohexyl]-3-[(4-fluorophenyl)amino]-1H-pyrazole-4-carboxamide | Calc'd 433, found 433 |

TABLE 34-continued

| Example | Compound Name | Exact Mass [M + H]+ |
|---|---|---|
| 40-104 | Cis or trans 1-[1-(cyanomethyl)-4-(3-fluoroazetidin-1-yl)cyclohexyl]-3-[(2-fluoropyridin-4-yl)amino]-1H-pyrazole-4-carboxamide | Calc'd 416, found 416 |
| 40-105 | Cis or trans 1-[1-(cyanomethyl)-4-(3-fluoroazetidin-1-yl)cyclohexyl]-3-({4-[(difluoromethyl)sulfonyl]phenyl}amino)-1H-pyrazole-4-carboxamide | Calc'd 511, found 511 |
| 40-106 | Cis or trans 1-{1-(cyanomethyl)-4-[(2,2-difluoroethyl)amino]cyclohexyl}-3-[(2-fluoropyridin-4-yl)amino]-1H-pyrazole-4-carboxamide | Calc'd 422, found 422 |
| 40-107 | Cis or trans 1-[1-(cyanomethyl)-4-(3-fluoroazetidin-1-yl)cyclohexyl]-3-[(4-fluorophenyl)amino]-1H-pyrazole-4-carboxamide | Calc'd 415, found 415 |

TABLE 34-continued

| Example | Structure | Compound Name | Exact Mass [M + H]+ |
|---|---|---|---|
| 40-108 | 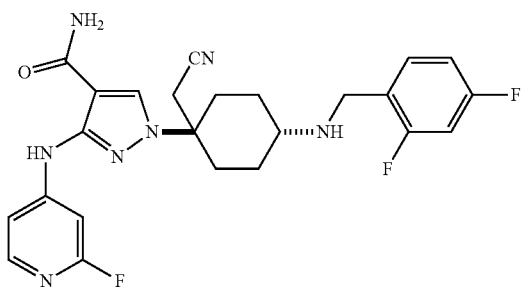 | 1-[cis-4-(benzylamino)-1-(cyanomethyl)cyclohexyl]-3-[(4-fluorophenyl)amino]-1H-pyrazole-4-carboxamide | Calc'd 447, found 447 |

Scheme #35

Example #41-1

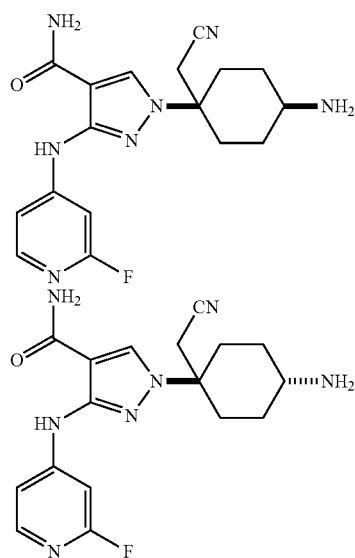

Trans 1-(1-(cyanomethyl)-4-((2,4-difluorobenzyl)amino)cyclohexyl)-3-((2-fluoropyridin-4-yl)amino)-1H-pyrazole-4-carboxamide (Example 41-1)

Step A: Cis or trans 1-(4-amino-1-(cyanomethyl)cyclohexyl)-3-((2-fluoropyridin-4yl)amino)-1H-pyrazole-4-carboxamide (Example 41-1A and 41-1B)

To a solution of 1-(1-(cyanomethyl)-4-oxocyclohexyl)-3-((2-fluoropyridin-4-yl)amino)-1H-pyrazole-4-carboxamide (1.5 g, 4.2 mmol) in MeOH (11.7 mL) and DMF (9.1 mL) was added $NH_4OAc$ (3.24 g, 42.1 mmol). The reaction mixture was allowed to stir at ambient temperature for 15 minutes. Sodium cyanoborohydride (0.265 g, 4.21 mmol) was added and the reaction mixture was allowed to stir for 20 hours at room temperature. The mixture was then purified directly by mass-triggered reverse-phase preparative HPLC (MeCN/water, with 0.1% v/v TFA modifier) to afford a diasteromeric mixture of the title compound. 1-(4-Amino-1-(cyanomethyl)cyclohexyl)-3-((2-fluoropyridin-4-yl)amino)-1H-pyrazole-4-carboxamide was chirally resolved to the constituent diastereomers by chiral SFC (Phenomenex Lux Cellulose-4, 5 µM, 2.1×25 cm, 30% MeOH+0.25% dimethyl ethylamine/70% $CO_2$, 70 mL/min). Desired fractions were identified, combined, and concentrated in vacuo to afford diastereomerically pure samples of the title compounds:

Example #41-1A

Cis 1-(4-amino-1-(cyanomethyl)cyclohexyl)-3-((2-fluoropyridin-4-yl)amino)-1H-pyrazole-4-carboxamide, first diastereomer to elute from column.
$^1$H NMR (500 MHz, DMSO-$d_6$): δ 10.10 (br s, 1H), 9.67 (s, 1H), 8.70 (s, 1H), 7.93-7.91 (m, 2H), 7.78 (br s, 1H), 7.36-7.32 (m, 2H), 3.06-3.02 (m, 2H), 2.69 (d, J=4 Hz, 2H), 2.63-2.60 (m, 2H), 1.94-1.89 (m, 2H), 1.32-1.26 (m, 1H), 1.18 (t, J=7.5 Hz, 3H).
LRMS (ESI) calc'd for $C_{17}H_{20}FN_7O$ [M+H]+: 358. Found: 358.

Example #41-1B

Trans 1-(4-amino-1-(cyanomethyl)cyclohexyl)-3-((2-fluoropyridin-4-yl)amino)-1H-pyrazole-4-carboxamide, second diastereomer to elute from column.
$^1$H NMR (500 MHz, DMSO-$d_6$): δ 9.67 (s, 1H), 8.54 (s, 1H), 7.93-7.91 (m, 2H), 7.73 (br s, 1H), 7.37-7.31 (m, 3H), 3.21 (s, 2H), 3.14 (m, 1H), 2.62 (m, 1H), 2.34-2.30 (m, 2H), 2.09-2.05 (m, 2H), 1.87-1.83 (m, 2H), 1.67-1.63 (m, 2H).

LRMS (ESI) calc'd for $C_{17}H_{20}FN_7O$ [M+H]$^+$: 358. Found: 358.

Step B: Trans 1-(1-(cyanomethyl)-4-((2,4-difluorobenzyl)amino)cyclohexyl)-3-((2-fluoropyridin-4-yl)amino)-1H-pyrazole-4-carboxamide (Example 41-1)

To a solution of trans 1-(4-amino-1-(cyanomethyl)cyclohexyl)-3-((2-fluoropyridin-4-yl)amino)-1H-pyrazole-4-carboxamide (10 mg, 0.028 mmol) in MeOH (0.23 mL) and DMF (0.047 mL) was added 2,4-difluorobenzaldehyde (0.003 mL, 0.028 mmol). The reaction mixture was allowed to stir at ambient temperature for 15 minutes. Sodium cyanoborohydride (2 mg, 0.03 mmol) was added and the reaction mixture was allowed to stir for 20 hours at ambient temperature. The mixture was then purified directly by mass-triggered reverse-phase preparative HPLC (MeCN/water, with 0.1% v/v TFA modifier) to afford the title compound.
$^1$H NMR (500 MHz, acetone-d$_6$): δ 9.62 (s, 1H), 8.49 (s, 1H), 7.89 (d, J=6 Hz, 1H), 7.67 (s, 1H), 7.51 (dd, J=15, 7.8 Hz, 1H), 7.34 (s, 1H), 7.28-7.25 (m, 2H), 7.15-7.11 (m, 1H), 7.03-7.01 (m, 1H), 3.69 (s, 2H), 3.15 (s, 2H), 2.58-2.56 (m, 1H), 2.23 (m, 2H), 2.02 (m, 2H), 1.82-1.80 (m, 1H), 1.63 (m, 2H), 1.51 (m, 2H). LRMS (ESI) calc'd for $C_{24}H_{24}FN_7O$ [M+H]$^+$: 484. Found: 484.

The following compounds shown in TABLE 35 were prepared according to Scheme #35 following similar procedures described for Example #41-1, which can be achieved by those of ordinary skill in the art of organic synthesis.

TABLE 35

| Example | Compound Name | Exact Mass [M + H]$^+$ |
|---|---|---|
| 41-2 | 1-[trans-4-amino-1-(cyanomethyl)cyclohexyl]-3-({4-(difluoromethyl)sulfonyl]phenyl}amino)-1H-pyrazole-4-carboxamide | Calc'd 453, Found 453 |
| 41-3 | 1-[cis-4-amino-1-(cyanomethyl)cyclohexyl]-3-({4-(difluoromethyl)sulfonyl]phenyl}amino)-1H-pyrazole-4-carboxamide | Calc'd 453, Found 453 |
| 41-4 | Cis or trans 1-{1-(cyanomethyl)-4-[(2,4-difluorobenzyl)amino]cyclohexyl}-3-[(2-fluoropyridin-4-yl)amino]-1H-pyrazole-4-carboxamide | Calc'd 484, Found 484 |

TABLE 35-continued

| Example | Structure | Compound Name | Exact Mass [M + H]+ |
|---|---|---|---|
| 41-5 | 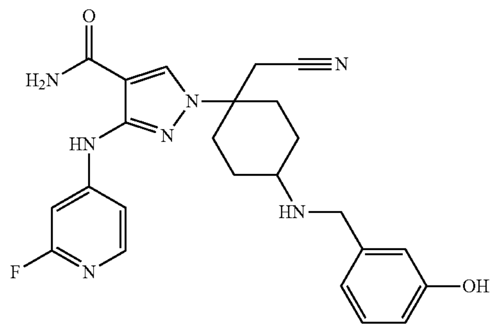 [SMILES: N#CCC1(n2cc(C(N)=O)c(Nc3ccnc(F)c3)n2)CCC(NCc2cccc(O)c2)CC1] | Cis or trans 1-{1-(cyanomethyl)-4-[(3-hydroxybenzyl)amino]cyclohexyl}-3-[(2-fluoropyridin-4-yl)amino]-1H-pyrazole-4-carboxamide | Calc'd 464, Found 464 |
| 41-6 | 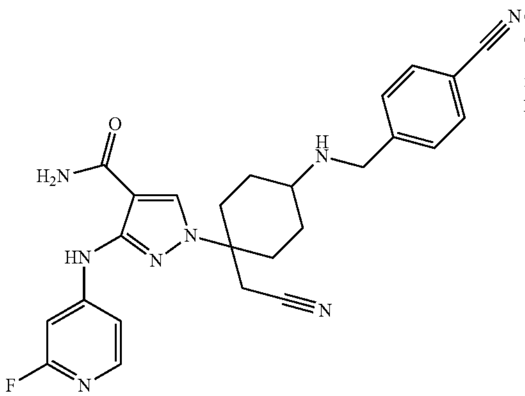 [SMILES: N#CCC1(n2cc(C(N)=O)c(Nc3ccnc(F)c3)n2)CCC(NCc2ccc(C#N)cc2)CC1] | Cis or trans 1-{4-[(4-cyanobenzyl)amino]-1-(cyanomethyl)cyclohexyl}-3-[(2-fluoropyridin-4-yl)amino]-1H-pyrazole-4-carboxamide | Calc'd 473, Found 473 |
| 41-7 | 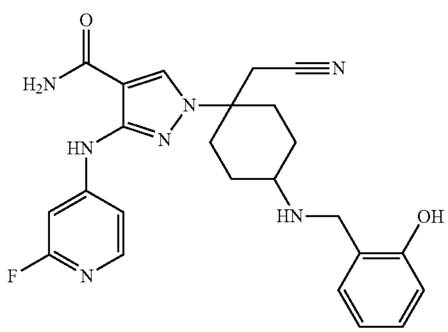 [SMILES: N#CCC1(n2cc(C(N)=O)c(Nc3ccnc(F)c3)n2)CCC(NCc2ccccc2O)CC1] | Cis or trans 1-{1-(cyanomethyl)-4-[(2-hydroxybenzyl)amino]cyclohexyl}-3-[(2-fluoropyridin-4-yl)amino]-1H-pyrazole-4-carboxamide | Calc'd 464, Found 464 |
| 41-8 | 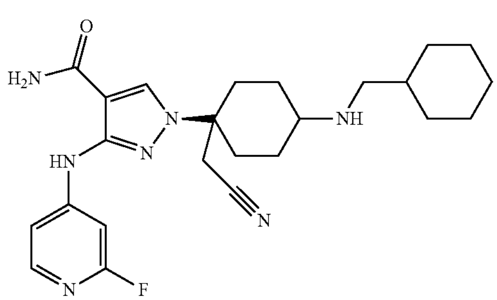 | Trans 1-{1-(cyanomethyl)-4-[(cyclohexylmethyl)amino]cyclohexyl}-3-[(2-fluoropyridin-4-yl)amino]-1H-pyrazole-4-carboxamide | Calc'd 454, Found 454 |

TABLE 35-continued

| Example | Structure | Compound Name | Exact Mass [M + H]+ |
|---|---|---|---|
| 41-9 | 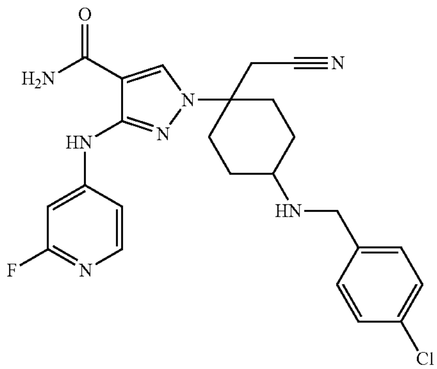 [SMILES: N#CCC1(n2cc(C(N)=O)c(Nc3ccnc(F)c3)n2)CCC(NCc2ccc(Cl)cc2)CC1] | Cis or trans 1-{4-[(4-chlorobenzyl)amino]-1-(cyanomethyl)cyclohexyl}-3-[(2-fluoropyridin-4-yl)amino]-1H-pyrazole-4-carboxamide | Calc'd 482, Found 482 |
| 41-10 | 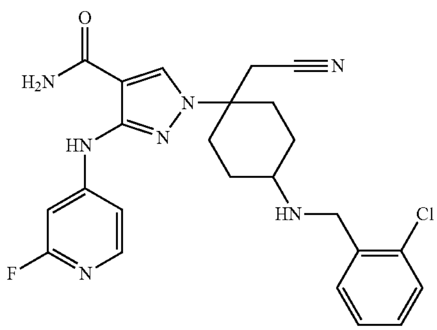 [SMILES: N#CCC1(n2cc(C(N)=O)c(Nc3ccnc(F)c3)n2)CCC(NCc2ccccc2Cl)CC1] | Cis or trans 1-{4-[(2-chlorobenzyl)amino]-1-(cyanomethyl)cyclohexyl}-3-[(2-fluoropyridin-4-yl)amino]-1H-pyrazole-4-carboxamide | Calc'd 482, Found 482 |
| 41-11 | 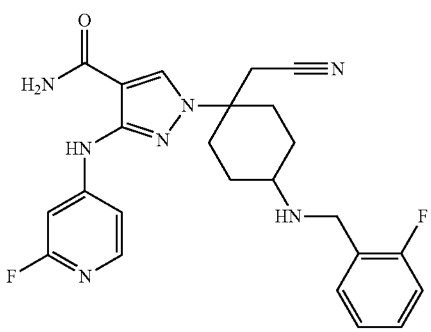 [SMILES: N#CCC1(n2cc(C(N)=O)c(Nc3ccnc(F)c3)n2)CCC(NCc2ccccc2F)CC1] | Cis or trans 1-{1-(cyanomethyl)-4-[(2-fluorobenzyl)amino]cyclohexyl}-3-[(2-fluoropyridin-4-yl)amino]-1H-pyrazole-4-carboxamide | Calc'd 466, Found 466 |
| 41-12 | 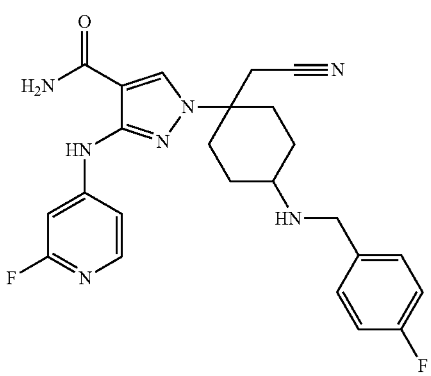 [SMILES: N#CCC1(n2cc(C(N)=O)c(Nc3ccnc(F)c3)n2)CCC(NCc2ccc(F)cc2)CC1] | Cis or trans 1-{1-(cyanomethyl)-4-[(4-fluorobenzyl)amino]cyclohexyl}-3-[(2-fluoropyridin-4-yl)amino]-1H-pyrazole-4-carboxamide | Calc'd 466, Found 466 |

TABLE 35-continued

| Example | Structure | Compound Name | Exact Mass [M + H]+ |
|---|---|---|---|
| 41-13 | 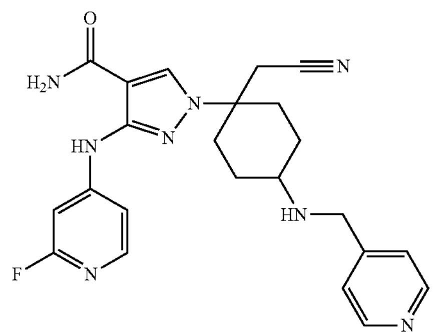 [SMILES: N#CCC1(n2cc(C(N)=O)c(Nc3ccnc(F)c3)n2)CCC(NCc2ccncc2)CC1] | Cis or trans 1-{1-(cyanomethyl)-4-[(pyridin-4-ylmethyl)amino]cyclohexyl}-3-[(2-fluoropyridin-4-yl)amino]-1H-pyrazole-4-carboxamide | Calc'd 449, Found 449 |
| 41-14 | 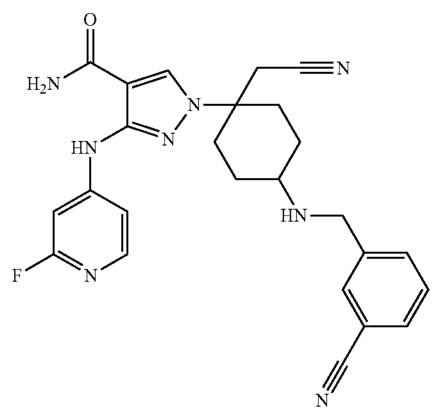 [SMILES: N#CCC1(n2cc(C(N)=O)c(Nc3ccnc(F)c3)n2)CCC(NCc2cccc(C#N)c2)CC1] | Cis or trans 1-{4-[(3-cyanobenzyl)amino]-1-(cyanomethyl)cyclohexyl}-3-[(2-fluoropyridin-4-yl)amino]-1H-pyrazole-4-carboxamide | Calc'd 473, Found 473 |
| 41-15 | 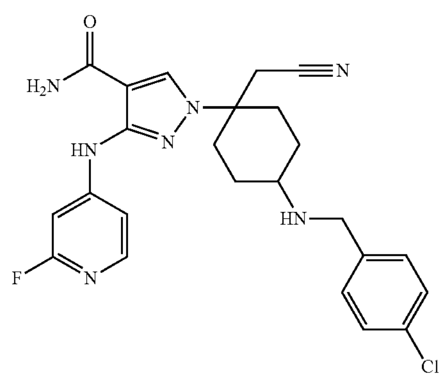 [SMILES: N#CCC1(n2cc(C(N)=O)c(Nc3ccnc(F)c3)n2)CCC(NCc2ccc(Cl)cc2)CC1] | Cis or trans 1-{4-[(4-chlorobenzyl)amino]-1-(cyanomethyl)cyclohexyl}-3-[(2-fluoropyridin-4-yl)amino]-1H-pyrazole-4-carboxamide | Calc'd 482, Found 482 |
| 41-16 | 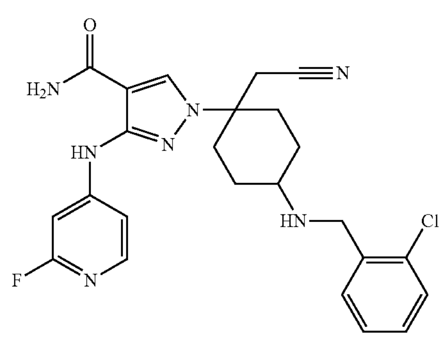 [SMILES: N#CCC1(n2cc(C(N)=O)c(Nc3ccnc(F)c3)n2)CCC(NCc2ccccc2Cl)CC1] | Cis or trans 1-{4-[(2-chlorobenzyl)amino]-1-(cyanomethyl)cyclohexyl}-3-[(2-fluoropyridin-4-yl)amino]-1H-pyrazole-4-carboxamide | Calc'd 482, Found 482 |

TABLE 35-continued

| Example | Structure | Compound Name | Exact Mass [M + H]+ |
|---|---|---|---|
| 41-17 | 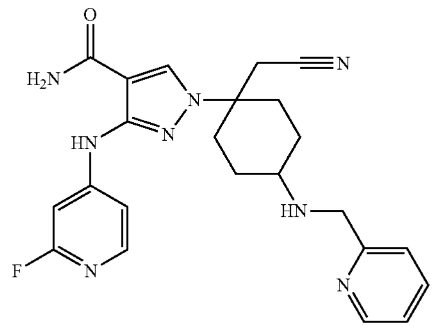 [SMILES: N#CCC1(n2cc(C(N)=O)c(Nc3ccnc(F)c3)n2)CCC(NCc2ccccn2)CC1] | Cis or trans 1-{1-(cyanomethyl)-4-[(pyridin-2-ylmethyl)amino]cyclohexyl}-3-[(2-fluoropyridin-4-yl)amino]-1H-pyrazole-4-carboxamide | Calc'd 449, Found 449 |
| 41-18 | 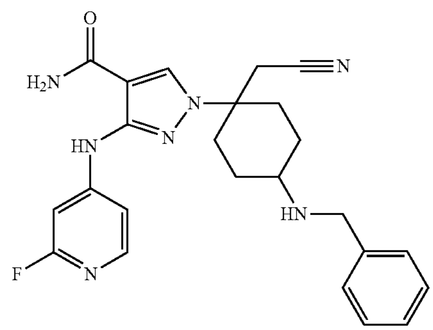 [SMILES: N#CCC1(n2cc(C(N)=O)c(Nc3ccnc(F)c3)n2)CCC(NCc2ccccc2)CC1] | Cis or trans 1-[4-(benzylamino)-1-(cyanomethyl)cyclohexyl]-3-[(2-fluoropyridin-4-yl)amino]-1H-pyrazole-4-carboxamide | Calc'd 448, Found 448 |
| 41-19 | 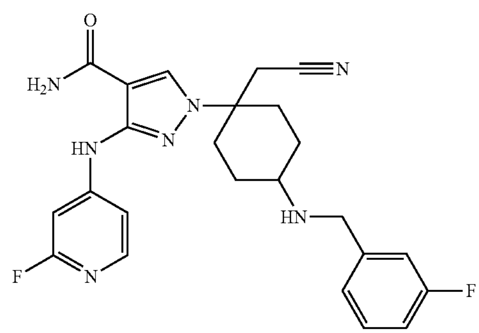 [SMILES: N#CCC1(n2cc(C(N)=O)c(Nc3ccnc(F)c3)n2)CCC(NCc2cccc(F)c2)CC1] | Cis or trans 1-{1-(cyanomethyl)-4-[(3-fluorobenzyl)amino]cyclohexyl}-3-[(2-fluoropyridin-4-yl)amino]-1H-pyrazole-4-carboxamide | Calc'd 466, Found 466 |
| 41-20 | 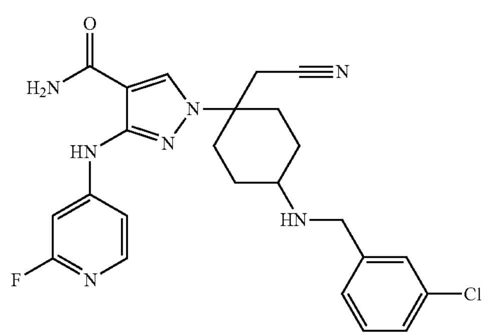 [SMILES: N#CCC1(n2cc(C(N)=O)c(Nc3ccnc(F)c3)n2)CCC(NCc2cccc(Cl)c2)CC1] | Cis or trans 1-{4-[(3-chlorobenzyl)amino]-1-(cyanomethyl)cyclohexyl}-3-[(2-fluoropyridin-4-yl)amino]-1H-pyrazole-4-carboxamide | Calc'd 482, Found 482 |

TABLE 35-continued

| Example | Compound Name | Exact Mass [M + H]+ |
|---|---|---|
| 41-21 | Cis or trans 1-{1-(cyanomethyl)-4-[(2-fluorobenzyl)amino]cyclohexyl}-3-[(2-fluoropyridin-4-yl)amino]-1H-pyrazole-4-carboxamide | Calc'd 466, Found 466 |
| 41-22 | Cis or trans 1-{1-(cyanomethyl)-4-[(pyridin-3-ylmethyl)amino]cyclohexyl}-3-[(2-fluoropyridin-4-yl)amino]-1H-pyrazole-4-carboxamide | Calc'd 449, Found 449 |
| 41-23 | Cis or trans 1-{4-[(3-chlorobenzyl)amino]-1-(cyanomethyl)cyclohexyl}-3-[(2-fluoropyridin-4-yl)amino]-1H-pyrazole-4-carboxamide | Calc'd 482, Found 482 |
| 41-24 | Cis or trans 1-{1-(cyanomethyl)-4-[(3-fluorobenzyl)amino]cyclohexyl}-3-[(2-fluoropyridin-4-yl)amino]-1H-pyrazole-4-carboxamide | Calc'd 466, Found 466 |

TABLE 35-continued

| Example | Structure | Compound Name | Exact Mass [M + H]+ |
|---|---|---|---|
| 41-25 | 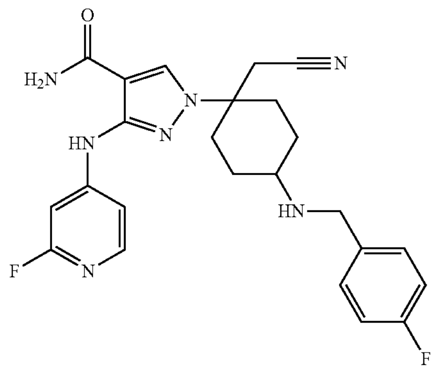 [SMILES: N#CCC1(n2cc(C(N)=O)c(Nc3ccnc(F)c3)n2)CCC(NCc2ccc(F)cc2)CC1] | Cis or trans 1-{1-(cyanomethyl)-4-[(4-fluorobenzyl)amino]cyclohexyl}-3-[(2-fluoropyridin-4-yl)amino]-1H-pyrazole-4-carboxamide | Calc'd 466, Found 466 |
| 41-26 | 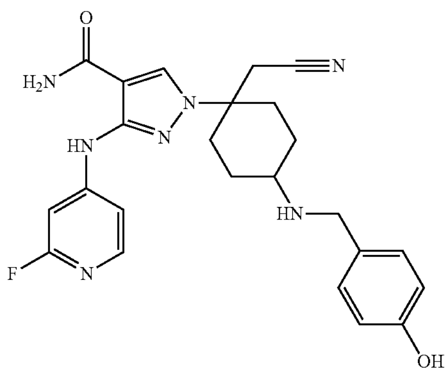 [SMILES: N#CCC1(n2cc(C(N)=O)c(Nc3ccnc(F)c3)n2)CCC(NCc2ccc(O)cc2)CC1] | Cis or trans 1-{1-(cyanomethyl)-4-[(4-hydroxybenzyl)amino]cyclohexyl}-3-[(2-fluoropyridin-4-yl)amino]-1H-pyrazole-4-carboxamide | Calc'd 464, Found 464 |
| 41-27 | 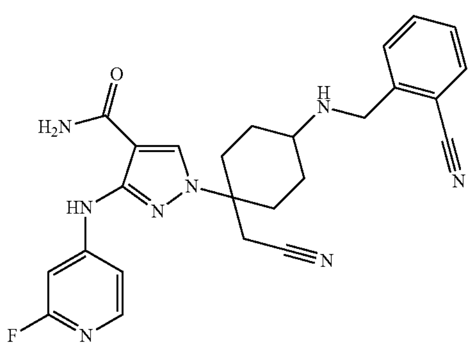 [SMILES: N#CCC1(n2cc(C(N)=O)c(Nc3ccnc(F)c3)n2)CCC(NCc2ccccc2C#N)CC1] | Cis or trans 1-{4-[(2-cyanobenzyl)amino]-1-(cyanomethyl)cyclohexyl}-3-[(2-fluoropyridin-4-yl)amino]-1H-pyrazole-4-carboxamide | Calc'd 473, Found 473 |
| 41-28 | 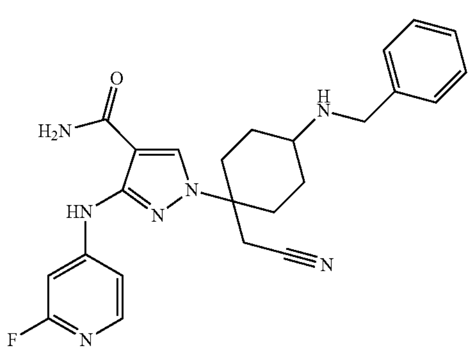 [SMILES: N#CCC1(n2cc(C(N)=O)c(Nc3ccnc(F)c3)n2)CCC(NCc2ccccc2)CC1] | Cis or trans 1-[4-(benzylamino)-1-(cyanomethyl)cyclohexyl]-3-[(2-fluoropyridin-4-yl)amino]-1H-pyrazole-4-carboxamide | Calc'd 448, Found 448 |

Scheme #28

Example #42

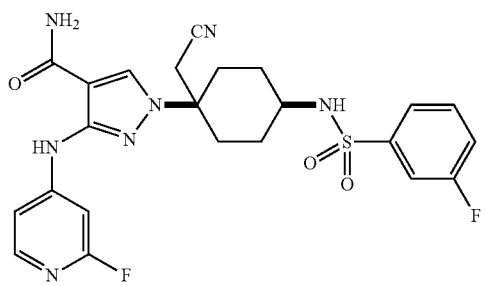

cis-1-(1-(Cyanomethyl)-4-(3-fluorophenylsulfona-
mido)cyclohexyl)-3-((2-fluoropyridin-4-yl)amino)-
1H-pyrazole-4-carboxamide To a solution of cis-1-(4-amino-1-(cyanomethyl)cyclo-hexyl)-3-((2-fluoropyridin-4-yl)amino)-1H-pyrazole-4-carboxamide (12 mg, 0.026 mmol) in DMF (0.26 mL) was added DIPEA (0.018 mL, 0.105 mmol) and DMAP (4 mg, 0.03 mmol). 3-Fluorobenzenesulfonyl chloride (0.005 mL. 0.04 mmol) was added and the reaction mixture was allowed to stir at ambient temperature for 20 hours. The mixture was then purified directly by mass-triggered reverse-phase preparative HPLC (MeCN/water, with 0.1% v/v TFA modifier). Desired fractions were identified, combined, and concentrated in vacuo. The residue was dissolved in a 1:1 mixture of MeOH/DMF and passed through a macroporous polystyrene-carbonate cartridge. The cartridge was washed with 1:1 MeOH/DMF, and the filtrate was concentrated in vacuo to afford the title compound. $^1$H NMR (500 MHz, DMSO-$d_6$): δ 9.64 (s, 1H), 8.53 (s, 1H), 7.93 (br s, 1H), 7.90 (d, J=6 Hz, 1H), 7.74 (d, J=7.5 Hz, 1H), 7.68 (br s, 1H), 7.64-7.62 (m, 2H), 7.57-7.55 (m, 1H), 7.52-7.47 (m, 1H), 7.32-7.30 (m, 3H), 3.15-3.13 (m, 1H), 2.98 (s, 2H), 2.62-2.61 (m, 1H), 1.83 (t, J=13 Hz, 2H), 1.59-1.57 (m, 2H), 1.16-1.09 (m, 2H).

LRMS (ESI) calc'd for $C_{23}H_{23}F_2N_7O_3S$ [M+H]$^+$: 516. Found: 516.

Scheme #28

Example #43-1 and 43-2

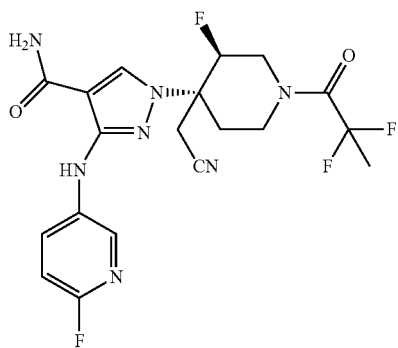

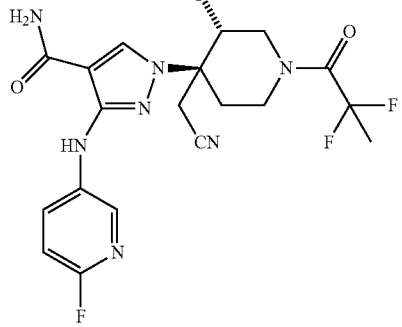

1-((3S,4R or 3R,4S)-4-(Cyanomethyl)-1-(2,2-difluo-ropropanoyl)-3-fluoropiperidin-4-yl)-3-((6-fluoropy-ridin-3-yl)amino)-1H-pyrazole-4-carboxamide

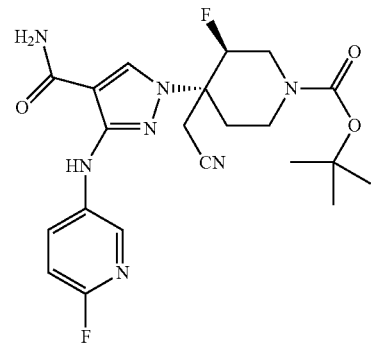

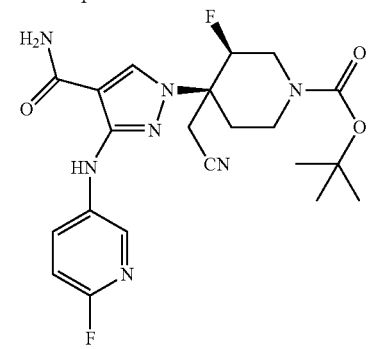

Step A: (3S,4R and 3R,4S)-tert-Butyl 4-(4-carbam-oyl-3-((6-fluoropyridin-3-yl)amino)-1H-pyrazol-1-yl)-4-(cyanomethyl)-3-fluoropiperidine-1-carboxy-late and (3S,4S and 3R,4R)-tert-butyl 4-(4-carbamoyl-3-((6-fluoropyridin-3-yl)amino)-1H-pyrazol-1-yl)-4-(cyanomethyl)-3-fluoropiperidine-1-carboxylate To a solution of tert-butyl (4E and 4Z)-4-(cyanometh-ylidene)-3-fluoropiperidine-1-carboxylate (158 mg, 0.656 mmol) in MeCN were added 3-[(6-fluoropyridin-3-yl)amino]-1H-pyrazole-4-carboxamide (145 mg, 0.656 mmol) and DBU (0.20 mL, 1.3 mmol). The solution was heated to 65° C. for 16 hours. Another batch of (4E and 4Z)-4-(cya-nomethylidene)-3-fluoropiperidine-1-carboxylate (790 mg, 3.28 mmol) was added and stirred for another 2 hours at ambient temperature. The reaction mixture was diluted with EtOAc and washed with brine, dried over anhydrous MgSO$_4$, filtered, and concentrated in vacuo to afford an oily residue. The residue was purified by MPLC on silica gel (using a gradient elution of 0-100% EtOAc/hexanes) to afford the title compounds.

Example 43-1-A1

(3S,4R and 3R,4S)-tert-Butyl 4-(4-carbamoyl-3-((6-fluoropyridin-3-yl)amino)-1H-pyrazol-1-yl)-4-(cyanomethyl)-3-fluoropiperidine-1-carboxylate
LRMS (ESI) calc'd for C$_{21}$H$_{26}$F$_2$N$_7$O$_3$ [M+H]$^+$: 462. Found: 462.

Example 43-1-A2

(3S,4S and 3R,4R)-tert-butyl 4-(4-carbamoyl-3-((6-fluoropyridin-3-yl)amino)-1H-pyrazol-1-yl)-4-(cyanomethyl)-3-fluoropiperidine-1-carboxylate
LRMS (ESI) calc'd for C$_{21}$H$_{26}$F$_2$N$_7$O$_3$ [M+11]$^+$: 462. Found: 462.

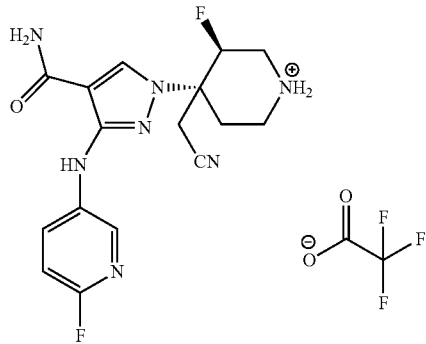 [SMILES: N#CC[C@]1(n2cc(C(N)=O)c(Nc3ccc(F)nc3)n2)CC[NH2+]C[C@@H]1F ; O=C([O-])C(F)(F)F]

Step B: (3S,4R and 3R,4S)-4-(4-carbamoyl-3-((6-fluoropyridin-3-yl)amino)-1H-pyrazol-1-yl)-4-(cyanomethyl)-3-fluoropiperidin-1-ium To a solution of (3S,4R and 3R,4S)-tert-Butyl 4-(4-carbamoyl-3-((6-fluoropyridin-3-yl)amino)-1H-pyrazol-1-yl)-4-(cyanomethyl)-3-fluoropiperidine-1-carboxylate (100 mg, 0.217 mmol) in DCM (1 mL) was added TFA (1 mL) and stirred for 30 min. The reaction mixture was then concentrated in vacuo and used without further purification.

LRMS (ESI) calc'd for C$_{16}$H$_{17}$F$_2$N$_7$O [M+H]$^+$: 362. Found: 362.

Step C: 1-((3S,4R or 3R,4S)-4-(Cyanomethyl)-1-(2,2-difluoropronanoyl)-3-fluoropiperidin-4-yl)-3-((6-fluoropyridin-3-yl)amino)-1H-pyrazole-4-carboxamide (3S,4R and 3R,4S)-4-(4-carbamoyl-3-((6-fluoropyridin-3-yl)amino)-1H-pyrazol-1-yl)-4-(cyanomethyl)-3-fluoropiperidin-1-ium (33 mg, 0.069 mmol) was dissolved in DMF (1 mL) and TEA (0.058 mL, 0.42 mmol), was added followed by 2,2-difluoropropanoic acid (23 mg, 0.21 mmol), and 2-(1H-7-Azabenzotriazol-1-yl)-1,1,3,3-tetramethyl uronium hexafluorophosphate methanaminium (HATU) (32 mg, 0.083 mmol). The resulting mixture was stirred for 16 hours. The reaction mixture was filtered and purified directly by reverse phase HPLC followed by chiral SFC to afford the chirally resolved title compound.

Example 43-1

First enantiomer to elute: 1-((3S,4R or 3R,4S)-4-(cyanomethyl)-1-(2,2-difluoropropanoyl)-3-fluoropiperidin-4-yl)-3-((6-fluoropyridin-3-yl)amino)-1H-pyrazole-4-carboxamide. $^1$H NMR (500 MHz, CD$_3$OD): δ 8.51 (d, J=11.5 Hz, 1H), 8.34 (s, 1H), 8.16 (m, 1H), 7.10-6.98 (dd, J=11, 2 Hz, 1H) 5.68-5.56 (dd, J=45, 13 Hz, 1H), 4.73-4.31 (m 2H), 3.46-3.00 (m, 4H), 2.66 (t, J=13 Hz, 1H), 2.40-2.30 (m, 1H), 1.86-1.77 (m, 3H).
LRMS (ESI) calc'd for C$_{19}$H$_{20}$F$_4$N$_7$O$_2$ [M+H]$^+$: 454. Found: 454.

Example 43-2

Second enantiomer to elute: 1-((3S,4R or 3R,4S)-4-(cyanomethyl)-1-(2,2-difluoropropanoyl)-3-fluoropiperidin-4-yl)-3-((6-fluoropyridin-3-yl)amino)-1H-pyrazole-4-carboxamide. $^1$H NMR (500 MHz, CD$_3$OD): 8.51 (d, J=11.5 Hz, 1H), 8.34 (s, 1H), 8.16 (m, 1H), 7.10-6.98 (dd, J=11, 2 Hz, 1H) 5.68-5.56 (dd, J=45, 13 Hz, 1H), 4.73-4.31 (m 2H), 3.46-3.00 (m, 4H), 2.66 (t, J=13 Hz, 1H), 2.40-2.30 (m, 1H), 1.86-1.77 (m, 3H).
LRMS (ESI) calc'd for C$_{19}$H$_{20}$F$_4$N$_7$O$_2$ [M+H]$^+$: 454. Found: 454.

The following compounds shown in TABLE 36 were prepared according to Scheme #28 following similar procedures described for Example #43-1 and 43-2, which can be achieved by those of ordinary skill in the art of organic synthesis.

TABLE 36

| Example | Structure | Compound Name | Exact Mass [M + H]$^+$ |
|---|---|---|---|
| 43-3 | 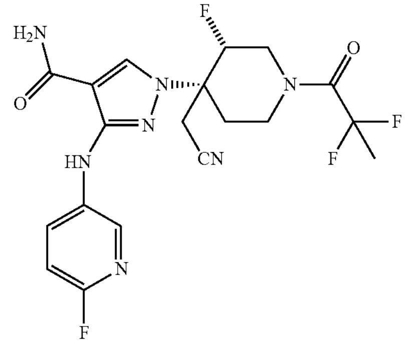 [SMILES: CC(F)(F)C(=O)N1CC[C@](CC#N)(n2cc(C(N)=O)c(Nc3ccc(F)nc3)n2)[C@H](F)C1] | 1-((3R,4R or 3S,4S)-4-(cyanomethyl)-1-(2,2-difluoropropanoyl)-3-fluoropiperidin-4-yl)-3-((6-fluoropyridin-3-yl)amino)-1H-pyrazole-4-carboxamide | Calc'd 454, Found 454 |

TABLE 36-continued

| Example | Structure | Compound Name | Exact Mass [M + H]+ |
|---------|-----------|---------------|---------------------|
| 43-4 | 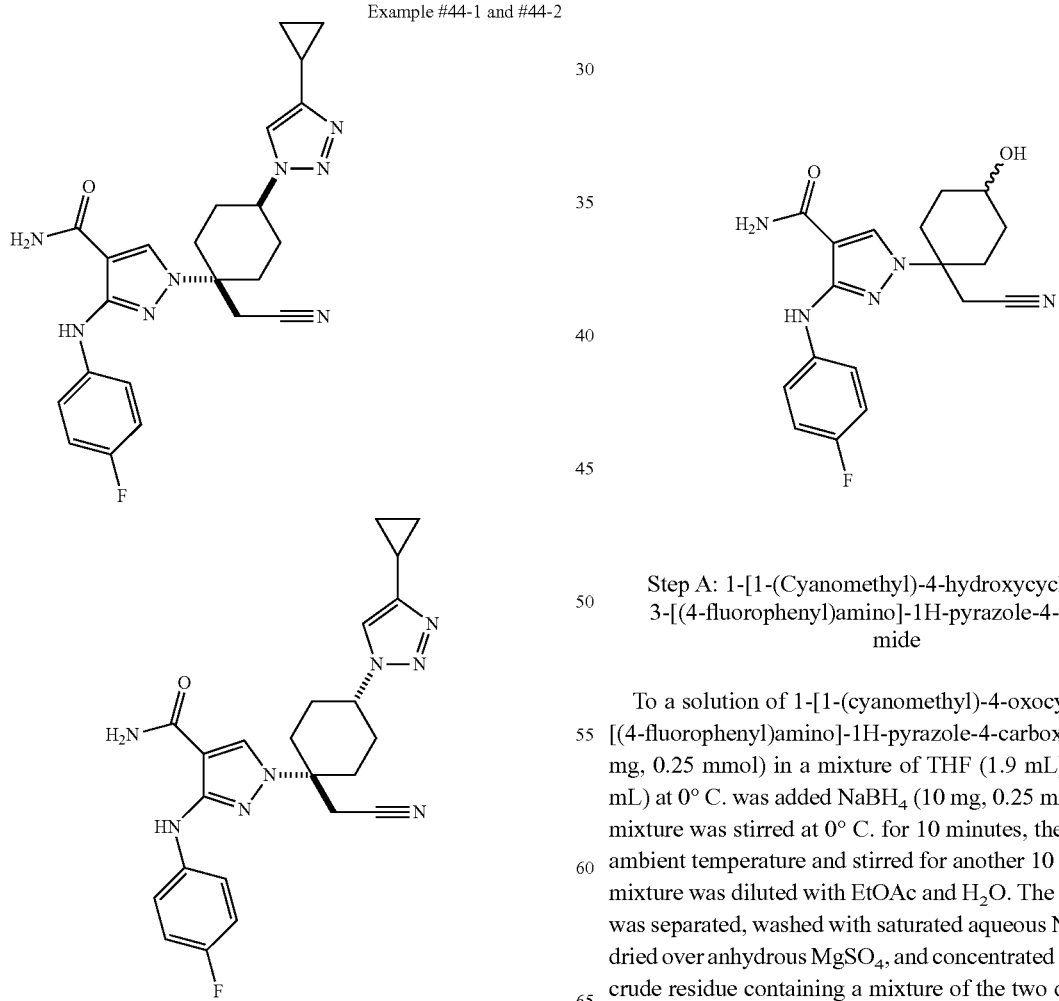 | 1-((3R,4R or 3S,4S)-4-(cyanomethyl)-1-(2,2-difluoropropanoyl)-3-fluoropiperidin-4-yl)-3-((6-fluoropyridin-3-yl)amino)-1H-pyrazole-4-carboxamide | Calc'd 454, Found 454 |

Cis or trans 1-[1-(cyanomethyl)-4-(4-cyclopropyl-1H-1,2,3-triazol-1-yl)cyclohexyl]-3-[(4-fluorophenyl)amino]-1H-pyrazole-4-carboxamide Step A: 1-[1-(Cyanomethyl)-4-hydroxycyclohexyl]-3-[(4-fluorophenyl)amino]-1H-pyrazole-4-carboxamide To a solution of 1-[1-(cyanomethyl)-4-oxocyclohexyl]-3-[(4-fluorophenyl)amino]-1H-pyrazole-4-carboxamide (90 mg, 0.25 mmol) in a mixture of THF (1.9 mL)/MeOH (0.6 mL) at 0° C. was added NaBH$_4$ (10 mg, 0.25 mmol), and the mixture was stirred at 0° C. for 10 minutes, then warmed to ambient temperature and stirred for another 10 minutes. The mixture was diluted with EtOAc and H$_2$O. The organic layer was separated, washed with saturated aqueous NH$_4$Cl, brine, dried over anhydrous MgSO$_4$, and concentrated in vacuo. The crude residue containing a mixture of the two diasteromeric alcohols was used for next step without purification. LRMS (ESI) calc'd for C$_{18}$H$_{20}$FN$_5$O$_2$ [M+H]+: 358. Found: 358.

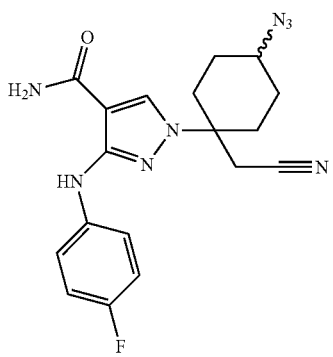 [SMILES: N#CCC1(n2cc(C(N)=O)c(Nc3ccc(F)cc3)n2)CCC(N=[N+]=[N-])CC1]

Step 2: 1-[4-Azido-1-(cyanomethyl)cyclohexyl]-3-[(4-fluorophenyl)amino]-1H-pyrazole-4-carboxamide To a solution of 1-[1-(cyanomethyl)-4-hydroxycyclohexyl]-3-[(4-fluorophenyl)amino]-1H-pyrazole-4-carboxamide (75 mg, 0.21 mmol) in DCM (2 mL) at ambient temperature was added TEA (0.059 mL, 0.42 mmol), and methanesulfonyl chloride (0.020 mL, 0.25 mmol). The mixture was stirred at ambient temperature for 10 minutes. The mixture was diluted with saturated aqueous NaHCO$_3$, and extracted with EtOAc. The organic layer was separated, washed with brine, dried over anhydrous MgSO$_4$ and concentrated in vacuo. The crude residue (90 mg, 0.207 mmol) was diluted in DMF (1.0 mL), NaN$_3$ (27 mg, 0.41 mmol) was added and the mixture was heated at 90° C. for 16 hours. The mixture was cooled to ambient temperature, diluted with H$_2$O and extracted with EtOAc. The organic layer was separated, washed with brine, dried over anhydrous MgSO$_4$ and concentrated in vacuo. The residue was purified by MPLC on silica gel (using a gradient elution of 30-100% EtOAc/hexanes) to give the title compound as a mixture of two diastereomers (ratio 1:3), which was used without further purification.
LRMS (ESI) calc'd for C$_{18}$H$_{20}$FN$_8$O [M+H]$^+$: 383. Found: 383.

Step C: Cis or Trans 1-[1-(cyanomethyl)-4-(4-cyclopropyl-1H-1,2,3-triazol-1-yl)cyclohexyl]-3-[(4-fluorophenyl)amino]-1H-pyrazole-4-carboxamide To a solution of 1-[4-azido-1-(cyanomethyl)cyclohexyl]-3-[(4-fluorophenyl)amino]-1H-pyrazole-4-carboxamide (60 mg, 0.16 mmol) in ethanol (0.8 mL) was added cyclopropylacetylene (0.013 mL, 0.16 mmol) and a mixture of sodium ascorbate (16 mg, 0.080 mmol) and CuSO$_4$ 5H$_2$O (16 mg, 0.060 mmol) in H$_2$O (0.8 mL) The heterogenous mixture was stirred vigorously at ambient temperature for 16 hours. The mixture was diluted with 2N ammonia and extracted with EtOAc. The combined organic layer was washed with brine, dried over anhydrous MgSO$_4$, and filtered. To the filtrate was added a spoon of silica gel and the volatiles were removed in vacuo. The resulting powder was subjected to MPLC purification (using a gradient elution of 40-100% EtOAc/hexanes followed by 10% MeOH/hexanes) to give the title compound as a mixture of two diastereomers (ratio 2:3). Further purification using chiral SFC (Chiral tech. IB-H 2.1×25 cm, eluting with 30% MeOH/CO$_2$) afforded the two pure diastereomers.

Example 44-1

1$^{st}$ diastereomer to elute: cis or Trans 1-[1-(cyanomethyl)-4-(4-cyclopropyl-1H-1,2,3-triazol-1-yl)cyclohexyl]-3-[(4-fluorophenyl)amino]-1H-pyrazole-4-carboxamide LRMS (ESI) calc'd for C$_{23}$H$_{26}$FN$_8$O [M+H]$^+$: 449. Found: 449.

Example 44-2

2$^{nd}$ diastereomer to elute: cis or Trans 1-[1-(cyanomethyl)-4-(4-cyclopropyl-1H-1,2,3-triazol-1-yl)cyclohexyl]-3-[(4-fluorophenyl)amino]-1H-pyrazole-4-carboxamide LRMS (ESI) calc'd for C$_{23}$H$_{26}$FN$_8$O [M+H]$^+$: 449. Found: 449.

Scheme #40

Example #45-1 and 45-2

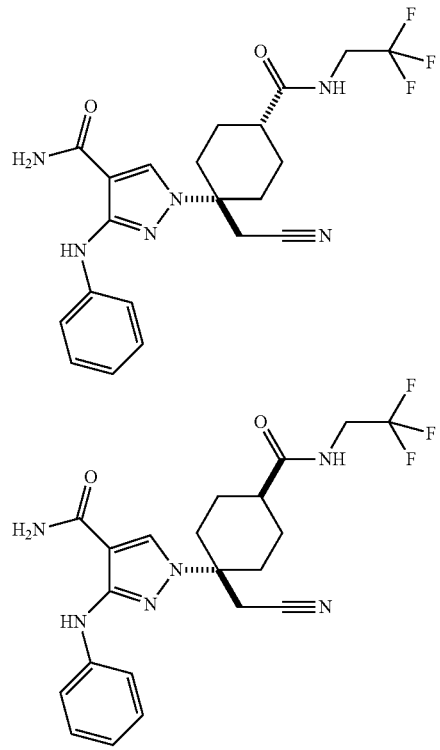

Cis or trans 1-{1-(cyanomethyl)-4-[(2,2,2-trifluoroethyl)carbamoyl]cyclohexyl}-3-(phenylamino)-1H-pyrazole-4-carboxamide To a solution of tert-butyl 4-[4-carbamoyl-3-(phenylamino)-1H-pyrazol-1-yl]-4-(cyanomethyl)cyclohexanecarboxylate (290 mg, 0.685 mmol) in DCM (3 mL) at ambient temperature was added TFA (1.0 mL), and the mixture was stirred at ambient temperature for 3 hours. The reaction mixture was concentrated in vacuo, and the residue was taken up in DMF (8 mL). To an aliquot (1.6 mL) of this solution was added DIPEA (0.071 mL, 0.41 mmol), 2,2,2-trifluoroethylamine hydrochloride (26 mg, 0.19 mmol), HOBT (29 mg, 0.19 mmol), and EDC (37 mg, 0.19 mmol). The mixture was stirred at ambient temperature for 18 hours. The reaction mixture was diluted with saturated aqueous NaHCO$_3$ and extracted with EtOAc. The organic layer was separated, dried over anhydrous MgSO$_4$, filtered and concentrated in vacuo. The residue was purified by reverse-phase preparative HPLC (MeCN/water, with 0.1% v/v TFA modifier) to afford the two pure disastereomers.

Example 45-1

1st diastereomer to elute, cis or trans 1-{1-(cyanomethyl)-4-[(2,2,2-trifluoroethyl)carbamoyl]cyclohexyl}-3-(phenylamino)-1H-pyrazole-4-carboxamide $^1$H NMR (600 MHz, DMSO-d$_6$): δ 9.06 (s, 1H), 8.46 (t, J=7.2 Hz, 1H), 8.40 (s, 1H), 7.59 (brs, 1H), 7.47 (d, J=7.8 Hz, 2H), 7.21 (t, J=7.8 Hz, 2H), 7.13 (brs, 1H), 6.79 (t, J=7.8 Hz, 1H), 3.76-3.83 (m, 2H), 3.0 (s, 2H), 2.58 (d, J=13.2 Hz, 2H), 2.25-2.30 (m, 1H), 1.78 (td, J=7.8, 3.6 Hz, 2H), 1.67-1.69 (m, 2H), 1.28-1.35 (m, 2H). LRMS (ESI) calc'd for C$_{21}$H$_{24}$F$_3$N$_6$O$_2$ [M+H]$^+$: 449. Found: 449.

Example 45-2

2nd diastereomer to elute, cis or trans 1-{1-(cyanomethyl)-4-[(2,2,2-trifluoroethyl)carbamoyl]cyclohexyl}-3-(phenylamino)-1H-pyrazole-4-carboxamide. 2. $^1$H NMR (600 MHz, DMSO-d$_6$): δ 9.06 (s, 1H), 8.48 (t, J=6.0 Hz, 1H), 8.41 (s, 1H), 7.56 (brs, 1H), 7.48 (d, J=7.8 Hz, 2H), 7.21 (t, J=7.8 Hz, 2H), 7.11 (brs, 1H), 6.79 (t, J=7.8 Hz, 1H), 3.84-3.92 (m, 2H), 3.22 (s, 2H), 2.32-2.46 (m, 2H), 2.25 (d, J=13.2 Hz, 2H), 1.92-1.97 (m, 2H), 1.74-1.77 (m, 2H), 1.64-1.72 (m, 2H).

LRMS (ESI) calc'd for C$_{21}$H$_{24}$F$_3$N$_6$O$_2$ [M+H]$^+$: 449. Found: 449.

Example #46

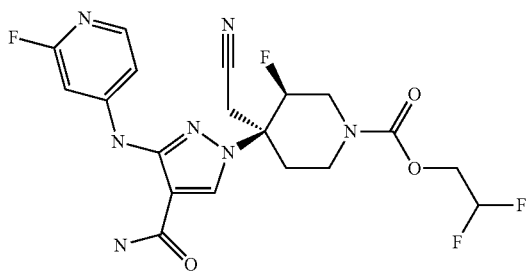

(3S,4S and 3R,4R)-2,2-Difluoroethyl 4-(4-carbamoyl-3-((2-fluoropyridin-4-yl)amino)-1H-pyrazol-1-yl)-4-(cyanomethyl)-3-fluoropiperidine-1-carboxylate

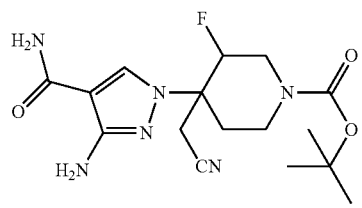 [SMILES: CC(C)(C)OC(=O)N1CCC(CC#N)(n2cc(C(N)=O)c(N)n2)C(F)C1]

Step A: tert-Butyl 4-(3-amino-4-carbamoyl-1H-pyrazol-1-yl)-4-(cyanomethyl)-3-fluoropiperidine-1-carboxylate To a solution of tert-butyl (4E and 4Z)-4-(cyanomethylidene)-3-fluoropiperidine-1-carboxylate (800 mg, 3.33 mmol) in MeCN (10 mL) were added 3-amino-1H-pyrazole-4-carboxamide (350 mg, 2.78 mmol) and DBU (0.837 mL, 5.55 mmol). The solution was stirred at ambient temperature for 16 hours. The reaction mixture was diluted with EtOAc and washed with brine, dried over anhydrous MgSO$_4$, filtered, and concentrated in vacuo. The oily residue was purified by MPLC on silica gel (0-100% EtOAc/hexanes) to afford the title compound as a mixture of diastereomers. LRMS (ESI) calc'd for C$_{16}$H$_{23}$FN$_6$O$_3$ [M+H]$^+$: 367. Found: 367.

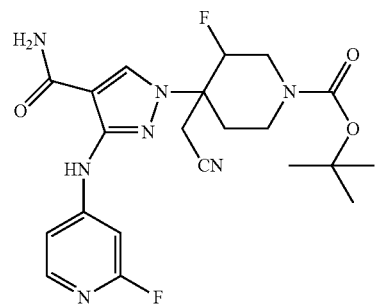 [SMILES: CC(C)(C)OC(=O)N1CCC(CC#N)(n2cc(C(N)=O)c(Nc3ccnc(F)c3)n2)C(F)C1]

Step B: tert-Butyl 4-(4-carbamoyl-3-((2-fluoropyridin-4-yl)amino)-1H-pyrazol-1-yl)-4-(cyanomethyl)-3-fluoropiperidine-1-carboxylate To a solution of tert-butyl 4-(4-carbamoyl-3-((2-fluoropyridin-4-yl)amino)-1H-pyrazol-1-yl)-4-(cyanomethyl)-3-fluoropiperidine-1-carboxylate (514 mg, 1.40 mmol) in dioxane (10 mL) were added 4-bromo-2-fluoropyridine (247 mg, 1.40 mmol) tetramethyl-t-butyl X-Phos (135 mg, 0.281 mmol), potassium phosphate tribasic (893 mg, 4.21 mmol), and Pd$_2$dba$_3$ (128 mg, 0.140 mmol). The solution was degassed by bubbling nitrogen gas and heated to 90° C. for 16 hours. The reaction was cooled to ambient temperature, diluted with EtOAc, washed with brine, dried over anhydrous MgSO$_4$, filtered, and concentrated in vacuo. The residue was purified by MPLC on silica gel (using a gradient elution of 0-100% MeOH/DCM) to afford the title compound as a mixture of diasteromers. LRMS (ESI) calc'd for C$_{21}$H$_{26}$F$_2$N$_7$O$_3$ [M+H]$^+$: 462. Found: 462

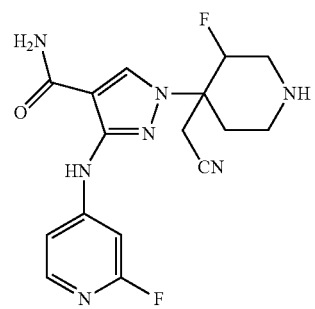 [SMILES: N#CCC1(n2cc(C(N)=O)c(Nc3ccnc(F)c3)n2)CCNCC1F]

Step C: 1-(4-(Cyanomethyl)-3-fluoropiperidin-4-yl1)-3-((2-fluoropyridin-4-yl)amino)-1H-pyrazole-4-carboxamide To a solution of tert-butyl 4-(4-carbamoyl-3-((2-fluoropyridin-4-yl)amino)-1H-pyrazol-1-yl)-4-(cyanomethyl)-3-fluoropiperidine-1-carboxylate (127 mg, 0.275 mmol) in DCM (3 mL) was added TFA (1 mL) and stirred for 30 min. The solution was quenched with saturated aqueous.NaHCO$_3$ and extracted with EtOAc. The organic layer was dried over anhydrous MgSO$_4$, filtered, and concentrated in vacuo to afford the title compound. This crude residue was used without further purification.

Step D: (3S,4S and 3R,4R)-2,2-Difluoroethyl 4-(4-carbamoyl-3-((2-fluoropyridin-4-yl)amino)-1H-pyrazol-1-yl)-4-(cyanomethyl)-3-fluoropiperidine-1-carboxylate To a solution of 1,1'-[carbonylbis(oxy)]dipyrrolidine-2,5-dione (51 mg, 0.20 mmol) in MeCN (0.5 mL) were added TEA (0.093 mL, 0.66 mmol) and 2,2-difluoroethanol (16 mg, 0.20 mmol). The resulting mixture was stirred for 2 hours at ambient temperature. 1-(4-(Cyanomethyl)-3-fluoropiperidin-4-yl)-3-((2-fluoropyridin-4-yl)amino)-1H-pyrazole-4-carboxamide (60 mg, 0.17 mmol) dissolved in DMSO (0.3 mL) and MeCN (0.5 mL) was added to the mixed carbonate solution and heated to 65° C. for 16 hours. The mixture was filtered and purified by reverse-phase preparative HPLC (MeCN/water, with 0.1% v/v TFA modifier) to afford the title compound. LRMS (ESI) calc'd for C$_{19}$H$_{19}$F$_4$N$_7$O$_3$ [M+H]$^+$: 470. Found: 470.

CHIRAL CHROMATOGRAPHY

The following experimental procedures exemplify the chiral chromatography and isolation of enantiopure or diastereomerically pure Examples of the instant invention. The following Examples are for illustrative purposes only and are not intended to limit the scope of the instant invention in any way.

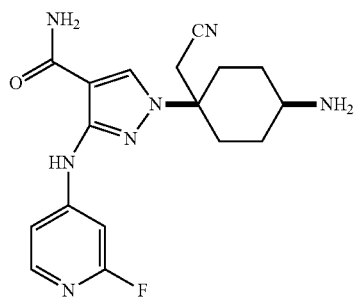

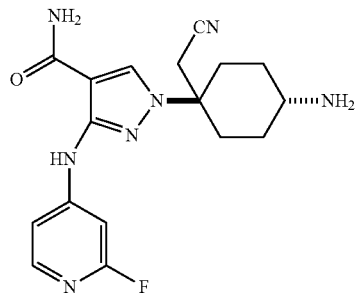

Cis-1-(4-amino-1-(cyanomethyl)cyclohexyl)-3-((2-fluoropyridin-4-yl)amino)-1H-pyrazole-4-carboxamide or Trans-1-(4-amino-1-(cyanomethyl)cyclohexyl)-3-((2-fluoropyridin-4-yl)amino)-1H-pyrazole-4-carboxamide (Examples 41-1A and 41-1B)

1-(4-amino-1-(cyanomethyl)cyclohexyl)-3-((2-fluoropyridin-4-yl)amino)-1H-pyrazole-4-carboxamide was separated to the constituent diastereomers by chiral SFC (Chiral Technology IA-H, 2.1×25 cm, 30% MeOH+0.25% dimethyl ethylamine/70% CO$_2$, 65 mL/min). Desired fractions were identified, combined, and concentrated in vacuo to afford diastereomerically pure samples of the title compounds:

Example #41-1A

Cis-1-(4-amino-1-(cyanomethyl)cyclohexyl)-3-((2-fluoropyridin-4-yl)amino)-1H-pyrazole-4-carboxamide, first diastereomer to elute from column.
$^1$H NMR (600 MHz, DMSO-d$_6$): δ 9.64 (s, 1H), 8.56 (s, 1H), 7.89 (d, J=5.4, 1H), 7.70 (br s, 1H), 7.34-7.29 (m, 3H), 3.01 (s, 2H), 2.81 (m, 1H), 2.57-2.50 (m, 2H), 1.84 (t, J=13.2 Hz, 2H), 1.77-1.75 (m, 2H), 1.19-1.07 (m, 4H).
LRMS (ESI) calc'd for C$_{17}$H$_{20}$FN$_7$O [M+H]$^+$: 358. Found: 358.

Example #41-1B

Trans-1-(4-amino-1-(cyanomethyl)cyclohexyl)-3-((2-fluoropyridin-4-yl)amino)-1H-pyrazole-4-carboxamide, second diastereomer to elute from column.
$^1$H NMR (600 MHz, DMSO-d$_6$): δ 9.64 (s, 1H), 8.49 (s, 1H), 7.89 (d, 1H), 7.68 (br s, 1H), 7.36-7.29 (m, 3H), 6.91 (br s, 2H), 3.18 (s, 2H), 3.12-3.09 (m, 1H), 2.28-2.26 (m, 2H), 2.04 (t, J=10.8 Hz, 2H), 1.84-1.82 (m, 2H), 1.61-1.55 (m, 2H).
LRMS (ESI) calc'd for C$_{17}$H$_{20}$FN$_7$O [M+H]$^+$: 358. Found: 358.

The following compounds shown in TABLE 37 were separated using a procedure similar to that reported above for Examples 41-1A and 41-1B, which can be achieved by those of ordinary skill in the art of organic synthesis.

TABLE 37

| Example | Structure | Compound Name | Exact Mass [M + H]+ |
|---|---|---|---|
| 41-2 | 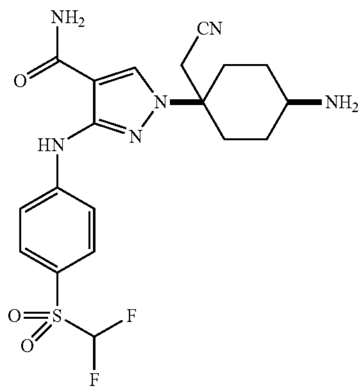 | Cis-4-amino-1-(cyanomethyl)cyclohexyl)-3-((4-((difluoromethyl)sulfonyl)phenyl)amino)-1H-pyrazole-4-carboxamide | Calc'd 453, Found 453 |
| 41-3 | 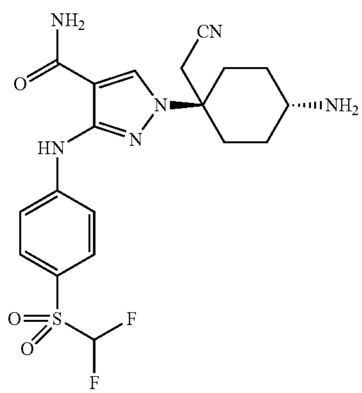 [SMILES: N#CC[C@]1(n2cc(C(N)=O)c(Nc3ccc(S(=O)(=O)C(F)F)cc3)n2)CC[C@H](N)CC1] | Trans-4-amino-1-(cyanomethyl)cyclohexyl)-3-((4-((difluoromethyl)sulfonyl)phenyl)amino)-1H-pyrazole-4-carboxamide | Calc'd 453, Found 453 |
| 47-3 | 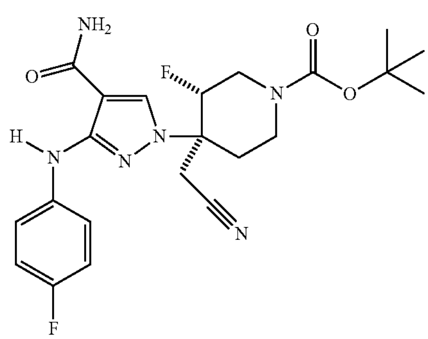 [SMILES: CC(C)(C)OC(=O)N1CC[C@@](CC#N)(n2cc(C(N)=O)c(Nc3ccc(F)cc3)n2)[C@H](F)C1] | tert-butyl (3R,4S or 3S,4R)-4-{4-carbamoyl-3-[(4-fluorophenyl)amino]-1H-pyrazol-1-yl}-4-(cyanomethyl)-3-fluoropiperidine-1-carboxylate | Calc'd 461, Found 461 |
| 47-4 | 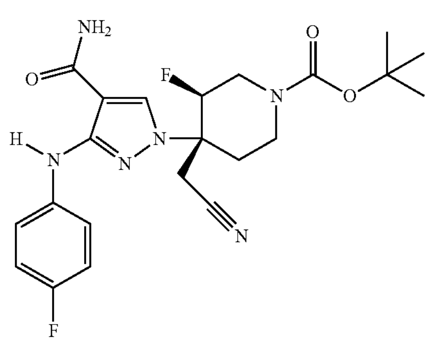 [SMILES: CC(C)(C)OC(=O)N1CC[C@](CC#N)(n2cc(C(N)=O)c(Nc3ccc(F)cc3)n2)[C@@H](F)C1] | tert-butyl (3S,4R or 3R,4S)-4-{4-carbamoyl-3-[(4-fluorophenyl)amino]-1H-pyrazol-1-yl}-4-(cyanomethyl)-3-fluoropiperidine-1-carboxylate | Calc'd 461, Found 461 |

Examples #48-1 and 48-2

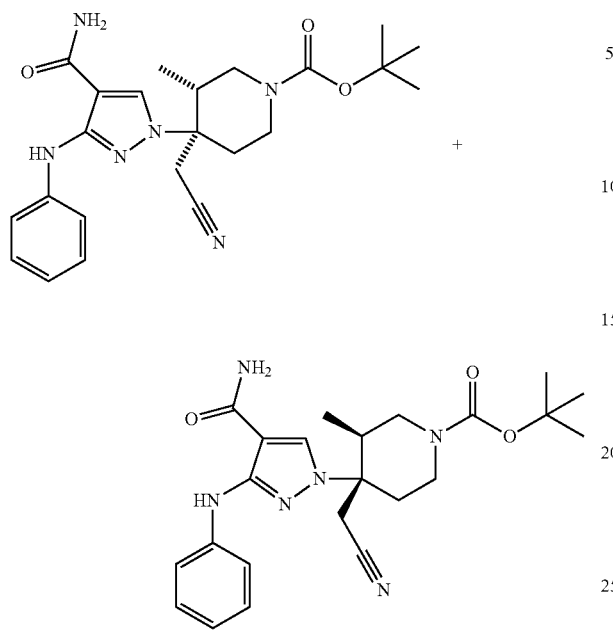

Examples 49-1 and 49-2

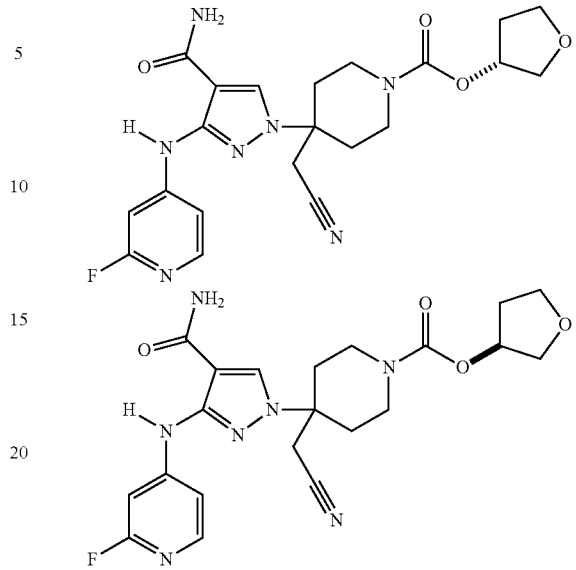

tert-Butyl (3S,4R or 3R,4S)-4-[4-carbamoyl-3-(phenylamino)-1H-pyrazol-1-yl]-4-(cyanomethyl)-3-methylpiperidine-1-carboxylate tert-Butyl (3S,4R and 3R,4S)-4-[4-carbamoyl-3-(phenylamino)-1H-pyrazol-1-yl]-4-(cyanomethyl)-3-methylpiperidine-1-carboxylate was chirally resolved to the two constituent enantiomers by chiral SFC (Chiral Technology IC-H, 2.1×25 cm, 25% MeOH—$CO_2$, 100 mL/min, 35° C., 100 bar). Desired fractions were identified, combined, and concentrated in vacuo to afford enantiomerically pure samples of the title compounds:

Example 48-1

First-eluting enantiomer, tert-Butyl (3S,4R or 3R,4S)-4-[4-carbamoyl-3-(phenylamino)-1H-pyrazol-1-yl]-4-(cyanomethyl)-3-methylpiperidine-1-carboxylate.

$^1$H-NMR data is consistent with spectral data reported for the racemic mixture, Example #2-10.

LRMS (ESI) calc'd for $C_{23}H_{31}N_6O_3$ [M+H]$^+$: 439. Found: 439.

Example 48-2

Second-eluting enantiomer, tert-Butyl (3S,4R or 3R,4S)-4-[4-carbamoyl-3-(phenylamino)-1H-pyrazol-1-yl]-4-(cyanomethyl)-3-methylpiperidine-1-carboxylate.

$^1$H-NMR data is consistent with spectral data reported for the racemic mixture, Example #2-10

LRMS (ESI) calc'd for $C_{23}H_{31}N_6O_3$ [M+H]$^+$: 439. Found: 439.

(3S or 3R)-Tetrahydrofuran-3-yl 4-{4-carbamoyl-3-[(2-fluoropyridin-4-yl)amino]-1H-pyrazol-1-yl}-4-(cyanomethyl)piperidine-1-carboxylate (3S and 3R)-Tetrahydrofuran-3-yl 4-{4-carbamoyl-3-[(2-fluoropyridin-4-yl)amino]-1H-pyrazol-1-yl}-4-(cyanomethyl)piperidine-1-carboxylate was chirally resolved by to the constituent enantiomers by chiral SFC (Chiral Technology IB-H, 2.1×25 cm, 20% MeOH+0.25% isobutylamine/$CO_2$, 70 mL/min). Desired fractions were identified, combined, and concentrated in vacuo to afford enantiomerically pure samples of the title compounds:

Example 49-1

(3S or 3R)-tetrahydrofuran-3-yl 4-{4-carbamoyl-3-[(2-fluoropyridin-4-yl)amino]-1H-pyrazol-1-yl}-4-(cyanomethyl)piperidine-1-carboxylate, first enantiomer to elute from column.

$^1$H NMR (600 MHz, acetone-$d_6$): δ 9.76 (s, 1H), 8.56 (s, 1H), 7.93 (d, J=5.7 Hz, 1H), 7.39 (s, 1H), 7.35-7.22 (m, 2H), 6.64 (br s, 1H), 5.19-5.15 (m, 1H), 3.93-3.87 (m, 2H), 3.83-3.77 (m, 2H), 3.75-3.66 (m, 2H), 3.25-3.12 (m, 4H), 2.66-2.60 (m, 2H), 2.19-1.91 (m, 4H).

LRMS (ESI) calc'd for $C_{21}H_{24}FN_7O_4$ [M+H]$^+$: 458. Found: 458.

Example 49-2

(3S or 3R)-tetrahydrofuran-3-yl 4-{4-carbamoyl-3-[(2-fluoropyridin-4-yl)amino]-1H-pyrazol-1-yl}-4-(cyanomethyl)piperidine-1-carboxylate, second enantiomer to elute from column.

$^1$H NMR (600 MHz, acetone-$d_6$): δ 9.76 (s, 1H), 8.56 (s, 1H), 7.93 (d, J=5.7 Hz, 1H), 7.39 (s, 1H), 7.35-7.22 (m, 2H), 6.64 (br s, 1H), 5.19-5.15 (m, 1H), 3.93-3.87 (m, 2H), 3.83-3.77 (m, 2H), 3.75-3.66 (m, 2H), 3.25-3.12 (m, 4H), 2.66-2.60 (m, 2H), 2.19-1.91 (m, 4H).

LRMS (ESI) calc'd for $C_{21}H_{24}FN_7O_4$ [M+11]$^+$: 458. Found: 458.

Examples 50-1 and 50-2

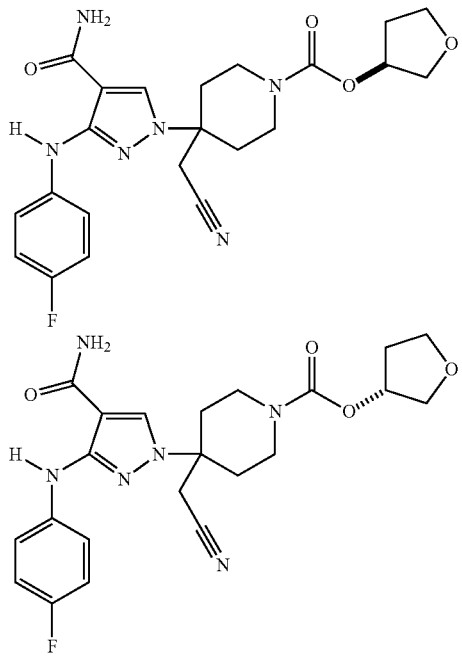

(3S or 3R)-tetrahydrofuran-3-yl 4-{4-carbamoyl-3-[(4-fluorophenyl)amino]-1H-pyrazol-1-yl}-4-(cyanomethyl)piperidine-1-carboxylate (3S and 3R)-Tetrahydrofuran-3-yl 4-{4-carbamoyl-3-[(4-fluorophenyl)amino]-1H-pyrazol-1-yl}-4-(cyanomethyl)piperidine-1-carboxylate was chirally resolved to the constituent enantiomers by chiral SFC (Chiral Technology OD-H, 2.1×25 cm, 20% 2-propanol/$CO_2$, 70 mL/min). Desired fractions were identified, combined, and concentrated in vacuo to afford enantiomerically pure samples of the title compounds:

Example 50-1

(3S or 3R)-tetrahydrofuran-3-yl 4-{4-carbamoyl-3-[(4-fluorophenyl)amino]-1H-pyrazol-1-yl}-4-(cyanomethyl)piperidine-1-carboxylate, first enantiomer to elute from column.

$^1$H NMR (600 MHz, acetone-$d_6$): δ 9.16 (s, 1H), 8.47 (s, 1H), 7.67-7.55 (m, 2H), 7.15 (br s, 1H), 7.05-6.96 (m, 2H), 6.48 (br s, 1H), 5.19-5.15 (m, 1H), 3.93-3.87 (m, 2H), 3.82-3.77 (m, 2H), 3.76-3.66 (m, 2H), 3.22-3.08 (m, 4H), 2.65-2.58 (m, 2H), 2.17-2.06 (m, 2H), 1.99-1.90 (m, 2H).

LRMS (ESI) calc'd for $C_{22}H_{25}FN_6O_4$ [M+H]$^+$: 457. Found: 457.

Example 50-2

(3S or 3R)-tetrahydrofuran-3-yl4-{4-carbamoyl-3-[(4-fluorophenyl)amino]-1H-pyrazol-1-yl}-4-(cyanomethyl)piperidine-1-carboxylate, second enantiomer to elute from column.

$^1$H NMR (600 MHz, acetone-$d_6$): 9.16 (s, 1H), 8.47 (s, 1H), 7.67-7.55 (m, 2H), 7.15 (br s, 1H), 7.05-6.96 (m, 2H), 6.48 (br s, 1H), 5.19-5.15 (m, 1H), 3.93-3.87 (m, 2H), 3.82-3.77 (m, 2H), 3.76-3.66 (m, 2H), 3.22-3.08 (m, 4H), 2.65-2.58 (m, 2H), 2.17-2.06 (m, 2H), 1.99-1.90 (m, 2H).

LRMS (ESI) calc'd for $C_{22}H_{25}FN_6O_4$ [M+H]$^+$: 457. Found: 457.

BIOLOGICAL ASSAYS

Jak Biochemical HTRF Assay Protocol

The ability of compounds to inhibit the activity of JAK1, JAK2, JAK3, and Tyk2 was measured using a recombinant purified GST-tagged catalytic domain for each enzyme (Invitrogen JAK1 #M4290, JAK2 #M4290, JAK3 #M4290, Tyk2 #M4290) in an HTRF format biochemical assay. The reactions employed a common peptide substrate, LCB-EQEDE-PEGDYFEWLW-$NH_2$ (in-house). The basic assay protocol is as follows: First, 250 nL of diluted compounds in DMSO were dispensed into the wells of a dry 384-well Black plate (Greiner #781076) using a Labcyte Echo 555 acoustic dispenser. Subsequent reagent additions employed an Agilent Bravo. Next, 18 μL of 1.11× enzyme and 1.11× substrate in 1× assay buffer (Invitrogen kinase buffer # PV3189, 2 mM DTT, 0.05% BSA) were added to the wells and shaken and then preincubated for 30 minutes at room temperature to allow compound binding to equilibrate. After equilibration, 2 μL of 10×ATP in 1× assay buffer was added to initiate the kinase reaction and the plates were shaken and then incubated at room temperature for 120 minutes. At the end of the incubation, 20 μL of 2× stop buffer (streptavidin-Dylight 650 (Thermo #84547B/100 mL), Eu-tagged pY20 antibody (Perkin Elmer #AD0067), EDTA, HEPES, and Triton) was added to quench the reaction. Plates were shaken and centrifuged and then incubated 60 minutes at room temperature and then read on a Perkin Elmer Envision ($\lambda_{ex}$=337 nm, $\lambda_{em}$=665 and 615 nm, TRF delay time=20 μs). HTRF signal=10,000*665 nm reading/615 nm reading. After normalization to untreated controls, the percent inhibition of the HTRF signal at each compound concentration was calculated. The plot of percent inhibition versus the log of compound concentration was fit with a 4-parameter dose response equation to calculate $IC_{50}$ values.

Final Reaction Conditions were:

| Enzyme | [E] (nM) | [S] (μM) | [ATP] (μM) | [Eu-pY20] (nM) | [SA-Dylight] (nM) |
|---|---|---|---|---|---|
| JAK1 | 1.405 | 0.75 | 31.8 | 9 | 312.5 |
| JAK2 | 0.052 | 0.75 | 8.5 | 9 | 312.5 |
| JAK3 | 0.031 | 0.75 | 2.9 | 9 | 312.5 |
| Tyk2 | 2.612 | 0.75 | 6.9 | 9 | 312.5 |

Compound concentrations tested were 1496, 499, 175, 49.9, 18.7, 6.2, 2.1, 0.75, 0.24, 0.075, and 0.0125 nM, with 1.25% residual DMSO.

BIOLOGICAL DATA

Examples of the instant invention were evaluated in JAK1 and JAK2 in vitro binding assays as described above. The following table tabulates the JAK1 $IC_{50}$ values and JAK2 $IC_{50}$ values disclosed for the instant invention.

| Example | JAK1 $IC_{50}$ | JAK2 $IC_{50}$ |
|---|---|---|
| 1 | 67 | 1481 |
| 2-1 | 1 | 27 |
| 2-2 | 0.5 | 23 |
| 2-3 | 8 | 57 |
| 2-4 | 0.5 | 18 |

| Example | JAK1 IC$_{50}$ | JAK2 IC$_{50}$ |
|---|---|---|
| 2-5 | 0.6 | 7 |
| 2-6 | 0.5 | 1 |
| 2-7 | 0.3 | 10 |
| 2-8 | 2 | 5 |
| 2-9 | 1 | 21 |
| 2-10 | 2 | 21 |
| 2-11 | 29 | 614 |
| 2-12 | 115 | 404 |
| 2-13 | 27 | 38 |
| 2-14 | 20 | 193 |
| 2-15 | 10 | 92 |
| 2-16 | 0.2 | 2 |
| 2-17 | 2 | 27 |
| 2-18 | 3 | 91 |
| 2-19 | 12 | 267 |
| 2-20 | 33 | 241 |
| 2-21 | 31 | 405 |
| 2-22 | 13 | 127 |
| 2-23 | 198 | 1481 |
| 3-1 | 4 | 154 |
| 3-2 | 6 | 414 |
| 3-3 | 5 | 488 |
| 3-4 | 8 | 174 |
| 3-5 | 0.2 | 4 |
| 3-6 | 0.2 | 5 |
| 3-7 | 0.3 | 22 |
| 3-8 | 1 | 54 |
| 3-9 | 1 | 37 |
| 3-10 | 3 | 47 |
| 3-11 | 4 | 74 |
| 3-12 | 2 | 40 |
| 3-13 | 0.7 | 21 |
| 3-14 | 2 | 49 |
| 3-15 | 191 | >1496 |
| 3-16 | 45 | 861 |
| 3-17 | 32 | 780 |
| 3-18 | 3 | 89 |
| 3-19 | 0.6 | 18 |
| 3-20 | 5 | 102 |
| 3-21 | 0.6 | 20 |
| 3-22 | 0.4 | 12 |
| 3-23 | 33 | 559 |
| 3-24 | 0.1 | 2 |
| 3-25 | 0.7 | 21 |
| 3-26 | 0.2 | 3 |
| 3-27 | 1 | 24 |
| 3-28 | 0.6 | 26 |
| 3-29 | 9 | 209 |
| 3-30 | 0.3 | 6 |
| 3-31 | 1 | 44 |
| 3-32 | 204 | >1496 |
| 3-33 | 7 | 102 |
| 3-34 | 5 | 215 |
| 3-35 | 19 | 280 |
| 3-36 | 3 | 46 |
| 3-37 | 0.6 | 17 |
| 3-38 | 2 | 37 |
| 3-39 | 4 | 117 |
| 3-40 | 3 | 67 |
| 3-41 | 213 | >1496 |
| 3-42 | 12 | 287 |
| 3-43 | 10 | 295 |
| 3-44 | 0.2 | 6 |
| 3-45 | 2 | 70 |
| 3-46 | 3 | 78 |
| 3-47 | 13 | 181 |
| 3-48 | 1 | 26 |
| 3-49 | 5 | 147 |
| 3-50 | 3 | 39 |
| 3-51 | 0.06 | 0.6 |
| 3-52 | 0.4 | 8 |
| 3-53 | 0.4 | 9 |
| 3-54 | 0.3 | 4 |
| 3-55 | 1 | 75 |
| 3-56 | 1 | 23 |
| 4-1 | 0.1 | 1 |
| 4-2 | 2 | 20 |
| 4-3 | 0.6 | 11 |
| 4-4 | 0.5 | 23 |
| 4-5 | 22 | 183 |
| 4-6 | 3 | 38 |
| 5-1 | 34 | 162 |
| 5-2 | 271 | 738 |
| 6-3 | 1 | 25 |
| 6-4 | 0.05 | 0.2 |
| 6-5 | 13 | 133 |
| 6-6 | 7 | 48 |
| 6-7 | 19 | 206 |
| 7 | 8 | 113 |
| 8 | 50 | 813 |
| 9-1 | 0.2 | 5 |
| 9-2 | 0.3 | 9 |
| 9-3 | 0.8 | 21 |
| 9-4 | 0.1 | 2 |
| 9-5 | 0.2 | 6 |
| 9-6 | 0.8 | 3 |
| 9-7 | 0.5 | 2 |
| 9-8 | 0.3 | 3 |
| 9-9 | 0.4 | 6 |
| 9-10 | 0.2 | 3 |
| 9-11 | 0.2 | 3 |
| 9-12 | 0.5 | 6 |
| 9-13 | 3 | 138 |
| 9-14 | 0.2 | 3 |
| 9-15 | 2 | 13 |
| 9-16 | 0.09 | 0.6 |
| 9-17 | 15 | 133 |
| 9-18 | 6 | 101 |
| 9-19 | 6 | 146 |
| 9-20 | 0.1 | 1 |
| 9-21 | 0.3 | 0.8 |
| 9-22 | 0.7 | 2 |
| 9-23 | 0.4 | 10 |
| 9-24 | 0.2 | 0.7 |
| 9-25 | 0.3 | 0.7 |
| 9-26 | 0.4 | 7 |
| 9-27 | 0.4 | 7 |
| 9-28 | 1 | 24 |
| 9-29 | 0.1 | 3 |
| 9-30 | 0.2 | 5 |
| 9-31 | 1 | 33 |
| 9-32 | 0.3 | 8 |
| 9-33 | 0.2 | 6 |
| 9-34 | 0.5 | 4 |
| 9-35 | 1 | 16 |
| 9-36 | 0.9 | 21 |
| 9-37 | 0.2 | 3 |
| 9-38 | 0.3 | 3 |
| 9-39 | 7 | 348 |
| 9-40 | 0.7 | 11 |
| 9-41 | 6 | 201 |
| 10-1 | 0.1 | 0.7 |
| 10-2 | 0.5 | 4 |
| 10-3 | 0.06 | 0.6 |
| 10-4 | 0.4 | 29 |
| 10-5 | 0.2 | 21 |
| 10-6 | 0.8 | 71 |
| 10-7 | 0.2 | 4 |
| 10-8 | 0.7 | 21 |
| 10-9 | 0.4 | 15 |
| 11-1 | 0.03 | 0.5 |
| 11-2 | 0.01 | 0.6 |
| 12-1 | 1 | 37 |
| 12-2 | 0.2 | 3 |
| 12-3 | 2 | 42 |
| 12-4 | 0.8 | 3 |
| 12-5 | 0.8 | 7 |
| 12-6 | 0.4 | 15 |
| 12-7 | 0.1 | 2 |
| 13-1 | 3 | 139 |
| 13-2 | 13 | 1009 |
| 13-3 | 8 | 466 |
| 13-4 | 4 | 183 |
| 13-5 | 15 | 903 |

| Example | JAK1 IC$_{50}$ | JAK2 IC$_{50}$ | Example | JAK1 IC$_{50}$ | JAK2 IC$_{50}$ |
|---|---|---|---|---|---|
| 13-6 | 26 | 179 | 22-27 | 6 | 157 |
| 13-7 | 8 | 210 | 22-28 | 3 | 73 |
| 13-8 | 9 | 176 | 22-29 | 2 | 37 |
| 13-9 | 10 | 186 | 22-30 | 86 | >1496 |
| 13-10 | 6 | 178 | 22-31 | 1 | 47 |
| 13-11 | 5 | 126 | 22-32 | 2 | 83 |
| 13-12 | 1 | 16 | 22-33 | 2 | 81 |
| 14 | 10 | 38 | 22-34 | 8 | 163 |
| 15-1 | 148 | 1481 | 22-35 | 6 | 145 |
| 15-2 | 51 | 1104 | 22-36 | 2 | 97 |
| 15-3 | 341 | 1050 | 22-37 | 88 | >1496 |
| 15-4 | 41 | 958 | 22-38 | 0.2 | 5 |
| 15-5 | 14 | 293 | 22-39 | 0.2 | 14 |
| 15-6 | 85 | 1481 | 22-40 | 23 | 582 |
| 15-7 | 127 | 1481 | 22-41 | 18 | 641 |
| 15-8 | 161 | 1481 | 22-42 | 18 | 582 |
| 15-9 | 644 | 1481 | 22-43 | 1 | 64 |
| 15-10 | 31 | 841 | 22-44 | 5 | 22 |
| 15-11 | 13 | 182 | 22-45 | 2 | 34 |
| 18 | 0.1 | 10 | 22-46 | 3 | 95 |
| 19 | 162 | 870 | 22-47 | 6 | 100 |
| 20 | 358 | 1481 | 22-48 | 2 | 73 |
| 21-1 | 6 | 46 | 22-49 | 2 | 29 |
| 21-2 | 3 | 11 | 22-50 | 0.6 | 16 |
| 21-3 | 79 | 234 | 22-51 | 0.4 | 9 |
| 21-4 | 29 | 243 | 22-52 | 1 | 25 |
| 21-5 | 46 | 314 | 22-53 | 4 | 87 |
| 21-6 | 3 | 55 | 22-54 | 1 | 28 |
| 21-7 | 11 | 135 | 22-55 | 4 | 53 |
| 21-8 | 89 | 1298 | 22-56 | 2 | 46 |
| 21-9 | 15 | 319 | 22-57 | 14 | 280 |
| 21-10 | 8 | 78 | 22-58 | 4 | 128 |
| 21-11 | 0.3 | 6 | 22-59 | 0.2 | 7 |
| 21-12 | 7 | 128 | 22-60 | 0.1 | 6 |
| 21-13 | 24 | 297 | 22-61 | 0.4 | 10 |
| 21-14 | 18 | 224 | 22-62 | 0.9 | 33 |
| 21-15 | 12 | 242 | 22-63 | 0.5 | 20 |
| 21-16 | 69 | 842 | 22-64 | 4 | 156 |
| 21-17 | 19 | 208 | 22-65 | 1 | 16 |
| 21-18 | 2 | 73 | 22-66 | 2 | 82 |
| 21-19 | 35 | 460 | 22-67 | 1 | 68 |
| 21-20 | 10 | 105 | 22-68 | 0.1 | 8 |
| 21-21 | 3 | 44 | 22-69 | 0.2 | 9 |
| 21-22 | 72 | 888 | 22-70 | 0.04 | 1 |
| 21-23 | 0.8 | 13 | 22-71 | 0.1 | 4 |
| 21-24 | 120 | 1053 | 22-72 | 0.3 | 13 |
| 21-25 | 83 | 747 | 23 | 4 | 105 |
| 21-26 | 0.7 | 11 | 24-1 | 10 | 59 |
| 21-27 | 36 | 809 | 24-2 | 41 | 917 |
| 21-28 | 39 | 453 | 25 | 0.08 | 2 |
| 21-29 | 21 | 400 | 26 | 0.4 | 5 |
| 22-1 | 30 | 447 | 27-1 | 0.3 | 2 |
| 22-2 | 0.2 | 5 | 27-2 | 0.3 | 6 |
| 22-3 | 1 | 57 | 27-3 | 1 | 16 |
| 22-4 | 74 | 1180 | 27-4 | 3 | 85 |
| 22-5 | 6 | 70 | 27-5 | 50 | 235 |
| 22-6 | 6 | 211 | 28 | 4 | 74 |
| 22-7 | 0.3 | 13 | 29 | 2 | 96 |
| 22-8 | 0.1 | 6 | 29-A | 1 | 40 |
| 22-9 | 0.06 | 2 | 30-1 | 0.2 | 8 |
| 22-10 | 0.07 | 3 | 30-2 | 0.3 | 15 |
| 22-11 | 0.1 | 4 | 30-3 | 0.8 | 28 |
| 22-12 | 124 | >1496 | 30-4 | 0.9 | 33 |
| 22-13 | 3 | 39 | 30-5 | 4 | 120 |
| 22-14 | 0.6 | 28 | 30-6 | 0.9 | 38 |
| 22-15 | 1 | 18 | 30-7 | 0.5 | 9 |
| 22-16 | 5 | 122 | 30-8 | 1 | 72 |
| 22-17 | 17 | 503 | 30-9 | 0.3 | 5 |
| 22-18 | 2 | 72 | 30-10 | 21 | 745 |
| 22-19 | 0.7 | 25 | 30-11 | 0.2 | 11 |
| 22-20 | 2 | 31 | 30-12 | 6 | 71 |
| 22-21 | 0.7 | 41 | 30-13 | 0.9 | 20 |
| 22-22 | 0.4 | 13 | 30-14 | 2 | 30 |
| 22-23 | 0.1 | 6 | 30-15 | 1 | 19 |
| 22-24 | 100 | >1496 | 30-16 | 0.9 | 38 |
| 22-25 | 6 | 208 | 30-17 | 3 | 96 |
| 22-26 | 6 | 117 | 30-18 | 2 | 44 |

| Example | JAK1 IC$_{50}$ | JAK2 IC$_{50}$ | Example | JAK1 IC$_{50}$ | JAK2 IC$_{50}$ |
|---|---|---|---|---|---|
| 30-19 | 1 | 37 | 34-14 | 0.3 | 8 |
| 30-20 | 8 | 240 | 34-15 | 5 | 194 |
| 30-21 | 6 | 145 | 34-16 | 2 | 35 |
| 30-22 | 5 | 123 | 34-17 | 10 | 158 |
| 30-23 | 2 | 40 | 34-18 | 8 | 137 |
| 30-24 | 4 | 96 | 34-19 | 11 | 184 |
| 30-25 | 4 | 120 | 34-20 | 13 | 115 |
| 30-26 | 0.2 | 3 | 34-21 | 4 | 63 |
| 30-27 | 0.07 | 5 | 34-22 | 6 | 176 |
| 30-28 | 3 | 102 | 34-23 | 14 | 230 |
| 30-29 | 6 | 249 | 34-24 | 7 | 84 |
| 30-30 | 1 | 50 | 34-25 | 28 | 350 |
| 30-31 | 8 | 318 | 34-26 | 10 | 238 |
| 30-32 | 4 | 88 | 34-27 | 32 | 448 |
| 30-33 | 2 | 40 | 34-28 | 92 | 1049 |
| 30-34 | 3 | 83 | 34-29 | 387 | 1481 |
| 30-35 | 4 | 71 | 34-30 | 35 | 363 |
| 30-36 | 1 | 40 | 34-31 | 61 | 704 |
| 30-37 | 3 | 103 | 34-32 | 6 | 166 |
| 30-38 | 7 | 156 | 34-33 | 153 | 711 |
| 30-39 | 2 | 38 | 34-34 | 60 | 830 |
| 30-40 | 2 | 58 | 34-35 | 44 | 248 |
| 30-41 | 31 | 336 | 34-36 | 42 | 298 |
| 30-42 | 41 | 798 | 34-37 | 138 | 570 |
| 30-43 | 12 | 318 | 34-38 | 59 | 542 |
| 30-44 | 11 | 318 | 34-39 | 0.9 | 42 |
| 30-45 | 3 | 97 | 34-40 | 0.1 | 2 |
| 30-46 | 1 | 37 | 34-41 | 3 | 48 |
| 30-47 | 3 | 103 | 34-42 | 3 | 96 |
| 30-48 | 4 | 71 | 34-43 | 11 | 234 |
| 30-49 | 0.3 | 18 | 34-44 | 2 | 63 |
| 30-50 | 2 | 27 | 34-45 | 1 | 46 |
| 30-51 | 14 | 298 | 34-46 | 2 | 139 |
| 30-52 | 3 | 76 | 34-47 | 2 | 79 |
| 30-53 | 11 | 262 | 34-48 | 0.3 | 13 |
| 30-54 | 375 | 1481 | 34-49 | 0.2 | 9 |
| 30-55 | 74 | 491 | 34-50 | 0.2 | 8 |
| 30-56 | 18 | 373 | 34-51 | 4 | 37 |
| 30-57 | 14 | 466 | 34-52 | 4 | 154 |
| 30-58 | 76 | 809 | 34-53 | 0.3 | 15 |
| 30-59 | 15 | 336 | 34-54 | 0.6 | 44 |
| 30-60 | 39 | 484 | 34-55 | 1 | 28 |
| 30-61 | 37 | 603 | 34-56 | 2 | 40 |
| 30-62 | 5 | 102 | 34-57 | 0.1 | 9 |
| 30-63 | 11 | 258 | 34-58 | 0.5 | 22 |
| 30-64 | 188 | 1481 | 34-59 | 0.2 | 3 |
| 30-65 | 12 | 271 | 34-60 | 8 | 115 |
| 30-66 | 19 | 353 | 34-61 | 2 | 38 |
| 30-67 | 108 | 849 | 34-62 | 1 | 47 |
| 30-68 | 45 | 445 | 35-1 | 0.1 | 5 |
| 30-69 | 31 | 671 | 35-2 | 0.2 | 10 |
| 30-70 | 21 | 423 | 35-3 | 3 | 35 |
| 30-71 | 200 | 1481 | 36-1 | 5 | 77 |
| 30-72 | 72 | 1186 | 36-2 | 0.6 | 10 |
| 30-73 | 130 | 1481 | 37-1 | 2 | 13 |
| 30-74 | 6 | 132 | 37-2 | 0.4 | 3 |
| 30-75 | 22 | 221 | 37-3 | 1 | 12 |
| 30-76 | 74 | 285 | 37-4 | 0.6 | 2 |
| 30-77 | 0.2 | 9 | 37-5 | 0.7 | 6 |
| 30-78 | 0.3 | 12 | 37-6 | 0.3 | 1 |
| 31 | 0.4 | 8 | 37-7 | 2 | 9 |
| 32 | 94 | 510 | 37-8 | 15 | 35 |
| 33-1 | 2 | 26 | 37-9 | 0.8 | 3 |
| 33-2 | 2 | 64 | 37-10 | 0.7 | 3 |
| 34-1 | 1 | 16 | 37-11 | 0.6 | 2 |
| 34-2 | 5 | 93 | 37-12 | 3 | 9 |
| 34-3 | 13 | 91 | 37-13 | 3 | 8 |
| 34-4 | 12 | 70 | 37-14 | 5 | 24 |
| 34-5 | 13 | 318 | 37-15 | 0.4 | 3 |
| 34-6 | 5 | 107 | 37-16 | 79 | 366 |
| 34-7 | 6 | 94 | 37-17 | 95 | 247 |
| 34-8 | 14 | 191 | 37-18 | 159 | 585 |
| 34-9 | 18 | 372 | 37-19 | 138 | 463 |
| 34-10 | 20 | 318 | 37-20 | 105 | 521 |
| 34-11 | 12 | 283 | 38-1 | 3 | 68 |
| 34-12 | 15 | 195 | 38-2 | 20 | 628 |
| 34-13 | 2 | 44 | 38-3 | 10 | 185 |

| Example | JAK1 IC$_{50}$ | JAK2 IC$_{50}$ | Example | JAK1 IC$_{50}$ | JAK2 IC$_{50}$ |
|---|---|---|---|---|---|
| 38-4 | 12 | 191 | 40-31 | 0.1 | 2 |
| 38-5 | 4 | 214 | 40-32 | 12 | 177 |
| 38-6 | 2 | 69 | 40-33 | 0.03 | 0.8 |
| 38-7 | 5 | 80 | 40-34 | 4 | 105 |
| 38-8 | 14 | 428 | 40-35 | 0.8 | 30 |
| 38-9 | 38 | 558 | 40-36 | 65 | >1496 |
| 38-10 | 5 | 158 | 40-37 | 16 | 506 |
| 38-11 | 4 | 78 | 40-38 | 1 | 103 |
| 38-12 | 128 | 1435 | 40-39 | 30 | 760 |
| 38-13 | 21 | 339 | 40-40 | 0.2 | 9 |
| 38-14 | 25 | 334 | 40-41 | 584 | >1496 |
| 38-15 | 0.9 | 21 | 40-42 | 64 | 775 |
| 38-16 | 7 | 111 | 40-43 | 0.3 | 14 |
| 38-17 | 11 | 149 | 40-44 | 0.1 | 0.8 |
| 38-18 | 7 | 106 | 40-45 | 38 | 770 |
| 38-19 | 23 | 334 | 40-46 | 1 | 60 |
| 38-20 | 19 | 326 | 40-47 | 215 | >1496 |
| 38-21 | 7 | 173 | 40-48 | 0.4 | 6 |
| 38-22 | 19 | 249 | 40-49 | 5 | 137 |
| 38-23 | 94 | 1194 | 40-50 | 0.1 | 6 |
| 38-24 | 5 | 179 | 40-51 | 598 | >1496 |
| 38-25 | 18 | 168 | 40-52 | 0.6 | 20 |
| 38-26 | 2 | 69 | 40-53 | 400 | >1496 |
| 38-27 | 11 | 162 | 40-54 | 0.9 | 24 |
| 38-28 | 6 | 79 | 40-55 | 13 | 409 |
| 38-29 | 185 | 1481 | 40-56 | 3 | 159 |
| 38-30 | 62 | 507 | 40-57 | 415 | >1496 |
| 38-31 | 33 | 656 | 40-58 | 0.2 | 7 |
| 38-32 | 4 | 86 | 40-59 | 0.5 | 3 |
| 38-33 | 26 | 265 | 40-60 | 45 | 758 |
| 38-34 | 2 | 28 | 40-61 | 0.06 | 3 |
| 38-35 | 8 | 144 | 40-62 | 38 | 832 |
| 38-36 | 15 | 233 | 40-63 | 0.03 | 1 |
| 38-37 | 8 | 114 | 40-64 | 0.05 | 2 |
| 38-38 | 13 | 183 | 40-65 | 2 | 129 |
| 38-39 | 16 | 303 | 40-66 | 344 | >1496 |
| 38-40 | 18 | 279 | 40-67 | 37 | 773 |
| 38-41 | 13 | 175 | 40-68 | 69 | 981 |
| 38-42 | 19 | 237 | 40-69 | 9 | 667 |
| 38-43 | 20 | 322 | 40-70 | 0.2 | 9 |
| 38-44 | 0.1 | 2 | 40-71 | 24 | 814 |
| 38-45 | 0.1 | 0.5 | 40-72 | 1 | 37 |
| 38-46 | 2 | 59 | 40-73 | 139 | >1496 |
| 38-47 | 0.2 | 6 | 40-74 | 1 | 35 |
| 39-1 | 0.09 | 2 | 40-75 | 0.2 | 7 |
| 39-2 | 0.1 | 3 | 40-76 | 13 | 225 |
| 40-1 | 272 | >1496 | 40-77 | 0.7 | 13 |
| 40-2 | 0.5 | 48 | 40-78 | 12 | 264 |
| 40-1A | 6 | 39 | 40-79 | 8 | 133 |
| 40-3 | 119 | >1496 | 40-80 | 14 | 325 |
| 40-4 | 102 | 1333 | 40-81 | 0.1 | 5 |
| 40-5 | 449 | >1496 | 40-82 | 26 | 444 |
| 40-6 | 12 | 365 | 40-84 | 0.04 | 3 |
| 40-7 | 7 | 36 | 40-85 | 0.02 | 0.2 |
| 40-8 | 0.3 | 6 | 40-86 | 0.06 | 0.6 |
| 40-9 | 12 | 352 | 40-87 | 13 | 524 |
| 40-10 | 14 | 355 | 40-88 | 200 | >1496 |
| 40-11 | 0.2 | 7 | 40-89 | 13 | 466 |
| 40-12 | 2 | 73 | 40-90 | 9 | 84 |
| 40-13 | 115 | >1496 | 40-91 | 67 | 323 |
| 40-14 | 1 | 65 | 40-92 | 0.04 | 0.2 |
| 40-15 | 0.08 | 2 | 40-93 | 166 | >1496 |
| 40-16 | 0.3 | 18 | 40-94 | 234 | >1496 |
| 40-17 | 0.04 | 1 | 40-95 | 28 | 794 |
| 40-18 | 235 | >1496 | 40-96 | 0.09 | 2 |
| 40-19 | 0.3 | 10 | 40-97 | 25 | 1037 |
| 40-20 | 1 | 43 | 40-98 | 1 | 31 |
| 40-21 | 171 | >1496 | 40-99 | 506 | >1496 |
| 40-22 | 4 | 195 | 40-100 | 18 | 216 |
| 40-23 | 2 | 237 | 40-101 | 18 | 276 |
| 40-24 | 8 | 184 | 40-102 | 0.05 | 1 |
| 40-25 | 63 | 940 | 40-103 | 0.1 | 3 |
| 40-26 | 0.08 | 5 | 40-104 | 0.2 | 11 |
| 40-27 | 8 | 273 | 40-105 | 0.08 | 1 |
| 40-28 | 0.2 | 32 | 40-106 | 4 | 31 |
| 40-29 | 0.07 | 4 | 40-108 | 0.09 | 2 |
| 40-30 | 326 | >1496 | 40-109 | 0.05 | 0.8 |

-continued

| Example | JAK1 IC$_{50}$ | JAK2 IC$_{50}$ |
|---|---|---|
| 40-110 | 2 | 64 |
| 41-1 | 8 | 218 |
| 41-1A | 106 | >1496 |
| 41-1B | 4 | 161 |
| 41-2 | 86 | >1496 |
| 41-3 | 1 | 33 |
| 41-4 | 0.09 | 2 |
| 41-5 | 10 | 595 |
| 41-6 | 23 | 851 |
| 41-7 | 12 | 468 |
| 41-8 | 0.8 | 153 |
| 41-9 | 15 | 440 |
| 41-10 | 0.03 | 2 |
| 41-11 | 0.08 | 2 |
| 41-12 | 0.2 | 9 |
| 41-13 | 86 | 1004 |
| 41-14 | 45 | 1419 |
| 41-15 | 0.1 | 2 |
| 41-16 | 24 | 912 |
| 41-17 | 46 | 1392 |
| 41-18 | 0.1 | 10 |
| 41-19 | 0.3 | 9 |
| 41-20 | 0.6 | 17 |
| 41-21 | 11 | 308 |
| 41-22 | 28 | 1053 |
| 41-23 | 46 | 1430 |
| 41-24 | 26 | 1029 |
| 41-25 | 27 | 1078 |
| 41-26 | 16 | 759 |
| 41-27 | 307 | >1496 |
| 41-28 | 20 | 735 |
| 42 | 8 | 336 |
| 43-1 | 4 | 13 |
| 43-2 | 18 | 67 |
| 43-3 | 0.9 | 5 |
| 43-4 | 0.05 | 0.1 |
| 44-1 | 155 | 1481 |
| 44-2 | 16 | 195 |
| 45-1 | 7 | 301 |
| 45-2 | 378 | 1481 |
| 46 | 0.03 | 0.1 |
| 47-3 | 2 | 32 |
| 47-4 | 2 | 83 |
| 48-1 | 1 | 24 |
| 48-2 | 113 | 487 |
| 49-1 | 0.6 | 20 |
| 49-2 | 0.4 | 22 |
| 50-1 | 1 | 47 |
| 50-2 | 2 | 62 |

What is claimed is:

1. A compound of formula I or a pharmaceutically acceptable salt, or a stereoisomer thereof:

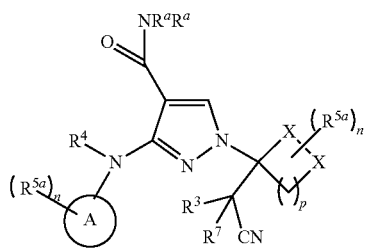

I $R^a$ and $R^4$ are each independently selected from hydrogen and $C_{1-4}$alkyl;
A is selected from aryl, and heteroaryl;
n is independently 0, 1, 2, 3, or 4;
p is 0, 1, 2, or 3;
X is independently selected from C, N, O and S;

$R^3$ and $R^7$ are each independently selected from
hydrogen,
halogen,
$C_{1-10}$ alkyl,
$C_{2-10}$ alkenyl,
$C_{1-10}$ heteroalkyl,
aryl $C_{0-10}$ alkyl$C_{0-10}$ alkyl,
$C_{3-8}$ cycloalkyl$C_{0-10}$ alkyl,
heteroaryl $C_{0-10}$ alkyl,
$(C_{3-8})$heterocycloalkyl $C_{0-10}$ alkyl,
and wherein each of $R^3$ and $R^7$ are independently substituted with 0, 1, 2, 3, or 4 $R^{5a}$ substituents;
$R^{5a}$ is selected from:
halogen,
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
aryl $C_{2-10}$ alkenyl(oxy)$_{0-1}$(carbonyl)$_{0-1}C_{0-10}$ alkyl,
aryl $C_{2-10}$ alkynyl(oxy)$_{0-1}$(carbonyl)$_{0-1}C_{0-10}$ alkyl,
$C_{3-8}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-8})$heterocycloalkyl $C_{0-10}$ alkyl(oxy)$_{0-1}$(carbonyl)$_{0-1}C_{0-10}$ alkyl,
$C_{1-10}$ alkyl(carbonyl)$_{0-1}$oxy$C_{0-10}$ alkyl,
$C_{1-10}$ heteroalkyl(carbonyl)$_{0-1}$oxy$C_{0-10}$ alkyl,
$C_{2-10}$ alkenyl(carbonyl)$_{0-1}$oxy$C_{0-10}$ alkyl,
$C_{1-10}$ heteroalkyl(carbonyl)$_{0-1}$oxy$C_{0-10}$ alkyl,
aryl $C_{0-10}$ alkyl (carbonyl)$_{0-1}$oxy$C_{0-10}$ alkyl,
$(C_{3-8})$cycloalkyl$C_{0-10}$ alkyl(carbonyl)$_{0-1}$oxy$C_{0-10}$ alkyl,
heteroaryl$C_{0-10}$ alkyl(carbonyl)$_{0-1}$oxy$C_{0-10}$ alkyl,
$(C_{3-8})$heterocycloalkyl $C_{0-10}$ alkyl(carbonyl)$_{0-1}$oxy$C_{0-10}$ alkyl,
$((C_{0-10})$alkyl$)_{1-2}$aminocarbonyloxy,
$(C_{0-10})$heteroalkylaminocarbonyloxy,
aryl $(C_{0-10})$alkylaminocarbonyloxy,
$(C_{3-8})$cycloalkyl$(C_{0-10})$alkylaminocarbonyloxy,
heteroaryl$(C_{0-10})$alkylaminocarbonyloxy,
$(C_{3-8})$heterocycloalkyl$(C_{0-10})$alkylaminocarbonyloxy,
$C_{0-10}$ alkylamino(oxy)$_{0-1}$carbonyl$C_{0-10}$ alkyl,
$(C_{0-10})$heteroalkylamino(oxy)$_{0-1}$carbonyl$C_{0-10}$ alkyl,
$C_{3-8}$ cycloalkyl $C_{0-10}$ alkylamino(oxy)$_{0-1}$carbonyl$C_{0-10}$ alkyl,
aryl $C_{0-10}$alkylamino(oxy)$_{0-1}$carbonyl$C_{0-10}$ alkyl,
heteroaryl$C_{0-1}$ alkylamino(oxy)$_{0-1}$carbonyl$C_{0-10}$ alkyl,
$(C_{3-8})$heterocycloalkyl$C_{0-10}$alkylamino(oxy)$_{0-1}$carbonyl$C_{0-10}$ alkyl,
$C_{1-10}$ alkyl(oxy)$_{0-1}$(carbonyl)$_{0-1}$amino$C_{0-10}$ alkyl,
$C_{1-10}$ heteroalkyl (oxy)$_{0-1}$(carbonyl)$_{0-1}$amino$C_{0-10}$ alkyl,
$C_{3-8}$ cycloalkyl $C_{0-10}$ alkyl (oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
$(C_{3-8})$heterocycloalkyl $C_{0-10}$ alkyl(oxy)$_{0-1}$(carbonyl)$_{0-1}$amino$C_{0-10}$ alkyl,
—CO$_2$($C_{0-10}$ alkyl),
—($C_{0-10}$ alkyl)CO$_2$H,
Oxo (=O);
$C_{1-10}$ alkylsulfonyl,
$C_{1-10}$ heteroalkylsulfonyl,
$(C_{3-8})$ cycloalkylsulfonyl,
$(C_{3-8})$ cycloheteroalkylsulfonyl,
heteroarylsulfonyl,
arylsulfonyl, aminosulfonyl,
—SO$_2$N(C$_{1-6}$alkyl)$_{1-2}$,
—SO$_2$C$_{1-6}$alkyl,
—SO$_2$CF$_3$,
—SO$_2$CF$_2$H,
C$_{1-10}$ alkylsulfinyl,
—Si(CH$_3$)$_3$,
amino,
(C$_{0-10}$ alkyl)$_{1-2}$ amino,
C$_{1-4}$acylamino C$_{0-10}$ alkyl,
hydroxy,
(C$_{1-10}$ alkyl)OH,
C$_{0-10}$ alkylalkoxy,
cyano,
(C$_{1-6}$alkyl)cyano, and
C$_{1-6}$haloalkyl;
wherein two R$^{5a}$ and the atom to which they are attached may optionally form a –4, –5, or –6 member saturated ring system;
wherein R$^{5a}$ is each optionally substituted with 1, 2, 3, or 4 R$^6$ substituents, and R$^6$ is independently selected from:
halogen,
C$_{1-10}$ alkyl(oxy)$_{0-1}$(carbonyl)$_{0-1}$C$_{0-10}$ alkyl,
C$_{1-10}$ heteroalkyl(oxy)$_{0-1}$(carbonyl)$_{0-1}$C$_{0-10}$ alkyl,
C$_{2-10}$ alkenyl(oxy)$_{0-1}$(carbonyl)$_{0-1}$C$_{0-10}$ alkyl,
aryl C$_{0-10}$ alkyl(oxy)$_{0-1}$(carbonyl)$_{0-1}$C$_{0-10}$ alkyl,
aryl C$_{2-10}$ alkenyl(oxy)$_{0-1}$(carbonyl)$_{0-1}$C$_{0-10}$ alkyl,
aryl C$_{2-10}$ alkynyl(oxy)$_{0-1}$(carbonyl)$_{0-1}$C$_{0-10}$ alkyl,
C$_{3-8}$ cycloalkyl C$_{0-10}$ alkyl(oxy)$_{0-1}$(carbonyl)$_{0-1}$C$_{0-10}$ alkyl,
heteroaryl C$_{0-10}$ alkyl(oxy)$_{0-1}$(carbonyl)$_{0-1}$C$_{0-10}$ alkyl,
(C$_{3-8}$)heterocycloalkyl C$_{0-10}$ alkyl(oxy)$_{0-1}$(carbonyl)$_{0-1}$C$_{0-10}$ alkyl,
C$_{1-10}$ alkyl(carbonyl)$_{0-1}$oxyC$_{0-10}$ alkyl,
C$_{2-10}$ alkenyl(carbonyl)$_{0-1}$oxyC$_{0-10}$ alkyl,
C$_{1-10}$ heteroalkyl(carbonyl)$_{0-1}$oxyC$_{0-10}$ alkyl,
aryl C$_{0-10}$ alkyl (carbonyl)$_{0-1}$oxyC$_{0-10}$ alkyl,
(C$_{3-8}$)cycloalkyl C$_{0-10}$ alkyl(carbonyl)$_{0-1}$oxyC$_{0-10}$ alkyl,
heteroarylC$_{0-10}$ alkyl(carbonyl)$_{0-1}$oxyC$_{0-10}$ alkyl,
(C$_{3-8}$)heterocycloalkyl C$_{0-10}$ alkyl(carbonyl)$_{0-1}$oxyC$_{0-10}$ alkyl,
((C$_{0-10}$)alkyl)$_{1-2}$aminocarbonyloxy,
aryl (C$_{0-10}$)alkylaminocarbonyloxy,
(C$_{3-8}$)cycloalkyl(C$_{0-10}$)alkylaminocarbonyloxy,
heteroaryl(C$_{0-10}$)alkylaminocarbonyloxy,
(C$_{3-8}$)heterocycloalkyl(C$_{0-10}$)alkylaminocarbonyloxy,
C$_{0-10}$ alkylamino(oxy)$_{0-1}$carbonylC$_{0-10}$ alkyl,
C$_{3-8}$ cycloalkyl C$_{0-10}$ alkylamino(oxy)$_{0-1}$carbonylC$_{0-10}$ alkyl,
aryl C$_{0-10}$ alkylamino(oxy)$_{0-1}$carbonylC$_{0-10}$ alkyl,
heteroaryl C$_{0-10}$ alkylamino(oxy)$_{0-1}$carbonylC$_{0-10}$ alkyl,
(C$_{3-8}$)heterocycloalkyl C$_{0-10}$ alkylamino(oxy)$_{0-1}$carbonylC$_{0-10}$ alkyl,
C$_{1-10}$ alkyl (oxy)$_{0-1}$carbonylaminoC$_{0-10}$ alkyl,
C$_{3-8}$ cycloalkyl C$_{0-10}$ alkyl (oxy)$_{0-1}$carbonylaminoC$_{0-10}$ alkyl,
aryl C$_{0-10}$ alkyl(oxy)$_{0-1}$carbonylaminoC$_{0-10}$ alkyl,
heteroaryl C$_{0-10}$ alkyl(oxy)$_{0-1}$carbonylaminoC$_{0-10}$ alkyl,
(C$_{3-8}$)heterocycloalkyl C$_{0-10}$ alkyl(oxy)$_{0-1}$carbonylaminoC$_{0-10}$ alkyl,
—CO$_2$(C$_{0-10}$ alkyl),
—(C$_{0-10}$ alkyl)CO$_2$H,
Oxo (=O),
C$_{1-10}$ alkylsulfonyl,
C$_{1-10}$ heteroalkylsulfonyl,
(C$_{3-8}$) cycloalkylsulfonyl,
(C$_{3-8}$) cycloheteroalkylsulfonyl,
heteroarylsulfonyl,
arylsulfonyl,
aminosulfonyl,
—SO$_2$N(C$_{1-6}$alkyl)$_{1-2}$,
—SO$_2$C$_{1-6}$alkyl,
—SO$_2$CF$_3$,
—SO$_2$CF$_2$H,
C$_{1-10}$ alkylsulfinyl,
—OSi(C$_{1-10}$alkyl)$_3$,
—Si(CH$_3$)$_3$,
amino,
(C$_{0-10}$ alkyl)$_{1-2}$ amino,
-(oxy)$_{0-1}$(carbonyl)$_{0-1}$N(C$_{0-10}$ alkyl)$_{1-2}$
C$_{1-4}$acylamino C$_{0-10}$ alkyl,
hydroxy,
(C$_{1-10}$ alkyl)OH,
C$_{1-10}$ alkoxy,
(C$_{1-10}$ alkyl)cyano,
cyano, and
C$_{1-6}$haloalkyl; and
wherein two R$^6$ and the atoms to which they are attached may optionally form a 3-, 4-, 5-, or 6-membered saturated ring system; and
R$^6$ is optionally substituted with 1, 2, or 3 substituents selected from hydrogen, hydroxy, (C$_{1-6}$)alkyl, (C$_{1-6}$) alkoxy, (C$_{1-10}$ alkyl)OH, halogen, CO$_2$H, —(C$_{0-6}$) alkylCN, —O(C=O)C$_1$-C$_6$ alkyl, NO$_2$, trifluoromethoxy, trifluoroethoxy, trifluoromethyl, trifluoroethyl, —N—C(O)O(C$_{0-6}$)alkyl, C$_{1-10}$ alkylsulfonyl, C$_{1-10}$ heteroalkylsulfonyl, oxo (O=), (C$_{3-8}$) cycloalkylsulfonyl, (C$_{3-8}$) cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —Si(CH$_3$)$_3$, —SO$_2$CF$_2$H, —C$_{1-10}$ alkylsulfinyl, —OSi(C$_{1-10}$alkyl)$_3$, —O$_{(0-1)}$(C$_{1-10}$)haloalkyl, amino (C$_{1-6}$alkyl)$_{0-2}$ and NH$_2$; with the proviso that the compound of formula I is other than:
1-[3-(cyanomethyl)-1-(ethylsulfonyl)azetidin-3-yl]-3-({4-[(1,1-dioxidothiomorpholin-4-yl)carbonyl]phenyl}amino)-1H-pyrazole-4-carboxamide; and
1-[3-(cyanomethyl)-1-(naphthalene-2-ylsulfonyl)azetidin-3-yl]-3-(phenylamino)-1H-pyrazole-4-carboxamide.

2. A compound or a pharmaceutically acceptable salt, or a stereoisomer thereof according to claim 1 selected from:
tert-Butyl 4-[4-carbamoyl-3-(phenylamino)-1H-pyrazol-1-yl]-4-(cyanomethyl)piperidine-1-carboxylate;
tert-butyl 4-{3-[(4-bromophenyl)amino]-4-carbamoyl-1H-pyrazol-1-yl}-4-(cyanomethyl)piperidine-1-carboxylate;
tert-butyl 3-[4-carbamoyl-3-(phenylamino)-1H-pyrazol-1-yl]-3-(cyanomethyl)azetidine-1-carboxylate;
tert-butyl 4-(3-{[3-(1H-benzotriazol-1-ylmethyl)phenyl]amino}-4-carbamoyl-1H-pyrazol-1-yl)-4-(cyanomethyl)piperidine-1-carboxylate;
tert-butyl 3-(4-carbamoyl-3-{[4-(methylsulfonyl)phenyl]amino}-1H-pyrazol-1-yl)-3-(cyanomethyl)azetidine-1-carboxylate;
tert-butyl 4-[4-carbamoyl-3-({4-[(1,1-dioxidothiomorpholin-4-yl)carbonyl]phenyl}amino)-1H-pyrazol-1-yl]-4-(cyanomethyl)piperidine-1-carboxylate;
tert-butyl 4-[4-carbamoyl-3-(pyridin-4-ylamino)-1H-pyrazol-1-yl]-4-(cyanomethyl)piperidine-1-carboxylate;

tert-butyl 3-[4-carbamoyl-3-({4-[(1,1-dioxidothiomorpholin-4-yl)carbonyl]phenyl}amino)-1H-pyrazol-1-yl]-3-(cyanomethyl)azetidine-1-carboxylate;
tert-Butyl-4-[4-carbamoyl-3-(phenylamino)-1H-pyrazol-1-yl]-4-(cyanomethyl)-3-methylpiperidine-1-carboxylate;
1-[3-(cyanomethyl)-1-(ethylsulfonyl)azetidin-3-yl]-3-(phenylamino)-1H-pyrazole-4-carboxamide;
1-[1-(cyanomethyl)cyclohexyl]-3-{[4-(methylsulfonyl)phenyl]amino}-1H-pyrazole-4-carboxamide;
1-[1-(cyanomethyl)cyclohexyl]-3-(phenylamino)-1H-pyrazole-4-carboxamide;
tert-butyl 3-(4-carbamoyl-3-{[4-(methylsulfonyl)phenyl]amino}-1H-pyrazol-1-yl)-3-(cyanomethyl)pyrrolidine-1-carboxylate;
tert-butyl 3-[4-carbamoyl-3-(phenylamino)-1H-pyrazol-1-yl]-3-(cyanomethyl)pyrrolidine-1-carboxylate;
tert-butyl 4-[4-carbamoyl-3-(phenylamino)-1H-pyrazol-1-yl]-4-(cyanomethyl)cyclohexanecarboxylate;
tert-butyl {4-[4-carbamoyl-3-(phenylamino)-1H-pyrazol-1-yl]-4-(cyanomethyl)cyclohexyl}carbamate;
1-[3-(cyanomethyl)oxetan-3-yl]-3-(phenylamino)-1H-pyrazole-4-carboxamide;
1-(3-cyano-1-(cyanomethyl)cyclobutyl)-3-(phenylamino)-1H-pyrazole-4-carboxamide;
1-(3-cyano-1-(cyanomethyl)cyclobutyl)-3-((4-(methylsulfonyl)phenyl)amino)-1H-pyrazole-4-carboxamide;
tert-butyl 6-[4-carbamoyl-3-(phenylamino)-1H-pyrazol-1-yl]-6-(cyanomethyl)-2-azaspiro[3.3]heptane-2-carboxylate;
1-[4-(Cyanomethyl)-1-(3,4-dimethoxyphenyl)piperidin-4-yl]-3-[(4-fluorophenyl)amino]-1H-pyrazole-4-carboxamide;
1-[4-(cyanomethyl)-1-isoquinolin-4-ylpiperidin-4-yl]-3-[(4-fluorophenyl)amino]-1H-pyrazole-4-carboxamide;
1-[4-(cyanomethyl)-1-quinolin-4-ylpiperidin-4-yl]-3-[(4-fluorophenyl)amino]-1H-pyrazole-4-carboxamide;
1-[4-(cyanomethyl)-1-(2-methylpyridin-4-yl)piperidin-4-yl]-3-[(4-fluorophenyl)amino]-1H-pyrazole-4-carboxamide;
1-[4-(cyanomethyl)-1-(5-fluoropyridin-3-yl)piperidin-4-yl]-3-[(4-fluorophenyl)amino]-1H-pyrazole-4-carboxamide;
1-[4-(cyanomethyl)-1-(2-methoxypyridin-4-yl)piperidin-4-yl]-3-[(4-fluorophenyl)amino]-1H-pyrazole-4-carboxamide;
1-{4-(cyanomethyl)-1-[6-(1-hydroxy-1-methylethyl)pyridin-2-yl]piperidin-4-yl}-3-[(4-fluorophenyl)amino]-1H-pyrazole-4-carboxamide;
1-{4-(cyanomethyl)-1-[5-(trifluoromethyl)pyridin-3-yl]piperidin-4-yl}-3-[(4-fluorophenyl)amino]-1H-pyrazole-4-carboxamide;
1-{4-(cyanomethyl)-1-[4-(2,2,2-trifluoro-1-hydroxyethyl)phenyl]piperidin-4-yl}-3-[(4-fluorophenyl)amino]-1H-pyrazole-4-carboxamide;
1-{4-(cyanomethyl)-1-[6-(2-hydroxyethoxy)pyridin-2-yl]piperidin-4-yl}-3-[(4-fluorophenyl)amino]-1H-pyrazole-4-carboxamide;
1-[4-(cyanomethyl)-1-(4-fluoro-3-methoxyphenyl)piperidin-4-yl]-3-[(4-fluorophenyl)amino]-1H-pyrazole-4-carboxamide;
1-[4-(cyanomethyl)-1-(3-fluoro-5-methoxyphenyl)piperidin-4-yl]-3-[(4-fluorophenyl)amino]-1H-pyrazole-4-carboxamide;
1-{4-(cyanomethyl)-1-[6-(difluoromethoxy)pyridin-3-yl]piperidin-4-yl}-3-[(4-fluorophenyl)amino]-1H-pyrazole-4-carboxamide;
1-[4-(cyanomethyl)-1-(5,6-dimethylpyridin-3-yl)piperidin-4-yl]-3-[(4-fluorophenyl)amino]-1H-pyrazole-4-carboxamide;
1-{4-(cyanomethyl)-1-[6-(1-methylethoxy)pyridin-2-yl]piperidin-4-yl}-3-[(4-fluorophenyl)amino]-1H-pyrazole-4-carboxamide;
1-[4-(cyanomethyl)-1-(6-ethoxypyridin-2-yl)piperidin-4-yl]-3-[(4-fluorophenyl)amino]-1H-pyrazole-4-carboxamide;
1-[4-(cyanomethyl)-1-(3-cyclopropylphenyl)piperidin-4-yl]-3-[(4-fluorophenyl)amino]-1H-pyrazole-4-carboxamide;
1-[4-(cyanomethyl)-1-(6-cyanopyridin-2-yl)piperidin-4-yl]-3-[(4-fluorophenyl)amino]-1H-pyrazole-4-carboxamide;
1-{4-(cyanomethyl)-1-[5-(difluoromethoxy)pyridin-2-yl]piperidin-4-yl}-3-[(4-fluorophenyl)amino]-1H-pyrazole-4-carboxamide;
1-[4-(cyanomethyl)-1-(6-methylpyridin-2-yl)piperidin-4-yl]-3-[(4-fluorophenyl)amino]-1H-pyrazole-4-carboxamide;
1-[4-(cyanomethyl)-1-(5-cyanopyridin-3-yl)piperidin-4-yl]-3-[(4-fluorophenyl)amino]-1H-pyrazole-4-carboxamide;
1-[4-(cyanomethyl)-1-(6-fluoropyridin-3-yl)piperidin-4-yl]-3-[(4-fluorophenyl)amino]-1H-pyrazole-4-carboxamide;
1-[4-(cyanomethyl)-1-(3-methoxypyridin-2-yl)piperidin-4-yl]-3-[(4-fluorophenyl)amino]-1H-pyrazole-4-carboxamide;
1-[4-(cyanomethyl)-1-pyrimidin-5-ylpiperidin-4-yl]-3-[(4-fluorophenyl)amino]-1H-pyrazole-4-carboxamide;
1-[4-(cyanomethyl)-1-(2-methoxypyrimidin-5-yl)piperidin-4-yl]-3-[(4-fluorophenyl)amino]-1H-pyrazole-4-carboxamide;
1-[4-(cyanomethyl)-1-(4-cyanophenyl)piperidin-4-yl]-3-[(4-fluorophenyl)amino]-1H-pyrazole-4-carboxamide;
1-[4-(cyanomethyl)-1-(3-fluorophenyl)piperidin-4-yl]-3-[(4-fluorophenyl)amino]-1H-pyrazole-4-carboxamide;
1-{4-(cyanomethyl)-1-[6-(trifluoromethyl)pyridin-3-yl]piperidin-4-yl}-3-[(4-fluorophenyl)amino]-1H-pyrazole-4-carboxamide;
1-[4-(cyanomethyl)-1-(2-methylpyridin-3-yl)piperidin-4-yl]-3-[(4-fluorophenyl)amino]-1H-pyrazole-4-carboxamide;
1-[4-(cyanomethyl)-1-pyridin-3-ylpiperidin-4-yl]-3-[(4-fluorophenyl)amino]-1H-pyrazole-4-carboxamide;
1-[4-(cyanomethyl)-1-(4-methylpyridin-2-yl)piperidin-4-yl]-3-[(4-fluorophenyl)amino]-1H-pyrazole-4-carboxamide;
1-[4-(cyanomethyl)-1-(5-fluoro-2-methylphenyl)piperidin-4-yl]-3-[(4-fluorophenyl)amino]-1H-pyrazole-4-carboxamide;
1-[4-(cyanomethyl)-1-(4-methylpyridin-3-yl)piperidin-4-yl]-3-[(4-fluorophenyl)amino]-1H-pyrazole-4-carboxamide;
1-[4-(cyanomethyl)-1-(3-fluoro-4-methylphenyl)piperidin-4-yl]-3-[(4-fluorophenyl)amino]-1H-pyrazole-4-carboxamide;
methyl 6-[4-{4-carbamoyl-3-[(4-fluorophenyl)amino]-1H-pyrazol-1-yl}-4-(cyanomethyl)piperidin-1-yl]pyridine-2-carboxylate;
1-[4-(cyanomethyl)-1-(6-ethoxypyridin-3-yl)piperidin-4-yl]-3-[(4-fluorophenyl)amino]-1H-pyrazole-4-carboxamide;

1-[4-(cyanomethyl)-1-(5-methoxypyridin-3-yl)piperidin-4-yl]-3-[(4-fluorophenyl)amino]-1H-pyrazole-4-carboxamide;
1-[4-(cyanomethyl)-1-(4-fluorophenyl)piperidin-4-yl]-3-[(4-fluorophenyl)amino]-1H-pyrazole-4-carboxamide;
1-[4-(cyanomethyl)-1-(4-methylphenyl)piperidin-4-yl]-3-[(4-fluorophenyl)amino]-1H-pyrazole-4-carboxamide;
1-[4-(cyanomethyl)-1-(3,5-difluorophenyl)piperidin-4-yl]-3-[(4-fluorophenyl)amino]-1H-pyrazole-4-carboxamide;
1-[4-(cyanomethyl)-1-(2-methoxyphenyl)piperidin-4-yl]-3-[(4-fluorophenyl)amino]-1H-pyrazole-4-carboxamide;
1-[4-(cyanomethyl)-1-(4-fluoro-3-methylphenyl)piperidin-4-yl]-3-[(4-fluorophenyl)amino]-1H-pyrazole-4-carboxamide;
1-[4-(cyanomethyl)-1-(2-fluoro-3-methylphenyl)piperidin-4-yl]-3-[(4-fluorophenyl)amino]-1H-pyrazole-4-carboxamide;
1-[4-(cyanomethyl)-1-(4-fluoropyridin-2-yl)piperidin-4-yl]-3-[(4-fluorophenyl)amino]-1H-pyrazole-4-carboxamide;
1-[4-(cyanomethyl)-1-(3,4-difluorophenyl)piperidin-4-yl]-3-[(4-fluorophenyl)amino]-1H-pyrazole-4-carboxamide;
1-[4-(cyanomethyl)-1-pyridin-4-ylpiperidin-4-yl]-3-[(4-fluorophenyl)amino]-1H-pyrazole-4-carboxamide;
1-[4-(cyanomethyl)-1-(4-methylpyrimidin-5-yl)piperidin-4-yl]-3-[(4-fluorophenyl)amino]-1H-pyrazole-4-carboxamide;
1-[4-(cyanomethyl)-1-(5-methylpyridin-3-yl)piperidin-4-yl]-3-[(4-fluorophenyl)amino]-1H-pyrazole-4-carboxamide;
1-{4-(cyanomethyl)-1-[6-(2-hydroxy-2-methylpropyl)pyridin-2-yl]piperidin-4-yl}-3-[(4-fluorophenyl)amino]-1H-pyrazole-4-carboxamide;
1-{4-(cyanomethyl)-1-[6-(fluoromethyl)pyridin-2-yl]piperidin-4-yl}-3-[(4-fluorophenyl)amino]-1H-pyrazole-4-carboxamide;
1-[4-(cyanomethyl)-1-(2-fluoropyridin-3-yl)piperidin-4-yl]-3-[(4-fluorophenyl)amino]-1H-pyrazole-4-carboxamide;
1-[4-(cyanomethyl)-1-(6-methylpyridin-3-yl)piperidin-4-yl]-3-[(4-fluorophenyl)amino]-1H-pyrazole-4-carboxamide;
1-[4-(cyanomethyl)-1-(6-methoxypyridin-3-yl)piperidin-4-yl]-3-[(4-fluorophenyl)amino]-1H-pyrazole-4-carboxamide;
1-[4-(cyanomethyl)-1-(6-fluoropyridin-2-yl)piperidin-4-yl]-3-[(4-fluorophenyl)amino]-1H-pyrazole-4-carboxamide;
1-{4-(cyanomethyl)-1-[4-(trifluoromethyl)pyridin-2-yl]piperidin-4-yl}-3-[(4-fluorophenyl)amino]-1H-pyrazole-4-carboxamide;
1-[4-(cyanomethyl)-1-(6-fluoro-5-methylpyridin-3-yl)piperidin-4-yl]-3-[(4-fluorophenyl)amino]-1H-pyrazole-4-carboxamide;
tert-Butyl 4-(4-carbamoyl-3-{[4-(methylsulfonyl)phenyl]amino}-1H-pyrazol-1-yl)-4-(cyanomethyl)piperidine-1-carboxylate;
tert-butyl 4-[4-carbamoyl-3-({4-[(1-methylethoxy)carbonyl]phenyl}amino)-1H-pyrazol-1-yl]-4-(cyanomethyl)piperidine-1-carboxylate;
tert-butyl 4-(4-carbamoyl-3-{[3-(1H-imidazol-1-ylmethyl)phenyl]amino}-1H-pyrazol-1-yl)-4-(cyanomethyl)piperidine-1-carboxylate;
2,2,2-trifluoroethyl 4-(3-{[3-(1H-benzotriazol-1-ylmethyl)phenyl]amino}-4-carbamoyl-1H-pyrazol-1-yl)-4-(cyanomethyl)piperidine-1-carboxylate;
1-[4-(cyanomethyl)tetrahydro-2H-pyran-4-yl]-3-{[4-(methylsulfonyl)phenyl]amino}-1H-pyrazole-4-carboxamide;
tert-butyl 4-{4-carbamoyl-3-[(2-cyanopyrimidin-5-yl)amino]-1H-pyrazol-1-yl}-4-(cyanomethyl)piperidine-1-carboxylate;
tert-Butyl 4-(4-carbamoyl-3-((4-fluorophenyl)amino)-1H-pyrazol-1-yl)-4-(1-cyanoethyl)piperidine-1-carboxylate;
tert-butyl 4-{4-carbamoyl-3-[(4-fluorophenyl)amino]-1H-pyrazol-1-yl}-4-[cyano(cyclopropyl)methyl]piperidine-1-carboxylate;
tert-butyl-4-{4-carbamoyl-3-[(4-fluorophenyl)amino]-1H-pyrazol-1-yl}-4-(cyanomethyl)-3-fluoropiperidine-1-carboxylate;
1-[4-(cyanomethyl)tetrahydro-2H-pyran-4-yl]-3-(phenylamino)-1H-pyrazole-4-carboxamide;
1-[8-(cyanomethyl)-1,4-dioxaspiro[4.5]dec-8-yl]-3-[(4-fluorophenyl)amino]-1H-pyrazole-4-carboxamide;
1-[8-(cyanomethyl)-1,4-dioxaspiro[4.5]dec-8-yl]-3-{[4-(methylsulfonyl)phenyl]amino}-1H-pyrazole-4-carboxamide;
1-(4-(Cyanomethyl)tetrahydro-2H-thiopyran-4-yl)-3-((4-fluorophenyl)amino)-1H-pyrazole-4-carboxamide;
1-(4-(Cyanomethyl)-1,1-dioxidotetrahydro-2H-thiopyran-4-yl)-3-((4-fluorophenyl)amino)-1H-pyrazole-4-carboxamide;
tert-Butyl 4-{4-carbamoyl-3-[(2-fluoropyridin-4-yl)amino]-1H-pyrazol-1-yl}-4-(cyanomethyl)-1-carboxylate;
tert-butyl 4-(4-carbamoyl-3-{[4-(methoxycarbonyl)phenyl]amino}-1H-pyrazol-1-yl)-4-(cyanomethyl)piperidine-1-carboxylate;
tert-butyl 4-{4-carbamoyl-3-[(4-fluorophenyl)amino]-1H-pyrazol-1-yl}-4-(cyanomethyl)piperidine-1-carboxylate;
tert-Butyl 4-[4-(aminocarbonyl)-3-({4-[(methylamino)carbonyl]phenyl}amino)-1H-pyrazol-1-yl]-4-(cyanoethyl)piperidine-1-carboxylate;
tert-butyl 4-{4-carbamoyl-3-[(4-cyanophenyl)amino]-1H-pyrazol-1-yl}-4-(cyanomethyl)piperidine-1-carboxylate;
tert-butyl 4-(4-carbamoyl-3-(6-(2-hydroxypropan-2-yl)pyridin-3-ylamino)-1H-pyrazol-1-yl)-4-(cyanomethyl)piperidine-1-carboxylate;
tert-butyl 4-(4-carbamoyl-3-(6-(1-hydroxyethyl)pyridin-3-ylamino)-1H-pyrazol-1-yl)-4-(cyanomethyl)piperidine-1-carboxylate;
tert-butyl 4-(4-carbamoyl-3-(4-(2-hydroxypropan-2-yl)phenylamino)-1H-pyrazol-1-yl)-4-(cyanomethyl)piperidine-1-carboxylate;
tert-butyl 4-(4-carbamoyl-3-(4-(1-hydroxyethyl)phenylamino)-1H-pyrazol-1-yl)-4-(cyanomethyl)piperidine-1-carboxylate;
tert-butyl 4-(3-(4-acetylphenylamino)-4-carbamoyl-1H-pyrazol-1-yl)-4-(cyanomethyl)piperidine-1-carboxylate;
tert-butyl 4-(4-carbamoyl-3-{[4-(trifluoroacetyl)phenyl]amino}-1H-pyrazol-1-yl)-4-(cyanomethyl)piperidine-1-carboxylate;
tert-butyl 4-{4-carbamoyl-3-[(6-cyanopyridin-3-yl)amino]-1H-pyrazol-1-yl}-4-(cyanomethyl)piperidine-1-carboxylate;

tert-butyl 4-(4-carbamoyl-3-{[4-(1-methyl-1H-pyrazol-3-yl)phenyl]amino}-1H-pyrazol-1-yl)-4-(cyanomethyl)piperidine-1-carboxylate;

tert-butyl 4-{3-[(2-aminopyridin-4-yl)amino]-4-carbamoyl-1H-pyrazol-1-yl}-4-(cyanomethyl)piperidine-1-carboxylate;

tert-butyl 4-[4-carbamoyl-3-({4-[(trifluoromethyl)sulfonyl]phenyl}amino)-1H-pyrazol-1-yl]-4-(cyanomethyl)piperidine-1-carboxylate;

tert-butyl 4-[4-carbamoyl-3-({4-[(difluoromethyl)sulfonyl]phenyl}amino)-1H-pyrazol-1-yl]-4-(cyanomethyl)piperidine-1-carboxylate;

tert-butyl 4-{4-carbamoyl-3-[(2-methylpyridin-4-yl)amino]-1H-pyrazol-1-yl}-4-(cyanomethyl)piperidine-1-carboxylate;

tert-butyl 4-(4-carbamoyl-3-{[2-(hydroxymethyl)pyridin-4-yl]amino}-1H-pyrazol-1-yl)-4-(cyanomethyl)piperidine-1-carboxylate;

tert-butyl 4-{4-carbamoyl-3-[(2-methoxypyridin-4-yl)amino]-1H-pyrazol-1-yl}-4-(cyanomethyl)piperidine-1-carboxylate;

tert-butyl 4-{4-carbamoyl-3-[(4-sulfamoylphenyl)amino]-1H-pyrazol-1-yl}-4-(cyanomethyl)piperidine-1-carboxylate;

tert-butyl 4-(4-carbamoyl-3-{[4-(dimethylsulfamoyl)phenyl]amino}-1H-pyrazol-1-yl)-4-(cyanomethyl)piperidine-1-carboxylate;

tert-butyl 4-{4-carbamoyl-3-{[4-(dimethylcarbamoyl)phenyl]amino}-1H-pyrazol-1-yl}-4-(cyanomethyl)piperidine-1-carboxylate;

tert-butyl 4-(4-carbamoyl-3-{[2-(trifluoromethyl)pyridin-4-yl]amino}-1H-pyrazol-1-yl)-4-(cyanomethyl)piperidine-1-carboxylate;

tert-butyl 4-(4-carbamoyl-3-{[3-fluoro-4-(morpholin-4-ylcarbonyl)phenyl]amino}-1H-pyrazol-1-yl)-4-(cyanomethyl)piperidine-1-carboxylate;

tert-butyl 4-(4-carbamoyl-3-{[[4-(morpholin-4-ylcarbonyl)phenyl]amino}-1H-pyrazol-1-yl)-4-(cyanomethyl)piperidine-1-carboxylate;

tert-butyl 4-{4-carbamoyl-3-[(4-cyano-3-fluorophenyl)amino]-1H-pyrazol-1-yl}-4-(cyanomethyl)piperidine-1-carboxylate;

tert-butyl 4-{4-carbamoyl-3-[(2-carbamoylpyridin-4-yl)amino]-1H-pyrazol-1-yl}-4-(cyanomethyl)piperidine-1-carboxylate;

tert-butyl 4-{4-carbamoyl-3-[(3,4-difluorophenyl)amino]-1H-pyrazol-1-yl}-4-(cyanomethyl)piperidine-1-carboxylate;

tert-butyl 4-{4-carbamoyl-3-[(2-chloropyridin-4-yl)amino]-1H-pyrazol-1-yl}-4-(cyanomethyl)piperidine-1-carboxylate;

tert-butyl 4-(4-carbamoyl-3-{[4-(3-methyl-1,2,4-oxadiazol-5-yl)phenyl]amino}-1H-pyrazol-1-yl)-4-(cyanomethyl)piperidine-1-carboxylate;

tert-butyl 4-{4-carbamoyl-3-[(2,6-dichloropyridin-4-yl)amino]-1H-pyrazol-1-yl}-4-(cyanomethyl)piperidine-1-carboxylate;

tert-butyl 4-(4-carbamoyl-3-{[4-(5-methyl-1,2,4-oxadiazol-3-yl)phenyl]amino}-1H-pyrazol-1-yl)-4-(cyanomethyl)piperidine-1-carboxylate;

tert-butyl 4-{4-carbamoyl-3-[(2-cyanopyridin-4-yl)amino]-1H-pyrazol-1-yl}-4-(cyanomethyl)piperidine-1-carboxylate;

tert-butyl 4-[4-carbamoyl-3-(pyridin-3-ylamino)-1H-pyrazol-1-yl]-4-(cyanomethyl)piperidine-1-carboxylate;

tert-butyl 4-{4-carbamoyl-3-[(5-fluoropyridin-3-yl)amino]-1H-pyrazol-1-yl}-4-(cyanomethyl)piperidine-1-carboxylate;

tert-butyl 4-{4-carbamoyl-3-[(5-chloropyridin-3-yl)amino]-1H-pyrazol-1-yl}-4-(cyanomethyl)piperidine-1-carboxylate;

2,2-difluoroethyl 4-(4-carbamoyl-3-{[6-(cyclobutyloxy)pyridin-3-yl]amino}-1H-pyrazol-1-yl)-4-(cyanomethyl)piperidine-1-carboxylate;

2,2-difluoroethyl 4-{4-carbamoyl-3-[(6-cyclobutylpyridin-3-yl)amino]-1H-pyrazol-1-yl}-4-(cyanomethyl)piperidine-1-carboxylate;

2,2-difluoroethyl 4-{4-carbamoyl-3-[(2-methoxypyridin-4-yl)amino]-1H-pyrazol-1-yl}-4-(cyanomethyl)piperidine-1-carboxylate;

2,2-difluoroethyl 4-{4-carbamoyl-3-[(6-cyclopropylpyridin-3-yl)amino]-1H-pyrazol-1-yl}-4-(cyanomethyl)piperidine-1-carboxylate;

2,2-difluoroethyl 4-{4-carbamoyl-3-[(2-cyclopropylpyridin-4-yl)amino]-1H-pyrazol-1-yl}-4-(cyanomethyl)piperidine-1-carboxylate;

2,2,2-Trifluoroethyl 4-(4-carbamoyl-3-(6-(2-hydroxypropan-2-yl)pyridin-3-ylamino)-1H-pyrazol-1-yl)-4-(cyanomethyl)piperidine-1-carboxylate;

2,2,2-trifluoroethyl 4-(4-carbamoyl-3-(4-(trifluoromethylsulfonyl)phenylamino)-1H-pyrazol-1-yl)-4-(cyanomethyl)piperidine-1-carboxylate;

2,2,2-trifluoroethyl 4-(4-carbamoyl-3-(6-(2,2,2-trifluoro-1-hydroxyethyl)pyridin-3-ylamino)-1H-pyrazol-1-yl)-4-(cyanomethyl)piperidine-1-carboxylate;

2,2,2-trifluoroethyl 4-(3-(3-(1H-pyrazol-3-yl)phenylamino)-4-carbamoyl-1H-pyrazol-1-yl)-4-(cyanomethyl)piperidine-1-carboxylate;

2,2,2-trifluoroethyl 4-(4-carbamoyl-3-(3-(1-methyl-1H-pyrazol-4-yl)phenylamino)-1H-pyrazol-1-yl)-4-(cyanomethyl)piperidine-1-carboxylate;

2,2,2-trifluoroethyl 4-(4-carbamoyl-3-(5-(1-methyl-1H-pyrazol-4-yl)pyridinl-3-ylamino)-1H-pyrazol-1-yl)-4-(cyanomethyl)piperidine-1-carboxylate;

2,2,2-trifluoroethyl 4-(4-carbamoyl-3-(pyridin-3-ylamino)-1H-pyrazol-1-yl)-4-(cyanomethyl)piperidine-1-carboxylate;

2,2,2-trifluoroethyl 4-(4-carbamoyl-3-(5-fluoropyridin-3-ylamino)-1H-pyrazol-1-yl)-4-(cyanomethyl)piperidine-1-carboxylate;

2,2,2-trifluoroethyl 4-{4-carbamoyl-3-[(5-chloropyridin-3-yl)amino]-1H-pyrazol-1-yl}-4-(cyanomethyl)piperidine-1-carboxylate;

2,2,2-Trifluoroethyl 4-(4-carbamoyl-3-{[6-(1-methyl-1H-pyrazol-4-yl)pyridin-3-yl]amino}-1H-pyrazol-1-yl)-4-(cyanomethyl)piperidine-1-carboxylate;

2,2,2-trifluoroethyl 4-(4-carbamoyl-3-{[6-(1H-pyrazol-4-yl)pyridin-3-yl]amino}-1H-pyrazol-1-yl)-4-(cyanomethyl)piperidine-1-carboxylate;

tert-Butyl 4-{3-[(3-bromophenyl)amino]-4-carbamoyl-1H-pyrazol-1-yl}-4-(cyanomethyl)piperidine-1-carboxylate;

tert-butyl 4-(4-carbamoyl-3-{[4-(2-methoxy-2-oxoethyl)phenyl]amino}-1H-pyrazol-1-yl)-4-(cyanomethyl)piperidine-1-carboxylate;

tert-butyl 4-{4-carbamoyl-3-[(3,5-difluorophenyl)amino]-H-pyrazol-1-yl}-4-(cyanomethyl)piperidine-1-carboxylate;

tert-butyl 4-(4-carbamoyl-3-{[6-(morpholin-4-yl)aphthal-3-yl]amino}-1H-pyrazol-1-yl)-4-(cyanomethyl)piperidine-1-carboxylate tert-butyl 4-{4-carbamoyl-3-[(6-fluoropyridin-3-yl)amino]-1H-pyrazol-1-yl}-4-(cyanomethyl)piperidine-1-carboxylate;
tert-butyl 4-[4-carbamoyl-3-(pyridazin-4-ylamino)-1H-pyrazol-1-yl]-4-(cyanomethyl)piperidine-1-carboxylate;
tert-butyl 4-{4-carbamoyl-3-[(1-oxo-2,3-dihydro-1H-isoindol-5-yl)amino]-1H-pyrazol-1-yl}-4-(cyanomethyl)piperidine-1-carboxylate;
tert-Butyl 4-(4-carbamoyl-3-(pyrimidin-4-ylamino)-1H-pyrazol-1-yl)-4-(cyanomethyl)piperidine-1-carboxylate;
tert-butyl 4-(4-carbamoyl-3-(6-methylpyridin-2-ylamino)-1H-pyrazol-1-yl)-4-(cyanomethyl)piperidine-1-carboxylate;
tert-butyl 4-(4-carbamoyl-3-(pyridin-2-ylamino)-1H-pyrazol-1-yl)-4-(cyanomethyl)piperidine-1-carboxylate;
tert-butyl 4-(4-carbamoyl-3-(5-fluoropyridin-2-ylamino)-1H-pyrazol-1-yl)-4-(cyanomethyl)piperidine-1-carboxylate;
tert-butyl 4-(4-carbamoyl-3-(4-fluoropyridin-2-ylamino)-1H-pyrazol-1-yl)-4-(cyanomethyl)piperidine-1-carboxylate;
tert-butyl 4-(4-carbamoyl-3-(pyridazin-3-ylamino)-1H-pyrazol-1-yl)-4-(cyanomethyl)piperidine-1-carboxylate;
tert-butyl 4-(4-carbamoyl-3-(pyrazine-2-ylamino)-1H-pyrazol-1-yl)-4-(cyanomethyl)piperidine-1-carboxylate;
tert-butyl 4-(4-carbamoyl-3-(6-methylpyrazine-2-ylamino)-1H-pyrazol-1-yl)-4-(cyanomethyl)piperidine-1-carboxylate;
tert-butyl 4-(4-carbamoyl-3-(6-methoxypyridin-2-ylamino)-1H-pyrazol-1-yl)-4-(cyanomethyl)piperidine-1-carboxylate;
tert-butyl 4-(4-carbamoyl-3-(2,6-dimethylpyrimidin-4-ylamino)-1H-pyrazol-1-yl)-4-(cyanomethyl)piperidine-1-carboxylate;
tert-butyl 4-(4-carbamoyl-3-(6-methylpyrimidin-4-ylamino)-1H-pyrazol-1-yl)-4-(cyanomethyl)piperidine-1-carboxylate;
tert-butyl 4-(4-carbamoyl-3-((5-fluoropyridin-3-yl)amino)-1H-pyrazol-1-yl)-4-(cyanomethyl)piperidine-1-carboxylate;
tert-Butyl 4-(4-carbamoyl-3-{[4-(3,5-dimethylisoxazol-4-yl)phenyl]amino}-1H-pyrazol-1-yl)-4-(cyanomethyl)piperidine-1-carboxylate;
tert-Butyl 4-{4-carbamoyl-3-[(4'-chlorobiphenyl-3-yl)amino]-1H-pyrazol-1-yl}-4-(cyanomethyl)piperidine-1-carboxylate;
tert-butyl 4-{4-carbamoyl-3-[(4'-fluorobiphenyl-3-yl)amino]-1H-pyrazol-1-yl}-4-(cyanomethyl)piperidine-1-carboxylate;
tert-butyl 4-[3-(biphenyl-3-ylamino)-4-carbamoyl-1H-pyrazol-1-yl]-4-(cyanomethyl)piperidine-1-carboxylate;
tert-butyl 4-{4-carbamoyl-3-[(4'-methoxybiphenyl-3-yl)amino]-1H-pyrazol-1-yl}-4-(cyanomethyl)piperidine-1-carboxylate;
tert-butyl 4-{4-carbamoyl-3-[(4'-hydroxybiphenyl-3-yl)amino]-1H-pyrazol-1-yl}-4-(cyanomethyl)piperidine-1-carboxylate;
tert-butyl 4-{4-carbamoyl-3-[(4'-methylbiphenyl-3-yl)amino]-1H-pyrazol-1-yl}-4-(cyanomethyl)piperidine-1-carboxylate;
tert-butyl 4-{4-carbamoyl-3-[(2'-methylbiphenyl-3-yl)amino]-1H-pyrazol-1-yl}-4-(cyanomethyl)piperidine-1-carboxylate;
tert-butyl 4-{4-carbamoyl-3-[(3'-chlorobiphenyl-3-yl)amino]-1H-pyrazol-1-yl}-4-(cyanomethyl)piperidine-1-carboxylate;
tert-butyl 4-{4-carbamoyl-3-[(3-naphthalen-2-ylphenyl)amino]-1H-pyrazol-1-yl}-4-(cyanomethyl)piperidine-1-carboxylate;
tert-butyl 4-{4-carbamoyl-3-[(2'-fluorobiphenyl-3-yl)amino]-1H-pyrazol-1-yl}-4-(cyanomethyl)piperidine-1-carboxylate;
tert-butyl 4-{4-carbamoyl-3-[(2'-hydroxybiphenyl-3-yl)amino]-1H-pyrazol-1-yl}-4-(cyanomethyl)piperidine-1-carboxylate;
[4-({1-[1-(tert-Butoxycarbonyl)-4-(cyanomethyl)piperidin-4-yl]-4-carbamoyl-1H-pyrazol-3-yl}amino)phenyl]acetic acid;
1-[3-(Cyanomethyl)-1-(2,2,2-trifluoroethyl)azetidin-3-yl]-3-(phenylamino)-1H-pyrazole-4-carboxamide;
1-[3-(Cyanomethyl)-1-methylazetidin-3-yl]-3-(phenylamino)-1H-pyrazole-4-carboxamide;
1-[1-(Biphenyl-4-ylmethyl)-4-(cyanomethyl)piperidin-4-yl]-3-(phenylamino)-1H-pyrazole-4-carboxamide;
1-[4-(cyanomethyl)-1-(pyridin-3-ylmethyl)piperidin-4-yl]-3-(phenylamino)-1H-pyrazole-4-carboxamide;
1-[1-(3-cyanobenzyl)-4-(cyanomethyl)piperidin-4-yl]-3-(phenylamino)-1H-pyrazole-4-carboxamide;
1-[1-(4-cyanobenzyl)-4-(cyanomethyl)piperidin-4-yl]-3-(phenylamino)-1H-pyrazole-4-carboxamide;
1-[4-(cyanomethyl)-1-(3-cyanopropyl)piperidin-4-yl]-3-(phenylamino)-1H-pyrazole-4-carboxamide;
1-[1-(2-chlorobenzyl)-4-(cyanomethyl)piperidin-4-yl]-3-(phenylamino)-1H-pyrazole-4-carboxamide;
1-[4-(cyanomethyl)-1-(4-methylbenzyl)piperidin-4-yl]-3-(phenylamino)-1H-pyrazole-4-carboxamide;
1-[4-(cyanomethyl)-1-(naphthalene-1-ylmethyl)piperidin-4-yl]-3-(phenylamino)-1H-pyrazole-4-carboxamide;
1-[4-(cyanomethyl)-1-(cyclohexylmethyl)piperidin-4-yl]-3-(phenylamino)-1H-pyrazole-4-carboxamide;
1-[1-(1,3-benzodioxol-5-ylmethyl)-4-(cyanomethyl)piperidin-4-yl]-3-(phenylamino)-1H-pyrazole-4-carboxamide;
1-[4-(cyanomethyl)-1-(3-hydroxybenzyl)piperidin-4-yl]-3-(phenylamino)-1H-pyrazole-4-carboxamide;
1-{1-[4-(acetylamino)benzyl]-4-(cyanomethyl)piperidin-4-yl}-3-(phenylamino)-1H-pyrazole-4-carboxamide;
1-{4-(cyanomethyl)-1-[(6-methoxynaphthalen-2-yl)methyl]piperidin-4-yl}-3-(phenylamino)-1H-pyrazole-4-carboxamide;
1-[4-(cyanomethyl)-1-(2,6-dichlorobenzyl)piperidin-4-yl]-3-(phenylamino)-1H-pyrazole-4-carboxamide;
1-{4-(cyanomethyl)-1-[3-(methylsulfanyl)propyl]piperidin-4-yl}-3-(phenylamino)-1H-pyrazole-4-carboxamide;
1-[4-(cyanomethyl)-1-(2-ethoxybenzyl)piperidin-4-yl]-3-(phenylamino)-1H-pyrazole-4-carboxamide;
1-{4-(cyanomethyl)-1-[(2E)-3-phenylprop-2-en-1-yl]piperidin-4-yl}-3-(phenylamino)-1H-pyrazole-4-carboxamide;
1-[4-(cyanomethyl)-1-(3-fluorobenzyl)piperidin-4-yl]-3-(phenylamino)-1H-pyrazole-4-carboxamide;
1-{4-(cyanomethyl)-1-[4-(trifluoromethyl)benzyl]piperidin-4-yl}-3-(phenylamino)-1H-pyrazole-4-carboxamide;

1-[1-(1-benzofuran-2-ylmethyl)-4-(cyanomethyl)piperidin-4-yl]-3-(phenylamino)-1H-pyrazole-4-carboxamide;

1-[1-(4-chloro-2-fluorobenzyl)-4-(cyanomethyl)piperidin-4-yl]-3-(phenylamino)-1H-pyrazole-4-carboxamide;

1-[4-(cyanomethyl)-1-(4-propylbenzyl)piperidin-4-yl]-3-(phenylamino)-1H-pyrazole-4-carboxamide;

1-[4-(cyanomethyl)-1-(2,6-difluorobenzyl)piperidin-4-yl]-3-(phenylamino)-1H-pyrazole-4-carboxamide;

1-{4-(cyanomethyl)-1-[4-(1-methylethyl)benzyl]piperidin-4-yl}-3-(phenylamino)-1H-pyrazole-4-carboxamide;

1-[4-(cyanomethyl)-1-(3-phenylprop-2-yn-1-yl)piperidin-4-yl]-3-(phenylamino)-1H-pyrazole-4-carboxamide;

1-[4-(cyanomethyl)-1-(2,3,6-trifluorobenzyl)piperidin-4-yl]-3-(phenylamino)-1H-pyrazole-4-carboxamide;

1-{4-(cyanomethyl)-1-[4-(1-methylethoxy)benzyl]piperidin-4-yl}-3-(phenylamino)-1H-pyrazole-4-carboxamide;

1-[4-(cyanomethyl)-1-(3,4-dimethylbenzyl)piperidin-4-yl]-3-(phenylamino)-1H-pyrazole-4-carboxamide;

methyl 2-({4-[4-carbamoyl-3-(phenylamino)-1H-pyrazol-1-yl]-4-(cyanomethyl)piperidin-1-yl}methyl)benzoate;

1-(4-(Cyanomethyl)-1-((1-ethyl-1H-imidazol-2-yl)methyl)piperidin-4-yl)-3-((2-fluoropyridin-4-yl)amino)-1H-pyrazole-4-carboxamide;

1-[4-(cyanomethyl)-1-(pyridin-3-ylmethyl)piperidin-4-yl]-3-[(2-fluoropyridin-4-yl)amino]-1H-pyrazole-4-carboxamide;

1-[4-(cyanomethyl)-1-(cyclohexylmethyl)piperidin-4-yl]-3-[(2-fluoropyridin-4-yl)amino]-1H-pyrazole-4-carboxamide;

1-{4-(cyanomethyl)-1-[(4-methyl-1H-imidazol-2-yl)methyl]piperidin-4-yl}-3-[(2-fluoropyridin-4-yl)amino]-1H-pyrazole-4-carboxamide;

1-[4-(cyanomethyl)-1-(1H-pyrazol-4-ylmethyl)piperidin-4-yl]-3-[(2-fluoropyridin-4-yl)amino]-1H-pyrazole-4-carboxamide;

1-[4-(cyanomethyl)-1-(cyclohexylmethyl)piperidin-4-yl]-3-[(4-fluorophenyl)amino]-1H-pyrazole-4-carboxamide;

1-[1-benzyl-4-(cyanomethyl)piperidin-4-yl]-3-[(4-fluorophenyl)amino]-1H-pyrazole-4-carboxamide;

1-[1-benzyl-4-(cyanomethyl)piperidin-4-yl]-3-[(2-fluoropyridin-4-yl)amino]-1H-pyrazole-4-carboxamide;

1-[4-(cyanomethyl)-1-(2-fluorobenzyl)piperidin-4-yl]-3-[(2-fluoropyridin-4-yl)amino]-1H-pyrazole-4-carboxamide;

1-[4-(cyanomethyl)-1-(3-fluorobenzyl)piperidin-4-yl]-3-[(2-fluoropyridin-4-yl)amino]-1H-pyrazole-4-carboxamide;

1-[4-(cyanomethyl)-1-(4-fluorobenzyl)piperidin-4-yl]-3-[(2-fluoropyridin-4-yl)amino]-1H-pyrazole-4-carboxamide;

1-[4-(cyanomethyl)-1-(imidazo[1,2-a]pyridin-2-ylmethyl)piperidin-4-yl]-3-[(2-fluoropyridin-4-yl)amino]-1H-pyrazole-4-carboxamide;

1-[4-(cyanomethyl)-1-(1H-pyrazol-5-ylmethyl)piperidin-4-yl]-3-[(2-fluoropyridin-4-yl)amino]-1H-pyrazole-4-carboxamide;

1-[4-(cyanomethyl)-1-(pyrazin-2-ylmethyl)piperidin-4-yl]-3-[(2-fluoropyridin-4-yl)amino]-1H-pyrazole-4-carboxamide;

1-{4-(cyanomethyl)-1-[(2-methyl-1,3-thiazol-5-yl)methyl]piperidin-4-yl}-3-[(2-fluoropyridin-4-yl)amino]-1H-pyrazole-4-carboxamide;

1-{4-(cyanomethyl)-1-[(2,2-dimethyltetrahydro-2H-pyran-4-yl)methyl]piperidin-4-yl}-3-[(2-fluoropyridin-4-yl)amino]-1H-pyrazole-4-carboxamide;

1-[4-(cyanomethyl)-1-(pyrazolo[1,5-a]pyridin-3-ylmethyl)piperidin-4-yl]-3-[(2-fluoropyridin-4-yl)amino]-1H-pyrazole-4-carboxamide;

1-[4-(cyanomethyl)-1-(1H-pyrrolo[2,3-b]pyridin-4-ylmethyl)piperidin-4-yl]-3-[(2-fluoropyridin-4-yl)amino]-1H-pyrazole-4-carboxamide;

1-[4-(cyanomethyl)-1-(furan-2-ylmethyl)piperidin-4-yl]-3-[(2-fluoropyridin-4-yl)amino]-1H-pyrazole-4-carboxamide;

1-[4-(cyanomethyl)-1-(1H-indol-5-ylmethyl)piperidin-4-yl]-3-[(2-fluoropyridin-4-yl)amino]-1H-pyrazole-4-carboxamide;

1-[4-(cyanomethyl)-1-(1H-indol-7-ylmethyl)piperidin-4-yl]-3-[(2-fluoropyridin-4-yl)amino]-1H-pyrazole-4-carboxamide;

1-{4-(cyanomethyl)-1-[(2-fluoro-5-methylpyridin-3-yl)methyl]piperidin-4-yl}-3-[(2-fluoropyridin-4-yl)amino]-1H-pyrazole-4-carboxamide;

1-{4-(cyanomethyl)-1-[(2-fluoropyridin-3-yl)methyl]piperidin-4-yl}-3-[(2-fluoropyridin-4-yl)amino]-1H-pyrazole-4-carboxamide;

1-[4-(cyanomethyl)-1-{[3-(1-hydroxy-1-methylethyl)cyclobutyl]methyl}piperidin-4-yl]-3-[(2-fluoropyridin-4-yl)amino]-1H-pyrazole-4-carboxamide;

1-[4-(cyanomethyl)-1-(1,3-thiazol-4-ylmethyl)piperidin-4-yl]-3-[(2-fluoropyridin-4-yl)amino]-1H-pyrazole-4-carboxamide;

1-[4-(cyanomethyl)-1-(1,3-oxazol-4-ylmethyl)piperidin-4-yl]-3-[(2-fluoropyridin-4-yl)amino]-1H-pyrazole-4-carboxamide;

1-{4-(cyanomethyl)-1-[(5-methylisoxazol-3-yl)methyl]piperidin-4-yl}-3-[(2-fluoropyridin-4-yl)amino]-1H-pyrazole-4-carboxamide;

1-[4-(cyanomethyl)-1-(1,3-oxazol-2-ylmethyl)piperidin-4-yl]-3-[(2-fluoropyridin-4-yl)amino]-1H-pyrazole-4-carboxamide;

1-{4-(cyanomethyl)-1-[(1-methyl-1H-pyrazol-5-yl)methyl]piperidin-4-yl}-3-[(2-fluoropyridin-4-yl)amino]-1H-pyrazole-4-carboxamide;

1-{4-(cyanomethyl)-1-[(1-methyl-1H-pyrazol-3-yl)methyl]piperidin-4-yl}-3-[(2-fluoropyridin-4-yl)amino]-1H-pyrazole-4-carboxamide;

1-[4-(cyanomethyl)-1-(isoxazol-3-ylmethyl)piperidin-4-yl]-3-[(2-fluoropyridin-4-yl)amino]-1H-pyrazole-4-carboxamide;

1-{4-(cyanomethyl)-1-[(6-fluoropyridin-2-yl)methyl]piperidin-4-yl}-3-[(2-fluoropyridin-4-yl)amino]-1H-pyrazole-4-carboxamide;

1-[4-(cyanomethyl)-1-(pyrazolo[1,5-a]pyridin-7-ylmethyl)piperidin-4-yl]-3-[(2-fluoropyridin-4-yl)amino]-1H-pyrazole-4-carboxamide;

1-[4-(cyanomethyl)-1-(pyrazolo[1,5-a]pyridin-2-ylmethyl)piperidin-4-yl]-3-[(2-fluoropyridin-4-yl)amino]-1H-pyrazole-4-carboxamide;

1-[4-(cyanomethyl)-1-(pyridazin-3-ylmethyl)piperidin-4-yl]-3-[(2-fluoropyridin-4-yl)amino]-1H-pyrazole-4-carboxamide;

1-{4-(cyanomethyl)-1-[(5-fluoropyridin-2-yl)methyl]piperidin-4-yl}-3-[(2-fluoropyridin-4-yl)amino]-1H-pyrazole-4-carboxamide;

1-{4-(cyanomethyl)-1-[(3-methoxycyclobutyl)methyl]piperidin-4-yl}-3-[(2-fluoropyridin-4-yl)amino]-1H-pyrazole-4-carboxamide;

1-{4-(cyanomethyl)-1-[(5-fluoropyridin-3-yl)methyl]piperidin-4-yl}-3-[(2-fluoropyridin-4-yl)amino]-1H-pyrazole-4-carboxamide;

1-[4-(cyanomethyl)-1-(1H-indol-2-ylmethyl)piperidin-4-yl]-3-[(2-fluoropyridin-4-yl)amino]-1H-pyrazole-4-carboxamide;

1-{4-(cyanomethyl)-1-[(1,5-dimethyl-1H-pyrazol-4-yl)methyl]piperidin-4-yl}-3-[(2-fluoropyridin-4-yl)amino]-1H-pyrazole-4-carboxamide;

1-[1-(1H-benzimidazol-2-ylmethyl)-4-(cyanomethyl)piperidin-4-yl]-3-[(2-fluoropyridin-4-yl)amino]-1H-pyrazole-4-carboxamide;

1-{4-(cyanomethyl)-1-[(3-methyl-4,5-dihydroisoxazol-5-yl)methyl]piperidin-4-yl}-3-[(2-fluoropyridin-4-yl)amino]-1H-pyrazole-4-carboxamide;

1-[4-(cyanomethyl)-1-(1H-indol-2-ylmethyl)piperidin-4-yl]-3-[(4-fluorophenyl)amino]-1H-pyrazole-4-carboxamide;

1-{4-(cyanomethyl)-1-[(2-fluoro-5-methylpyridin-3-yl)methyl]piperidin-4-yl}-3-[(4-fluorophenyl)amino]-1H-pyrazole-4-carboxamide;

1-[4-(cyanomethyl)-1-(isoxazol-3-ylmethyl)piperidin-4-yl]-3-[(4-fluorophenyl)amino]-1H-pyrazole-4-carboxamide;

1-{4-(cyanomethyl)-1-[(6-fluoropyridin-2-yl)methyl]piperidin-4-yl}-3-[(4-fluorophenyl)amino]-1H-pyrazole-4-carboxamide;

1-[4-(cyanomethyl)-1-(pyridazin-3-ylmethyl)piperidin-4-yl]-3-[(4-fluorophenyl)amino]-1H-pyrazole-4-carboxamide;

1-{4-(cyanomethyl)-1-[(5-fluoropyridin-2-yl)methyl]piperidin-4-yl}-3-[(4-fluorophenyl)amino]-1H-pyrazole-4-carboxamide;

1-{4-(cyanomethyl)-1-[(5-fluoropyridin-3-yl)methyl]piperidin-4-yl}-3-[(4-fluorophenyl)amino]-1H-pyrazole-4-carboxamide;

1-{4-(cyanomethyl)-1-[(4-fluoropyridin-2-yl)methyl]piperidin-4-yl}-3-[(4-fluorophenyl)amino]-1H-pyrazole-4-carboxamide;

1-[4-(cyanomethyl)-1-(pyridin-3-ylmethyl)piperidin-4-yl]-3-[(4-fluorophenyl)amino]-1H-pyrazole-4-carboxamide;

1-[4-(cyanomethyl)-1-(pyrazin-2-ylmethyl)piperidin-4-yl]-3-[(4-fluorophenyl)amino]-1H-pyrazole-4-carboxamide;

1-[4-(cyanomethyl)-1-(1H-pyrrolo[2,3-b]pyridin-4-ylmethyl)piperidin-4-yl]-3-[(4-fluorophenyl)amino]-1H-pyrazole-4-carboxamide;

1-[4-(cyanomethyl)-1-(furan-2-ylmethyl)piperidin-4-yl]-3-[(4-fluorophenyl)amino]-1H-pyrazole-4-carboxamide;

1-[4-(cyanomethyl)-1-(1H-indol-5-ylmethyl)piperidin-4-yl]-3-[(4-fluorophenyl)amino]-1H-pyrazole-4-carboxamide;

1-[4-(cyanomethyl)-1-(1H-indol-6-ylmethyl)piperidin-4-yl]-3-[(4-fluorophenyl)amino]-1H-pyrazole-4-carboxamide;

1-[4-(cyanomethyl)-1-(1H-indol-4-ylmethyl)piperidin-4-yl]-3-[(4-fluorophenyl)amino]-1H-pyrazole-4-carboxamide;

1-[4-(cyanomethyl)-1-(1H-indol-7-ylmethyl)piperidin-4-yl]-3-[(4-fluorophenyl)amino]-1H-pyrazole-4-carboxamide;

1-[1-(2-chlorobenzyl)-4-(cyanomethyl)piperidin-4-yl]-3-[(2-fluoropyridin-4-yl)amino]-1H-pyrazole-4-carboxamide;

1-[4-(cyanomethyl)-1-(4-hydroxybenzyl)piperidin-4-yl]-3-[(2-fluoropyridin-4-yl)amino]-1H-pyrazole-4-carboxamide;

1-[1-(3-chlorobenzyl)-4-(cyanomethyl)piperidin-4-yl]-3-[(2-fluoropyridin-4-yl)amino]-1H-pyrazole-4-carboxamide;

1-[1-(3-cyanobenzyl)-4-(cyanomethyl)piperidin-4-yl]-3-[(2-fluoropyridin-4-yl)amino]-1H-pyrazole-4-carboxamide;

1-[4-(cyanomethyl)-1-(3-methoxybenzyl)piperidin-4-yl]-3-[(2-fluoropyridin-4-yl)amino]-1H-pyrazole-4-carboxamide;

1-[4-(cyanomethyl)-1-(2-phenylethyl)piperidin-4-yl]-3-[(2-fluoropyridin-4-yl)amino]-1H-pyrazole-4-carboxamide;

1-[4-(cyanomethyl)-1-(4-methoxybenzyl)piperidin-4-yl]-3-[(2-fluoropyridin-4-yl)amino]-1H-pyrazole-4-carboxamide;

1-[4-(cyanomethyl)-1-(2-methoxybenzyl)piperidin-4-yl]-3-[(2-fluoropyridin-4-yl)amino]-1H-pyrazole-4-carboxamide;

1-{4-(cyanomethyl)-1-[(6-oxo-1,6-dihydropyridin-2-yl)methyl]piperidin-4-yl}-3-[(2-fluoropyridin-4-yl)amino]-1H-pyrazole-4-carboxamide;

1-{4-(cyanomethyl)-1-[(6-hydroxypyridin-3-yl)methyl]piperidin-4-yl}-3-[(2-fluoropyridin-4-yl)amino]-1H-pyrazole-4-carboxamide;

1-[1-(4-cyanobenzyl)-4-(cyanomethyl)piperidin-4-yl]-3-[(2-fluoropyridin-4-yl)amino]-1H-pyrazole-4-carboxamide;

1-[4-(cyanomethyl)-1-(3-hydroxybenzyl)piperidin-4-yl]-3-[(2-fluoropyridin-4-yl)amino]-1H-pyrazole-4-carboxamide;

1-[1-(4-chlorobenzyl)-4-(cyanomethyl)piperidin-4-yl]-3-[(2-fluoropyridin-4-yl)amino]-1H-pyrazole-4-carboxamide;

1-[1-(2-cyanobenzyl)-4-(cyanomethyl)piperidin-4-yl]-3-[(2-fluoropyridin-4-yl)amino]-1H-pyrazole-4-carboxamide;

1-(4-(Cyanomethyl)-1-(1-phenylethyl)piperidin-4-yl)-3-((4-fluorophenyl)amino)-1H-pyrazole-4-carboxamide;

1-(4-(Cyanomethyl)-1-(2-fluoroethyl)piperidin-4-yl)-3-((4-fluorophenyl)amino)-1H-pyrazole-4-carboxamide;

1-[4-(cyanomethyl)-1-(cyclopropylmethyl)piperidin-4-yl]-3-[(4-fluorophenyl)amino]-1H-pyrazole-4-carboxamide;

1-(4-(Cyanomethyl)-1-(pyridin-2-yl)piperidin-4-yl)-3-(4-fluorophenylamino)-1H-pyrazole-4-carboxamide;

1-[4-(Cyanomethyl)-1-pyrimidin-4-ylpiperidin-4-yl]-3-[(4-fluorophenyl)amino]-1H-pyrazole-4-carboxamide;

Methyl 4-(4-carbamoyl-3-(4-(trifluoromethylsulfonyl)phenylamino)-1H-pyrazol-1-yl)-4-(cyanomethyl)piperidine-1-carboxylate;

2-methoxyethyl 4-(4-carbamoyl-3-(4-(trifluoromethylsulfonyl)phenylamino)-1H-pyrazol-1-yl)-4-(cyanomethyl)piperidine-1-carboxylate;

methyl 4-(4-carbamoyl-3-{[4-(methylsulfonyl)phenyl]amino}-1H-pyrazol-1-yl)-4-(cyanomethyl)piperidine-1-carboxylate;

benzyl 4-[4-carbamoyl-3-(phenylamino)-1H-pyrazol-1-yl]-4-(cyanomethyl)piperidine-1-carboxylate;

methyl 4-[4-carbamoyl-3-(phenylamino)-1H-pyrazol-1-yl]-4-(cyanomethyl)piperidine-1-carboxylate;

2-Methoxy-1,1-dimethylethyl 4-{4-carbamoyl-3-[(4-fluorophenyl)amino]-1H-pyrazol-1-yl}-4-(cyanomethyl)piperidine-1-carboxylate;
1-Hydroxy-2-methylpropan-2-yl 4-{4-carbamoyl-3-[(4-fluorophenyl)amino]-1H-pyrazol-1-yl}-4-(cyanomethyl)piperidine-1-carboxylate;
2,2,2-Trifluoroethyl 4-{4-carbamoyl-3-[(2-fluoropyridin-4-yl)amino]-1H-pyrazol-1-yl}-4-(cyanomethyl)piperidine-1-carboxylate;
2,2,2-trifluoroethyl 4-(4-carbamoyl-3-(4-fluorophenylamino)-1H-pyrazol-1-yl)-4-(cyanomethyl)piperidine-1-carboxylate;
1,1,1-trifluoropropan-2-yl 4-(4-carbamoyl-3-(4-fluorophenylamino)-1H-pyrazol-1-yl)-4-(cyanomethyl)piperidine-1-carboxylate;
cyclobutyl 4-(4-carbamoyl-3-(4-fluorophenylamino)-1H-pyrazol-1-yl)-4-(cyanomethyl)piperidine-1-carboxylate;
cyclobutylmethyl 4-(4-carbamoyl-3-(4-fluorophenylamino)-1H-pyrazol-1-yl)-4-(cyanomethyl)piperidine-1-carboxylate;
(2,2-difluorocyclopropyl)methyl 4-(4-carbamoyl-3-(4-fluorophenylamino)-1H-pyrazol-1-yl)-4-(cyanomethyl)piperidine-1-carboxylate;
2,2-difluoroethyl 4-(4-carbamoyl-3-(4-fluorophenylamino)-1H-pyrazol-1-yl)-4-(cyanomethyl)piperidine-1-carboxylate;
(1-methylcyclopropyl)methyl 4-(4-carbamoyl-3-(4-fluorophenylamino)-1H-pyrazol-1-yl)-4-(cyanomethyl)piperidine-1-carboxylate;
1,3-difluoropropan-2-yl 4-(4-carbamoyl-3-(4-fluorophenylamino)-1H-pyrazol-1-yl)-4-(cyanomethyl)piperidine-1-carboxylate;
(trimethylsilyl)methyl 4-(4-carbamoyl-3-(4-fluorophenylamino)-1H-pyrazol-1-yl)-4-(cyanomethyl)piperidine-1-carboxylate;
2,2-difluoro-3-hydroxypropyl 4-(4-carbamoyl-3-(4-fluorophenylamino)-1H-pyrazol-1-yl)-4-(cyanomethyl)piperidine-1-carboxylate;
1-cyclopropylethyl 4-(4-carbamoyl-3-(4-fluorophenylamino)-1H-pyrazol-1-yl)-4-(cyanomethyl)piperidine-1-carboxylate;
(1-hydroxycyclopropyl)methyl 4-(4-carbamoyl-3-(4-fluorophenylamino)-1H-pyrazol-1-yl)-4-(cyanomethyl)piperidine-1-carboxylate;
1,1,1-trifluoropropan-2-yl 4-(4-carbamoyl-3-(4-fluorophenylamino)-1H-pyrazol-1-yl)-4-(cyanomethyl)piperidine-1-carboxylate;
2,2-difluoroethyl 4-(4-carbamoyl-3-(5-fluoropyridin-3-ylamino)-1H-pyrazol-1-yl)-4-(cyanomethyl)piperidine-1-carboxylate;
tetrahydrofuran-3-yl 4-{4-carbamoyl-3-[(2-fluoropyridin-4-yl)amino]-1H-pyrazol-1-yl}-4-(cyanomethyl)piperidine-1-carboxylate;
tetrahydro-2H-pyran-4-yl 4-{4-carbamoyl-3-[(2-fluoropyridin-4-yl)amino]-1H-pyrazol-1-yl}-4-(cyanomethyl)piperidine-1-carboxylate;
oxetan-3-yl 4-{4-carbamoyl-3-[(4-fluorophenyl)amino]-1H-pyrazol-1-yl}-4-(cyanomethyl)piperidine-1-carboxylate;
cyclopropylmethyl 4-{4-carbamoyl-3-[(4-fluorophenyl)amino]-1H-pyrazol-1-yl}-4-(cyanomethyl)piperidine-1-carboxylate;
(3-methyloxetan-3-yl)methyl 4-{4-carbamoyl-3-[(4-fluorophenyl)amino]-1H-pyrazol-1-yl}-4-(cyanomethyl)piperidine-1-carboxylate;
tetrahydro-2H-pyran-4-ylmethyl 4-{4-carbamoyl-3-[(4-fluorophenyl)amino]-1H-pyrazol-1-yl}-4-(cyanomethyl)piperidine-1-carboxylate;
tetrahydrofuran-3-ylmethyl 4-{4-carbamoyl-3-[(4-fluorophenyl)amino]-1H-pyrazol-1-yl}-4-(cyanomethyl)piperidine-1-carboxylate;
1-methoxypropan-2-yl 4-{4-carbamoyl-3-[(4-fluorophenyl)amino]-1H-pyrazol-1-yl}-4-(cyanomethyl)piperidine-1-carboxylate;
2-methoxypropyl 4-{4-carbamoyl-3-[(4-fluorophenyl)amino]-1H-pyrazol-1-yl}-4-(cyanomethyl)piperidine-1-carboxylate;
tetrahydro-2H-pyran-3-yl 4-{4-carbamoyl-3-[(4-fluorophenyl)amino]-1H-pyrazol-1-yl}-4-(cyanomethyl)piperidine-1-carboxylate;
oxetan-3-yl 4-(4-carbamoyl-3-(4-(trifluoromethylsulfonyl)phenylamino)-1H-pyrazol-1-yl)-4-(cyanomethyl)piperidine-1-carboxylate;
2,2-difluoroethyl 4-(4-carbamoyl-3-(2-fluoropyridin-4-ylamino)-1H-pyrazol-1-yl)-4-(cyanomethyl)piperidine-1-carboxylate;
2-methylpropyl 4-[4-carbamoyl-3-(phenylamino)-1H-pyrazol-1-yl]-4-(cyanomethyl)piperidine-1-carboxylate;
2,2-dimethylpropyl 4-[4-carbamoyl-3-(phenylamino)-1H-pyrazol-1-yl]-4-(cyanomethyl)piperidine-1-carboxylate;
cyclopentyl 4-[4-carbamoyl-3-(phenylamino)-1H-pyrazol-1-yl]-4-(cyanomethyl)piperidine-1-carboxylate;
cyclohexyl 4-[4-carbamoyl-3-(phenylamino)-1H-pyrazol-1-yl]-4-(cyanomethyl)piperidine-1-carboxylate;
3-fluorobenzyl 4-[4-carbamoyl-3-(phenylamino)-1H-pyrazol-1-yl]-4-(cyanomethyl)piperidine-1-carboxylate;
2-fluorobenzyl 4-[4-carbamoyl-3-(phenylamino)-1H-pyrazol-1-yl]-4-(cyanomethyl)piperidine-1-carboxylate;
2,3-dihydro-1H-inden-2-yl 4-[4-carbamoyl-3-(phenylamino)-1H-pyrazol-1-yl]-4-(cyanomethyl)piperidine-1-carboxylate;
2-methoxyethyl 4-[4-carbamoyl-3-(phenylamino)-1H-pyrazol-1-yl]-4-(cyanomethyl)piperidine-1-carboxylate;
4-carbamoyl-1-[4-(cyanomethyl)-1-{[tetrahydrofuran-3-yloxy]carbonyl}piperidin-4-yl]-3-(phenylamino)-1H-pyrazol-2-ium;
tetrahydro-2H-pyran-4-yl 4-[4-carbamoyl-3-(phenylamino)-1H-pyrazol-1-yl]-4-(cyanomethyl)piperidine-1-carboxylate;
pyridin-3-ylmethyl 4-[4-carbamoyl-3-(phenylamino)-1H-pyrazol-1-yl]-4-(cyanomethyl)piperidine-1-carboxylate;
pyridin-3-ylmethyl 4-[4-carbamoyl-3-(phenylamino)-1H-pyrazol-1-yl]-4-(cyanomethyl)piperidine-1-carboxylate;
pyridin-4-ylmethyl 4-[4-carbamoyl-3-(phenylamino)-1H-pyrazol-1-yl]-4-(cyanomethyl)piperidine-1-carboxylate;
2-morpholin-4-ylethyl 4-[4-carbamoyl-3-(phenylamino)-1H-pyrazol-1-yl]-4-(cyanomethyl)piperidine-1-carboxylate;
1-methylpiperidin-4-yl 4-[4-carbamoyl-3-(phenylamino)-1H-pyrazol-1-yl]-4-(cyanomethyl)piperidine-1-carboxylate;
2-(4-methylpiperazin-1-yl)ethyl 4-[4-carbamoyl-3-(phenylamino)-1H-pyrazol-1-yl]-4-(cyanomethyl)piperidine-1-carboxylate;

(1-methylpiperidin-4-yl)methyl 4-[4-carbamoyl-3-(phenylamino)-1H-pyrazol-1-yl]-4-(cyanomethyl)piperidine-1-carboxylate;

3,3,3-Trifluoropropyl 4-{4-carbamoyl-3-[(4-fluorophenyl)amino]-H-pyrazol-1-yl}-4-(cyanomethyl)piperidine-1-carboxylate;

tetrahydrofuran-3-yl 4-{4-carbamoyl-3-[(4-fluorophenyl)amino]-1H-pyrazol-1-yl}-4-(cyanomethyl)piperidine-1-carboxylate;

tetrahydro-2H-pyran-4-yl 4-{4-carbamoyl-3-[(4-fluorophenyl)amino]-1H-pyrazol-1-yl}-4-(cyanomethyl)piperidine-1-carboxylate;

2-methoxyethyl 4-{4-carbamoyl-3-[(4-fluorophenyl)amino]-1H-pyrazol-1-yl}-4-(cyanomethyl)piperidine-1-carboxylate;

Cyclopropylmethyl 4-{4-carbamoyl-3-[(2-fluoropyridin-4-yl)amino]-1H-pyrazol-1-yl}-4-(cyanomethyl)piperidine-1-carboxylate;

2-fluoroethyl 3-[4-carbamoyl-3-(phenylamino)-1H-pyrazol-1-yl]-3-(cyanomethyl)azetidine-1-carboxylate;

2-methylpropyl 3-[4-carbamoyl-3-(phenylamino)-1H-pyrazol-1-yl]-3-(cyanomethyl)azetidine-1-carboxylate;

cyclopentyl 3-[4-carbamoyl-3-(phenylamino)-1H-pyrazol-1-yl]-3-(cyanomethyl)azetidine-1-carboxylate;

benzyl 3-[4-carbamoyl-3-(phenylamino)-1H-pyrazol-1-yl]-3-(cyanomethyl)azetidine-1-carboxylate;

2-naphthalen-1-ylethyl 3-[4-carbamoyl-3-(phenylamino)-1H-pyrazol-1-yl]-3-(cyanomethyl)azetidine-1-carboxylate;

2-morpholin-4-ylethyl 3-[4-carbamoyl-3-(phenylamino)-1H-pyrazol-1-yl]-3-(cyanomethyl)azetidine-1-carboxylate;

2,2-dimethylpropyl 3-[4-carbamoyl-3-(phenylamino)-1H-pyrazol-1-yl]-3-(cyanomethyl)azetidine-1-carboxylate;

cyclohexyl 3-[4-carbamoyl-3-(phenylamino)-1H-pyrazol-1-yl]-3-(cyanomethyl)azetidine-1-carboxylate;

2-phenylethyl 3-[4-carbamoyl-3-(phenylamino)-1H-pyrazol-1-yl]-3-(cyanomethyl)azetidine-1-carboxylate;

2-methoxyethyl 3-[4-carbamoyl-3-(phenylamino)-1H-pyrazol-1-yl]-3-(cyanomethyl)azetidine-1-carboxylate;

2-ethoxy-2-oxoethyl 3-[4-carbamoyl-3-(phenylamino)-1H-pyrazol-1-yl]-3-(cyanomethyl)azetidine-1-carboxylate;

3-methoxypropyl 3-[4-carbamoyl-3-(phenylamino)-1H-pyrazol-1-yl]-3-(cyanomethyl)azetidine-1-carboxylate;

tetrahydrofuran-3-yl 3-[4-carbamoyl-3-(phenylamino)-1H-pyrazol-1-yl]-3-(cyanomethyl)azetidine-1-carboxylate;

tetrahydro-2H-pyran-4-yl 3-[4-carbamoyl-3-(phenylamino)-1H-pyrazol-1-yl]-3-(cyanomethyl)azetidine-1-carboxylate;

2-(2-oxopyrrolidin-1-yl)ethyl 3-[4-carbamoyl-3-(phenylamino)-1H-pyrazol-1-yl]-3-(cyanomethyl)azetidine-1-carboxylate;

pyridin-3-ylmethyl 3-[4-carbamoyl-3-(phenylamino)-1H-pyrazol-1-yl]-3-(cyanomethyl)azetidine-1-carboxylate;

pyridin-4-ylmethyl 3-[4-carbamoyl-3-(phenylamino)-1H-pyrazol-1-yl]-3-(cyanomethyl)azetidine-1-carboxylate;

2-pyridin-2-ylethyl 3-[4-carbamoyl-3-(phenylamino)-1H-pyrazol-1-yl]-3-(cyanomethyl)azetidine-1-carboxylate;

3-pyridin-3-ylpropyl 3-[4-carbamoyl-3-(phenylamino)-1H-pyrazol-1-yl]-3-(cyanomethyl)azetidine-1-carboxylate;

2-methoxybenzyl 3-[4-carbamoyl-3-(phenylamino)-1H-pyrazol-1-yl]-3-(cyanomethyl)azetidine-1-carboxylate;

3-methoxybenzyl 3-[4-carbamoyl-3-(phenylamino)-1H-pyrazol-1-yl]-3-(cyanomethyl)azetidine-1-carboxylate;

3-(dimethylamino)propyl 3-[4-carbamoyl-3-(phenylamino)-1H-pyrazol-1-yl]-3-(cyanomethyl)azetidine-1-carboxylate;

2-(4-methylpiperazin-1-yl)ethyl 3-[4-carbamoyl-3-(phenylamino)-1H-pyrazol-1-yl]-3-(cyanomethyl)azetidine-1-carboxylate;

(1-methylpiperidin-4-yl)methyl 3-[4-carbamoyl-3-(phenylamino)-1H-pyrazol-1-yl]-3-(cyanomethyl)azetidine-1-carboxylate;

cyclopentyl 3-(4-carbamoyl-3-{[4-(methylsulfonyl)phenyl]amino}-1H-pyrazol-1-yl)-3-(cyanomethyl)azetidine-1-carboxylate;

tetrahydrofuran-3-yl 3-(4-carbamoyl-3-{[4-(methylsulfonyl)phenyl]amino}-1H-pyrazol-1-yl)-3-(cyanomethyl)azetidine-1-carboxylate;

tetrahydro-2H-pyran-4-yl 3-(4-carbamoyl-3-{[4-(methylsulfonyl)phenyl]amino}-1H-pyrazol-1-yl)-3-(cyanomethyl)azetidine-1-carboxylate;

1-cyclopropylethyl 4-{4-carbamoyl-3-[(2-fluoropyridin-4-yl)amino]-1H-pyrazol-1-yl}-4-(cyanomethyl)piperidine-1-carboxylate;

2-Hydroxy-1-methylethyl 4-{4-carbamoyl-3-[(4-fluorophenyl)amino]-1H-pyrazol-1-yl}-4-(cyanomethyl)piperidine-1-carboxylate;

1-[1-Acetyl-3-(cyanomethyl)azetidin-3-yl]-3-(phenylamino)-1H-pyrazole-4-carboxamide;

1-[4-(Cyanomethyl)-1-propanoylpiperidin-4-yl]-3-(phenylamino)-1H-pyrazole-4-carboxamide;

1-{1-[(2E)-but-2-enoyl]-4-(cyanomethyl)piperidin-4-yl}-3-(phenylamino)-1H-pyrazole-4-carboxamide;

1-[4-(Cyanomethyl)-1-(cyclopropylcarbonyl)piperidin-4-yl]-3-(phenylamino)-1H-pyrazole-4-carboxamide;

1-[4-(cyanomethyl)-1-(methoxyacetyl)piperidin-4-yl]-3-(phenylamino)-1H-pyrazole-4-carboxamide;

1-[4-(cyanomethyl)-1-(2,2-dimethylpropanoyl)piperidin-4-yl]-3-(phenylamino)-1H-pyrazole-4-carboxamide;

1-[4-(cyanomethyl)-1-pentanoylpiperidin-4-yl]-3-(phenylamino)-1H-pyrazole-4-carboxamide;

1-[4-(cyanomethyl)-1-(N,N-dimethylglycyl)piperidin-4-yl]-3-(phenylamino)-1H-pyrazole-4-carboxamide;

1-[4-(cyanomethyl)-1-(tetrahydrofuran-2-ylcarbonyl)piperidin-4-yl]-3-(phenylamino)-1H-pyrazole-4-carboxamide;

1-[4-(cyanomethyl)-1-(phenylcarbonyl)piperidin-4-yl]-3-(phenylamino)-1H-pyrazole-4-carboxamide;

1-[4-(cyanomethyl)-1-(pyridin-3-ylcarbonyl)piperidin-4-yl]-3-(phenylamino)-1H-pyrazole-4-carboxamide;

1-[4-(cyanomethyl)-1-(pyridin-2-ylcarbonyl)piperidin-4-yl]-3-(phenylamino)-1H-pyrazole-4-carboxamide;

1-[4-(cyanomethyl)-1-(pyridin-4-ylcarbonyl)piperidin-4-yl]-3-(phenylamino)-1H-pyrazole-4-carboxamide;

1-[4-(cyanomethyl)-1-(pyrazin-2-ylcarbonyl)piperidin-4-yl]-3-(phenylamino)-1H-pyrazole-4-carboxamide;

1-{4-(cyanomethyl)-1-[(5-methylisoxazol-3-yl)carbonyl]piperidin-4-yl}-3-(phenylamino)-1H-pyrazole-4-carboxamide;

1-[4-(cyanomethyl)-1-(cyclohexylcarbonyl)piperidin-4-yl]-3-(phenylamino)-1H-pyrazole-4-carboxamide;

1-[4-(cyanomethyl)-1-(thiophen-2-ylcarbonyl)piperidin-4-yl]-3-(phenylamino)-1H-pyrazole-4-carboxamide;

1-{4-(cyanomethyl)-1-[(2-oxopyrrolidin-1-yl)acetyl]piperidin-4-yl}-3-(phenylamino)-1H-pyrazole-4-carboxamide;

1-[4-(cyanomethyl)-1-(thiophen-3-ylcarbonyl)piperidin-4-yl]-3-(phenylamino)-1H-pyrazole-4-carboxamide;

1-{4-(cyanomethyl)-1-[(2E)-3-pyridin-3-ylprop-2-enoyl]piperidin-4-yl}-3-(phenylamino)-1H-pyrazole-4-carboxamide;

1-{4-(cyanomethyl)-1-[(4-methoxyphenyl)carbonyl]piperidin-4-yl}-3-(phenylamino)-1H-pyrazole-4-carboxamide;

1-{1-[(4-chlorophenyl)carbonyl]-4-(cyanomethyl)piperidin-4-yl}-3-(phenylamino)-1H-pyrazole-4-carboxamide;

1-{1-[(2-chlorophenyl)carbonyl]-4-(cyanomethyl)piperidin-4-yl}-3-(phenylamino)-1H-pyrazole-4-carboxamide;

1-{1-[(3-chlorophenyl)carbonyl]-4-(cyanomethyl)piperidin-4-yl}-3-(phenylamino)-1H-pyrazole-4-carboxamide;

1-[4-(cyanomethyl)-1-(1H-indol-2-ylcarbonyl)piperidin-4-yl]-3-(phenylamino)-1H-pyrazole-4-carboxamide;

1-[4-(cyanomethyl)-1-{[4-(dimethylamino)phenyl]carbonyl}piperidin-4-yl]-3-(phenylamino)-1H-pyrazole-4-carboxamide;

1-{4-(cyanomethyl)-1-[(4-methoxyphenyl)acetyl]piperidin-4-yl}-3-(phenylamino)-1H-pyrazole-4-carboxamide;

1-[4-(cyanomethyl)-1-(naphthalene-1-ylcarbonyl)piperidin-4-yl]-3-(phenylamino)-1H-pyrazole-4-carboxamide;

1-{4-(cyanomethyl)-1-[(1-methyl-1H-indol-2-yl)carbonyl]piperidin-4-yl}-3-(phenylamino)-1H-pyrazole-4-carboxamide;

1-{4-(cyanomethyl)-1-[(3,4-dimethoxyphenyl)carbonyl]piperidin-4-yl}-3-(phenylamino)-1H-pyrazole-4-carboxamide;

1-{4-(cyanomethyl)-1-[(3-morpholin-4-ylphenyl)carbonyl]piperidin-4-yl}-3-(phenylamino)-1H-pyrazole-4-carboxamide;

1-[1-(biphenyl-2-ylcarbonyl)-4-(cyanomethyl)piperidin-4-yl]-3-(phenylamino)-1H-pyrazole-4-carboxamide;

1-[4-(cyanomethyl)-1-{[4-(trifluoromethyl)phenyl]acetyl}piperidin-4-yl]-3-(phenylamino)-1H-pyrazole-4-carboxamide;

1-{4-(cyanomethyl)-1-[(4-morpholin-4-ylphenyl)carbonyl]piperidin-4-yl}-3-(phenylamino)-1H-pyrazole-4-carboxamide;

1-[4-(cyanomethyl)-1-(quinolin-2-ylcarbonyl)piperidin-4-yl]-3-(phenylamino)-1H-pyrazole-4-carboxamide;

1-[4-(cyanomethyl)-1-(diphenylacetyl)piperidin-4-yl]-3-(phenylamino)-1H-pyrazole-4-carboxamide;

1-[4-(cyanomethyl)-1-{[4-(4-methylpiperazin-1-yl)phenyl]carbonyl}piperidin-4-yl]-3-(phenylamino)-1H-pyrazole-4-carboxamide;

1-[4-(cyanomethyl)-1-(hydroxyacetyl)piperidin-4-yl]-3-(phenylamino)-1H-pyrazole-4-carboxamide;

1-[3-(cyanomethyl)-1-propanoylazetidin-3-yl]-3-(phenylamino)-1H-pyrazole-4-carboxamide;

1-[3-(cyanomethyl)-1-(2,2-dimethylpropanoyl)azetidin-3-yl]-3-(phenylamino)-1H-pyrazole-4-carboxamide;

1-[3-(cyanomethyl)-1-(pyridin-2-ylcarbonyl)azetidin-3-yl]-3-(phenylamino)-1H-pyrazole-4-carboxamide;

1-[4-(cyanomethyl)-1-(tetrahydrofuran-2-ylacetyl)piperidin-4-yl]-3-[(2-fluoropyridin-4-yl)amino]-1H-pyrazole-4-carboxamide;

1-[4-(cyanomethyl)-1-(2,2-difluoropropanoyl)piperidin-4-yl]-3-[(2-fluoropyridin-4-yl)amino]-1H-pyrazole-4-carboxamide;

1-{4-(cyanomethyl)-1-[3-fluoro-2-(fluoromethyl)-2-methylpropanoyl]piperidin-4-yl}-3-[(2-fluoropyridin-4-yl)amino]-1H-pyrazole-4-carboxamide;

1-[4-(cyanomethyl)-1-(methoxyacetyl)piperidin-4-yl]-3-[(2-fluoropyridin-4-yl)amino]-1H-pyrazole-4-carboxamide;

1-[4-(cyanomethyl)-1-(2-hydroxy-2-methylpropanoyl)piperidin-4-yl]-3-[(2-fluoropyridin-4-yl)amino]-1H-pyrazole-4-carboxamide;

1-{4-(cyanomethyl)-1-[(1-methyl-1H-pyrazol-4-yl)carbonyl]piperidin-4-yl}-3-[(2-fluoropyridin-4-yl)amino]-1H-pyrazole-4-carboxamide;

1-[4-(cyanomethyl)-1-(cyclopropylacetyl)piperidin-4-yl]-3-[(2-fluoropyridin-4-yl)amino]-1H-pyrazole-4-carboxamide;

1-{4-(cyanomethyl)-1-[(2R)-2-hydroxy-3-methylbutanoyl]piperidin-4-yl}-3-[(2-fluoropyridin-4-yl)amino]-1H-pyrazole-4-carboxamide;

1-{4-(cyanomethyl)-1-[(2S)-2-hydroxy-3-methylbutanoyl]piperidin-4-yl}-3-[(2-fluoropyridin-4-yl)amino]-1H-pyrazole-4-carboxamide;

1-{4-(cyanomethyl)-1-(3,3,3-trifluoro-2-methylpropanoyl)piperidin-4-yl}-3-[(2-fluoropyridin-4-yl)amino]-1H-pyrazole-4-carboxamide;

1-[1-(cyanoacetyl)-4-(cyanomethyl)piperidin-4-yl]-3-[(2-fluoropyridin-4-yl)amino]-1H-pyrazole-4-carboxamide;

1-[4-(cyanomethyl)-1-(3-hydroxy-3-methylbutanoyl)piperidin-4-yl]-3-[(2-fluoropyridin-4-yl)amino]-1H-pyrazole-4-carboxamide;

1-[4-(cyanomethyl)-1-{[1-(trifluoromethyl)cyclobutyl]carbonyl}piperidin-4-yl]-3-[(2-fluoropyridin-4-yl)amino]-1H-pyrazole-4-carboxamide;

1-[4-(cyanomethyl)-1-(1H-imidazol-1-ylacetyl)piperidin-4-yl]-3-[(2-fluoropyridin-4-yl)amino]-1H-pyrazole-4-carboxamide;

1-{4-(cyanomethyl)-1-[(3,3-difluorocyclobutyl)carbonyl]piperidin-4-yl}-3-[(2-fluoropyridin-4-yl)amino]-1H-pyrazole-4-carboxamide;

1-[4-(cyanomethyl)-1-(3,3-dimethylbutanoyl)piperidin-4-yl]-3-[(2-fluoropyridin-4-yl)amino]-1H-pyrazole-4-carboxamide;

1-[4-(cyanomethyl)-1-(3,3,3-trifluoro-2,2-dimethylpropanoyl)piperidin-4-yl]-3-[(2-fluoropyridin-4-yl)amino]-1H-pyrazole-4-carboxamide;

1-[4-(cyanomethyl)-1-{[1-(trifluoromethyl)cyclopropyl]carbonyl}piperidin-4-yl]-3-[(2-fluoropyridin-4-yl)amino]-1H-pyrazole-4-carboxamide;

1-[4-(cyanomethyl)-1-(4,4,4-trifluorobutanoyl)piperidin-4-yl]-3-[(2-fluoropyridin-4-yl)amino]-1H-pyrazole-4-carboxamide;

1-{4-(cyanomethyl)-1-[(methylsulfonyl)acetyl]piperidin-4-yl}-3-[(2-fluoropyridin-4-yl)amino]-1H-pyrazole-4-carboxamide;

1-[4-(cyanomethyl)-1-(2,2-difluorobutanoyl)piperidin-4-yl]-3-[(2-fluoropyridin-4-yl)amino]-1H-pyrazole-4-carboxamide;

1-{4-(cyanomethyl)-1-[(1-methylcyclobutyl)carbonyl]piperidin-4-yl}-3-[(2-fluoropyridin-4-yl)amino]-1H-pyrazole-4-carboxamide;

1-[4-(cyanomethyl)-1-(3,3-difluoro-2-hydroxy-2-methylpropanoyl)piperidin-4-yl]-3-[(2-fluoropyridin-4-yl)amino]-1H-pyrazole-4-carboxamide;

1-{4-(cyanomethyl)-1-[(3R)-3-hydroxybutanoyl]piperidin-4-yl}-3-[(2-fluoropyridin-4-yl)amino]-1H-pyrazole-4-carboxamide;

1-(4-(Cyanomethyl)-1-(3,3,3-trifluoropropanoyl)piperidin-4-yl)-3-(4-fluorophenylamino)-1H-pyrazole-4-carboxamide;

1-(4-(cyanomethyl)-1-(3,3,3-trifluoropropanoyl)piperidin-4-yl)-3-(2-fluoropyridin-4-ylamino)-1H-pyrazole-4-carboxamide;
1-(4-(cyanomethyl)-1-(3,3,3-trifluoropropanoyl)piperidin-4-yl)-3-(5-fluoropyridin-3-ylamino)-1H-pyrazole-4-carboxamide;
1-[1-(Cyanoacetyl)-4-(cyanomethyl)piperidin-4-yl]-3-(phenylamino)-1H-pyrazole-4-carboxamide;
1-[1-(cyanoacetyl)-4-(cyanomethyl)piperidin-4-yl]-3-{[4-(methylsulfonyl)phenyl]amino}-1H-pyrazole-4-carboxamide;
1-[4-(Cyanomethyl)-1-(isopropylsulfonyl)piperidin-4-yl]-3-(phenylamino)-1H-pyrazole-4-carboxamide;
1-[4-(cyanomethyl)-1-(methylsulfonyl)piperidin-4-yl]-3-(phenylamino)-1H-pyrazole-4-carboxamide;
1-[4-(cyanomethyl)-1-(ethylsulfonyl)piperidin-4-yl]-3-(phenylamino)-1H-pyrazole-4-carboxamide;
1-[4-(cyanomethyl)-1-(furan-2-ylsulfonyl)piperidin-4-yl]-3-(phenylamino)-1H-pyrazole-4-carboxamide;
1-{4-(cyanomethyl)-1-[(trifluoromethyl)sulfonyl]piperidin-4-yl}-3-(phenylamino)-1H-pyrazole-4-carboxamide;
1-[4-(cyanomethyl)-1-(phenylsulfonyl)piperidin-4-yl]-3-(phenylamino)-1H-pyrazole-4-carboxamide;
1-{4-(cyanomethyl)-1-[(1-methyl-1H-imidazol-4-yl)sulfonyl]piperidin-4-yl}-3-(phenylamino)-1H-pyrazole-4-carboxamide;
1-[1-(benzylsulfonyl)-4-(cyanomethyl)piperidin-4-yl]-3-(phenylamino)-1H-pyrazole-4-carboxamide;
1-{4-(cyanomethyl)-1-[(4-methoxyphenyl)sulfonyl]piperidin-4-yl}-3-(phenylamino)-1H-pyrazole-4-carboxamide;
1-{4-(cyanomethyl)-1-[(3-methoxyphenyl)sulfonyl]piperidin-4-yl}-3-(phenylamino)-1H-pyrazole-4-carboxamide;
1-{1-[(3-chlorophenyl)sulfonyl]-4-(cyanomethyl)piperidin-4-yl}-3-(phenylamino)-1H-pyrazole-4-carboxamide;
1-{1-[(2-chlorophenyl)sulfonyl]-4-(cyanomethyl)piperidin-4-yl}-3-(phenylamino)-1H-pyrazole-4-carboxamide
1-[4-(cyanomethyl)-1-{[4-(trifluoromethyl)phenyl]sulfonyl}piperidin-4-yl]-3-(phenylamino)-1H-pyrazole-4-carboxamide;
1-[1-(biphenyl-4-ylsulfonyl)-4-(cyanomethyl)piperidin-4-yl]-3-(phenylamino)-1H-pyrazole-4-carboxamide;
1-[4-(cyanomethyl)-1-(cyclopropylsulfonyl)piperidin-4-yl]-3-(phenylamino)-1H-pyrazole-4-carboxamide;
1-[3-(cyanomethyl)-1-(methylsulfonyl)azetidin-3-yl]-3-(phenylamino)-1H-pyrazole-4-carboxamide;
1-[3-(cyanomethyl)-1-(furan-2-ylsulfonyl)azetidin-3-yl]-3-(phenylamino)-1H-pyrazole-4-carboxamide;
1-{3-(cyanomethyl)-1-[(trifluoromethyl)sulfonyl]azetidin-3-yl}-3-(phenylamino)-1H-pyrazole-4-carboxamide;
1-[3-(cyanomethyl)-1-(phenylsulfonyl)azetidin-3-yl]-3-(phenylamino)-1H-pyrazole-4-carboxamide;
1-[1-(benzylsulfonyl)-3-(cyanomethyl)azetidin-3-yl]-3-(phenylamino)-1H-pyrazole-4-carboxamide;
1-{3-(Cyanomethyl)-1-[(3-fluorophenyl)carbamoyl]azetidin-3-yl}-3-(phenylamino)-1H-pyrazole-4-carboxamide;
1-[3-(cyclohexylcarbamoyl)azetidin-3-yl]-3-(phenylamino)-1H-pyrazole-4-carboxamide;
1-{3-(cyanomethyl)-1-[(1-methylethyl)carbamoyl]azetidin-3-yl}-3-(phenylamino)-1H-pyrazole-4-carboxamide;
1-{3-(cyanomethyl)-1-[(3,4-dimethylphenyl)carbamoyl]azetidin-3-yl}-3-(phenylamino)-1H-pyrazole-4-carboxamide;
1-[1-(butylcarbamoyl)-3-(cyanomethyl)azetidin-3-yl]-3-(phenylamino)-1H-pyrazole-4-carboxamide;
1-{3-(cyanomethyl)-1-[(4-methylphenyl)carbamoyl]azetidin-3-yl}-3-(phenylamino)-1H-pyrazole-4-carboxamide;
1-[3-(cyanomethyl)-1-{[4-(1-methylethyl)phenyl]carbamoyl}azetidin-3-yl]-3-(phenylamino)-1H-pyrazole-4-carboxamide;
1-[3-(cyanomethyl)-1-{[2-(1-methylethyl)phenyl]carbamoyl}azetidin-3-yl]-3-(phenylamino)-1H-pyrazole-4-carboxamide;
ethyl N-({3-[4-carbamoyl-3-(phenylamino)-1H-pyrazol-1-yl]-3-(cyanomethyl)azetidin-1-yl}carbonyl)alaninate;
1-{3-(cyanomethyl)-1-[(2,5-difluorophenyl)carbamoyl]azetidin-3-yl}-3-(phenylamino)-1H-pyrazole-4-carboxamide;
1-{3-(cyanomethyl)-1-[(3-methylphenyl)carbamoyl]azetidin-3-yl}-3-(phenylamino)-1H-pyrazole-4-carboxamide;
1-{3-(cyanomethyl)-1-[(2,4,6-trimethylphenyl)carbamoyl]azetidin-3-yl}-3-(phenylamino)-1H-pyrazole-4-carboxamide;
1-{1-[(3-chloro-4-methylphenyl)carbamoyl]-3-(cyanomethyl)azetidin-3-yl}-3-(phenylamino)-1H-pyrazole-4-carboxamide;
1-{1-[(4-chloro-2-methylphenyl)carbamoyl]-3-(cyanomethyl)azetidin-3-yl}-3-(phenylamino)-1H-pyrazole-4-carboxamide;
1-{3-(cyanomethyl)-1-[(4-cyanophenyl)carbamoyl]azetidin-3-yl}-3-(phenylamino)-1H-pyrazole-4-carboxamide;
1-{3-(cyanomethyl)-1-[(2,5-dimethylphenyl)carbamoyl]azetidin-3-yl}-3-(phenylamino)-1H-pyrazole-4-carboxamide;
1-{1-[(5-chloro-2-methylphenyl)carbamoyl]-3-(cyanomethyl)azetidin-3-yl}-3-(phenylamino)-1H-pyrazole-4-carboxamide;
1-[3-(cyanomethyl)-1-(propylcarbamoyl)azetidin-3-yl]-3-(phenylamino)-1H-pyrazole-4-carboxamide;
1-{3-(cyanomethyl)-1-[(2,4-dimethylphenyl)carbamoyl]azetidin-3-yl}-3-(phenylamino)-1H-pyrazole-4-carboxamide;
1-{3-(cyanomethyl)-1-[(3,5-dimethylphenyl)carbamoyl]azetidin-3-yl}-3-(phenylamino)-1H-pyrazole-4-carboxamide;
1-{3-(cyanomethyl)-1-[(3,4-difluorophenyl)carbamoyl]azetidin-3-yl}-3-(phenylamino)-1H-pyrazole-4-carboxamide;
1-{1-[(3-chloro-2-methylphenyl)carbamoyl]-3-(cyanomethyl)azetidin-3-yl}-3-(phenylamino)-1H-pyrazole-4-carboxamide;
1-{3-(cyanomethyl)-1-[(2-ethyl-6-methylphenyl)carbamoyl]azetidin-3-yl}-3-(phenylamino)-1H-pyrazole-4-carboxamide;
1-{1-[(2-chloro-6-methylphenyl)carbamoyl]-3-(cyanomethyl)azetidin-3-yl}-3-(phenylamino)-1H-pyrazole-4-carboxamide;
1-{3-(cyanomethyl)-1-[(2-methoxy-5-methylphenyl)carbamoyl]azetidin-3-yl}-3-(phenylamino)-1H-pyrazole-4-carboxamide;
1-{3-(cyanomethyl)-1-[(4-ethoxyphenyl)carbamoyl]azetidin-3-yl}-3-(phenylamino)-1H-pyrazole-4-carboxamide;

1-{3-(cyanomethyl)-1-[(2-methylphenyl)carbamoyl]azetidin-3-yl}-3-(phenylamino)-1H-pyrazole-4-carboxamide;
1-{3-(cyanomethyl)-1-[(2,4-difluorophenyl)carbamoyl]azetidin-3-yl}-3-(phenylamino)-1H-pyrazole-4-carboxamide;
1-{3-(cyanomethyl)-1-[(1,1,3,3-tetramethylbutyl)carbamoyl]azetidin-3-yl}-3-(phenylamino)-1H-pyrazole-4-carboxamide;
1-{3-(cyanomethyl)-1-[(2-ethoxyphenyl)carbamoyl]azetidin-3-yl}-3-(phenylamino)-1H-pyrazole-4-carboxamide;
1-{3-(cyanomethyl)-1-[(2,6-dimethylphenyl)carbamoyl]azetidin-3-yl}-3-(phenylamino)-1H-pyrazole-4-carboxamide;
1-{1-[(3-acetylphenyl)carbamoyl]-3-(cyanomethyl)azetidin-3-yl}-3-(phenylamino)-1H-pyrazole-4-carboxamide;
1-[3-(cyanomethyl)-1-{[(1R)-1-phenylethyl]carbamoyl}azetidin-3-yl]-3-(phenylamino)-1H-pyrazole-4-carboxamide;
1-{3-(cyanomethyl)-1-[(4-ethylphenyl)carbamoyl]azetidin-3-yl}-3-(phenylamino)-1H-pyrazole-4-carboxamide;
1-{3-(cyanomethyl)-1-[(3-ethylphenyl)carbamoyl]azetidin-3-yl}-3-(phenylamino)-1H-pyrazole-4-carboxamide;
1-{3-(cyanomethyl)-1-[(4-methoxy-2-methylphenyl)carbamoyl]azetidin-3-yl}-3-(phenylamino)-1H-pyrazole-4-carboxamide;
1-{3-(cyanomethyl)-1-[(3-fluoro-4-methylphenyl)carbamoyl]azetidin-3-yl}-3-(phenylamino)-1H-pyrazole-4-carboxamide;
1-{3-(cyanomethyl)-1-[(5-fluoro-2-methylphenyl)carbamoyl]azetidin-3-yl}-3-(phenylamino)-1H-pyrazole-4-carboxamide;
1-{3-(cyanomethyl)-1-[(2-ethylphenyl)carbamoyl]azetidin-3-yl}-3-(phenylamino)-1H-pyrazole-4-carboxamide;
1-{1-[(3-chloro-4-fluorophenyl)carbamoyl]-3-(cyanomethyl)azetidin-3-yl}-3-(phenylamino)-1H-pyrazole-4-carboxamide;
1-{3-(cyanomethyl)-1-[(4-methylphenyl)carbamoyl]azetidin-3-yl}-3-{[4-(methylsulfonyl)phenyl]amino}-1H-pyrazole-4-carboxamide;
1-{3-(cyanomethyl)-1-[(2,5-difluorophenyl)carbamoyl]azetidin-3-yl}-3-{[4-(methylsulfonyl)phenyl]amino}-1H-pyrazole-4-carboxamide;
1-[1-(butylcarbamoyl)-3-(cyanomethyl)azetidin-3-yl]-3-{[4-(methylsulfonyl)phenyl]amino}-1H-pyrazole-4-carboxamide;
4-(4-carbamoyl-3-(4-(trifluoromethylsulfonyl)phenylamino)-1H-pyrazol-1-yl)-4-(cyanomethyl)-N-isopropylpiperidine-1-carboxamide;
4-(4-carbamoyl-3-(4-(trifluoromethylsulfonyl)phenylamino)-1H-pyrazol-1-yl)-4-(cyanomethyl)-N-(4-cyanophenyl)piperidine-1-carboxamide;
4-[4-Carbamoyl-3-(phenylamino)-1H-pyrazol-1-yl]-4-(cyanomethyl)-N-(1-methylethyl)piperidine-1-carboxamide;
4-[4-carbamoyl-3-(phenylamino)-1H-pyrazol-1-yl]-4-(cyanomethyl)-N-(4-cyanophenyl)piperidine-1-carboxamide;
3-((4-chlorophenyl)amino)-1-(1-(cyanomethyl)-4-(3-fluoroazetidin-1-yl)cyclohexyl)-1H-pyrazole-4-carboxamide;
1-[1-(cyanomethyl)-4-(3-fluoroazetidin-1-yl)cyclohexyl]-3-{[4-(trifluoromethyl)phenyl]amino}-1H-pyrazole-4-carboxamide;
1-(1-(cyanomethyl)-4-(cyclohexylamino)cyclohexyl)-3-((4-fluorophenyl)amino)-1H-pyrazole-4-carboxamide;
1-{1-(cyanomethyl)-4-[(3-fluorophenyl)amino]cyclohexyl}-3-[(4-fluorophenyl)amino]-1H-pyrazole-4-carboxamide;
1-[1-(cyanomethyl)-4-(pyridin-2-ylamino)cyclohexyl]-3-[(2-fluoropyridin-4-yl)amino]-1H-pyrazole-4-carboxamide;
1-[1-(cyanomethyl)-4-(tetrahydro-2H-pyran-4-ylamino)cyclohexyl]-3-[(4-fluorophenyl)amino]-1H-pyrazole-4-carboxamide;
1-[1-(cyanomethyl)-4-(pyridin-3-ylamino)cyclohexyl]-3-[(2-fluoropyridin-4-yl)amino]-1H-pyrazole-4-carboxamide;
1-{1-(cyanomethyl)-4-[(4-hydroxyphenyl)amino]cyclohexyl}-3-({4-[(difluoromethyl)sulfonyl]phenyl}amino)-1H-pyrazole-4-carboxamide;
1-[1-(cyanomethyl)-4-(pyridin-3-ylamino)cyclohexyl]-3-({4-[(difluoromethyl)sulfonyl]phenyl}amino)-1H-pyrazole-4-carboxamide;
1-[1-(cyanomethyl)-4-(pyridin-3-ylamino)cyclohexyl]-3-({4-[(difluoromethyl)sulfonyl]phenyl}amino)-1H-pyrazole-4-carboxamide;
1-{1-(cyanomethyl)-4-[(2,5-difluorophenyl)amino]cyclohexyl}-3-[(2-fluoropyridin-4-yl)amino]-1H-pyrazole-4-carboxamide;
1-{4-[(2-chlorophenyl)amino]-1-(cyanomethyl)cyclohexyl}-3-[(2-fluoropyridin-4-yl)amino]-1H-pyrazole-4-carboxamide;
1-[1-(cyanomethyl)-4-(pyridin-2-ylamino)cyclohexyl]-3-[(4-fluorophenyl)amino]-1H-pyrazole-4-carboxamide;
1-[1-(cyanomethyl)-4-(4-hydroxypiperidin-1-yl)cyclohexyl]-3-[(2-fluoropyridin-4-yl)amino]-1H-pyrazole-4-carboxamide;
1-{1-(cyanomethyl)-4-[(3-hydroxyphenyl)amino]cyclohexyl}-3-({4-[(difluoromethyl)sulfonyl]phenyl}amino)-1H-pyrazole-4-carboxamide;
1-{1-(cyanomethyl)-4-[methyl(phenyl)amino]cyclohexyl}-3-[(2-fluoropyridin-4-yl)amino]-1H-pyrazole-4-carboxamide;
1-{1-(cyanomethyl)-4-[(3-fluorophenyl)amino]cyclohexyl}-3-[(4-fluorophenyl)amino]-1H-pyrazole-4-carboxamide;
1-{1-(cyanomethyl)-4-[(2-fluorophenyl)amino]cyclohexyl}-3-[(2-fluoropyridin-4-yl)amino]-1H-pyrazole-4-carboxamide;
1-{1-(cyanomethyl)-4-[(4-fluorophenyl)amino]cyclohexyl}-3-[(4-fluorophenyl)amino]-1H-pyrazole-4-carboxamide;
1-{1-(cyanomethyl)-4-[(4-fluorophenyl)amino]cyclohexyl}-3-[(4-fluorophenyl)amino]-1H-pyrazole-4-carboxamide;
1-{1-(cyanomethyl)-4-[(3,4-difluorophenyl)amino]cyclohexyl}-3-[(2-fluoropyridin-4-yl)amino]-1H-pyrazole-4-carboxamide;
1-[1-(cyanomethyl)-4-(2,3-dihydro-1H-indol-1-yl)cyclohexyl]-3-[(4-fluorophenyl)amino]-1H-pyrazole-4-carboxamide;
1-[1-(cyanomethyl)-4-(pyridin-2-ylamino)cyclohexyl]-3-[(2-fluoropyridin-4-yl)amino]-1H-pyrazole-4-carboxamide;
1-[1-(cyanomethyl)-4-(cyclohexylamino)cyclohexyl]-3-[(2-fluoropyridin-4-yl)amino]-1H-pyrazole-4-carboxamide;

1-{1-(cyanomethyl)-4-[(2-fluorophenyl)amino]cyclohexyl}-3-[(2-fluoropyridin-4-yl)amino]-1H-pyrazole-4-carboxamide;
1-{4-[(2-chlorophenyl)amino]-1-(cyanomethyl)cyclohexyl}-3-[(2-fluoropyridin-4-yl)amino]-1H-pyrazole-4-carboxamide;
1-[1-(cyanomethyl)-4-(tetrahydro-2H-pyran-4-ylamino)cyclohexyl]-3-({4-[(difluoromethyl)sulfonyl]phenyl}amino)-1H-pyrazole-4-carboxamide;
1-[1-(cyanomethyl)-4-(4-hydroxypiperidin-1-yl)cyclohexyl]-3-[(4-fluorophenyl)amino]-1H-pyrazole-4-carboxamide;
1-[1-(cyanomethyl)-4-(cyclohexylamino)cyclohexyl]-3-({4-[(difluoromethyl)sulfonyl]phenyl}amino)-1H-pyrazole-4-carboxamide;
1-{4-[(3-chlorophenyl)amino]-1-(cyanomethyl)cyclohexyl}-3-[(2-fluoropyridin-4-yl)amino]-1H-pyrazole-4-carboxamide;
1-[1-(cyanomethyl)-4-(2,3-dihydro-1H-indol-1-yl)cyclohexyl]-3-[(2-fluoropyridin-4-yl)amino]-1H-pyrazole-4-carboxamide;
1-[1-(cyanomethyl)-4-(4,4-difluoropiperidin-1-yl)cyclohexyl]-3-({4-[(difluoromethyl)sulfonyl]phenyl}amino)-1H-pyrazole-4-carboxamide;
1-{1-(cyanomethyl)-4-[(2-hydroxyphenyl)amino]cyclohexyl}-3-({4-[(difluoromethyl)sulfonyl]phenyl}amino)-1H-pyrazole-4-carboxamide;
1-{1-(cyanomethyl)-4-[(2,4-difluorophenyl)amino]cyclohexyl}-3-[(2-fluoropyridin-4-yl)amino]-1H-pyrazole-4-carboxamide;
1-{1-(cyanomethyl)-4-[methyl(phenyl)amino]cyclohexyl}-3-[(2-fluoropyridin-4-yl)amino]-1H-pyrazole-4-carboxamide;
1-{1-(cyanomethyl)-4-[(3,4-difluorophenyl)amino]cyclohexyl}-3-[(4-fluorophenyl)amino]-1H-pyrazole-4-carboxamide;
1-{1-(cyanomethyl)-4-[(3,4-difluorophenyl)amino]cyclohexyl}-3-[(2-fluoropyridin-4-yl)amino]-1H-pyrazole-4-carboxamide;
1-{1-(cyanomethyl)-4-[(2,4-difluorophenyl)amino]cyclohexyl}-3-[(2-fluoropyridin-4-yl)amino]-1H-pyrazole-4-carboxamide;
1-[1-(cyanomethyl)-4-(tetrahydro-2H-pyran-4-ylamino)cyclohexyl]-3-[(2-fluoropyridin-4-yl)amino]-1H-pyrazole-4-carboxamide;
1-[1-(cyanomethyl)-4-(pyridin-3-ylamino)cyclohexyl]-3-[(4-fluorophenyl)amino]-1H-pyrazole-4-carboxamide;
1-{1-(cyanomethyl)-4-[(4-fluorophenyl)amino]cyclohexyl}-3-[(2-fluoropyridin-4-yl)amino]-1H-pyrazole-4-carboxamide;
1-[1-(cyanomethyl)-4-(4-hydroxypiperidin-1-yl)cyclohexyl]-3-[(4-fluorophenyl)amino]-1H-pyrazole-4-carboxamide;
1-[1-(cyanomethyl)-4-(4,4-difluoropiperidin-1-yl)cyclohexyl]-3-({4-[(difluoromethyl)sulfonyl]phenyl}amino)-1H-pyrazole-4-carboxamide;
1-[1-(cyanomethyl)-4-(4-hydroxypiperidin-1-yl)cyclohexyl]-3-({4-[(difluoromethyl)sulfonyl]phenyl}amino)-1H-pyrazole-4-carboxamide;
1-{1-(cyanomethyl)-4-[(3-hydroxyphenyl)amino]cyclohexyl}-3-({4-[(difluoromethyl)sulfonyl]phenyl}amino)-1H-pyrazole-4-carboxamide;
1-{4-[(4-chlorophenyl)amino]-1-(cyanomethyl)cyclohexyl}-3-[(2-fluoropyridin-4-yl)amino]-1H-pyrazole-4-carboxamide;
1-{4-[(3-chlorophenyl)amino]-1-(cyanomethyl)cyclohexyl}-3-[(4-fluorophenyl)amino]-1H-pyrazole-4-carboxamide;
1-{1-(cyanomethyl)-4-[(4-furphenyl)amino]cyclohexyl}-3-[(2-fluoropyridin-4-yl)amino]-1H-pyrazole-4-carboxamide;
1-{1-(cyanomethyl)-4-[(2-hydroxyphenyl)amino]cyclohexyl}-3-({4-[(difluoromethyl)sulfonyl]phenyl}amino)-1H-pyrazole-4-carboxamide;
1-[1-(cyanomethyl)-4-(2,3-dihydro-1H-indol-1-yl)cyclohexyl]-3-[(4-fluorophenyl)amino]-1H-pyrazole-4-carboxamide;
1-{1-(cyanomethyl)-4-[(2,5-difluorophenyl)amino]cyclohexyl}-3-[(4-fluorophenyl)amino]-1H-pyrazole-4-carboxamide;
1-[1-(cyanomethyl)-4-(cyclohexylamino)cyclohexyl]-3-[(2-fluoropyridin-4-yl)amino]-1H-pyrazole-4-carboxamide;
1-{4-[(4-chlorophenyl)amino]-1-(cyanomethyl)cyclohexyl}-3-[(4-fluorophenyl)amino]-1H-pyrazole-4-carboxamide;
1-{4-[(4-chlorophenyl)amino]-1-(cyanomethyl)cyclohexyl}-3-[(4-fluorophenyl)amino]-1H-pyrazole-4-carboxamide;
1-[1-(cyanomethyl)-4-(2,3-dihydro-1H-indol-1-yl)cyclohexyl]-3-[(2-fluoropyridin-4-yl)amino]-1H-pyrazole-4-carboxamide;
1-{1-(cyanomethyl)-4-[(3-fluorophenyl)amino]cyclohexyl}-3-[(2-fluoropyridin-4-yl)amino]-1H-pyrazole-4-carboxamide;
1-[1-(cyanomethyl)-4-(4-hydroxypiperidin-1-yl)cyclohexyl]-3-[(2-fluoropyridin-4-yl)amino]-1H-pyrazole-4-carboxamide;
1-[1-(cyanomethyl)-4-(cyclohexylamino)cyclohexyl]-3-({4-[(difluoromethyl)sulfonyl]phenyl}amino)-1H-pyrazole-4-carboxamide;
1-{1-(cyanomethyl)-4-[(2-fluorophenyl)amino]cyclohexyl}-3-[(4-fluorophenyl)amino]-1H-pyrazole-4-carboxamide;
1-{1-(cyanomethyl)-4-[(4-hydroxyphenyl)amino]cyclohexyl}-3-({4-[(difluoromethyl)sulfonyl]phenyl}amino)-1H-pyrazole-4-carboxamide;
1-{1-(cyanomethyl)-4-[(2-fluorophenyl)amino]cyclohexyl}-3-[(4-fluorophenyl)amino]-1H-pyrazole-4-carboxamide;
1-{4-[(4-chlorophenyl)amino]-1-(cyanomethyl)cyclohexyl}-3-[(2-fluoropyridin-4-yl)amino]-1H-pyrazole-4-carboxamide;
1-{4-[(3-chlorophenyl)amino]-1-(cyanomethyl)cyclohexyl}-3-[(2-fluoropyridin-4-yl)amino]-1H-pyrazole-4-carboxamide;
1-{1-(cyanomethyl)-4-[(2,5-difluorophenyl)amino]cyclohexyl}-3-[(2-fluoropyridin-4-yl)amino]-1H-pyrazole-4-carboxamide;
1-{1-(cyanomethyl)-4-[(3-fluorophenyl)amino]cyclohexyl}-3-[(2-fluoropyridin-4-yl)amino]-1H-pyrazole-4-carboxamide;
1-[1-(cyanomethyl)-4-(tetrahydro-2H-pyran-4-ylamino)cyclohexyl]-3-[(4-fluorophenyl)amino]-1H-pyrazole-4-carboxamide;
1-[1-(cyanomethyl)-4-(tetrahydro-2H-pyran-4-ylamino)cyclohexyl]-3-({4-[(difluoromethyl)sulfonyl]phenyl}amino)-1H-pyrazole-4-carboxamide;
1-[1-(cyanomethyl)-4-(4-hydroxypiperidin-1-yl)cyclohexyl]-3-({4-[(difluoromethyl)sulfonyl]phenyl}amino)-1H-pyrazole-4-carboxamide;

1-{1-(cyanomethyl)-4-[(2-hydroxyethyl)amino]cyclohexyl}-3-[(4-fluorophenyl)amino]-1H-pyrazole-4-carboxamide;
1-{1-(cyanomethyl)-4-[(cyclopropylmethyl)amino]cyclohexyl}-3-[(4-fluorophenyl)amino]-1H-pyrazole-4-carboxamide;
1-[1-(cyanomethyl)-4-(4,4-difluoropiperidin-1-yl)cyclohexyl]-3-[(4-fluorophenyl)amino]-1H-pyrazole-4-carboxamide;
1-{1-(cyanomethyl)-4-[(2-methoxyethyl)amino]cyclohexyl}-3-[(4-fluorophenyl)amino]-1H-pyrazole-4-carboxamide;
1-[1-(cyanomethyl)-4-{methyl[2-(methylsulfonyl)ethyl]amino}cyclohexyl]-3-[(4-fluorophenyl)amino]-1H-pyrazole-4-carboxamide;
1-[1-(cyanomethyl)-4-{[4-(trifluoromethyl)phenyl]amino}cyclohexyl]-3-[(4-fluorophenyl)amino]-1H-pyrazole-4-carboxamide;
1-[1-(cyanomethyl)-4-(3-methoxyazetidin-1-yl)cyclohexyl]-3-[(4-fluorophenyl)amino]-1H-pyrazole-4-carboxamide;
1-[1-(cyanomethyl)-4-(pyridin-3-ylamino)cyclohexyl]-3-[(4-fluorophenyl)amino]-1H-pyrazole-4-carboxamide;
1-[4-(4-acetylpiperazin-1-yl)-1-(cyanomethyl)cyclohexyl]-3-[(4-fluorophenyl)amino]-1H-pyrazole-4-carboxamide;
1-{1-(cyanomethyl)-4-[(2,2-difluoroethyl)amino]cyclohexyl}-3-[(4-fluorophenyl)amino]-1H-pyrazole-4-carboxamide;
1-[1-(cyanomethyl)-4-(methylamino)cyclohexyl]-3-[(4-fluorophenyl)amino]-1H-pyrazole-4-carboxamide;
1-{1-(cyanomethyl)-4-[(2-fluoroethyl)amino]cyclohexyl}-3-[(4-fluorophenyl)amino]-1H-pyrazole-4-carboxamide;
1-[4-azetidin-1-yl-1-(cyanomethyl)cyclohexyl]-3-[(4-fluorophenyl)amino]-1H-pyrazole-4-carboxamide;
1-[1-(cyanomethyl)-4-(3-methoxyazetidin-1-yl)cyclohexyl]-3-[(2-fluoropyridin-4-yl)amino]-1H-pyrazole-4-carboxamide;
1-[1-(cyanomethyl)-4-(3-fluoroazetidin-1-yl)cyclohexyl]-3-[(2-fluoropyridin-4-yl)amino]-1H-pyrazole-4-carboxamide;
1-[1-(cyanomethyl)-4-(phenylamino)cyclohexyl]-3-[(2-fluoropyridin-4-yl)amino]-1H-pyrazole-4-carboxamide;
1-{1-(cyanomethyl)-4-[(2,2-difluoroethyl)amino]cyclohexyl}-3-({4-[(difluoromethyl)sulfonyl]phenyl}amino)-1H-pyrazole-4-carboxamide;
1-{1-(cyanomethyl)-4-[(2,2,2-trifluoroethyl)amino]cyclohexyl}-3-({4-[(difluoromethyl)sulfonyl]phenyl}amino)-1H-pyrazole-4-carboxamide;
1-[1-(cyanomethyl)-4-(phenylamino)cyclohexyl]-3-[(2-fluoropyridin-4-yl)amino]-1H-pyrazole-4-carboxamide;
1-{1-(cyanomethyl)-4-[(2,2-difluoroethyl)amino]cyclohexyl}-3-[(2-fluoropyridin-4-yl)amino]-1H-pyrazole-4-carboxamide;
1-[1-(cyanomethyl)-4-(phenylamino)cyclohexyl]-3-({4-[(difluoromethyl)sulfonyl]phenyl}amino)-1H-pyrazole-4-carboxamide;
1-{1-(cyanomethyl)-4-[(2,2,2-trifluoroethyl)amino]cyclohexyl}-3-({4-[(difluoromethyl)sulfonyl]phenyl}amino)-1H-pyrazole-4-carboxamide;
1-[1-(cyanomethyl)-4-(1,3-dihydro-2H-isoindol-2-yl)cyclohexyl]-3-[(4-fluorophenyl)amino]-1H-pyrazole-4-carboxamide;
1-[1-(cyanomethyl)-4-(3-fluoroazetidin-1-yl)cyclohexyl]-3-({4-[(difluoromethyl)sulfonyl]phenyl}amino)-1H-pyrazole-4-carboxamide;
1-[4-(benzylamino)-1-(cyanomethyl)cyclohexyl]-3-[(4-fluorophenyl)amino]-1H-pyrazole-4-carboxamide;
1-{1-(cyanomethyl)-4-[(2,2,2-trifluoroethyl)amino]cyclohexyl}-3-[(2-fluoropyridin-4-yl)amino]-1H-pyrazole-4-carboxamide;
1-[1-(cyanomethyl)-4-(3-methoxyazetidin-1-yl)cyclohexyl]-3-[(2-fluoropyridin-4-yl)amino]-1H-pyrazole-4-carboxamide;
1-{1-(cyanomethyl)-4-[(2,2,2-trifluoroethyl)amino]cyclohexyl}-3-[(2-fluoropyridin-4-yl)amino]-1H-pyrazole-4-carboxamide;
1-[1-(cyanomethyl)-4-(phenylamino)cyclohexyl]-3-[(4-fluorophenyl)amino]-1H-pyrazole-4-carboxamide;
1-{4-[(4-cyanobenzyl)amino]-1-(cyanomethyl)cyclohexyl}-3-[(4-fluorophenyl)amino]-1H-pyrazole-4-carboxamide;
1-{1-(cyanomethyl)-4-[(2,2,2-trifluoroethyl)amino]cyclohexyl}-3-[(4-fluorophenyl)amino]-1H-pyrazole-4-carboxamide;
1-{1-(cyanomethyl)-4-[(2,2-difluoroethyl)amino]cyclohexyl}-3-({4-[(difluoromethyl)sulfonyl]phenyl}amino)-1H-pyrazole-4-carboxamide;
1-[1-(cyanomethyl)-4-(3-fluoroazetidin-1-yl)cyclohexyl]-3-[(4-fluorophenyl)amino]-1H-pyrazole-4-carboxamide;
1-{1-(cyanomethyl)-4-[(2,2,2-trifluoroethyl)amino]cyclohexyl}-3-[(4-fluorophenyl)amino]-1H-pyrazole-4-carboxamide;
1-[1-(cyanomethyl)-4-(phenylamino)cyclohexyl]-3-({4-[(difluoromethyl)sulfonyl]phenyl}amino)-1H-pyrazole-4-carboxamide;
1-[1-(cyanomethyl)-4-(phenylamino)cyclohexyl]-3-[(4-fluorophenyl)amino]-1H-pyrazole-4-carboxamide;
1-[1-(cyanomethyl)-4-(3-fluoroazetidin-1-yl)cyclohexyl]-3-[(2-fluoropyridin-4-yl)amino]-1H-pyrazole-4-carboxamide;
1-[1-(cyanomethyl)-4-(3-fluoroazetidin-1-yl)cyclohexyl]-3-({4-[(difluoromethyl)sulfonyl]phenyl}amino)-1H-pyrazole-4-carboxamide;
1-{1-(cyanomethyl)-4-[(2,2-difluoroethyl)amino]cyclohexyl}-3-[(2-fluoropyridin-4-yl)amino]-1H-pyrazole-4-carboxamide;
1-[1-(cyanomethyl)-4-(3-fluoroazetidin-1-yl)cyclohexyl]-3-[(4-fluorophenyl)amino]-1H-pyrazole-4-carboxamide;
1-[cis-4-(benzylamino)-1-(cyanomethyl)cyclohexyl]-3-[(4-fluorophenyl)amino]-1H-pyrazole-4-carboxamide;
1-(1-(cyanomethyl)-4-((2,4-difluorobenzyl)amino)cyclohexyl)-3-((2-fluoropyridin-4-yl)amino)-1H-pyrazole-4-carboxamide;
1-[4-amino-1-(cyanomethyl)cyclohexyl]-3-({4-[(difluoromethyl)sulfonyl]phenyl}amino)-1H-pyrazole-4-carboxamide;
1-{1-(cyanomethyl)-4-[(2,4-difluorobenzyl)amino]cyclohexyl}-3-[(2-fluoropyridin-4-yl)amino]-1H-pyrazole-4-carboxamide;
1-{1-(cyanomethyl)-4-[(3-hydroxybenzyl)amino]cyclohexyl}-3-[(2-fluoropyridin-4-yl)amino]-1H-pyrazole-4-carboxamide;
1-{4-[(4-cyanobenzyl)amino]-1-(cyanomethyl)cyclohexyl}-3-[(2-fluoropyridin-4-yl)amino]-1H-pyrazole-4-carboxamide;

1-{1-(cyanomethyl)-4-[(2-hydroxybenzyl)amino]cyclohexyl}-3-[(2-fluoropyridin-4-yl)amino]-1H-pyrazole-4-carboxamide;
1-{1-(cyanomethyl)-4-[(cyclohexylmethyl)amino]cyclohexyl}-3-[(2-fluoropyridin-4-yl)amino]-1H-pyrazole-4-carboxamide;
1-{4-[(4-chlorobenzyl)amino]-1-(cyanomethyl)cyclohexyl}-3-[(2-fluoropyridin-4-yl)amino]-1H-pyrazole-4-carboxamide;
1-{4-[(2-chlorobenzyl)amino]-1-(cyanomethyl)cyclohexyl}-3-[(2-fluoropyridin-4-yl)amino]-1H-pyrazole-4-carboxamide;
1-{1-(cyanomethyl)-4-[(2-fluorobenzyl)amino]cyclohexyl}-3-[(2-fluoropyridin-4-yl)amino]-1H-pyrazole-4-carboxamide;
1-{1-(cyanomethyl)-4-[(4-fluorobenzyl)amino]cyclohexyl}-3-[(2-fluoropyridin-4-yl)amino]-1H-pyrazole-4-carboxamide;
1-{1-(cyanomethyl)-4-[(pyridin-4-ylmethyl)amino]cyclohexyl}-3-[(2-fluoropyridin-4-yl)amino]-1H-pyrazole-4-carboxamide;
1-{4-[(3-cyanobenzyl)amino]-1-(cyanomethyl)cyclohexyl}-3-[(2-fluoropyridin-4-yl)amino]-1H-pyrazole-4-carboxamide;
1-{4-[(4-chlorobenzyl)amino]-1-(cyanomethyl)cyclohexyl}-3-[(2-fluoropyridin-4-yl)amino]-1H-pyrazole-4-carboxamide;
1-{4-[(2-chlorobenzyl)amino]-1-(cyanomethyl)cyclohexyl}-3-[(2-fluoropyridin-4-yl)amino]-1H-pyrazole-4-carboxamide;
1-{1-(cyanomethyl)-4-[(pyridin-2-ylmethyl)amino]cyclohexyl}-3-[(2-fluoropyridin-4-yl)amino]-1H-pyrazole-4-carboxamide;
1-[4-(benzylamino)-1-(cyanomethyl)cyclohexyl]-3-[(2-fluoropyridin-4-yl)amino]-1H-pyrazole-4-carboxamide;
1-{1-(cyanomethyl)-4-[(3-fluorobenzyl)amino]cyclohexyl}-3-[(2-fluoropyridin-4-yl)amino]-1H-pyrazole-4-carboxamide;
1-{4-[(3-chlorobenzyl)amino]-1-(cyanomethyl)cyclohexyl}-3-[(2-fluoropyridin-4-yl)amino]-1H-pyrazole-4-carboxamide;
1-{1-(cyanomethyl)-4-[(2-fluorobenzyl)amino]cyclohexyl}-3-[(2-fluoropyridin-4-yl)amino]-1H-pyrazole-4-carboxamide;
1-{1-(cyanomethyl)-4-[(pyridin-3-ylmethyl)amino]cyclohexyl}-3-[(2-fluoropyridin-4-yl)amino]-1H-pyrazole-4-carboxamide;
1-{4-[(3-chlorobenzyl)amino]-1-(cyanomethyl)cyclohexyl}-3-[(2-fluoropyridin-4-yl)amino]-1H-pyrazole-4-carboxamide;
1-{1-(cyanomethyl)-4-[(3-fluorobenzyl)amino]cyclohexyl}-3-[(2-fluoropyridin-4-yl)amino]-1H-pyrazole-4-carboxamide;
1-{1-(cyanomethyl)-4-[(4-fluorobenzyl)amino]cyclohexyl}-3-[(2-fluoropyridin-4-yl)amino]-1H-pyrazole-4-carboxamide;
1-{1-(cyanomethyl)-4-[(4-hydroxybenzyl)amino]cyclohexyl}-3-[(2-fluoropyridin-4-yl)amino]-1H-pyrazole-4-carboxamide;
1-{4-[(2-cyanobenzyl)amino]-1-(cyanomethyl)cyclohexyl}-3-[(2-fluoropyridin-4-yl)amino]-1H-pyrazole-4-carboxamide;
1-[4-(benzylamino)-1-(cyanomethyl)cyclohexyl]-3-[(2-fluoropyridin-4-yl)amino]-1H-pyrazole-4-carboxamide;
1-(1-(Cyanomethyl)-4-(3-fluorophenylsulfonamido)cyclohexyl)-3-((2-fluoropyridin-4-yl)amino)-1H-pyrazole-4-carboxamide;
1-(4-(Cyanomethyl)-1-(2,2-difluoropropanoyl)-3-fluoropiperidin-4-yl)-3-((6-fluoropyridin-3-yl)amino)-1H-pyrazole-4-carboxamide;
1-(4-(cyanomethyl)-1-(2,2-difluoropropanoyl)-3-fluoropiperidin-4-yl)-3-((6-fluoropyridin-3-yl)amino)-1H-pyrazole-4-carboxamide;
1-(4-(cyanomethyl)-1-(2,2-difluoropropanoyl)-3-fluoropiperidin-4-yl)-3-((6-fluoropyridin-3-yl)amino)-1H-pyrazole-4-carboxamide;
1-[1-(cyanomethyl)-4-(4-cyclopropyl-1H-1,2,3-triazol-1-yl)cyclohexyl]-3-[(4-fluorophenyl)amino]-1H-pyrazole-4-carboxamide;
1-{1-(cyanomethyl)-4-[(2,2,2-trifluoroethyl)carbamoyl]cyclohexyl}-3-(phenylamino)-1H-pyrazole-4-carboxamide;
2,2-Difluoroethyl 4-(4-carbamoyl-3-((2-fluoropyridin-4-yl)amino)-1H-pyrazol-1-yl)-4-(cyanomethyl)-3-fluoropiperidine-1-carboxylate;
1-(4-amino-1-(cyanomethyl)cyclohexyl)-3-((2-fluoropyridin-4-yl)amino)-1H-pyrazole-4-carboxamide;
4-amino-1-(cyanomethyl)cyclohexyl)-3-((4-((difluoromethyl)sulfonyl)phenyl)amino)-1H-pyrazole-4-carboxamide;
tert-butyl-4-{4-carbamoyl-3-[(4-fluorophenyl)amino]-1H-pyrazol-1-yl}-4-(cyanomethyl)-3-fluoropiperidine-1-carboxylate;
tert-butyl-4-[4-carbamoyl-3-(phenylamino)-1H-pyrazol-1-yl]-4-(cyanomethyl)-3-methylpiperidine-1-carboxylate;
tetrahydrofuran-3-yl 4-{4-carbamoyl-3-[(2-fluoropyridin-4-yl)amino]-1H-pyrazol-1-yl}-4-(cyanomethyl)piperidine-1-carboxylate; and
tetrahydrofuran-3-yl 4-{4-carbamoyl-3-[(4-fluorophenyl)amino]-1H-pyrazol-1-yl}-4-(cyanomethyl)piperidine-1-carboxylate.

3. A compound according to claim 1, wherein $R^a$ is hydrogen or methyl.

4. A compound according to claim 3, wherein $R^4$ is hydrogen or methyl.

5. A compound according to claim 4, wherein A is selected from: furanyl, thienyl, pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridinyl, thienopyridinyl, benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl, imidazo(2,1-b)(1,3)thiazole, and benzo-1,3-dioxolyl, phenyl, indenyl, and naphthyl.

6. A compound according to claim 5, wherein $R^{5a}$ is selected from:
halogen,
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl, aryl $C_{0-10}$ alkyl(oxy)$_{0-1}$(carbonyl)$_{0-1}$$C_{0-10}$ alkyl,
aryl $C_{2-10}$ alkenyl(oxy)$_{0-1}$(carbonyl)$_{0-1}$$C_{0-10}$ alkyl,
aryl $C_{2-10}$ alkynyl(oxy)$_{0-1}$(carbonyl)$_{0-1}$$C_{0-10}$ alkyl,
$C_{3-8}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
$(C_{3-8})$heterocycloalkyl $C_{0-10}$ alkyl(oxy)$_{0-1}$(carbonyl)$_{0-1}$$C_{0-10}$ alkyl,
$C_{1-10}$ alkyl(carbonyl)$_{0-1}$oxy$C_{0-10}$ alkyl,
$C_{1-10}$ heteroalkyl(carbonyl)$_{0-1}$oxy$C_{0-10}$ alkyl, $((C_{0-10})$ alkyl)$_{1-2}$aminocarbonyloxy,
$(C_{0-10})$heteroalkylaminocarbonyloxy, $C_{0-10}$ alkylamino (oxy)$_{0-1}$carbonyl$C_{0-10}$ alkyl,
$(C_{0-10})$heteroalkylamino(oxy)$_{0-1}$carbonyl$C_{0-10}$ alkyl,
$C_{3-8}$ cycloalkyl $C_{0-10}$ alkylamino(oxy)$_{0-1}$carbonyl$C_{0-10}$ alkyl,
aryl $C_{0-10}$alkylamino(oxy)$_{0-1}$carbonyl$C_{0-10}$ alkyl,
heteroaryl$C_{0-10}$alkylamino(oxy)$_{0-1}$carbonyl$C_{0-10}$ alkyl,
$(C_{3-8})$heterocycloalkyl$C_{0-10}$alkylamino(oxy)$_{0-1}$carbonyl$C_{0-10}$ alkyl,
$C_{1-10}$ alkyl(oxy)$_{0-1}$(carbonyl)$_{0-1}$amino$C_{0-10}$ alkyl,
$C_{1-10}$ heteroalkyl (oxy)$_{0-1}$(carbonyl)$_{0-1}$amino$C_{0-10}$ alkyl,
—$CO_2(C_{0-10}$ alkyl),
—$(C_{0-10}$ alkyl)$CO_2H$, Oxo (=O); $C_{1-10}$ alkylsulfonyl,
$C_{1-10}$ heteroalkylsulfonyl,
$(C_{3-8})$cycloalkylsulfonyl, $(C_{3-8})$ cycloheteroalkylsulfonyl, heteroarylsulfonyl, arylsulfonyl,
aminosulfonyl, —$SO_2N(C_{1-6}$alkyl)$_{1-2}$, —$SO_2C_{1-6}$alkyl, —$SO_2CF_3$, —$SO_2CF_2H$, —$Si(CH_3)_3$,
$(C_{0-10}$ alkyl)$_{1-2}$ amino, hydroxy, $(C_{1-10}$ alkyl)OH, $C_{0-10}$ alkylalkoxy, cyano, $(C_{1-6}$alkyl)cyano,
and $C_{1-6}$haloalkyl; wherein two $R^{5a}$ and the atom to which they are attached may optionally form a −4, −5, or −6 member saturated ring system and wherein $R^{5a}$ is each optionally substituted with 1, 2, 3, or 4 $R^6$ substituents.

7. A compound according to claim 6, wherein $R^{5a}$ is independently selected from: tert-butyloxycarbonyl, fluoro, ethoxy, methoxy, methylsulfonyl, oxo, methoxycarbonyl, (methylamino)carbonyl, cyano, 2-hydroxypropanyl, hydroxyethyl, acetyl, methylcarbonyl, trifluoromethylcabonyl, methyl, pyrazolyl, amino, (trifluoromethyl)sulfonyl, (difluoromethyl)sulfonyl, hydroxymethyl, sulfamoyl, dimethylsulfamoyl, dimethylaminocarbonyl, trifluoromethyl, morpholinylcarbonyl, aminocarbonyl, chloro, 1,2,4-oxadiazolyl, cyclobutyloxy, ethoxycarbonyl, cyclopropyl, hydroxypropanyl, trifluoroethyl, bromo, methoxyoxoethyl, morpholinyl, isoxazolyl, phenyl, naphthalenyl, methylCOOH, trifluoroethyl, pyridinylmethyl, benzyl, cyanopropyl, napthalenylmethyl, cyclohexylmethyl, 1,3-benzodioxolylmethyl, propyl, methylsulfonyl, (2E)-3-phenylprop-2-enyl, benzofuranylmethyl, phenylprop-2-ynyl, imidazolylmethyl, pyrazolylmethyl, imidazo[I,2-a]pyridinylmethyl, pyrazinylmethyl, thiazoylmethyl, 1,3-thiazolylmethyl, tetrahydro-2H-pyranylmethyl, pyrazolo[1,5-a]pyridinylmethyl, pyrrolo[2,3-b]pyridinylmethyl, furanylmethyl, indolylmethyl, cyclobutylmethyl, 1,3-oxazolylmethyl, isoxazolylmethyl, benzimidazolylmethyl, 4,5-dyhydroisoxazolylmethyl, phenylethyl, 1-phenylethyl, 2-fluoroethyl, methylsulfonyl, benzyloxycarbonyl, propyloxycarbonyl, cyclobutyloxycarbonyl, cyclobutylmethyloxycarbonyl, isopropyloxycarbonyl, tetrahydrofuranyloxycarbonyl, tetrahydropyranyloxycarbonyl, oxetanyloxycarbonyl, oxetanylmethyloxycarbonyl, propyloxycarbonyl, cyclopentyloxycarbonyl, cyclopropyloxycarbonyl, cyclohexyloxycarbonyl, 2,3-dihydro-1H-indenyloxycarbonyl, pyridinylmethyloxycarbonyl, morpholinylethyloxycarbonyl, piperidinyloxycarbonyl, piperazinylethyloxycarbonyl, piperidinylmethyloxycarbonyl, ethyloxycarbonyl, cyclopropylmethyloxycarbonyl, naphthalenylethyloxycarbonyl, phenylethyloxycarbonyl, ethyloxycarbonyl, pyrrolidinylethyloxycarbonyl, pyridinylethyloxycarbonyl, pyridinylpropyloxycarbonyl, cyclopropylethyloxycarbonyl, ethylcarbonyl, (2E)-prop-2-enylcarbonyl methylcarbonyl, tert-butylcarbonyl, butylcarbonyl, methylcarbonyl, tetrahydrofuranylcarbonyl, pyridinylcarbonyl, pyrazinylcarbonyl, isoxazolylcarbonyl, cyclohexylcarbonyl, thiophenylcarbonyl, pyrrolidinylmethylcarbonyl, (1E)-ethylenylcarbonyl, phenylcarbonyl, indolylcarbonyl, benzylcarbonyl, naphthalenylcarbonyl, quinolinylcarbonyl, methylcarbonyl, tetrahydrofuranylmethylcarbonyl, methylethylcarbonyl, pyrazolylcarbonyl, cyclobutylcarbonyl, dimethylpropylcarbonyl, isopropylsulfonyl, furanylsulfonyl, tert-butylsulfonyl, phenylsulfonyl, imidazolylsulfonyl, cyclopropylsulfonyl, naphthalenylsulfonyl, trifluoromethylsulfonyl, phenylaminocarbonyl, cyclohexylaminocarbonyl, methylethylaminocarbonyl, butylaminocarbonyl, ethylaminocarbonyl, (1,1,3,3,-tetramethylbutyl)aminocarbonyl, phenylethylaminocarbonyl, azetidinyl, cyclohexylamino; phenylamino, pyridinylamino, tetrahydro-2H-pyranylamino, difluoromethylsulfonyl, ethylamino, cyclopropylmethylamino, methylamino, benzylamino, amino, tert-butylcarbonyl, 1,2,3,-tiazolyl, and tetrahydrofuranyloxycarbonyl; wherein two $R^{5a}$ and the atom to which they are attached may optionally form a −4, −5, or −6 member saturated and wherein $R^{5a}$ is each optionally substituted with 1, 2, 3, or 4 $R^6$ substituents.

8. A compound according to claim 6, wherein, X is selected from N and C.

9. A compound according to claim 6, wherein X is selected from O and S.

10. A pharmaceutical composition comprising a compound of claim 1 or a pharmaceutically acceptable salt thereof and a pharmaceutically acceptable carrier.

11. A method for the treatment of a JAK-mediated disease comprising administering to a patient in need thereof a therapeutically effective amount of a compound of claim 1 or a pharmaceutically acceptable thereof.

12. A method of treating a condition in a mammal that can be ameliorated by the selective inhibition of a Janus kinase JAK1 relative to JAK 2 and JAK 3 which condition is selected from arthritis, asthma, obstructive airways diseases, autoimmune diseases or disorders, and cancer comprising administering to the mammal in need of such treatment, a therapeutically effective amount of a compound according to claim 1 or a pharmaceutically acceptable salt or a stereoisomer thereof.

13. A method according to claim 12, wherein said condition is arthritis.

14. A method according to claim 13, wherein said condition is selected from rheumatoid arthritis, juvenile arthritis, and psoriatic arthritis.

15. A method according to claim 12, wherein said condition is asthma or obstructive airways diseases.

16. A method according to claim 15, wherein said condition is selected from: chronic asthma, late asthma, airway hyper-responsiveness, bronchitis, bronchial asthma, allergic asthma, intrinsic asthma, extrinsic asthma, dust asthma, recurrent airway obstruction, chronic obstruction pulmonary disease (COPD), and emphysema.

17. A method according to claim 12, wherein said condition is autoimmune diseases or disorders.

18. A method of treating asthma in a mammal in need thereof, comprising administering a therapeutically effective amount of a compound according to claim 1 or a pharmaceutically acceptable salt thereof.

19. A method of treating arthritis in a mammal in need thereof, comprising administering a therapeutically effective amount of a compound according to claim 1 or a pharmaceutically acceptable salt thereof.

* * * * *